US008354092B2

(12) United States Patent
Kolb et al.

(10) Patent No.: US 8,354,092 B2
(45) Date of Patent: Jan. 15, 2013

(54) DEVELOPMENT OF MOLECULAR IMAGING PROBES FOR CARBONIC ANHYDRASE-IX USING CLICK CHEMISTRY

(75) Inventors: Hartmuth C. Kolb, Playa Del Rey, CA (US); Joseph C. Walsh, Pacific Palisades, CA (US); Dhanalakshmi Kasi, Los Angeles, CA (US); Vani P. Mocharla, Los Angeles, CA (US); Bing Wang, San Jose, CA (US); Umesh B. Gangadharmath, Los Angeles, CA (US); Brian A. Duclos, Kalamazoo, MI (US); Kai Chen, Rockville, MD (US); Wei Zhang, Norwood, MA (US); Gang Chen, Los Angeles, CA (US); Henry Clifton Padgett, Hermosa Beach, CA (US); Farhad Karimi, Mansfield, MA (US); Peter J. H. Scott, Ypsilanti, MI (US); Zhiyong Gao, Wynnewood, PA (US); Qianwa Liang, Hacienda Heights, CA (US); Thomas Lee Collier, Perkasie, PA (US); Tieming Zhao, Los Angeles, CA (US); Chunfang Xia, Los Angeles, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 92 days.

(21) Appl. No.: 12/862,955

(22) Filed: Aug. 25, 2010

(65) Prior Publication Data
US 2010/0317842 A1 Dec. 16, 2010

Related U.S. Application Data

(62) Division of application No. 12/099,135, filed on Apr. 7, 2008, now Pat. No. 7,829,063.

(60) Provisional application No. 60/922,065, filed on Apr. 5, 2007.

(51) Int. Cl.
*A61K 51/00* (2006.01)
*C07D 249/00* (2006.01)
*C07D 343/00* (2006.01)

(52) U.S. Cl. ....... 424/1.53; 514/359; 514/449; 514/461; 530/330; 548/255; 549/429

(58) Field of Classification Search ................. 424/1.53; 530/330; 514/359, 449, 461; 548/255; 549/429
See application file for complete search history.

(56) References Cited

U.S. PATENT DOCUMENTS
6,562,319 B2 5/2003 Mishani et al.

FOREIGN PATENT DOCUMENTS
| WO | WO 2006/116736 A | 11/2006 |
|---|---|---|
| WO | WO 2006135233 A1 | 12/2006 |
| WO | WO 2007018431 A2 | 2/2007 |
| WO | WO 2008/027162 A | 3/2008 |
| WO | WO 2008033557 A2 | 3/2008 |

OTHER PUBLICATIONS

Wang et al., Integrated Microfluidics for Parallel Screening of an In Situ Click Chemistry Library, Angew. Chem. Int. Ed., 2006, vol. 45, 5276-5281, in particular p. 5280, Table 1, compound 10.*
Wheeler, et al., Microfluidic labeling of biomolecules with radiometals for use in nuclear medicine, Lab. Chip., 2010, vol. 10, 3387-3396.*
Mocharla Vani P et al.: "In Situ Click Chemistry: Enzyme-Generated Inhibitors of Carbonic Anhydrase II", Angew Andte Chemie. International Edition, VCH Verlag, Weinheim, DE, vol. 44, No. 1, Dec. 17, 2004 , pp. 116-120, XP009072498, ISSN: 0570-0833, p. 119, right-hand column; tables 1, 2; p. 117, right-hand column.
Wilkinson Brendan L. et al.: "A novel class of carbonic anhydrase inhibitors: glycoconjugate benzene sulfonamides prepared by "click-tailing".", Journal of Medicinal Chemistry, Nov. 2, 2006, vol. 49, No. 22, Nov. 2, 2006, pp. 6539-6548, XP002496737, ISSN: 0022-2653, p. 6539, left-hand column; figure 2; compounds 2,3, p. 6540, left-hand column, paragraph 1.
Schmidt, et al. "Synthesis of Entantriomerically Pure and Compatibly Protected (2S, 3R)- and (2S, 3S)-Diaminobutyric Acids" Published in Synthesis, No. 12, 1992 (pp. 1201-1202); Magazine.
Kuijpers, et al. "Expedient synthesis of triazole-linked glycosyl amino acids and peptides" Published by Organic Letters, American Chemical Society, vol. 6, No. 18, Sep. 2, 2004 (pp. 3123-3126); Magazine.
Oppolzer, et al. "Non-destructive Cleavage of N-Acylsultams Under Neutral Conditions: Preparation of Enantiomerically Pure Fmoc-Protected alpha-Amino Acids" Published by Helvetica Chimica Acta, vol. 75, 1992 (pp. 2572-2582); Magazine.
Franke, et al. "Peptide ligation through click chemistry for the generation of assembled and scaffolded peptides" Published in Tetrahedron Letters, Elsevier, Science Direct, vol. 46, No. 26, Jun. 27, 2005 (pp. 4479-4482); Magazine.
International Search Report in Application No. PCT/US2009/003309 dated Nov. 12, 2009.
Office Action dated Jun. 15, 2011 in Korean Patent Application No. 10-2009-7022869 (English translation attached), 15 pages.

* cited by examiner

*Primary Examiner* — Susannah Chung
(74) *Attorney, Agent, or Firm* — Joshua Ryan

(57) ABSTRACT

The present application discloses methods for identifying inhibitors with high binding-affinity for the carbonic anhydrase-IX (CA-IX) enzyme using click chemistry and uses the candidates thereof as positron emission tomography (PET) imaging agents.

38 Claims, 25 Drawing Sheets

| Entry | Code Name | Chemical Structure | Mol. Wt. | QPLogPo/w (Calc.)[a] | In Vitro Binding Affinity IC₅₀ (nM) | | | K_d (nM) | | Red Blood Cell Uptake | |
|---|---|---|---|---|---|---|---|---|---|---|---|
| | | | | | CA-IX | CA-II | CA-IX | CA-II | (−) Ethoxzo-lamide | (+) 1mM Ethoxzo-lamide |
| 1 | DHK7 | (structure) | 462.52 | 2.54 | 1157 | 59 | 17 | 1.1 | 15.13[b] | 2.58 |
| 2 | DHK19 | (structure) | 403.50 | 1.92 | 960 | 57 | 14 | 1 | 15.53 | 7.15 |
| 3 | DHK25 | (structure) | 403.46 | 0.80 | 348 | 36 | 5 | 0.5 | 23.48 | 6.81 |
| 4 | DHK29 | (structure) | 355.37 | 1.05 | 944 | 36 | 20 | 1 | 10.04 | 4.01 |

FIG. 3A

| Entry | Code Name | Chemical Structure | Mol. Wt. | QPLogPo/w (Calc.)[a] | In Vitro Binding Affinity IC$_{50}$ (nM) | | K$_d$ (nM) | | Red Blood Cell Uptake | |
|---|---|---|---|---|---|---|---|---|---|---|
| | | | | | CA-IX | CA-II | CA-IX | CA-II | (−) Ethoxzo-lamide | (+) 1mM Ethoxzo-lamide |
| 5 | DHK113 | (structure) | 576.67 | 2.07 | 586 | 81 | 10 | 1.3 | 19.97 | 5.18 |
| 6 | DHK117 | (structure) | 536.57 | 2.28 | 1011 | 89 | 14.1 | 1.6 | 4.52 | 2.21 |
| 7 | DHK121 | (structure) | 480.36 | 2.35 | 1197 | 81 | 25 | 1.1 | 7.58 | 3.26 |

| Entry | Code Name | Chemical Structure | Mol. Wt. | QPLogPo/w(Calc.)a | In Vitro Binding Affinity | | | | | Red Blood Cell Uptake | |
|---|---|---|---|---|---|---|---|---|---|---|---|
| | | | | | IC₅₀ (nM) | | | K_d (nM) | | | |
| | | | | | CA-IX | CA-II | | CA-IX | CA-II | (-) Ethoxzo | (+) 1mM Ethoxzo |
| 8 | DHK123 | 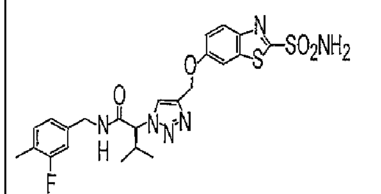 | 532.61 | 2.17 | 961 | 83 | | 12.5 | 1 | 9.59 | 3.78 |
| 9 | DHK125 | 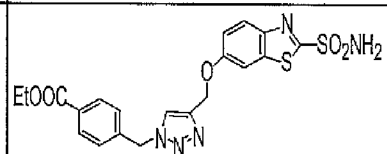 | 473.53 | 1.62 | 1000 | 74 | | 16.7 | 1.4 | 14.27 | 4.35 |
| 10 | DHK127 | 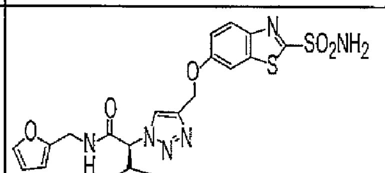 | 490.56 | 1.30 | 1653 | 27.7 | | 25 | 0.5 | 15.68 | 4.64 |
| 11 | DHK128 | 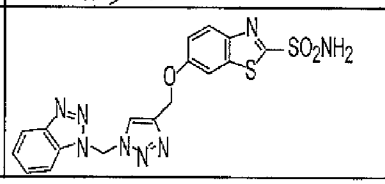 | 442.47 | 0.92 | 737 | 81 | | 12.5 | 0.2 | 20.41 | 5.31 |

| Entry | Code Name | Chemical Structure | Mol. Wt. | QPLogPo/w (Calc.)a | In Vitro Binding Affinity | | | | | Red Blood Cell Uptake | |
|---|---|---|---|---|---|---|---|---|---|---|---|
| | | | | | IC$_{50}$ (nM) | | | K$_d$ (nM) | | (−) Ethoxzo-lamide | (+) 1mM Ethoxzo-lamide |
| | | | | | CA-IX | CA-II | | CA-IX | CA-II | | |
| 1 | DHK-2-24 | 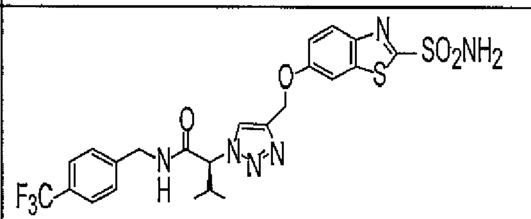 | 568.59 | 2.82 | 196 | 61 | | 1 | 0.25 | — | — |
| 2 | DHK-2-41 | 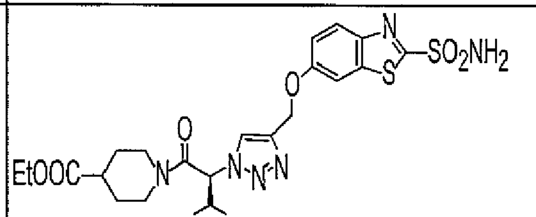 | 550.65 | 0.84 | 620 | 74 | | 5 | 1 | — | — |
| 3 | DHK-2-44 | 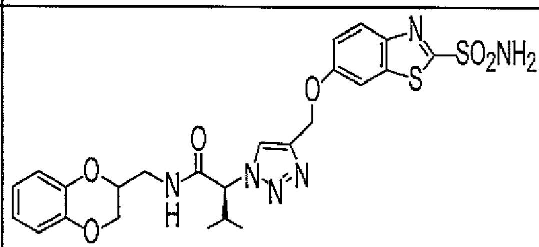 | 558.63 | 1.85 | 198 | 56 | | 5 | 0.5 | — | — |

FIG. 5A

| Entry | Code Name | Chemical Structure | Mol. Wt. | QPLogPo/w (Calc.)a | In Vitro Binding Affinity | | | | | Red Blood Cell Uptake | |
|---|---|---|---|---|---|---|---|---|---|---|---|
| | | | | | IC$_{50}$ (nM) | | | K$_d$ (nM) | | (−) Ethoxzo-lamide | (+) 1mM Ethoxzo-lamide |
| | | | | | CA-IX | CA-II | | CA-IX | CA-II | | |
| 4 | DHK-2-51 | 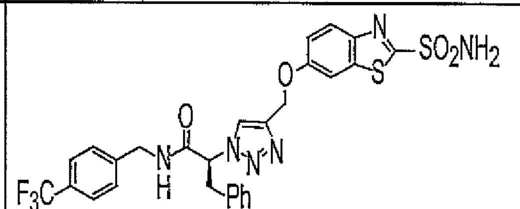 | 616.63 | 3.74 | 82 | 56 | | 2.5 | 0.2 | — | — |
| 5 | DHK-2-66 | 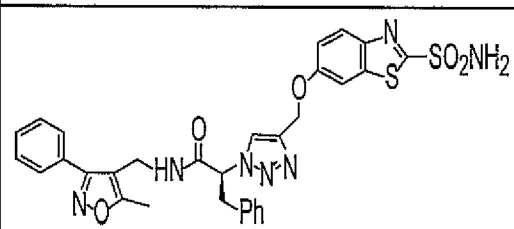 | 629.71 2 | 3.04 | 212 | 62 | | 2 | 0.34 | — | — |

FIG. 5B

| Entry | Code Name | Chemical Structure | Mol. Wt. | QPLogPo/w(Calc.)a | In Vitro Binding Affinity | | | | Red Blood Cell Uptake | |
|---|---|---|---|---|---|---|---|---|---|---|
| | | | | | IC$_{50}$ (nM) | | K$_d$ (nM) | | (−) Ethoxzo-lamide | (+) 1mM Ethoxzo-lamide |
| | | | | | CA-IX | CA-II | CA-IX | CA-II | | |
| 6 | DHK-2-68 | 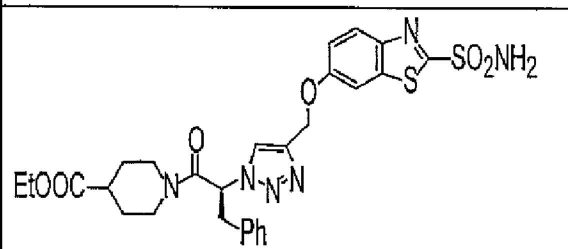 | 598.69 | 1.91 | 469 | 68 | 3.4 | 0.5 | — | — |
| 7 | DHK-2-71 | 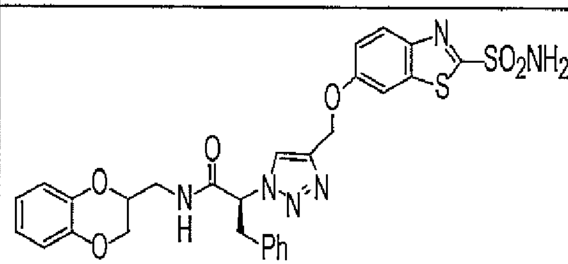 | 606.67 | 2.89 | 118 | 56 | 2.5 | 0.25 | — | — |

FIG. 5C

| Entry | Code Name | Chemical Structure | Mol. Wt. | In Vitro Binding Affinity | | | | Red Blood Cell Uptake | |
|---|---|---|---|---|---|---|---|---|---|
| | | | | IC$_{50}$ (nM) | | K$_d$ (nM) | | (−) Ethoxzo-lamide | (+) 1mM Ethoxzo-lamide |
| | | | | CA-IX | CA-II | CA-IX | CA-II | | |
| 1 | DHK149 | 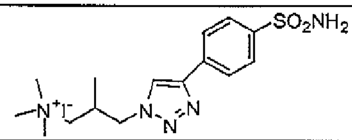 | 465.35 | 2083 | 745 | 100 | 10 | 0.06$^a$ | 0.02 |
| 2 | DHK159 | 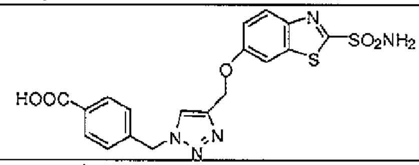 | 445.47 | 982 | 120 | 14.1 | 2 | 0.04 | 0.03 |
| 3 | DHK160 | 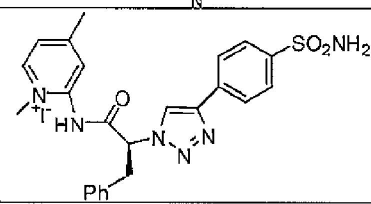 | 604.46 | 1467 | 46 | 20 | 1 | 0.02 | 0.01 |
| 4 | DHK161 |  | 562.64 | 625 | 99 | 10 | 1.4 | 0.03 | 0.02 |

# DEVELOPMENT OF MOLECULAR IMAGING PROBES FOR CARBONIC ANHYDRASE-IX USING CLICK CHEMISTRY

CROSS-REFERENCE TO RELATED PATENT APPLICATIONS

This application is a divisional of U.S. Ser. No. 12/099,135, filed on Apr. 7, 2008. The entire content of U.S. Ser. No. 12/099,135 is incorporated by reference herein. This application also claims priority from Provisional Application U.S. Application 60/922,065, filed Apr. 5, 2007, incorporated herein by reference in its entirety.

FIELD OF THE INVENTION

The present invention relates to radioactively labeled high affinity CA-IX ligands that identify enzymatic activity of cell-surface expressed CA-IX, a protein over expressed in patients in with tumor growth. These cell impermeable tracers have high affinity for CA-IX, and are thus selective for CA-IX over CA-II, and exhibit favorable imaging properties. In addition, these tracers bind to tumors expressing CA-IX. Because these tracers provide biochemical information related to CA-IX enzymatic activity, these tracers may provide valuable information regarding a patient's potential response to therapy, outcome prognosis and treatment regimen.

BACKGROUND OF THE INVENTION

Positron Emission Tomography (PET), a molecular imaging technology, detects a myriad of diseases non-invasively. PET imaging systems create images based on the distribution of positron-emitting isotopes in the tissue of the patient. The isotopes are typically administered to a patient by injection of probe molecules that are comprised of a positron-emitting isotope, such as F-18, C-11, N-13 or O-15, covalently attached to a molecule that metabolizes or localizes in the body, or that binds to receptor sites within the body.

One of the most widely used positron-emitter labeled PET molecular imaging probes is 2-deoxy-2-[$^{18}$F]fluoro-D-glucose ([$^{18}$F]FDG). [$^{18}$F]FDG, which primarily targets glucose transporters, is an accurate clinical tool for the early detection, staging, and restaging of cancer. PET-FDG imaging is increasingly used to monitor cancer chemo- and radio-therapy because early changes in glucose utilization have been shown to correlate with outcome predictions. A characteristic feature of tumor cells is their accelerated glycolysis rate, which results from the high metabolic demands of rapidly proliferating tumor tissue. Like glucose, FDG is taken up by cancer cells via glucose transporters and is phosphorylated by hexokinase to FDG-6 phosphate. The latter cannot proceed any further in the glycolysis chain or leave the cell, due to its charge, allowing cells with high glycolysis rates to be detected.

Although useful in many contexts, several limitations of FDG-PET imaging for monitoring cancer exist as well. Accumulation of FDG in inflammatory tissue limits the specificity of FDG-PET. Conversely, nonspecific FDG uptake may also limit the sensitivity of PET for tumor response prediction. Therapy-induced cellular stress reactions have been shown to cause a temporary increase in FDG-uptake in tumor cell lines treated by radiotherapy and chemotherapeutic drugs. Furthermore, physiologically-high normal background activity (e.g. FDG uptake in the brain) can render the quantification of cancer-related FDG-uptake impossible in some areas of the body.

Due to these limitations, other PET imaging tracers are being developed to target a variety of enzyme-mediated transformations in cancer tissue, such as 6-[F-18]-fluoro-L-DOPA for dopamine synthesis, 3'-[F-18]Fluoro-3'-deoxythymidine (FLT) for DNA replication, and [C-11](methyl)choline for choline kinase, as well as ultra-high specific activity receptor-ligand binding (e.g., 16α [F-18]fluoroestradiol). Molecularly targeted agents have demonstrated great potential value for the non-invasive PET imaging of specific metabolic targets in cancers. Despite the clear clinical value of incorporating PET imaging into patient management, limitations do exist. In certain instances, current imaging probes lack specificity or have inadequate signal to background characteristics. In addition, new biological targets that are being tested for therapeutic intervention will require new imaging probes to evaluate their therapeutic potential. Additional biomarkers are needed that show a very high affinity to, and specificity for, tumor targets to support cancer drug development and to provide health care providers with a means to accurately diagnose disease and monitor treatment.

The carbonic anhydrases (CAs, EC 4.2.1.1) form a large family of genes encoding zinc metalloenzymes of great physiological importance. As catalysts for the reversible hydration of carbon dioxide, these enzymes participate in many diverse biological processes, including respiration, calcification, acid-base balance, bone resorption and in the formation of both cerebrospinal fluid and gastric acid. As a reflection of the importance of these enzymes, the carbonic anhydrases are widely distributed in many different living organisms. In higher vertebrates, including humans, 16 isozymes have been identified so far that differ in their subcellular localization, catalytic activity and susceptibility to different classes of inhibitors. Some of these isozymes are cytosolic (CA-I, CA-II, CA-III, CA-VII and CA-XIII), others are membrane bound (CA-IV, CA-IX, CA-XII and CA-XIV), two are mitochondrial (CA-VA and CA-VB), and one is secreted in saliva (CA-VI). The CAs and CA-related proteins show extensive diversity in their tissue distribution, levels of expression, and putative or established biological functions. Some CAs are ubiquitously expressed in almost all tissues, such as CA-II, while the expression of other CAs appear to be restricted in their tissue expression patterns.

Recently, it has been shown that two CA isozymes (CA-IX and CA-XII) are prominently associated with, and over expressed in, many tumors, where they are involved in crucial processes connected with cancer progression. The first CA found to be associated with cancers was CA-IX, as reported in 1992 (Pastorekova S., et al., Virology, 1992, 187, 620-626). The strong association between CA-IX expression and intratumorial hypoxia has been demonstrated in the cervical, breast, head and neck, bladder and non-small cell lung carcinomas. In addition, in breast carcinomas and non-small cell lung carcinomas, correlation between CA-IX and a constellation of proteins involved in angiogenesis, apoptosis inhibition and cell-cell adhesion disruption has been observed. Hypoxia is linked with acidification of the extracellular milieu that facilitates tumor invasion and CA-IX is believed to play a role in this process via its catalytic activity. Thus, there are several reasons that CA-IX is considered as one of the best targets for cancer diagnosis and therapy. For instance, CA-IX is an integral plasma membrane protein with an extracellularly exposed enzyme active site. Also, CA-IX has a very high catalytic activity with the highest proton transfer rate among the known CAs. In addition, CA-IX is present in few normal tissues such as the gall bladder and stomach, but its over expression is strongly associated with many tumor tissues such as lung, head and neck, renal and cervical carcinomas. Finally, CA-IX levels dramatically increase in response to hypoxia via a direct transcriptional activation of the CA-IX gene by HIF-1 (Giatromanolaki et al., *Cancer Res.*, 2001, 61, 7992-7998; Dubois et al., *Br. J. Cancer*, 2004, 91, 1947-1954), and the expression of CA-IX in certain tumors can be a sign of poor prognosis. Consequently, discovery of specific inhibitors for CA-IX constitutes a novel approach to the diagnosis and treatment of cancers in which CA-IX is expressed.

The enzymatic activity of carbonic anhydrases can be efficiently blocked by sulfonamide inhibitors, a fact that has been therapeutically exploited in diseases caused by excessive activities of certain CA isoforms (e.g. CA-II in glaucoma). There is also experimental evidence that sulfonamides block both tumor cell proliferation and invasion in vitro, and tumor growth in vivo, but the targets of those sulfonamides have not yet been identified. Unfortunately, the sulfonamides available thus far indiscriminately inhibit various CA isoenzymes and the sulfonamides' lack of selectivity compromises their clinical utilization presenting a major drawback for the application of sulfonamides in specific CA-IX-targeted therapies.

Currently, there exists very few reported PET imaging agents that are both selective for the CA-IX enzyme and which have provided useful in vivo images. For example, the use of the radiolabeled monoclonal antibody $^{124}$I-G250 for targeting CA-IX in hypoxic tumors and CA-IX expression in xenografted human renal cell carcinoma animal models (Lawrentschuk, N., et al, *British Journal of Urology*, 2006, 97, Suppl. 1, 10-10(1)) has been reported. However, it is well documented that the application of monoclonal antibodies has substantial limitations, such as slow clearance.

SUMMARY OF THE INVENTION

We have identified a need for developing methods for identifying membrane-impermeable, high-affinity CA-IX inhibitors and for the development of inhibitors into useful candidates as PET tracers for imaging CA-IX expression in vivo. The present invention addresses these needs. In one aspect, the present invention provides novel sulfonamide compounds that are particularly active in inhibiting carbonic anhydrase (CA), especially those selectively targeting the cancer-related, hypoxia-induced CA-IX isozyme. Such sulfonamide compounds and their derivatives are useful for the development of in vivo positron emission tomography (PET) imaging agents for the diagnosis of diseases such as cancer.

In one embodiment of the present application, there is provided a compound of the Formula I:

Z—X-A-Y—B—SO$_2$NH$_2$     Formula I wherein:

A is 3- to 7-membered saturated or unsaturated heterocycle,

B is aryl, heteroaryl, $C_3$-$C_7$cycloalkyl, $C_3$-$C_7$cycloalkenyl, $C_3$-$C_7$saturated heterocyclic, or $C_3$-$C_7$ unsaturated heterocyclic;

X is a linker, including alkyl, alkyloxyl, $C_3$-$C_7$ cycloalkyl, $C_3$-$C_7$ cycloalkenyl, aryl, or 3- to 7-membered heterocycle, each of which may be optionally substituted with one or more halogen, $C_1$-$C_6$ alkyl, $C_1$-$C_6$ alkenyl, ($C_1$-$C_6$ alkylene)-aryl, $C_1$-$C_6$ alkynyl, —N(R$_1$)$_2$, —CN, —OR$_1$, —SR$_1$, —S(O)—R$_1$, —SO$_2$—R$_1$, —SO$_2$NH—R$_1$, —SO$_3$H, —NH—SO$_2$—R$_1$, —C(O)R$_2$, P(O)(OR$_1$)$_2$, or —NHC(O)R$_2$ group;

Y is a linker, including a bond, alkyl, alkyloxy, $C_3$-$C_7$ cycloalkyl, $C_3$-$C_7$ cycloalkenyl, or 3- to 7-membered heterocycle, each of which may be optionally substituted with one or more halogen, $C_1$-$C_6$ alkyl, $C_1$-$C_6$ alkenyl, ($C_1$-$C_6$ alkylene)-aryl, $C_1$-$C_6$ alkynyl, poly(alkoxy), —N(R$_1$)$_2$, —CN, —OR$_1$, —SR$_1$, —S(O)—R$_1$, —SO$_2$—R$_1$, —SO$_2$NH—R$_1$, —SO$_3$H, —NH—SO$_2$—R$_1$, —C(O)R$_2$, —P(O)(OR$_1$)$_2$, or —NHC(O)R$_2$ group;

each R$_1$ is independently H, $C_1$-$C_6$ alkyl, $C_1$-$C_6$ alkenyl, $C_1$-$C_6$ alkynyl, aryl, heteroaryl, ($C_1$-$C_6$ alkylene)-aryl, $C_3$-$C_7$ cycloaryl, $C_3$-$C_7$ cycloalkenyl or 3- to 7-membered heterocycle;

each R$_2$ is independently —R$_1$, —N(R$_1$)$_2$ or —OR$_1$;

Z is optionally substituted aryl, optionally substituted heteroaryl, optionally substituted $C_3$-$C_7$ cycloalkyl, optionally substituted $C_3$-$C_7$ cycloalkenyl, or optionally substituted 3- to 7-membered heterocycle;

C is a charged component or species, which is optionally present in X, or Y, or Z;

W is a radionuclide, which is optionally present in X, or Y, or Z; and including single stereoisomers and mixtures of stereoisomers and the pharmaceutically acceptable salts thereof.

In one embodiment, A is a triazole, B is an optionally substituted aryl, Y is a bond, X is independently a bond, optionally substituted alkyl, optionally substituted aryl, optionally substituted heterocycle, optionally substituted amino carbonyl, and Z is optionally substituted aryl, optionally substituted heteroaryl, or optionally substituted heterocycle. The substituted groups are selected from hydroxyl, amino or substituted amino, lower alkyl, lower alkenyl, alkoxy, aryl, alkoxyaryl, heteroaryl, halogen, carboxy, substituted amino carbonyl, cyano, nitro, sulfonyl, substituted amino acid, such as Ala, Asn, Cys, Glu, Gly, Gln, His, Lys, Ser, Tyr, Val or Phe, especially Cys, His and Phe.

In another embodiment, A is methyl triazole, B is an optionally substituted aryl, Y is an amino carbonyl, X is independently a covalent bond, optionally substituted alkyl, optionally substituted aryl, optionally substituted heterocycle, optionally substituted amino carbonyl, and Z is optionally substituted aryl, optionally substituted heteroaryl, or optionally substituted heterocycle. The substituted groups are selected from hydroxyl, amino or substituted amino, lower alkyl, lower alkenyl, alkoxy, aryl, alkoxyaryl, heterocycloalkyl, heteroaryl, halogen, optionally substituted carboxy, substituted amino carbonyl, cyano, nitro, sulfonyl, substituted amino acid, such as Ala, Asn, Cys, Glu, Gly, Gln, His, Lys, Ser, Tyr, Val or Phe, especially Cys, His and Phe.

In yet another embodiment, A is a triazole, B is an optionally substituted heteroaryl, Y is an alkoxy, preferably methyleneoxy, X is independently a covalent bond, optionally substituted alkyl, optionally substituted aryl, optionally substituted heterocycle, optionally substituted acyl, or optionally substituted amino carbonyl, and Z is optionally substituted aryl, optionally substituted heteroaryl, optionally substituted heterocycle, or optionally substituted amino acid, preferably Ala, Val, Phe, Cys, Pro or Trp. The substituted groups are selected from hydroxyl, amino or substituted amino, substituted lower alkyl, substituted lower alkenyl, alkoxy, aryl, alkoxyaryl, heterocycloalkyl, heteroaryl, halogen, optionally substituted carboxy, substituted amino carbonyl, cyano, nitro, sulfonyl, substituted amino acid, such as Ala, Asn, Cys, Glu, Gly, Gln, His, Lys, Ser, Tyr Val or Phe, especially Cys, His and Phe.

In all these embodiments, a charged moiety that is either a cation or anion, can be optionally incorporated into X, Y and Z. Without being bound by any theory proposed herein, it is believed that the charged moiety is important for achieving cellular impermeability of the said compounds, and hence allows for selective binding to the extracellularly located CA-IX enzyme. The cation moiety can be selected from quaternary ammonium salts, imidate salts, thiolate salts, oxonium cations, lewis-acid base complexes such as boronamine salts, or pyridinium salts, and the like. The anion moiety can be selected from such acidic groups that become charged at physiological pH as carboxylic acid, sulfonic acid, phosphoric acid, phosphonic acid, N-oxides, sulfinates, or boronic acid.

In another embodiment, there is provided the compounds represented in formula above, but the compounds have been converted into radiolabeled derivatives. In one embodiment, A is a triazole, B is an optionally substituted heteroaryl, Y is an alkoxy, preferably methyleneoxy, X is independently a covalent bond, optionally substituted alkyl, optionally substituted aryl, optionally substituted heterocycle, optionally substituted acyl, or optionally substituted amino carbonyl, and Z is optionally substituted aryl, optionally substituted heteroaryl, optionally substituted heterocycle, or optionally substituted amino acid, preferably Ala, Val, Phe, Cys, Pro or Trp. The substituted groups are selected from hydroxyl, amino or substituted amino, substituted lower alkyl, substituted lower alkenyl, alkoxy, aryl, alkoxyaryl, heterocycloalkyl, heteroaryl, halogen, optionally substituted carboxy, substituted amino carbonyl, cyano, nitro, sulfonyl, substituted amino acid, such as Ala, Asn, Cys, Glu, Gly, Gln, His, Lys, Ser, Tyr or Phe, especially Cys, His and Phe. A charged moiety, either a cation or anion, is incorporated into either X, Y or Z. The cation moiety can be selected from quaternary ammonium salts or pyridinium salts, and the like. The anion moiety can be selected from such acidic groups that become charged at physiological pH as carboxylic acid, sulfonic acid, phosphoric acid, phosphonic acid, or boronic acid. A radioactive element or nuclide may be incorporated on either X, Y or Z. The radioactive elements may be selected from $^{18}F$, $^{11}C$, $^{13}N$ or $^{15}O$, preferably an $^{18}F$.

In another embodiment, there is provided a compound comprising the Formula Ia, Ib, IIa or IIb:

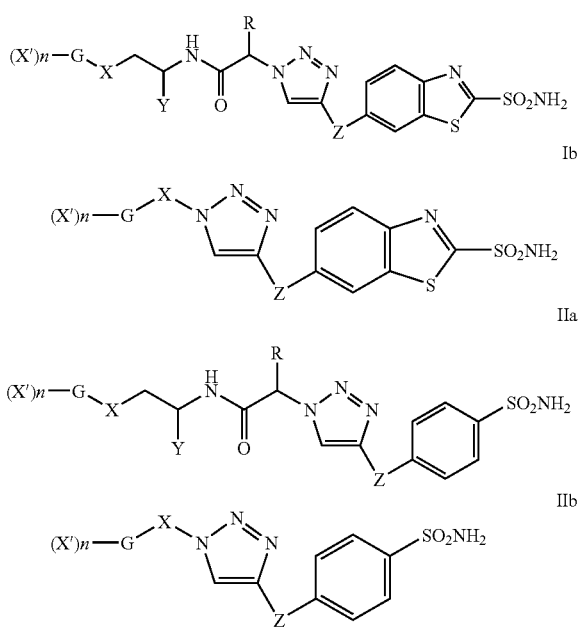

wherein for Ia and IIa:
each G is independently a bond or is independently selected from the group consisting of substituted or unsubstituted heterocyclyl, aryl and heteroaryl;
n is 0, 1, 2 or 3;
X is a bond, an amino acid residue, or is selected from the group consisting of —O—, —S—, —S(O)—, —S(O)$_2$—, —NR$^o$— where R$^o$ is H or $C_{1-5}$alkyl, heterocyclyl, aryl, heteroaryl, $C_{1-6}$alkyl, $C_{1-6}$alkyl wherein 1 or 2 carbon atoms of the $C_{1-6}$alkyl is replaced by a —O—, —C(O)—, —S—, —S(O)—, —S(O)$_2$— or —NR'''— where R''' is H or $C_{1-5}$alkyl, and where the $C_{1-6}$alkyl is optionally substituted with 1 or 2 substituents selected from the group consisting of —OH, —SH, NH$_2$, heterocyclyl, aryl and heteroaryl;
X' is selected from the group consisting of a charged species, —OH, amino, halo, —CF$_3$, —CH$_2$F, —CHF$_2$, —COON, —COOC$_{1-5}$alkyl, —COC$_{1-5}$alkyl, —CO-aryl, —CO-heteroaryl, $C_{1-6}$alkyl, amino-$C_{1-5}$alkyl-, optionally substituted aryl, optionally substituted heteroaryl, halo-$C_{1-5}$alkyl, halo-$C_{1-5}$alkoxy-; Z'—$C_{2-6}$alkyl, Z'—$C_{2-6}$alkyl-O—, Z'—$C_{2-6}$alkyl-O—$C_{1-3}$alkyl-, Z'—$C_{2-6}$alkyl-S—, Z'—$C_{2-6}$alkyl-NH—, Z'—$C_{2-6}$alkyl-NH—$C_{1-3}$ alkyl-, Z'—$C_{2-6}$alkyl-N($C_{1-3}$ alkyl)-$C_{1-3}$ alkyl-, Z'—(CH$_2$CH$_2$—O)$_{1-5}$—, wherein Z' is selected from the group consisting of halo, —CF$_3$, —CH$_2$F, —CHF$_2$, aryl and heteroaryl;
Y is H or is selected from the group consisting of a charged species, —COOR'', —SO$_3$R'', —P(O)$_2$OR'' and —OP(O)$_2$OR'' wherein R'' is H or $C_{1-3}$alkyl;
R is H or a side chain of an amino acid or a derivative thereof, —$C_{1-5}$alkyl-o, m, or p-aryl-(O—CH$_2$CH$_2$)$_{1-5}$-halo or —$C_{1-5}$alkyl-o, m, or p-aryl-(CH$_2$CH$_2$)$_{1-5}$-halo; and
Z is a bond or is selected from the group consisting of —O—, —C(O)—, —C(O)NR'—, —S—, —S(O)—, —S(O)$_2$—, —NR$^o$— where R$^o$ is H or $C_{1-5}$alkyl, $C_{1-3}$alkyl, $C_{1-3}$alkyl wherein 1 or 2 carbon atoms of the $C_{1-5}$alkyl is replaced by a —O—, —S—, —C(O)—, —C(O)NR'''—, —S(O)—, —S(O)$_2$—, —S(O)$_2$NR'''— or —NR'''—, where R''' is H or $C_{1-5}$alkyl; and wherein for Ib and IIb:
each G is independently a bond or is independently selected from the group consisting of substituted or unsubstituted heterocyclyl, aryl and heteroaryl;
n is 0, 1, 2 or 3;
X is a bond, an amino acid residue, or is selected from the group consisting of —O—, —S—, —S(O)—, —S(O)$_2$—, —NR$^o$— where R$^o$ is H or $C_{1-5}$alkyl, heterocyclyl, aryl, heteroaryl, $C_{1-6}$alkyl and $C_{1-6}$alkyl wherein 1 or 2 carbon atoms of the $C_{1-6}$alkyl is replaced by a —O—, —C(O)—, —S—, —S(O)—, —S(O)$_2$— or —NR'''— where R''' is H or $C_{1-5}$alkyl, and where the $C_{1-6}$alkyl is optionally substituted with 1 or 2 substituents selected from the group consisting of —OH, —SH, NH$_2$, heterocyclyl, aryl and heteroaryl;
X' is selected from the group consisting of a charged species, —OH, amino, halo, —CF$_3$, —CH$_2$F, —CHF$_2$, —COON, —COOC$_{1-5}$alkyl, —COC$_{1-5}$alkyl, —CO-aryl, —CO-heteroaryl, $C_{1-6}$alkyl, amino-$C_{1-5}$alkyl-, optionally substituted aryl, optionally substituted heteroaryl, halo-$C_{1-5}$alkyl, halo-$C_{1-5}$alkoxy-; Z'—$C_{2-6}$alkyl, Z'—$C_{2-6}$alkyl-O—, Z'—$C_{2-6}$alkyl-O—$C_{1-3}$alkyl-, Z'—$C_{2-6}$alkyl-S—, Z'—$C_{2-6}$alkyl-NH—, Z'—$C_{2-6}$alkyl-NH—$C_{1-3}$ alkyl-, Z'—$C_{2-6}$alkyl-N($C_{1-3}$ alkyl)-$C_{1-3}$ alkyl-, Z'—(CH$_2$CH$_2$—O)$_{1-5}$—, wherein Z' is selected from the group consisting of halo, —CF$_3$, —CH$_2$F, —CHF$_2$, aryl and heteroaryl;
Z is a bond or is selected from the group consisting of —O—, —C(O)—, —C(O)NR'—, —S—, —S(O)—, —S(O)$_2$—, —NR'— where R' is H or $C_{1-5}$alkyl, $C_{1-3}$alkyl, $C_{1-3}$alkyl wherein 1 or 2 carbon atoms of the $C_{1-5}$alkyl is replaced by a —O—, —S—, —C(O)—, —C(O)NR'''—, —S(O)—, —S(O)$_2$—, —S(O)$_2$NR'''— or —NR'''—, where R''' is H or C$_{1-5}$alkyl; and wherein at least one of the group X, X', G, X and Y comprises a radionuclide or a non-radioactive element;

or a pharmaceutically acceptable salt thereof, optionally in the form of a single stereoisomer or mixtures of stereoisomers thereof.

In one variation, the compound is of the Formula Ia, or a pharmaceutically acceptable salt thereof, optionally in the form of a single stereoisomer or mixtures of stereoisomers thereof. In another variation, the compound is of the Formula Ib, or a pharmaceutically acceptable salt thereof, optionally in the form of a single stereoisomer or mixtures of stereoisomers thereof. In another variation, the compound is of the Formula Ia, or a pharmaceutically acceptable salt thereof, optionally in the form of a single stereoisomer or mixtures of stereoisomers thereof. In another variation, the compound is of the Formula IIb, or a pharmaceutically acceptable salt thereof, optionally in the form of a single stereoisomer or mixtures of stereoisomers thereof. In one aspect of the compound of Formula Ia, Ib, IIa or IIb, the radionuclide is selected from the group consisting of $^{11}$C, $^{18}$F, $^{13}$N and $^{15}$O.

In another aspect, Z is a bond or is selected from the group consisting of C$_{1-3}$alkyl and C$_{1-3}$alkyl wherein 1 or 2 carbon atoms of the C$_{1-5}$alkyl is replaced by a —O—, —S—, —C(O)—, —C(O)NR'''—, —S(O)—, —S(O)$_2$—, —S(O)$_2$NR'''— or —NR'''—, where R''' is H or C$_{1-5}$alkyl. In one variation of the above, the charged species is selected from the group consisting of carboxylic acids, sulfonic acids, phosphonic acid and ammonium ion and their respective salts. In another variation, the charged species comprises a group selected from —COOH, —SO$_3$H, —PO$_3$H, —N(C$_{1-6}$alkyl)$_3$$^+$X$^-$ wherein X$^-$ is a counter anion. In certain variations of the compound of the present application, the charged species exclude 1,2,3,5-substituted pyrylium salts of 4-alkylenylbenzensulfonamides, 2-(1,2,3,5-substituted pyrylium)-5-(sulfonamide)-1,3,4-thiadiazoles, and aryl and heteroaryl sulfonamides of 2,4,6-trisubstituted-pyridinium-methylcarboxylic acids and their derivatives.

In yet another variation of the above compound, Z is a bond or is selected form the group consisting of —CH$_2$—O—, —CH$_2$CH$_2$—O—, —CH$_2$—O—CH$_2$—, —(CH$_2$)$_{2-3}$O—CH$_2$— and —CH$_2$—O—(CH$_2$)$_{2-3}$—. In a particular variation, X is a bond, an amino acid residue, or is selected from the group consisting of heterocyclyl, aryl, heteroaryl, C$_{1-6}$alkyl, C$_{1-6}$alkyl wherein 1 or 2 carbon atoms of the C$_{1-6}$alkyl is replaced by a —O—, —C(O)—, —S—, —S(O)—, —S(O)$_2$— or —NR'''— where R''' is H or C$_{1-5}$alkyl, and where the C$_{1-6}$alkyl is optionally substituted with 1 or 2 substituents selected from the group consisting of —OH, —SH, NH$_2$, heterocyclyl, aryl and heteroaryl. In another variation of the above, each G is independently a bond or is independently selected from the group consisting of substituted or unsubstituted heterocyclyl, aryl and heteroaryl; and Z is a bond or is selected from the group consisting of C$_{1-3}$alkyl and C$_{1-3}$alkyl wherein 1 or 2 carbon atoms of the C$_{1-5}$alkyl is replaced by a —O—, —S—, —C(O)—, —C(O)NR'''—, —S(O)—, —S(O)$_2$—, —S(O)$_2$NR'''— or —NR'''— where R''' is H or C$_{1-5}$alkyl.

In yet another aspect of the above compound, each G is independently a bond or is independently selected from the group consisting of substituted or unsubstituted heterocyclyl, aryl and heteroaryl; Z is a bond or is selected from the group consisting of C$_{1-3}$alkyl wherein 1 or 2 carbon atoms of the C$_{1-5}$alkyl is replaced by a —O—, —S—, —C(O)—, —C(O)NR'''—, —S(O)—, —S(O)$_2$—, —S(O)$_2$NR'''— or —NR'''—, where R''' is H or C$_{1-5}$alkyl; and X' is selected from the group consisting of a charged species, halo, —CF$_3$, —CH$_2$F, —CHF$_2$, —COOH, halo-C$_{1-5}$alkyl, halo-C$_{1-5}$alkoxy-; Z'—C$_{2-6}$alkyl, Z'—C$_{2-6}$alkyl-O—, Z'—C$_{2-6}$alkyl-O—C$_{1-3}$alkyl-, Z'—C$_{2-6}$alkyl-S—, Z'—C$_{2-6}$alkyl-NH—, Z'—C$_{2-6}$alkyl-NH—C$_{1-3}$alkyl-, Z'—C$_{2-6}$alkyl-N(C$_{1-3}$ alkyl)-C$_{1-3}$alkyl-, Z'—(CH$_2$CH$_2$—O)$_{1-5}$—, wherein Z' is selected from the group consisting of halo, —CF$_3$, —CH$_2$F, —CHF$_2$, aryl and heteroaryl.

In one aspect of the above for the compound of Formula Ia or IIa, Y is H or is selected from the group consisting of a charged species, —COOR'', —SO$_3$R'', —P(O)$_2$OR'' and —OP(O)$_2$OR'' wherein R'' is H or C$_{1-3}$alkyl; R is H or a side chain of an amino acid or a derivative thereof, —C$_{1-5}$alkyl-o, m, or p-aryl-(—O—CH$_2$CH$_2$)$_{1-5}$-halo or —C$_{1-5}$ alkyl-o, m, or p-aryl-(CH$_2$CH$_2$)$_{1-5}$-halo; and Z is a bond or is selected from the group consisting of C$_{1-3}$alkyl and C$_{1-3}$alkyl wherein 1 or 2 carbon atoms of the C$_{1-5}$alkyl is replaced by a —O—, —S—, —C(O)—, —C(O)NR'''—, —S(O)—, —S(O)$_2$—, —S(O)$_2$NR'''— or —NR'''—, where R''' is H or C$_{1-5}$alkyl.

In another embodiment of the compound of Formula Ia, Ib, IIa or IIb, X' is selected from the group consisting of a charged species, halo, —CF$_3$, —CH$_2$F, —CHF$_2$, halo-C$_{1-5}$alkyl, halo-C$_{1-5}$alkoxy-; Z'—C$_{2-6}$alkyl, Z'—C$_{2-6}$alkyl-O—, Z'—C$_{2-6}$alkyl-O—C$_{1-3}$alkyl-, Z'—C$_{2-6}$alkyl-S—, Z'—C$_{2-6}$alkyl-NH—, Z'—C$_{2-6}$alkyl-NH—C$_{1-3}$ alkyl-, Z'—C$_{2-6}$alkyl-N(C$_{1-3}$ alkyl)-C$_{1-3}$ alkyl-, Z'—(CH$_2$CH$_2$—O)$_{1-5}$—, wherein Z' is selected from the group consisting of halo, —CF$_3$, —CH$_2$F, —CHF$_2$, aryl and heteroaryl.

In another embodiment, there is provided a method for detecting hypoxic tumors in a mammal, the method comprising: a) administering to the mammal the compound of the above; and b) obtaining a diagnostic image of the hypoxic tumors. In one variation of the method, the diagnostic image is obtained using positron emission tomography (PET). In another variation, the radionuclide is $^{11}$C or $^{18}$F.

In yet another embodiment, there is provided a method for detecting carbonic anhydrase IX (CA-IX) activity of a tissue, the method comprising: a) administering a compound as disclosed herein to the tissue; and b) detecting the CA-IX activity in the tissue. In one variation of the above, the detection of the CA-IX activity is performed using positron emission tomography (PET). In another embodiment, there is provided a method for the diagnostic imaging of hypoxic tissue in a mammal, the method comprising: a) administering to the mammal pharmaceutical formulation comprising a compound of the Formula Ia, Ib, IIa or IIb, or a pharmaceutically acceptable salt thereof, optionally in the form of a single stereoisomer or mixtures of stereoisomers thereof; and b) obtaining a diagnostic image of the hypoxic tissue. In one variation, the tissue is selected from a heart, a lung, a kidney, a liver and a brain tissue. In another variation of the method, the method is employed for the diagnose of hypoxic tissue in tumors.

In another aspect, there is provided a method of using the radio-labeled compounds of the present application as positron emission tomography (PET) imaging agents for the detection of CA IX over-expression in a subject, which allows monitoring the progress or regression of a cancerous disease in the subject. The method comprises of the steps:

a) administering the radio-labeled compounds as described herein to a subject, b) detecting the radioactive emission of the compound administered in step (a).

In the present method, the radioactive emission from a radioisotope, such as $^{18}$F, can be detected using positron emission tomography for imaging CA-IX expression in a subject. The radioactive emission can be detected anywhere in the body of the subject. In one embodiment, the subject can be known or suspected to have one or more of the following conditions: a preneoplastic or neoplastic disease, including carcinomas, such as, colorectal, ovarian, uterine, cervical, endometrial, squamous cell and adenosquamous carcinomas; head and neck cancers; mesodermal tumors, such as, neuroblastomas and retinoblastomas; sarcomas, such as osteosarcomas; and melanomas. Of particular interest are cancers of the breast, of the gastrointestinal tract, of the stomach including esophagus, of the colon, of the kidney, of the prostate, of the liver, of the urinary tract including bladder, of the lung, and of the head and neck. Also of particular interest are gynecological cancers including ovarian, uterine, cervical, vaginal, vulval and endometrial cancers, particularly ovarian, uterine, cervical and endometrial cancers. In another embodiment, there is provided a method of using click chemistry to generate combinatorial compound libraries represented in Formula I, Ia, Ib, IIa and IIb, which are potent inhibitors for CA IX enzyme.

In one embodiment, 'traditional' combinatorial chemistry libraries were synthesized through a click chemistry approach. The identification process involved in using various azide reagents and a series of alkyne-bearing moieties, as exemplified by benzenesulfonamide alkyne (Formula IIa), N-(prop-2-ynyl)-4-sulfamoylbenzamide (Formula IIb), and 6-(prop-2-ynyloxy)benzo[d]-thiazole-2-sulfonamide (Formula IIe). These scaffolds generated a total of 109 compounds in these three exemplary combinatorial libraries, which were then subjected to screening at 1 µM concentration using a standard competitive fluorescence-based assay (A. Jain, S. G. Huang, G. M. Whitesides, *J. Am. Chem. Soc.* 1994, 116, 5057) against carbonic anhydrase enzymes. Sixteen of them were identified to be active and with binding affinity Kd's from 5-20 nM for CA IX enzyme.

In another embodiment, 'focused' combinatorial chemistry libraries were synthesized using click chemistry generated triazole building blocks. The identification process involved uses various amine reagents and a number of triazole-bearing acid moieties (FIG. 2), as exemplified by (S)-3-methyl-2-(4-(4-sulfamoylphenyl)-1H-1,2,3-triazol-1-yl)butanoic acid (Formula IIIa), (S)-3-phenyl-2-(4-(4-sulfamoylphenyl)-1H-1,2,3-triazol-1-yl)propanoic acid (Formula IIIb), (S)-3-methyl-2-(4-((2-sulfamoylbenzo[d]thiazol-6-yloxy)methyl)-1H-1,2,3-triazol-1-yl)butanoic acid (Formula IIIc), and (S)-3-phenyl-2-(4-((2-sulfamoylbenzo[d]-thiazol-6-yloxy)methyl)-1H-1,2,3-triazol-1-yl)propanoic acid (Formula IIId). A total of 118 triazole-bearing amide compounds (Table 2) in four combinatorial libraries were made and screened at 1 µM concentration using a standard competitive fluorescence-based assay (A. Jain, S. G. Huang, G. M. Whitesides, J. Am. Chem. Soc. 1994, 116, 5057) against carbonic anhydrase enzymes. Twenty two of them were identified to be active and with binding affinity Kds from 0.5-10 nM for CA-IX, with exemplary compounds with their binding affinities shown in FIGS. 5A-5B. Inhibition assay results are shown in FIGS. 4A-1-4C and FIGS. 6A-6D.

In another embodiment, a small subset of four compounds, derived from lead CA-IX binders, were converted into either ammonium salts or free carboxylic acids (FIG. 7). Three of the four compounds were shown to have Kds ranging from 10-20 nM and displayed high cell impermeability characteristics in both the ethoxazolamide blocked and unblocked cells uptake assays (FIG. 7).

BRIEF DESCRIPTION OF THE DRAWINGS

FIG. 3A is a table containing various compounds with the corresponding in vitro activity.
FIG. 3B is a continuation of the table shown in FIG. 3A.
FIG. 3C is a continuation of the tables shown in FIGS. 3A and 3B.
FIG. 4A-1 is a graph showing the percent inhibition of various compounds.
FIG. 4A-2 is a graph showing the percent inhibition of various compounds.
FIG. 4B-1 is a graph showing the percent inhibition of various compounds.
FIG. 4B-2 is a graph showing the percent inhibition of various compounds.
FIG. 5A is a table showing various compounds with the corresponding in vitro activity.
FIGS. 5B and 5C are continuations of the table shown in FIG. 5A.

DETAILED DESCRIPTION OF THE PREFERRED EMBODIMENTS

Figure 1:
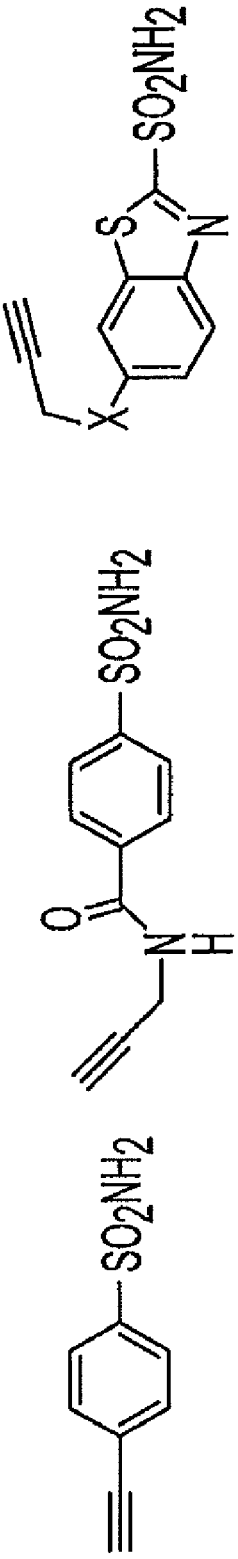
FIG. 1 shows formulas IIa, IIb and IIc.
Figure 2:
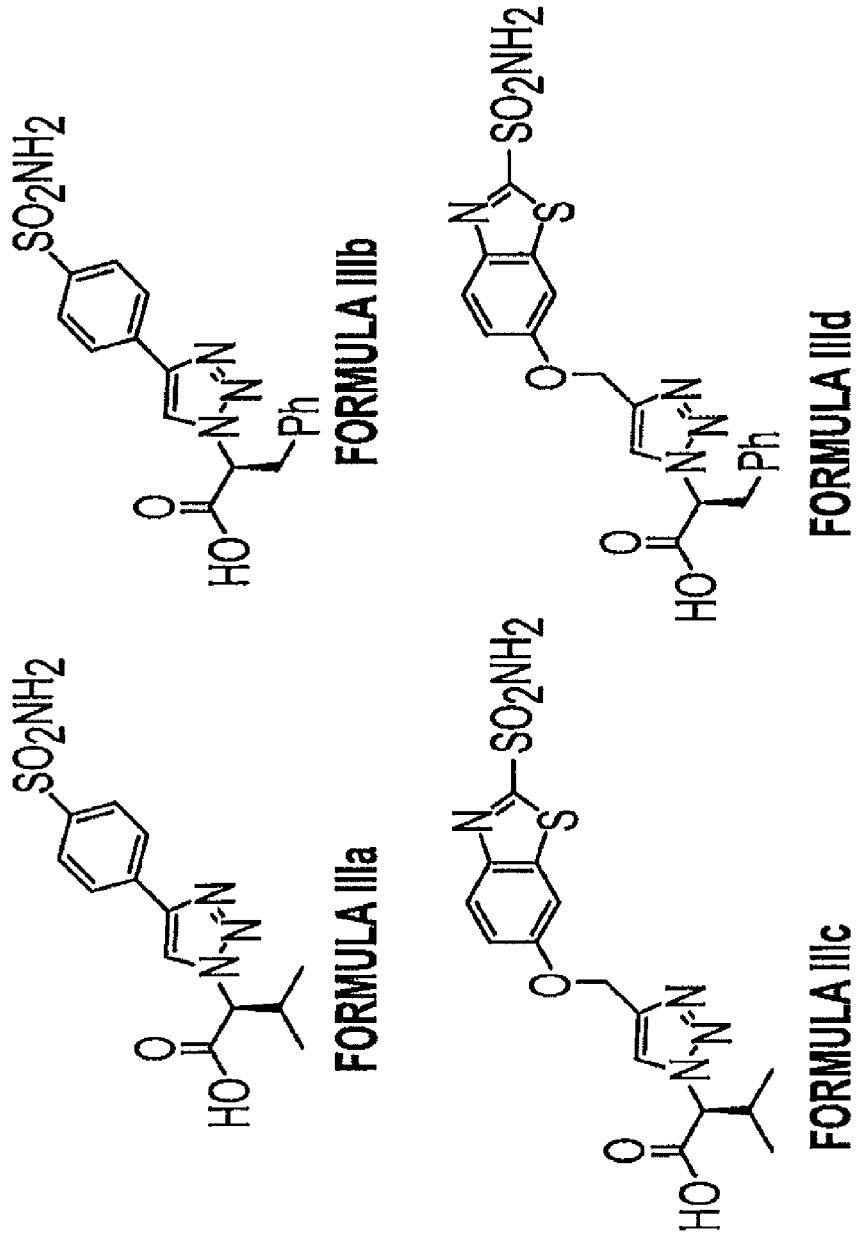
FIG. 2 shows formulas IIIa, IIIb, IIIc and IIId.
Figures 1, 4A:
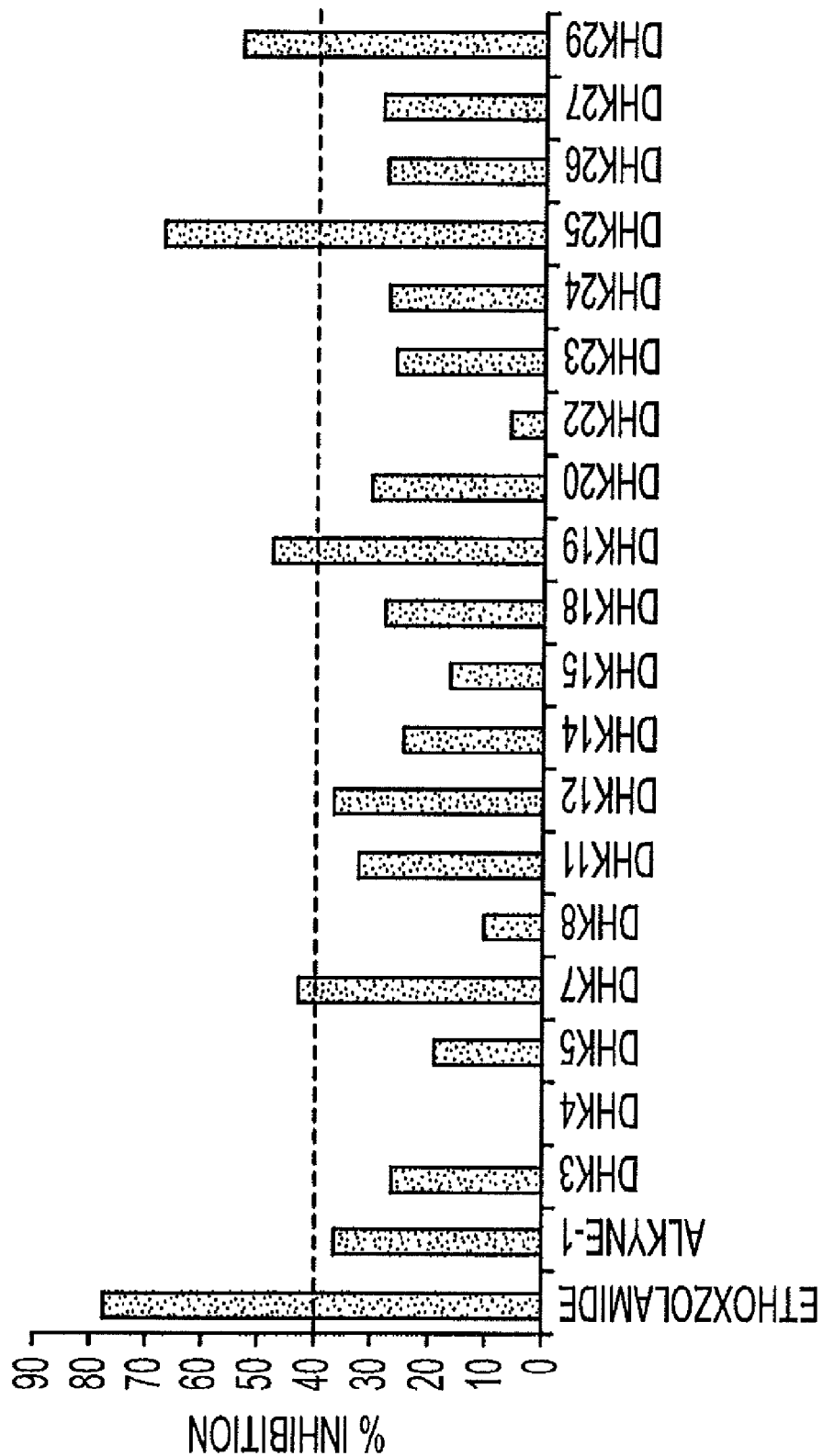
Figures 2, 4A:
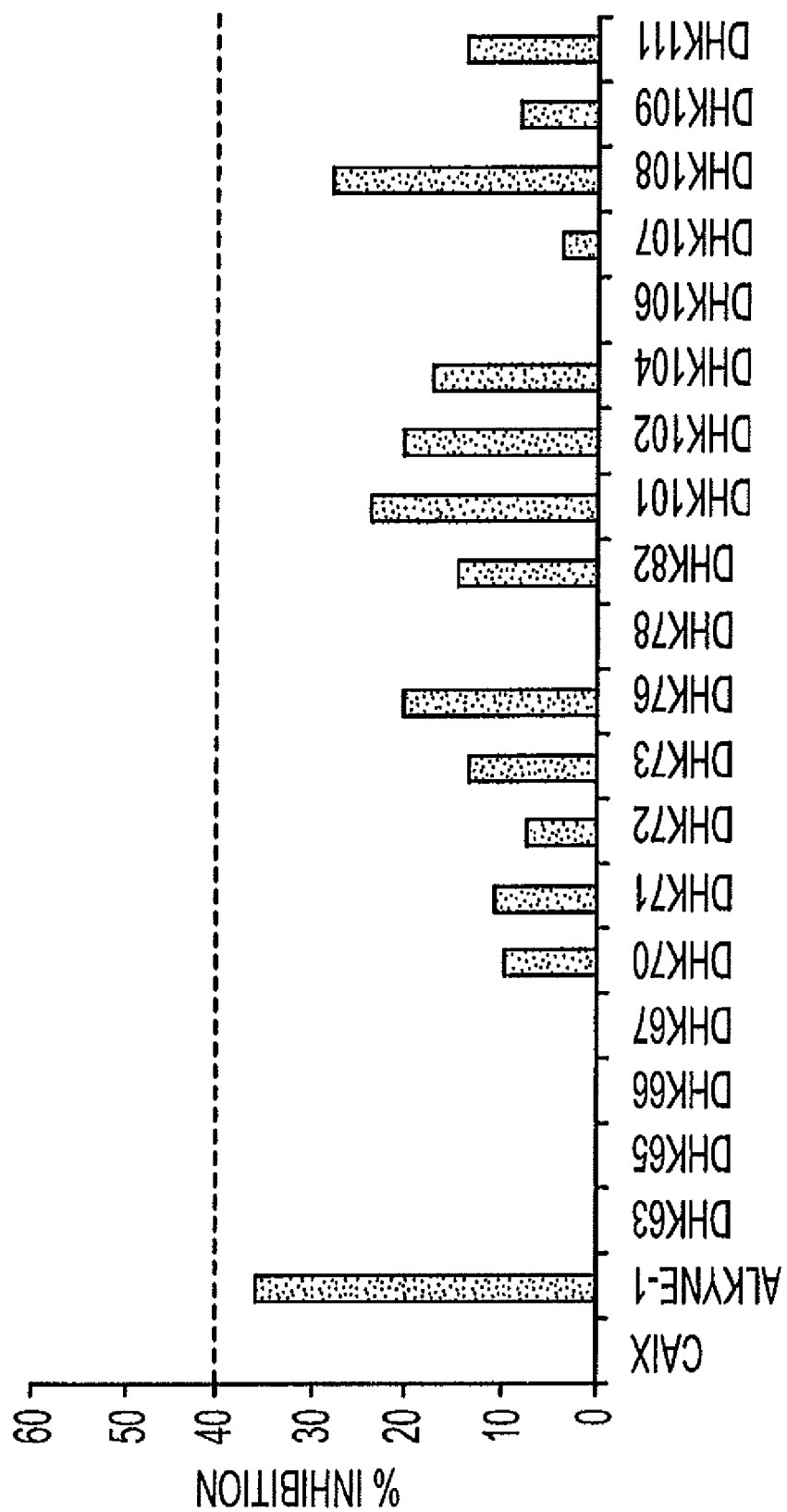
Figures 1, 4B:
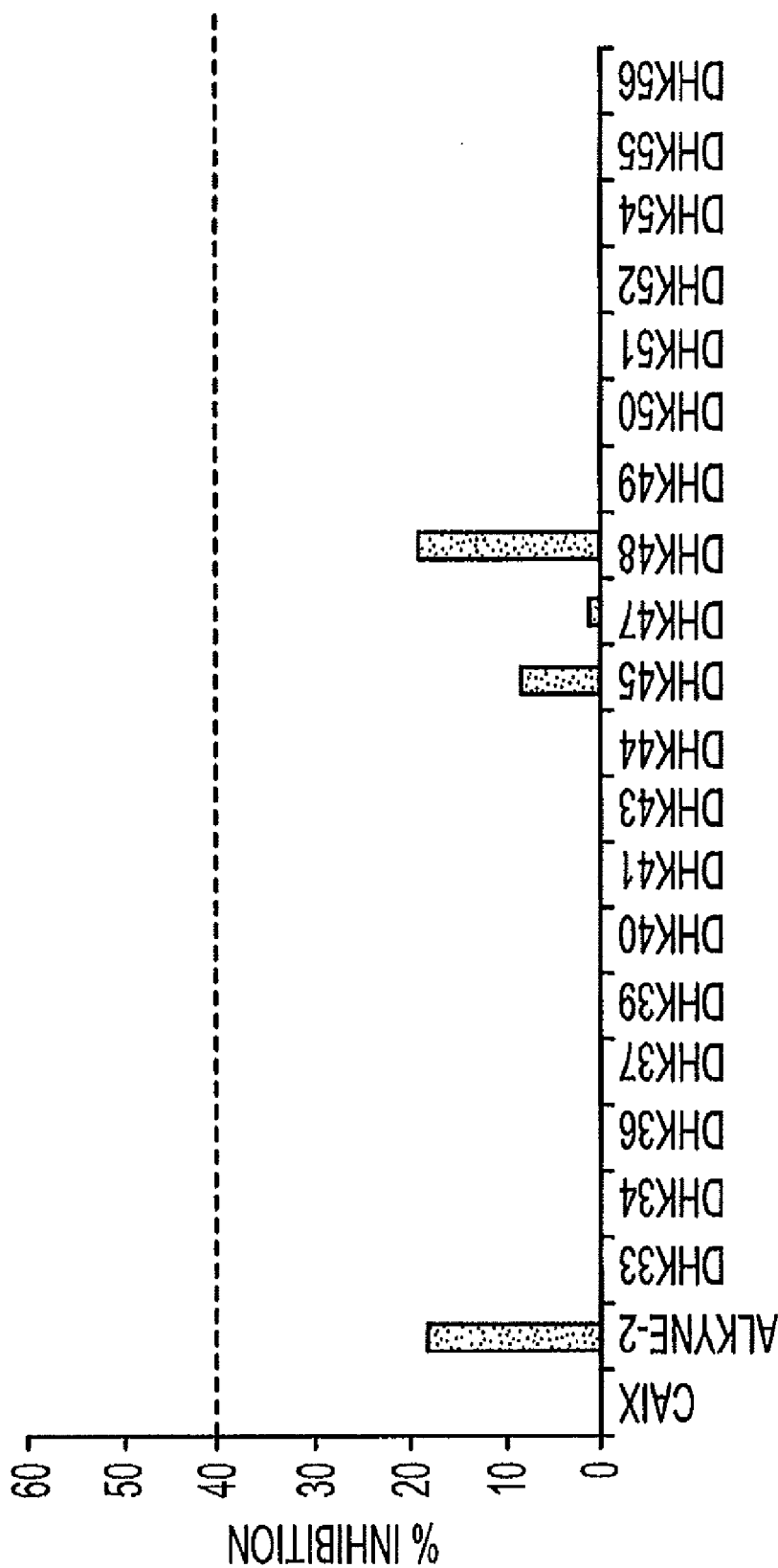
Figures 2, 4B:
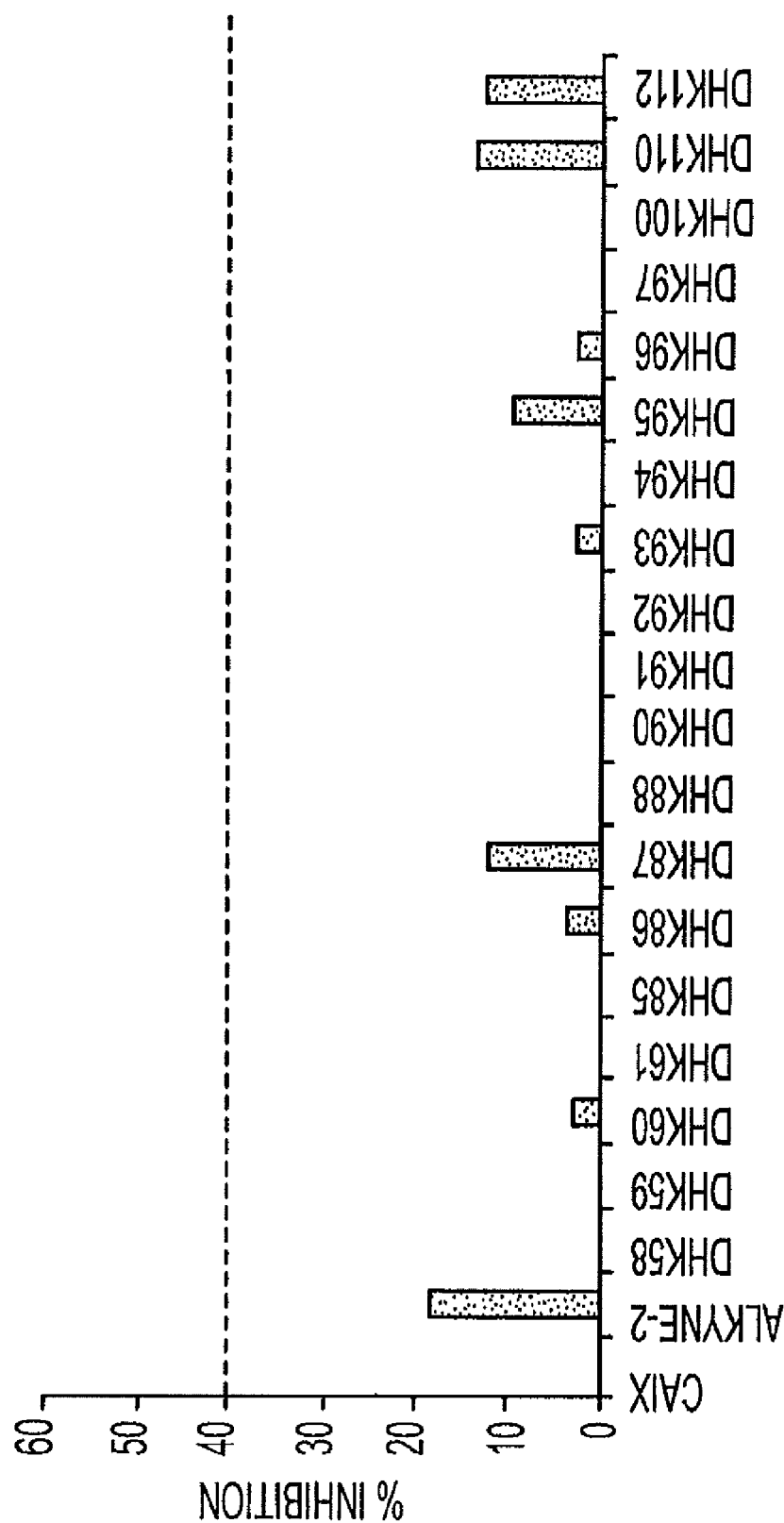
Figure 4C:
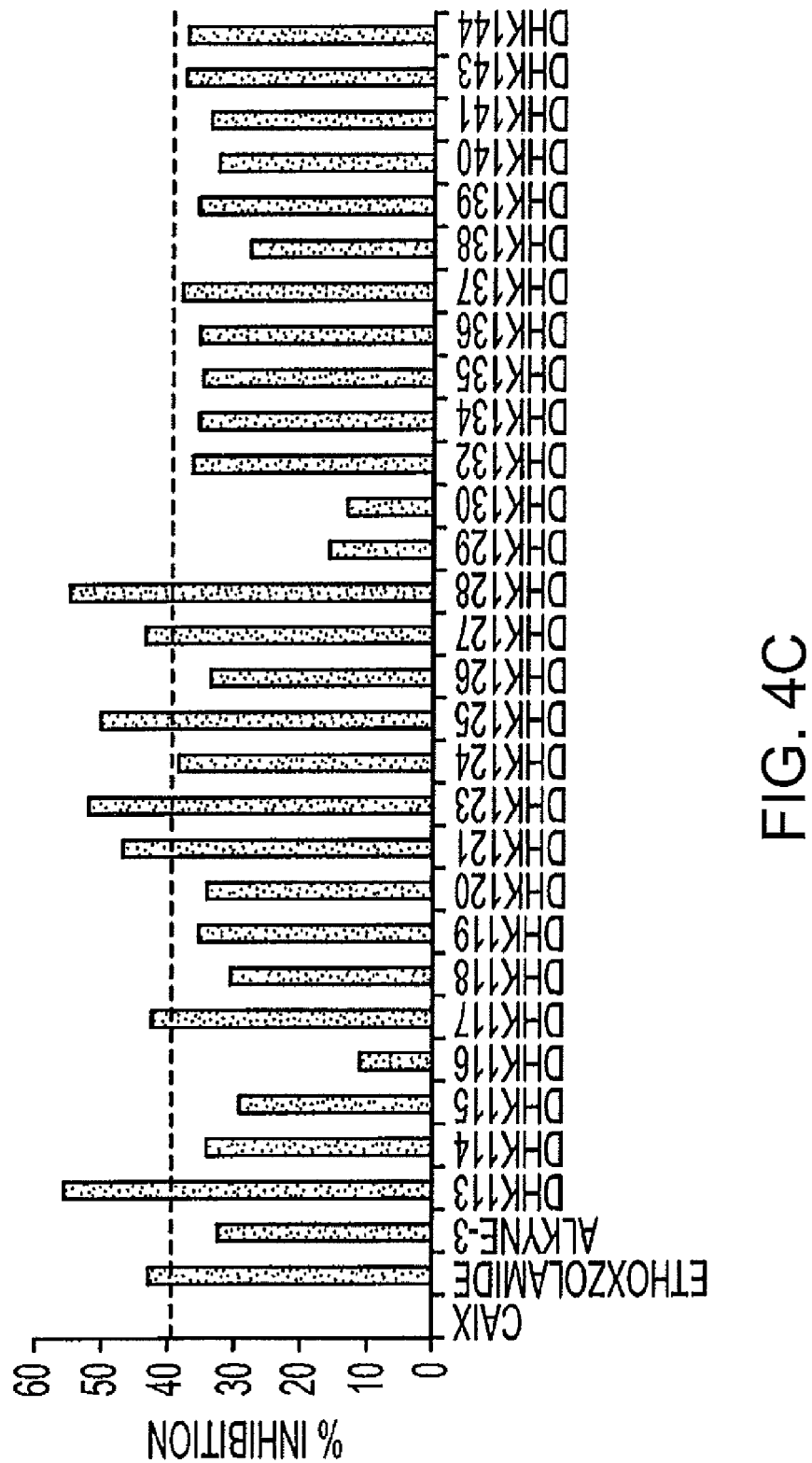
FIG. 4C is a graph showing the percent inhibition of various compounds.
Figure 6A:
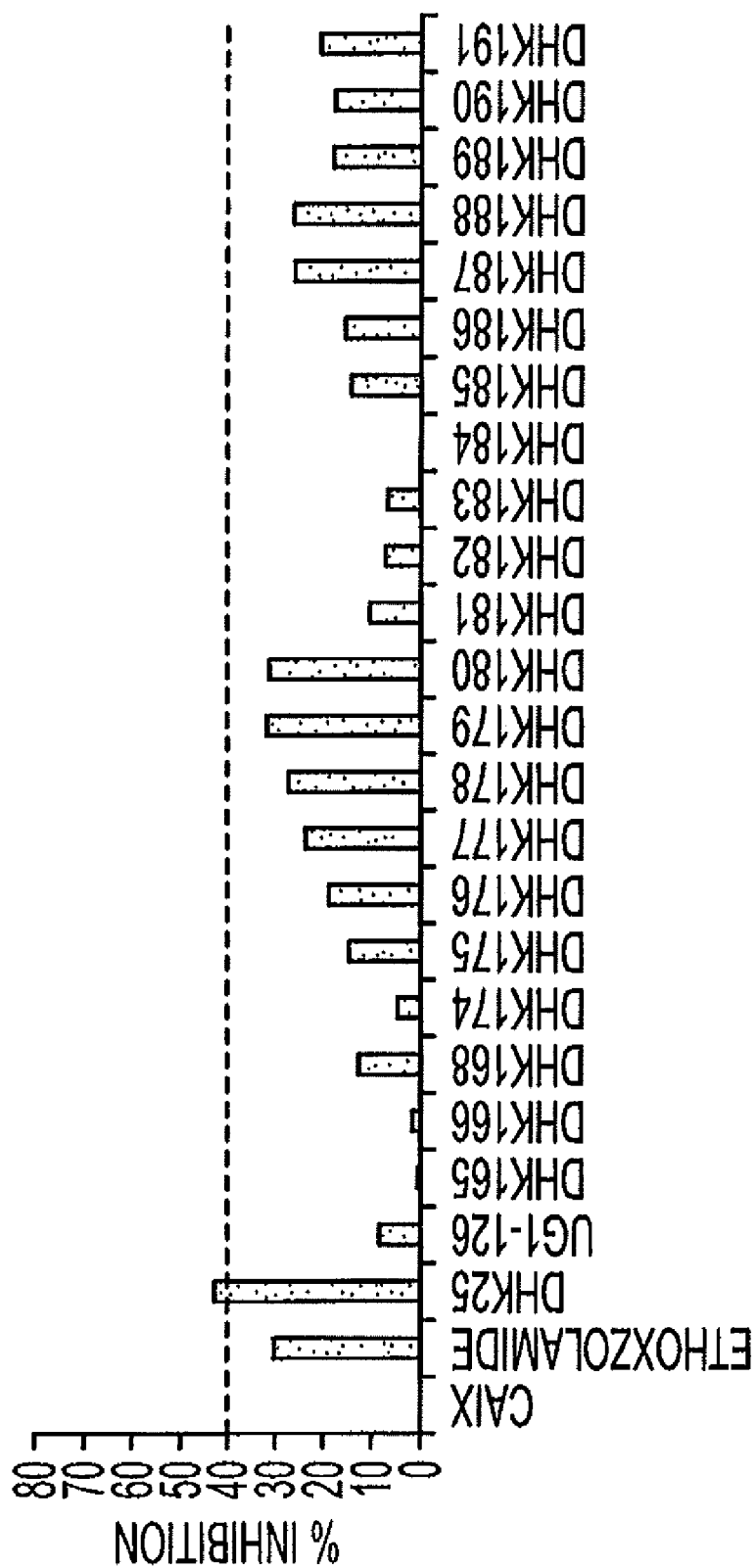
FIG. 6A is a graph showing the percent inhibition of various compounds.
Figure 6B:
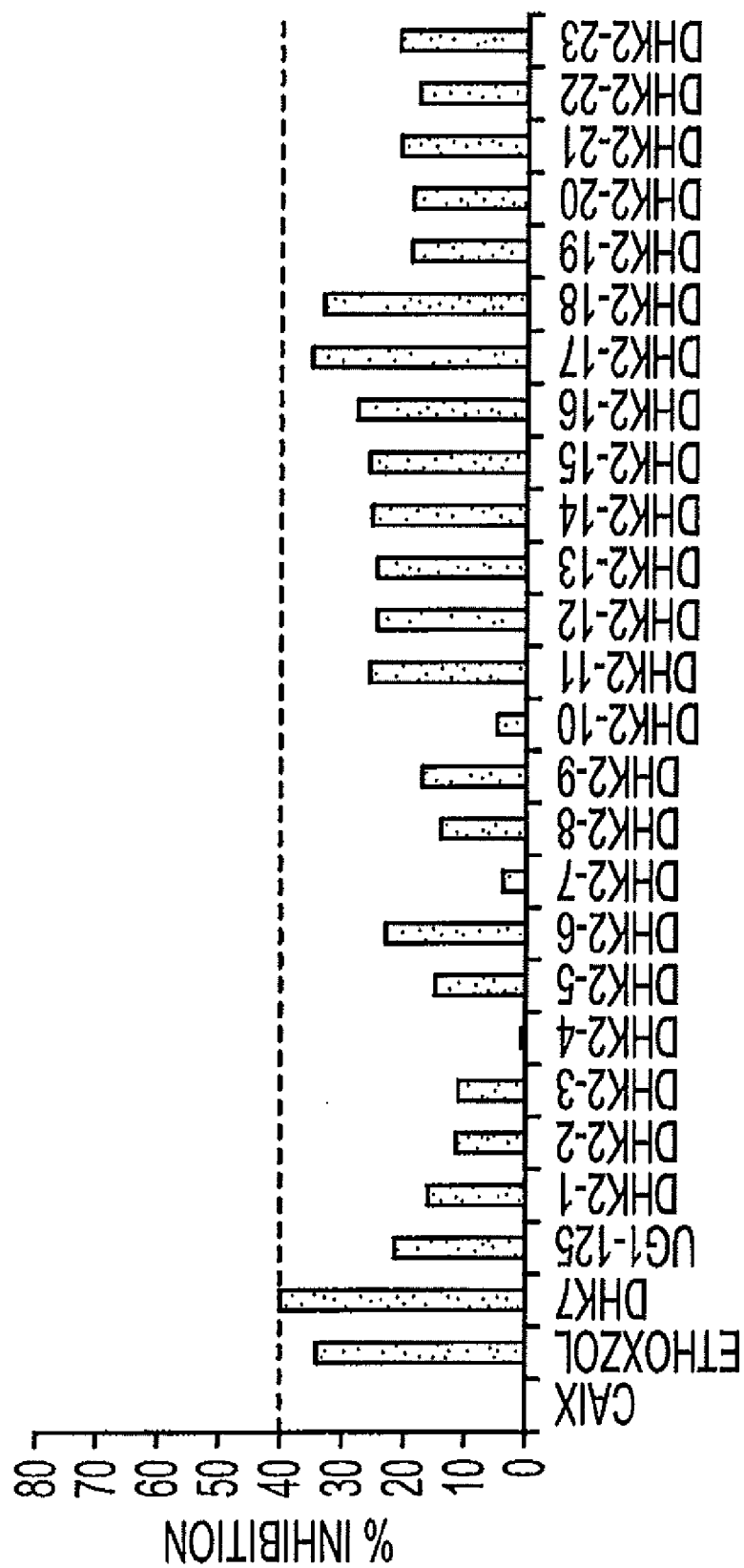
FIG. 6B is a graph showing the percent inhibition of various compounds.
Figure 6C:
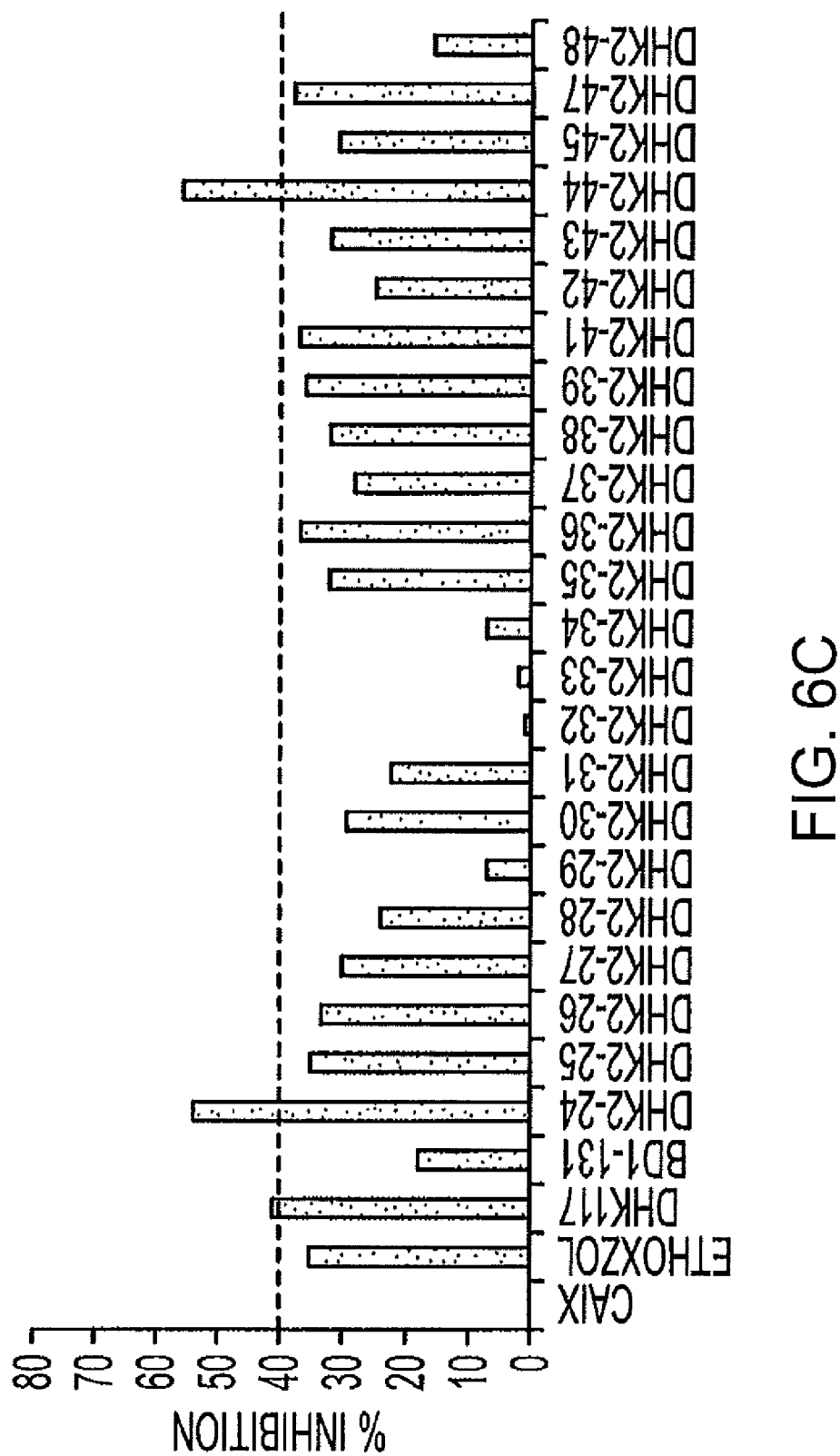
FIG. 6C is a graph showing the percent inhibition of various compounds.
Figure 6D:
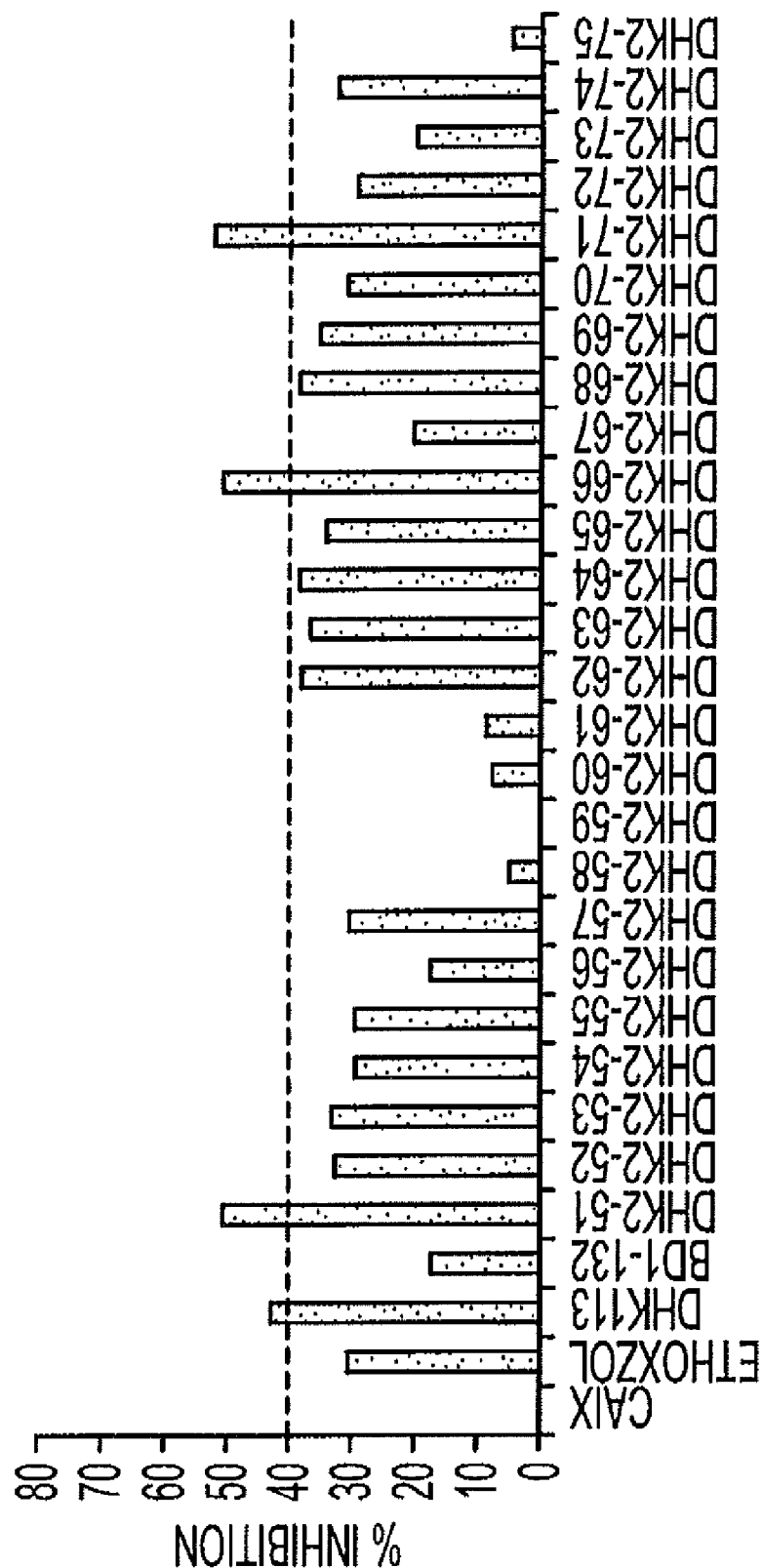
FIG. 6D is a graph showing the percent inhibition of various compounds.
Figure 7:
FIG. 7 is a table showing various compounds with the corresponding in vitro activity.
Figure 7:
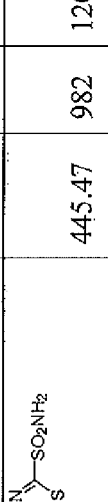
Figure 7:
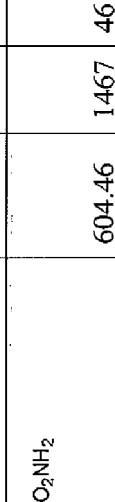
Figure 7:
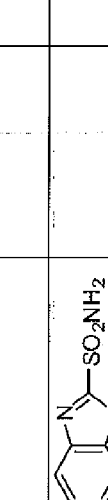
Figure 8:
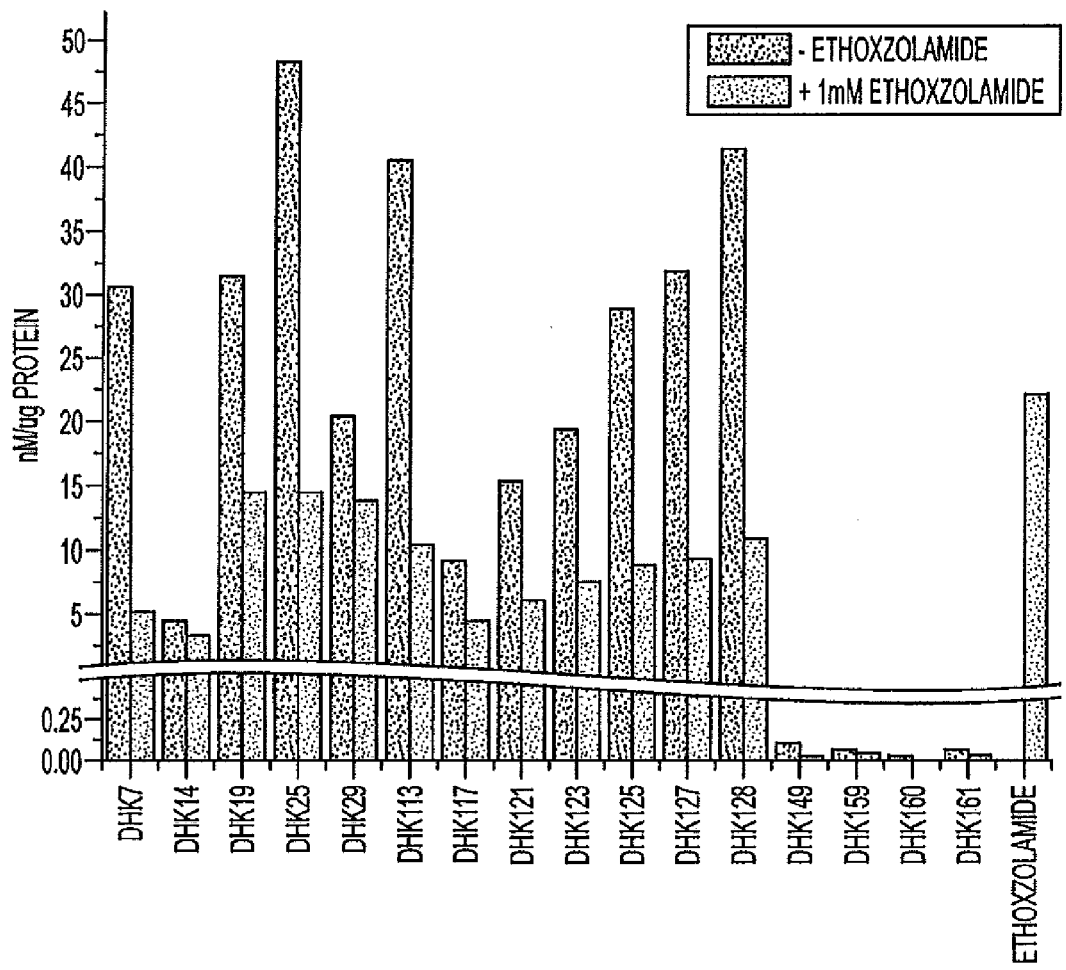
FIG. 8 is a graph showing the cell impermeability characteristics in both the ethoxazolamide blocked and unblocked cells uptake assays for various compounds.
Figure 9A:
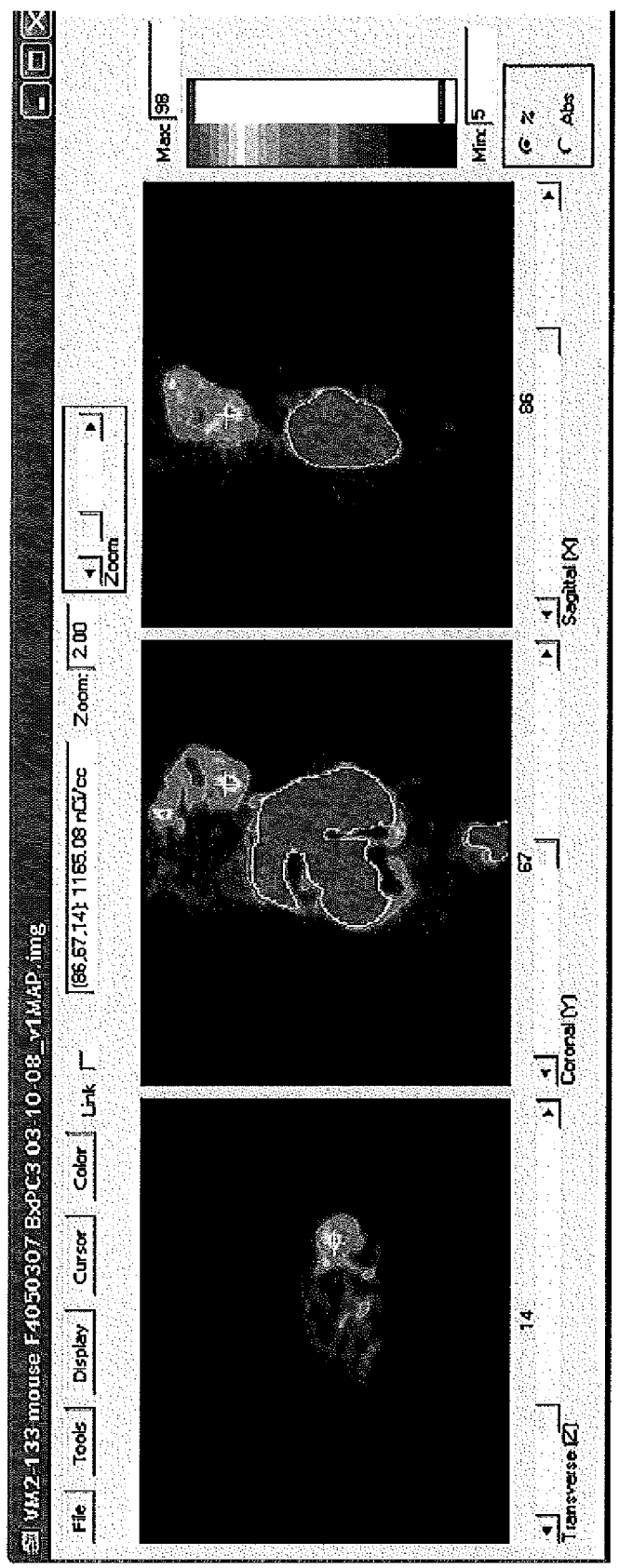
FIG. 9A is a "screen shot" showing PET images two CA-IX tracers in athymic mice bearing CA-IX expressing xenograph tumors.
Figure 9B:
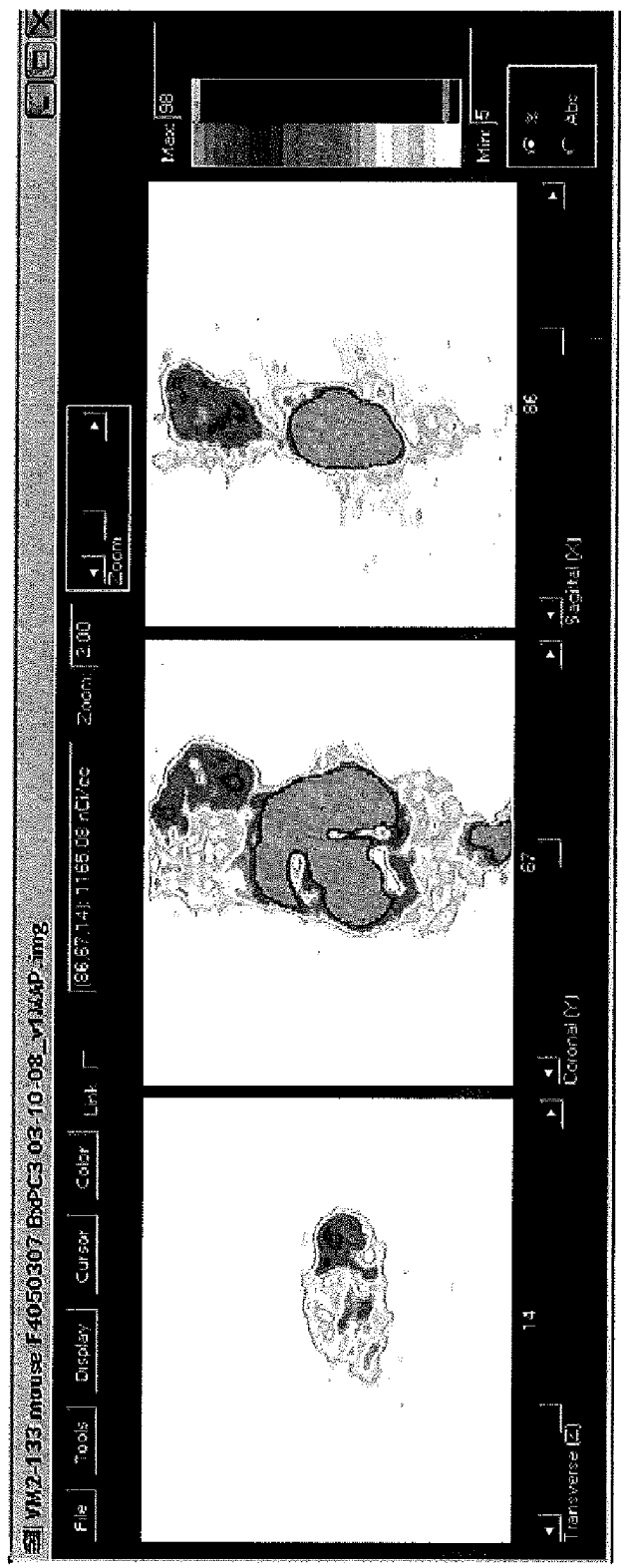
FIG. 9B is the "screen shot" of FIG. 9A but with the colors inverted for further clarity.
Figure 10A:
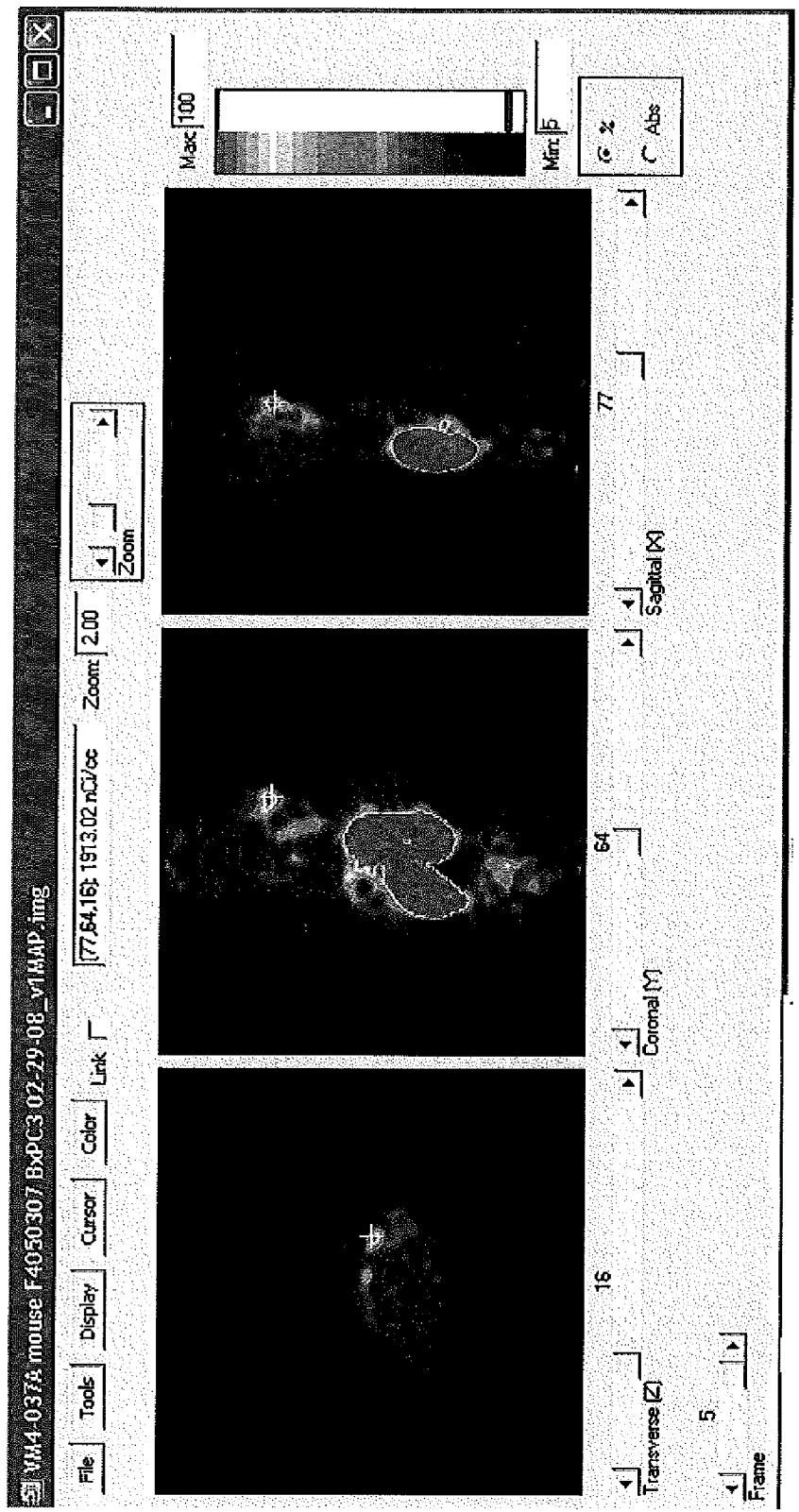
FIG. 10A is a "screen shot" showing PET images two CA-IX tracers in athymic mice bearing CA-IX expressing xenograph tumors.
Figure 10B:
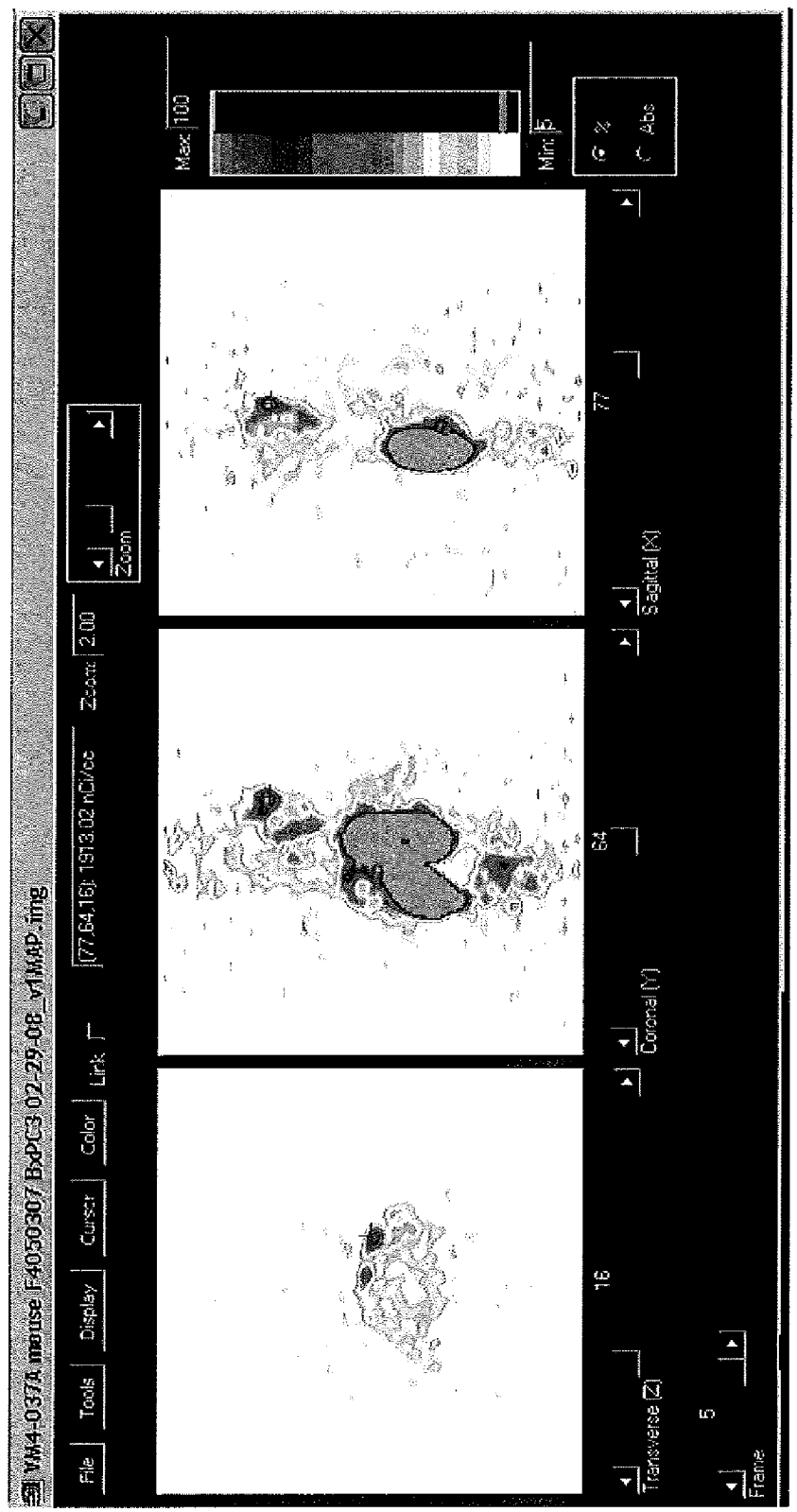
FIG. 10B is the "screen shot" of FIG. 10A but with the colors inverted for further clarity.
Figure 11A:
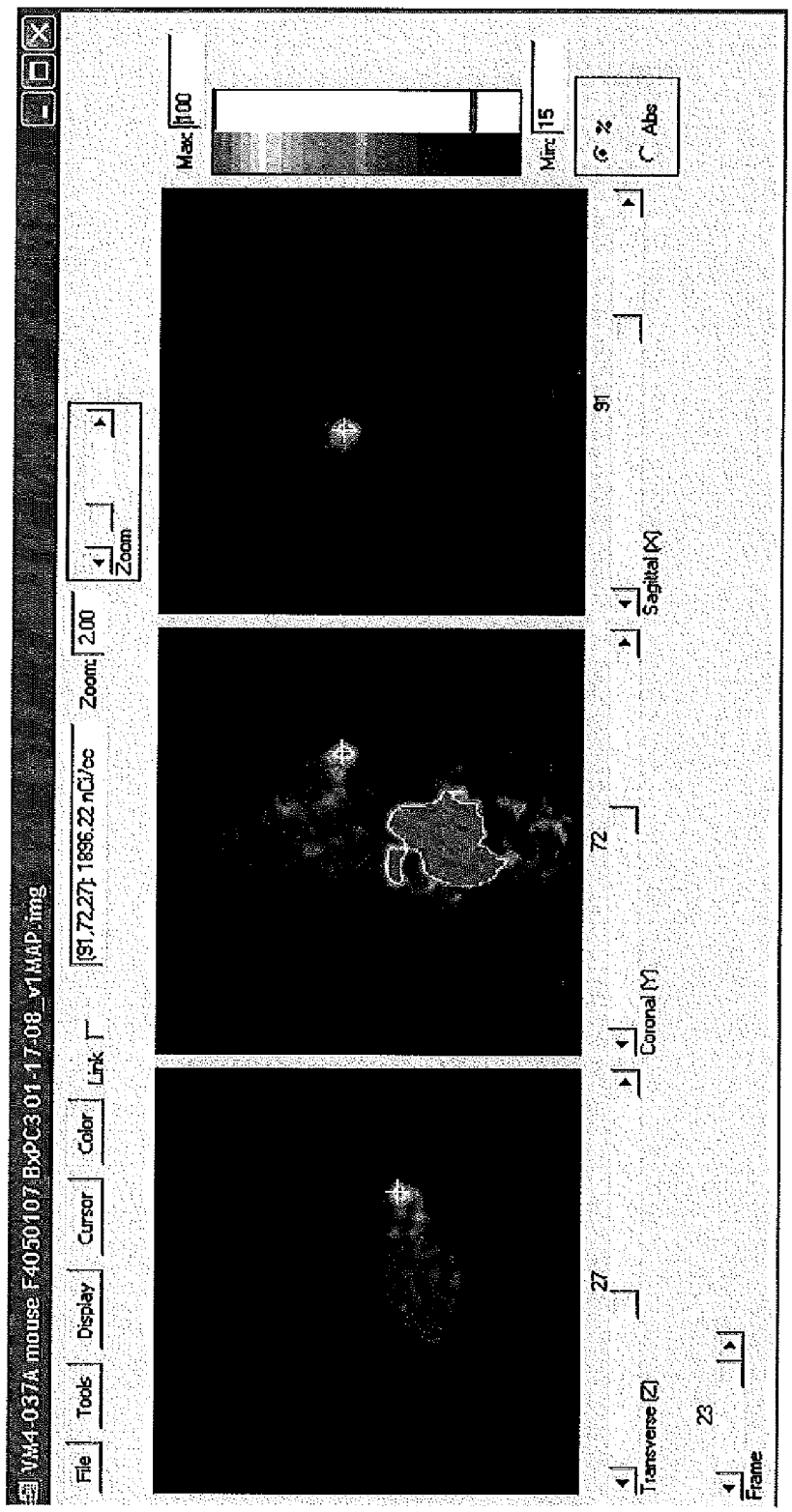
FIG. 11A is a "screen shot" showing PET images two CA-IX tracers in athymic mice bearing CA-IX expressing xenograph tumors.
Figure 11B:
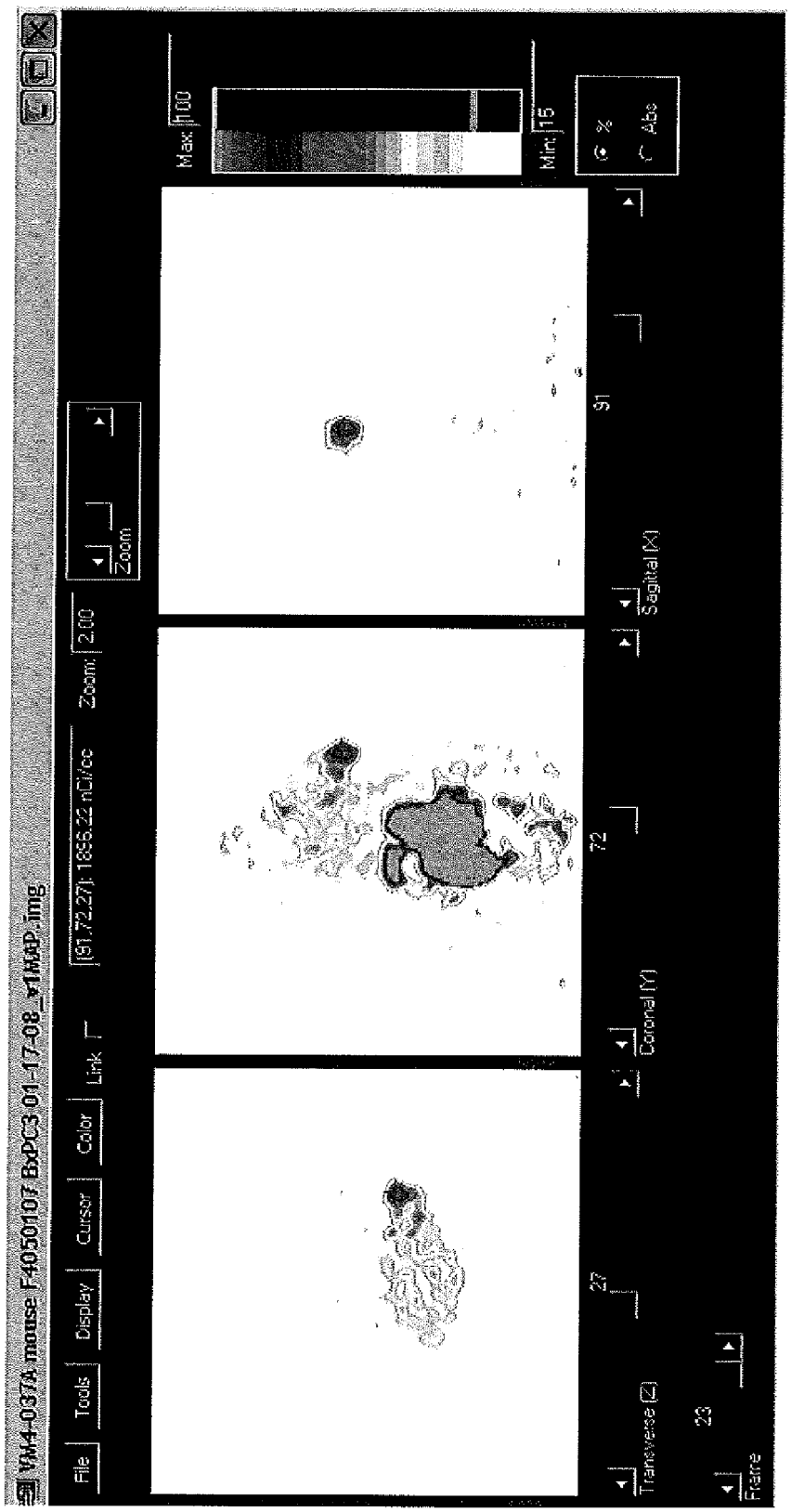
FIG. 11B is the "screen shot" of FIG. 11A but with the colors inverted for further clarity.

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art.
Definitions:
As used in the present specification, the following words and phrases are generally intended to have the meanings as set forth below, except to the extent that the context in which they are used indicates otherwise.
The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl," as defined below. It will be understood by those skilled in the art with respect to any group containing one or more substituents that such groups are not intended to introduce any substitution or substitution patterns that are sterically impractical and/or synthetically non-feasible.

Certain compound, reactant, or reaction parameter abbreviations are defined as follows:

"DCM" refers to dichloromethane or methylene chloride
"t-Bu" refers to t-butyl
"Boc" refers to tert-butoxycarbonyl
"DIC" refers to N,N-diisopropylcarbodiimide
"DIPEA" refers to diisopropyl ethylamine
"DMAP" refers to 4-N,N-dimethylamino pyridine
"DMF" refers to N,N-dimethyl formamide
"Eq." refers to equivalent
"MeOH" refers to methanol
"TsOH" refers to toluene sulfonic acid
"EtOH" refers to ethanol
"PSC" refers to poly(styrene)carbodiimide
"HOBt" refers to 1-hydroxybenzotriazole
"DMTr" refers to dimethoxy trityl
"TBDMS" refers to t-butyl di-methyl silyl
"THF" refers to tetrahydrofuran
"TBAF" refers to tetrabutyl ammonium fluoride
"TMEDA" refers to N,N,N',N'-tetramethylethylenediamine
"EtOAc" refers to ethyl acetate.
"TEA" refers to triethylamine
"DCM" refers to dichloromethane
"DMSO" refers to dimethylsulfoxide The term "acyl" refers to the groups —C(O)—H, —C(O)-(optionally substituted alkyl), —C(O)-(optionally substituted cycloalkyl), —C(O)-(optionally substituted alkenyl), —C(O)-(optionally substituted cycloalkenyl), —C(O)-(optionally substituted aryl), —C(O)-(optionally substituted heteroaryl) and —C(O)-(optionally substituted heterocyclyl).

The term "alkenyl" refers to a monoradical branched or unbranched, unsaturated or polyunsaturated hydrocarbon chain, having from about 2 to 20 carbon atoms (i.e. $C_{2\text{-}20}$alkenyl), more preferably about 2 to 10 carbon atoms. This term is exemplified by groups such as ethenyl, but-2-enyl, 3-methyl-but-2-enyl (also referred to as "prenyl"), octa-2,6-dienyl, 3,7-dimethyl-octa-2,6-dienyl (also referred to as "geranyl"), and the like.

The term "amino" refers to a nitrogen moiety having two further substituents where a hydrogen or carbon atom is attached to the nitrogen. For example, representative amino groups include —$NH_2$, —$NHCH_3$, —$N(CH_3)_2$, —$NHC_{2\text{-}3}$-alkyl, —$N(C_{2\text{-}3}$-alkyl$)_2$ and the like. Unless indicated otherwise, the compounds of the invention containing amino moieties may include protected derivatives thereof. Suitable protecting groups for amino moieties include acetyl, tert-butoxycarbonyl, benzyloxycarbonyl and the like.

The term "substituted amino" refers to the group —NHR or —NRR where each R is independently selected from the group: optionally substituted alkyl, optionally substituted cycloalkyl, optionally substituted alkenyl, optionally substituted cycloalkenyl, optionally substituted alkynyl, optionally substituted aryl, optionally substituted heteroaryl, optionally substituted heterocyclyl, acyl, optionally substituted alkoxy, carboxy and alkoxycarbonyl.

The term "amino acid residue" means the divalent group —NH—CHR—COO— or —OOC—CHR—NH—, where R is the side chain of an amino acid as known in the art.

The term "substituted alkenyl" refers to an alkenyl group in which 1 or more (up to about 5, preferably up to about 3) hydrogen atoms is replaced by a substituent independently selected from the group: optionally substituted anthraquinone, optionally substituted aryl, (optionally substituted aryl)carbonyl, optionally substituted heteroaryl, or optionally substituted heterocyclyl. Preferred optional substituents for alkenyl are substituted aryl and substituted heteroaryl.

The term "alkoxy" refers to the groups —O-alkyl, —O-alkenyl, —O-cycloalkyl, —O-cycloalkenyl, and —O-alkynyl. Preferred alkoxy groups are —O-alkyl and —O-alkenyl and include, by way of example, methoxy, ethoxy, n-propoxy, iso-propoxy, n-butoxy, tert-butoxy, sec-butoxy, n-pentoxy, n-hexoxy, 1,2-dimethylbutoxy, 3,7-dimethyl-octa-2,6-dienyloxy and the like.

The term "substituted alkoxy" refers to the groups —O-(substituted alkyl), —O-(substituted alkenyl), —O-(substituted cycloalkyl), —O-(substituted cycloalkenyl), —O-(substituted alkynyl) and —O-(optionally substituted alkylene)-alkoxy. One preferred substituted alkoxy group is "polyalkoxy" or —O-(substituted alkylene)-alkoxy, and includes groups such as, —$OCH_2CH_2OCH_3$, and (or PEG) groups such as —$O(CH_2CH_2O)_xCH_3$ and —$O(CH_2CH_2O)_xH$ where x is an integer of about 2-20, preferably about 2-10, and more preferably about 2-5. Another preferred substituted alkoxy group is trifluoromethoxy.

The term "alkyl" refers to a monoradical branched or unbranched saturated hydrocarbon chain preferably having from about 1 to 20 carbon atoms, more preferably about 1 to 10 carbon atoms, and even more preferably about 1 to 6 carbon atoms. This term is exemplified by groups such as methyl, ethyl, n-propyl, iso-propyl, n-butyl, iso-butyl, n-hexyl, n-decyl, tetradecyl, and the like.

The term "substituted alkyl" refers to an alkyl group in which 1 or more (up to about 5, preferably up to about 3) hydrogen atoms is replaced by a substituent independently selected from the group: =O, =S, acyl, acyloxy, optionally substituted alkoxy, optionally substituted amino, azido, carboxyl, (optionally substituted alkoxy)carbonyl, (optionally substituted amino)carbonyl, cyano, optionally substituted cycloalkyl, optionally substituted cycloalkenyl, halogen, hydroxyl, sulfanyl, sulfinyl and sulfonyl. One of the preferred optional substituents for alkyl is hydroxy, exemplified by hydroxyalkyl groups, such as 2-hydroxyethyl, 3-hydroxypropyl, 3-hydroxybutyl, 4-hydroxybutyl, and the like; dihydroxyalkyl groups (glycols), such as 2,3-dihydroxypropyl, 3,4-dihydroxybutyl, 2,4-dihydroxybutyl, and the like; mixed hydroxy and carboxy substituted alkyl groups, such as pyruvates; and those compounds known as polyethylene glycols, polypropylene glycols and polybutylene glycols, and the like.

The term "alkylene" refers to a diradical derived from the above-defined monoradical, alkyl. This term is exemplified by groups such as methylene (—$CH_2$—), ethylene (—$CH_2CH_2$—), the propylene isomers [e.g., —$CH_2CH_2CH_2$— and —$CH(CH_3)CH_2$—] and the like.

The term "substituted alkylene" refers to a diradical derived from the above-defined monoradical, substituted alkyl. Examples of substituted alkylenes are chloromethylene (—CH(Cl)—), aminoethylene (—$CH(NH_2)CH_2$—), methylaminoethylene (—$CH(NHMe)CH_2$—), 2-carboxypropylene isomers (—$CH_2CH(CO_2H)CH_2$—), ethoxyethylene (—$CH_2CH_2O—CH_2CH_2$—), ethyl(N-methyl)aminoethylene (—$CH_2CH_2N(CH_3)CH_2CH_2$—), 1-ethoxy-2-(2-ethoxyethoxy)ethylene (—$CH_2CH_2O—CH_2CH_2—OCH_2CH_2—OCH_2CH_2$—), and the like.

The term "aromatic" refers to a cyclic or polycyclic moiety having a conjugated unsaturated (4n+2) π electron system (where n is a positive integer), sometimes referred to as a delocalized π electron system.

The term "aryl" refers to an aromatic cyclic hydrocarbon group of from 6 to 20 carbon atoms having a single ring (e.g., phenyl) or multiple condensed (fused) rings (e.g., naphthyl or anthryl). Preferred aryls include phenyl, naphthyl and the like.

The term "substituted aryl" refers to an aryl group as defined above, which unless otherwise constrained by the definition for the aryl substituent, is substituted with from 1 to 5 substituents, and preferably 1 to 3 substituents, independently selected from the group consisting of: =O, =S, acyl, acyloxy, optionally substituted alkenyl, optionally substituted alkoxy, optionally substituted alkyl (such as tri-halomethyl), optionally substituted alkynyl, optionally substituted amino, optionally substituted aryl, optionally substituted aryloxy, azido, carboxyl, (optionally substituted alkoxy)carbonyl, (optionally substituted amino)carbonyl, cyano, optionally substituted cycloalkyl, optionally substituted cycloalkenyl, halogen, optionally substituted heteroaryl, optionally substituted heteroaryloxy, optionally substituted heterocyclyl, optionally substituted heterocyclooxy, hydroxyl, hydroxylamino, nitro, nitroso, phosphoryl, sulfanyl, sulfinyl, and sulfonyl. Preferred aryl substituents include: =O (e.g., anthracenone and anthraquinone), optionally substituted alkenyl, optionally substituted alkyl, alkoxy, substituted amino, halo, hydroxyl, alkoxycarbonyl, carboxy, cyano, nitro, phosphoryl, 2,4-dihydro-pyrazol-3-one, thiazolidine-2,4-dione, trihalomethyl, sulfinyl, sulfonamide, methyl-sulfonamide.

The term "carbonyl" refers to the di-radical "—C(=O)-", which is also illustrated as "—C(O)—".

The term "(optionally substituted alkoxy)carbonyl" refers to the groups: —C(O)O-(optionally substituted alkyl), —C(O)O-(optionally substituted cycloalkyl), —C(O)O-(optionally substituted alkenyl), —C(O)O-(optionally substituted alkynyl), —C(O)O-(optionally substituted aryl), —C(O)O-(optionally substituted heteroaryl), and —C(O)O-(optionally substituted heterocyclyl). These moieties are also referred to as esters.

The term "(optionally substituted amino)carbonyl" refers to the group —C(O)-(optionally substituted amino). This moiety is also referred to as a primary, secondary or tertiary carboxamide.

The term "carboxy" or "carboxyl" refers to the moiety "—C(O)O—", which is also illustrated as "—COO—".

The term "compound of Formula" is intended to encompass the derivatives of the invention as disclosed, and/or the pharmaceutically acceptable salts of such compounds. In addition, the compounds employed in this invention include the individual stereochemical isomers (arising from the selection of substituent groups) and mixtures of isomers. For the sake of brevity, except where specifically indicated to the contrary (e.g., by designation of a single salt, isomer or mixture) the term should be understood to include single stereoisomers, mixtures of stereoisomers, and the pharmaceutically acceptable salts thereof.

The term "cycloalkyl" refers to non-aromatic cyclic hydrocarbon groups of having 3 to about 20 (preferably about 4 to 10) carbon atoms having a single ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

The term "halo" or "halogen" refers to fluoro, chloro, bromo and iodo.

In certain aspect of the present application, for the radiolabeled compounds of the present application, a radionuclide may be attached to the variable X' of the compound of the present application, or a 2-($^{18}$F-fluoroethyl)-, 2-($^{18}$F-fluoromethyl)-, a $^{11}$C-methoxy-group that is attached to a compound of Formula I, Ia, Ib, IIa or IIb, for example, and/or the radionuclide may be attached to any one or more of the variables X, Y, R and/or Z of a $^{18}$F-fluoroethyl-group, a $^{18}$F-fluoromethyl-group, a $^{18}$F-fluoroethoxy-group, a $^{11}$C-methoxy-group, a $^{18}$F-fluoropropyloxy-group and the like, a $^{123}$I, a $^{124}$I, a $^{125}$I or a $^{131}$I group, and the like. Unless otherwise noted, a compound represented as being substituted by an atom, such as the generic representation by the atom fluorine in F—CH$_2$CH$_2$— or F—CH$_2$CH$_2$O— as attached to a compound of the Formula I, Ia, Ib, IIa or IIb, for example, is intended to cover both the naturally occurring element $^{19}$F (fluorine-19) as well as the $^{18}$F (fluorine-18) isotope(s) of the element itself.

The term "heteroaryl" refers to an aromatic cyclic hydrocarbon group having about 1 to 40 (preferably from about 3 to 15) carbon atoms and about 1 to 10 hetero atoms (preferably about 1 to 4 heteroatoms, selected from nitrogen, sulfur, phosphorus, and/or oxygen) within at least one ring. Such heteroaryl groups can have a single ring (e.g., pyridyl) or multiple condensed rings (e.g., indolizinyl, benzothiazolyl, and benzo[1,3]dioxo-5-yl). Preferred heteroaryls include pyridyl, pyrrolyl and benzothiazolyl.

The term "substituted heteroaryl" refers to a heteroaryl group as defined above, which unless otherwise constrained by the definition for the heteroaryl substituent, is substituted with from 1 to 5 substituents, and preferably 1 to 3 substituents, independently selected from the group consisting of: =O, =S, acyl, acyloxy, optionally substituted alkenyl, optionally substituted alkoxy, optionally substituted alkyl (such as tri-halomethyl), optionally substituted alkynyl, optionally substituted amino, optionally substituted aryl, optionally substituted aryloxy, azido, carboxyl, (optionally substituted alkoxy)carbonyl, (optionally substituted amino)carbonyl, cyano, optionally substituted cycloalkyl, optionally substituted cycloalkenyl, halogen, optionally substituted heteroaryl, optionally substituted heteroaryloxy, optionally substituted heterocyclyl, optionally substituted heterocyclooxy, hydroxyl, nitro, sulfanyl, sulfinyl, and sulfonyl.

The term "heteroaralkyl" refers to the moiety "-alkyleneheteroaryl" each having the meaning as defined herein.

The term "substituted heteroaralkyl" refers to the moiety "-(optionally substituted alkylene)-(optionally substituted heteroaryl)", each having the meaning as defined herein.

The terms "heterocycle", "heterocyclic" and "heterocyclyl" refer to a monoradical, saturated or unsaturated, non-aromatic cyclic hydrocarbon group having about 1 to 40 (preferably from about 3 to 15) carbon atoms and about 1 to 10 hetero atoms (preferably about 1 to 4 heteroatoms, selected from nitrogen, sulfur, phosphorus, and/or oxygen) within the ring. Such heterocyclic groups can have a single ring or multiple condensed rings. The heterocycle may include pyrrolidinyl, tetrahydrofuranyl, oxazolidinyl and imidazolidinyl and the like. The heterocycle may also include carbohydrates and their derivatives. Preferred heterocyclics include morpholino, piperidinyl, furanyl, thiazolyl, imidazolidinyl, and the like.

The terms "substituted heterocycle", "substituted heterocyclic" and "substituted heterocyclyl" refer to a heterocyclyl group as defined above, which unless otherwise constrained by the definition for the heterocycle, is substituted with from 1 to 5 substituents, and preferably 1 to 3 substituents, independently selected from the group consisting of: =O, =S, acyl, acyloxy, optionally substituted alkenyl, optionally substituted alkoxy, optionally substituted alkyl (such as tri-halomethyl), optionally substituted alkynyl, optionally substituted amino, optionally substituted aryl, optionally substituted aryloxy, azido, carboxyl, (optionally substituted alkoxy)carbonyl, (optionally substituted amino)carbonyl, cyano, optionally substituted cycloalkyl, optionally substituted cycloalkenyl, halogen, optionally substituted heteroaryl, optionally substituted heteroaryloxy, optionally substituted heterocyclyl, optionally substituted heterocyclooxy, hydroxyl, nitro, sulfanyl, sulfinyl, and sulfonyl. Preferred substituted heterocycles include 2-thioxo-thiazolidin-4-one and thiazolidine-2,4-dione.

The term "heterocycloalkyl" refers to the moiety "-alkylene-heterocycle" each having the meaning as defined herein.

The term "substituted heterocycloalkyl" refers to the moiety "-(optionally substituted alkylene)-(optionally substituted heterocycle)", each having the meaning as defined herein.

The term "pharmaceutically acceptable salt" refers to salts which retain the biological effectiveness and properties of the compounds of this invention and which are not biologically or otherwise undesirable. In many cases, the compounds of this invention are capable of forming acid and/or base salts by virtue of the presence of amino and/or carboxyl groups or groups similar thereto. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl)amines, alkenyl amines, dialkenyl amines, trialkenyl amines, substituted alkenyl amines, di(substituted alkenyl)amines, tri(substituted alkenyl) amines, cycloalkyl amines, di(cycloalkyl)amines, tri(cycloalkyl)amines, substituted cycloalkyl amines, disubstituted cycloalkyl amine, trisubstituted cycloalkyl amines, cycloalkenyl amines, di(cycloalkenyl)amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, trimethyl amine, diethyl amine, tri(iso-propyl)amine, tri(n-propyl)amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

The term "phosphoryl" refers to the group —P(O)(OR")$_2$, where R" is independently selected from hydrogen or alkyl and aryl, which group is sometimes also referred to as "phosphono" or as a "phosphate" or "phosphonic acid."

The term "sulfonyl" refers to the groups: —S(O$_2$)-(optionally substituted alkyl), —S(O$_2$)-(optionally substituted amino), —S(O$_2$)-optionally substituted aryl), —S(O$_2$)-(optionally substituted heteroaryl), —S(O$_2$)-(optionally substituted heterocyclyl). Preferred sulfonyl groups include, by way of example, methylsulfonyl, ethylsulfonyl, aminosulfonyl, piperidin-1-sulfonyl and morpholine-4-sulfonyl.

The term "biological target" can be any biological molecule involved in biological pathways associated with any of various diseases and conditions, including cancer (e.g., leukemia, lymphomas, brain tumors, breast cancer, lung cancer, prostate cancer, gastric cancer, as well as skin cancer, bladder cancer, bone cancer, cervical cancer, colon cancer, esophageal cancer, eye cancer, gallbladder cancer, liver cancer, kidney cancer, laryngeal cancer, oral cancer, ovarian cancer, pancreatic cancer, penile cancer, glandular tumors, rectal cancer, small intestine cancer, sarcoma, testicular cancer, urethral cancer, uterine cancer, and vaginal cancer), diabetes, neurodegenerative diseases, cardiovascular diseases, respiratory diseases, digestive system diseases, infectious diseases, inflammatory diseases, autoimmune diseases, and the like. Exemplary biological pathways include, for example, cell cycle regulation (e.g., cellular proliferation and apoptosis), angiogenesis, signaling pathways, tumor suppressor pathways, inflammation (COX-2), oncogenes, hypoxia-related pathways and growth factor receptors. The biological target may also be referred to as the "target biomacromolecule" or the "biomacromolecule." The biological target can be a receptor, such as enzyme receptors, ligand-gated ion channels, G-protein-coupled receptors, and transcription factors. The biologically target is preferably a protein or protein complex, such as enzymes, membrane transport proteins, hormones, and antibodies. In one particularly preferred embodiment, the protein biological target is an enzyme, such as carbonic anhydrase-II and its related isozymes such as carbonic anhydrase IX and XII.

The term "leaving group", as used herein refers to groups that are readily displaced, for example, by a nucleophile, such as an amine, a thiol or an alcohol nucleophile or its salt. Such leaving groups are well known and include, for example carboxylates, N-hydroxysuccinimide, N-hydroxybenzotriazole, halides, triflates, tosylates, nosylates, —OR and —SR and the like.

The term "ligand" is a molecule, preferably having a molecular weight of less than about 800 Da., more preferably less than about 600 Da., comprising a first group exhibiting affinity for a first binding site on a biological target molecule, such as a protein, and a second group exhibiting affinity for a second binding site on the same biological target molecule. The two binding sites can be separate areas within the same binding pocket on the target molecule. The ligands preferably exhibit nanomolar binding affinity for the biological target molecule. In certain aspects as disclosed herein, a ligand is used synonomously with a "substrate." A ligand may comprise a "molecular structure" as defined herein.

The term "linker" as used herein refers to a chain comprising 1 to 10 atoms and may comprise of the atoms or groups, such as C, —NR—, O, S, —S(O)—, —S(O)₂—, CO, —C(NR)— and the like, and wherein R is H or is selected from the group consisting of $(C_{1-10})$alkyl, $(C_{3-8})$cycloalkyl, aryl$(C_{1-5})$alkyl, heteroaryl$(C_{1-5})$alkyl, amino, aryl, heteroaryl, hydroxy, $(C_{1-10})$alkoxy, aryloxy, heteroaryloxy, each substituted or unsubstituted. The linker chain may also comprise part of a saturated, unsaturated or aromatic ring, including polycyclic and heteroaromatic rings.

The terms "patient" and "subject" refer to any human or animal subject, particularly including all mammals.

The term "radiochemical" is intended to encompass any organic, inorganic or organometallic compound comprising a covalently-attached radioactive isotope, any inorganic radioactive ionic solution (e.g., Na[$^{18}$F]F ionic solution), or any radioactive gas (e.g., [$^{11}$C]CO₂), particularly including radioactive molecular imaging probes intended for administration to a patient (e.g., by inhalation, ingestion, or intravenous injection) for tissue imaging purposes, which are also referred to in the art as radiopharmaceuticals, radiotracers, or radioligands. Although the present invention is primarily directed to synthesis of positron-emitting molecular imaging probes for use in PET imaging systems, the invention could be readily adapted for synthesis of any radioactive compound comprising a radionuclide, including radiochemicals useful in other imaging systems, such as single photon emission computed tomography (SPECT).

The term "radioactive isotope" refers to isotopes exhibiting radioactive decay (i.e., emitting positrons) and radiolabeling agents comprising a radioactive isotope (e.g., [$^{11}$C]methane, [$^{11}$C]carbon monoxide, [$^{11}$C]carbon dioxide, [$^{11}$C]phosgene, [$^{11}$C]urea, [$^{11}$C]cyanogen bromide, as well as various acid chlorides, carboxylic acids, alcohols, aldehydes, and ketones containing carbon-11). Such isotopes are also referred to in the art as radioisotopes or radionuclides. Radioactive isotopes are named herein using various commonly used combinations of the name or symbol of the element and its mass number (e.g., $^{18}$F, F-18, or fluorine-18). Exemplary radioactive isotopes include I-124, F-18 fluoride, C-11, N-13, and O-15, which have half-lives of 4.2 days, 110 minutes, 20 minutes, 10 minutes, and 2 minutes, respectively. The radioactive isotope is preferably dissolved in an organic solvent, such as a polar aprotic solvent. Preferably, the radioactive isotopes used in the present method include F-18, C-11, I-123, I-124, I-127, I-131, Br-76, Cu-64, Tc-99m, Y-90, Ga-67, Cr-51, Ir-192, Mo-99, Sm-153 and Tl-201. Other radioactive isotopes that may be employed include: As-72, As-74, Br-75, Co-55, Cu-61, Cu-67, Ga-68, Ge-68, I-125, I-132, In-111, Mn-52, Pb-203, Ru-97.

The term "optical imaging agent" refers to molecules that have wavelength emission greater than 400 nm and below 1200 nm. Examples of optical imaging agents are Alex Fluor, BODIPY, Nile Blue, COB, rhodamine, Oregon green, fluorescein and acridine.

In a particular aspect of the method with the ligand radiochemical embodiment, one of the precursor molecules may also comprise a leaving group that can be readily displaced by nucleophilic substitution in order to covalently attach a radioisotope to the precursor. Exemplary reactive precursors include small molecules bearing structural similarities to existing PET probe molecules, EGF, cancer markers (e.g., p 185HER2 for breast cancer, CEA for ovarian, lung, breast, pancreas, and gastrointestinal tract cancers, and PSCA for prostrate cancer), growth factor receptors (e.g., EGFR and VEGFR), glycoproteins related to autoimmune diseases (e.g., HC gp-39), tumor or inflammation specific glycoprotein receptors (e.g., selectins), integrin specific antibody, virus-related antigens (e.g., HSV glycoprotein D, EV gp), and organ specific gene products.

Nomenclature

In general, the nomenclature used in this Application was generated using the AUTONOM™ naming package within the ChemOffice® version 10.0 suite of programs by CambridgeSoft Corp (Cambridge, Mass.). A compound in Formula I, for example, wherein B is a benzothiazolesulfonamide, Y is methyleneoxy, A is a triazole, X is butanamide, and Z is 4-trifluorobenzyl may be named (S)-3-methyl-2-(4-((2-sulfamoylbenzo[d]thiazol-6-yloxy)methyl)-1H-1,2,3-triazol-1-yl)-N-(4-(trifluoromethyl)benzyl)butanamide.

Synthesis of the Compounds of the Invention

Synthetic Reaction Parameters

The terms "solvent", "inert organic solvent" or "inert solvent" mean a solvent inert under the conditions of the reaction being described in conjunction therewith. Solvents employed in synthesis of the compounds of the invention include, for example, methanol, acetone, water, acetonitrile, 1,4-dioxane, dichloromethane ("DCM"), dimethylformamide ("DMF"), benzene, toluene, tetrahydrofuran ("THF"), chloroform, diethyl ether, pyridine and the like, as well as mixtures thereof. Unless specified to the contrary, the solvents used in the reactions of the present invention are inert organic solvents.

Unless specified to the contrary, the reactions described herein take place at atmospheric pressure within a temperature range from 0° C. to 110° C. (preferably from 0° C. to 25° C.; most preferably at "room" or "ambient" temperature, e.g., 20° C.). Further, unless otherwise specified, the reaction times and conditions are intended to be approximate, e.g., taking place at about atmospheric pressure within a temperature range of about 0° C. to about 110° C. (preferably from about 0° C. to about 25° C.; most preferably at about "room" or "ambient" temperature, e.g., approximately 20° C.) over a period of about 1 to about 20 hours (preferably about 5 hours). Parameters given in the Examples are intended to be specific, not approximate.

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples herein below. However, asymmetric synthetic approaches and other equivalent separation or isolation procedures can, of course, also be used.

Synthesis of Compound Libraries

Compounds of Formula I of the present invention wherein A is a triazole, B is a benzene or benzothiazole, X and Z taken together by R, and Y are as described above, can be prepared following the Synthetic Scheme I.

Synthetic Scheme I

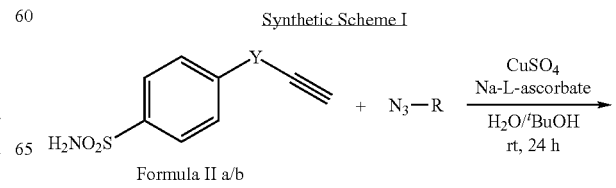

Formula II a/b

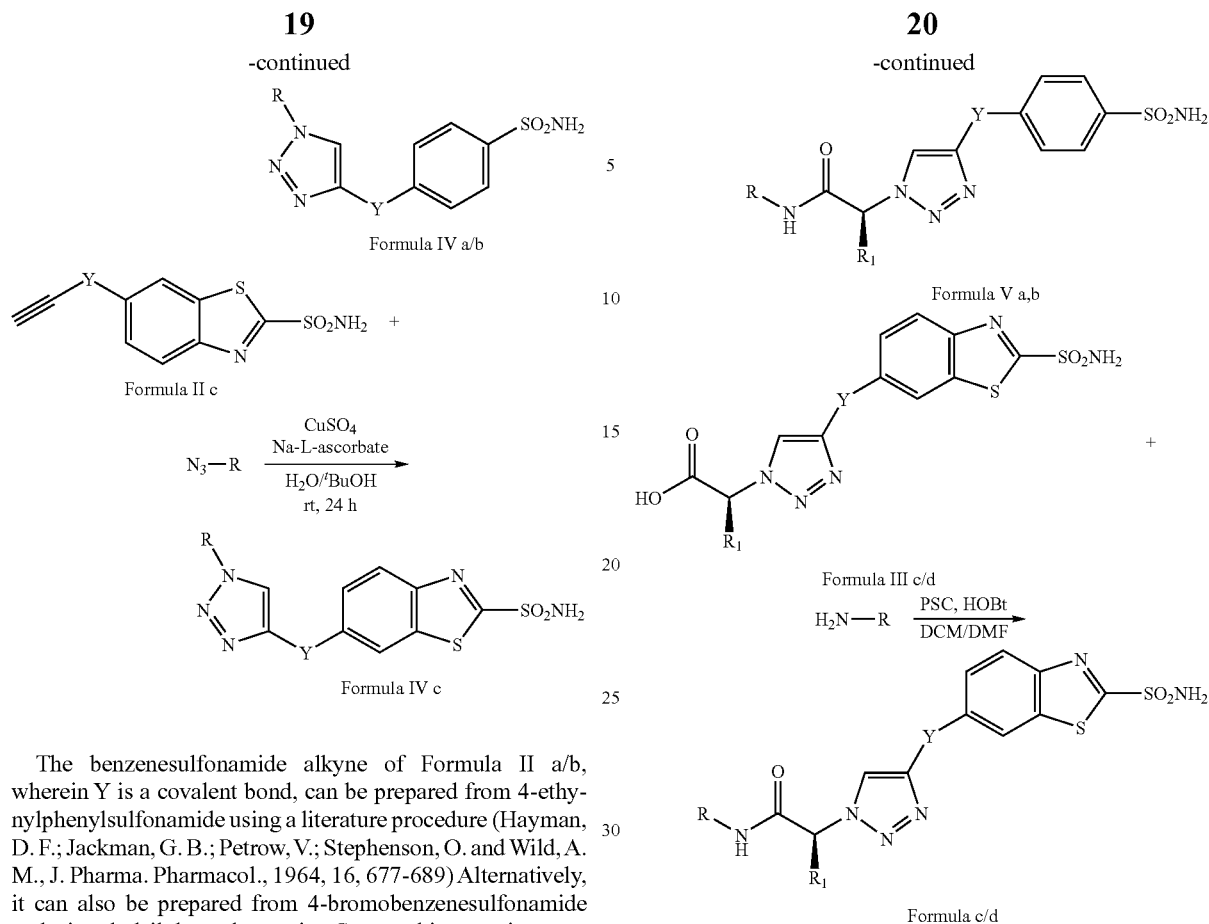

The benzenesulfonamide alkyne of Formula II a/b, wherein Y is a covalent bond, can be prepared from 4-ethynylphenylsulfonamide using a literature procedure (Hayman, D. F.; Jackman, G. B.; Petrow, V.; Stephenson, O. and Wild, A. M., J. Pharma. Pharmacol., 1964, 16, 677-689) Alternatively, it can also be prepared from 4-bromobenzenesulfonamide and trimethylsilylacetelene using Sonogashira reaction conditions. The benzenesulfonamide alkyne of Formula II a/b, wherein Y is a methylene amido carbonyl (—CH$_2$NHC (O)—), can be prepared from 4-sulfamoylbenzoic acid and propargyl amine. The azido compounds of R—N3, wherein R is taken together of X and Z in Formula I are either commercially available or can be made using the methods well known in the art. The benzothiazolesulfonamide alkyne of Formula II c, wherein Y is methyleneoxy (—CH$_2$O—), can be prepared from 4-hydroxybenzothiazolesulfonamide and propargyl bromide under inert condition using a base, such as potassium carbonate. The alkynes, such as in Formula II a/b and II c, and azides (R—N3) in the presence of Cu(I) salts can undergo 1,3-dioplar cycloaddition forming 1,4-disubstituted 1,2,3-triazoles, as shown in Formula IV a/b and Formula IV c. The Cu (I) salts can be generated from Cu(II) SO4 and Na-L-ascorbate, or can be used directly from Cu(I)I or CuOAc, and the like.

Synthetic Scheme II

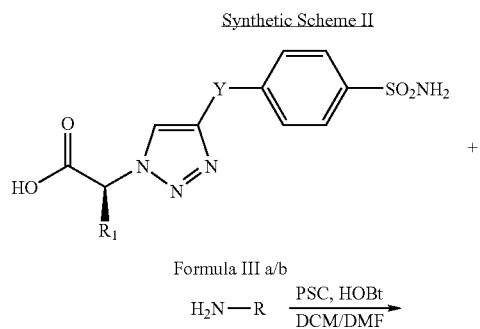

Compounds of Formula I of the present invention wherein A is a triazole, B is a benzene or benzothiazole, X is α-substituted acetamide, Y is the same as described above, and Z equals R and as the same as described above, can be prepared following the Synthetic Scheme II. The precursors of Formula III a/b and Formula III c/d can both be prepared in the same way as illustrated in Synthetic Scheme I, wherein R—N$_3$ is a R$_1$ substituted azidoacetic acid. These R$_1$ substituted azidoacetic acid in general can be made from various amino acids using a diazo transfer reaction (Lundquist IV, J. T. and Pelletier, J. C. Org. Lett., 2001, 3, 781-783). Alternatively, they can be also synthesized using nucleophilic replacement reaction of NaN$_3$ with α-bromo-substituted acids. Reaction of these precursors with a wide variety of amines (R—NH$_2$) in the presence of the coupling reagents, for example Poly(styrene)carbodiimide (PSC), in suitable solvents, such as dichloromethane (DCM) and DMF, can give the desired compound libraries of Formula V a/b and Formula V c/d.

Synthesis of Radio-Labeled Compounds

Radio-labeling a small molecule usually involves displacement of a suitably activated precursor with a radioactive moiety in a compatible reaction media. In the case of $^{18}$F-labeling, the [$^{18}$F] fluoride attachment to the precursor occurs via nucleophilic substitution of a leaving group, such as mesylate, tosylate, bromide, iodide, or diazonium salt, or nitro. The preparation of a radio-labeled compound hence generally consists of two sequences. The first sequence involves the preparation of radio-labeling precursor, in which various functional groups have been appropriately protected and a proper leaving group has been incorporated. The second sequence then involves the radio-labeling, and removal of the

Synthetic Scheme III

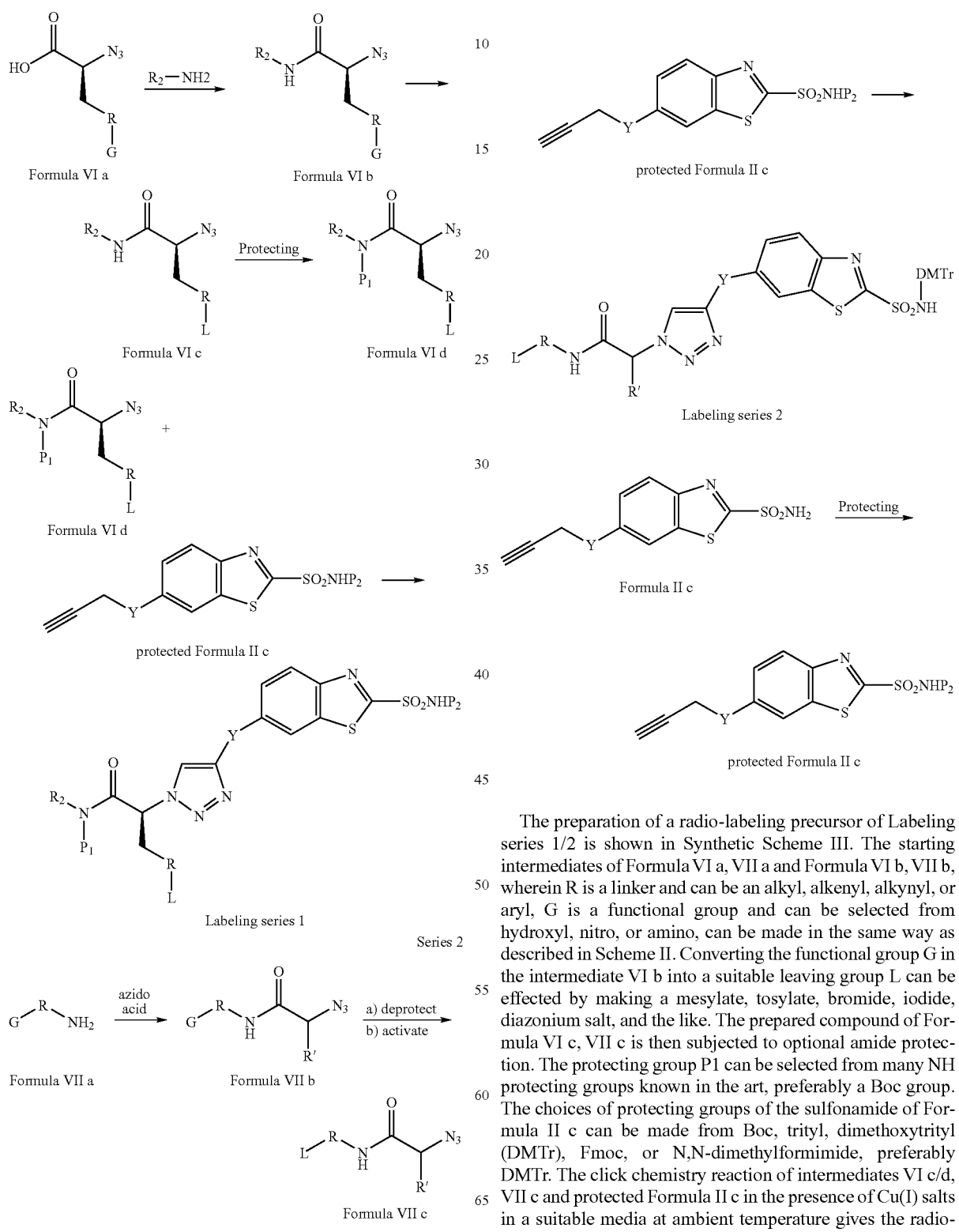

The preparation of a radio-labeling precursor of Labeling series 1/2 is shown in Synthetic Scheme III. The starting intermediates of Formula VI a, VII a and Formula VI b, VII b, wherein R is a linker and can be an alkyl, alkenyl, alkynyl, or aryl, G is a functional group and can be selected from hydroxyl, nitro, or amino, can be made in the same way as described in Scheme II. Converting the functional group G in the intermediate VI b into a suitable leaving group L can be effected by making a mesylate, tosylate, bromide, iodide, diazonium salt, and the like. The prepared compound of Formula VI c, VII c is then subjected to optional amide protection. The protecting group P1 can be selected from many NH protecting groups known in the art, preferably a Boc group. The choices of protecting groups of the sulfonamide of Formula II c can be made from Boc, trityl, dimethoxytrityl (DMTr), Fmoc, or N,N-dimethylformimide, preferably DMTr. The click chemistry reaction of intermediates VI c/d, VII c and protected Formula II c in the presence of Cu(I) salts in a suitable media at ambient temperature gives the radio-labeling precursor of Labeling series 1/2.

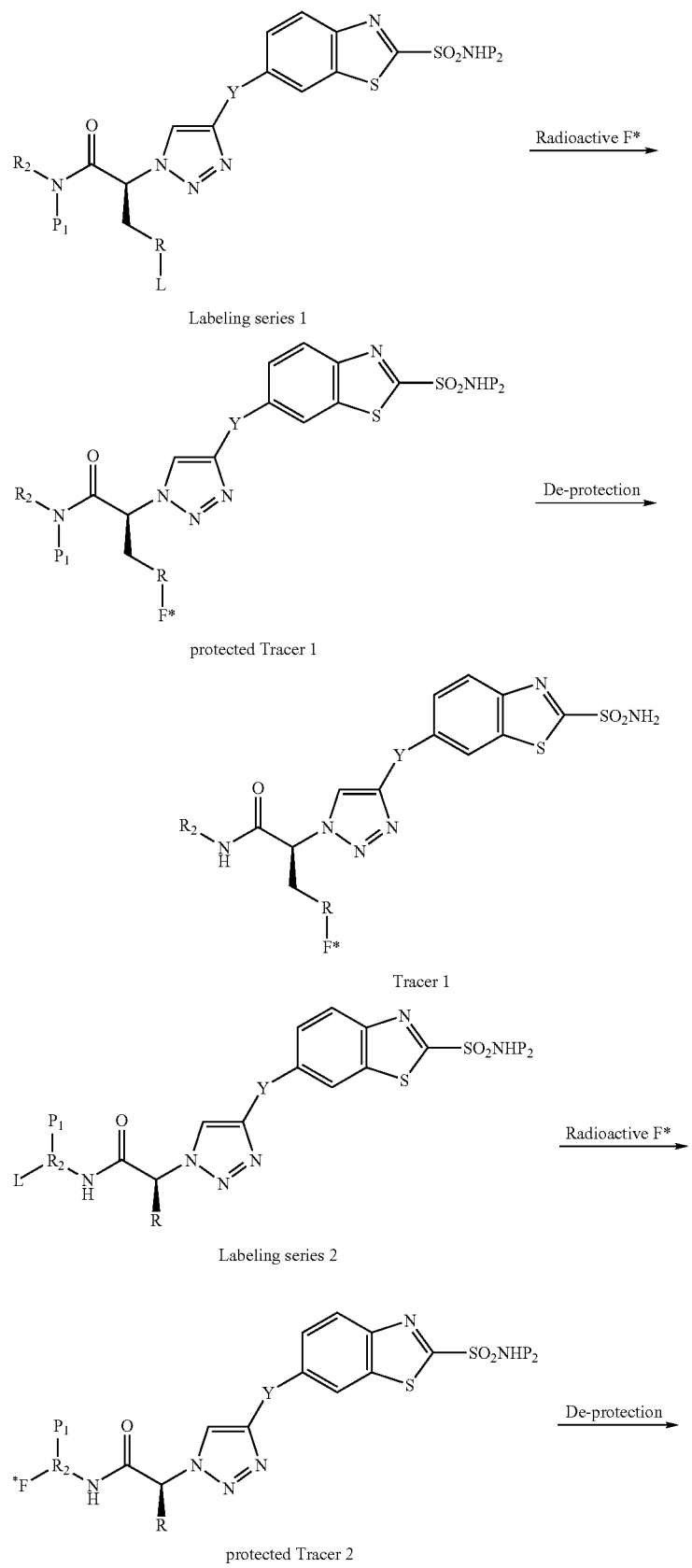

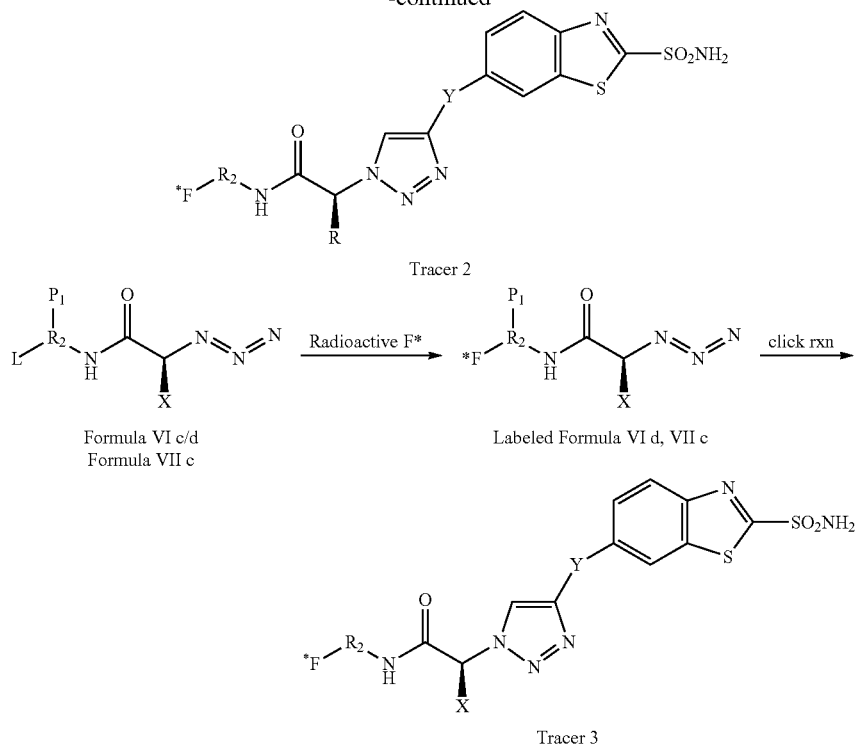

Tracer 2

Formula VI c/d
Formula VII c

Labeled Formula VI d, VII c

Tracer 3

X = R-L or R

The radio-labeling process involves two sequential steps. The first is the radioactive nucleophilic F* displacement of the leaving group L of the labeling series 1/2. Then, the protecting groups of $P_1$ and $P_2$ are removed under appropriate conditions, leading to a radio-labeled, PET imaging probe Protected Tracer 1/2. In a preferred embodiment of the present invention, the radioactive element is [$^{18}$F] and the leaving group L is a nosylate or tosylate. In this case, the radio-labeling step is generally affected in the presence of tetra-N-butyl ammonium bicarbonate or K222, $K_2CO_3$ at an elevated temperature for 5-10 minutes in acetonitrile. The removal of protecting groups is achieved using either a) an aqueous HCl solution at an elevated temperature for 5-10 minutes or b) LiOH saponification at RT for 30 min followed by treatment with an aqueous HCl solution at an elevated temperature for 5-10 minutes. It must be understood, however, that as described above, the radioactive element can be incorporated in either X, Y, or Z of Formula I. The structures used herein can only serve to show the general process of preparing the radio-labeled PET imaging agents and should not be used as the description of the scope of the present invention.

Alternatively, the azide may be radiolabeled by nucleophilic displacement of F* of the leaving group L of the labeling precursor Formula VI c/d and VII c. Then the protecting groups are removed and the material is then clicked with an alkyne to afford radiolabled Tracer 3. In a preferred embodiment of the present invention, the radioactive element is [$^{18}$F] and the leaving group L is a tosylate. In this case, the radio-labeling step is generally affected in the presence of tetra-N-butyl ammonium bicarbonate or K222, $K_2CO_3$ at an elevated temperature for 5-10 minutes in acetonitrile. The removal of protecting groups is achieved using either a) an aqueous HCl solution at an elevated temperature for 5-10 minutes or b) LiOH saponification at RT for 30 min followed by treatment with an aqueous HCl solution at an elevated temperature for 5-10 minutes. The click reaction is performed in the presence of an alkyne and heat and/or a metal catalyst to effect the coupling. A reducing agent such as sodium ascorbate may be added. A preferred metal catalyst is copper in the Cu(I) oxidation state.

Preferred Compounds

The following combinations and permutations of substituent groups (sub-grouped, respectively, in increasing order of preference) define compounds that are preferred as composition of matter and compounds for use in the methods as PET imaging agents according to the invention.

The compounds of any of Formula I where B is cycloalkyl, cycloalkenyl, heterocyclyl, aryl, heteroaryl, particularly B is a benzne, and preferably B is a benzothiazole.

The compounds of any of Formula I where Y is optionally substituted alkyl, alkoxy, alkenyl, cycloalkyl, cycloalkenyl, aryl. The preferred substituent groups are H, lower alkyl, haloalkyl, hydroxyalkyl, carboxyalkyl, aminoalkyl and arylalkyl. Particularly those where Y is an alkyl (amido carbonyl), preferably Y is a covalent bond, and more preferably Y is a methyleneoxy. The compounds of any of Formula I where A is 3- to 7-membered heterocycle, more preferably a triazole, and most preferably a 1,4-substituted triazole. The compounds of any of Formula I where X is optionally substituted lower alkyl, alkoxy, $C_3$-$C_7$ cycloalkyl, cycloalkenyl, and 3- to 7-membered heterocycle, preferably (amido carbonyl)alkyl, more preferably optionally substituted acetamide. The preferred substitutent groups are halo, lower alkyl, alkoxy, haloalkyl, carboxyalkyl, aminoalkyl, hydroxyalkyl, cyanoalkyl, sulfonylalkyl, sulfamoylalkyl, (amido carbonyl) alkyl, alkenyl, alkynyl, optionally substituted aryl, arylalkyl and amino acid. The more preferred substituent groups are H, isopropyl, methylene carboxylate, and benzyl. The most preferred are 4-(2-fluoroethoxy)benzyl, 4-(4-fluoro-2,3-dihydroxybutoxy)benzyl, 4-(3-fluoro-2-hydroxypropoxy)benzyl, 2-fluoroethyl and 3-fluoro-2-hydroxypropyl. The compounds of any of Formula I where Z is optionally substituted aryl, optionally substituted heteroaryl, optionally substituted heterocycle, or optionally substituted amino acid. The more preferred Z include trifluorobenzyl, furan-2-yl-methyl, pyridinium salt, piperidine-4-carboxylic acid, and substituted amino acid Phe, Cys and Pro. The preferred substituted groups are hydroxyl, amino or substituted amino, substituted lower alkyl, substituted lower alkenyl, alkoxy, halogen, optionally substituted carboxy, substituted amino carbonyl, nitro and sulfonyl. The more preferred substituent groups are haloalkyl, hydroxyalkyl, aminoalkyl, haloalkoxy and cyano. The most preferred groups are trifluoromethyl, 2-fluoroethoxy, 4-fluoro-2,3-dihydrobutoxy and 3-fluoro-2-hydroxypropoxy.

The compounds of any of Formula I wherein a charged moiety is included in either X, Y, or Z. The preferred location of the charged moiety is in X or Z. The preferred charged moieties include quaternary ammonium salts, pyridinium salts, boronic acids, sulfonic acids, phosphonic acids, and carboxylic acids.

The compounds of any of Formula I wherein a radioactive element is included in either X, Y, or Z. The preferred location of the radioactive element is in X or Z. The preferred radioactive element includes $^{11}C$, $^{13}N$, $^{15}O$, and $^{18}F$. The most preferred one is $^{18}F$.

The preferred compounds include the following, as well as their stereoisomers, tautomers, salts, and mixtures thereof:
(R)-2-(S)-3-(4-(2-fluoroethoxy)phenyl)-2-(4-((2-sulfamoylbenzo[d]thiazol-6-yloxy)methyl)-1H-1,2,3-triazol-1-yl)propanamido)-3-(4-(trifluoromethyl)phenyl)propanoic acid;
(2S)-2-((2S)-3-(4-(3-fluoro-2-hydroxypropoxy)phenyl)-2-(4-((2-sulfamoylbenzo[d]thiazol-6-yloxy)methyl)-1H-1,2,3-triazol-1-yl)propanamido)-3-(4-(trifluoromethyl)phenyl)propanoic acid;
(S)-3-(4-(2-fluoroethoxy)phenyl)-2-(4-((2-sulfamoylbenzo[d]thiazol-6-yloxy)methyl)-1H-1,2,3-triazol-1-yl)-N-(4-(trifluoromethoxy)benzyl)propanamide;
(S)-2-(S)-3-(4-(2-fluoroethoxy)phenyl)-2-(4-((2-sulfamoylbenzo[d]thiazol-6-yloxy)methyl)-1H-1,2,3-triazol-1-yl)propanamido)-3-(1H-indol-3-yl)propanoic acid;
(S)-2-(S)-3-(4-(2-fluoroethoxy)phenyl)-2-(4-((2-sulfamoylbenzo[d]thiazol-6-yloxy)methyl)-1H-1,2,3-triazol-1-yl)propanamido)-3-(3-(trifluoromethyl)phenyl)propanoic acid;
(S)-3-(4-cyanophenyl)-2-((S)-3-(4-(2-fluoroethoxy)phenyl)-2-(4-((2-sulfamoylbenzo[d]thiazol-6-yloxy)methyl)-1H-1,2,3-triazol-1-yl)propanamido)propanoic acid;
(S)-methyl 3-(3-(2-fluoroethoxy)benzylthio)-2-((S)-4-hydroxy-2-(4-((2-sulfamoylbenzo[d]thiazol-6-yloxy)methyl)-1H-1,2,3-triazol-1-yl)butanamido)propanoate;
(R)-3-(3-(2-fluoroethoxy)benzylthio)-2-((R)-4-hydroxy-2-(4-((2-sulfamoylbenzo[d]thiazol-5-yloxy)methyl)-1H-1,2,3-triazol-1-yl)butanamido)propanoic acid;
(R)-3-(3-(2-fluoroethoxy)benzylthio)-2-((S)-4-hydroxy-2-(4-((2-sulfamoylbenzo[d]thiazol-5-yloxy)methyl)-1H-1,2,3-triazol-1-yl)butanamido)propanoic acid;
(S)-2-((S)-3-(4-(((4S,5R)-5-(fluoromethyl)-2,2-dimethyl-1,3-dioxolan-4-yl)methoxy)phenyl)-2-(4-((2-sulfamoylbenzo[d]thiazol-6-yloxy)methyl)-1H-1,2,3-triazol-1-yl)propanamido)-3-(4-(trifluoromethyl)phenyl)propanoic acid;
(S)-2-((R)-3-(4-(((4S,5R)-5-(fluoromethyl)-2,2-dimethyl-1,3-dioxolan-4-yl)methoxy)phenyl)-2-(4-((2-sulfamoylbenzo[d]thiazol-6-yloxy)methyl)-1H-1,2,3-triazol-1-yl)propanamido)-3-(4-(trifluoromethyl)phenyl)propanoic acid;
3-(3-(2-fluoroethoxy)benzylthio)-2-(4-hydroxy-2-(4-((2-sulfamoylbenzo[d]thiazol-5-yloxy)methyl)-1H-1,2,3-triazol-1-yl)butanamido)propanoic acid;
(S)-2-((S)-3-(4-((2S,3R)-4-fluoro-2,3-dihydroxybutoxy)phenyl)-2-(4-((2-sulfamoylbenzo[d]thiazol-6-yloxy)methyl)-1H-1,2,3-triazol-1-yl)propanamido)-3-(4-(trifluoromethyl)phenyl)propanoic acid;
(S)-2-((R)-3-(4-((2S,3R)-4-fluoro-2,3-dihydroxybutoxy)phenyl)-2-(4-((2-sulfamoylbenzo[d]thiazol-6-yloxy)methyl)-1H-1,2,3-triazol-1-yl)propanamido)-3-(4-(trifluoromethyl)phenyl)propanoic acid;
(2R)-3-(3-((1-(1-fluoro-3-hydroxypropan-2-yl)-1H-1,2,3-triazol-4-yl)methoxy)benzylthio)-2-(2-(4-((2-sulfamoylbenzo[d]thiazol-5-yloxy)methyl)-1H-1,2,3-triazol-1-yl)acetamido)propanoic acid;
(2R)-3-(3-(2-fluoroethoxy)benzylsulfinyl)-2-(2-(4-((2-sulfamoylbenzo[d]thiazol-5-yloxy)methyl)-1H-1,2,3-triazol-1-yl)acetamido)propanoic acid;
(S)-3-(3-(2-fluoroethoxy)benzyloxy)-2-(2-(4-((2-sulfamoylbenzo[d]thiazol-5-yloxy)methyl)-1H-1,2,3-triazol-1-yl)acetamido)propanoic acid;
(2S)-3-(3-(3-fluoro-2-hydroxypropoxy)benzyloxy)-2-(2-(4-((2-sulfamoylbenzo[d]thiazol-5-yloxy)methyl)-1H-1,2,3-triazol-1-yl)acetamido)propanoic acid;
(2S)-3-(4-(3-fluoro-2-hydroxypropoxy)phenyl)-2-((R)-3-methyl-2-(4-((2-sulfamoylbenzo[d]thiazol-6-yloxy)methyl)-1H-1,2,3-triazol-1-yl)butanamido)propanoic acid;
(2S)-3-(4-(3-fluoro-2-hydroxypropoxy)phenyl)-2-((R)-3-methyl-2-(4-((2-sulfamoylbenzo[d]thiazol-6-yloxy)methyl)-1H-1,2,3-triazol-1-yl)butanamido)propanoic acid;
(S)-3-(4-(2-fluoroethoxy)phenyl)-2-((R)-3-methyl-2-(4-((2-sulfamoylbenzo[d]thiazol-6-yloxy)methyl)-1H-1,2,3-triazol-1-yl)butanamido)propanoic acid;
(S)-3-(4-(2-fluoroethoxy)phenyl)-2-((R)-3-methyl-2-(4-((2-sulfamoylbenzo[d]thiazol-6-yloxy)methyl)-1H-1,2,3-triazol-1-yl)butanamido)propanoic acid;
(S)-3-(4-(2-fluoroethoxy)phenyl)-2-(2-(4-((2-sulfamoylbenzo[d]thiazol-6-yloxy)methyl)-1H-1,2,3-triazol-1-yl)acetamido)propanoic acid;
(2S)-3-(4-(3-fluoro-2-hydroxypropoxy)phenyl)-2-(2-(4-((2-sulfamoylbenzo[d]thiazol-6-yloxy)methyl)-1H-1,2,3-triazol-1-yl)acetamido)propanoic acid;
(2S)-3-(4-(1-fluoro-3-hydroxypropan-2-yloxy)phenyl)-2-((S)-3-methyl-2-(4-((2-sulfamoylbenzo[d]thiazol-6-yloxy)methyl)-1H-1,2,3-triazol-1-yl)butanamido)propanoic acid; and
S)-3-(4-(1-fluoro-3-hydroxypropan-2-yloxy)phenyl)-2-((R)-3-methyl-2-(4-((2-sulfamoylbenzo[d]thiazol-6-yloxy)methyl)-1H-1,2,3-triazol-1-yl)butanamido)propanoic acid.

Also provided herein are the following compounds:
Propyl 4-(2-(4-(4-sulfamoylphenyl)-1H-1,2,3-triazol-1-yl)acetamido)benzoate;
(R)-Methyl 3-(benzylthio)-2-(2-(4-(4-sulfamoylphenyl)-1H-1,2,3-triazol-1-yl)acetamido)propanoate;
4-(1-(2-Morpholinoethyl)-1H-1,2,3-triazol-4-yl)benzenesulfonamide;
(S)—N-(4-Methylpyridin-2-yl)-3-phenyl-2-(4-(4-sulfamoylphenyl)-1H-1,2,3-triazol-1-yl)propanamide;
4-(1-(3-(1,3-Dioxoisoindolin-2-yl)-2-hydroxypropyl)-1H-1,2,3-triazol-4-yl)benzenesulfonamide;

(S)—N-Benzyl-4-methyl-2-(4-(4-sulfamoylphenyl)-1H-1,2,3-triazol-1-yl)pentanamide;
4-(1-(3-(Dimethylamino)-2-methylpropyl)-1H-1,2,3-triazol-4-yl)benzenesulfonamide;
4-(1-(3-Bromobenzyl)-1H-1,2,3-triazol-4-yl)benzenesulfonamide;
Ethyl 4-((4-(4-sulfamoylphenyl)-1H-1,2,3-triazol-1-yl)methyl)benzoate;
4-(1-(3-(6-Chloro-2-methoxyacridin-9-ylamino)propyl)-1H-1,2,3-triazol-4-yl)benzenesulfonamide;
N-(1,3-Dimethyl-1H-pyrazol-5-yl)-2-(4-(4-sulfamoylphenyl)-1H-1,2,3-triazol-1-yl)acetamide;
4-(1-((1H-Benzo[d]imidazol-2-yl)methyl)-1H-1,2,3-triazol-4-yl)benzenesulfonamide;
4-(1-(2-(2-oxo-2H-chromen-7-yloxy)ethyl)-1H-1,2,3-triazol-4-yl)benzenesulfonamide;
4-(1-(2-(1H-Indazol-1-yl)-2-oxoethyl)-1H-1,2,3-triazol-4-yl)benzenesulfonamide;
4-(3-Methoxy-3-oxo-2-(4-(4-sulfamoylphenyl)-1H-1,2,3-triazol-1-yl)propyl)benzoic acid;
4-(1-(4-((1S,2R)-1,2-Dihydroxyoctyl)benzyl)-1H-1,2,3-triazol-4-yl)benzenesulfonamide;
4-(1-(7-Chloroquinolin-4-yl)-1H-1,2,3-triazol-4-yl)benzenesulfonamide;
4-(1-((1R)-(6-Methoxyquinolin-4-yl)((2R)-8-vinylquinuclidin-2-yl)methyl)-1H-1,2,3-triazol-4-yl)benzenesulfonamide;
4-(1-(6-Hydroxyhexyl)-1H-1,2,3-triazol-4-yl)benzenesulfonamide;
4-(1-(2-(2,4-Dioxo-1,2-dihydroquinazolin-3(4H)-yl)ethyl)-1H-1,2,3-triazol-4-yl)benzenesulfonamide;
(E)-4-(1-(1-Cinnamoylpiperidin-4-yl)-1H-1,2,3-triazol-4-yl)benzenesulfonamide;
2-(4-(4-Sulfamoylphenyl)-1H-1,2,3-triazol-1-yl)-N-(thiazol-2-yl)acetamide;
N-Phenyl-3-(4-(4-sulfamoylphenyl)-1H-1,2,3-triazol-1-yl)propanamide;
N-Morpholino-3-(4-(4-sulfamoylphenyl)-1H-1,2,3-triazol-1-yl)benzamide;
3-(1H-Imidazol-5-yl)-2-(2-(4-(4-sulfamoylphenyl)-1H-1,2,3-triazol-1-yl)acetamido)propanoic acid;
4-(1-(2-(4-(3,5-Dichlorophenyl)piperazin-1-yl)-2-oxoethyl)-1H-1,2,3-triazol-4-yl)benzenesulfonamide;
4-(1-(3-Aminopropyl)-1H-1,2,3-triazol-4-yl)benzenesulfonamide;
(E)-4-(1-(1-(Styrylsulfonyl)piperidin-4-yl)-1H-1,2,3-triazol-4-yl)benzenesulfonamide;
4-(1-(2-(1,2-Dihydroxyethyl)-4,5-dihydroxytetrahydrofuran-3-yl)-1H-1,2,3-triazol-4-yl)benzenesulfonamide;
(R)-Methyl 3-(benzylthio)-2-(2-(4-((4-sulfamoylbenzamido)methyl)-1H-1,2,3-triazol-1-yl)acetamido)propanoate;
N-((1-(2-Morpholinoethyl)-1H-1,2,3-triazol-4-yl)methyl)-4-sulfamoylbenzamide;
(S)—N-((1-(1-(4-Methylpyridin-2-ylamino)-1-oxo-3-phenylpropan-2-yl)-1H-1,2,3-triazol-4-yl)methyl)-4-sulfamoylbenzamide;
N-Morpholino-3-(4-((4-sulfamoylbenzamido)methyl)-1H-1,2,3-triazol-1-yl)benzamide;
(S)—N-((1-(1-(2,5-Difluorobenzylamino)-3-methyl-1-oxobutan-2-yl)-1H-1,2,3-triazol-4-yl)methyl)-4-sulfamoylbenzamide;
(S)—N-((1-(1-(Benzylamino)-4-methyl-1-oxopentan-2-yl)-1H-1,2,3-triazol-4-yl)methyl)-4-sulfamoylbenzamide;
N-((1-(3-(Dimethylamino)-2-methylpropyl)-1H-1,2,3-triazol-4-yl)methyl)-4-sulfamoylbenzamide;
N-((1-((2R)-3-Methyl-1-(3-methylpiperidin-1-yl)-1-oxobutan-2-yl)-1H-1,2,3-triazol-4-yl)methyl)-4-sulfamoylbenzamide;
(S)—N-((1-(1-(2,5-Dimethylbenzylamino)-1-oxo-3-phenylpropan-2-yl)-1H-1,2,3-triazol-4-yl)methyl)-4-sulfamoylbenzamide;
N-((1-(3-Bromobenzyl)-1H-1,2,3-triazol-4-yl)methyl)-4-sulfamoylbenzamide;
4-Sulfamoyl-N-((1-((2-thioxobenzo[d]thiazol-3(2H)-yl)methyl)-1H-1,2,3-triazol-4-yl)methyl)benzamide;
N-((1-(1-(3-Fluoro-4-methylbenzylamino)-3-methyl-1-oxobutan-2-yl)-1H-1,2,3-triazol-4-yl)methyl)-4-sulfamoylbenzamide;
(S)—N-((1-(1-(Cyclohexylamino)-3-methyl-1-oxobutan-2-yl)-1H-1,2,3-triazol-4-yl)methyl)-4-sulfamoylbenzamide;
Ethyl 4-((4-((4-Sulfamoylbenzamido)methyl)-1H-1,2,3-triazol-1-yl)methyl)benzoate;
(S)—N-((1-(1-(Benzylamino)-3-methyl-1-oxobutan-2-yl)-1H-1,2,3-triazol-4-yl)methyl)-4-sulfamoylbenzamide;
(S)—N-((1-(1-(Furan-2-ylmethylamino)-3-methyl-1-oxobutan-2-yl)-1H-1,2,3-triazol-4-yl)methyl)-4-sulfamoylbenzamide;
N-((1-((1H-Benzo[d][1,2,3]triazol-1-yl)methyl)-1H-1,2,3-triazol-4-yl)methyl)-4-sulfamoylbenzamide;
4-(3-Methoxy-3-oxo-2-(4-((4-sulfamoylbenzamido)methyl)-1H-1,2,3-triazol-1-yl)propyl)benzoic acid
Propyl 4-(2-(4-((4-sulfamoylbenzamido)methyl)-1H-1,2,3-triazol-1-yl)acetamido)benzoate;
(S)—N-((1-(3-Methyl-1-(3-morpholinopropylamino)-1-oxobutan-2-yl)-1H-1,2,3-triazol-4-yl)methyl)-4-sulfamoylbenzamide;
N-((1-(2-(3,5-Di-tert-butyl-4-hydroxyphenyl)-2-oxoethyl)-1H-1,2,3-triazol-4-yl)methyl)-4-sulfamoylbenzamide;
(S)-3-Methyl-2-(4-((4-sulfamoylbenzamido)methyl)-1H-1,2,3-triazol-1-yl)butanoic acid;
(S)—N-((1-(1-(Biphenyl-4-ylamino)-3-methyl-1-oxobutan-2-yl)-1H-1,2,3-triazol-4-yl)methyl)-4-sulfamoylbenzamide;
N-((1-(4-((1S,2R)-1,2-Dihydroxyoctyl)benzyl)-1H-1,2,3-triazol-4-yl)methyl)-4-sulfamoylbenzamide;
N-((1-(7-Chloroquinolin-4-yl)-1H-1,2,3-triazol-4-yl)methyl)-4-sulfamoylbenzamide;
N-((1-((1R)-(6-Methoxyquinolin-4-yl)((2R)-8-vinylquinuclidin-2-yl)methyl)-1H-1,2,3-triazol-4-yl)methyl)-4-sulfamoylbenzamide;
N-((1-(6-Hydroxyhexyl)-1H-1,2,3-triazol-4-yl)methyl)-4-sulfamoylbenzamide;
N-((1-((1S,2S)-2-(Cinnamyloxy)-1,2-diphenylethyl)-1H-1,2,3-triazol-4-yl)methyl)-4-sulfamoylbenzamide;
(S)—N-((1-(3-Methyl-1-oxo-1-(2-(thiophen-3-yl)ethylamino)butan-2-yl)-1H-1,2,3-triazol-4-yl)methyl)-4-sulfamoylbenzamide;
3-(1H-Imidazol-5-yl)-2-(2-(4-((4-sulfamoylbenzamido)methyl)-1H-1,2,3-triazol-1-yl)acetamido)propanoic acid;
N-((1-(2-(2,4-Dioxo-1,2-dihydroquinazolin-3(4H)-yl)ethyl)-1H-1,2,3-triazol-4-yl)methyl)-4-sulfamoylbenzamide;
N-((1-(2-(4-(3,5-Dichlorophenyl)piperazin-1-yl)-2-oxoethyl)-1H-1,2,3-triazol-4-yl)methyl)-4-sulfamoylbenzamide;
N-((1-(3-Aminopropyl)-1H-1,2,3-triazol-4-yl)methyl)-4-sulfamoylbenzamide;
(E)-N-((1-(1-(Styrylsulfonyl)piperidin-4-yl)-1H-1,2,3-triazol-4-yl)methyl)-4-sulfamoylbenzamide;
(E)-N-((1-(1-Cinnamoylpiperidin-4-yl)-1H-1,2,3-triazol-4-yl)methyl)-4-sulfamoylbenzamide;

(S)-3-Methyl-2-(4-((4-sulfamoylbenzamido)methyl)-1H-1,2,3-triazol-1-yl)butanoic acid;
2-(4-((4-Sulfamoylbenzamido)methyl)-1H-1,2,3-triazol-1-yl)dodecanoic acid;
N-((1-(2-(1,2-Dihydroxyethyl)-4,5-dihydroxytetrahydrofuran-3-yl)-1H-1,2,3-triazol-4-yl)methyl)-4-sulfamoylbenzamide;
6-((1-(2-Morpholinoethyl)-1H-1,2,3-triazol-4-yl)methoxy)benzo[d]thiazole-2-sulfonamide;
(S)—N-(4-Methylpyridin-2-yl)-3-phenyl-2-(4-((2-sulfamoylbenzo[d]thiazol-6-yloxy)methyl)-1H-1,2,3-triazol-1-yl)propanamide;
N-Morpholino-3-(4-((2-sulfamoylbenzo[d]thiazol-6-yloxy)methyl)-1H-1,2,3-triazol-1-yl)benzamide;
(S)—N-Benzyl-4-methyl-2-(4-((2-sulfamoylbenzo[d]thiazol-6-yloxy)methyl)-1H-1,2,3-triazol-1-yl)pentanamide;
6-((1-((2R)-3-Methyl-1-(3-methylpiperidin-1-yl)-1-oxobutan-2-yl)-1H-1,2,3-triazol-4-yl)methoxy)benzo[d]thiazole-2-sulfonamide;
(S)—N-(2,5-Dimethylbenzyl)-3-phenyl-2-(4-((2-sulfamoylbenzo[d]thiazol-6-yloxy)methyl)-1H-1,2,3-triazol-1-yl)propanamide;
(S)—N-Cyclohexyl-3-methyl-2-(4-((2-sulfamoylbenzo[d]thiazol-6-yloxy)methyl)-1H-1,2,3-triazol-1-yl)butanamide;
(S)—N-Benzyl-3-methyl-2-(4-((2-sulfamoylbenzo[d]thiazol-6-yloxy)methyl)-1H-1,2,3-triazol-1-yl)butanamide;
4-(3-Methoxy-3-oxo-2-(4-((2-sulfamoylbenzo[d]thiazol-6-yloxy)methyl)-1H-1,2,3-triazol-1-yl)propyl)benzoic acid;
Propyl 4-(2-(4-((2-sulfamoylbenzo[d]thiazol-6-yloxy)methyl)-1H-1,2,3-triazol-1-yl)acetamido)benzoate;
6-((1-(2-(3,5-Di-tert-butyl-4-hydroxyphenyl)-2-oxoethyl)-1H-1,2,3-triazol-4-yl)methoxy)benzo[d]thiazole-2-sulfonamide;
(R)—N-(Biphenyl-4-yl)-3-methyl-2-(4-((2-sulfamoylbenzo[d]thiazol-6-yloxy)methyl)-1H-1,2,3-triazol-1-yl)butanamide;
6-((1-(4-((1S,2R)-1,2-Dihydroxyoctyl)benzyl)-1H-1,2,3-triazol-4-yl)methoxy)benzo[d]thiazole-2-sulfonamide;
6-((1-(7-Chloroquinolin-4-yl)-1H-1,2,3-triazol-4-yl)methoxy)benzo[d]thiazole-2-sulfonamide;
6-((1-(6-Hydroxyhexyl)-1H-1,2,3-triazol-4-yl)methoxy)benzo[d]thiazole-2-sulfonamide;
6-((1-((1S,2S)-2-(Cinnamyloxy)-1,2-diphenylethyl)-1H-1,2,3-triazol-4-yl)methoxy)benzo[d]thiazole-2-sulfonamide;
(S)-3-Methyl-2-(4-((2-sulfamoylbenzo[d]thiazol-6-yloxy)methyl)-1H-1,2,3-triazol-1-yl)-N-(2-(thiophen-3-yl)ethyl)butanamide;
6-((1-(2-(2,4-Dioxo-1,2-dihydroquinazolin-3(4H)-yl)ethyl)-1H-1,2,3-triazol-4-yl)methoxy)benzo[d]thiazole-2-sulfonamide;
6-((1-(2-(4-(3,5-Dichlorophenyl)piperazin-1-yl)-2-oxoethyl)-1H-1,2,3-triazol-4-yl)methoxy)benzo[d]thiazole-2-sulfonamide;
(E)-6-((1-(1-(Styrylsulfonyl)piperidin-4-yl)-1H-1,2,3-triazol-4-yl)methoxy)benzo[d]thiazole-2-sulfonamide;
(E)-6-((1-(1-Cinnamoylpiperidin-4-yl)-1H-1,2,3-triazol-4-yl)methoxy)benzo[d]thiazole-2-sulfonamide;
4-(1-((2R)-3-Methyl-1-(3-methylpiperidin-1-yl)-1-oxobutan-2-yl)-1H-1,2,3-triazol-4-yl)benzenesulfonamide;
(S)—N-(2,5-Difluorobenzyl)-3-methyl-2-(4-(4-sulfamoylphenyl)-1H-1,2,3-triazol-1-yl)butanamide;
(S)—N-(3-Fluoro-4-methylbenzyl)-3-methyl-2-(4-(4-sulfamoylphenyl)-1H-1,2,3-triazol-1-yl)butanamide;
(S)—N-Benzyl-3-methyl-2-(4-(4-sulfamoylphenyl)-1H-1,2,3-triazol-1-yl)butanamide;
(S)-3-Methyl-2-(4-(4-sulfamoylphenyl)-1H-1,2,3-triazol-1-yl)butanoic acid;
(S)-3-Methyl-2-(4-(4-sulfamoylphenyl)-1H-1,2,3-triazol-1-yl)-N-(2-(thiophen-3-yl)ethyl)butanamide;
(S)—N-(4-Fluorobenzyl)-3-methyl-2-(4-(4-sulfamoylphenyl)-1H-1,2,3-triazol-1-yl)butanamide;
(S)—N-Benzyl-N,3-dimethyl-2-(4-(4-sulfamoylphenyl)-1H-1,2,3-triazol-1-yl)butanamide;
(S)-3-Methyl-2-(4-(4-sulfamoylphenyl)-1H-1,2,3-triazol-1-yl)-N-(4-(trifluoromethyl)benzyl)butanamide;
(S)-4-(1-(3-Methyl-1-oxo-1-(4-(pyridin-2-yl)piperazin-1-yl)butan-2-yl)-1H-1,2,3-triazol-4-yl)benzenesulfonamide;
(R)-Ethyl 2-((S)-3-methyl-2-(4-(4-sulfamoylphenyl)-1H-1,2,3-triazol-1-yl)butanamido)-3-phenylpropanoate;
(S)-Ethyl 3-methyl-2-((S)-3-methyl-2-(4-(4-sulfamoylphenyl)-1H-1,2,3-triazol-1-yl)butanamido)butanoate;
(S)-Methyl 2-((S)-3-methyl-2-(4-(4-sulfamoylphenyl)-1H-1,2,3-triazol-1-yl)butanamido)propanoate;
(S)-3-Methyl-N-(pyridin-2-ylmethyl)-2-(4-(4-sulfamoylphenyl)-1H-1,2,3-triazol-1-yl)butanamide;
(S)—N-Cyclohexyl-3-methyl-2-(4-(4-sulfamoylphenyl)-1H-1,2,3-triazol-1-yl)butanamide;
(S)—N-(Cyclopropylmethyl)-3-methyl-2-(4-(4-sulfamoylphenyl)-1H-1,2,3-triazol-1-yl)butanamide;
(S)—N-(3-Hydroxypropyl)-3-methyl-2-(4-(4-sulfamoylphenyl)-1H-1,2,3-triazol-1-yl)butanamide;
(S)-3-Methyl-N-((5-methyl-3-phenylisoxazol-4-yl)methyl)-2-(4-(4-sulfamoylphenyl)-1H-1,2,3-triazol-1-yl)butanamide;
(S)-Ethyl 3-(N-(furan-2-ylmethyl)-3-methyl-2-(4-(4-sulfamoylphenyl)-1H-1,2,3-triazol-1-yl)butanamido)propanoate;
(S)-Ethyl 1-(3-methyl-2-(4-(4-sulfamoylphenyl)-1H-1,2,3-triazol-1-yl)butanoyl)piperidine-4-carboxylate;
(S)-4-(1-(1-(4-(2-Hydroxyethyl)piperazin-1-yl)-3-methyl-1-oxobutan-2-yl)-1H-1,2,3-triazol-4-yl)benzenesulfonamide;
(S)—N-((1R,2S)-2-Hydroxy-2,3-dihydro-1H-inden-1-yl)-3-methyl-2-(4-(4-sulfamoylphenyl)-1H-1,2,3-triazol-1-yl)butanamide;
(2S)—N-((2,3-Dihydrobenzo[b][1,4]dioxin-2-yl)methyl)-3-methyl-2-(4-(4-sulfamoylphenyl)-1H-1,2,3-triazol-1-yl)butanamide;
(S)-4-(1-(3-Methyl-1-oxo-1-(4-(pyrrolidin-1-yl)piperidin-1-yl)butan-2-yl)-1H-1,2,3-triazol-4-yl)benzenesulfonamide;
(S)-3-Methyl-N-((1-methyl-1H-benzo[d]imidazol-2-yl)methyl)-2-(4-(4-sulfamoylphenyl)-1H-1,2,3-triazol-1-yl)butanamide;
(S)-4-(1-(3-Methyl-1-oxo-1-(4-(pyrimidin-2-yl)piperazin-1-yl)butan-2-yl)-1H-1,2,3-triazol-4-yl)benzenesulfonamide;
(S)—N-(2-(4-Benzylpiperazin-1-yl)ethyl)-3-methyl-2-(4-(4-sulfamoylphenyl)-1H-1,2,3-triazol-1-yl)butanamide;
(S)-2-Fluoro-N,N-dimethyl-N-((5-((3-methyl-2-(4-(4-sulfamoylphenyl)-1H-1,2,3-triazol-1-yl)butanamido)methyl)furan-2-yl)methyl)ethanaminium bromide;
(S)—N-(4-Fluorobenzyl)-3-phenyl-2-(4-(4-sulfamoylphenyl)-1H-1,2,3-triazol-1-yl)propanamide;
(S)—N-Benzyl-N-methyl-3-phenyl-2-(4-(4-sulfamoylphenyl)-1H-1,2,3-triazol-1-yl)propanamide;
(S)—N-(2-((5-((Dimethylamino)methyl)furan-2-yl)methylthio)ethyl)-3-phenyl-2-(4-(4-sulfamoylphenyl)-1H-1,2,3-triazol-1-yl)propanamide;

(S)-4-(1-(1-Oxo-3-phenyl-1-(4-(pyrimidin-2-yl)piperazin-1-yl)propan-2-yl)-1H-1,2,3-triazol-4-yl)benzenesulfonamide;
(S)-3-Phenyl-N-((5-(pyridin-2-yl)thiophen-2-yl)methyl)-2-(4-(4-sulfamoylphenyl)-1H-1,2,3-triazol-1-yl)propanamide;
4-(1-((S)-1-((R)-2-(Hydroxymethyl)pyrrolidin-1-yl)-1-oxo-3-phenylpropan-2-yl)-1H-1,2,3-triazol-4-yl)benzenesulfonamide;
(S)-4-(1-(1-Oxo-3-phenyl-1-(4-(pyridin-2-yl)piperazin-1-yl)propan-2-yl)-1H-1,2,3-triazol-4-yl)benzenesulfonamide;
(R)-Ethyl 3-phenyl-2-((S)-3-phenyl-2-(4-(4-sulfamoylphenyl)-1H-1,2,3-triazol-1-yl)propanamido)propanoate;
(S)-Ethyl 3-methyl-2-((S)-3-phenyl-2-(4-(4-sulfamoylphenyl)-1H-1,2,3-triazol-1-yl)propanamido)butanoate;
(S)-Methyl 2-((S)-3-phenyl-2-(4-(4-sulfamoylphenyl)-1H-1,2,3-triazol-1-yl)propanamido)propanoate;
(S)-3-Phenyl-N-(pyridin-2-ylmethyl)-2-(4-(4-sulfamoylphenyl)-1H-1,2,3-triazol-1-yl)propanamide;
(S)—N-Cyclohexyl-3-phenyl-2-(4-(4-sulfamoylphenyl)-1H-1,2,3-triazol-1-yl)propanamide;
(S)—N-(Cyclopropylmethyl)-3-phenyl-2-(4-(4-sulfamoylphenyl)-1H-1,2,3-triazol-1-yl)propanamide;
(S)—N-(3-Hydroxypropyl)-3-phenyl-2-(4-(4-sulfamoylphenyl)-1H-1,2,3-triazol-1-yl)propanamide;
(S)—N-((5-Methyl-3-phenylisoxazol-4-yl)methyl)-3-phenyl-2-(4-(4-sulfamoylphenyl)-1H-1,2,3-triazol-1-yl)propanamide;
(S)-Ethyl 3-(N-(furan-2-ylmethyl)-3-phenyl-2-(4-(4-sulfamoylphenyl)-1H-1,2,3-triazol-1-yl)propanamido)propanoate;
(S)-Ethyl 1-(3-phenyl-2-(4-(4-sulfamoylphenyl)-1H-1,2,3-triazol-1-yl)propanoyl)piperidine-4-carboxylate;
(S)-4-(1-(1-(4-(2-Hydroxyethyl)piperazin-1-yl)-1-oxo-3-phenylpropan-2-yl)-1H-1,2,3-triazol-4-yl)benzenesulfonamide;
(S)—N-((1R,2S)-2-Hydroxy-2,3-dihydro-1H-inden-1-yl)-3-phenyl-2-(4-(4-sulfamoylphenyl)-1H-1,2,3-triazol-1-yl)propanamide;
(2S)—N-((2,3-Dihydrobenzo[b][1,4]dioxin-2-yl)methyl)-3-phenyl-2-(4-(4-sulfamoylphenyl)-1H-1,2,3-triazol-1-yl)propanamide;
(S)-4-(1-(1-Oxo-3-phenyl-1-(4-(pyrrolidin-1-yl)piperidin-1-yl)propan-2-yl)-1H-1,2,3-triazol-4-yl)benzenesulfonamide;
(S)—N-((1-Methyl-1H-benzo[d]imidazol-2-yl)methyl)-3-phenyl-2-(4-(4-sulfamoylphenyl)-1H-1,2,3-triazol-1-yl)propanamide;
(S)—N-(2-(4-Benzylpiperazin-1-yl)ethyl)-3-phenyl-2-(4-(4-sulfamoylphenyl)-1H-1,2,3-triazol-1-yl)propanamide;
(S)—N-(4-Fluorobenzyl)-3-methyl-2-(4-((2-sulfamoylbenzo[d]thiazol-6-yloxy)methyl)-1H-1,2,3-triazol-1-yl)butanamide;
(S)—N-Benzyl-N,3-dimethyl-2-(4-((2-sulfamoylbenzo[d]thiazol-6-yloxy)methyl)-1H-1,2,3-triazol-1-yl)butanamide;
(S)—N-(2-((5-((Dimethylamino)methyl)furan-2-yl)methylthio)ethyl)-3-methyl-2-(4-((2-sulfamoylbenzo[d]thiazol-6-yloxy)methyl)-1H-1,2,3-triazol-1-yl)butanamide;
(S)-6-((1-(3-Methyl-1-oxo-1-(4-(pyrimidin-2-yl)piperazin-1-yl)butan-2-yl)-1H-1,2,3-triazol-4-yl)methoxy)benzo[d]thiazole-2-sulfonamide;
(S)-3-Methyl-N-((5-(pyridin-2-yl)thiophen-2-yl)methyl)-2-(4-((2-sulfamoylbenzo[d]thiazol-6-yloxy)methyl)-1H-1,2,3-triazol-1-yl)butanamide;
6-((1-((S)-1-((R)-2-(Hydroxymethyl)pyrrolidin-1-yl)-3-methyl-1-oxobutan-2-yl)-1H-1,2,3-triazol-4-yl)methoxy)benzo[d]thiazole-2-sulfonamide;
(S)-6-((1-(3-Methyl-1-oxo-1-(4-(pyridin-2-yl)piperazin-1-yl)butan-2-yl)-1H-1,2,3-triazol-4-yl)methoxy)benzo[d]thiazole-2-sulfonamide;
(S)-Ethyl 2-((S)-3-methyl-2-(4-((2-sulfamoylbenzo[d]thiazol-6-yloxy)methyl)-1H-1,2,3-triazol-1-yl)butanamido)-3-phenylpropanoate;
(S)-Ethyl 3-methyl-2-((S)-3-methyl-2-(4-((2-sulfamoylbenzo[d]thiazol-6-yloxy)methyl)-1H-1,2,3-triazol-1-yl)butanamido)butanoate;
(S)-Methyl 2-((S)-3-methyl-2-(4-((2-sulfamoylbenzo[d]thiazol-6-yloxy)methyl)-1H-1,2,3-triazol-1-yl)butanamido)propanoate;
(S)-3-Methyl-N-(pyridin-2-ylmethyl)-2-(4-((2-sulfamoylbenzo[d]thiazol-6-yloxy)methyl)-1H-1,2,3-triazol-1-yl)butanamide;
(S)—N-Cyclohexyl-3-methyl-2-(4-((2-sulfamoylbenzo[d]thiazol-6-yloxy)methyl)-1H-1,2,3-triazol-1-yl)butanamide;
(S)—N-(Cyclopropylmethyl)-3-methyl-2-(4-((2-sulfamoylbenzo[d]thiazol-6-yloxy)methyl)-1H-1,2,3-triazol-1-yl)butanamide;
(S)—N-(3-Hydroxypropyl)-3-methyl-2-(4-((2-sulfamoylbenzo[d]thiazol-6-yloxy)methyl)-1H-1,2,3-triazol-1-yl)butanamide;
(S)-3-Methyl-N-((5-methyl-3-phenylisoxazol-4-yl)methyl)-2-(4-((2-sulfamoylbenzo[d]thiazol-6-yloxy)methyl)-1H-1,2,3-triazol-1-yl)butanamide;
(S)-6-((1-(1-(4-(2-Hydroxyethyl)piperazin-1-yl)-3-methyl-1-oxobutan-2-yl)-1H-1,2,3-triazol-4-yl)methoxy)benzo[d]thiazole-2-sulfonamide;
(S)—N-((1R,2S)-2-Hydroxy-2,3-dihydro-1H-inden-1-yl)-3-methyl-2-(4-((2-sulfamoylbenzo[d]thiazol-6-yloxy)methyl)-1H-1,2,3-triazol-1-yl)butanamide;
(S)-6-((1-(3-Methyl-1-oxo-1-(4-(pyrrolidin-1-yl)piperidin-1-yl)butan-2-yl)-1H-1,2,3-triazol-4-yl)methoxy)benzo[d]thiazole-2-sulfonamide;
(S)—N-(2-(4-Benzylpiperazin-1-yl)ethyl)-3-methyl-2-(4-((2-sulfamoylbenzo[d]thiazol-6-yloxy)methyl)-1H-1,2,3-triazol-1-yl)butanamide;
(S)-Ethyl 3-(1H-indol-3-yl)-2-((S)-3-methyl-2-(4-((2-sulfamoylbenzo[d]thiazol-6-yloxy)methyl)-1H-1,2,3-triazol-1-yl)butanamido)propanoate;
(S)—N-(4-Fluorobenzyl)-3-phenyl-2-(4-((2-sulfamoylbenzo[d]thiazol-6-yloxy)methyl)-1H-1,2,3-triazol-1-yl)propanamide;
(S)—N-Benzyl-N-methyl-3-phenyl-2-(4-((2-sulfamoylbenzo[d]thiazol-6-yloxy)methyl)-1H-1,2,3-triazol-1-yl)propanamide;
(S)—N-(2-((5-((Dimethylamino)methyl)furan-2-yl)methylthio)ethyl)-3-phenyl-2-(4-((2-sulfamoylbenzo[d]thiazol-6-yloxy)methyl)-1H-1,2,3-triazol-1-yl)propanamide;
(S)-6-((1-(1-Oxo-3-phenyl-1-(4-(pyrimidin-2-yl)piperazin-1-yl)propan-2-yl)-1H-1,2,3-triazol-4-yl)methoxy)benzo[d]thiazole-2-sulfonamide;
(S)-3-Phenyl-N-((5-(pyridin-2-yl)thiophen-2-yl)methyl)-2-(4-((2-sulfamoylbenzo[d]thiazol-6-yloxy)methyl)-1H-1,2,3-triazol-1-yl)propanamide;
6-((1-((S)-1-((R)-2-(Hydroxymethyl)pyrrolidin-1-yl)-1-oxo-3-phenylpropan-2-yl)-1H-1,2,3-triazol-4-yl)methoxy)benzo[d]thiazole-2-sulfonamide;
(S)-6-((1-(1-Oxo-3-phenyl-1-(4-(pyridin-2-yl)piperazin-1-yl)propan-2-yl)-1H-1,2,3-triazol-4-yl)methoxy)benzo[d]thiazole-2-sulfonamide;

(R)-ethyl 3-Phenyl-2-((S)-3-phenyl-2-(4-((2-sulfamoyl-benzo[d]thiazol-6-yloxy)methyl)-1H-1,2,3-triazol-1-yl)propanamido)propanoate;

(S)-Ethyl 3-methyl-2-((S)-3-phenyl-2-(4-((2-sulfamoyl-benzo[d]thiazol-6-yloxy)methyl)-1H-1,2,3-triazol-1-yl)propanamido)butanoate;

(S)-3-Phenyl-N-(pyridin-2-ylmethyl)-2-(4-((2-sulfamoyl-benzo[d]thiazol-6-yloxy)methyl)-1H-1,2,3-triazol-1-yl)propanamide;

(S)—N-Cyclohexyl-3-phenyl-2-(4-((2-sulfamoylbenzo[d]thiazol-6-yloxy)methyl)-1H-1,2,3-triazol-1-yl)propanamide;

(S)—N-(Cyclopropylmethyl)-3-phenyl-2-(4-((2-sulfamoyl-benzo[d]thiazol-6-yloxy)methyl)-1H-1,2,3-triazol-1-yl)propanamide;

(S)—N-(3-Hydroxypropyl)-3-phenyl-2-(4-((2-sulfamoyl-benzo[d]thiazol-6-yloxy)methyl)-1H-1,2,3-triazol-1-yl)propanamide;

(S)-6-((1-(1-(4-(2-Hydroxyethyl)piperazin-1-yl)-1-oxo-3-phenylpropan-2-yl)-1H-1,2,3-triazol-4-yl)methoxy)benzo[d]thiazole-2-sulfonamide;

(S)—N-((1R,2S)-2-Hydroxy-2,3-dihydro-1H-inden-1-yl)-3-phenyl-2-(4-((2-sulfamoylbenzo[d]thiazol-6-yloxy)methyl)-1H-1,2,3-triazol-1-yl)propanamide;

(2S)—N-((2,3-Dihydrobenzo[b][1,4]dioxin-2-yl)methyl)-3-phenyl-2-(4-((2-sulfamoylbenzo[d]thiazol-6-yloxy)methyl)-1H-1,2,3-triazol-1-yl)propanamide;

(S)-6-((1-(1-(4-(2-Hydroxyethyl)piperazin-1-yl)-1-oxo-3-phenylpropan-2-yl)-1H-1,2,3-triazol-4-yl)methoxy)benzo[d]thiazole-2-sulfonamide;

(S)—N-((1R,2S)-2-Hydroxy-2,3-dihydro-1H-inden-1-yl)-3-phenyl-2-(4-((2-sulfamoylbenzo[d]thiazol-6-yloxy)methyl)-1H-1,2,3-triazol-1-yl)propanamide;

(S)-6-((1-(1-(4-(2-Hydroxyethyl)piperazin-1-yl)-1-oxo-3-phenylpropan-2-yl)-1H-1,2,3-triazol-4-yl)methoxy)benzo[d]thiazole-2-sulfonamide;

(S)—N-((1R,2S)-2-Hydroxy-2,3-dihydro-1H-inden-1-yl)-3-phenyl-2-(4-((2-sulfamoylbenzo[d]thiazol-6-yloxy)methyl)-1H-1,2,3-triazol-1-yl)propanamide;

(S)—N,N,N-Trimethyl-2-oxo-2-(6-oxo-5-(4-((2-sulfamoyl-benzo[d]thiazol-6-yloxy)methyl)-1H-1,2,3-triazol-1-yl)-6-(4-(trifluoromethyl)benzylamino)hexylamino)ethanaminium;

(S)-3,10-Dioxo-4-(4-((2-sulfamoylbenzo[d]thiazol-6-yloxy)methyl)-1H-1,2,3-triazol-1-yl)-1-(4-(trifluoromethyl)phenyl)-13,16,19,22,25-pentaoxa-2,9-diazaoctacosan-28-oic acid;

(S)-4-Oxo-4-(6-oxo-5-(4-((2-sulfamoylbenzo[d]thiazol-6-yloxy)methyl)-1H-1,2,3-triazol-1-yl)-6-(4-(trifluoromethyl)benzylamino)hexylamino)butanoic acid;

(S)-4-(6-(4-(Ethoxycarbonyl)cyclohexyl)-6-oxo-5-(4-((2-sulfamoylbenzo[d]thiazol-6-yloxy)methyl)-1H-1,2,3-triazol-1-yl)hexylamino)-4-oxobutanoic acid; and (S)-6-((S)-2-Amino-3-hydroxypropanamido)-2-(4-((2-sulfamoylbenzo[d]thiazol-6-yloxy)methyl)-1H-1,2,3-triazol-1-yl)-N-(4-(Trifluoromethyl)benzyl)hexanamide hydrochloride.

The more preferred compounds include the following, as well as their stereoisomers, tautomers, salts, and mixtures thereof:

(S)—N-(4-Methylpyridin-2-yl)-3-phenyl-2-(4-(4-sulfamoylphenyl)-1H-1,2,3-triazol-1-yl)propanamide 4-(1-((2-Thioxobenzo[d]thiazol-3(2H)-yl)methyl)-1H-1,2,3-triazol-4-yl)benzenesulfonamide 4-(1-((1H-Benzo[d][1,2,3]triazol-1-yl)methyl)-1H-1,2,3-triazol-4-yl)benzenesulfonamide (S)—N-(2,5-Difluorobenzyl)-3-methyl-2-(4-((2-sulfamoyl-benzo[d]thiazol-6-yloxy)methyl)-1H-1,2,3-triazol-1-yl)butanamide 6-((1-(3-Bromobenzyl)-1H-1,2,3-triazol-4-yl)methoxy)benzo[d]thiazole-2-sulfonamide (S)—N-(3-Fluoro-4-methylbenzyl)-3-methyl-2-(4-((2-sulfamoylbenzo[d]thiazol-6-yloxy)methyl)-1H-1,2,3-triazol-1-yl)butanamide Ethyl 4-((4-((2-sulfamoylbenzo[d]thiazol-6-yloxy)methyl)-1H-1,2,3-triazol-1-yl)methyl)benzoate (S)—N-(Furan-2-ylmethyl)-3-methyl-2-(4-((2-sulfamoyl-benzo[d]thiazol-6-yloxy)methyl)-1H-1,2,3-triazol-1-yl)butanamide 6-((1-((1H-Benzo[d][1,2,3]triazol-1-yl)methyl)-1H-1,2,3-triazol-4-yl)methoxy)benzo[d]thiazole-2-sulfonamide 4-((4-((2-Sulfamoylbenzo[d]thiazol-6-yloxy)methyl)-1H-1,2,3-triazol-1-yl)methyl)benzoic acid (S)-1,4-Dimethyl-2-(3-phenyl-2-(4-(4-sulfamoylphenyl)-1H-1,2,3-triazol-1-yl)propanamido)pyridinium iodide (R)-3-(Benzylthio)-2-(2-(4-((2-sulfamoylbenzo[d]thiazol-6-yloxy)methyl)-1H-1,2,3-triazol-1-yl)acetamido)propanoic acid (R)-Methyl 3-(3-(2-fluoro ethoxy)benzylthio)-2-(2-(4-((2-sulfamoylbenzo[d]thiazol-5-yloxy)methyl)-1H-1,2,3-triazol-1-yl)acetamido)propanoate (S)-1-(3-Methyl-2-(4-((2-sulfamoylbenzo[d]thiazol-6-yloxy)methyl)-1H-1,2,3-triazol-1-yl)butanoyl)piperidine-4-carboxylic acid (S)-Methyl 2-((S)-3-phenyl-2-(4-((2-sulfamoylbenzo[d]thiazol-6-yloxy)methyl)-1H-1,2,3-triazol-1-yl)propanamido)propanoate (S)-1-(3-Phenyl-2-(4-((2-sulfamoylbenzo[d]thiazol-6-yloxy)methyl)-1H-1,2,3-triazol-1-yl)propanoyl)piperidine-4-carboxylic acid (S)-Methyl 3-((S)-3-(4-(2-fluoroethoxy)phenyl)-2-(4-((2-sulfamoylbenzo[d]thiazol-6-yloxy)methyl)-1H-1,2,3-triazol-1-yl)propanamido)-3-phenylpropanoate (R)-2-Hydroxy-N,N,N-trimethyl-4-oxo-4-((S)-6-oxo-5-(4-((2-sulfamoylbenzo[d]thiazol-6-yloxy)methyl)-1H-1,2,3-triazol-1-yl)-6-(4-(trifluoromethyl)benzylamino)hexylamino)butan-1-aminium chloride.

The most preferred compounds include the following, as well as their stereoisomers, tautomers, salts, and mixtures thereof:

(S)—N-(Furan-2-ylmethyl)-3-methyl-2-(4-(4-sulfamoylphenyl)-1H-1,2,3-triazol-1-yl)butanamide (R)-Methyl 3-(benzylthio)-2-(2-(4-((2-sulfamoylbenzo[d]thiazol-6-yloxy)methyl)-1H-1,2,3-triazol-1-yl)acetamido)propanoate (R)-3-(3-(2-Fluoroethoxy)benzylthio)-2-(2-(4-((2-sulfamoylbenzo[d]thiazol-5-yloxy)methyl)-1H-1,2,3-triazol-1-yl)acetamido)propanoic acid (2S)—N-((2,3-Dihydrobenzo[b][1,4]dioxin-2-yl)methyl)-3-methyl-2-(4-((2-sulfamoylbenzo[d]thiazol-6-yloxy)methyl)-1H-1,2,3-triazol-1-yl)butanamide (S)-Methyl 2-((S)-3-methyl-2-(4-((2-sulfamoylbenzo[d]thiazol-6-yloxy)methyl)-1H-1,2,3-triazol-1-yl)butanamido)-3-(4-(trifluoromethyl)phenyl)propanoate (S)-Methyl 3-((S)-3-methyl-2-(4-((2-sulfamoylbenzo[d]thiazol-6-yloxy)methyl)-1H-1,2,3-triazol-1-yl)butanamido)-3-(4-(trifluoromethyl)phenyl)propanoate (S)-3-((S)-3-Methyl-2-(4-((2-sulfamoylbenzo[d]thiazol-6-yloxy)methyl)-1H-1,2,3-triazol-1-yl)butanamido)-3-(4-(trifluoromethyl)phenyl)propanoic acid (S)-3-Phenyl-2-(4-((2-sulfamoylbenzo[d]thiazol-6-yloxy)methyl)-1H-1,2,3-triazol-1-yl)-N-(4-(trifluoromethyl)benzyl)propanamide (S)—N-((5-Methyl-3-phenylisoxazol-4-yl)methyl)-3-phenyl-2-(4-((2-sulfamoylbenzo[d]thiazol-6-yloxy)methyl)-1H-1,2,3-triazol-1-yl)propanamide (S)-Ethyl 1-(3-phenyl-2-(4-((2-sulfamoylbenzo[d]thiazol-6-yloxy)methyl)-1H-1,2,3-triazol-1-yl)propanoyl)piperidine-4-carboxylate (2S)—N-((2,3-Dihydrobenzo[b][1,4]dioxin-2-yl)methyl)-3-phenyl-2-(4-((2-sulfamoylbenzo[d]thiazol-6-yloxy)methyl)-1H-1,2,3-triazol-1-yl)propanamide (S)-ethyl 1-(3-(4-(2-Fluoroethoxy)phenyl)-2-(4-((2-sulfamoylbenzo[d]thiazol-6-yloxy)methyl)-1H-1,2,3-triazol-1-yl)propanoyl)piperidine-4-carboxylate (S)-3-(4-(2-Fluoroethoxy)phenyl)-2-(4-((2-sulfamoylbenzo[d]thiazol-6-yloxy)methyl)-1H-1,2,3-triazol-1-yl)-N-(4-(trifluoromethyl)benzyl)propanamide (S)-1-(3-(4-(2-Fluoroethoxy)phenyl)-2-(4-((2-sulfamoylbenzo[d]thiazol-6-yloxy)methyl)-1H-1,2,3-triazol-1-yl)propanoyl)piperidine-4-carboxylic acid (S)-Methyl 2-((S)-3-(4-(2-fluoroethoxy)phenyl)-2-(4-((2-sulfamoylbenzo[d]thiazol-6-yloxy)methyl)-1H-1,2,3-triazol-1-yl)propanamido)-3-(4-(trifluoromethyl)phenyl)propanoate (S)-2-((S)-3-Methyl-2-(4-((2-sulfamoylbenzo[d]thiazol-6-yloxy)methyl)-1H-1,2,3-triazol-1-yl)butanamido)-3-(4-(trifluoromethyl)phenyl)propanoic acid (S)-2-((S)-3-(4-(2-Fluoroethoxy)phenyl)-2-(4-((2-sulfamoylbenzo[d]thiazol-6-yloxy)methyl)-1H-1,2,3-triazol-1-yl)propanamido)-3-(4-(trifluoromethyl)phenyl)propanoic acid.

(R)-2-((S)-3-(4-(2-fluoroethoxy)phenyl)-2-(4-((2-sulfamoylbenzo[d]thiazol-6-yloxy)methyl)-1H-1,2,3-triazol-1-yl)propanamido)-3-(4-(trifluoromethyl)phenyl)propanoic acid;

(2S)-2-((2S)-3-(4-(3-fluoro-2-hydroxypropoxy)phenyl)-2-(4-((2-sulfamoylbenzo[d]thiazol-6-yloxy)methyl)-1H-1,2,3-triazol-1-yl)propanamido)-3-(4-(trifluoromethyl)phenyl)propanoic acid;

(S)-3-(4-(2-fluoroethoxy)phenyl)-2-(4-((2-sulfamoylbenzo[d]thiazol-6-yloxy)methyl)-1H-1,2,3-triazol-1-yl)-N-(4-(trifluoromethoxy)benzyl)propanamide;

(S)-2-((S)-3-(4-(2-fluoroethoxy)phenyl)-2-(4-((2-sulfamoylbenzo[d]thiazol-6-yloxy)methyl)-1H-1,2,3-triazol-1-yl)propanamido)-3-(1H-indol-3-yl)propanoic acid;

(S)-2-((S)-3-(4-(2-fluoroethoxy)phenyl)-2-(4-((2-sulfamoylbenzo[d]thiazol-6-yloxy)methyl)-1H-1,2,3-triazol-1-yl)propanamido)-3-(3-(trifluoromethyl)phenyl)propanoic acid;

(S)-3-(4-cyanophenyl)-2-((S)-3-(4-(2-fluoroethoxy)phenyl)-2-(4-((2-sulfamoylbenzo[d]thiazol-6-yloxy)methyl)-1H-1,2,3-triazol-1-yl)propanamido)propanoic acid;

(S)-methyl 3-(3-(2-fluoroethoxy)benzylthio)-2-((S)-4-hydroxy-2-(4-((2-sulfamoylbenzo[d]thiazol-6-yloxy)methyl)-1H-1,2,3-triazol-1-yl)butanamido)propanoate;

(R)-3-(3-(2-fluoroethoxy)benzylthio)-2-((R)-4-hydroxy-2-(4-((2-sulfamoylbenzo[d]thiazol-5-yloxy)methyl)-1H-1,2,3-triazol-1-yl)butanamido)propanoic acid;

(R)-3-(3-(2-fluoroethoxy)benzylthio)-2-((S)-4-hydroxy-2-(4-((2-sulfamoylbenzo[d]thiazol-5-yloxy)methyl)-1H-1,2,3-triazol-1-yl)butanamido)propanoic acid;

(S)-2-((S)-3-(4-(((4S,5R)-5-(fluoromethyl)-2,2-dimethyl-1,3-dioxolan-4-yl)methoxy)phenyl)-2-(4-((2-sulfamoylbenzo[d]thiazol-6-yloxy)methyl)-1H-1,2,3-triazol-1-yl)propanamido)-3-(4-(trifluoromethyl)phenyl)propanoic acid;

(S)-2-((R)-3-(4-(((4S,5R)-5-(fluoromethyl)-2,2-dimethyl-1,3-dioxolan-4-yl)methoxy)phenyl)-2-(4-((2-sulfamoylbenzo[d]thiazol-6-yloxy)methyl)-1H-1,2,3-triazol-1-yl)propanamido)-3-(4-(trifluoromethyl)phenyl)propanoic acid;

3-(3-(2-fluoroethoxy)benzylthio)-2-(4-hydroxy-2-(4-((2-sulfamoylbenzo[d]thiazol-5-yloxy)methyl)-1H-1,2,3-triazol-1-yl)butanamido)propanoic acid;

(S)-2-((S)-3-(4-((2S,3R)-4-fluoro-2,3-dihydroxybutoxy)phenyl)-2-(4-((2-sulfamoylbenzo[d]thiazol-6-yloxy)methyl)-1H-1,2,3-triazol-1-yl)propanamido)-3-(4-(trifluoromethyl)phenyl)propanoic acid;

(S)-2-((R)-3-(4-((2S,3R)-4-fluoro-2,3-dihydroxybutoxy)phenyl)-2-(4-((2-sulfamoylbenzo[d]thiazol-6-yloxy)methyl)-1H-1,2,3-triazol-1-yl)propanamido)-3-(4-(trifluoromethyl)phenyl)propanoic acid;

(2R)-3-(3-((1-(1-fluoro-3-hydroxypropan-2-yl)-1H-1,2,3-triazol-4-yl)methoxy)benzylthio)-2-(2-(4-((2-sulfamoylbenzo[d]thiazol-5-yloxy)methyl)-1H-1,2,3-triazol-1-yl)acetamido)propanoic acid;

(2R)-3-(3-(2-fluoroethoxy)benzylsulfinyl)-2-(2-(4-((2-sulfamoylbenzo[d]thiazol-5-yloxy)methyl)-1H-1,2,3-triazol-1-yl)acetamido)propanoic acid;

(S)-3-(3-(2-fluoroethoxy)benzyloxy)-2-(2-(4-((2-sulfamoylbenzo[d]thiazol-5-yloxy)methyl)-1H-1,2,3-triazol-1-yl)acetamido)propanoic acid;

(2S)-3-(3-(3-fluoro-2-hydroxypropoxy)benzyloxy)-2-(2-(4-((2-sulfamoylbenzo[d]thiazol-5-yloxy)methyl)-1H-1,2,3-triazol-1-yl)acetamido)propanoic acid;

(2S)-3-(4-(3-fluoro-2-hydroxypropoxy)phenyl)-2-(R)-3-methyl-2-(4-((2-sulfamoylbenzo[d]thiazol-6-yloxy)methyl)-1H-1,2,3-triazol-1-yl)butanamido)propanoic acid;

(2S)-3-(4-(3-fluoro-2-hydroxypropoxy)phenyl)-2-(R)-3-methyl-2-(4-((2-sulfamoylbenzo[d]thiazol-6-yloxy)methyl)-1H-1,2,3-triazol-1-yl)butanamido)propanoic acid;

(S)-3-(4-(2-fluoroethoxy)phenyl)-2-((R)-3-methyl-2-(4-((2-sulfamoylbenzo[d]thiazol-6-yloxy)methyl)-1H-1,2,3-triazol-1-yl)butanamido)propanoic acid;

(S)-3-(4-(2-fluoroethoxy)phenyl)-2-((R)-3-methyl-2-(4-((2-sulfamoylbenzo[d]thiazol-6-yloxy)methyl)-1H-1,2,3-triazol-1-yl)butanamido)propanoic acid;

(S)-3-(4-(2-fluoroethoxy)phenyl)-2-(2-(4-((2-sulfamoylbenzo[d]thiazol-6-yloxy)methyl)-1H-1,2,3-triazol-1-yl)acetamido)propanoic acid;

(2S)-3-(4-(3-fluoro-2-hydroxypropoxy)phenyl)-2-(2-(4-((2-sulfamoylbenzo[d]thiazol-6-yloxy)methyl)-1H-1,2,3-triazol-1-yl)acetamido)propanoic acid;

(2S)-3-(4-(1-fluoro-3-hydroxypropan-2-yloxy)phenyl)-2-((S)-3-methyl-2-(4-((2-sulfamoylbenzo[d]thiazol-6-yloxy)methyl)-1H-1,2,3-triazol-1-yl)butanamido)propanoic acid;

(2S)-3-(4-(1-fluoro-3-hydroxypropan-2-yloxy)phenyl)-2-((R)-3-methyl-2-(4-((2-sulfamoylbenzo[d]thiazol-6-yloxy)methyl)-1H-1,2,3-triazol-1-yl)butanamido)propanoic acid.

Utility, Testing, and Administration

Utility

The radiolabeled triazole compounds can be used as imaging agents to image CA-IX expression in a subject.

In one aspect, the radiolabeled triazole compounds have a high affinity and specificity to CA-IX. As reflected in $K_d$ values, lead compounds bind to CA-IX at the nanomolar level. In addition, the CA-IX-based and CA-II-based assay determined that lead compounds are good inhibitors for CA-IX as well as for CA-II. The selectivity between CA-IX and CA-II is about 10-fold. The red blood cell membrane permeability assay indicated that the lead compounds exhibit minimal penetration of the red blood cell membrane, and thus the lead compounds are unlikely to participate in a CA-II cross-reaction.

In addition, the present invention relates to the use of radiolabeled triazole compounds for detecting CA-IX expression in vivo. In particular, the present methods for detecting CA-IX expression in vivo utilize PET, where the imaging tracer is a radiolabeled triazole compound of the present invention. PET is useful for visualizing a subject's condition in relation to various tissues, especially bone and soft tissues, such as cartilage, synovium and organs. Specific organs and tissues including, but not limited to, the brain, heart, kidney, liver, spleen, colon, spinal cord, lymph nodes, or any combination thereof, of the subject. By using PET, a computer tomogram can be obtained of the desired organ tissue, enabling the localization and quantification of CA-IX.

The radiolabeled triazole compounds of the present invention can be used to detect and/or quantitatively measure CA-IX levels in a subject, including humans. The radiolabeled triazole compounds can also be used to measure and/or detect CA-IX in CA-IX associated diseases, disorders and conditions, including, but not limited to, a preneoplastic/neoplastic disease, including carcinomas, such as, colorectal, ovarian, uterine, cervical, endometrial, squamous cell and adenosquamous carcinomas; head and neck cancers; mesodermal tumors, such as, neuroblastomas and retinoblastomas; sarcomas, such as osteosarcomas; and melanomas. Of particular interest are cancers of the breast, of the gastrointestinal tract, of the stomach including esophagus, of the colon, of the kidney, of the prostate, of the liver, of the urinary tract including bladder, of the lung, and of the head and neck. Also of particular interest are gynecological cancers including ovarian, uterine, cervical, vaginal, vulval and endometrial cancers, particularly ovarian, uterine cervical and endometrial cancers. Furthermore, the radiolabeled triazole compounds can be used to screen for individuals to determine the efficacy of CA-IX inhibitors administered to treat a disease or disorder that involve the upregulation of CA-IX expression.

Administration of the Radiolabeled Triazole Compounds

As described above, the radiolabeled triazole compounds are useful for imaging a CA-IX subject. When administered to a subject, the radiolabeled triazole compounds can be administered as a component of a composition that comprises a physiologically acceptable carrier or vehicle. The present compositions, which comprise a radiolabeled triazole compound, can be administered by any convenient route, for example, by infusion, bolus injection, or by absorption through epithelial or mucocutaneous linings and can be administered together with another biologically active agent. Administration can be systemic or local. Methods of administration include, but are not limited to, intradermal, intramuscular, intraperitoneal, intravenous, subcutaneous, intranasal, sublingual, epidural, intracerebral, intravaginal, transdermal, rectal, or topical.

In one embodiment, it can be desirable to administer the radiolabeled triazole compounds locally. This can be achieved, for example, and not by way of limitation, by local infusion during surgery, by injection, by means of a catheter, by means of a suppository or enema, or by means of an implant, with said implant being of a porous, non-porous, or gelatinous material, including membranes, such as sialastic membranes, or fibers.

In another embodiment, the radiolabeled triazole compounds can be delivered in a controlled-release system or sustained-release system. The controlled-release system or sustained-release system can be placed in proximity to a target of the radiolabeled triazole compounds, e.g., the spinal column, brain, heart, kidney or gastrointestinal tract, thus requiring only a fraction of the systemic dose.

The compositions can optionally comprise a suitable amount of a physiologically acceptable excipient so as to provide the form for proper administration to the subject. Such physiologically acceptable excipients can be liquids, such as water for injection, bactereostatic water for injection, or sterile water for injection. The physiologically acceptable excipients are sterile when administered to a subject. Water is a particularly useful excipient when the radiolabeled triazole compound is administered intravenously. Saline solutions can also be employed as liquid excipients, particularly for injectable solutions. The pharmaceutical excipients can be saline, gum acacia, starch, glucose, lactose, glycerol, ethanol and the like.

The radiolabeled triazole compounds can be formulated for intravenous administration. Typically, compositions for intravenous administration comprise sterile isotonic aqueous buffer. Where the radiolabeled triazole compounds are administered by injection, an ampule of sterile water for injection or saline can be provided so that the ingredients can be mixed prior to administration. Where the radiolabeled triazole compounds are to be administered by infusion, they can be dispensed, for example, with an infusion bottle containing sterile pharmaceutical grade water or saline.

The amount of the radiolabeled triazole compound that is effective as an imaging agent to detect CA-IX in a subject can be determined using standard clinical and nuclear medicine techniques. In addition, in vitro or in vivo testing can optionally be employed to help identify optimal dosage ranges. The precise dose to be employed will also depend on the route of administration, the identity of the subject and the identity of the particular radionuclide being detected and should be decided according to the judgment of the practitioner and each subject's circumstances in view of published clinical studies. The radiolabeled triazole compounds will have a specific activity of >1000 Ci/mmol at the time of administration to insure a low injected mass and adequate counts for imaging.

EXAMPLES

General. CA-IX human recombinant enzyme was expressed with a C-terminal His tag in a mouse myeloma cell line, NS0 (R&D Systems Inc., catalog number 2188-CA). The human red blood cells were obtained from Research Blood Components, LLC. All absorbance measurements were performed on a SPECTRA MAX M2 plate reader at 25° C. The LC/MS analyses were performed on an Agilent 1100 series LC/MSD (SL) using a 30×2.1 mm Zorbax C8 column with a Phenomenex C18 pre-column. Compound detection was accomplished by electrospray mass spectroscopy in positive selected ion mode (LC/MS-SIM). The elution solvents were acetonitrile and water, contained 0.05% TFA. Nuclear magnetic resonance (NMR) spectra were obtained on a Bruker AMX 300 MHz spectrometer or a Varian 400. 19F NMR spectra were recorded on a Bruker AMX 282.35 MHz or a Varian 400 spectrometer. The mass spectra were recorded on an Agilent 1100 series LC/MSD with electrospray mass spectroscopic detection. Flash column chromatography was performed on Merck silica gel (40-63 µm) using the solvent system indicated. The radiochemical and chemical purities were analyzed by RP-HPLC.

General Combinatorial Library Screening Protocol for CA-IX

The CA-IX screening assay was employed for testing libraries derived from the various "anchor" molecules, using ethoxzolamide as a positive control. The assay was performed at a substrate (dansylamide, DNSA) concentration of 200 µM, and sample concentrations of 100 nM and 1000 nM, respectively. A modified competitive fluorescence-based assay (A. Jain, S. G. Huang, G. M. Whitesides, *J. Am. Chem. Soc.* 1994, 116, 5057) was used to measure CA-IX activity. The enzymatic assay was carried out in a 96-well plate. To the wells, deionized water, 40 µL of phosphate buffer (250 mM, pH 7.4), 2.4 µL of CA-IX (17 µM), and 2 µL or 20 µL of inhibitor (concentration of 100 nM or 1000 nM) were added to achieve a final volume of 180 µL. Reactions were initiated by adding 20 µL DNSA (200 µM) to each well and the plate was incubated at 25° C. for 1 hour. The fluorescence intensities from each well of the plate were then read at 460 nm using a plate reader with an excitation wavelength of 290 nm.

General Procedure of Binding Affinity ($K_d$) Determination for CA-IX Inhibitors The fluorescence competition assay developed by Whitesides et al. (A. Jain, S. G. Huang, G. M. Whitesides, *J. Am. Chem. Soc.* 1994, 116, 5057) and J. C. Kernohan (R. F. Chen, J. C. Kernohan, *J. Biol. Chem.* 1967, 242, 5813) using DNSA as a reporting ligand that is displaced by the test compound was used for the measurement of binding affinities. The assay was based on the observation that the only fluorescence signal detected at 460 nm upon excitation at 290 nm, an absorption minimum for DNSA, was that of the DNSA.CA complex. With increasing sample concentration, the fluorescence intensity due to DNSA.CA decreases as a result of competition with the test compound, allowing the determination of dissociation constants from Scatchard plots. The latter were developed for each test compound using mass balance for calculating the concentration of CA bound to DNSA [DNSA.CA], bound to the non-fluorescent sample [CA.Inh] and free CA [CA] in solution. The $K_d$ values were determined from Scatchard plots using the equation below as described by Whitesides et al.

$$[CA.Inh]/[CA]_{tot}[Inh]=K_{11}^{inh}-K_{11}^{inh}\{[CA.Inh]+[CA.DNSA]\}/([CA]_{tot})$$

The terms [CA·DNSA], [CA.Inh], and free CA were calculated using the mass balance based on the known values for the dissociation constant of CA.DNSA and the total concentration of CA in each reaction.

General Procedure of Red Blood Cell Membrane Permeability Assay

The isolated human red blood cells were treated with or without 1 mM ethoxzolamide for 30 minutes, followed by incubation with 0.2 mM of individual compound, respectively, for 60 minutes. After the incubation, the red blood cells were washed three times to eliminate all unbound inhibitor. The cells were then lysed and centrifuged and the supernatants were analyzed by LC/MS to measure the levels of the compounds within red blood cells.

Preparation of Compounds

Equivalents (equiv) refer to molar equivalents. Volumes (vol) refer to ml to gram equivalents of the limiting reagent.

General Experimental Procedure for Phenolic Alkylation: (A)

To a round bottomed flask equipped with a magnetic stir bar, rubber septum, and argon inlet containing DMF (10 vol) was placed phenol (1 equiv). To this solution was added alkylating agent (1.1 equiv), $Cs_2CO_3$ (1.2 equiv) and the reaction was allowed to stir at 90° C. for 15 h. The reaction was then poured into water (25 vol) and extracted into EtOAc (3×20 vol). The combined organic extracts were washed with brine (25 vol), dried ($Na_2SO_4$) and concentrated in vacuo. The residue was purified over silica gel using Hexanes:EtOAc as an eluent to afford the final product.

General Experimental Procedure for Boc, THP and Ketal Deprotections: (B)

To a round bottomed flask equipped with a magnetic stir bar was placed protected material (1 equiv). To this compound was added HCl (4M solution in dioxane, 3.8 vol) and the reaction was allowed to stir at room temperature for 2 h. To this solution was added conc. HCl (0.08 vol) in MeOH (3.8 vol) and the reaction was allowed to stir at room temperature for 2 h. After the reaction was complete, the solvents were removed in vacuo to afford the final compound.

General Experimental Procedure for Coupling: (C)

To a round bottomed flask equipped with a magnetic stir bar, rubber septum, and argon inlet containing DMF (20 vol) was placed amine (1 equiv). To this solution was added the azidoacid (1 equiv), EDC (1 equiv), HOBt (1 equiv), $NaHCO_3$ or TEA (5 equiv using $NaHCO_3$ or 2 equiv using TEA) and the reaction was allowed to stir at room temperature for 15 h. The reaction was then poured into water (50 vol) and extracted into EtOAc (4×40 vol). The combined organic extracts were washed with $H_2O$ (3×40 vol) brine (50 vol), dried ($Na_2SO_4$) and concentrated in vacuo. The residue was purified over silica gel using Hexanes:EtOAc as the eluent to afford the final coupled product.

General Experimental Procedure of Tosylation of Alcohol: (D)

To a round bottomed flask equipped with a magnetic stir bar containing DCM (17 vol) was placed alcohol (1 equiv) cooled to 0° C. To this solution was added $Ts_2O$ (1.5 equiv), $Et_3N$ (3 equiv) and the reaction was allowed to stir at room temperature for 1 h. After the reaction was complete, DCM was removed in vacuo. The residue was purified over silica gel using Hexanes:EtOAc as the eluent to afford the final tosylate.

General Experimental Procedure for Click Reaction Between Azides and Acetylenes Using CuI and DIPEA: (E)

To a round bottomed flask equipped with a magnetic stir bar, rubber septum, and argon inlet containing THF (29 vol) was placed azide (1 equiv). To this solution was added acetylene (1 equiv), CuI (0.2 equiv), DIPEA (0.4 equiv) and the reaction was allowed to stir at room temperature for until deemed complete by LCMS. After the reaction was complete, the solvents were removed in vacuo. The residue was purified over silica gel (that was neutralized with 5-10% triethylamine:Hexanes mixture) using Hexanes:EtOAc as the eluent to afford the final triazole.

General Experimental Procedure of Serine Alkylation with Sodium Hydride: (F)

To a round bottomed flask equipped with a magnetic stir bar, rubber septum, and argon inlet containing DMF (17 vol) was placed N-Boc-Serine (1.2 equiv). To this solution was added NaH (60% dispersion in oil, 3 equiv) at 0° C. and the reaction was allowed to stir at 0° C. for 30 min. To this reaction was added the alkylating agent (1 equiv) at 0° C. and the reaction was allowed to stir at room temperature for 15 h. After the reaction was complete by LCMS, solvent was removed in vacuo. The reaction was then poured into water (54 vol), pH was adjusted to >10 and extracted into EtOAc (2×21 vol). Organic layer was discarded and the pH of the aqueous layer was adjusted to pH=4 with 1N HCl and extracted into EtOAc (3×27 vol). The combined organic extracts were washed with brine (11 vol), dried ($Na_2SO_4$) and concentrated in vacuo to afford the alkylated product.

General Experimental Procedure of Acid Esterification with Trimethylsilyl Azide: (G)

To a round bottomed flask equipped with a magnetic stir bath containing toluene:MeOH (2:1.5, 23 vol) was placed the acid (1 equiv). To this solution was added $TMSCHN_2$ (2M solution in ether, 1.5 equiv) and the reaction was allowed to stir at room temperature for 30 min. After the reaction was complete, solvent was removed in vacuo. The residue was purified over silica gel using Hexanes:EtOAc as the eluent to afford the esterified material.

General Experimental Procedure for Selective Monotosylation of Diol: (H)

To a round bottomed flask equipped with a magnetic stir bar containing ACN or DCM (67 vol) was placed diol (1 equiv). To this solution was added $Bu_2SnO$ (0.2 equiv), TsCl (0.95 equiv), $Et_3N$ (1 equiv) and the reaction was allowed to stir at room temperature for 1 h. After the reaction was complete, the solvent was removed in vacuo. The residue was purified over silica gel using Hexanes:EtOAc as the eluent to afford the monotosylate.

General Experimental Procedure for Acetylation of Alcohols: (I)

To a round bottomed flask equipped with a magnetic stir bar containing DCM (26 vol) was placed alcohol (1 equiv), cooled to 0° C. To this solution was added $Ac_2O$ (2 equiv), DMAP (1 equiv), $Et_3N$ (2 equiv) and the reaction was allowed to stir at room temperature for 1 h. The reaction was then poured into water (53 vol) and extracted into DCM (3×53 vol). The combined organic extracts were washed with brine (53 vol), NaHCO$_3$ solution (53 vol), dried (Na$_2$SO$_4$) and concentrated in vacuo. The residue was purified over silica gel using Hexanes:EtOAc as the eluent to afford the acetylated material.

General Experimental Procedure for Fluorination: (J)

To a round bottomed flask or vial equipped with a magnetic stir bar, was placed the precursor (1 equiv). To this compound was added Bu$_4$NF (4M solution in THF, 20 vol) and the reaction was allowed to stir at 90° C. for 30 min. To this reaction was added HCl (1N, 40 vol) and the reaction was allowed to stir at 65° C. for 30 min. The reaction mixture was diluted with water/acetonitrile (1 mL), filtered through 0.45 µm filter prior to purification by HPLC using ACN: Water both containing 0.05% TFA to afford the fluorinated product.

General Experimental Procedure for Ester Hydrolysis Using LiOH: (K)

To a round bottomed flask equipped with a magnetic stir bar containing THF:Water (1:1) (20 vol) was placed the ester (1 equiv) and LiOH (2-5 equiv), and the reaction was allowed to stir at room temperature for 30 min to 1 h. The reaction was then concentrated and product was isolated by HPLC purification as a colorless solid.

General Experimental Procedure for Boc and Ketal Deprotections Using TFA: (L)

To a round bottomed flask equipped with a magnetic stir bar was placed protected material (1 equiv) in DCM (200 vol). To this compound was added TFA (10 vol) and the reaction was allowed to stir at room temperature for 15 h. The reaction was then poured into water (200 vol) and extracted into DCM (2×100 vol). The combined organic extracts were washed with brine (50 vol), NaHCO$_3$ solution (50 vol), dried (Na$_2$SO$_4$) and concentrated in vacuo. The residue was purified over silica gel using Hexanes:EtOAc as the eluent to afford the deeprotected material.

General Experimental Procedure for Azidation: (M)

To a round bottomed flask equipped with a magnetic stir bar containing pyridine (12 vol) was placed NaN$_3$ (5 equiv) at 0° C. The reaction was stirred at 0° C. for 5 h. To this solution was added amine (1 equiv) in MeOH (100 vol), CuSO$_4$ (0.3 equiv) and the reaction was allowed to stir at room temperature for 15 h. The reaction was then poured into NaHCO$_3$ solution (100 vol) and extracted into EtOAc (3×100 vol). The combined organic extracts were washed with CuSO$_4$ solution (100 vol), dil. HCl solution (100 vol), brine (2×100 vol), dried (Na$_2$SO$_4$) and concentrated in vacuo. The residue was purified over silica gel using Hexanes:EtOAc as the eluent to afford the azide.

General Procedures Used in the Combinatorial Library Synthesis:

General Experimental Procedure for Click Reaction Between Azides and Acetylenes Using CuSO$_4$.H$_2$O and Sodium Ascorbate: (N)

To a round bottomed flask equipped with a magnetic stir bar, rubber septum, and argon inlet containing t-BuOH: H$_2$O (1:1, 100 vol) was placed azide (1 equiv). To this solution was added acetylene (0.9 equiv), CuSO$_4$.5H$_2$O (0.2 equiv), sodium L-ascorbate (0.4 equiv) and the reaction was allowed to stir at room temperature for until deemed complete by LCMS. After the reaction was complete, the solvents were removed in vacuo. The residue was washed with water (100 vol), cooled at 0° C., filtered, washed with ether (50 vol) dried in vacuo to afford the final triazole. If the solid appeared to contain trace amounts of copper, as was evidenced by a green color, the solid was washed with an add'n portion of 0.1% NH$_4$OH (100 vol), with water (100 vol), washed with ether (50 vol) and dried in vacuo. All library members were submitted for LC/MS analysis to evaluate purity. Compounds with purities above 85% were submitted for biological assay. Compounds with purities below 85% were re-purified via flash chromatography and then subjected to biological assay.

General Experimental Procedure for Amide Coupling with Ps-Carbodiimide (O)

A 5 mL microwave tube was charged with acid (1 equiv), PS-Carbodiimide (2 equiv), 1-hydroxybenzotriazole (0.99 equiv) and amine (0.95 equiv) in dichloromethane (50 vol) and dimethylformamide (5 vol). The suspension was irradiated in a Biotage Emrys Optimizer microwave reactor (250 W) at 100° C. for 10 min After cooling to room temperature the reaction mixture was filtered through an SPE-cartridge (pre-packed with 500 mg silica-bound carbonate and preconditioned with CH$_2$Cl$_2$ (100 vol) and washed with dichloromethane (100 vol)). The dichloromethane washes were discarded. The cartridge was further washed with methanol (3×100 vol) and the eluents were collected via gravity filtration in a scintillation vial. Evaporation of all volatile components in a centrifugal vacuum evaporator (Genevac HT-4) provided the amide. All library members were submitted for LC/MS analysis to evaluate purity. Compounds with purities above 85% were submitted for biological assay. Compounds with purities below 85% were re-purified via flash chromatography and then subjected to biological assay.

HPLC Purifications:

All the HPLC purifications were done on a Shimadzu semi prep system using a gradient acetonitrile:water mixture (with 0.05-0.1% TFA) as the eluent starting from 5% ACN: 95% Water (both containing 0.05-1% TFA) at T$_o$ and going to 100% ACN (containing 0.05-0.1% TFA) over 30 to 40 minutes.

Preparation of
6-Hydroxybenzo[d]thiazole-2-sulfonamide (1)

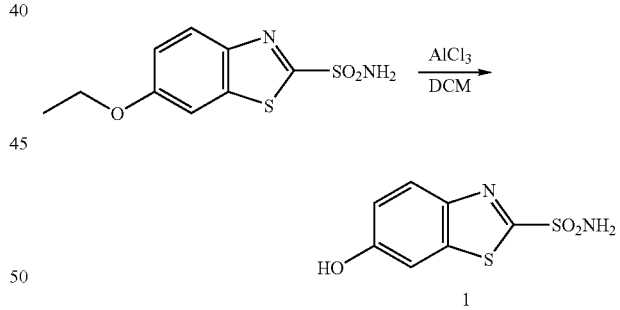

To a 1 L round bottomed flask equipped with a magnetic stir bar, rubber septum, and argon inlet containing DCM (500 mL) was placed 6-ethoxybenzo[d]thiazole-2-sulfonamide (25 g, 108.7 mmol). To this solution at 0° C. (ice bath) was added AlCl$_3$ (50 g, 376 mmol) portion-wise and the reaction was allowed to stir at rt for 24 h. Solvent was removed in vacuo and the residue was cautiously quenched into 3 M HCl (600 mL). The mixture was filtered and the solid was washed with cooled 3 M HCl (2×50 mL). The product was dried under high vacuum for 48 h to afford compound 1 as a yellow solid (24 g).

$^1$H NMR (300 MHz, CD$_3$OD) δ: 7.91 (d, J=9.2 Hz, 1H), 7.37 (d, J=2.4 Hz, 1H), 7.10 (dd, J=9.2, 2.4 Hz, 1H); MS (ESI) m/z 231 (M+H$^+$).

Preparation of 6-(Prop-2-ynyloxy)benzo[d]thiazole-2-sulfonamide (3)

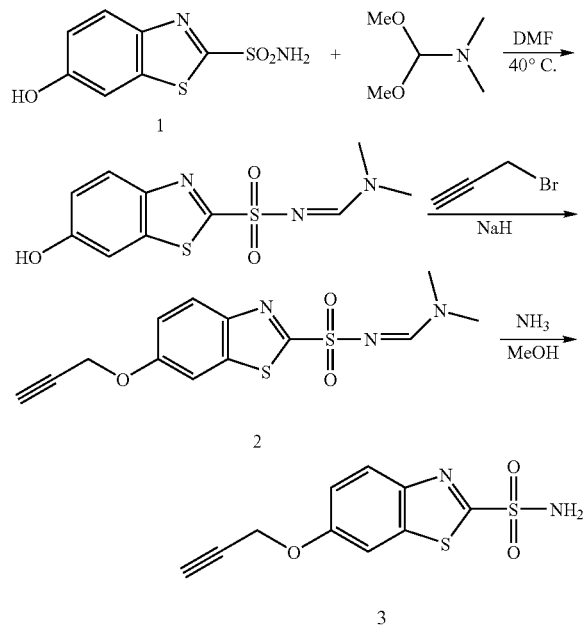

Preparation of N,N-Dimethyl-N'-(6-(prop-2-ynyloxy)benzo[d]thiazol-2-ylsulfonyl)formimidamide (2)

To a 100 mL round bottomed flask equipped with a magnetic stir bar, rubber septum, and argon inlet containing DMF (25 mL) in an ice bath was placed 1 (17.5 g, 76.1 mmol) and the reaction was stirred at rt until the solid dissolved. To this solution was added N,N-dimethylformamide dimethyl acetal (60 g) and the mixture was heated at 40° C. for 4 h. Solvent was removed in vacuo at 42° C. and the residue was dissolved in anhydrous DMF (60 mL). To this solution at 0° C. was added portion wise NaH (4.56 g, 60% in oil, 114 mmol) and the reaction was stirred at 0° C. for 30 min. To this mixture was added propargyl bromide (18 g, 80% toluene solution, 121.7 mmol) dropwise. Ice bath was removed and the mixture was stirred at rt for 1 h. The residue was poured into a mixture of water and EtOAc (200 mL/200 mL). The mixture was filtered and solid was collected and dissolved in DCM (300 mL) and washed with saturated NaHCO$_3$ (3×200 mL) and water (200 mL). To this solution was added 100 g of silica gel and dried in vacuo. The solid mixture was loaded on silica gel column and eluted with 10% EtOAc in DCM to afford compound 2 as a yellow solid (9.2 g, 37.4%).

$^1$H NMR (300 MHz, acetone-d$_6$) δ: 8.29 (s, 1H), 8.00 (d, J=9.2 Hz, 1H), 7.76 (d, J=2.4 Hz, 1H), 7.27 (dd, J=9.2, 2.4 Hz, 1H), 4.92 (d, J=2.8 Hz, 2H), 3.34 (s, 3H), 3.14 (t, J=2.4 Hz, 1H), 3.07 (s, 3H); MS (ESI) m/z 324 (M+H$^+$).

Preparation of 6-(Prop-2-ynyloxy)benzo[d]thiazole-2-sulfonamide (3)

To a 500 mL round bottomed flask equipped with a magnetic stir bar, rubber septum, and argon inlet was placed 2 (9 g, 27.8 mmol) and 200 mL of ammonia in methanol (7 N). The mixture was stirred at rt for 24 h. The solution was bubbled with air for 1 h and filtered. The filtrate was acidified with concentrated HCl to pH=2 and concentrated and dried. This solid was again treated with ammonia methanol solution (7 N, 200 mL) for 24 h at rt. The solution was bubbled with air for 1 h and filtered. The filtrate was added concentrated HCl to pH=2 and concentrated. It was filtered and the solid was washed with cooled water and dried to afford compound 3 as a yellow solid (5.2 g, 70%).

$^1$H NMR (300 MHz, acetone-d$_6$) δ: 8.03 (d, J=9.2 Hz, 1H), 7.78 (d, J=2.8 Hz, 1H), 7.38 (s, 2H), 7.30 (dd, J=9.2, 2.4 Hz, 1H), 4.93 (d, J=2.4 Hz, 2H), 3.15 (t, J=2.4 Hz, 1H); MS (ESI) m/z 269 (M+H$^+$).

Alternate preparation of 6-(Prop-2-ynyloxy)benzo[d]thiazole-2-sulfonamide (3)

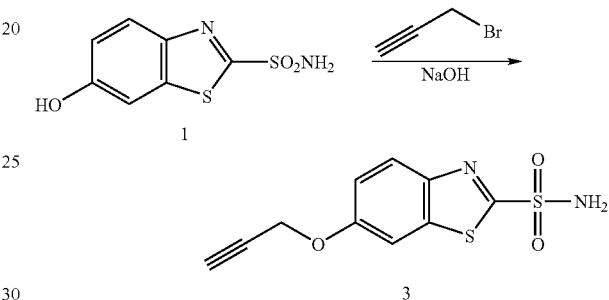

To a stirring solution of NaOH in MeOH (2.5 M, 18.8 mL) and DMF (60 mL) was added 1 (4.33 g, 18.8 mmol). The mixture was allowed to stir for 45 min at 23° C. before propargyl bromide (80% in PhMe, 3.36 mL, 22.56 mmol) was added slowly over 10 min. After 2.5 h, an aqueous solution of 1 M HCl was added to achieve pH=6, where upon a white precipitate forms. Water was then added and the organic layer was extracted 3×EtOAc and the combined organic extracts washed 1×H$_2$O, 1×brine, and then dried over MgSO$_4$. The solvents were removed in vacuo and the crude residue purified by flash chromatography using Hexanes:EtOAc on a Biotage purification system to yield 3 as a pale yellow solid (1.43 g, 29%).

$^1$H NMR (300 MHz, CDCl$_3$) δ: 8.27 (2H, s), 8.09 (d, J=9.0 Hz, 1H), 7.86 (d, J=2.6 Hz, 1H), 7.31 (dd, J=9.0, 2.6 Hz, 1H), 4.93 (d, J=2.3 Hz, 2H), 3.65 (t, J=2.3 Hz, 1H).

Preparation of N-(bis(4-Methoxyphenyl)(phenyl)methyl)-6-(prop-2-ynyloxy)benzo[d]thiazole-2-sulfonamide (4)

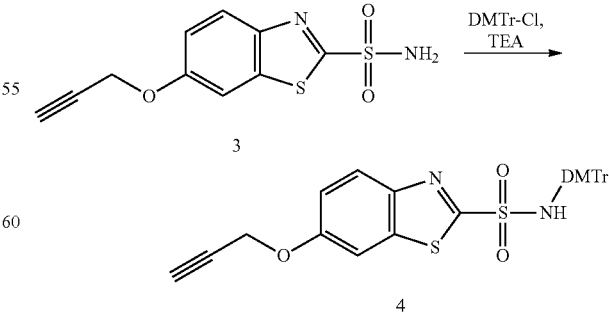

To a stirring slurry of 3 (0.2 g, 0.76 mmol) and dimethoxytrityl chloride (0.31 g, 0.91 mmol) (DMTr-Cl) in DCM (15 mL) was added TEA (0.15 mL). The resulting clear solution was allowed to stir at room temperature for 4 h. Silica gel (0.5 g) was added to the solution and followed by rotary evaporation of solvent in vacuo. The sample absorbed silica gel was then loaded onto a pre-equilibrated column (with 10% TEA in hexanes). Flash chromatography using 0-50% EtOAc in hexane as the eluent gave the product 4 as a yellow solid (0.30 g, 69%).

Preparation of N-(bis(4-Methoxyphenyl)(phenyl)methyl)-4-ethynylbenzenesulfonamide (5)

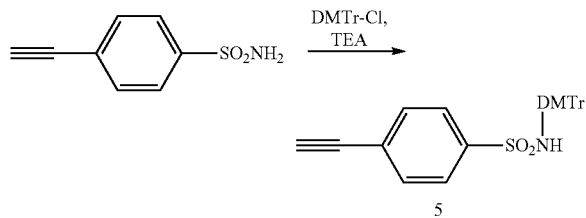

To a stirring slurry of 4-ethynylbenzenesulfonamide (1.81 g, 10.0 mmol) and DMTr-Cl (4.07 g, 12.0 mmol) in DCM (100 mL) was added TEA (2.8 mL). The resulting solution was allowed to stir at room temperature for overnight. Silica gel (3 g) was added to the solution followed by rotary evaporation of solvent in vacuo. The sample was absorbed onto silica gel was then loaded onto a pre-equilibrated column (with 10% TEA in hexane). Flash chromatography using 0-30% EtOAc in hexane as the gradient eluents gave the product 5 as a yellow solid (4.8 g, 99%).

Preparation of (S)-2-(4-(4-(N-(bis(4-Methoxyphenyl)(phenyl)methyl)sulfamoyl)phenyl)-1H-1,2,3-triazol-1-yl)-3-methylbutanoic acid (6)

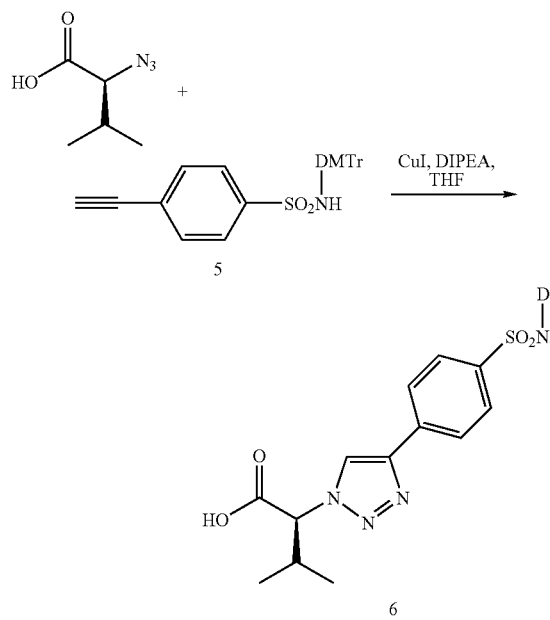

Click reaction was done according to the general procedure (E). Performed on a 0.97 g scale with DIEA in 1.1 equiv. After evaporation of THF, the residue was dissolved in DCM, washed with water (2×), dried over anhydrous sodium sulfate, and concentrated before loading onto the column Flash chromatography on a silica gel column (40 g) using 5-20% MeOH in DCM gave the desired product 6 (0.545 g, 65%).

Preparation of 2-(4-((2-sulfamoylbenzo[d]thiazol-6-yloxy)methyl)-1H-1,2,3-triazol-1-yl)acetic acid (7), (S)-3-methyl-2-(4-((2-sulfamoylbenzo[d]thiazol-6-yloxy)methyl)-1H-1,2,3-triazol-1-yl)butanoic acid (8), and (S)-3-phenyl-2-(4-((2-sulfamoylbenzo[d]thiazol-6-yloxy)methyl)-1H-1,2,3-triazol-1-yl)propanoic acid (9)

Compounds 7, 8 and 9 were prepared via general procedure (N). The crude reaction mixture for each compound was independently concentrated in vacuo onto silical gel and purified by flash chromatography first using Hexanes:EtOAc followed by dichloromethane/methanol on a Biotage purification system, furnishing triazoles 7-9 as off-white crystalline solids (77-100%).

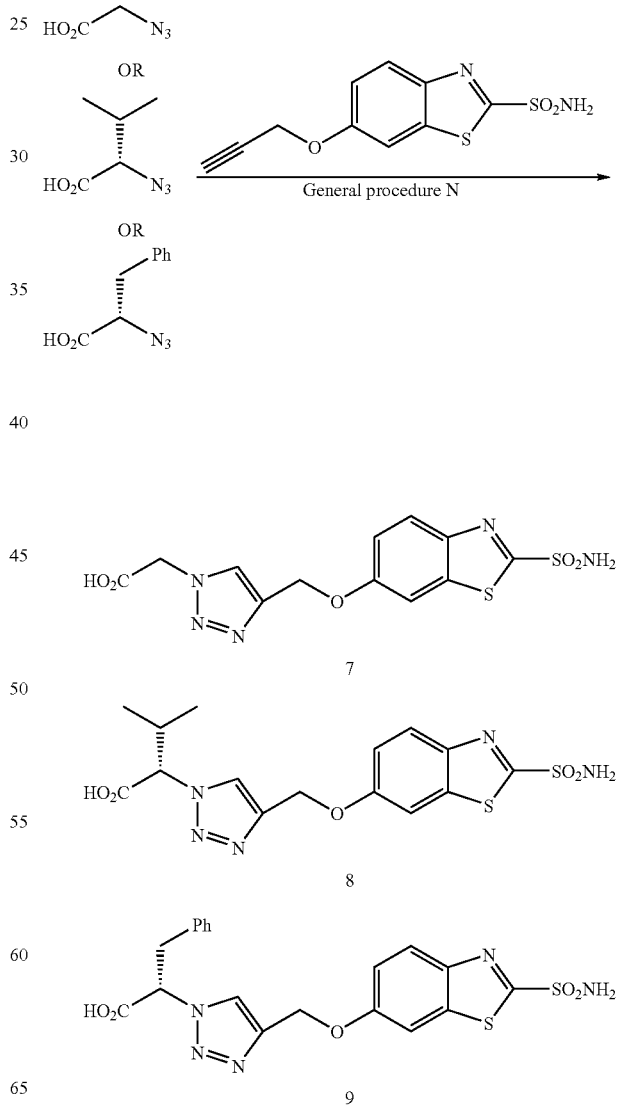

Preparation of VM4047 Precursor

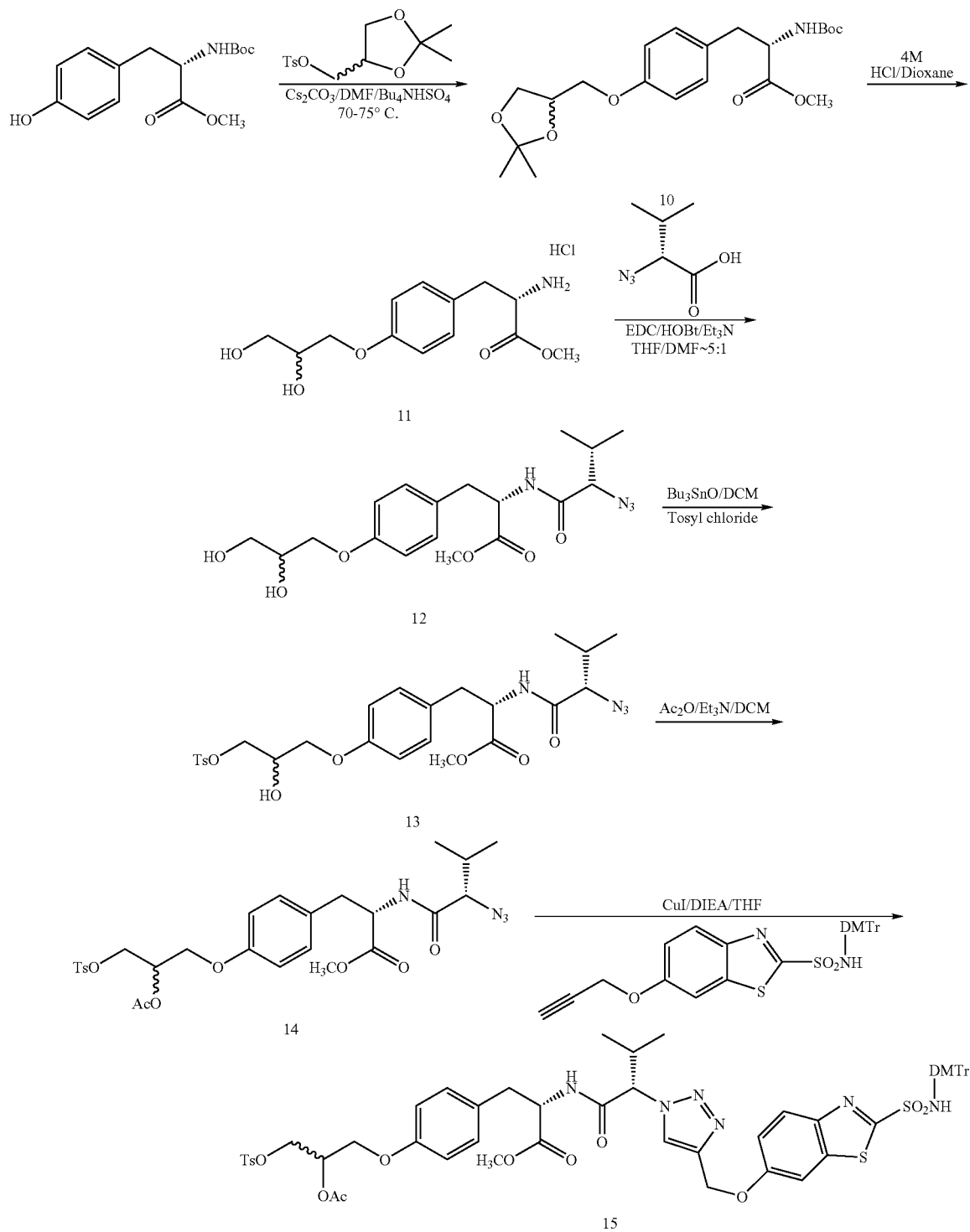

Preparation of (S)-methyl-2-(tert-butoxycarbonylamino)-3-(4-((2,2-dimethyl-1,3-dioxolan-4-yl)methoxy)phenyl)propanoate (10)

General experimental procedure for alkylation (A) was followed. Performed on a 5 g scale, using the ketal tosylate, and tetrabutylammonium sulfate. Reaction mixture was purified over silica gel using DCM first followed by Hexanes:EtOAc to afford 10 (6 g, 85%) as a yellow liquid. MS: [M+Na]$^+$: 432

Preparation of (S)-methyl 2-amino-3-(4-(2,3-dihydroxypropoxy)phenyl)propanoate (11)

General procedure for deprotection (B) was followed. Performed on a 1.5 g scale. After the completion of the reaction, solvent was evaporated, triturated with Et$_2$O, washed and the resulting product 11 was obtained as a white solid (100% yield).

Preparation of (S)-methyl-2((S)-2-azido-3-methylbutanamido)-3-(4-(2,3-dihydroxy propoxy)phenyl) propanoate (12)

Coupling reaction was done according to the general procedure (C). Performed on a 0.5 g scale using valine azido acid and triethyl amine as base. In this specific case, racemization at the valine centre occurred during this step. Isolated 0.65 g (86%) of 12 as mixture of isomers. MS: [M+H]+: 353.4

Preparation of (S)-methyl 2-((S)-2-azido-3-methylbutanamido)-3-(4-(2-hydroxy-3-(tosyloxy)propoxy)phenyl)propanoate (13)

Tosylation was done according to the general procedure (H). Performed on a 0.55 g scale. Isolated 0.6 g (100%) of 13. MS: [M+H]+: 549.2

Preparation of (S)-methyl 3-(4-(2-acetoxy-3-(tosyloxy)propoxy)phenyl)-2-((S)-2-azido-3-methylbutanamido)propanoate (14)

Acetylation was done according to the general procedure (I). Performed on a 0.55 g scale. EtOAc:Hexanes (45:55) were used as the eluent. Isolated 0.6 g (100%) of 14 as a colorless oil. MS: [M+H]+: 591.1

Preparation of (S)-methyl 3-(4-(2-acetoxy-3-(tosyloxy)propoxy)phenyl)-2-((S)-2-(4-(2-(N-(bis(4-methoxyphenyl)(phenyl)methyl)sulfamoyl)benzo[d]thiazol-6-yloxy)methyl)-1H-1,2,3-triazol-1-yl)-3-methylbutanamido)propanoate (15)

Click reaction was done according to the general procedure (E). Performed on a 0.5 g scale with DIEA in 1.1 eq. Product 15 was obtained (0.7 g, 75%) as off colorless solid.

LCMS for $C_{58}H_{60}N_6O_{14}S_3$, calc'd: 1160.33. found: 1161.4, 1183.4 (M+H, M+Na)

Preparation of VM4047 Standard (VM4047A and VM4047B)

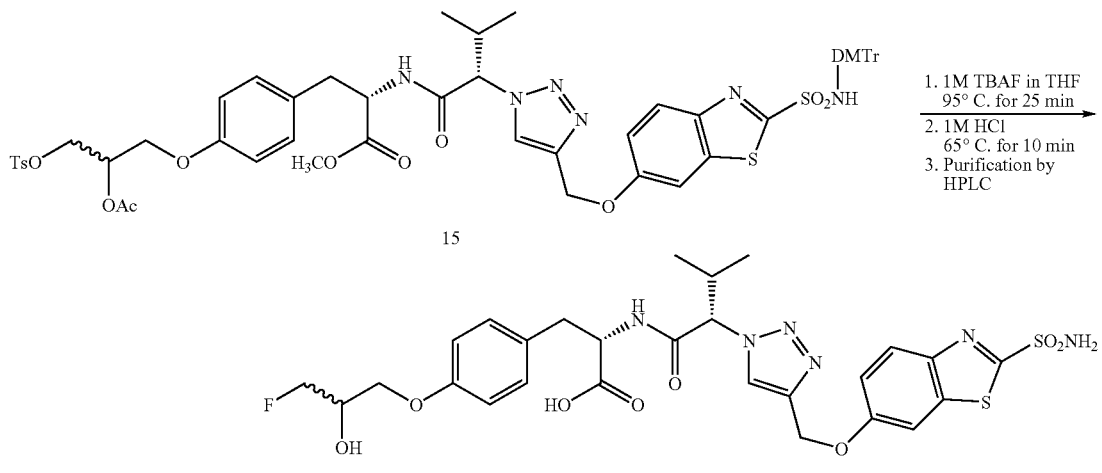

VM4047A and VM4047B

Preparation of (S)-3-(4-(3-fluoro-2-hydroxypropoxy)phenyl)-2-((R)-3-methyl-2-(4-((2-sulfamoylbenzo[d]thiazol-6-yloxy)methyl)-1H-1,2,3-triazol-1-yl)butanamido) propanoic acid (VM4047A and VM4047B)

General experimental procedure for fluorination (J) was followed. Performed on a 0.6 g scale. The reaction mixture purified by HPLC to afford two isomers in a 3:2 ratio (16% overall, A: 2.51 mg, B: 2.95 mg) as colorless solid. MS: for A and B [M+H]+: 651.2 (M+H).

VM4047A: $^1$H NMR (400 MHz, Acetone-d$_6$) δ: 8.21 (d, J=2.2 Hz, 1H), 8.03 (d, J=9.0 Hz, 2H), 7.91 (d, J=2.5 Hz, 1H), 7.39 (s, 2H), 7.34 (dd, J=9.2, 2.5 Hz, 1H), 6.99 (d, J=8.4 Hz, 2H), 6.75 (d, J=8.6 Hz, 2H), 5.35 (s, 2H), 5.13 (d, J=10 Hz, 1H), 4.74-4.68 (m, 1H), 4.60 (dq, J=9.6, 3.2 Hz, 1H), 4.49 (dq, J=9.8, 4.3 Hz, 1H), 4.20-4.12 (m, 1H), 4.03-3.99 (m, 2H), 3.48-3.44 (m, 1H), 3.12 (dd, J=13.9, 5.3 Hz, 2H), 2.95 (dd, J=14.3, 8.0 Hz, 2H), 2.49-2.44 (m, 1H), 1.84-1.82 (m, 1H), 1.47-1.41 (m, 1H), 1.04 (d, J=6.7 Hz, 3H), 0.68 (d, J=6.7 Hz, 3H).

VM4047B: $^1$H NMR (400 MHz, Acetone-d$_6$) δ: 8.25 (s, 1H), 8.08 (d, J=8.2 Hz, 1H), 8.02 (d, J=9.0 Hz, 1H), 7.95 (d, J=2.5 Hz, 1H), 7.40 (s, 1H), 7.33 (dd, J=9.0, 2.5 Hz, 1H), 7.16 (d, J=8.6 Hz, 1H), 5.33 (s, 2H), 5.05 (d, J=9.8 Hz, 1H), 4.74-4.69 (m, 1H), 4.62 (dq, J=9.6, 3.9 Hz, 1H), 4.49 (dq, J=9.6, 3.9 Hz, 1H), 4.21-4.14 (m, 1H), 4.04-4.01 (m, 1H), 3.19 (dd, J=14.1, 4.7 Hz, 2H), 2.97 (dd, J=14.0, 9.4 Hz, 2H), 2.40-2.35 (m, 1H), 0.81 (d, J=6.7 Hz, 3H), 0.63 (d, J=6.7 Hz, 3H).

Alternate Preparation of VM4047 Standard (VM4047)
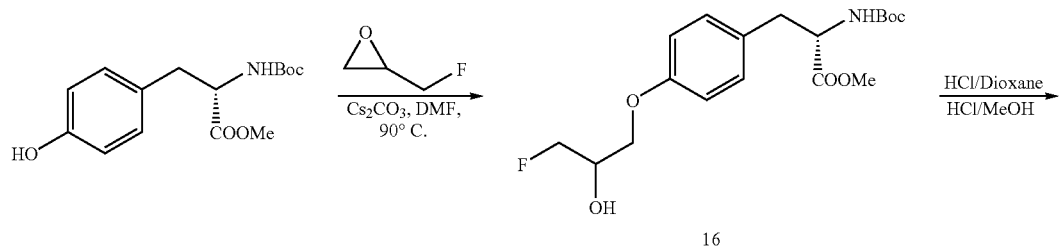
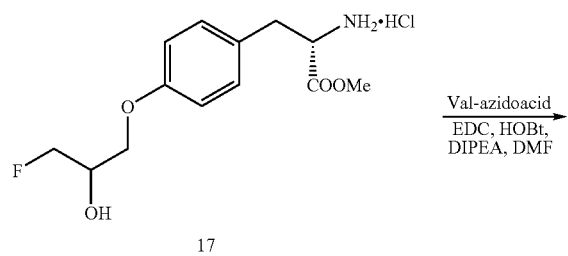
17
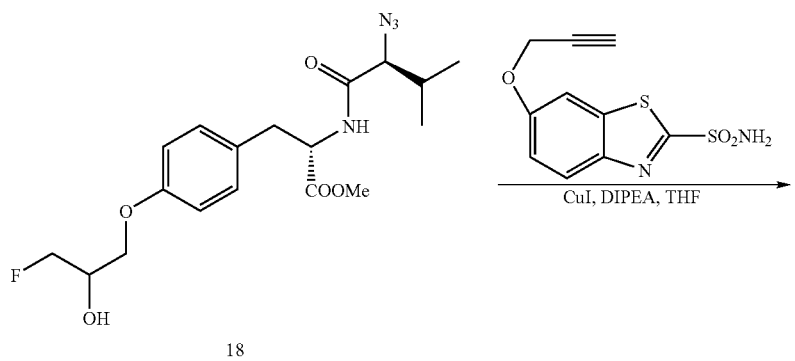
18
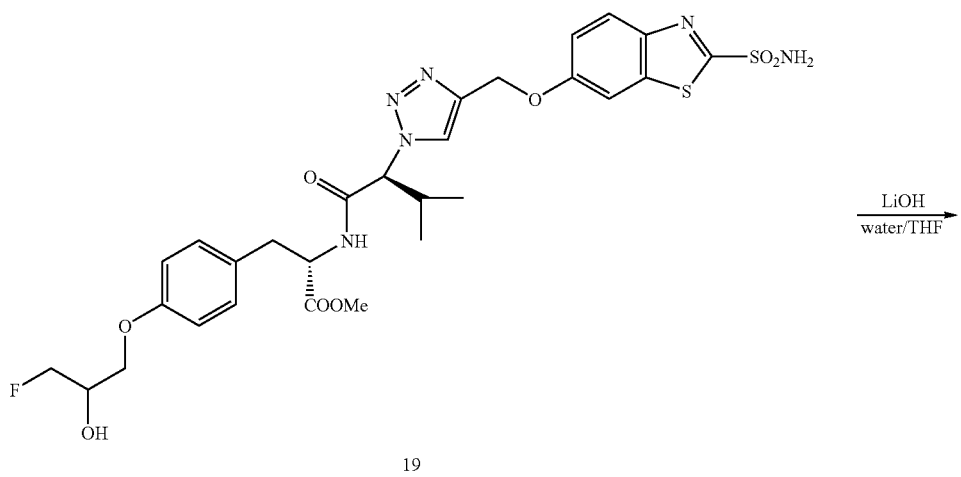
19

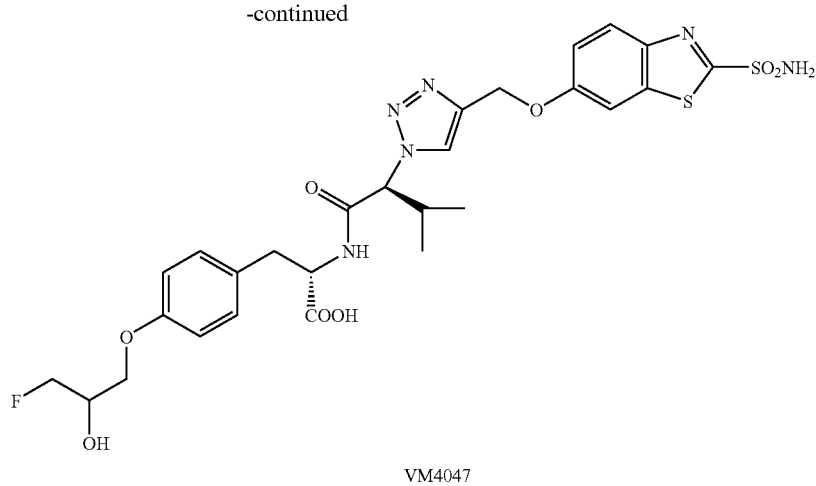

VM4047

Preparation of (2S)-methyl 2-(tert-butoxycarbonylamino)-3-(4-(3-fluoro-2-hydroxypropoxy)phenyl)propanoate (16)

General experimental procedure for phenolic alkylation (A) was followed. Reaction was performed on a 2 g scale. Hexanes:EtOAc (50:50) used as the eluent for purification. Isolated 1.9 g (76%) of 16 as a colorless oil. MS: [M-Boc+H]$^+$: 271.

Preparation of (2S)-methyl2-amino-3-(4-(3-fluoro-2-hydroxypropoxy)phenyl)propanoate hydrochloride (17)

General experimental procedure for deprotection (B) was followed. Reaction was performed on a 2.4 g scale. Isolated 1.9 g (96%) of 17 as a colorless solid. MS: [M+H]$^+$: 308.

Preparation of (2S)-methyl2-((S)-2-azido-3-methylbutanamido)-3-(4-(3-fluoro-2-hydroxypropoxy)phenyl)propanoate (18)

General experimental procedure for coupling (C) was followed. Reaction was performed on a 1.9 g scale. Hexanes:EtOAc (60:40) used as the eluent for purification. Isolated 1.6 g (67%) of 18 as a colorless solid. MS: [M+H]$^+$: 397.

Preparation of (2S)-methyl 3-(4-(3-fluoro-2-hydroxypropoxy)phenyl)-2-((S)-3-methyl-2-(4-((2-sulfamoylbenzo[d]thiazol-6-yloxy)methyl)-1H-1,2,3-triazol-1-yl)butanamido)propanoate (19)

General experimental procedure for click reaction (E) was followed. Reaction was performed on a 0.025 g scale. Hexanes:EtOAc (10:90) used as the eluent for purification. Isolated 0.02 g (48%) of 19 as a colorless solid. MS: [M+H]$^+$: 665

Preparation of VM4047a

General experimental procedure for hydrolysis (K) can be used to prepare VM4047a.

Preparation of VM391 Precursor

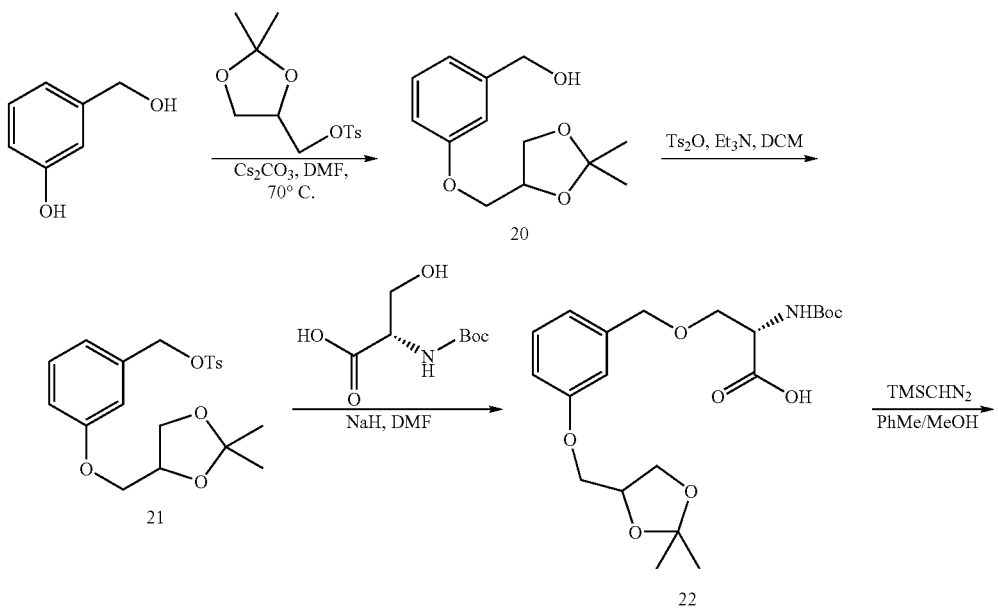

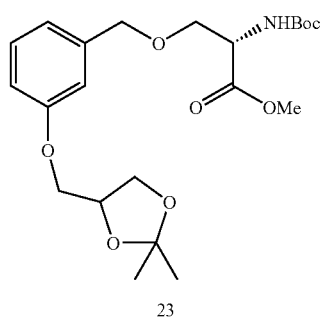
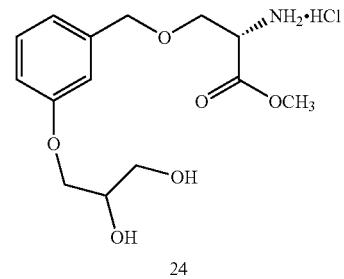

Preparation of (3-((2,2-dimethyl-1,3-dioxolan-4-yl)methoxy)phenyl)methanol (20)

General experimental procedure for phenolic alkylation (A) was followed. Reaction was performed on a 20 g scale. Hexanes:EtOAc (40:60) used as the eluent for purification. Isolated 17 g (72%) of 20. MS: [M+H]$^+$: 239.

Preparation of 3-((2,2-dimethyl-1,3-dioxolan-4-yl)methoxy)benzyl-4-methylbenzene sulfonate (21)

General experimental procedure for tosylation (D) was followed. Reaction was performed on a 17 g scale. Hexanes:EtOAc (50:50) used as the eluent for purification. Isolated 9.5 g (35%) of 21. MS: [M+H]$^+$: 393.

Preparation of (2S)-2-(tert-butoxycarbonylamino)-3-(3-((2,2-dimethyl-1,3-dioxolan-4-yl)methoxy)benzyloxy)propanoic acid (22)

General experimental procedure for serine alkylation (F) was followed. Reaction was performed on a 5.8 g scale. Isolated 6 g (60%) of 22. MS: [M-Boc+H]$^+$: 326.

Preparation of (2S) methyl 2-(tert-butoxycarbonylamino)-3-(3-((2,2-dimethyl-1,3-dioxolan-4-yl)methoxy)benzyloxy)propanoate (23)

General experimental procedure for esterification (G) was followed. Reaction was performed on a 6 g scale. Hexanes:EtOAc (60:40) was used as the eluent for purification. Isolated 4 g (66%) of 23. MS: [M-Boc+H]$^+$: 340.

Preparation of (2S) methyl 2-amino-3-(3-(2,3-dihydroxypropoxy)benzyloxy)propanoate hydrochloride (24)

General experimental procedure for deprotection (B) was followed. Reaction was performed on a 4 g scale. Isolated 2.7 g (90%) of 24 as a colorless solid. MS: [M+H]$^+$: 300.

Preparation of (2S) methyl 2-(2-azidoacetamido)-3-(3-(2,3-dihydroxypropoxy)benzyloxy)propanoate (25)

General experimental procedure for coupling (C) was followed. Reaction was performed on a 2.7 g scale. EtOAc was used as the eluant for purification. Isolated 1.5 g (50%) of 25. MS: [M+H]$^+$: 383.

Preparation of (2S) methyl 2-(2-azidoacetamido)-3-(3-(2-hydroxy-3-(tosyloxy)propoxy)benzyloxy)propanoate (26)

General experimental procedure for selective monotosylation of diol (H) was followed. Reaction was performed on a 1.5 g scale. Hexanes:EtOAc (30:70) used as the eluent for purification. Isolated 1.9 g (90%) of 26. MS: [M+H]$^+$: 537.

Preparation of (2S)-methyl 3-(3-(2-acetoxy-3-(tosyloxy)propoxy)benzyloxy)-2-(2-azidoacetamido)propanoate (27)

General experimental procedure for acetylation of alcohols (I) was followed. Reaction was performed on a 1.9 g scale. Hexanes:EtOAc (30:70) used as the eluent for purification. Isolated 1.9 g (95%) of 27. MS: [M+H]$^+$: 579.

Preparation of methyl 3-(3-(2-acetoxy-3-(tosyloxy)propoxy)benzyloxy)-2-(2-(4-((2-(N-(bis(4-methoxyphenyl)(phenyl)methyl)sulfamoyl)benzo[d]thiazol-6-yloxy)methyl)-1H-1,2,3-triazol-1-yl)acetamido)propanoate (28)

General experimental procedure for click reaction (E) was followed. Reaction was performed on a 0.45 g scale. Hexanes:EtOAc (20:80) was used as the eluent for purification. Isolated 0.88 g (99%) of 28 as a colorless solid. MS: [M+H]$^+$: 1149.

Preparation of VM391 Standard

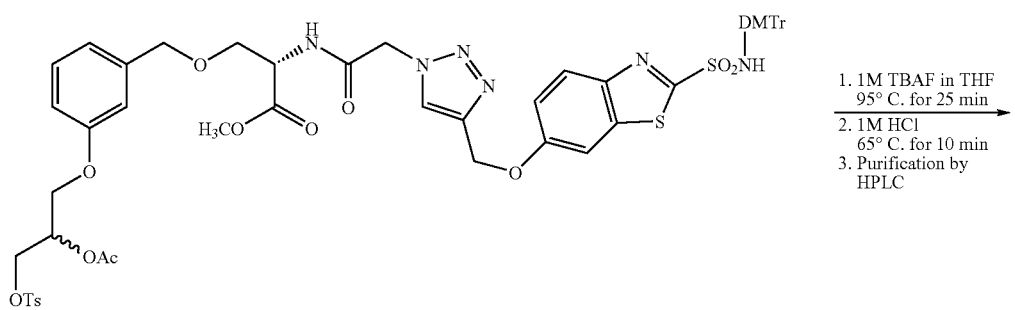

28

1. 1M TBAF in THF 95° C. for 25 min
2. 1M HCl 65° C. for 10 min
3. Purification by HPLC

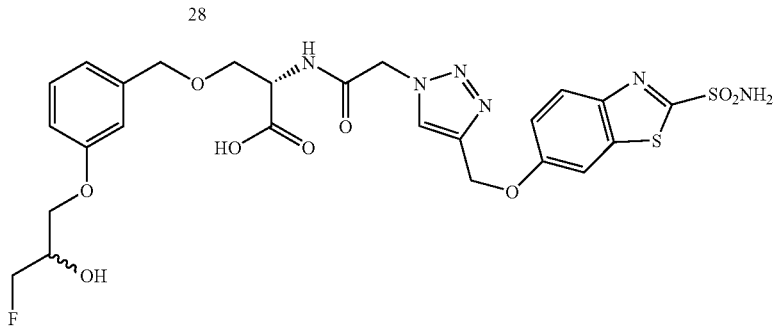

VM391

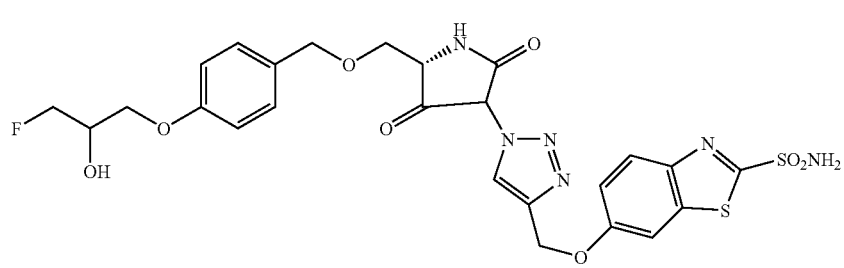

29

Preparation of (S)-3-(3-(3-fluoro-2-hydroxypropoxy) benzyloxy)-2-(2-(4-((2-sulfamoylbenzo[d]thiazol-6-yloxy)methyl)-1H-1,2,3-triazol-1-yl)acetamido) propanoic acid (VM391)

General experimental procedure for fluorination (J) was followed. Performed on a 0.1 g scale. The reaction mixture purified by HPLC to afford two compounds (yield not determined) (VM391 and compound 29) as colorless solids. MS: (VM391) [M+H]$^+$: 639.1. MS: (compound 29) [M+H]$^+$: 621.0

Preparation of VM2133 Precursor

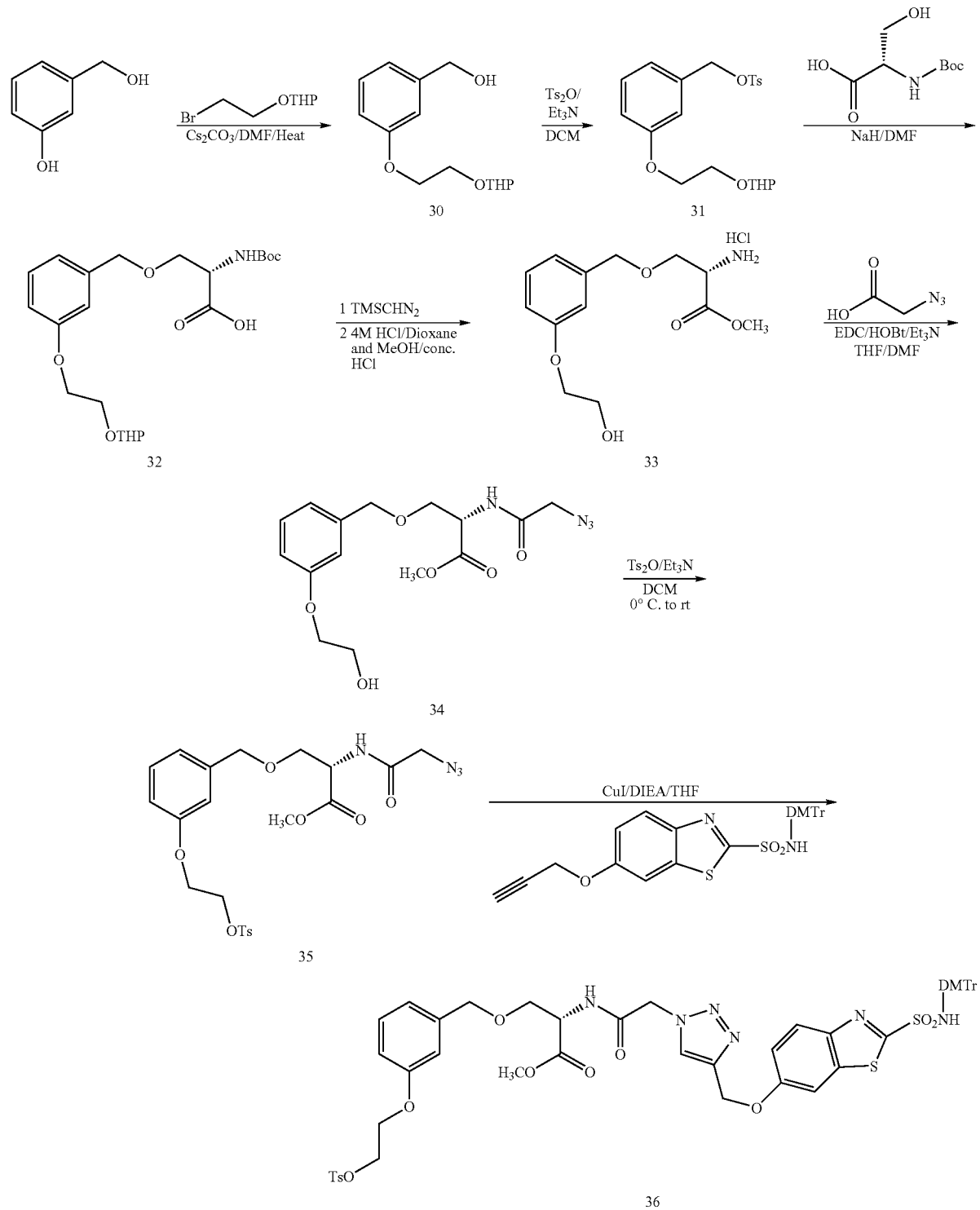

Preparation of (3-(2-(tetrahydro-2H-pyran-2-yloxy) ethoxy)phenyl)methanol (30)

General alkylation procedure (A) was followed. Performed on a 15 g scale. Product eluted out in 65:35 Hexanes:EtOAc in a gradient elution on a Combiflash purification system. Product 30 was isolated as a yellow oil (24 g, 79%).

Preparation of 3-(2-(tetrahydro-2H-pyran-2-yloxy) ethoxy)benzyl 4-methylbenzene sulfonate (31)

General tosylation procedure (D) was followed. Performed on a 23 g scale. Reaction time 10 min. Product eluted out in about 25% EtOAc: Hexanes using a gradient elution on a Combiflash system. Product isolated as yellow color oil (17 g, 45%)

Preparation of (2S)-2-(tert-butoxycarbonylamino)-3-(3-(2-(tetrahydro-2H-pyran-2-yloxy)ethoxy)benzyloxy)propanoic acid (32)

General experimental procedure for alkylation using NaH (F) was followed. Performed on a 5 g scale using N-boc L-serine. After work up, product was isolated as a thick yellow oil (~7 g, 62%) and used as is for next step. MS: [M+Na]$^+$: 462.4

Preparation of (S)-methyl 2-amino-3-(3-(2-hydroxyethoxy)benzyloxy)propanoate (33)

General experimental procedure for acid esterification (G) using TMS-diazomethane was followed. Reaction was performed on a 7 g scale and the addition was done at 0° C. and TMS-diazomethane was added slowly dropwise. Compound eluted out in 28% EtOAc: Hexanes using gradient elution on a Combiflash purification system. Isolated product as a colorless oil (4.9 g, 72%). MS: [M+Na]$^+$: 476.2

Boc and THP groups were removed using the general experimental procedure (B). Performed on a 4.9 g scale. After removal of solvent, the residue was triturated with ether. Product 33 was isolated as the HCl salt (colorless solid, 3.1 g, 94%). MS: [M+Na]$^+$: 270.1

Preparation of (S)-methyl 2-(2-azidoacetamido)-3-(3-(2-hydroxyethoxy)benzyloxy) propanoate (34)

General experimental procedure for coupling reactions (C) was followed. Performed on a 2 g scale, using Et$_3$N as base and THF:DMF (1:1) as solvent. Compound eluted out in 65% EtOAc: Hexanes in a gradient elution on a Combiflash purification system. Isolated 34 (1.6 g, 70%) as light yellow oil. MS: [M+Na]$^+$: 375.1, [M+H]$^+$: 353.2

Preparation of (S)-methyl 2-(2-azidoacetamido)-3-(3-(2-(tosyloxy)ethoxy)benzyloxy) propanoate (35)

General experimental procedure for tosylation (D) was followed. Performed on a 1 g scale and at 0° C. for 10 min. Product eluted out in 58% EtOAc: Hexanes in a gradient elution on a Combiflash purification system. Isolated 35 (1.4 g, 95%) as yellow oil.

Preparation of (S)-methyl2-(2-(4-((2-(N-(bis(4-methoxyphenyl)(phenyl)methyl)sulfamoyl)-benzo[d]thiazol-6-yloxy)methyl)-1H-1,2,3-triazol-1-yl)acetamido)-3-(3-(2-(tosyloxy)ethoxy)benzyloxy) propanoate (36)

General experimental procedure for click reaction (E) was followed. Performed on a 0.3 g scale and 1.1 eq of base. Product eluted out in 78% EtOAc:Hexanes mixture in a gradient elution on a Combiflash purification system. Isolated 36 (pure 0.5 g, impure 0.13 g, overall quantitative) as an off colorless solid. MS: [M+Na]$^+$: 1099.6, [M+H]$^+$: 1077.5

$^1$H NMR (400 MHz, Acetone-d$_6$) δ: 8.15 (s, 1H), 8.08 (br s, 2H), 7.91 (d, J=9.0 Hz, 1H), 7.83 (d, J=8.4 Hz, 2H), 7.37 (d, J=2.5 Hz, 1H), 7.49-7.46 (m, 4H), 7.30-7.16 (m, 9H), 6.90-6.78 (m, 3H), 6.35 (d, J=8.8 Hz, 4H), 5.33 (d, J=6.1 Hz, 4H), 4.75-4.73 (m, 1H), 4.52 (d, J=12.3 Hz, 1H), 4.43-4.41 (m, 2H), 4.26-4.24 (m, 2H), 3.90 (dd, J=9.8, 4.1 Hz, 1H), 3.74 (dd, J=9.8, 3.3 Hz, 1H), 3.70 (s, 3H), 3.65 (s, 6H), 2.46 (s, 3H).

Preparation of VM2131 and VM2133 including alternate preparation of VM2133

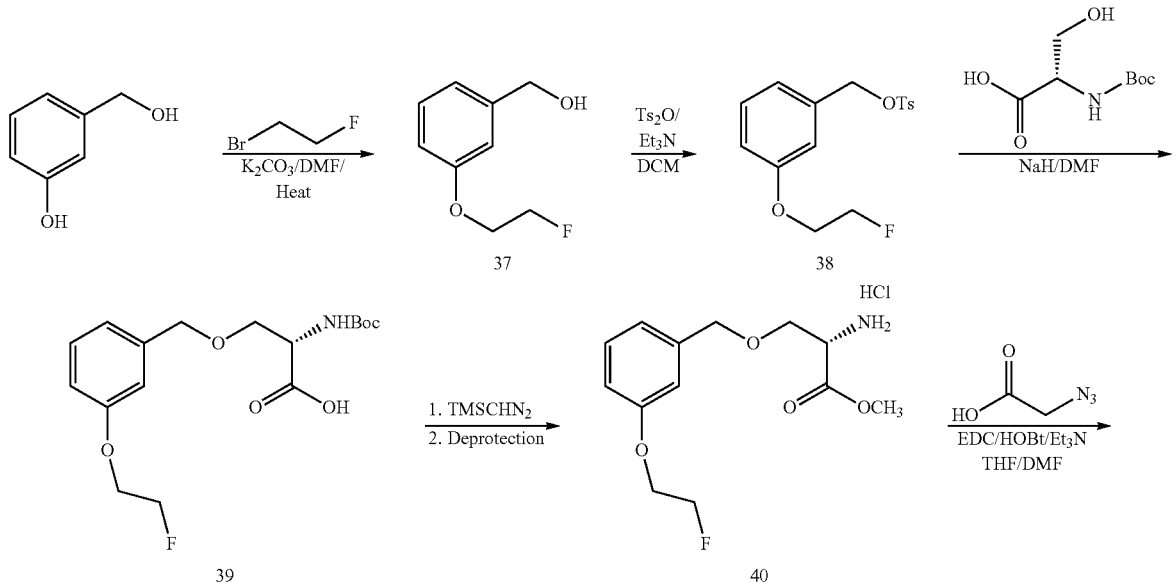

-continued
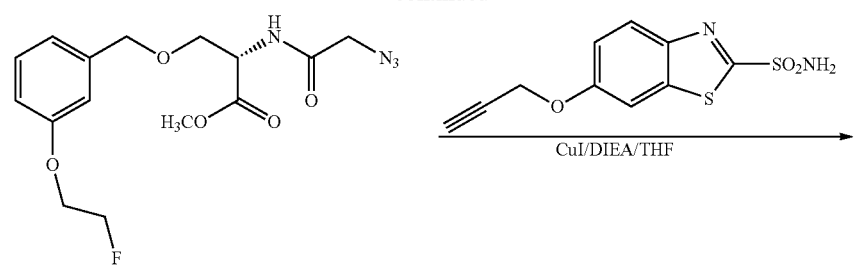
41
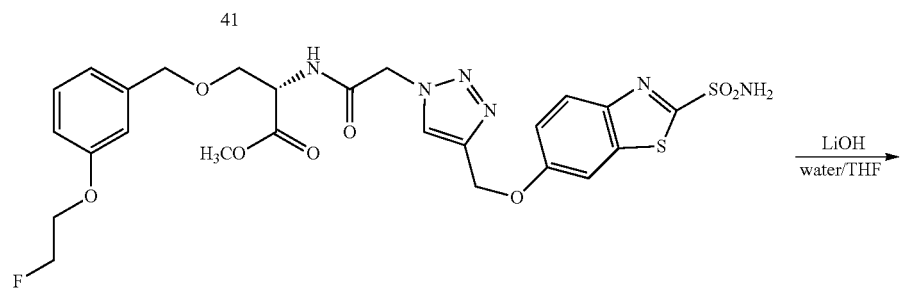
VM2131
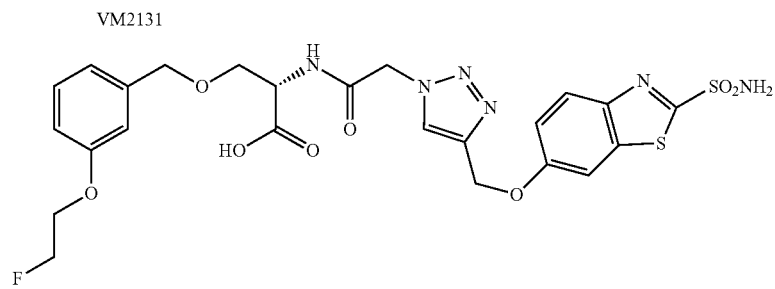
VM2133
Alternate procedure:
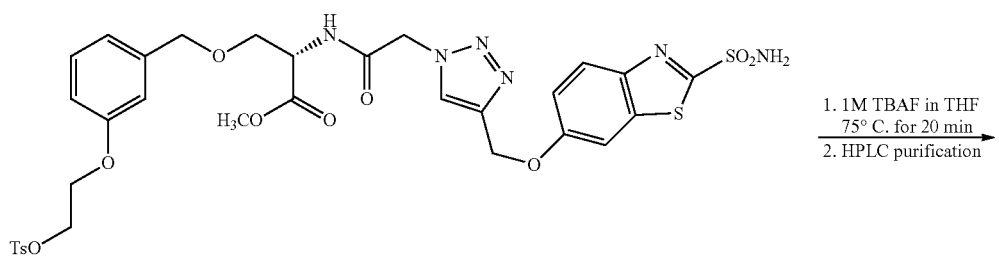
36
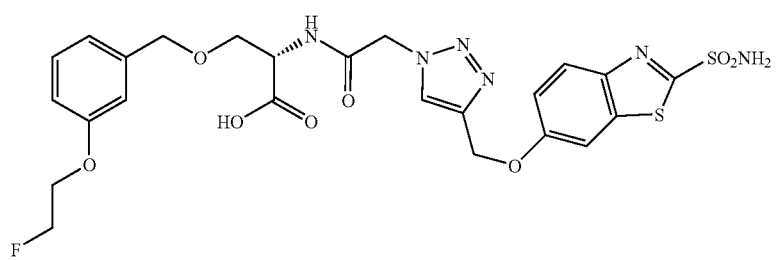
VM2133

Preparation of (3-(2-fluoroethoxy)phenyl)methanol (37)

General procedure for alkylation of phenol (A) was followed. Performed on a 10 g scale using $K_2CO_3$ as base. Isolated 37 as a brown oil after work up (13 g, 95% yield).

Preparation of 3-(2-fluoroethoxy)benzyl 4-methylbenzenesulfonate (38)

General experimental procedure for tosylation (D) was followed. Performed on a 12 g scale. Product eluted out in 30% EtOAc:Hexanes mixture in a gradient elution on a Combiflash purification system. Isolated 38 (14.2 g, 62% yield) as a yellow oil.
MS: $[M+Na]^+$: 347.1

Preparation of (S)-2-(tert-butoxycarbonylamino)-3-(3-(2-fluoroethoxy)benzyloxy)-propanoic acid (39)

General experimental procedure for alkylation (F) was followed. Performed on a 10 g scale. Adjusted pH to 3-4. Product eluted out in 45% EtOAc:Hexanes mixture in a gradient elution on a Combiflash purification system. Isolated 39 (pure 6.2 g, 36%) as a thick yellowish oil.
MS: $[M+Na]^+$: 380.1, $[M-Boc]^+$: 258.1

Preparation of (S)-methyl 2-amino-3-(3-(2-fluoroethoxy)benzyloxy)propanoate (40)

General experimental procedure for esterification of acids (G) and deprotection (B) was followed. Performed on 3 g of Boc-acid. Isolated 40 (2.25 g, 100% yield) product as a colorless solid as the HCl salt. MS: $[M+Na]^+$: 294.0, $[M+H]^+$: 272.1

Preparation of (S)-methyl 2-(2-azidoacetamido)-3-(3-(2-fluoroethoxy)benzyloxy)-propanoate (41)

General experimental procedure for coupling (C) was followed. Performed on 0.125 g scale, $Et_3N$ as base and THF as solvent. Product eluted out in 51% EtOAc:Hexanes mixture in a gradient elution on a Combiflash purification system. Isolated 41 (0.27 g, 68%) as an off colorless solid. MS: $[M+H]^+$: 355.1

Preparation of (S)-methyl 3-(3-(2-fluoroethoxy)benzyloxy)-2-(2-(4-((2-sulfamoylbenzo[d]thiazol-6-yloxy)methyl)-1H-1,2,3-triazol-1-yl)acetamido)propanoate (VM2131)

General experimental procedure for click reaction (E) was followed. Performed on 0.09 g scale and 1.1 eq of base. Product eluted out in 96% EtOAc:Hexanes mixture in a gradient elution on a Combiflash purification system. Isolated VM2131 (0.074 g, 45%) as a colorless solid. MS: $[M+H]^+$: 623

Preparation of (S)-3-(3-(2-fluoroethoxy)benzyloxy)-2-(2-(4-((2-sulfamoyl benzo[d]thiazol-6-yloxy)methyl)-1H-1,2,3-triazol-1-yl)acetamido)propanoic acid (VM2133)

General experimental procedure for ester hydrolysis (K) was followed. Performed on 0.03 g scale. HPLC purification afforded (0.017 g, 55%) VM2133 as a colorless solid.
MS: $[M+H]^+$: 609.1

Preparation of (S)-3-(3-(2-fluoroethoxy)benzyloxy)-2-(2-(4-((2-sulfamoyl-benzo[d]thiazol-6-yloxy)methyl)-1H-1,2,3-triazol-1-yl)acetamido)propanoate (VM2133) starting from 36

General experimental procedure for fluorination (J) was followed. Performed on a 0.1 g scale. The reaction mixture purified by HPLC to afford VM2133 (30, 38%) as a colorless solid. $[M+H]^+$: 609.0
$^1$H NMR (400 MHz, Acetone-$d_6$) δ: 8.17 (s, 1H), 8.06 (br s, 1H), 8.03 (d, J=9.0 Hz, 1H), 7.90 (d, J=2.5 Hz, 1H), 7.39 (s, 2H), 7.32 (dd, J=9.0, 2.4 Hz, 1H), 7.27 (t, J=8.0 Hz, 1H), 6.97-6.88 (m, 3H), 5.37 (d, J=16.4 Hz, 1H), 5.34 (s, 2H), 5.33 (d, J=16.6 Hz, 1H), 4.84-4.82 (m, 1H), 4.76-4.70 (m, 2H), 4.55 (d, J=12.5 Hz, 1H), 4.52 (d, J=12.5 Hz, 1H), 4.32-4.30 (m, 1H), 4.25-4.23 (m, 1H), 3.98 (dd, J=9.6, 3.9 Hz, 1H), 3.78 (dd, J=9.6, 3.3 Hz, 1H).

Preparation of VM241 Precursor

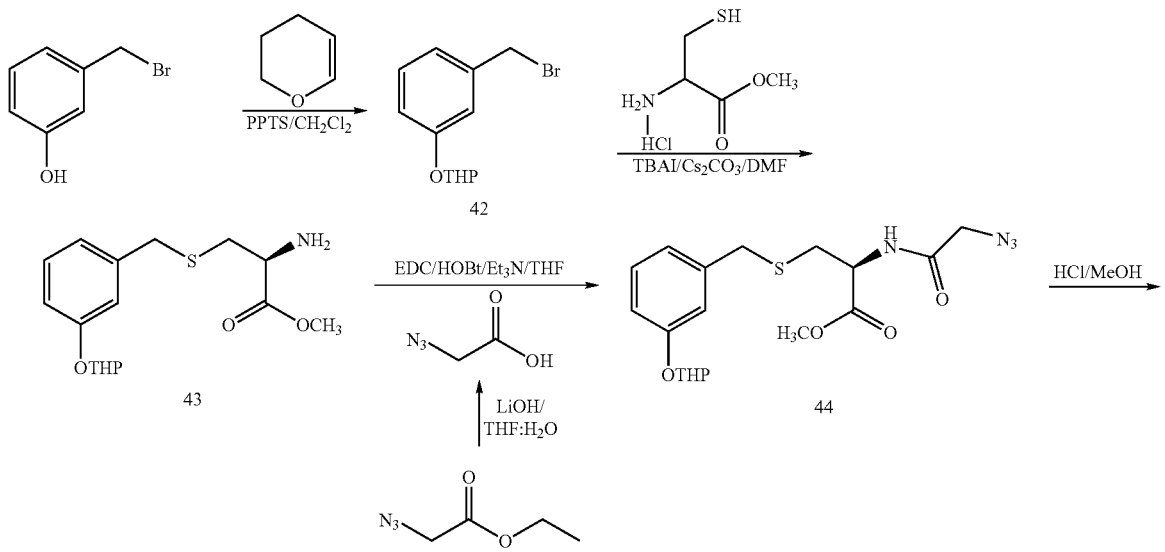

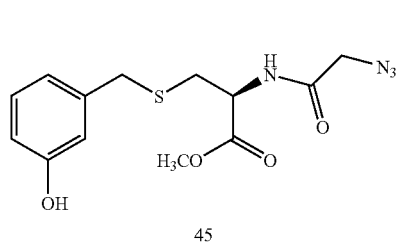
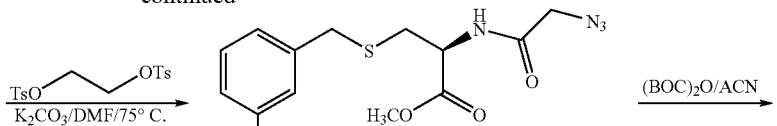

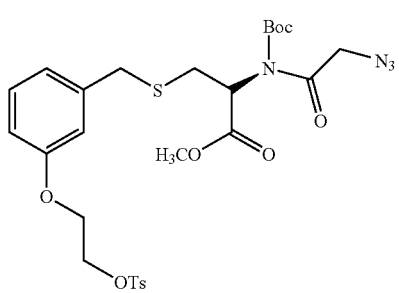
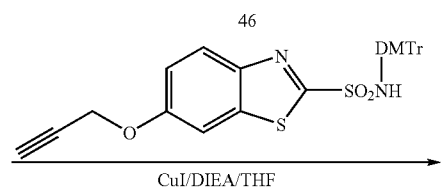

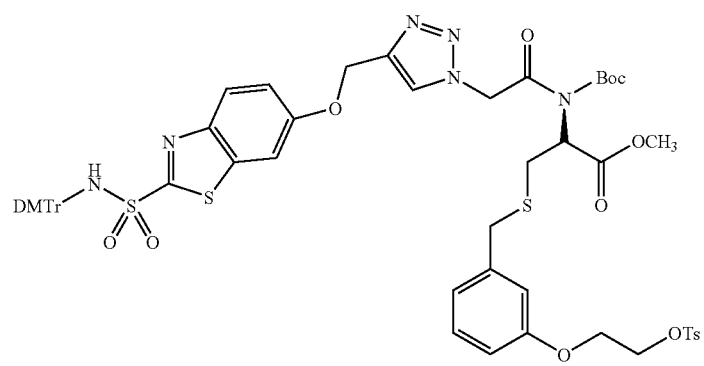

Preparation of Azido Acetic Acid

To a solution of ethyl azido acetate (30% by weight in dichloromethane, 63 g, 146 mmol, 1 equiv) in THF (90 ml) and water (90 ml), was added LiOH monohydrate (12.3 g, 293 mmol, 2 equiv). The reaction was stirred at room temperature for 2 h. Reaction was then quenched by slow addition of HCl (conc. 22.5 ml, 293 mmol, 2 equiv) at ice bath temperature. The mixture was stirred in ice bath for another 20 min and poured into a separation funnel. The aqueous layers was separated from organic layers, and extracted with dichloromethane (3×100 mL). The combined organic layers were washed with brine (2×40 mL). The organic layers was dried over MgSO$_4$ and filtered. The solution was carefully concentrated to remove 100-150 mL of dichloromethane under vacuum without heating to afford 2-azidoacetic acid solution in THF and dichloromethane (5.65% by weight (c.a.), 223 g, 125 mmol, 85% yield). $^1$H NMR (400 MHz, DMSO-d$_6$), δ: 13.16 (br s, 1H), 3.95 (s, 2H).

Preparation of 2-(3-(bromomethyl)phenoxy)tetrahydro-2H-pyran (42)

3-Hydroxybenzyl bromide (1.00 g, 5.35 mmol), DHP (0.89 g, 10.09 mmol), pyridinium-p-toluenesulfonate (0.20 g, 0.80 mmol) were dissolved in methylene chloride (20 mL) and stirred at room temperature for 5 h. The mixture was concentrated and chromatographed without workup. The product 42 was obtained as colorless oil (1.25 g, 87% yield).

Preparation of Methyl-2-amino-3-(3-(tetrahydro-2H-pyran-2-yloxy)benzylthio)propanoate (43)

To the cysteine methyl ester hydrochloride (0.63 g, 3.69 mmol) dissolved in DMF and cooled to 0° C., Cs$_2$CO$_3$ (1.21 g, 3.69 mmol) and tetrabutylammonium iodide (1.36 g, 3.69 mmol) were added and stirred. After 10 min, the ice bath was removed and the reaction mixture was allowed to react for 1 h at room temperature. It was then cooled to 0° C. and bromide (1.00 g, 3.69 mmol) was added. Ice bath was removed after 10 min and the mixture was allowed to react at room temperature. After 2 h, the reaction was quenched with water, extracted with ethyl acetate, washed with water, brine and dried over MgSO$_4$. After evaporation of the solvent, the reaction mixture was chromatographed (5% methanol/methylene chloride) to yield product 43 as thick colorless oil (0.74 g, 62% yield).

Preparation of Methyl 2-(2-azidoacetamido)-3-(3-(tetrahydro-2H-pyran-2-yloxy)benzylthio)propanoate (44)

General peptide coupling procedure (C) was followed. Azidoacetic acid (0.9 g of ~40% solution in THF/CH$_2$Cl$_2$), Et$_3$N and THF were used. After purification, 44 was isolated as colorless oil (0.89 g, 95% yield).

Preparation of Methyl 2-(2-azidoacetamido)-3-(3-hydroxybenzylthio)propanoate (45)

Few drops of conc. HCl (5 drops) were added to the 44 (0.25 g) in methanol and stirred for 30 min until no starting material was seen by LCMS. After evaporation of methanol, brine was added to the reaction mixture and extracted with ethyl acetate, dried over MgSO$_4$, concentrated and chromatographed (Hexanes/EtOAc) then 5% methanol/methylene chloride) to obtain the 0.2 g of 45 as colorless oil in quantitative yield.

Preparation of Methyl 2-(2-azidoacetamido)-3-(3-(2-(tosyloxy)ethoxy)benzylthio)propanoate (46)

Phenol (0.47 g, 1.45 mmol), Ethylene glycol ditosylate (1.62 g, 4.37 mmol) and K$_2$CO$_3$ (1.01 g, 7.27 mmol) were taken in a round bottom flask and dissolved in DMF (4 mL). The slurry was heated to 75° C. for 2 h. The reaction was then quenched with water, extracted with ethyl acetate. The organic layer washed several times with water followed by brine and dried over MgSO$_4$. After concentration and purification by flash chromatography (methylene chloride/ethyl acetate) 46 was obtained as light yellow colored oil (0.11 g).

Preparation of Methyl 2-(2-azido-N-(tert-butoxycarbonyl)acetamido)-3-(3-(2-(tosyloxy)ethoxy)benzylthio)propanoate (47)

To the amide 46 (0.11 g, 0.21 mmol) in acetonitrile (3 mL), Boc anhydride (0.07 g, 0.32 mmol) and DMAP (0.002 g, 0.011 mmol) were added. The reaction was allowed to stir at room temperature for 18 h. Solvent was evaporated and the reaction mixture purified by flash chromatography (Hexanes/ethyl acetate) to afford 47 as an oil (0.05 g).

Preparation of methyl 2-(2-(4-((2-(N-(bis(4-methoxyphenyl)(phenyl)methyl)sulfamoyl)benzo[d]thiazol-6-yloxy)methyl)-1H-1,2,3-triazol-1-yl)-N-(tert-butoxycarbonyl)acetamido)-3-(3-(2-(tosyloxy)ethoxy)benzylthio)propanoate (48)

General experimental procedure for click reaction (E) was followed. Performed on 0.046 g scale and 1.1 eq of base. Purified by Combiflash purification system using EtOAc: Hexanes as the gradient eluent. Isolated 48 (0.027 g) as a colorless solid.

MS: [M+H]$^+$: 1193.5

$^1$H NMR (400 MHz, Acetone-d$_6$) δ: 8.15 (s, 1H), 7.90 (d, J=9.0 Hz, 1H), 7.80 (d, J=8.2 Hz, 2H), 7.33 (d, J=2.4 Hz, 1H), 7.47-7.44 (m, 4H), 7.29-7.15 (m, 9H), 6.87 (d, J=8.0 Hz, 1H), 7.69 (t, J=2.4 Hz, 1H), 6.73-6.71 (m, 1H), 6.15 (d, J=9.0 Hz, 1H), 5.97 (d, J=18.2 Hz, 1H), 5.90 (d, J=18.2 Hz, 1H), 5.52-5.48 (m, 1H), 5.33 (s, 2H), 4.41-4.39 (m, 2H), 4.21-4.18 (m, 1H), 3.70 (s, 3H), 3.66 (s, 2H), 3.64 (s, 6H), 3.18 (dd, J=14.5, 5.5 Hz, 1H), 2.93 (dd, J=14.5, 9.6 Hz, 1H), 1.52 (s, 9H).

Preparation of VM241 Standard

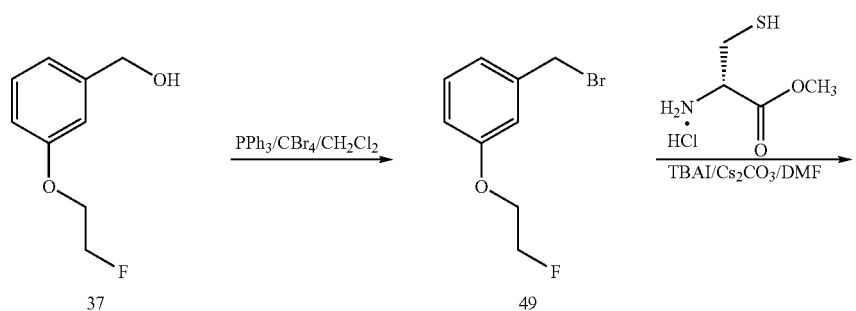

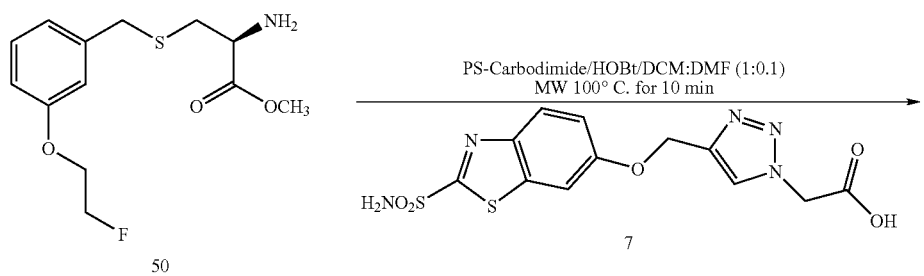

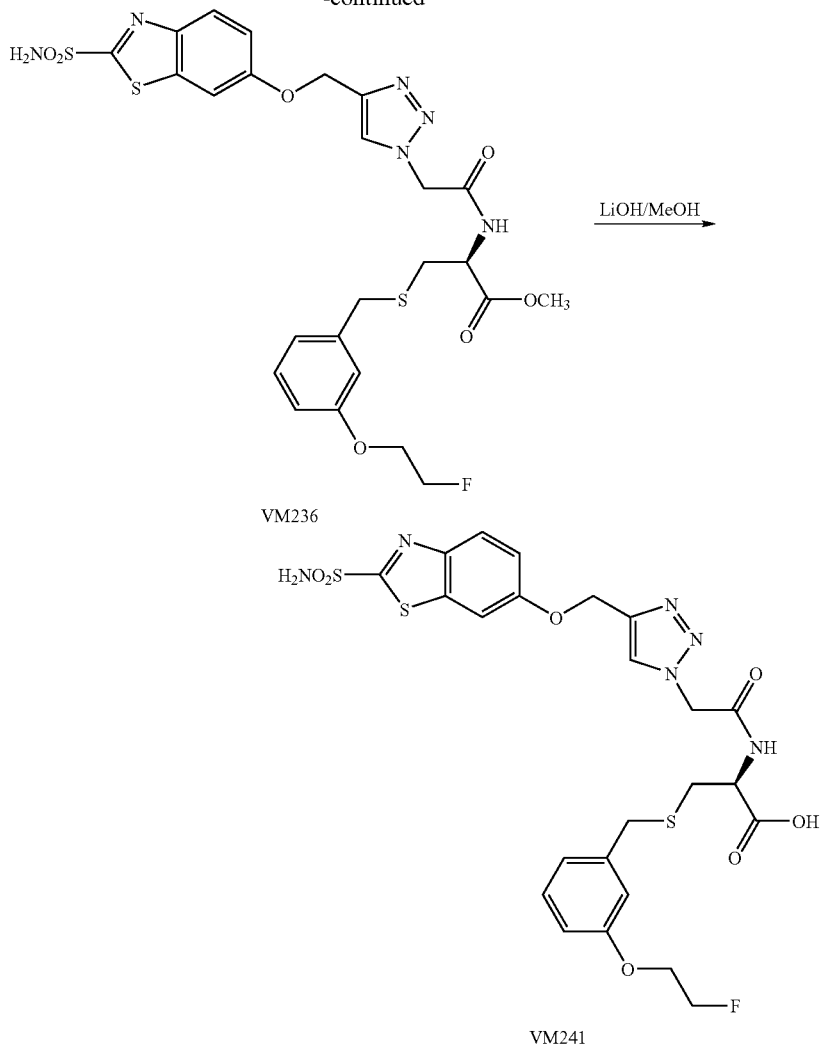

VM236

VM241

Preparation of 1-(bromomethyl)-3-(2-fluoroethoxy)benzene (49)

PPh$_3$ (3.08 g, 11.8 mmol) and CBr$_4$ (2.93 g, 8.82 mmol) were added to a solution of 37 (1.00 g, 5.88 mmol) in DCM (20 mL) under nitrogen and stirred at room temperature for 1 h. The reaction mixture was filtered, concentrated and chromatographed to isolate the 49 as a colorless solid (0.85 g, 62% yield).

Preparation of Methyl-2-amino-3-(3-(2-fluoroethoxy)benzylthio)propanoate (50)

To the L-cysteine methyl ester hydrochloride (0.037 g, 0.215 mmol) dissolved in DMF and cooled to 0° C., Cs$_2$CO$_3$ (0.069 g, 0.215 mmol) and tetrabutyl ammonium iodide (0.079 g, 0.215 mmol) were added and stirred. After 10 min, the ice bath was removed and the reaction mixture was allowed to react for 1 hr at room temperature. It was then cooled to 0° C. and bromide (0.05 g, 0.215 mmol) was added. Ice bath was removed after 10 min and the mixture was allowed to react at room temperature. After 2 h, the reaction was quenched with water, extracted with ethyl acetate, washed with water, brine and dried over MgSO$_4$. After evaporation of the solvent, the reaction mixture was chromatographed to yield 50 as thick colorless oil (0.025 g, 41% yield).

Preparation of Methyl 3-(3-(2-fluoroethoxy)benzylthio)-2-(2-(4-((2-sulfamoyl bezo[d]thazol-6-yloxy)methyl)-1H-1,2,3-triazol-1-yl)acetamido)propanoate (VM236)

General experimental procedure for coupling (O) was followed. Performed on 0.01 g scale and 1.1 eq of base. Purified by Combiflash purification system using EtOAc:Hexanes as the gradient eluent. Isolated VM236 (20%) as a colorless solid.

Preparation of Methyl 3-(3-(2-fluoroethoxy)benzylthio)-2-(2-(4-((2-sulfamoyl bezo[d]thazol-6-yloxy)methyl)-1H-1,2,3-triazol-1-yl)acetamido)propanoic acid (VM241)

General experimental procedure for ester hydrolysis (K) was followed. Reaction was carried out on a 0.008 g scale. Isolated VM241 (0.005 g, 64% yield) as a colorless solid. MS: [M+H]$^+$: 625.2

$^1$H NMR (400 MHz, Acetone-d$_6$) δ: 8.35 (s, 1H), 8.19 (d, J=9.0 Hz, 1H), 8.06 (d, J=2.5 Hz, 1H), 7.55 (s, 2H), 7.48 (dd, J=9.0, 2.5 Hz, 2H), 7.39 (t, J=7.8 Hz, 1H), 7.12-7.09 (m, 3H), 7.01-6.99 (m, 1H), 5.5 (s, 4H), 4.98-4.96 (m, 1H), 4.93-4.91 (m, 1H), 4.86-4.85 (m, 1H), 4.45-4.43 (m, 1H), 4.38-4.36 (m, 1H), 3.94 (s, 2H), 3.16 (dd, J=14.1, 5.1 Hz, 1H), 2.91 (dd, J=14.2, 5.2 Hz, 1H).

VM4037 Nosylate Precursor:
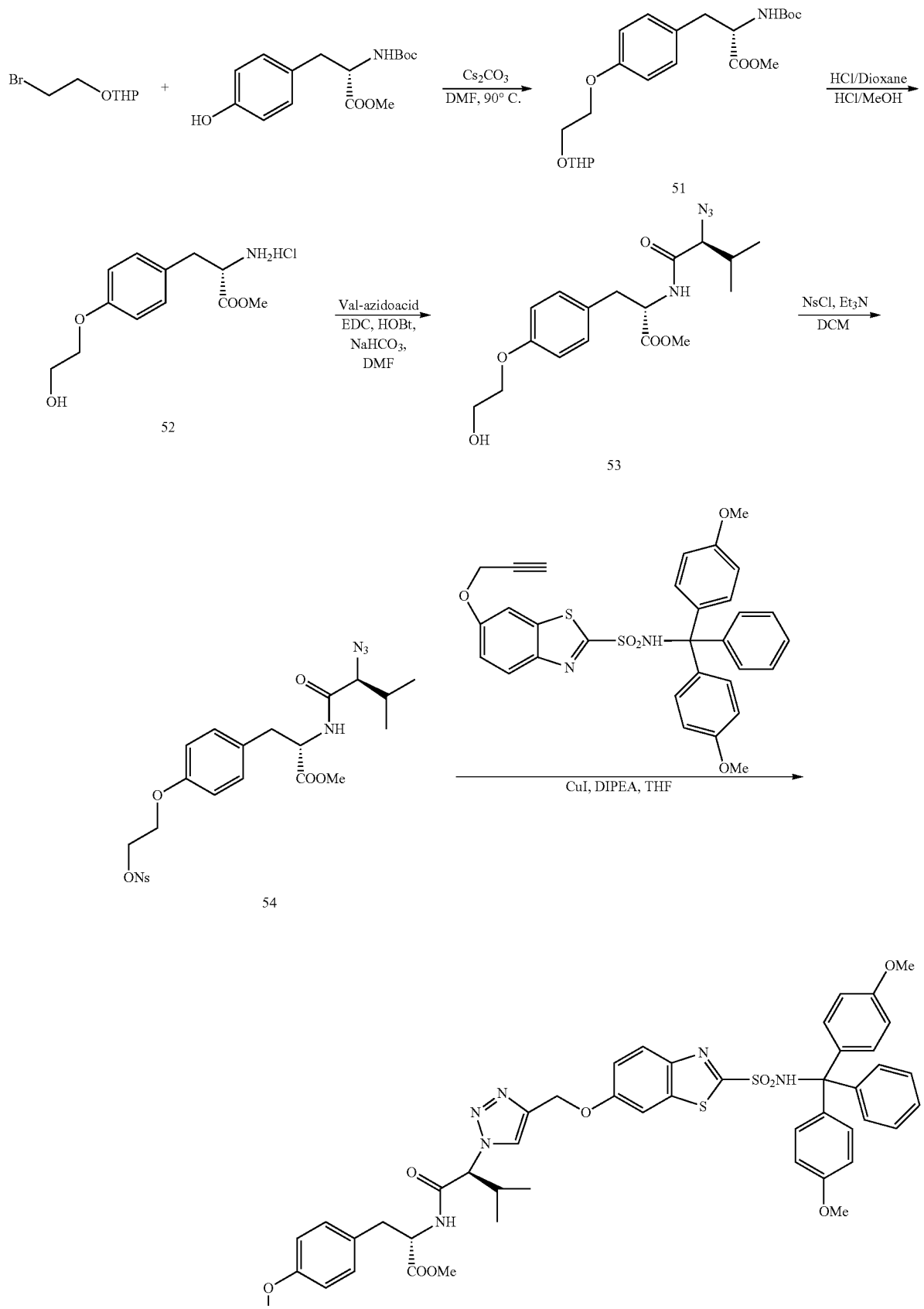

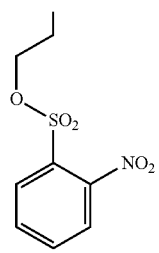

55

Preparation of (2S)-methyl 2-(tert-butoxycarbonylamino)-3-(4-(2-(tetrahydro-2H-pyran-2-yloxy)ethoxy)phenyl)propanoate (51)

General experimental procedure for phenolic alkylation (A) was followed. Reaction was performed on a 10 g scale. Product eluted out in 30% EtOAc:Hexanes mixture in a gradient elution on a Combiflash purification system. Isolated 13 g (91% yield) of 51 as a colorless oil. MS: [M+H]$^+$: 424.

Preparation of (S)-methyl 2-amino-3-(4-(2-hydroxyethoxy)phenyl)propanoate hydrochloride (52)

General experimental procedure for deprotection (B) was followed. Reaction was performed on a 13 g scale. Isolated 7.5 g (69% yield) of 52 as a colorless solid. MS: [M+H]$^+$: 240.

Preparation of (S)-methyl 2-((S)-2-azido-3-methylbutanamido)-3-(4-(2-hydroxy ethoxy)phenyl)propanoate (53)

General experimental procedure for coupling (C) was followed. Reaction was performed on a 5 g scale. Product eluted out in 50% EtOAc:Hexanes mixture in a gradient elution on a Combiflash purification system. Isolated 5.2 g (79% yield) of 53 as a colorless oil. MS: [M+H]$^+$: 365.

Preparation of (S)-methyl 2-((S)-2-azido-3-methylbutanamido)-3-(4-(2-(2-nitrophenylsulfonyloxy)ethoxy)phenyl)propanoate (54)

To a 100 mL round bottomed flask equipped with a magnetic stir bar containing DCM (100 mL) was placed 62 (1.3 g, 3.6 mmol). To this solution was added nosyl chloride (0.87 g, 3.9 mmol), Et$_3$N (0.4 g, 3.9 mmol) and the reaction was allowed to stir at room temperature for 15 h. After the reaction was complete, DCM was removed in vacuo. The residue was purified over silica gel using Hexanes:EtOAc (50:50) as the eluent to afford 54 (1.5 g, 77% yield) as a colorless oil. MS: [M+H]$^+$: 560.

Preparation of (S)-methyl 2-((S)-2-(4-((2-(N-(bis(4-methoxyphenyl) (phenyl)methyl)sulfamoyl)benzo[d]thiazol-6-yloxy)methyl)-1H-1,2,3-triazol-1-yl)-3-methylbutanamido)-3-(4-(2-(2-nitrophenylsulfonyloxy)ethoxy)phenyl)propanoate (55)

General experimental procedure for click reaction (E) was followed. Reaction was performed on a 0.34 g scale. Product eluted out in 90% EtOAc:Hexanes mixture in a gradient elution on a Combiflash purification system. Isolated 0.55 g (79% yield) of 55 as a colorless solid. MS: [M+H]$^+$: 1120.

Preparation of VM 4037a

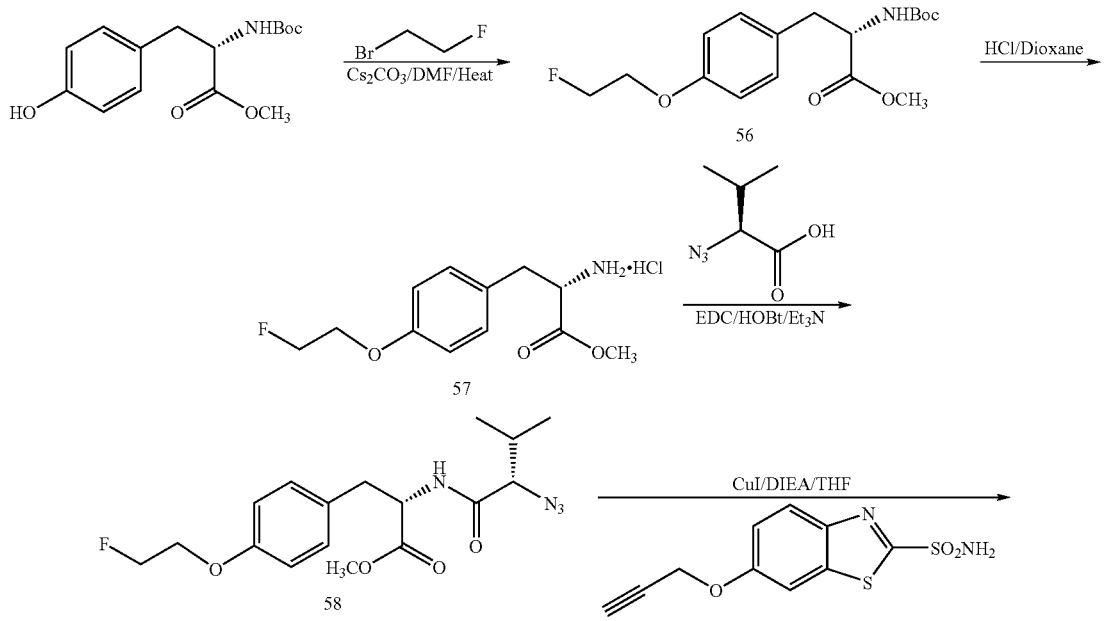

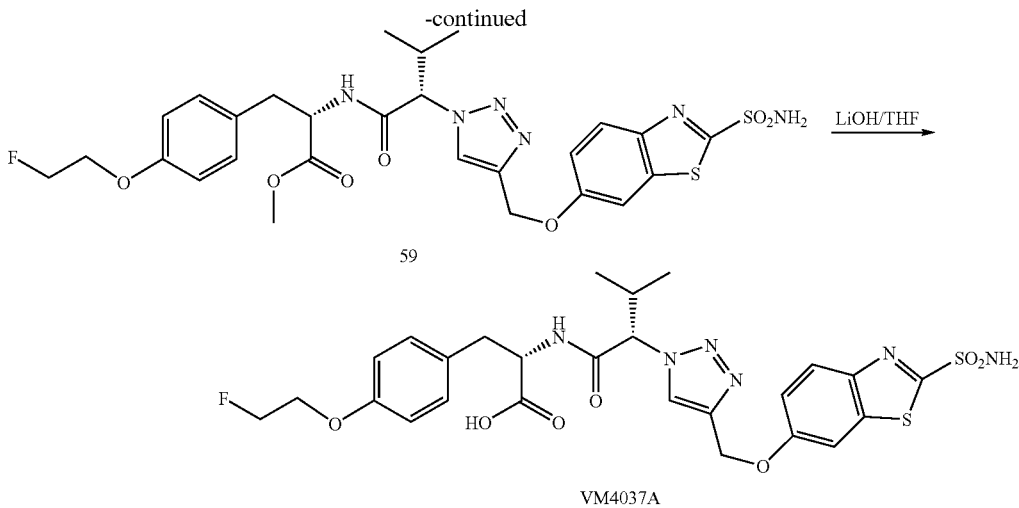

Preparation of (methyl 2-(tert-butoxycarbonylamino)-3-(4-(2-fluoroethoxy)phenyl)propanoate (56)

Compound 56 was prepared through general experimental procedure (A) and isolated 56 as a colorless solid (6 g scale, yield 80%). LRMS for $C_{17}H_{24}FNO_5+H^+$, calc'd: 342.2. found: 342.2 (M+H$^+$), 364.1 (M+Na).

$^1$H NMR (CDCl$_3$, 400 MHz) δ: 7.04 (d, J=8.8 Hz, 2H), 6.85 (d, J=8.8 Hz, 2H), 4.96 (d, J=8.4 Hz, 1H), 4.79-4.82 (m, 1H), 4.67-4.70 (m, 1H), 4.53-4.56 (m, 1H), 4.21-4.24 (m, 1H), 4.09-4.17 (m, 1H), 3.72 (s, 3H), 3.00-3.05 (m, 2H), 1.42 (s, 9H).

Preparation of methyl 2-amino-3-(4-(2-fluoroethoxy)phenyl)propanoate hydrochloride (57)

57 was prepared through general experimental procedure (B) and isolated as a colorless solid (5.5 g scale, yield 99%). LRMS for $C_{12}H_{16}FNO_3+H^+$, calc'd: 242.2. found: 242.2 (M+H$^+$).

Preparation of (S)-methyl 2-((S)-2-azido-3-methylbutanamido)-3-(4-(2-fluoroethoxy)phenyl)propanoate (58)

Compound 58 was prepared through general experimental procedure (C) and isolated as a colorless solid (4.5 g scale, yield 72%). LRMS for $C_{17}H_{23}FN_4O_4+H^+$, calc'd: 367.2. found: 367.2 (M+H$^+$).

$^1$H NMR (400 MHz, DMSO-d$_6$) δ: 8.60 (br s, 1H), 7.12 (d, J=8.8 Hz, 2H), 6.82 (d, J=8.4 Hz, 2H), 4.75-4.60 (m, 2H), 4.45-4.40 (m, 1H), 4.20-4.10 (m, 2H), 3.56 (s, 3H), 3.44 (d, J=8.0 Hz, 1H), 3.00-2.80 (m, 2H), 2.00-1.90 (m, 1H); 0.84 (d, J=2.0 Hz, 3H), 0.82 (d, J=2.0 Hz, 3H).

Preparation of (S)-methyl 3-(4-(2-fluoroethoxy)phenyl)-2-((S)-3-methyl-2-(4-((2-sulfamoylbenzo[d]thiazol-6-yloxy)methyl)-1H-1,2,3-triazol-1-yl)butanamido) propanoate (59)

Compound 59 was prepared through general experimental procedure (E) and isolated as a colorless solid (4.1 g scale, yield 98%). LRMS for $C_{27}H_{31}FN_6O_7S_2+H^+$, calc'd: 635.2. found: 635.2 (M+H$^+$).

$^1$H NMR (400 MHz, DMSO-d$_6$) δ: 9.05 (br s, 1H), 8.31 (s, 1H), 8.27 (s, 2H), 8.05 (d, J=9.2 Hz, 1H), 7.96 (d, J=2.8 Hz, 1H), 7.36 (m, 1H), 7.06 (d, J=8.8 Hz, 2H), 6.78 (d, J=8.4 Hz, 2H), 5.24 (s, 2H), 5.06 (d, J=9.2 Hz, 1H), 4.75-4.60 (m, 2H), 4.42-4.40 (m, 1H), 4.21-4.10 (m, 2H), 3.58 (s, 3H), 3.00-2.80 (m, 2H), 2.40-2.30 (m, 1H); 0.98 (d, J=6.0 Hz, 3H) 0.63 (d, J=6.0 Hz, 3H).

Preparation of (S)-3-(4-(2-fluoroethoxy)phenyl)-2-((S)-3-methyl-2-(4-((2-sulfamoylbenzo[d]thiazol-6-yloxy)methyl)-1H-1,2,3-triazol-1-yl)butanamido) propanoic acid (4037a)

VM-4037a was prepared through general experimental procedure (K) and isolated as a colorless solid (7.0 g scale, yield 60%). LRMS for $C_{26}H_{29}FN_6O_7S_2+H^+$, calc'd: 621.2. found: 621.2 (M+H$^+$).

$^1$H NMR (400 MHz, DMSO-d$_6$) δ: 8.90 (br s, 1H), 8.26 (s, 1H), 8.24 (s, 2H), 8.01 (d, J=9.2 Hz, 1H), 7.92 (d, J=2.4 Hz, 1H), 7.30 (m, 1H), 6.99 (d, J=9.2 Hz, 2H), 6.72 (d, J=8.4 Hz, 2H), 5.20 (s, 2H), 5.03 (d, J=9.6 Hz, 1H), 4.70-4.58 (m, 2H), 4.38-4.30 (m, 1H), 4.17-4.07 (m, 2H), 2.95-2.75 (m, 2H), 2.40-2.30 (m, 1H); 0.93 (d, J=6.0 Hz, 3H) 0.58 (d, J=6.0 Hz, 3H).

$^{13}$C NMR (100 MHz, DMSO-d$_6$) δ: 173.0, 168.0, 167.2, 158.9, 158.6, 158.1, 157.4, 146.9, 142.8, 138.0, 129.9, 125.6, 124.5, 118.6, 118.4, 115.5, 114.8, 106.6, 83.6, 82.0, 69.0 (d), 67.3 (d), 62.3, 54.5, 36.3, 31.9, 19.3. $^{19}$F NMR (376 MHz, DMSO-d$_6$) δ: −222.4.

Preparation of VM4041 Precursor

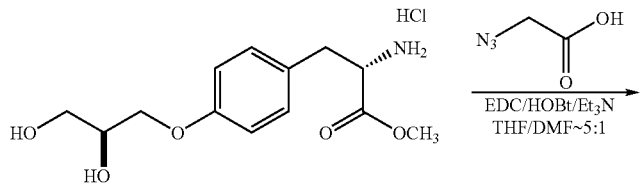

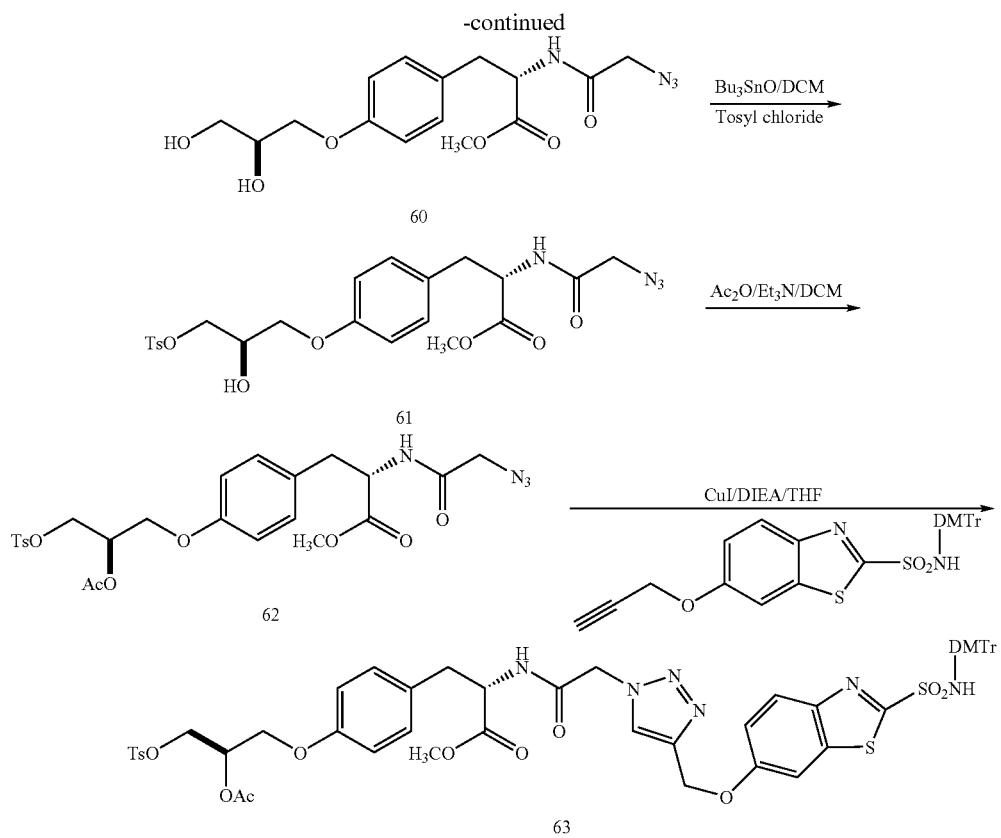

Preparation of (S)-methyl 2-(2-azidoacetamido)-3-(4-(2,3-dihydroxypropoxy)phenyl) propanoate (60)

Coupling reaction was done according to the general procedure (C). Performed on a 0.8 g scale using glycine azido acid and triethyl amine as base. EtOAc:Hexanes (95:5) used as the eluent. Product 60 was isolated (0.52 g, 60%) as a colorless solid. MS: [M+H]$^+$: 353.4

Preparation of (S)-methyl 2-(2-azidoacetamido)-3-(4-(2-hydroxy-3-(tosyloxy)propoxy)-phenyl)propanoate (61)

Tosylation was done according to the general procedure (H). Performed on a 0.5 g scale. EtOAc: Product eluted out in 50% EtOAc:Hexanes mixture in a gradient elution on a Combiflash purification system. 61 was isolated as colorless oil in 88% yield. MS: [M+H]$^+$: 507.1

Preparation of (S)-methyl 3-(4-(2-acetoxy-3-(tosyloxy)propoxy)phenyl)-2-(2-azido acetamido)propanoate (62)

Acetylation was done according to the general procedure (I). Performed on a 0.6 g scale. Product eluted out in 55% EtOAc:Hexanes mixture in a gradient elution on a Combiflash purification system. 62 isolated as a colorless oil in 95% yield. LCMS for $C_{24}H_{28}N_4O_9S$, calc'd: 548.16. found: 549.1 (M+H).

Preparation of (S)-methyl 3-(4-(2-acetoxy-3-(tosyloxy)propoxy)phenyl)-2-(2-(4-(2-(N-(bis(4-methoxyphenyl)(phenyl)methyl)sulfamoyl)benzo[d]thiazol-6-yloxy)methyl)-1H-1,2,3-triazol-1-yl)acetamido) propanoate (63)

Click reaction was done according to the general procedure (E). Performed on a 0.6 g scale and 1.1 eq of base. Product eluted out in 80% EtOAc:Hexanes mixture in a gradient elution on a Combiflash purification system. 63 was obtained (1.0 g, 87%) as a yellow solid. MS: [M+Na]$^+$: 1141.2
$^1$H NMR (400 MHz, Acetone-d$_6$) δ: 8.09 (s, 1H), 7.92 (d, J=9.0 Hz, 1H), 7.86-7.80 (m, 3H), 7.74 (d, J=2.5 Hz, 1H), 7.50-7.45 (m, 4H), 7.30-7.10 (m, 9H), 6.80 (d, J=8.6 Hz, 2H), 6.63 ((d, J=9.0 Hz, 4H), 5.32 (s, 2H), 5.32-5.29 (m, 1H), 5.25 (s, 2H), 4.74-4.69 (m, 1H), 4.36 (d, J=4.5 Hz, 2H), 4.10 (t$_{br}$, J=4.3 Hz, 2H), 3.68 (s, 3H), 3.65 (s, 6H), 3.10 (dd, J=25.5, 13.9 Hz, 1H), 2.98 (dd, J=13.9, 7.6 Hz, 1H), 1.98 (s, 3H).

Preparation of VM4041 Standard

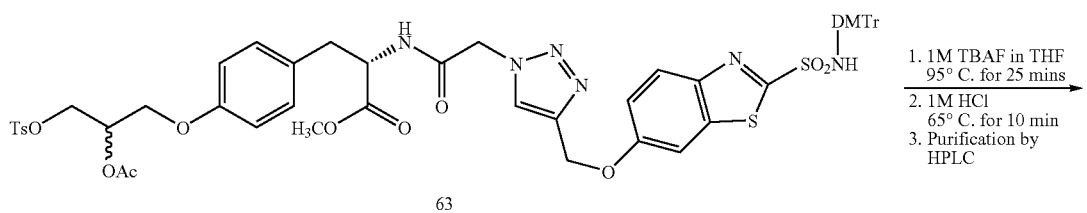

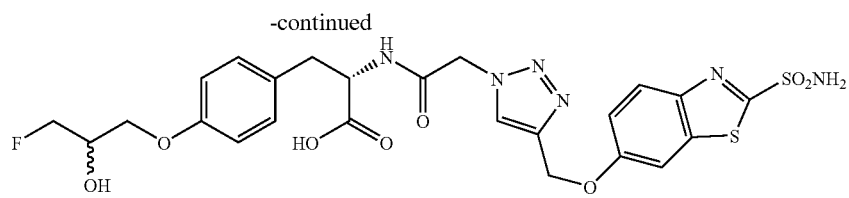

VM4041

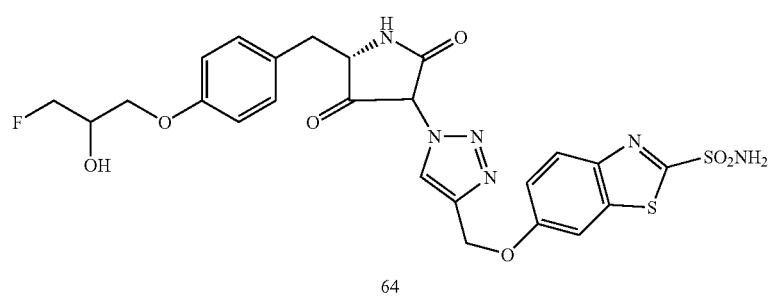

64

Preparation of (S)-3-(4-(3-fluoro-2-hydroxypropoxy) phenyl)-2-(2-(4-((2-sulfamoyl benzo[d]thiazol-6-yloxy)methyl)-1H-1,2,3-triazol-1-yl)acetamido)propanoic acid (VM4041)

General experimental procedure for fluorination (J) was followed. Performed on a 0.1 g scale. The reaction mixture purified by HPLC to afford two compounds (64 and VM4041) (yield not determined) as colorless solids.

MS: (VM4041) [M+H]$^+$: 609.1
MS: (compound 64) [M+H]$^+$: 591.1
VM4041: $^1$H NMR (400 MHz, Acetone-d$_6$) δ: 8.11 (s, 1H), 8.03 (d, J=9.2 Hz, 1H), 7.91 (d, J=2.5 Hz, 1H), 7.76 (d, J=7.2 Hz, 1H), 7.33 (dd, J=9.0, 2.5 Hz, 1H), 7.15 (d, J=8.6 Hz, 2H), 6.87 (d, J=8.6 Hz, 2H), 5.34 (s, 2H), 5.24 (s, 2H), 4.73-4.68 (m, 1H), 4.57-4.67 (m, 1H), 4.50 (dq, J=9.6, 3.9 Hz, 1H), 4.23-4.14 (m, 1H), 4.04-4.02 (m, 2H), 3.15 (dd, J=14.1, 5.3 Hz, 1H), 3.01 (dd, J=13.9, 7.6 Hz, 1H).

Preparation of VM4021

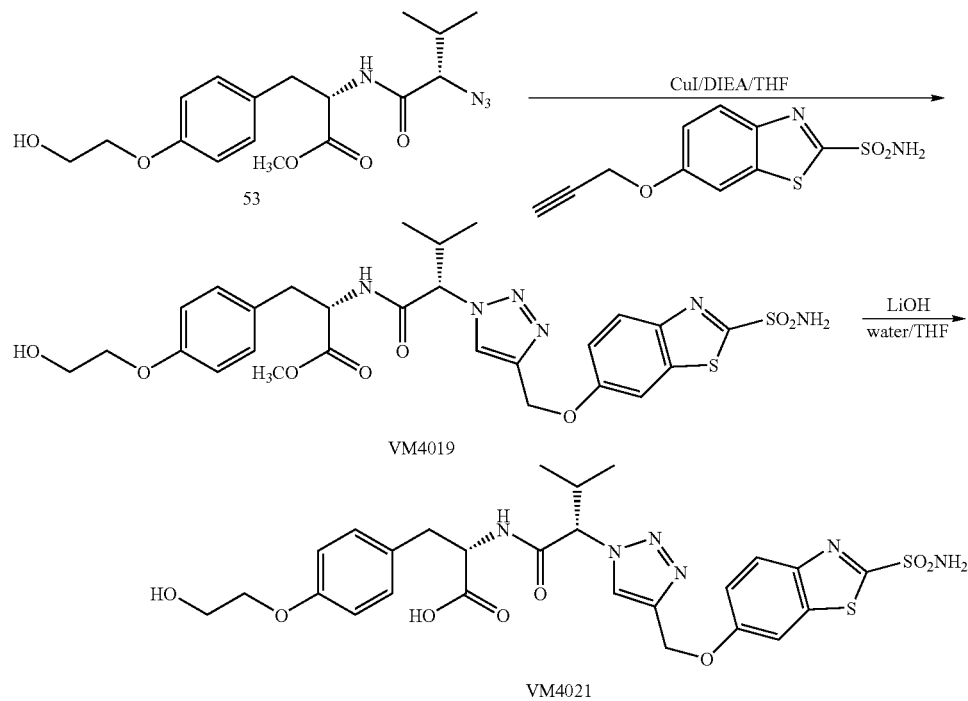

Preparation of (S)-methyl3-(4-(2-hydroxyethoxy) phenyl)-2-((S)-3-methyl-2-(4-((2-sulfamoylbenzo[d] thiazol-6-yloxy)methyl)-1H-1,2,3-triazol-1-yl)butanamido) propanoate (64)

Click reaction was done according to the general procedure (E). Performed on a 0.05 g scale. The reaction was not purified by chromatography rather triturated with ether/EtOAc mixture after removal of THF from the reaction mixture. Isolated 0.05 g, (58%) of 64 greenish solid. MS: [M+H]$^+$: 633.5

Preparation of (S)-3-(4-(2-hydroxyethoxy)phenyl)-2-((S)-3-methyl-2-(4-((2-sulfamoyl benzo[d]thiazol-6-yloxy)methyl)-1H-1,2,3-triazol-1-yl)butanamido) propanoic acid (VM4021)

Hydrolysis was done using the general procedure (K). After HPLC purification, the product was obtained as colorless solid. The yield was not calculated. MS: [M+H]$^+$: 619.1.

$^1$H NMR (400 MHz, Acetone-d$_6$) δ: 8.12 (br s, 1H), 8.03 (d, J=9.0 Hz, 1H), 8.00 (d, J=7.6 Hz, 1H), 7.92 (d, J=2.5 Hz, 1H), 7.39 (s, 1H), 7.34 (dd, J=9.0, 2.5 Hz, 1H), 6.98 (d, J=8.6 Hz, 2H), 6.72 (d, J=8.8 Hz, 2H), 5.35 (s, 2H), 5.12 (d, J=10.0 Hz, 1H), 4.74-4.69 (m, 1H), 3.98 (t, J=4.7 Hz, 2H), 3.83 (t, J=9.6 Hz, 2H), 3.12 (dd, J=14.1, 5.3 Hz, 1H), 2.95 (dd, J=13.9, 7.8 Hz, 1H), 2.49-2.43 (m, 1H), 1.04 (d, J=6.7 Hz, 3H), 0.68 (d, J=6.6 Hz, 3H).

Preparation of VM4009

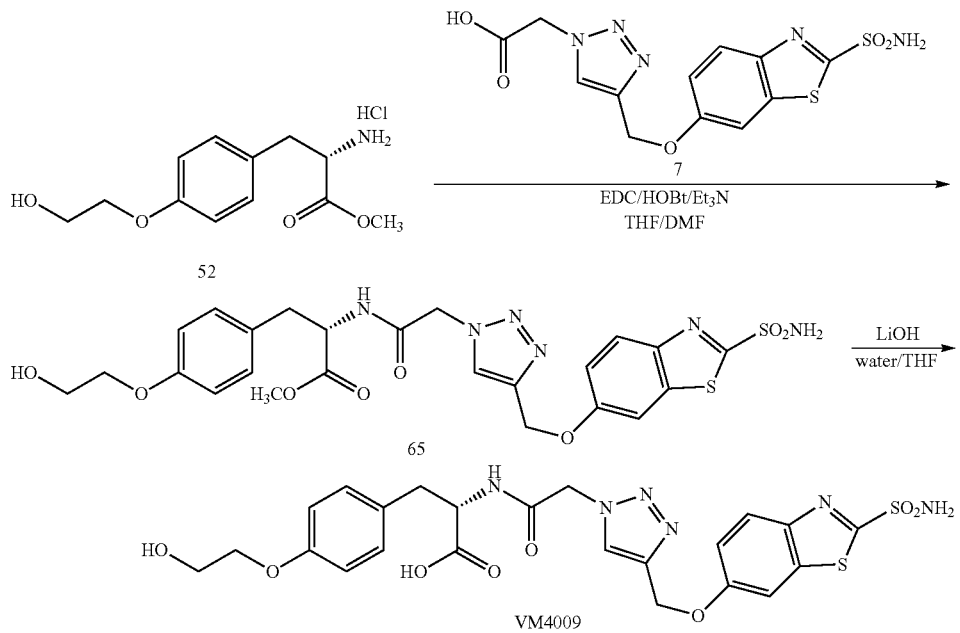

Preparation of (S)-methyl 3-(4-(2-hydroxyethoxy)phenyl)-2-(2-(4-((2-sulfamoyl benzo[d]thiazol-6-yloxy)methyl)-1H-1,2,3-triazol-1-yl)acetamido)propanoate (65)

Coupling reaction was done according to the general procedure (C). Performed on 0.1 g scale, using Et$_3$N as base and THF/DMF as solvent (5:1). During the work up, the solid that was not soluble, was also collected and mixed along with the organic layer. After evaporation, the residue was carried over to the next step, hydrolysis without further purification. The yield was not determined. MS: [M+H]$^+$: 591.2

Preparation of (S)-3-(4-(2-hydroxyethoxy)phenyl)-2-(2-(4-((2-sulfamoyl benzo[d]thiazol-6-yloxy)methyl)-1H-1,2,3-triazol-1-yl)acetamido)propanoic acid (VM4009)

Hydrolysis was done using the general procedure (K). After HPLC purification, the product was obtained as colorless solid. Yield not calculated. MS: [M+H]$^+$. found: 577.0

$^1$H NMR (400 MHz, Acetone-d$_6$) δ: 8.09 (s, 1H), 8.03 (d, J=9.0, Hz, 1H), 7.92 (d, J=2.5 Hz, 1H), 7.70 (d, J=8.0 Hz, 1H), 7.38 (s, 1H), 7.34 (dd, J=9.0, 2.5 Hz, 1H), 7.14 (d, J=8.4 Hz, 2H), 7.85 (d, J=8.8 Hz, 2H), 5.34 (s, 2H), 5.25 (s, 2H), 4.75-4.70 (m, 1H), 4.04-4.02 (m, 2H), 3.84 (m, 2H), 3.15 (dd, J=14.1, 5.3 Hz, 1H), 3.00 (dd, J=14.1, 7.8 Hz, 1H).

Preparation of VM3167
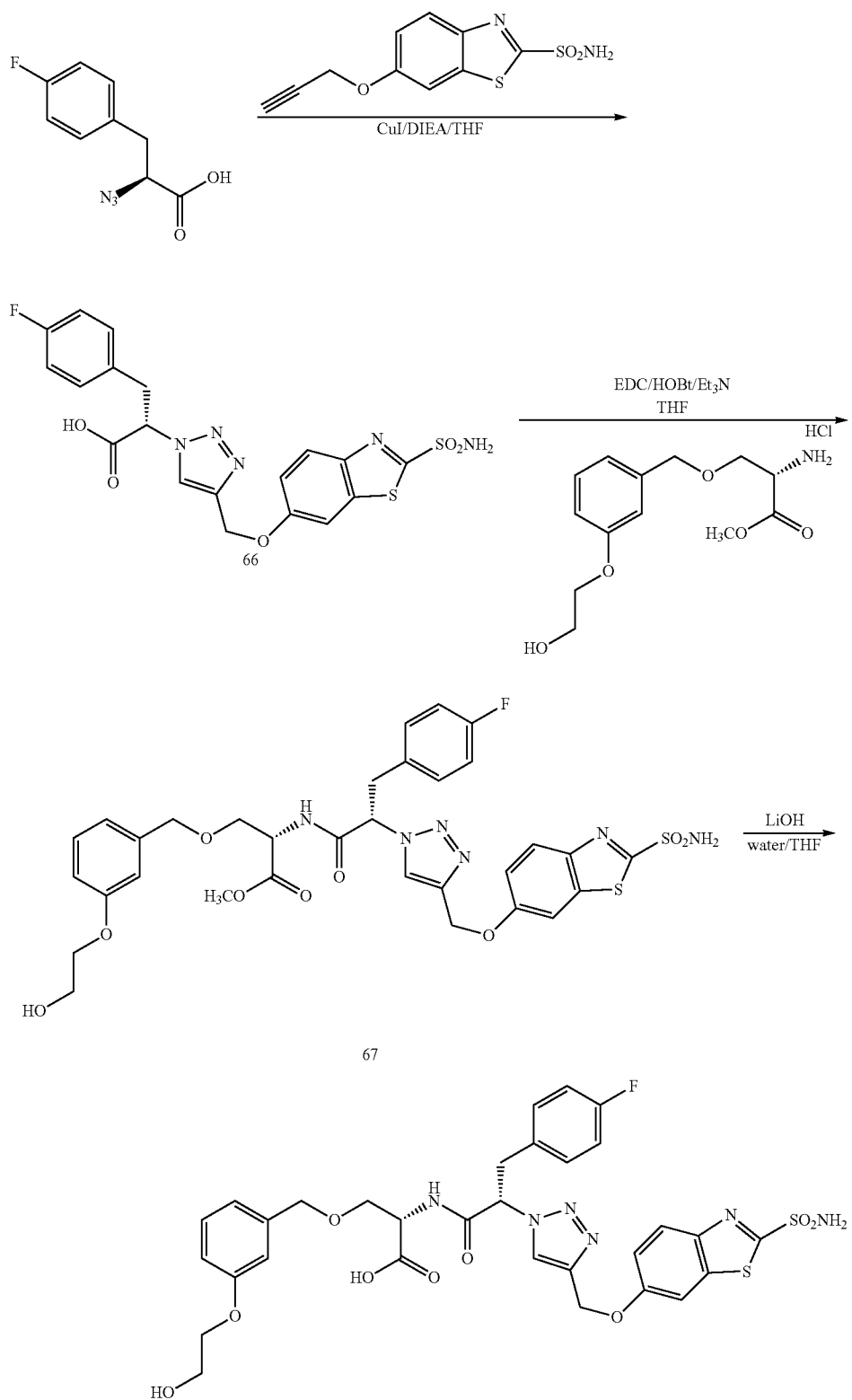

Preparation of (S)-3-(4-fluorophenyl)-2-(4-((2-sulfa-moylbenzo[d]thiazol-6-yloxy)methyl)-1H-1,2,3-triazol-1-yl)propanoic acid (66)

Click reaction was done with according to the general procedure (E). Performed on a 0.1 g scale. Reaction mixture was triturated with ether/EtOAc mixture after removal of THF under vacuum. Isolated 0.2 g (100%) of 66 as greenish solid. MS: [M+H]$^+$: 478.3

Preparation of (S)-methyl 2-((S)-3-(4-fluorophenyl)-2-(4-((2-sulfamoyl benzo[d]thiazol-6-yloxy)methyl)-1H-1,2,3-triazol-1-yl)propanamido)-3-(3-(2-hydroxyethoxy)benzyloxy)propanoate (67)

Coupling reaction was done with according to the general procedure (C). Product was isolated as colorless solid (yield not calculated) after chromatography. MS: [M+H]$^+$: 729.1

Preparation of (S)-2-((S)-3-(4-fluorophenyl)-2-(4-((2-sulfamoylbenzo[d]thiazol-6-yloxy)methyl)-1H-1,2,3-triazol-1-yl)propanamido)-3-(3-(2-hydroxyethoxy)benzyloxy)propanoic acid (VM4167A and VM4167B)

Hydrolysis of ester was done according the general procedure (K). Performed on a 0.03 g scale. After HPLC purification, two isomers (A:B, 2:1) were isolated as colorless solids in 73% overall yield. MS: [M+H]$^+$: 715.1

VM4167A: $^1$H NMR (400 MHz, Acetone-d$_6$) δ: 8.37 (s, 1H), 8.25 (d, J=8.3 Hz, 1H), 8.03 (d, J=9.0 Hz, 1H), 7.87 (d, J=2.5 Hz, 1H), 7.34 (s, 2H), 7.30 (dd, J=9.0, 2.5 Hz, 1H), 7.24-7.17 (m, 3H), 6.89-6.82 (m, 5H), 5.93 (dd, J=10.2, 5.5 Hz, 1H), 5.29 (s, 2H), 4.74-4.71 (m, 1H), 4.48 (s, 1H), 4.47 (s, 1H), 4.06 (t, J=4.7 Hz, 2H), 3.96 (dd, J=9.8, 4.1 Hz, 1H), 3.86 (t, J=5.1 Hz, 2H), 3.74 (dd, J=9.8, 3.3 Hz, 1H), 3.58 (dd, J=14.3, 5.5 Hz, 1H), 3.44 (dd, J=14.3, 10.2 Hz 1H).

VM4167B: $^1$H NMR (400 MHz, Acetone-d$_6$) δ: 8.36 (s, 1H), 8.21 (d, J=8.2 Hz, 2H), 8.03 (d, J=9.0 Hz, 2H), 7.88 (d, J=2.5 Hz, 2H), 7.39 (s, 2H), 7.31 (dd, J=9.2, 2.7 Hz, 1H), 7.26-7.21 (m, 3H), 6.95-6.84 (m, 5H), 5.91 (dd, J=9.4, 6.5 Hz, 1H), 5.31 (s, 2H), 4.73-4.69 (m, 1H), 4.46 (s, 2H), 4.05 (t, J=4.9 Hz, 2H), 3.93 (dd, J=9.6, 3.9 Hz, 1H), 3.84 (t, J=5.1 Hz, 2H), 3.64 (dd, J=9.6, 3.3 Hz, 1H), 3.55 (dd, J=13.0, 6.5 Hz, 1H), 3.44 (dd, J=14.1, 9.4 Hz, 1H).

Preparation of VM3165

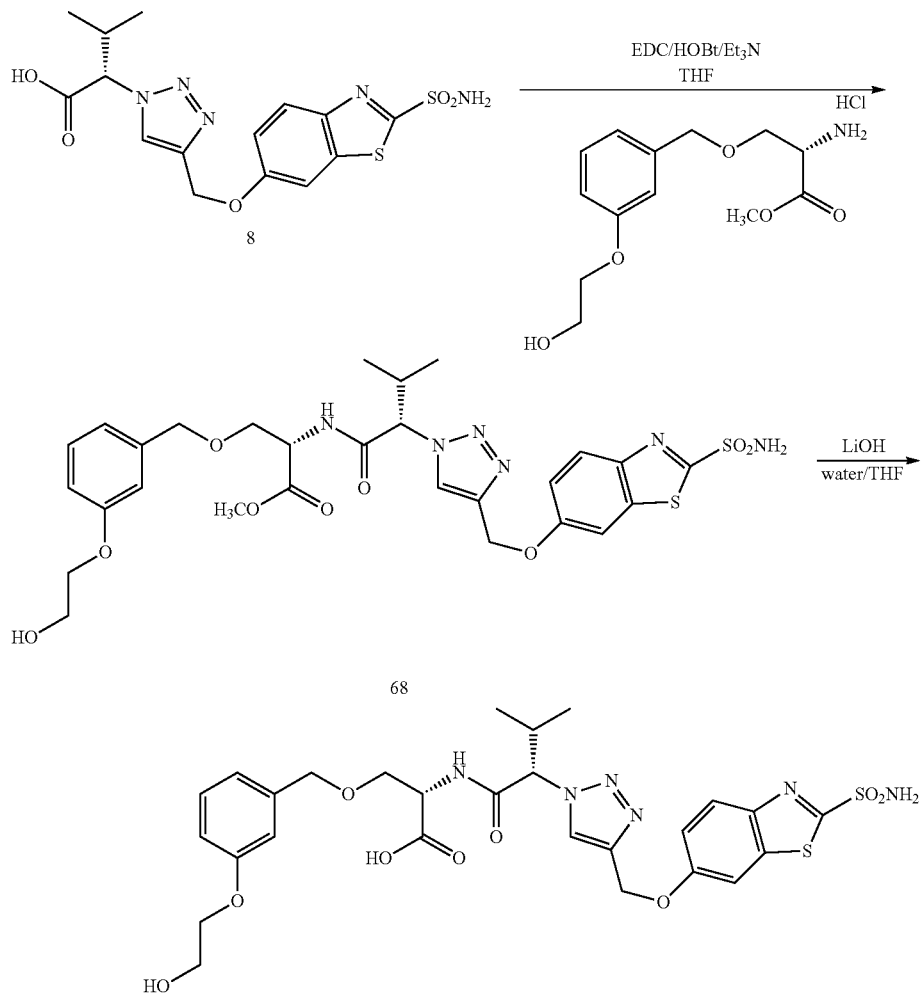

VM3165A and VM3165B

Preparation of (S)-methyl 3-(3-(2-hydroxyethoxy)
benzyloxy)-2-((S)-3-methyl-2-(4-((2-sulfamoyl-
benzo[d]thiazol-6-yloxy)methyl)-1H-1,2,3-triazol-1-
yl)butanamido) propanoate (68)

Coupling reaction was done according to the general procedure (C). Performed on a 0.12 g scale using Et₃N as base and THF as solvent. Product eluted out in 85% EtOAc:Hexanes mixture in a gradient elution on a Combiflash purification system. 68 was isolated as colorless solid (yield not calculated). MS: [M+H]⁺: 663.6

Preparation of (S)-3-(3-(2-hydroxyethoxy)benzyloxy)-2-((S)-3-methyl-2-(4-((2-sulfamoylbenzo[d]
thiazol-6-yloxy)methyl)-1H-1,2,3-triazol-1-yl)butanamido) propanoic acid (VM3165A and VM3165B)

Hydrolysis of ester was done according the general procedure (K). Performed on a 0.01 g scale. After HPLC purification, two isomers (A:B, 2:1) were isolated as colorless solids (A: 4.4 mg, B: 2.1 mg, 67% overall). MS: (A and B)[M+H]⁺: 649.1

VM3165B: ¹H NMR (400 MHz, Acetone-d₆) δ: 8.32 (s, 1H), 8.29 (s, 1H), 8.02 (d, J=9.0 Hz, 1H), 7.91 (d, J=2.5 Hz, 1H), 7.39 (s$_{br}$, 2H), 7.33 (dd, J=9.0, 2.5 Hz, 1H), 7.24 (t, J=7.8 Hz, 1H), 6.93-6.85 (m, 3H), 5.34 (s, 2H), 5.30 (d, J=9.8 Hz, 1H), 4.78-4.74 (m, 1H), 4.53 (s, 2H), 4.07 (t, J=4.7 Hz, 2H), 3.97 (dd, J=9.6, 4.3 Hz, 1H), 3.87 (t, J=5.1 Hz, 2H), 3.80 (dd, J=9.6, 3.3 Hz, 1H), 2.52-2.46 (m, 1H), 1.07 (d, J=6.7 Hz, 3H), 0.73 (d, J=6.7 Hz, 3H).

Preparation of VM3163

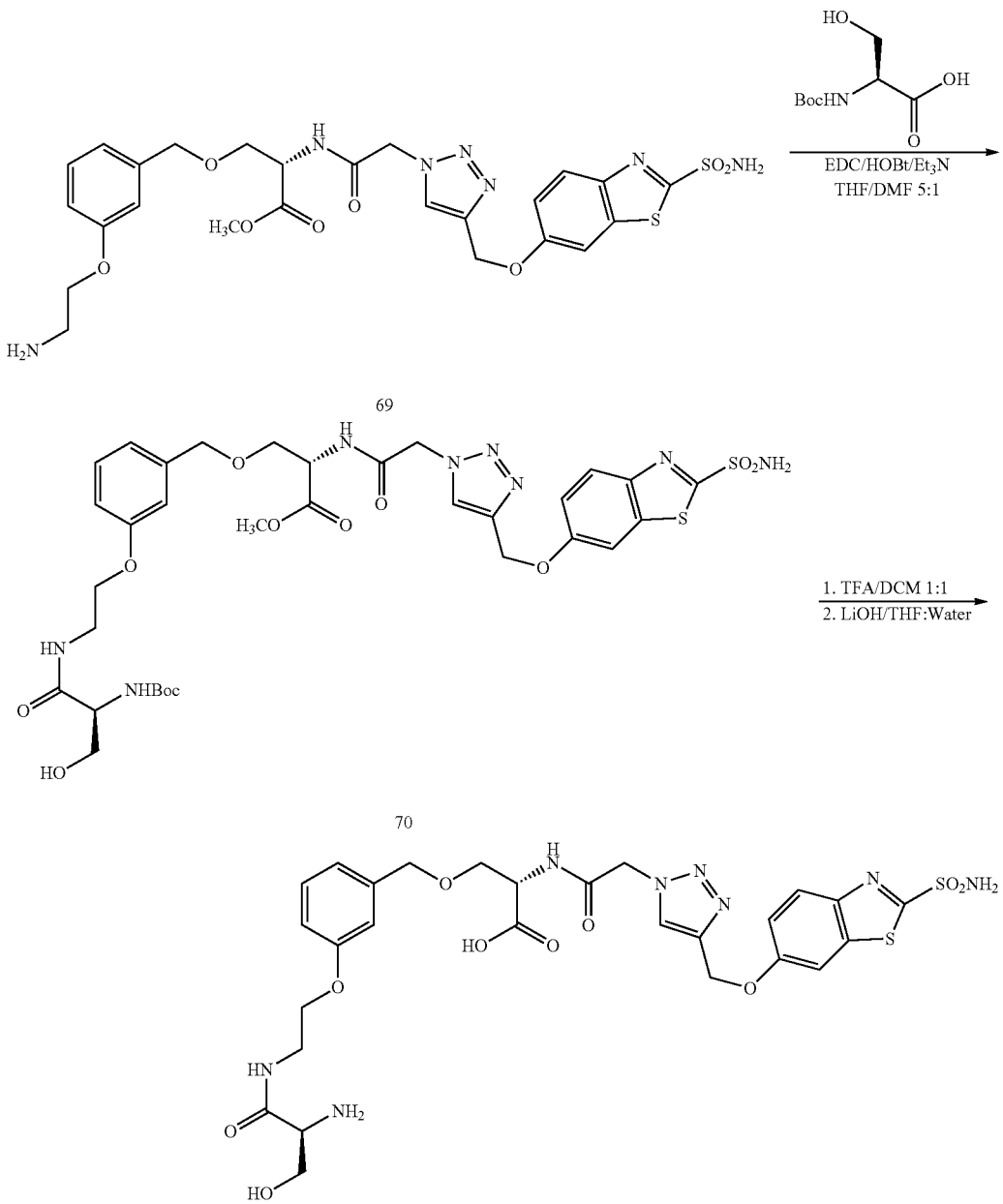

VM3163

Preparation of (S)-methyl 3-(3-(2-((S)-2-(tert-butoxycarbonylamino)-3-hydroxy propanamido)ethoxy)benzyloxy)-2-(2-(4-((2-sulfamoylbenzo[d]thiazol-6-yloxy)methyl)-1H-1,2,3-triazol-1-yl)acetamido)propanoate (70)

Coupling reaction was done with amine 69 and N-Boc serine according to the general procedure (C). Performed on a 0.02 g scale. Isolated 0.02 g (67%) of 70. MS: [M+H]$^+$: 707.1

Preparation of (S)-3-(3-(2-((S)-2-amino-3-hydroxypropanamido)ethoxy)benzyloxy)-2-(2-(4-((2-sulfamoylbenzo[d]thiazol-6-yloxy)methyl)-1H-1,2,3-triazol-1-yl)acetamido)propanoic acid (VM3163)

To a 10 mL vial with magnetic stir bar was added DCM (0.5 mL) and TFA (0.5 mL). To this, compound 70 was added and let to react for 30 min. After the completion of the reaction, solvents were removed in vacuo, THF was added (0.2 mL) followed by aq. LiOH (0.4 mL) and the reaction stirred for 30 min. After completion of the reaction, THF was removed and the crude residue was purified by HPLC to afford VM3163 (33%) as a colorless solid. LCMS for $C_{27}H_{32}N_8O_{10}S_2$, calc'd: 692.17. found: 693.0 (M+H).

Preparation of VM2126 and VM2128

Preparation of (S)-methyl 2-(2-azidoacetamido)-3-(3-(2-fluoroethoxy)benzylthio) propanoate (71)

General procedure for peptide coupling (C) was followed. Performed on 0.33 g scale, Et$_3$N as base and THF as solvent with 2 equiv of azido acid. Product eluted out in 55% EtOAc: Hexanes mixture in a gradient elution on a Combiflash purification system.

Isolated (0.42 g, 100%) of 71 as a colorless solid. MS: [M+H]$^+$: 371.1

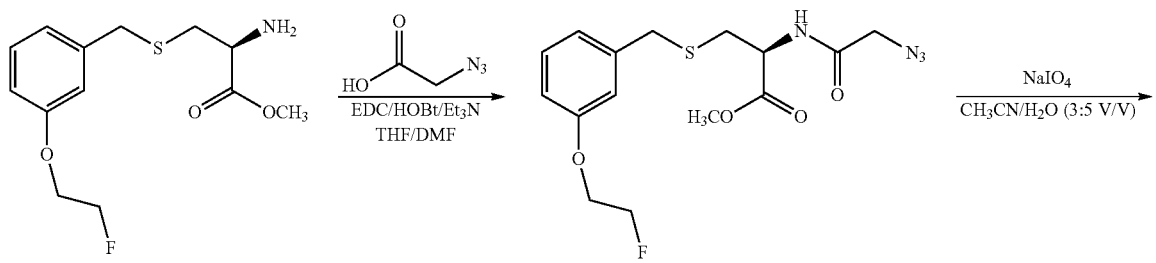

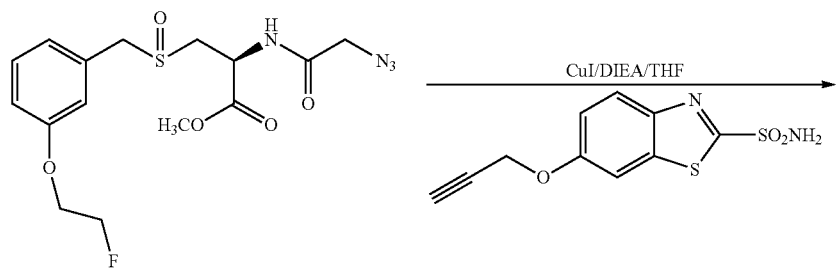

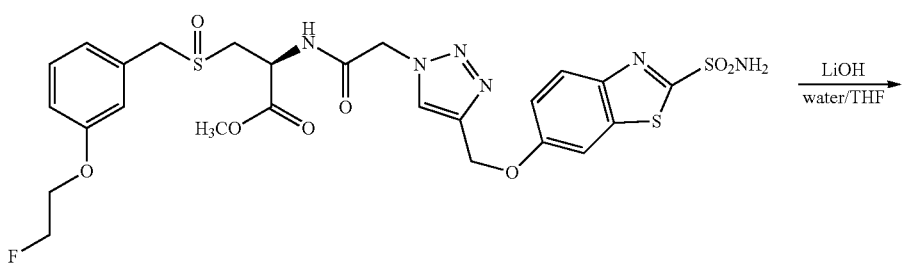

VM2126

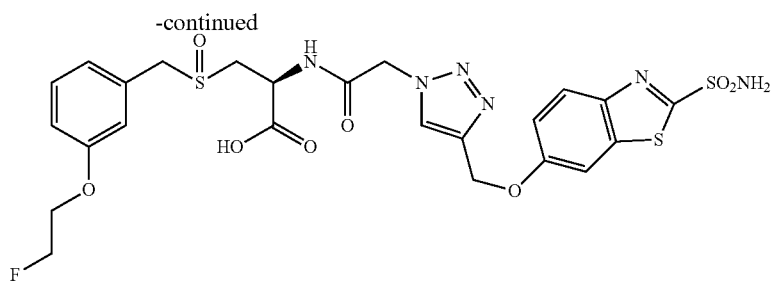

VM2128B and VM2128C

Preparation of (2S)-methyl 2-(2-azidoacetamido)-3-(3-(2-fluoroethoxy)benzyl sulfinyl)propanoate (72)

To a round bottomed flask equipped with a magnetic stir bar, rubber septum, and argon inlet containing acetonitrile/water (10 mL, 3:5 v/v) was placed thioether 71 (0.2 g, 0.54 mmol). To this solution was added sodium metaperiodate (0.23 g, 1.08 mmol) and the reaction was allowed to stir at room temperature for until deemed complete by LCMS (2-3 h). After the reaction was complete, the solvents were removed in vacuo. The reaction was then poured into water and extracted into EtOAc (4×20 mL). The combined organic extracts were washed with $H_2O$, brine, dried ($MgSO_4$) and concentrated in vacuo, to afford the final coupled product 72 (0.12 g, 58%) as colorless solid. MS: [M+H]$^+$: 387.1

Preparation of ((2S)-methyl 3-(3-(2-fluoroethoxy)benzylsulfinyl)-2-(2-(4-((2-sulfamoylbenzo[d]thiazol-6-yloxy)methyl)-1H-1,2,3-triazol-1-yl)acetamido)propanoate (VM2126)

General experimental procedure for click reaction (E) was followed. Performed on 0.10 g scale and 1.1 eq of base. Methanol:DCM (eluted out in 20% methanol) was used as the eluent. Isolated 0.123 g (73%) of VM126 as an yellow solid. MS: [M+H]$^+$: 654.9

$^1$H NMR (400 MHz, Acetone-d$_6$) δ: 8.17 (s, 1H), 8.15 (s, 1H), 8.02 (d, J=9.0 Hz, 1H), 7.89 (d, J=2.6 Hz, 1H), 7.36-7.28 (m, 4H), 7.01-6.95 (m, 3H), 5.34 (s, 2H), 5.28 (s, 2H), 4.92-4.88 (m, 1H), 4.84-4.82 (m, 1H), 4.72-4.70 (m, 1H), 4.33-4.30 (m, 1H), 4.26-4.23 (m, 1H), 4.20-3.99 (m, 2H), 3.69 (s, 3H), 3.25 (dd, J=13.4, 9.2 Hz, 1H), 3.16 (dd, J=13.5, 3.9 Hz, 1H).

Preparation of (2S)-3-(3-(2-fluoroethoxy)benzylsulfinyl)-2-(2-(4-((2-sulfamoyl benzo[d]thiazol-6-yloxy)methyl)-1H-1,2,3-triazol-1-yl)acetamido) propanoic acid (VM2128B and VM2128C)

General experimental procedure for ester hydrolysis (K) was followed. Performed on a 0.02 g scale. HPLC purification afforded two isomers as colorless solids (yield not determined). MS: B and C [M+H]$^+$: 641.1

VM128B: $^1$H NMR (400 MHz, Acetone-d$_6$) δ: 8.19 (br s, 1H), 8.16 (s, 1H), 8.02 (d, J=8.8 Hz, 1H), 7.89 (d, J=2.35, 1H), 7.37 (s, 2H), 7.33-7.29 (m, 2H), 7.03-6.95 (m, 2H), 5.35 (s, 2H), 5.32 (d, J=19.4, 2H), 4.92-4.91 (m, 1H), 4.84-4.82 (m, 1H), 4.72-4.70 (m, 1H), 4.33-4.31 (m, 1H), 4.25-4.22 (m, 1H), 4.21 (d, J=12.7 Hz, 1H), 4.09 (d, J=12.9 Hz, 1H), 3.29-3.12 (m, 4H).

Preparation of VM2106 Precursor

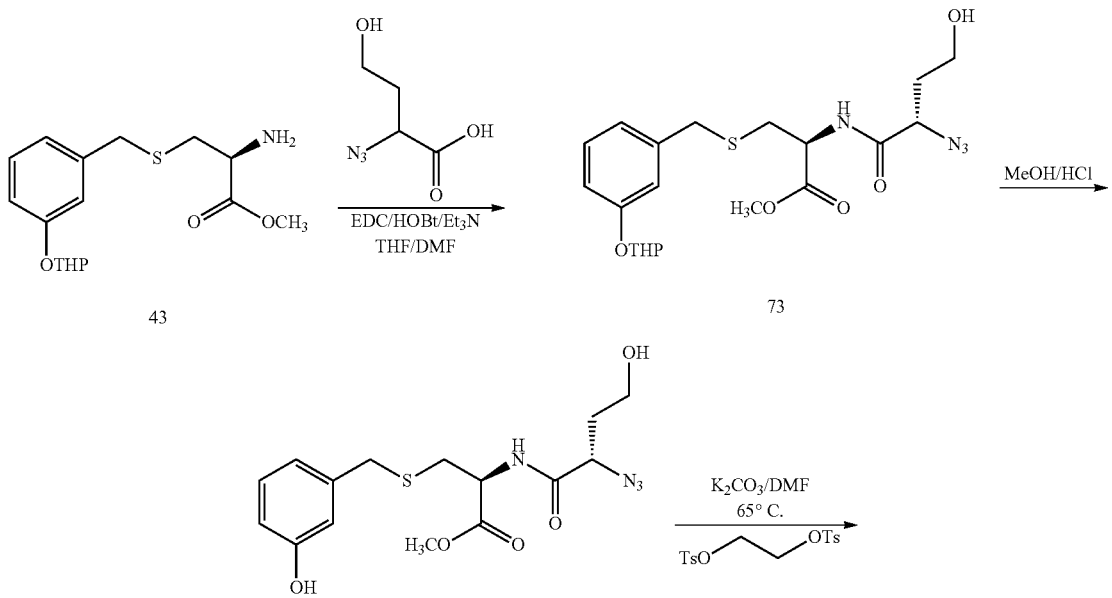

-continued

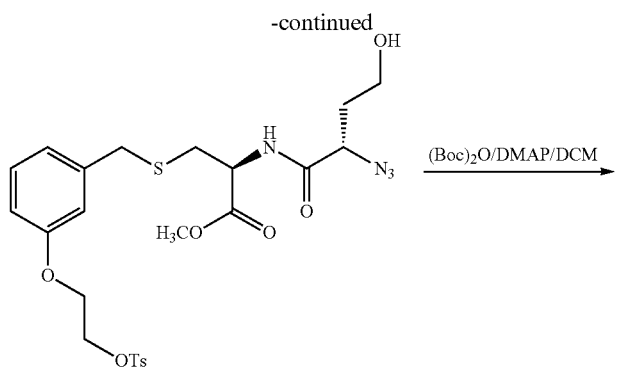

75

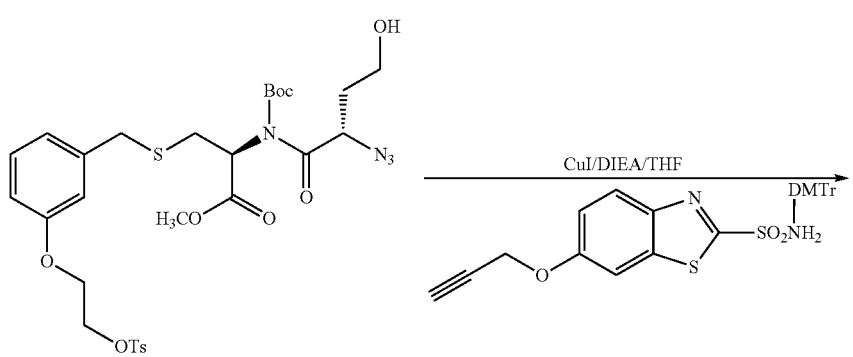

76

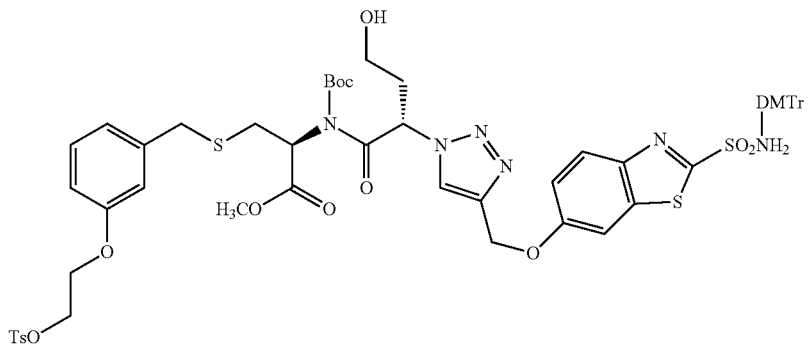

77

Preparation of (2S)-methyl 2-((S)-2-azido-4-hydroxybutanamido)-3-(3-(tetrahydro-2H-pyran-2-yloxy)benzylthio)propanoate (73)

General procedure for peptide coupling (C) was followed. Performed on 0.05 g scale, $Et_3N$ as base and THF as solvent with 2 equiv of azido acid. Product eluted out in 65% EtOAc: Hexanes mixture in a gradient elution on a Combiflash purification system.

Isolated 0.06 g (86%) of 73 as an yellow oil. MS: $[M+Na]^+$: 475.2

Preparation of (S)-methyl 2-((S)-2-azido-4-hydroxybutanamido)-3-(3-hydroxybenzyl thio)propanoate (74)

THP group was removed using the general experimental procedure (B). Performed on a 0.06 g scale, using HCl/MeOH. Product eluted out in 65% EtOAc:Hexanes mixture in a gradient elution on a Combiflash purification system.

Isolated 0.018 g (40%) of 74 as a colorless oil. MS: $[M+Na]^+$: 369.2

Preparation of (S)-methyl 2-((S)-2-azido-4-hydroxybutanamido)-3-(3-(2-(tosyloxy)ethoxy)benzylthio)propanoate (75)

General procedure for alkylation of phenol (A) was followed. Performed on a 0.57 g scale using $K_2CO_3$ as the base and ethylene glycol ditosylate. Product eluted out in 30% EtOAc:DCM mixture in a gradient elution on a Combiflash purification system. Isolated 0.09 g of 75 as an yellow oil. MS: $[M+H]^+$: 567.1

Preparation of (S)-methyl 2-((S)-2-azido-N-(tert-butoxycarbonyl)-4-(tert-butoxy carbonyloxy)butanamido)-3-(3-(2-(tosyloxy)ethoxy)benzylthio)propanoate (76)

To a round bottomed flask equipped with a magnetic stir bar containing DCM (26 vol) was placed azido alcohol 75 (0.09 g, 0.16 mmol). To this solution was added (Boc)$_2$O (0.1 g, 0.47 mmole), DMAP (0.1 equiv) and the reaction was allowed to stir at room temperature for 3 h. After evaporation of the solvent, the residue was purified over silica gel using Hexanes:EtOAc as the eluent to afford the Diboc protected compound 76 (0.07 g) as a thick colorless oil.

Preparation of (S)-2-((S)-2-(4-((2-(N-(bis(4-methoxyphenyl)(phenyl)methyl)sulfamoyl)benzo[d]thiazol-6-yloxy)methyl)-1H-1,2,3-triazol-1-yl)-N-(tert-butoxycarbonyl)-4-(tert-butoxycarbonyloxy)butanamido)-3-(3-(2-(tosyloxy)ethoxy)benzylthio)propanoic acid (77)

General experimental procedure for click reaction (E) was followed. Performed on a 0.07 g scale and 1.1 eq of base. Product eluted out in 55% EtOAc:Hexanes mixture in a gradient elution on a Combiflash purification system. Isolated 0.07 g (56%) of 77 as an off colorless foam. MS: $[M+H]^+$: 1337.5

Preparation of VM2-106 and VM2-107

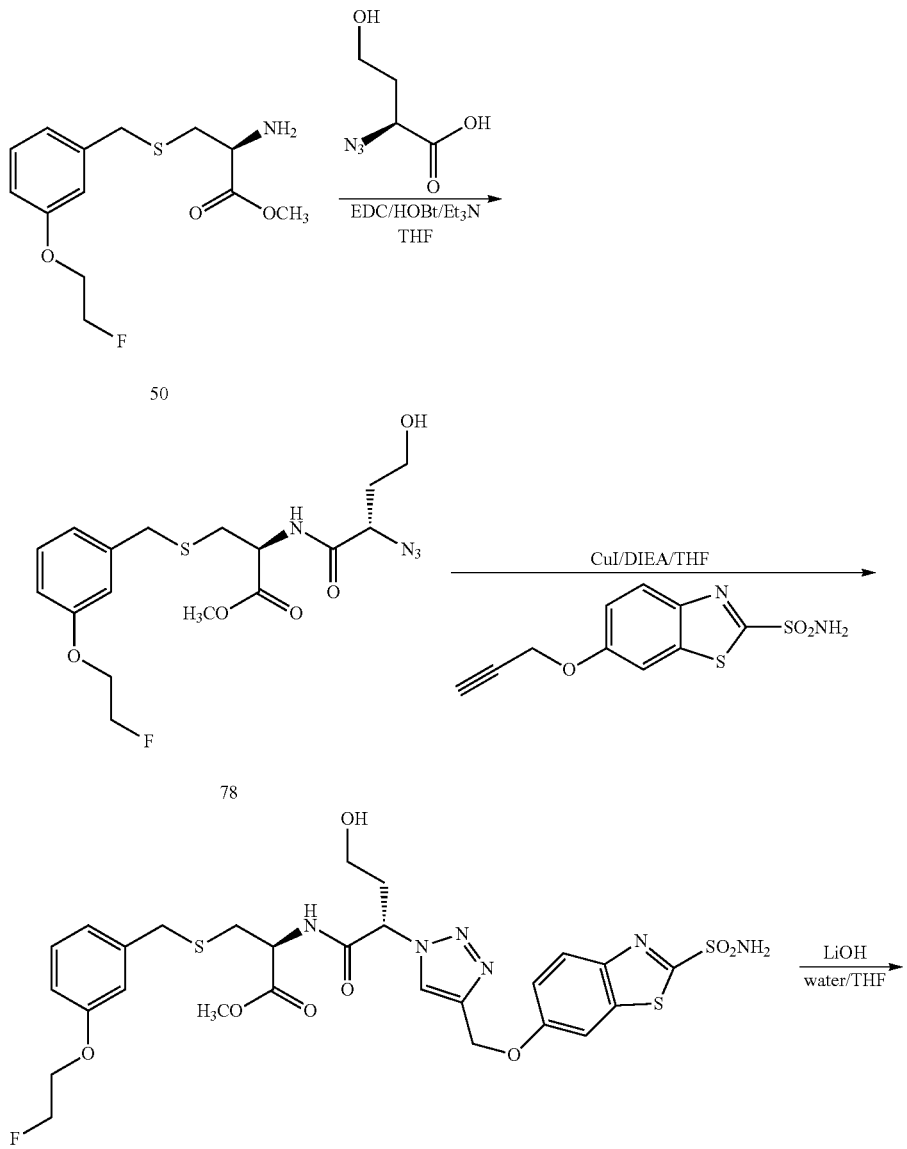

VM2106

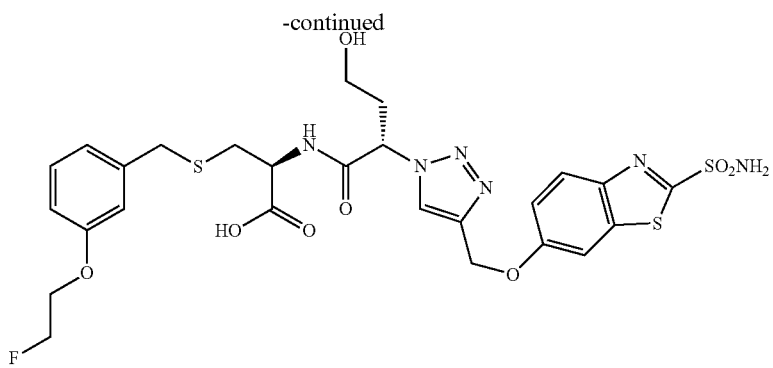

VM2-107A and VM2107B

Preparation of (S)-methyl 2-((S)-2-azido-4-hydroxybutanamido)-3-(3-(2-fluoroethoxy)benzylthio)propanoate (78)

General procedure for peptide coupling (C) was followed. Performed on 0.18 g scale, Et₃N as base and THF as solvent with 2 equiv of azido acid. Product eluted out in 65% EtOAc: Hexanes mixture in a gradient elution on a Combiflash purification system. Isolated 0.07 g (28%) of 78 as a colorless oil. MS: [M+H]⁺: 415.2

Preparation of (S)-methyl 3-(3-(2-fluoroethoxy)benzylthio)-2-((S)-4-hydroxy-2-(4-((2-sulfamoylbenzo[d]thiazol-6-yloxy)methyl)-1H-1,2,3-triazol-1-yl)butanamido) propanoate (VM2106)

General experimental procedure for click reaction (E) was followed. Performed on a 0.07 g scale and 1.1 eq of base. Product eluted out in 55% EtOAc:Hexanes mixture in a gradient elution on a Combiflash purification system. Isolated 0.1 g (84%) of VM2106 as light yellow solid. MS: [M+H]⁺: 682.2

Preparation of (S)-3-(3-(2-fluoroethoxy)benzylthio)-2-((S)-4-hydroxy-2-(4-((2-sulfamoylbenzo[d]thiazol-6-yloxy)methyl)-1H-1,2,3-triazol-1-yl)butanamido) propanoic acid (VM2107A and VM2107B)

General experimental procedure for ester hydrolysis (K) was followed. Performed on a 0.08 g scale. THF removal followed by acidification and EtOAc extraction afforded pure VM2107A and VM2107B (0.05 g, 66%) as off colorless solids. MS: A and B[M+H]⁺: 669.5

Preparation of VM3143

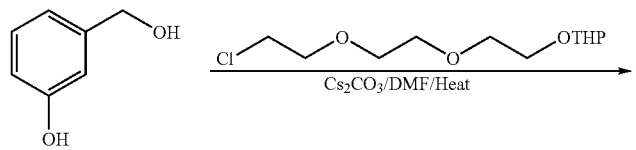

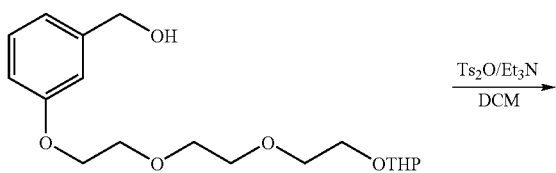

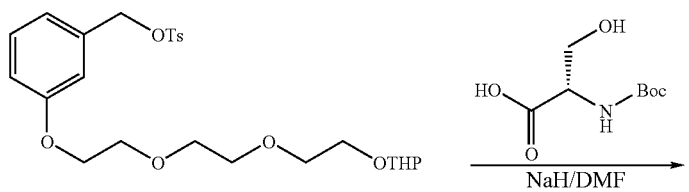

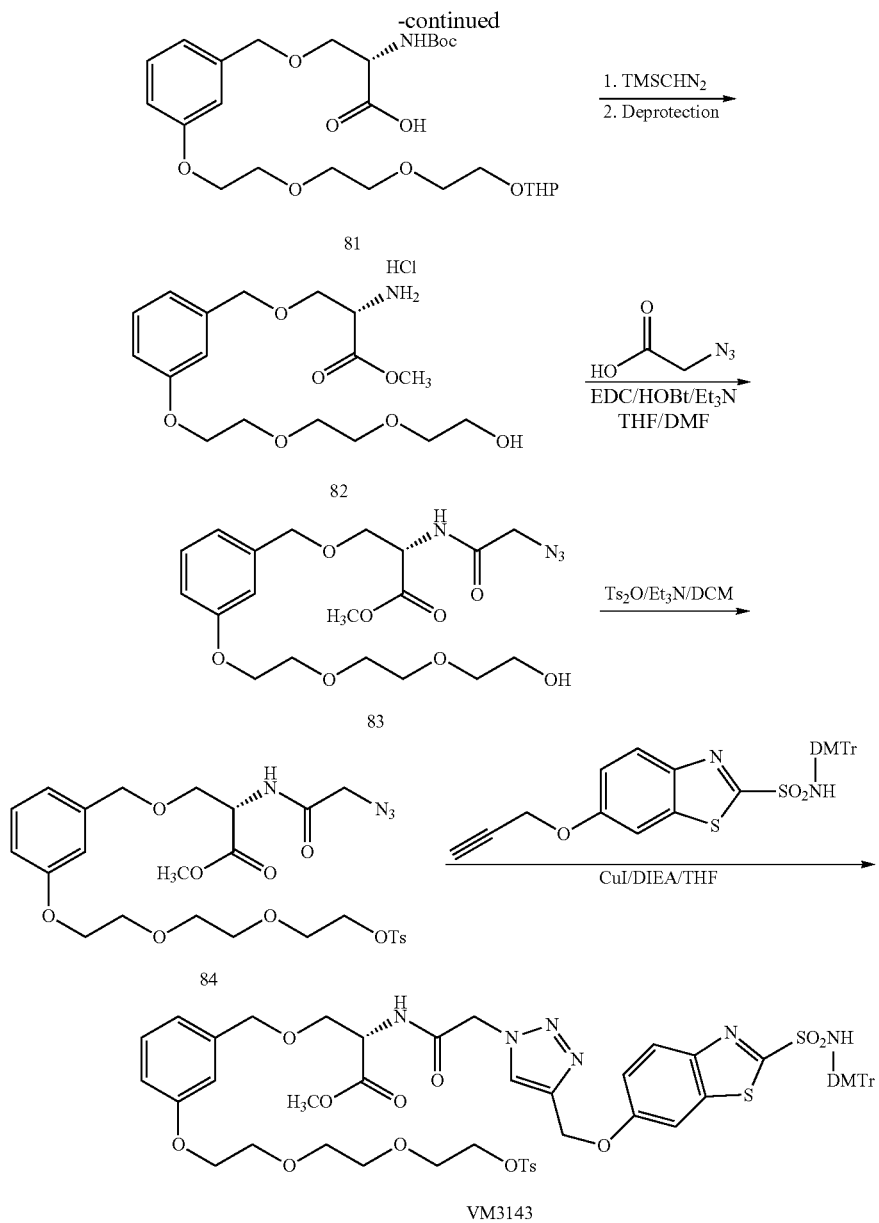

Preparation of (3-(2-(2-(2-(tetrahydro-2H-pyran-2-yloxy)ethoxy)ethoxy)ethoxy)phenyl)methanol (79)

General procedure for alkylation of phenol (A) was followed. Yield was not calculated. MS: [M+Na]⁺: 363.2

Preparation of 3-(2-(2-(2-(tetrahydro-2H-pyran-2-yloxy)ethoxy)ethoxy)ethoxy)benzyl 4-methylbenzenesulfonate (80)

General procedure for tosylation (D) was followed. Yield was not calculated. MS: [M+Na]⁺: 517.4

Preparation of (2S)-2-(tert-butoxycarbonylamino)-3-(3-(2-(2-(2-(tetrahydro-2H-pyran-2-yloxy)ethoxy)ethoxy)ethoxy)benzyloxy)propanoic acid (81)

General experimental procedure for alkylation (F) was followed. Adjusted reaction to pH=4.5-5. Product eluted out in 55% EtOAc:Hexanes mixture in a gradient elution on a Combiflash purification system. Isolated 81 as a thick colorless oil. The yield was not calculated.

Preparation of (S)-methyl 2-amino-3-(3-(2-(2-(2-hydroxyethoxy)ethoxy)ethoxy)benzyloxy)propanoate (82)

General experimental procedure for esterification of acid (G) and deprotection (B) was followed. Performed on 1.45 g of Boc-acid. Isolated 1.4 g, (quantitative) of 82 as a colorless solid. MS: [M+H]⁺: 358.2

Preparation of (S)-methyl 2-(2-azidoacetamido)-3-(3-(2-(2-(2-hydroxyethoxy)ethoxy)ethoxy)benzyloxy)propanoate (83)

General procedure for peptide coupling (C) was followed. Performed on 1.4 g scale, using Et₃N as base and THF as solvent with 1.5 equi of azido acid. Product eluted out in 75% EtOAc:Hexanes mixture in a gradient elution on a Combiflash purification system. Isolated 0.36 g (23%) of 83 as yellow oil. MS: [M+H]$^+$: 441.2

Preparation of (S)-methyl 2-(2-azidoacetamido)-3-(3-(2-(2-(2-(tosyloxy)ethoxy)ethoxy)ethoxy)benzyloxy)propanoate (84)

General experimental procedure for tosylation (D) was followed. Performed on a 0.34 g scale and at 0° C. for 10 min Product eluted out in 58% EtOAc:Hexanes mixture in a gradient elution on a Combiflash purification system. Isolated 0.33 g (72%) of 84 as a colorless oil. MS: [M+H]$^+$: 595.2

Preparation of (S)-methyl2-(2-(4-((2-(N-(bis(4-methoxyphenyl)(phenyl)methyl)sulfamoyl)benzo[d]thiazol-6-yloxy)methyl)-1H-1,2,3-triazol-1-yl)acetamido)-3-(3-(2-(2-(2-(tosyloxy)ethoxy)ethoxy)ethoxy)benzyloxy)propanoate (VM3143)

General experimental procedure for click reaction (E) was followed. Performed on 0.14 g scale and 1.1 equiv of base. Product eluted out in 85% EtOAc:Hexanes mixture in a gradient elution on a Combiflash purification system. Isolated 0.13 g (48%) of VM3143 as an off colorless foam. MS: [M+Na]$^+$: 1187.2

Preparation of VM3147

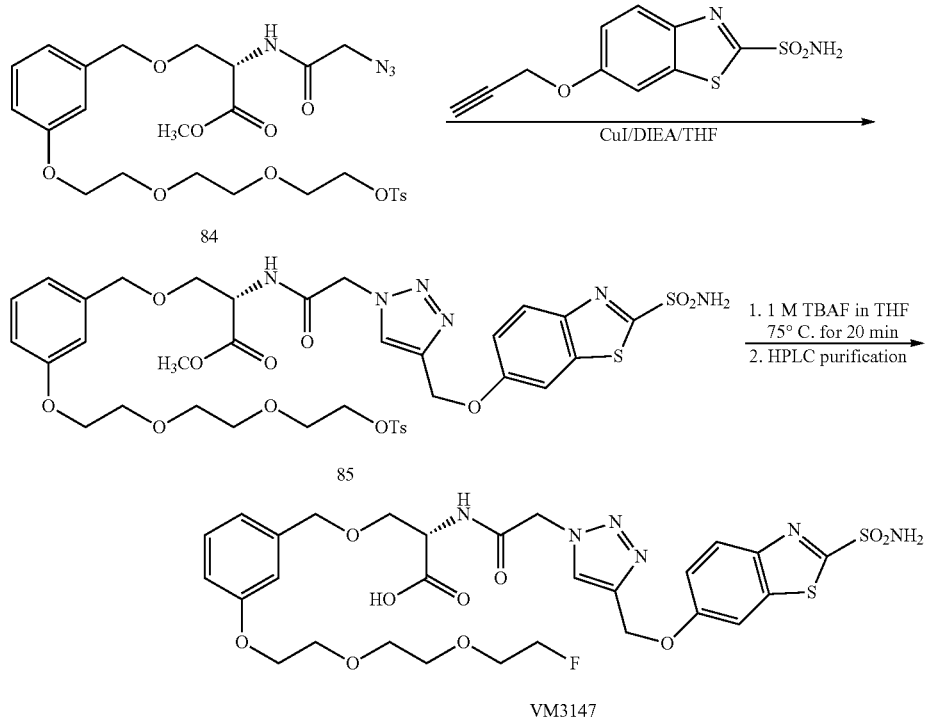

Preparation of (S)-methyl 2-(2-(4-((2-sulfamoylbenzo[d]thiazol-6-yloxy)methyl)-1H-1,2,3-triazol-1-yl)acetamido)-3-(3-(2-(2-(2-(tosyloxy)ethoxy)ethoxy)ethoxy)benzyloxy)propanoate (85)

General experimental procedure for click reaction (E) was followed. Performed on 0.12 g (alkyne) scale and 1.1 equiv of base. Reaction mixture was triturated with ether/DCM mixture after removal of THF under vacuum. Isolated 0.04 g (93%) of 85 as green solid. MS: [M+Na]$^+$: 863.1

Preparation of (S)-3-(3-(2-(2-(2-fluoroethoxy)ethoxy)ethoxy)benzyloxy)-2-(2-(4-((2-sulfamoylbenzo[d]thiazol-6-yloxy)methyl)-1H-1,2,3-triazol-1-yl)acetamido) propanoic acid (VM3147)

General experimental procedure for fluorination (J) was followed. Performed on 0.04 g scale. Reaction mixture was triturated with ether/DCM mixture after removal of THF in vacuo. Isolated 8.7 mg (27%) of VM3147 as colorless solid. MS: [M+H]$^+$: 697.1

Preparation of DHK3183 precursor
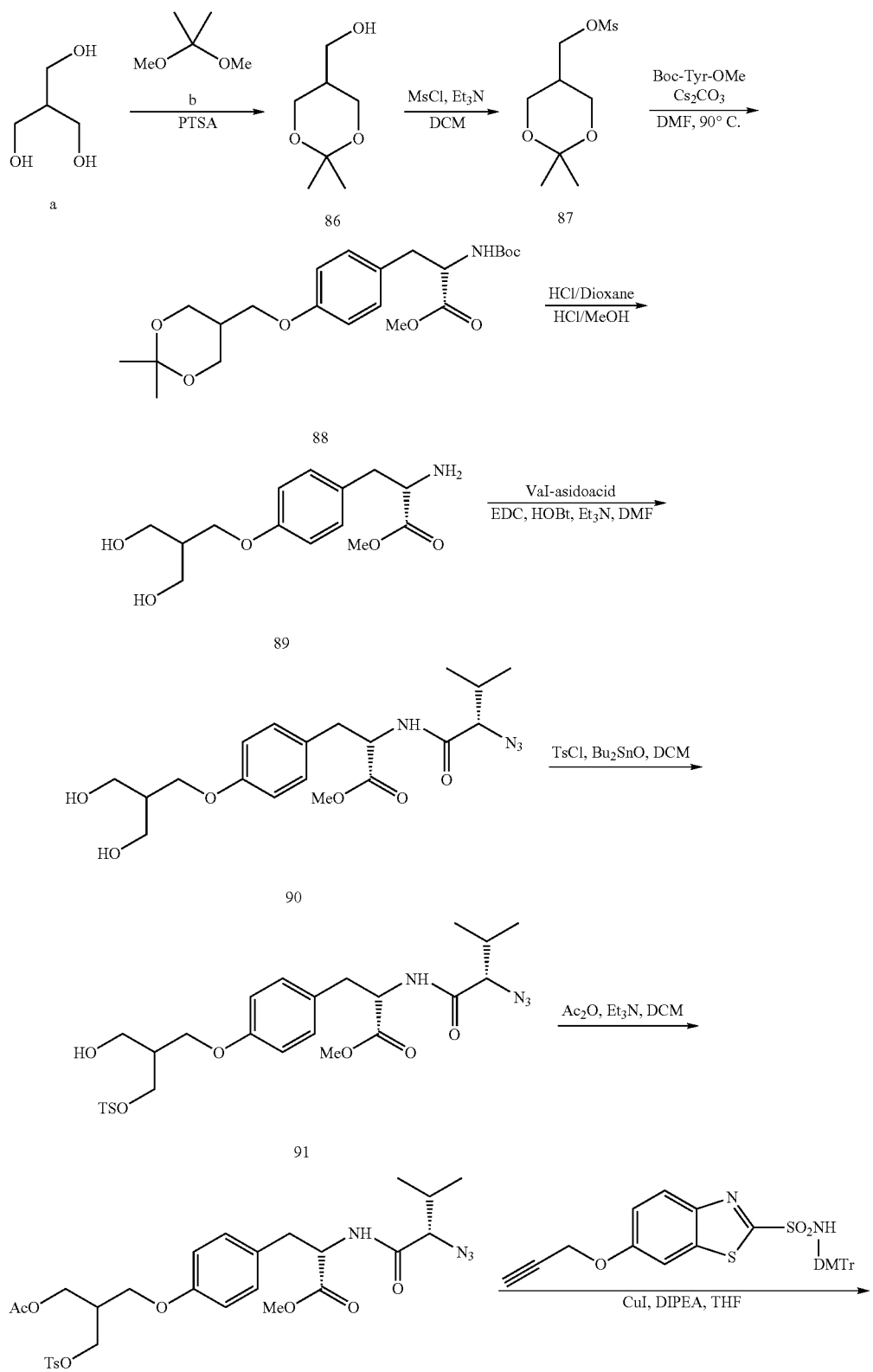

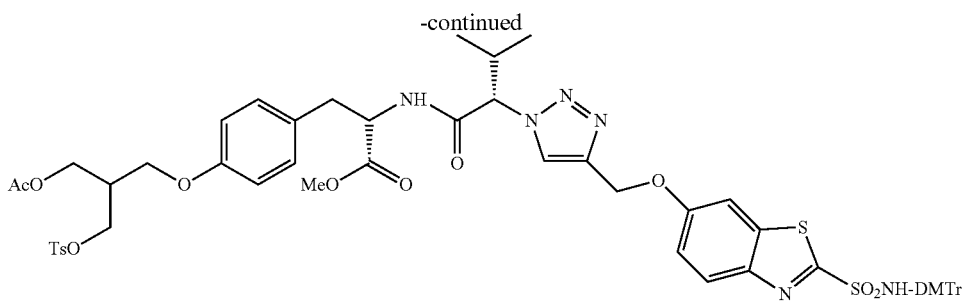

93

Preparation of (2,2-dimethyl-1,3-dioxan-5-yl)methanol (86)

To a 100 mL round bottomed flask equipped with a magnetic stir bar containing THF (75 mL) was placed a (4 g, 38 mmol, 1 equiv). To this solution was added b (4.5 g, 43 mmol, 1.15 equiv), PTSA (0.2 g, 1.1 mmol, 0.03 equiv) and the reaction was allowed to stir at room temperature for 2 h. After the reaction was complete, solvent was removed in vacuo. The residue was purified over silica gel. Product eluted out in 60% EtOAc:Hexanes mixture in a gradient elution on a Combiflash purification system. Isolated 86 (5 g, 91%) as a colorless oil. MS: [M+H]$^+$: 147.

Preparation of 2,2-dimethyl-1,3-dioxan-5-yl)methyl methanesulfonate (87)

To a 500 mL round bottomed flask equipped with a magnetic stir bar containing DCM (200 mL) was placed 87 (5 g, 34 mmol, 1 equiv). To this solution was added mesyl chloride (4.3 g, 38 mmol, 1.1 equiv), Et$_3$N (5 g, 51 mmol, 1.5 equiv) and the reaction was allowed to stir at room temperature for 3 h. The reaction was then poured into water (100 mL) and extracted into DCM (3×100 mL). The combined organic extracts were washed with brine (100 mL), NaHCO$_3$ solution (100 mL), dried (Na$_2$SO$_4$) and concentrated in vacuo. The residue was purified over silica gel. Product eluted out in 50% EtOAc:Hexanes mixture in a gradient elution on a Combiflash purification system. Isolated 87 (7 g, 91%) as a colorless solid. MS: [M+H]$^+$: 225.

Preparation of (S)-methyl 2-(tert-butoxycarbonylamino)-3-(4-((2,2-dimethyl-1,3-dioxan-5-yl)methoxy)phenyl)propanoate (88)

General experimental procedure for phenolic alkylation: (A) was followed. Reaction was performed on a 3.5 g scale. Product eluted out in 40% EtOAc:Hexanes mixture in a gradient elution on a Combiflash purification system. Isolated 4.5 g (100%) of 88 as a colorless oil. MS: [M+H]$^+$: 424.

Preparation of (S)-methyl 2-amino-3-(4-(3-hydroxy-2-(hydroxymethyl)propoxy)phenyl)propanoate (89)

General experimental procedure for deprotection (B) was followed. Reaction was performed on a 4.3 g scale. Isolated 3 g (92%) of 89 as a colorless solid. MS: [M+H]$^+$: 284.

Preparation of (S)-methyl 2-((S)-2-azido-3-methylbutanamido)-3-(4-(3-hydroxy-2-(hydroxymethyl)propoxy)phenyl)propanoate (90)

General experimental procedure for coupling (C) was followed. Reaction was performed on a 1.7 g scale. Product eluted out in 100% EtOAc:Hexanes mixture in a gradient elution on a Combiflash purification system. Isolated 1 g (46%) of 90 as a colorless oil. MS: [M+H]$^+$: 409.

Preparation of (2S)-methyl 2-((S)-2-azido-3-methylbutanamido)-3-(4-(3-hydroxy-2-(tosyloxymethyl)propoxy)phenyl)propanoate (91)

General experimental procedure for selective monotosylation of diol (H) was followed. Reaction was performed on a 0.9 g scale. Product eluted out in 60% EtOAc:Hexanes mixture in a gradient elution on a Combiflash purification system. Isolated 0.7 g (57%) of 91 as a colorless oil. MS: [M+H]$^+$: 563.

Preparation of (2S)-methyl 3-(4-(3-acetoxy-2-(tosyloxymethyl)propoxy)phenyl)-2-((S)-2-azido-3-methylbutanamido)propanoate (92)

General experimental procedure for acetylation of alcohols (I) was followed. Reaction was performed on a 0.7 g scale. Product eluted out in 40% EtOAc:Hexanes mixture in a gradient elution on a Combiflash purification system. Isolated 0.68 g (42%) of 92 as a colorless oil. MS: [M+H]$^+$: 605.

Preparation of 3-acetoxy-2-(tosyloxymethyl)propoxy)phenyl)-2-(S)-2-(4-(2-(N-(bis(4-methoxyphenyl)(phenyl)methyl)sulfamoyl)benzo[d]thiazol-6-yloxy)methyl)-1H-1,2,3-triazol-1-yl)-3-methylbutanamido)propanoate (93)

General experimental procedure for click reaction (E) was followed. Reaction was performed on a 0.15 g scale. Product eluted out in 65% EtOAc:Hexanes mixture in a gradient elution on a Combiflash purification system. Isolated 0.24 g (82%) of 93 as a colorless solid. MS: [M+H]$^+$: 1176.

Preparation of DHK3183
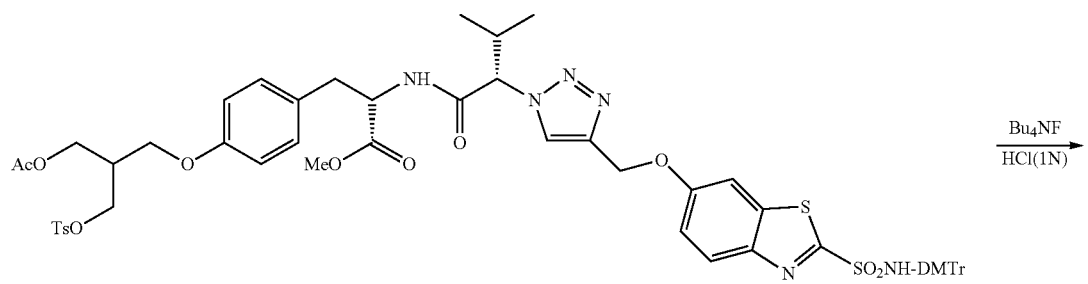
93
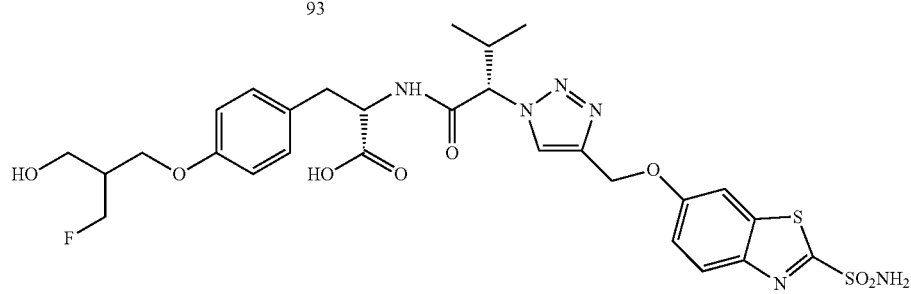
DHK3183
General experimental procedure for fluorination (J) was followed. Reaction was performed on a 0.024 g scale. Isolated 0.013 g (56%) of DHK3183 as a colorless solid. MS: [M+H]$^+$: 665.
Preparation of DHK2173 Precursor
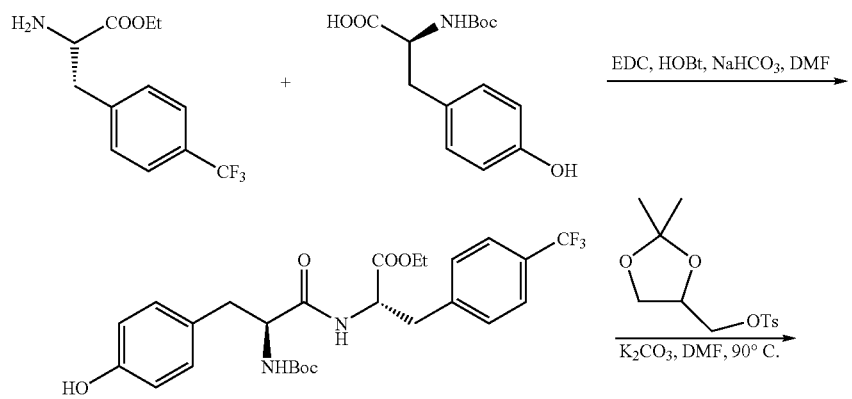
94
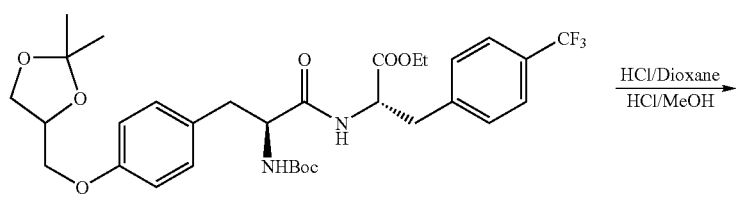
95

-continued
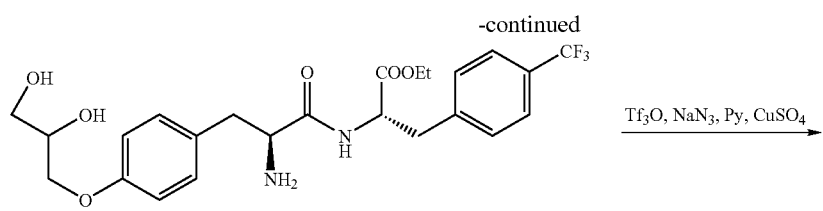
96
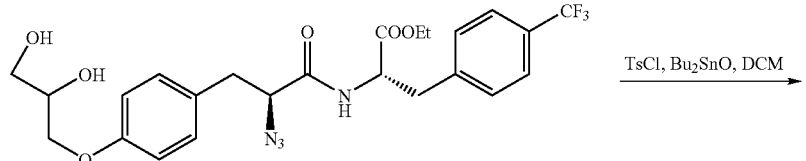
97
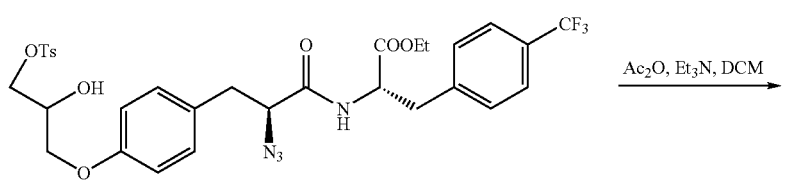
98
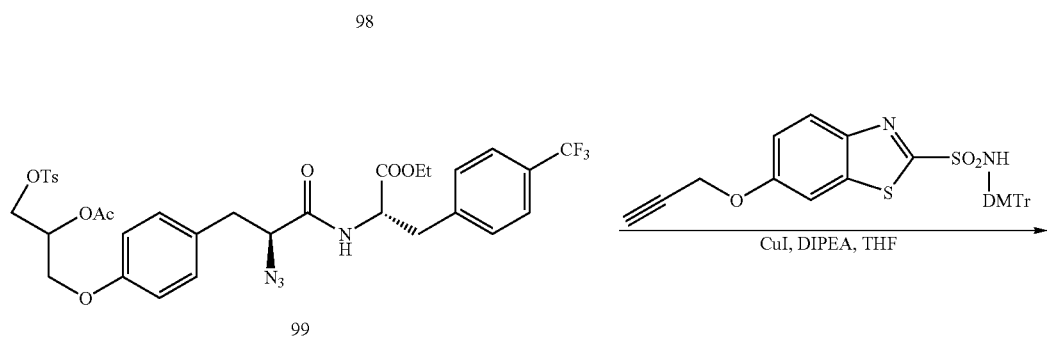
99
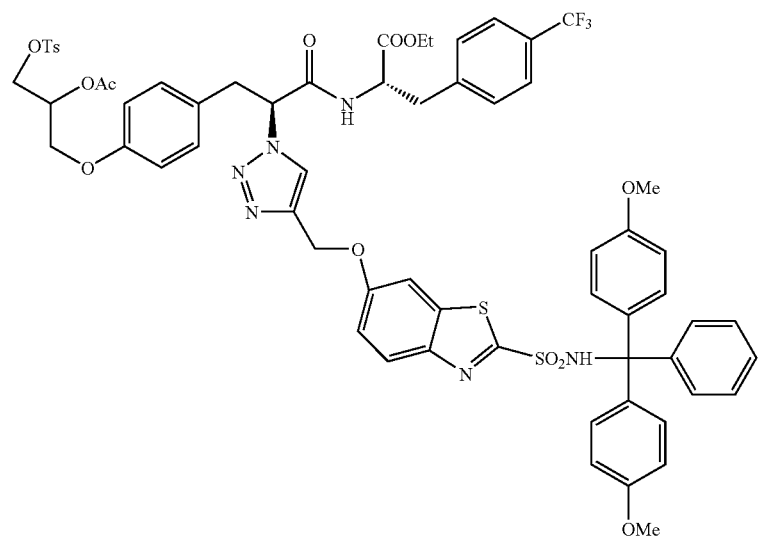
100

Preparation of (S)-ethyl 2-((S)-2-(tert-butoxycarbonylamino)-3-(4-hydroxy phenyl)propanamido)-3-(4-(trifluoromethyl)phenyl)propanoate (94)

General experimental procedure for coupling (C) was followed. Reaction was performed on a 4 g scale. Product eluted out in 50% EtOAc:Hexanes mixture in a gradient elution on a Combiflash purification system. Isolated 1 g (81%) of 94 as a colorless solid. MS: [M-Boc+H]$^+$: 425.

Preparation of (2S)-ethyl 2-42S)-2-(tert-butoxycarbonylamino)-3-(4-((2,2-dimethyl-1,3-dioxolan-4-yl)methoxy)phenyl)propanamido)-3-(4-(trifluoromethyl)phenyl) propanoate (95)

General experimental procedure for phenolic alkylation (A) was followed. Reaction was performed on a 5 g scale. K$_2$CO$_3$ was used as a base. Product eluted out in 50% EtOAc:Hexanes mixture in a gradient elution on a Combiflash purification system. Isolated 1.5 g (25%) of 95. MS: [M-Boc+H]$^+$: 539.

Preparation of (2S)-ethyl 2-((2S)-2-amino-3-(4-(2,3-dihydroxypropoxy)phenyl)propanamido)-3-(4-(trifluoromethyl)phenyl)propanoate (96)

General experimental procedure for deprotection (B) was followed. Reaction was performed on a 1.5 g scale. Isolated 1.1 g (100%) of 96 as a colorless solid. MS: [M+H]$^+$: 499.

Preparation of (2S)-ethyl 2-((2S)-2-azido-3-(4-(2,3-dihydroxypropoxy)phenyl)propanamido)-3-(4-(trifluoromethyl)phenyl)propanoate (97)

General experimental procedure for azidation (M) was followed. Reaction was performed on a 0.04 g scale. Product eluted out in 80% EtOAc:Hexanes mixture in a gradient elution on a Combiflash purification system. Isolated 0.25 g, 25% of 97 as a colorless solid. MS: [M+H]$^+$: 525.

Preparation of (2S)-ethyl 2-((2S)-2-azido-3-(4-(2-hydroxy-3-(tosyloxy)propoxy)phenyl)propanamido)-3-(4-(trifluoromethyl)phenyl)propanoate (98)

General experimental procedure for selective monotosylation of diol (H) was followed. Reaction was performed on a 0.22 g scale. Product eluted out in 60% EtOAc:Hexanes mixture in a gradient elution on a Combiflash purification system. Isolated 0.23 g (82%) of 98. MS: [M+H]$^+$: 679.

Preparation of (2S)-ethyl 2-42S)-3-(4-(2-acetoxy-3-(tosyloxy)propoxy)phenyl)-2-azidopropanamido)-3-(4-(trifluoromethyl)phenyl)propanoate (99)

General experimental procedure for acetylation of alcohols (I) was followed. Reaction was performed on a 0.043 g scale. Product eluted out in 40% EtOAc:Hexanes mixture in a gradient elution on a Combiflash purification system. Isolated 0.032 g (71%) of 99. MS: [M+H]$^+$: 721.

Preparation of (2S)-ethyl 2-((2S)-3-(4-(2-acetoxy-3-(tosyloxy)propoxy)phenyl)-2-(4-((2-(N-(bis(4-methoxyphenyl)(phenyl)methyl)sulfamoyl)benzo[d]thiazol-6-yloxy)methyl)-1H-1,2,3-triazol-1-yl)propanamido)-3-(4-(trifluoromethyl)phenyl)propanoate (100)

General experimental procedure for click reaction (E) was followed. Reaction was performed on a 0.044 g scale. Product eluted out in 70% EtOAc:Hexanes mixture in a gradient elution on a Combiflash purification system. Isolated 0.075 g (96%) of 100 as a colorless solid. MS: [M+H]$^+$: 1192

Preparation of DHK2173

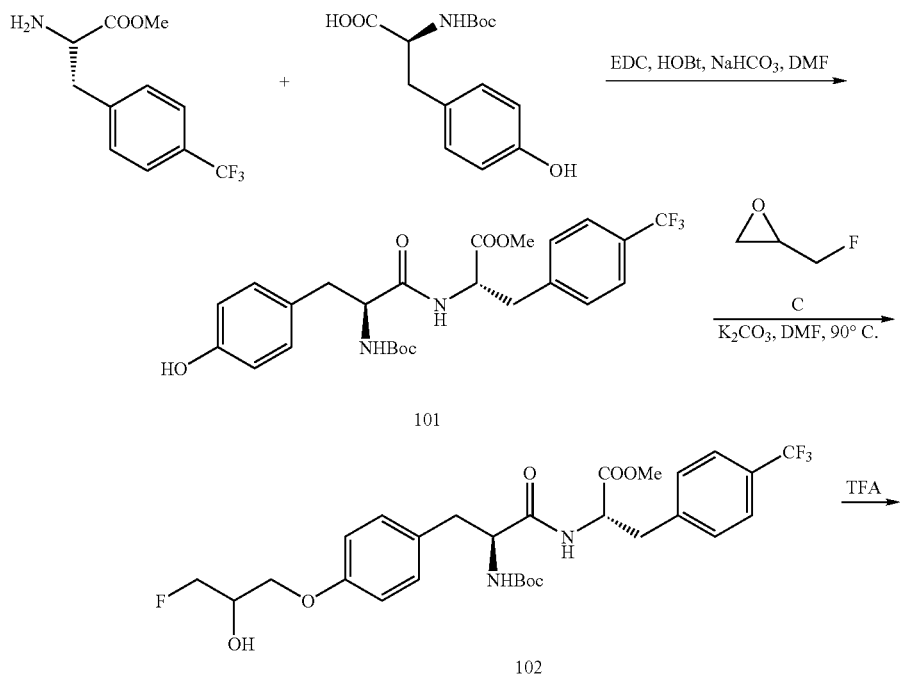

-continued
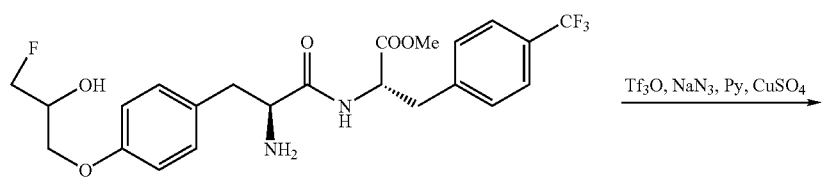
103
Tf₃O, NaN₃, Py, CuSO₄ →
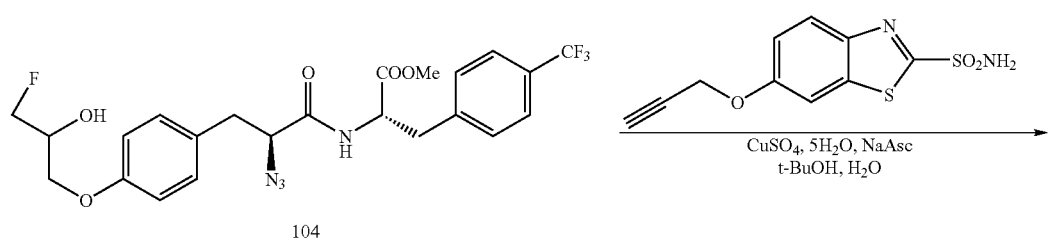
104
CuSO₄, 5H₂O, NaAsc
t-BuOH, H₂O →
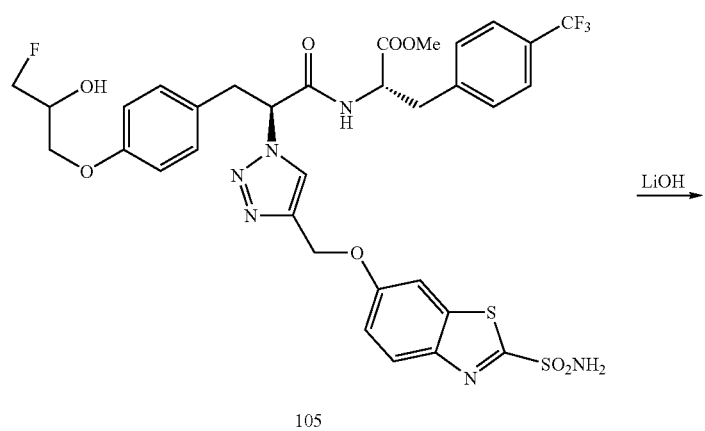
105
LiOH →
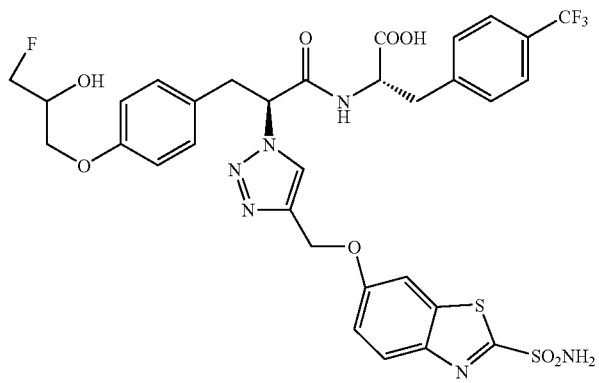
DHK2173

Preparation of (S)-methyl 2-((S)-2-(tert-butoxycarbonylamino)-3-(4-hydroxyphenyl)propanamido)-3-(4-(trifluoromethyl)phenyl)propanoate (101)

General experimental procedure for coupling (C) was followed. Reaction was performed on a 5 g scale. Product eluted out in 50% EtOAc:Hexanes mixture in a gradient elution on a Combiflash purification system. Isolated 6.1 g (81%) of 101 as a colorless solid. MS: [M-Boc+H]$^+$: 411.

Preparation of (2S)-methyl 2-((2S)-2-(tert-butoxycarbonylamino)-3-(4-(3-fluoro-2-hydroxypropoxy)phenyl)propanamido)-3-(4-(trifluoromethyl)phenyl)propanoate (102)

General experimental procedure for phenolic alkylation (A) was followed. Reaction was performed on a 0.22 g scale. $K_2CO_3$ was used as a base. Product eluted out in 30% EtOAc:Hexanes mixture in a gradient elution on a Combiflash purification system. Isolated 0.053 g (23%) of 102. MS: [M-Boc+H]$^+$: 487.

Preparation of (2S)-methyl 2-((2S)-2-amino-3-(4-(3-fluoro-2-hydroxypropoxy)phenyl)propanamido)-3-(4-(trifluoromethyl)phenyl)propanoate (103)

General experimental procedure for deprotection (L) was followed. Reaction was performed on a 0.05 g scale. Isolated 0.04 g (75%) of 103. MS: [M+H]$^+$: 487.

Preparation of (2S)-methyl 2-((2S)-2-azido-3-(4-(3-fluoro-2-hydroxypropoxy)phenyl)propanamido)-3-(4-(trifluoromethyl)phenyl)propanoate (104)

General experimental procedure for azidation (M) was followed. Reaction was performed on a 0.04 g scale. Isolated 0.042 g (100%) of 104. MS: [M+H]$^+$: 513.

Preparation of (2S)-methyl 2-((2S)-3-(4-(3-fluoro-2-hydroxypropoxy)phenyl)-2-(4-((2-sulfamoylbenzo[d]thiazol-6-yloxy)methyl)-1H-1,2,3-triazol-1-yl)propanamido)-3-(4-(trifluoromethyl)phenyl)propanoate (105)

General experimental procedure for click reaction (N) was followed. Reaction was performed on a 0.036 g scale. Isolated 0.037 g (69%) of 105 as a colorless solid.
MS: [M+H]$^+$: 781

Preparation of (2S)-2-((2S)-3-(4-(3-fluoro-2-hydroxypropoxy)phenyl)-2-(4-((2-sulfamoylbenzo[d]thiazol-6-yloxy)methyl)-1H-1,2,3-triazol-1-yl)propanamido)-3-(4-(trifluoromethyl)phenyl)propanoic acid (DHK2173)

General experimental procedure for ester hydrolysis (K) was followed. Reaction was performed on a 0.035 g scale. Isolated 0.0132 g (39%) of DHK2173 as a colorless solid. MS: [M+H]$^+$: 767

Preparation of DHK2134

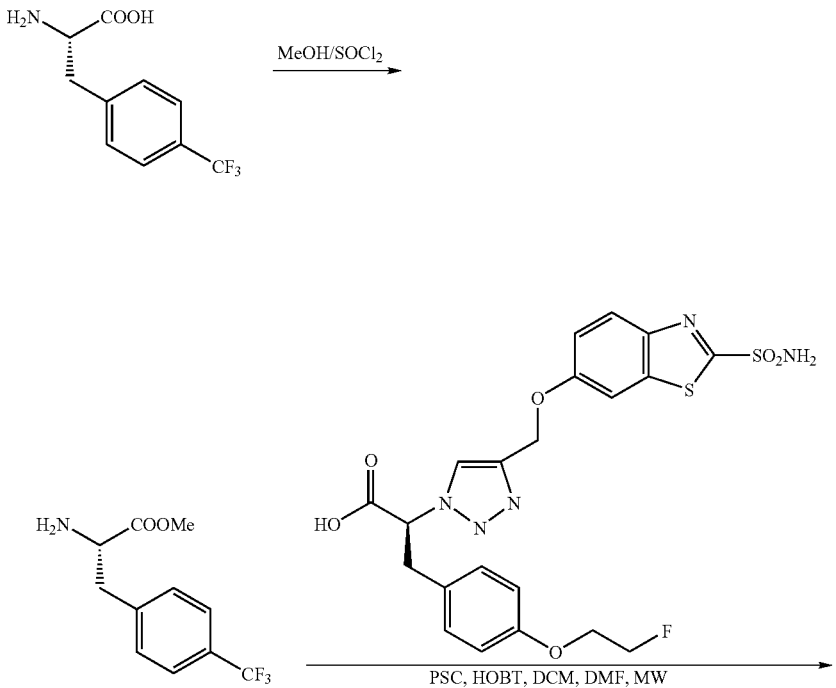

-continued

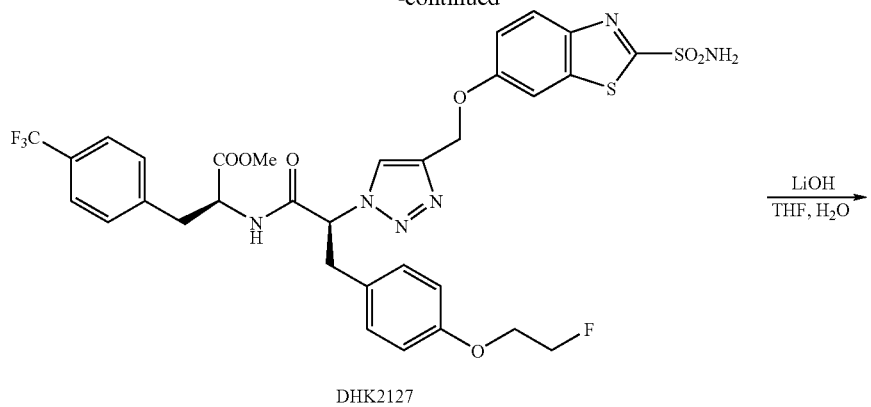

DHK2127

DHK2134

Preparation of (S)-methyl 2-amino-3-(4-(trifluoromethyl)phenyl)propanoate (105)

To a 50 mL round bottomed flask equipped with a magnetic stir bar, rubber septum, and argon inlet containing MeOH (5 mL) was placed acid (0.13 g, 0.56 mmol). To this solution was added thionyl chloride (2M solution in DCM, 5 mL) at 0° C. and the reaction was allowed to stir at room temperature for 24 h. After the reaction was complete, MeOH was removed in vacuo, diluted with DCM (50 mL). The DCM layer was washed with 10% NaHCO$_3$ solution (25 mL), H$_2$O (2×25 mL) dried (Na$_2$SO$_4$) and concentrated in vacuo to afford 105 (0.08 g, 58%) as a colorless solid. MS: [M+H]$^+$: 248

Preparation of (S)-methyl 2-((S)-3-(4-(2-fluoroethoxy)phenyl)-2-(4-((2-sulfamoylbenzo[d]thiazol-6-yloxy)methyl)-1H-1,2,3-triazol-1-yl)propanamido)-3-(4-(trifluoromethyl)phenyl)propanoate (DHK2127)

General experimental procedure for amide coupling (O) was followed. Reaction was performed on a 0.007 g scale. Isolated 0.010 g (43%) of DHK2127 as a colorless solid. MS: [M+H]$^+$: 751

Preparation of (S)-2-((S)-3-(4-(2-fluoroethoxy)phenyl)-2-(4-((2-sulfamoylbenzo[d]thiazol-6-yloxy)methyl)-1H-1,2,3-triazol-1-yl)propanamido)-3-(4-(trifluoromethyl)phenyl)propanoic acid (DHK2134)

General experimental procedure for ester hydrolysis (K) was followed. Reaction was performed on a 0.007 g scale. Isolated 0.003 g (40%) of DHK2134 as a colorless solid. MS: [M+H]$^+$: 737

Preparation of BW96

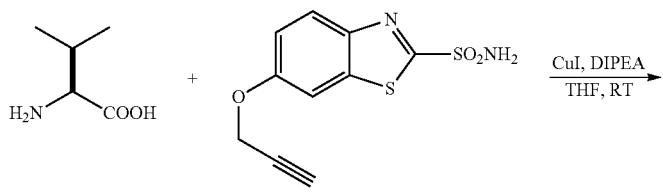

-continued

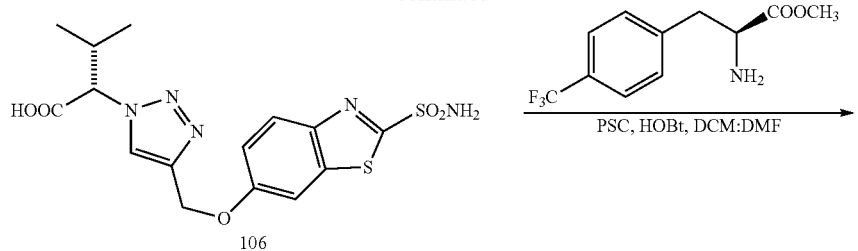

106

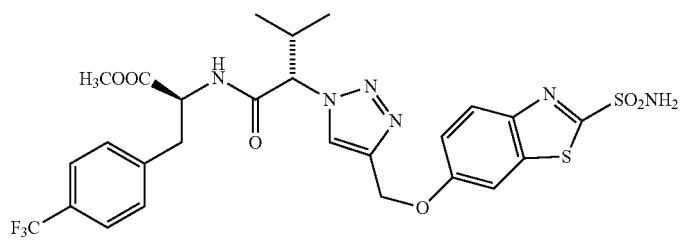

BW-96

Preparation of (S)-3-methyl 2(4-((2-sulfamoylbenzo[d]thiazol-6-yloxy)methyl)-1H-1,2,3-triazol-1-yl)butanoic acid (106)

General experimental procedure for click reaction (E) was followed. Reaction was performed on a 0.14 g scale. 0% to 40% MeOH in DCM was used as the eluent for purification. Isolated 0.40 g (98%) of 106 as a solid. MS: [M+H]: 412.

Preparation of (S)-methyl 2-((S)-3-methyl-2-(4-((2-sulfamoylbenzo[d]thiazol-6-yloxy)methyl)-1H-1,2,3-triazol-1-yl)butanamido)-3-(4-(trifluoromethyl)phenyl)propanoate (BW96)

General experimental procedure for amide coupling (O) was followed. Reaction was performed on a 0.015 g scale. 0% to 80% EtOAc in DCM was used as the eluent for purification. Isolated 0.019 g (49%) of BW96 as a solid. MS: [M+H]: 641.

Preparation of BW1391A and BW1391B

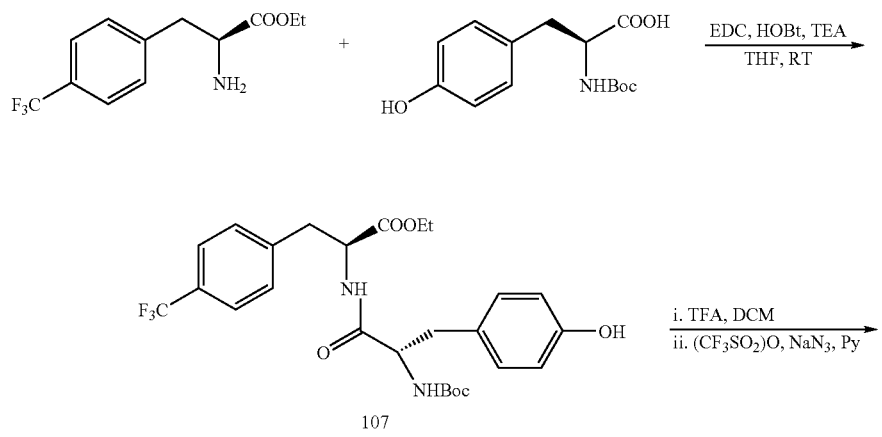

107

-continued
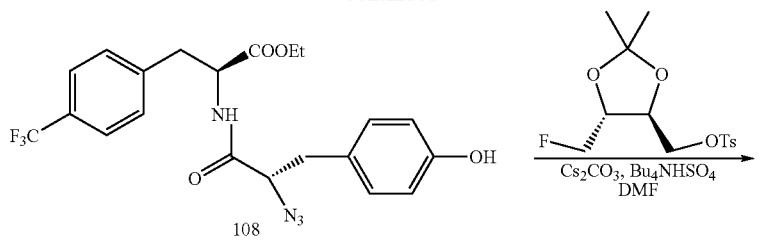
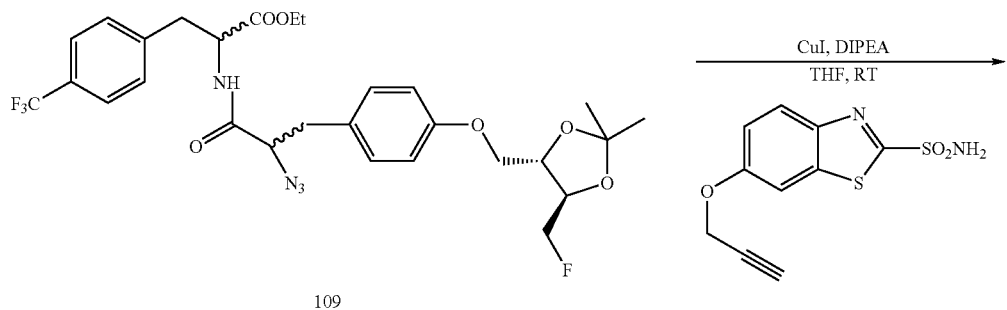
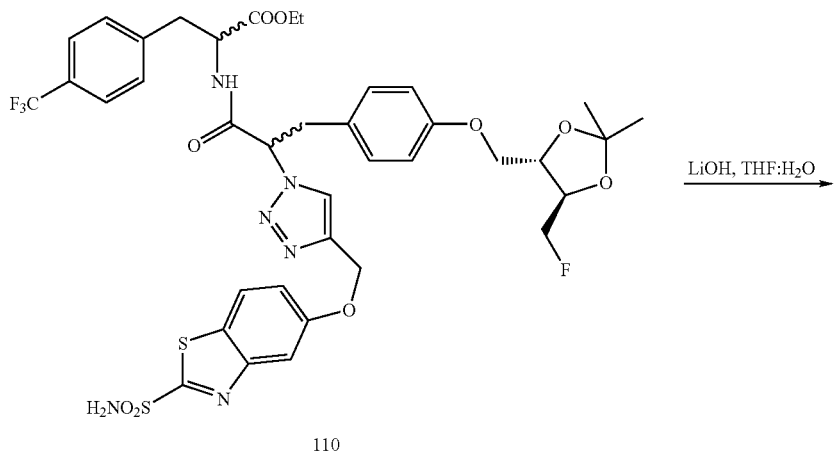
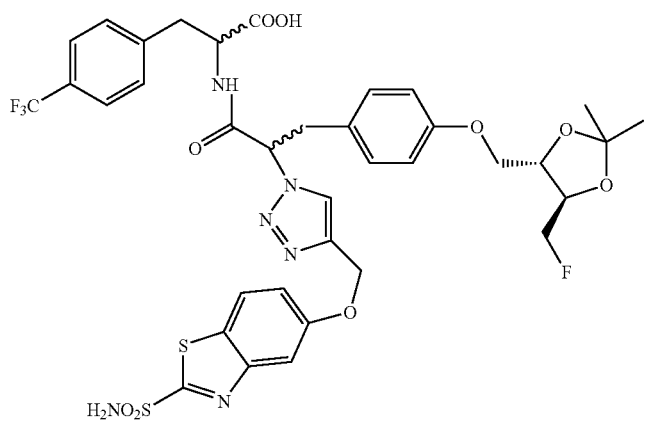
BW1391A and BW1391B

Preparation of (S)-ethyl 2-((S)-2-(tert-butoxycarbonylamino)-3-(4-hydroxyphenyl)propanamido)-3-(4-(trifluoromethyl)phenyl)propanoate (107)

General experimental procedure for coupling (C) was followed. Reaction was performed on a 3.9 g scale. 50% to 100% EtOAc in DCM was used as the eluent for purification. Isolated 7.0 g (90%) of 107 as a solid. MS: [M+Na]: 547.

Preparation of (S)-ethyl 2-((S)-2-azido-3-(4-hydroxyphenyl)propanamido)-3-(4-(trifluoromethyl)phenyl)propanoate (108)

General experimental procedures for deprotection (L) was followed by azidation (M). Reaction was performed on a 1.1 g scale. 0% to 45% EtOAc in DCM was used as the eluent for purification. Isolated 0.31 g (41%) of 108 as a solid. MS: [M+H]: 551.

Preparation of ethyl 2-(2-azido-3-(4-(((4S,5R)-5-(fluoromethyl)-2,2-dimethyl-1,3-dioxolan-4-yl)methoxy)phenyl)propanamido)-3-(4-(trifluoromethyl)phenyl)propanoate (109)

General experimental procedures for phenolic alkylation (A) was followed. Reaction was performed on a 0.1 g scale and tetrabutylammonium sulfate was used. The residue was purified over silica gel using 0% to 50% EtOAc in Hexanes as an eluent to afford 0.07 g (49%) of 109. MS: [M+H]: 597.

Preparation of ethyl 2-(3-(4-(((4S,5R)-5-(fluoromethyl)-2,2-dimethyl-1,3-dioxolan-4-yl)methoxy)phenyl)-2-(4-((2-sulfamoylbenzo[d]thiazol-5-yloxy)methyl)-1H-1,2,3-triazol-1-yl)propanamido)-3-(4-(trifluoromethyl)phenyl)propanoate (110)

General experimental procedure for click reaction (E) was followed. Reaction was performed on a 0.07 g scale. 50% to 80% EtOAc in Hexanes was used as the eluent for purification. Isolated 0.009 g (9%) of 110 as a solid. MS: [M+H]: 865.

Preparation of 2-(3-(4-(((4S,5R)-5-(fluoromethyl)-2,2-dimethyl-1,3-dioxolan-4-yl)methoxy)phenyl)-2-(4-((2-sulfamoylbenzo[d]thiazol-5-yloxy)methyl)-1H-1,2,3-triazol-1-yl)propanamido)-3-(4-(trifluoromethyl)phenyl)propanoic acid (BW1391A and BW1391B)

General experimental procedure for hydrolysis (K) was followed. Reaction was performed on a 0.009 g scale. HPLC was used as the purification method. Isolated 0.004 g (43%) of BW139 (A and B) as colorless solids. MS: [M+H]: 839.

Preparation of BW1411 and BW1412

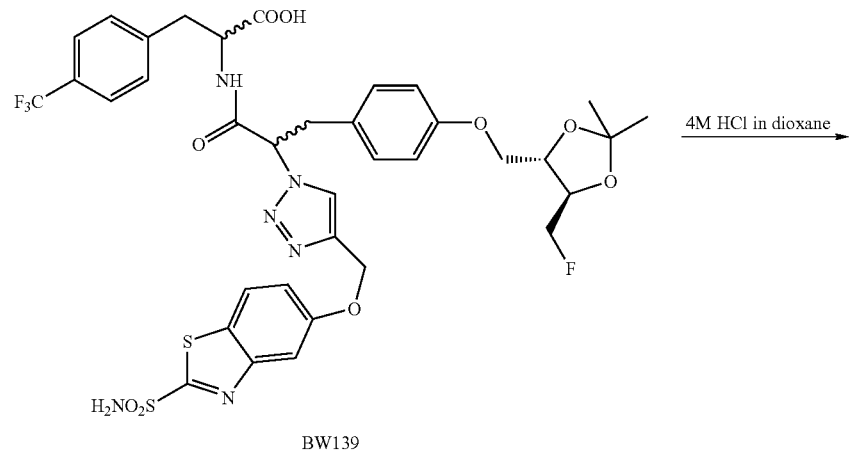

BW139

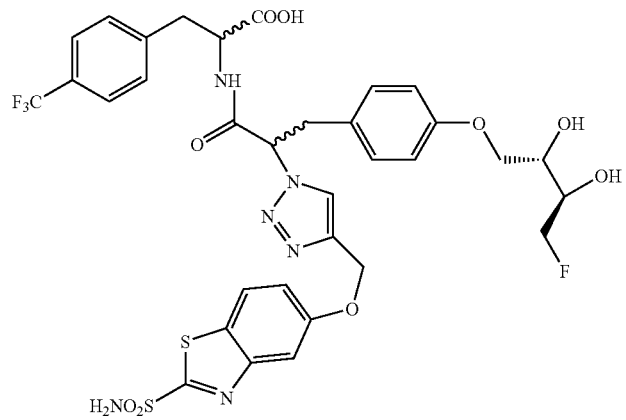

BW1411 and BW1412

Preparation of 2-(3-(4-((2S,3R)-4-fluoro-2,3-dihydroxybutoxy)phenyl)-2-(4-((2-sulfamoylbenzo[d]thiazol-5-yloxy)methyl)-1H-1,2,3-triazol-1-yl)propanamido)-3-(4-(trifluoromethyl)phenyl)propanoic acid (BW-141-1 and BW-141-2)

General experimental procedure for deprotection (B) was followed. Reaction was performed on a 0.004 g scale. HPLC was used as the purification method. Isolated 0.002 g (43%) of BW1411 and BW1412 as colorless solids. MS: [M+H]: 797.

Preparation of BW1392C and BW1392D

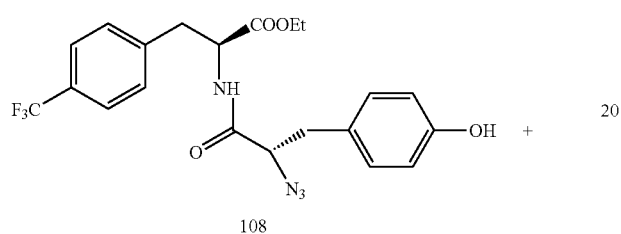

108

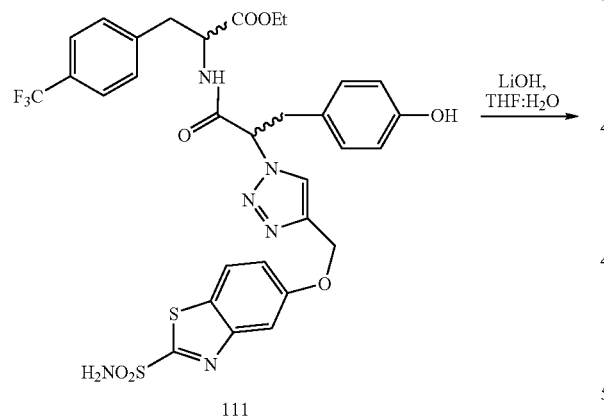

111

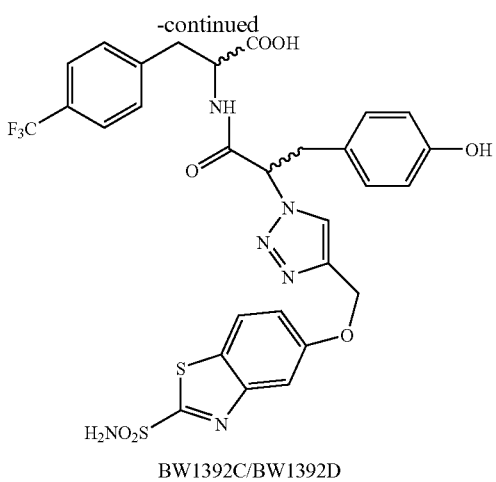

BW1392C/BW1392D

Preparation of ethyl 2-(3-(4-hydroxyphenyl)-2-(4-((2-sulfamoylbenzo[d]thiazol-5-yloxy)methyl)-1H-1,2,3-triazol-1-yl)propanamido)-3-(4-(trifluoromethyl)phenyl)propanoate (111)

General experimental procedure for click reaction (E) was followed. Reaction was performed on a 0.07 g scale. 50% to 80% EtOAc in Hexanes was used as the eluent for purification. Isolated 0.01 g (8%) of 111 as a colorless solid. MS: [M+H]: 719.

Preparation of 2-(3-(4-hydroxyphenyl)-2-(4-((2-sulfamoylbenzo[d]thiazol-5-yloxy)methyl)-1H-1,2,3-triazol-1-yl)propanamido)-3-(4-(trifluoromethyl)phenyl)propanoic acid (BW1392C and BW1392D)

General experimental procedure for hydrolysis (K) was followed. Reaction was performed on a 10 mgs scale. HPLC was used as the purification method. Isolated 4 mg (40%) of BW1392C and BW1392D as colorless solids. MS: [M+H]: 691.

Preparation of BW223

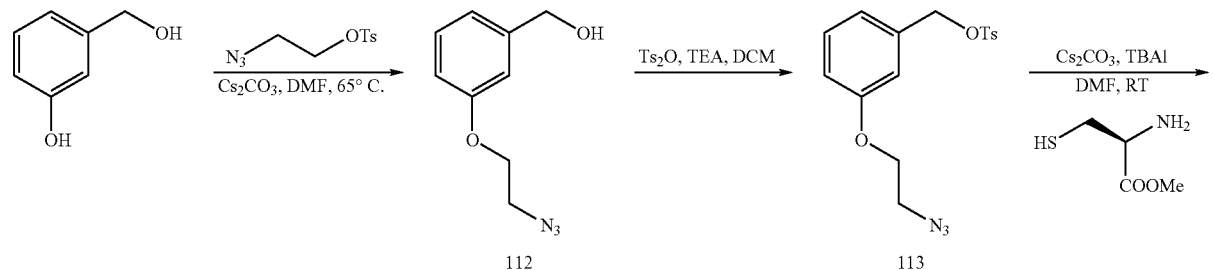

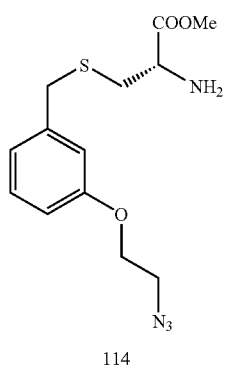

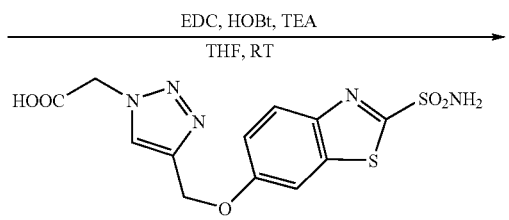

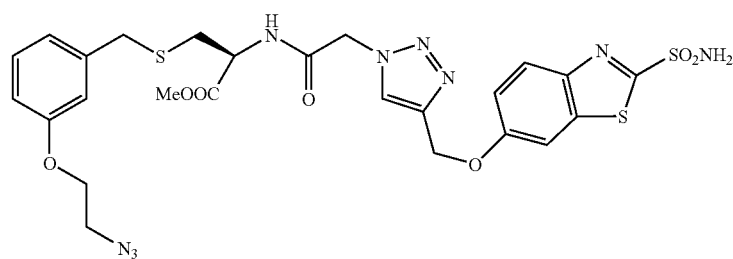

BW223

Preparation (3-(2-azidoethoxy)phenyl)methanol (112)

General experimental procedure for phenolic alkylation (A) was followed. Reaction was performed on a 1.2 g scale. 0% to 50% EtOAc in Hexanes was used as the eluent for purification. Isolated 0.61 g (63%) of 112 as a colorless oil. MS: [M+Na]: 216.

Preparation (3-(2-azidoethoxy)benzyl 4-methylbenzenesulfonate (113)

General experimental procedure for tosylation (D) was followed. Reaction was performed on a 0.59 g scale. Isolated 1.0 g (99%) of 113 as a solid. MS: [M+Na]: 370.

Preparation (S)-methyl 2-amino-3-(3-(2-azidoethoxy)benzylthio)propanoate (114)

To a round bottomed flask equipped with a magnetic stir bar, rubber septum, and argon inlet containing DMF (10 mL) was placed tosylate (1.0 g, 3.1 mmol). The reaction was cooled to 0° C. To this pre-cooled solution was added thiol (0.53 g, 3.1 mmol), $Cs_2CO_3$ (1.1 g, 3.4 mmol), tetrabutylammonium iodide (1.1 g, 3.1 mmol) and stirred at 0° C. After 1 h, the reaction was allowed to stir at room temperature for 4 h. The reaction was then poured into water (25 vol) and extracted into EtOAc (3×20 vol). The combined organic extracts were washed with brine (25 vol), dried ($Na_2SO_4$) and concentrated in vacuo to afford 0.34 g (36%) of 114. MS: [M+H]: 311.

Preparation (S)-methyl 3-(3-(2-azidoethoxy)benzylthio)-2-(2-(4-((2-sulfamoylbenzo[d]thiazol-6-yloxy)methyl)-1H-1,2,3-triazol-1-yl)acetamido)propanoate (BW223)

General experimental procedure for coupling (C) was followed. Reaction was performed on a 0.1 g scale. 100% EtOAc used as the eluent for purification. Isolated 0.068 g (32%) of BW223 as a solid. MS: [M+H]: 662.

Preparation of BW227

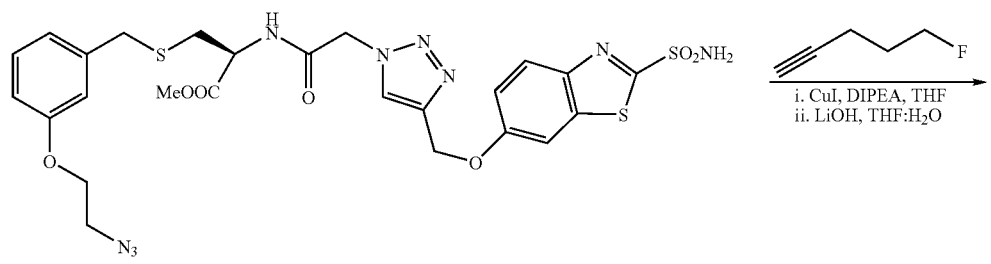

BW223

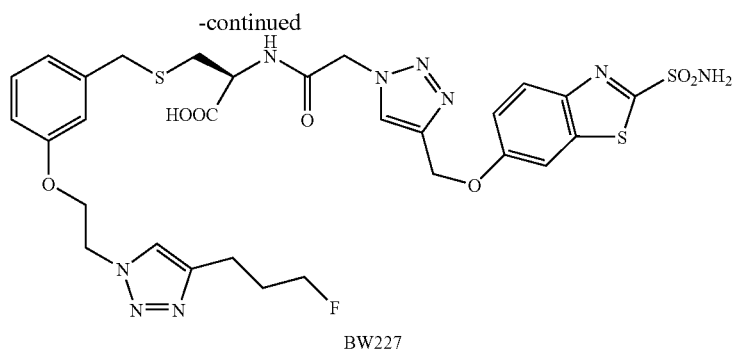

Preparation (S)-3-(3-(2-(4-(3-fluoropropyl)-1H-1,2,3-triazol-1-yl)ethoxy)benzylthio)-2-(2-(4-((2-sulfamoylbenzo[d]thiazol-6-yloxy)methyl)-1H-1,2,3-triazol-1-yl)acetamido)propanoic acid (BW227)

General experimental procedures for click reaction (E) was followed by hydrolysis (K). Reaction was performed on a 0.044 g scale. HPLC was used as the purification method. Isolated 0.005 g (10%) of BW227 as a colorless solid. MS: [M+H]: 734.

Preparation of BW241

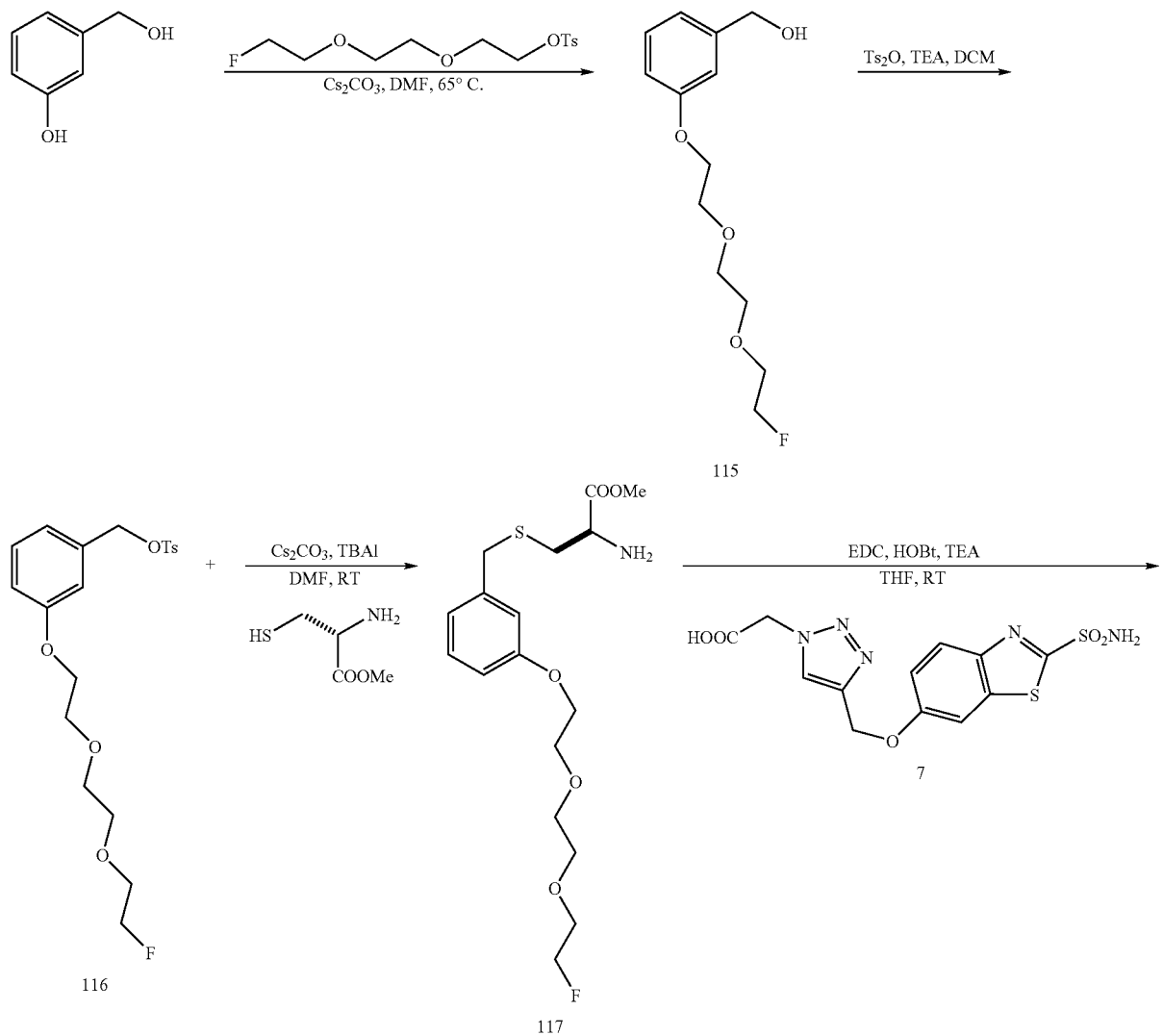

-continued

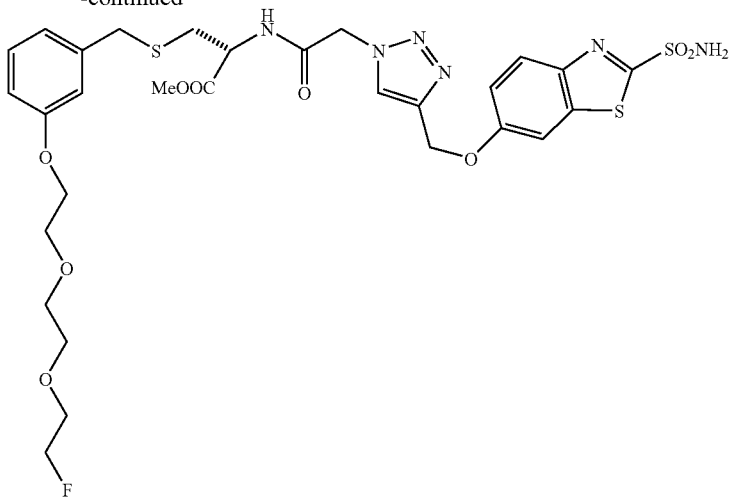

BW241

Preparation of (3-(2-(2-(2-fluoroethoxy)ethoxy)ethoxy)phenyl)methanol (115)

General experimental procedure for phenolic alkylation (A) was followed. Reaction was performed on a 3.2 g scale. Isolated 4.1 g (62%) of 115 as a crude oil. MS: [M+H]: 281.

Preparation 3-(2-(2-(2-fluoroethoxy)ethoxy)ethoxy)benzyl 4-methylbenzenesulfonate (116)

General experimental procedure for tosylation (D) was followed. Reaction was performed on a 3.3 g scale. 0% to 50% EtOAc in Hexanes was used as the eluent for purification. Isolated 3.3 g (63%) of 116 as a colorless oil. MS: [M+Na]: 435.

Preparation of (S)-methyl 2-amino-3-(3-(2-(2-(2-fluoroethoxy)ethoxy)ethoxy)benzylthio)propanoate (117)

To a round bottomed flask equipped with a magnetic stir bar, rubber septum, and argon inlet containing DMF (10 mL) was placed tosylate (0.94 g, 2.2 mmol). The reaction was cooled to 0° C. To this pre-cooled solution was added thiol (0.39 g, 2.2 mmol), $Cs_2CO_3$ (0.79 g, 2.4 mmol), tetrabutylammonium iodide (0.81 g, 2.2 mmol) and stirred at 0° C. After 1 h, the reaction was allowed to stir at room temperature for 4 h. The reaction was then poured into water (25 vol) and extracted into EtOAc (3×20 vol). The combined organic extracts were washed with brine (25 vol), dried ($Na_2SO_4$) and concentrated in vacuo. Purified by silica gel column using 0% to 50% EtOAc in DCM to afford 0.34 g (46%) of 117 as a colorless oil. MS: [M+H]: 376.

Preparation (S)-methyl 3-(3-(2-(2-(2-fluoroethoxy)ethoxy)ethoxy)benzylthio)-2-(2-(4-((2-sulfamoyl-benzo[d]thiazol-6-yloxy)methyl)-1H-1,2,3-triazol-1-yl)acetamido)propanoate (BW241)

General experimental procedure for coupling (C) was followed. Reaction was performed on a 0.35 g scale. 0% to 100% EtOAc in DCM was used as the eluent for purification. Isolated 0.1 g (15%) of BW241 as a solid. MS: [M+H]: 749.

Preparation of BW245

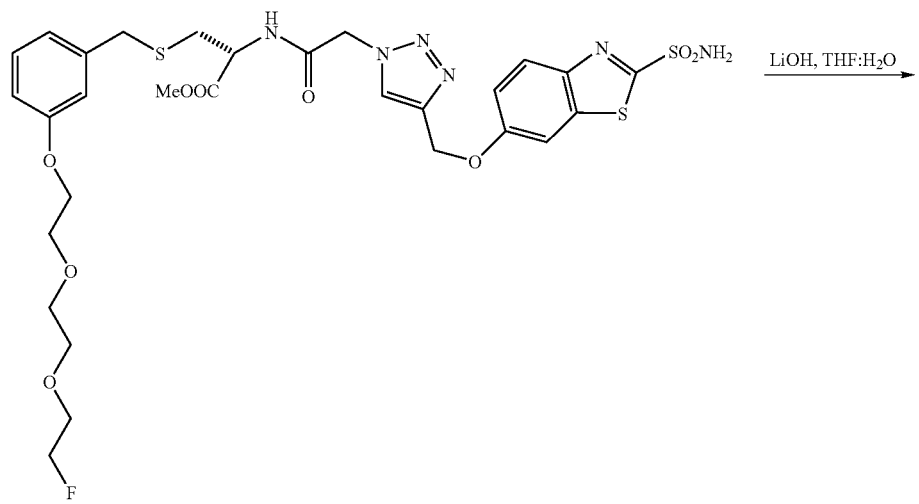

BW241

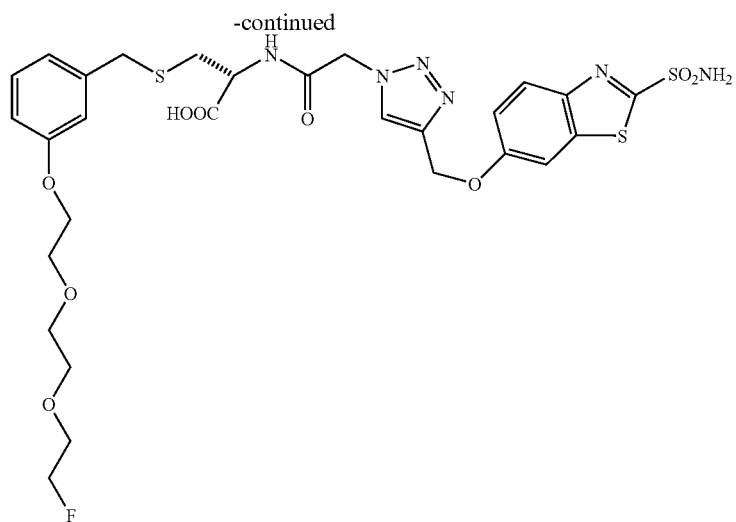
BW245
Preparation of (S)-3-(3-(2-(2-(2-fluoroethoxy)ethoxy)ethoxy)benzylthio)-2-(2-(4-((2-sulfamoylbenzo[d]thiazol-6-yloxy)methyl)-1H-1,2,3-triazol-1-yl)acetamido) propanoic acid (BW245)
General experimental procedure for hydrolysis (K) was followed. Reaction was performed on a 10 mgs scale. Prep-HPLC was used as the purification method. Isolated 0.005 g (50%) of BW245 as a solid. MS: [M+H]: 713.
Preparation of GC117a and GC117b
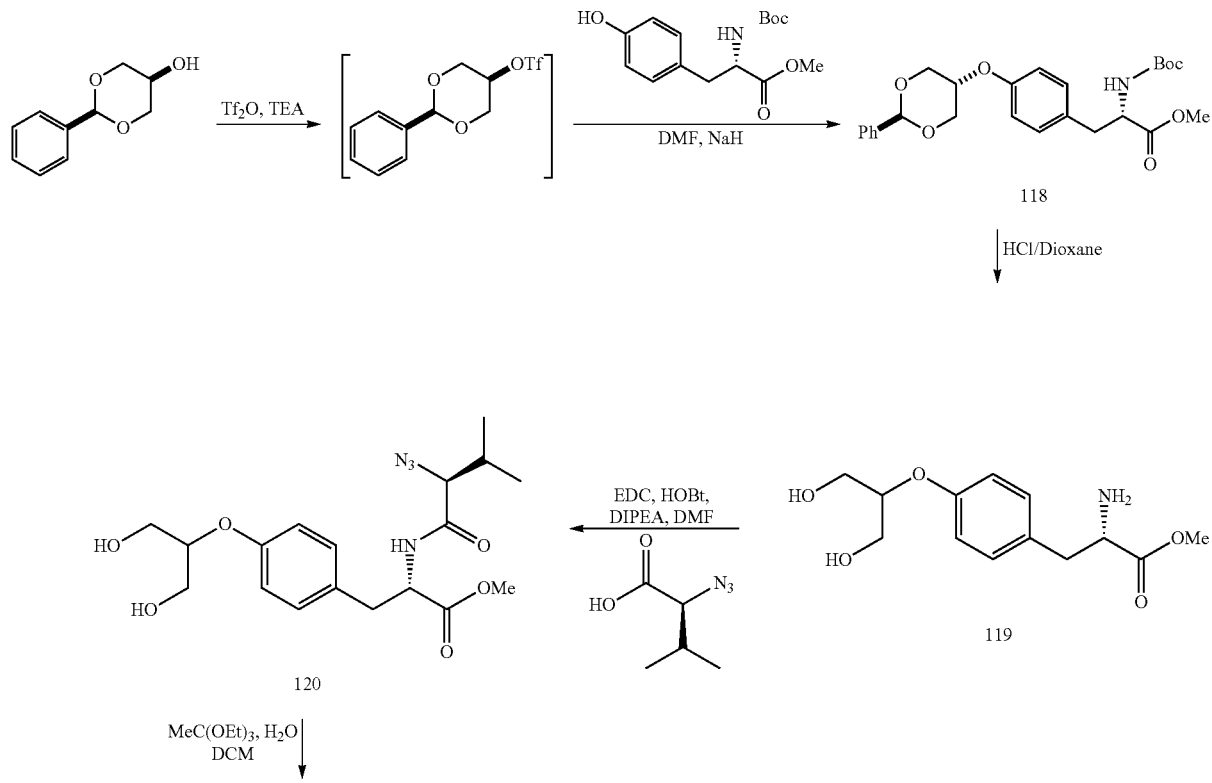

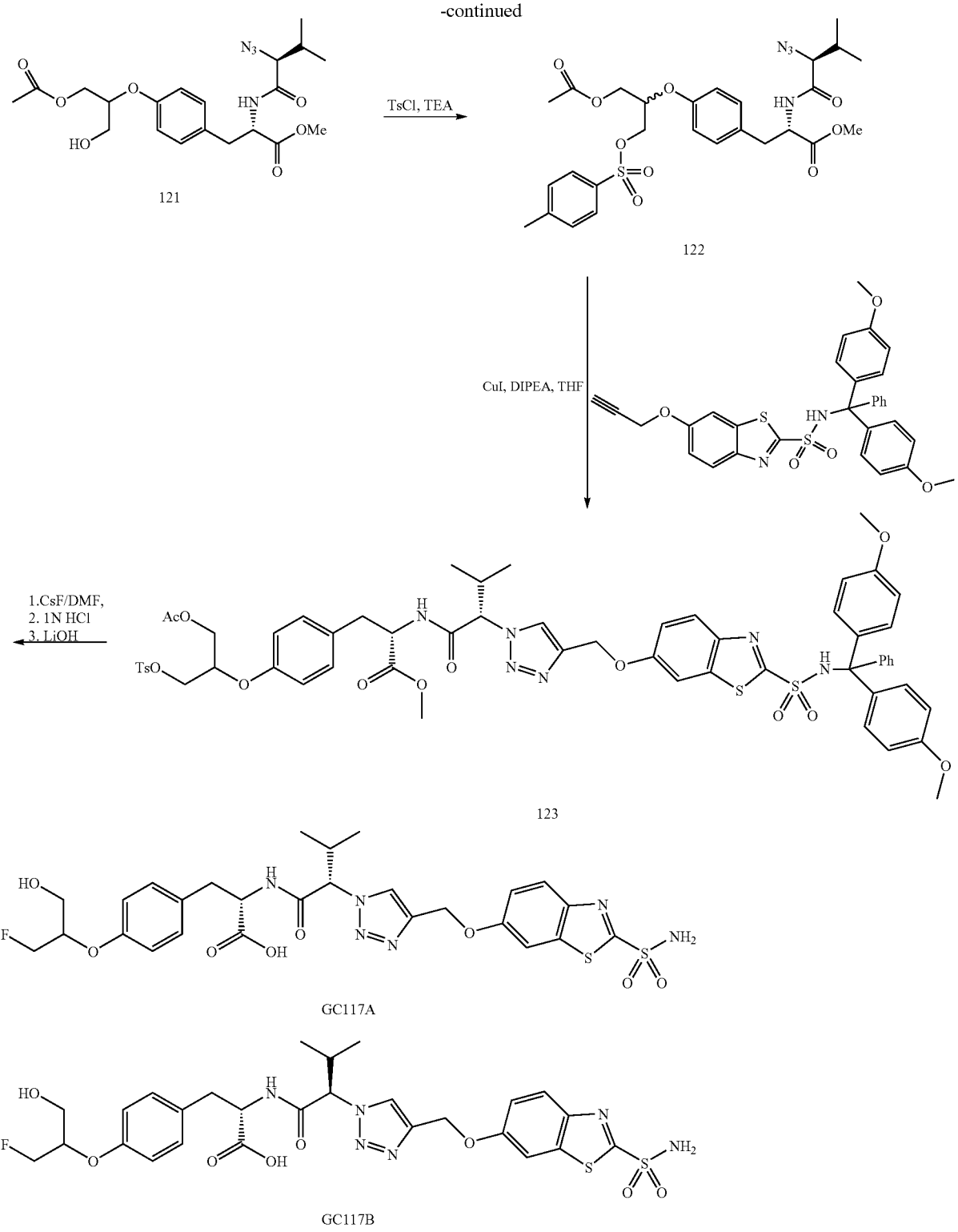

Preparation of (S)-methyl 2-(tert-butoxycarbonylamino)-3-(4-((2s,5r)-2-phenyl-1,3-dioxan-5-yloxy)phenyl)propanoate (118)

To a 200 mL round bottomed flask equipped with a magnetic stir bar, rubber septum, and argon inlet containing DCM (150 mL) was placed trans-2-phenyl-1,3-dioxan-5-ol (8.0 g, 44 mmol). To this solution was added TEA (13.5 g, 133 mmol) and the reaction was allowed to stir at ice bath temperature for 30 min. Trifluoromethanesulfonic anhydride (15 ml, 89 mmol) was added drop wise in 30 min. After the reaction was complete (30 min), it was concentrated in vacuo. The residue was purified over silica gel using Hexanes:EtOAc (5:1) as an eluent to afford trans-2-phenyl-1,3-dioxan-5-yl trifluoromethanesulfonate (5.7 g, 41%) as a yellow solid. (S)-methyl 2-(tert-butoxycarbonylamino)-3-(4-hydroxyphenyl)propanoate (6.4 g, 22 mmol) and sodium hydride (95% suspended in mineral oil) (0.51 g, 20 mmol) were dissolved in DMF (45 mL). After stirred at room temperature for 5 min, the above trans-2-phenyl-1,3-dioxan-5-yl trifluoromethanesulfonate (5.2 g, 17 mmol) was added into the reaction in the DMF (45 mL) solution. The reaction was allowed to stir at room temperature 15 h. The reaction was concentrated in vacuo. The residue was diluted with EtOAc (150 mL) and washed with brine (50 mL). The organic layer was concentrated again and purified on a silica gel. Product eluted out in 50% EtOAc:Hexanes mixture in a gradient elution on a Combiflash purification system. Isolated 118 (1.9 g, 25%) as a yellow solid.

LRMS for $C_{25}H_{31}NO_7+Na^+$, calc'd: 480.2. found: 480.2 (M+Na$^+$)

$^1$H NMR (400 MHz, CDCl$_3$) δ: 7.49 (d, J=2.0 Hz, 2H), 7.37 (m, 3H), 7.04, (d, J=8.4 Hz, 1H), 6.88 (d, J=8.4 Hz, 1H), 5.50 (s, 1H), 4.93 (br s, 1H), 4.50-4.44 (m, 4H), 3.81 (t, J=10.2 Hz, 2H), 3.72 (s, 3H), 3.10-2.98 (m, 2H), 1.42 (s, 9H).

Preparation of (S)-methyl 2-amino-3-(4-(1,3-dihydroxypropan-2-yloxy)phenyl)propanoate (119)

119 was prepared through general experimental procedure (B) and isolated as a colorless solid (40 mg scale, yield 85%).
$^1$H NMR (400 MHz, D$_2$O) δ: 7.03 (d, J=8.8 Hz, 2H), 6.87 (d, J=8.4 Hz, 3H), 4.36 (m, 1H), 4.20 (t, J=4.0 Hz, 1H), 3.70-3.55 (m, 7H), 3.15-2.97 (m, 2H); LRMS for $C_{13}H_{19}NO_5+H^+$, calc'd: 269.1. found: 269.2 (M+H$^+$)

Preparation of (S)-methyl 2-((S)-2-azido-3-methylbutanamido)-3-(4-(1,3-dihydroxypropan-2-yloxy)phenyl)propanoate (120)

120 was prepared through general experimental procedure (C) and isolated as a colorless solid (320 mg scale, yield 65%).
$^1$H NMR (400 MHz, CDCl$_3$) δ: 7.03 (d, J=8.8 Hz, 2H), 6.87 (d, J=8.8 Hz, 3H), 6.70 (b, 1H), 4.85 (m, 1H), 4.40 (t, J=4.8 Hz, 1H), 3.90 (m, 4H), 3.79 (d, J=4.4 Hz, 3H), 3.75 (s, 3H), 3.16-2.99 (m, 2H), 2.30-2.25 (m, 1H), 1.02 (d, J=7.2 Hz, 3H), 0.79 (d, J=7.2 Hz, 3 Hz); LRMS for $C_{18}H_{26}N_4O_6+H^+$, calc'd: 395.4. found: 395.6 (M+H+).

Preparation of (S)-methyl 3-(4-(1-acetoxy-3-hydroxypropan-2-yloxy)phenyl)-2-((S)-2-azido-3-methylbutanamido)propanoate (121)

To a 25 mL round bottomed flask equipped with a magnetic stir bar, rubber septum, and argon inlet containing dichloromethane (5 mL) was placed (S)-methyl 2-((S)-2-azido-3-methylbutanamido)-3-(4-(1,3-dihydroxypropan-2-yloxy)phenyl)propanoate (320 mg, 0.811 mmol). To this solution was added was added triethyloxy orthoacetate (197 mg, 1.22 mmol). The reaction was allowed to stir at room temperature for 20 min.

To the reaction was added water (21.9 mg, 1.22 mmol). The reaction was allowed to stir at room temperature 15 h. Product eluted out in 30% EtOAc:Hexanes mixture in a gradient elution on a Combiflash purification system. Isolated 121 (230 mg, 65.0%) as a colorless solid.

$^1$H NMR (400 MHz, CDCl$_3$) δ: 7.03 (d, J=8.8 Hz, 2H), 6.90 (d, J=8.8 Hz, 3H), 6.70 (b, 1H), 4.85 (m, 1H), 4.51 (m, 1H), 4.40 (m, 1H), 4.23-4.20 (m, 2H), 3.85-3.79 (m, 3H), 3.74 (s, 3H), 3.16-2.99 (m, 2H), 2.30-2.25 (m, 1H), 2.08 (s, 3H), 1.02 (d, J=6.8, 3H), 0.79 (d, J=7.2 Hz, 3 Hz).

LRMS for $C_{20}H_{28}N_4O_7+H^+$, calc'd: 437.2. found: 437.3 (M+H$^+$)

Preparation of (2S)-methyl 3-(4-(1-acetoxy-3-(tosyloxy)propan-2-yloxy)phenyl)-2-(S)-2-azido-3-methylbutanamido)propanoate (122)

122 was prepared through general experimental procedure (D) and isolated as a colorless solid (230 mg scale, yield 77%).
$^1$H NMR (400 MHz, CDCl$_3$) δ: 7.04 (d, J=8.8 Hz, 2H), 6.90 (d, J=8.8 Hz, 3H), 6.70 (br s, 1H), 4.87 (m, 1H), 4.40 (t, J=4.8 Hz, 1H), 3.90-3.79 (m, 4H), 3.78 (d, J=4.4 Hz, 1H), 3.75 (s, 3H), 3.16-2.97 (m, 2H), 2.30-2.25 (m, 1H), 1.02 (d, J=7.2 Hz, 3H), 0.79 (d, J=7.2 Hz, 3 Hz)

LRMS for $C_{27}H_{34}N_4O_9S+H^+$, calc'd: 591.2. found: 395.6 (M+H$^+$)

Preparation of (2S)-methyl 3-(4-(1-acetoxy-3-(tosyloxy)propan-2-yloxy)phenyl)-2-((S)-2-(4-((2-(N-(bis(4-methoxyphenyl)(phenyl)methyl)sulfamoyl)benzo[d]thiazol-6-yloxy)methyl)-1H-1,2,3-triazol-1-yl)-3-methylbutanamido)propanoate (123)

Compound 123 was prepared through general experimental procedure (E) and isolated as a colorless solid (225 mg scale, yield 77%).
$^1$H NMR (400 MHz, (CD$_3$)$_2$CO) δ: 8.21 (s, 1H), 8.10 (m, 2H), 7.89 (d, J=7.2 Hz, 1H), 7.80-7.70, (m, 3H), 7.45-7.41 (m, 4H), 7.30-7.12 (m, 8H), 6.95 (m, 2H), 6.75 (m, 2H), 6.60 (d, J=6.8 Hz, 4H), 5.30 (s, 2H), 5.10 (d, J=8.8 Hz, 1H), 4.71-4.65 (m, 2H), 4.35-4.15 (m, 4H), 3.84 (s, 1H), 3.79 (s, 1H), 3.66 (s, 3H), 3.62 (6H), 3.06-2.90 (m, 2H), 2.65 (s, 2H), 2.59 (s, 3H), 2.42 (s, 3H), 1.02 (d, J=7.2 Hz, 3H), 0.79 (d, J=7.2 Hz, 3H) LRMS for $C_{58}H_{60}N_6O_{14}S_3+H^+$, calc'd: 1161.3. found: 1161.3 (M+H$^+$)

Preparation of (2S)-3-(4-(1-fluoro-3-hydroxypropan-2-yloxy)phenyl)-2-((S)-3-methyl-2-(4-42-sulfamoylbenzo[d]thiazol-6-yloxy)methyl)-1H-1,2,3-triazol-1-yl)butanamido)propanoic acid (GC2117a)

GC2117a was prepared through general experimental procedure (J) and isolated as a colorless solid (10 mg scale, yield 23%).
$^1$H NMR (400 MHz, (CD$_3$)$_2$CO) δ: 8.08 (d, J=2.8 Hz, 1H), 7.91 (s, 1H), 7.80 (s, 1H), 7.78 (d, J=2.8, 1H), 7.27-7.10 (m, 3H), 6.86 (d, J=7.6 Hz, 2H), 6.67 (d, J=7.6 Hz, 2H), 5.23 (s, 2H), 5.00 (m, 1H), 4.61-4.30 (m, 4H), 3.63 (m, 2H), 2.40-2.30 (m, 2H), 0.91 (d, J=6.8 Hz, 3H), 0.56 (d, J=6.8 Hz, 3H).

LRMS for $C_{27}H_{31}FN_6O_8S_2+H^+$, calc'd: 651.2. found: 651.2 (M+H$^+$)

Preparation of (2S)-3-(4-(1-fluoro-3-hydroxypropan-2-yloxy)phenyl)-2-4R)-3-methyl-2-(4-42-sulfamoylbenzo[d]thiazol-6-yloxy)methyl)-1H-1,2,3-triazol-1-yl)butanamido)propanoic acid (GC2117B)

GC2117b was prepared through general experimental procedure (J) and isolated as a colorless solid (10 mg scale, yield 23%).
$^1$H NMR (400 MHz, (CD$_3$)$_2$CO) δ: 8.12 (s, 1H), 8.00-7.88 (m, 2H), 7.80 (s, 1H), 7.27, (s, 2H), 7.20 (d, J=6.4 Hz, 2H), 7.02 (d, J=6.0 Hz, 2H), 6.80 (d, J=6.0 Hz, 1H), 5.21 (s, 2H), 4.90 (d, J=7.2 Hz, 1H), 4.61-4.40 (m, 4H), 3.63 (m, 2H), 2.40-2.30 (m, 2H), 0.65 (d, J=6.8 Hz, 3H), 0.50 (d, J=6.8 Hz, 3H).

LRMS for $C_{27}H_{31}FN_6O_8S_2+H^+$, calc'd: 651.2. found: 651.2 (M+H$^+$).

Preparation of BD209

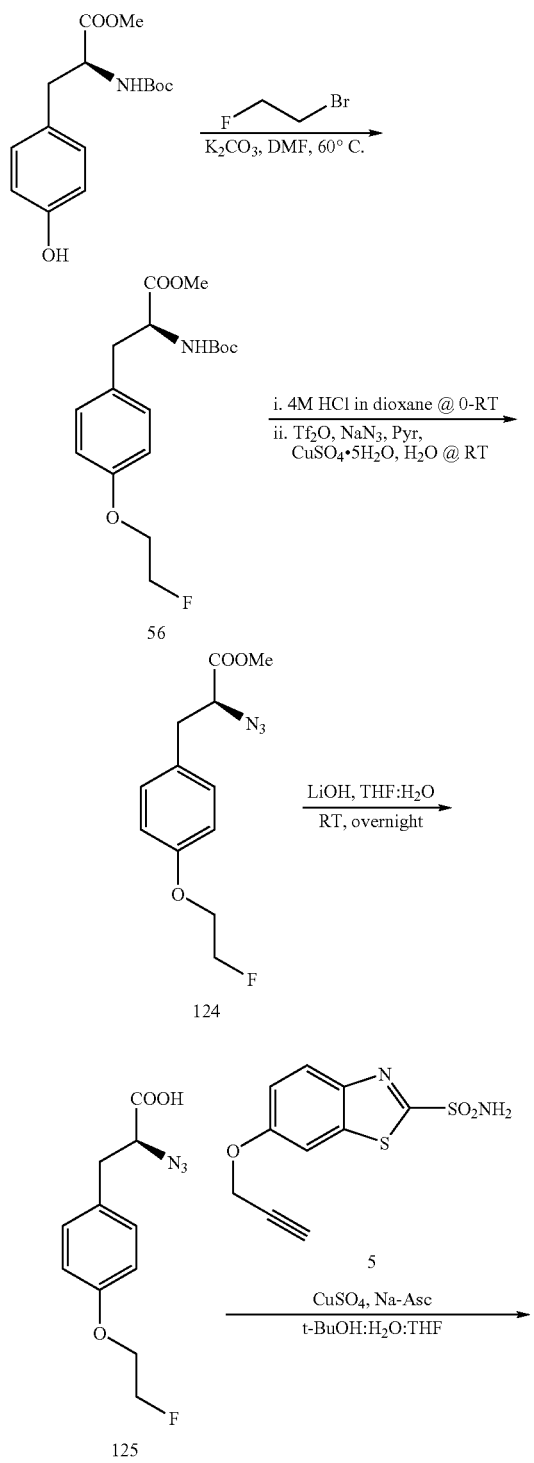

Preparation of (S)-methyl 2-azido-3-(4-(2-fluoroethoxy)phenyl)propanoate (124)

To a 500 mL round bottom flask containing 56 (5.3 g, 15.5 mmol) at 0° C., was added 4M HCl in dioxane (310 mL). The temperature was raised to RT and stirred for 2.5 h. After the reaction is done, dioxane removed in vacuo to get the colorless salt (4.29 g, 100%) and used for next step. To this, a slurry of NaN$_3$ (1.51 g, 23.25 mmol) in pyridine (23 mL) at 0° C., Tf$_2$O (3.91 mL, 23.25 mmol) was added, the reaction warmed to RT and stir for 1 hr. To this water (11 mL), CuSO$_4$.5H$_2$O (0.579 g, 2.325 mmol) were added and stirred at RT for 12 h. Reaction was carefully quenched with sat. NaHCO$_3$ (50 mL), taken up in EtOAc (100 mL) washed with 10% CuSO$_4$.5H$_2$O (2×30 mL), brine (30 mL), dried over MgSO$_4$ and concentrated in vacuo. The residue was purified over silica gel using EtOAc:Hexanes (1:1) as an eluent to afford 124 (4.13 g, 100%) as a colorless oil. LC/MS: Expected for $C_{12}H_{14}FN_3O_3$: 267.1. found: 290.1 (M+Na).

$^1$H NMR (400 MHz, CDCl$_3$) δ: 7.15 (d, J=8.8 Hz, 2H), 6.89 (d, J=8.8 Hz, 2H), 4.80-4.82 (m, 1H), 4.68-4.70 (m, 1H), 4.23-4.25 (m, 1H), 4.16-4.18 (m, 1H), 4.01-4.05 (m, 1H), 3.77 (s, 3H), 3.1-3.15 (m, 1H), 2.94-2.99 (m, 1H).

Preparation of (S)-2-azido-3-(4-(2-fluoroethoxy)phenyl)propanoic acid (125)

General experimental procedure for hydrolysis (K) was followed. Reaction was performed on a 4.13 g scale. After the reaction was done, THF was removed and the aqueous layer was acidified to pH=3 with 6M HCl. The reaction was then poured into brine (50 mL) and extracted into CHCl$_3$ (3×30 mL). The combined organic extracts were washed with water (50 mL), brine (50 mL), dried over MgSO$_4$ and concentrated in vacuo to afford 125 (3.92 g, 100%) as a colorless oil.

LC/MS: Expected for $C_{11}H_{12}FN_3O_3$: 253.09. found: 276.1 (M+Na).

Preparation of (S)-3-(4-(2-fluoroethoxy)phenyl)-2-(4-((2-sulfamoylbenzo[d]thiazol-6-yloxy)methyl)-1H-1,2,3-triazol-1-yl)propanoic acid (BD209)

General experimental procedure for click reaction (N) was followed. Performed on 0.7 g (alkyne) scale, purified over silica gel using MeOH:CH$_2$Cl$_2$ (1:4) as an eluent to afford BD209 (0.55 g, 42%) as a yellow crystalline solid.

LC/MS: Expected for $C_{21}H_{20}FN_5O_6S_2$: 521.08. found: 522.1 (M+H).

$^1$H NMR (400 MHz, CDCl$_3$) δ: 8.34 (s, 1H), 8.27 (br, s, 2H), 8.05 (d, J=9.2 Hz, 1H), 7.94 (d, J=2.4 Hz, 1H), 7.30 (dd, J=2.8, 9.2 Hz, 1H), 6.96 (d, J=8.8 Hz, 2H), 6.64 (d, J=8.8 Hz, 2H), 5.21 (d, J=2.0 Hz, 2H), 4.72-4.76 (m, 1H), 4.61-4.63 (m, 1H), 4.37-4.38 (m, 1H), 4.02-4.11 (m, 1H), 3.81-3.85 (m, 2H), 3.15-3.17 (m, 2H).

Preparation of BD246

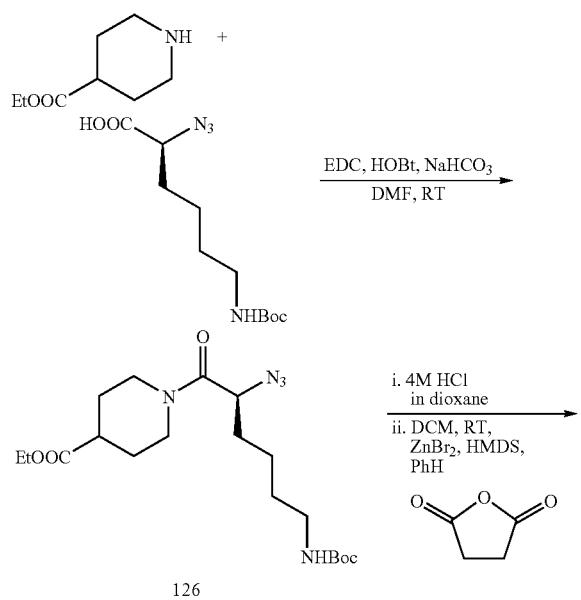

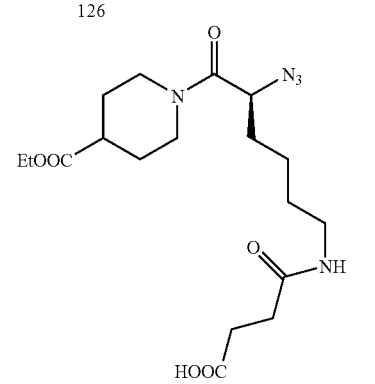

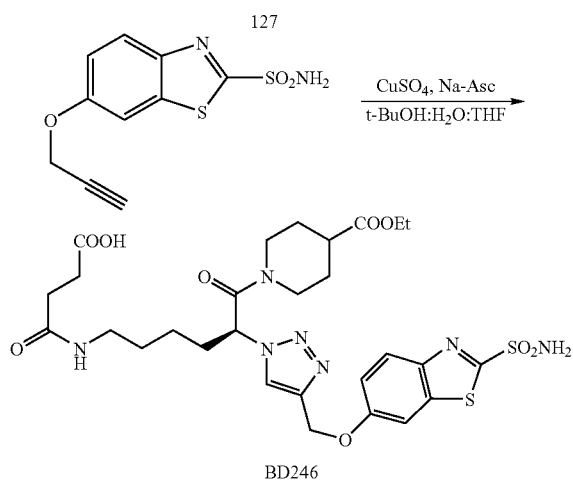

BD246

Preparation of (S)-ethyl 1-(2-azido-6-(tert-butoxycarbonylamino)hexanoyl)piperidine-4-carboxylate (126)

General experimental procedure for couplin reaction (C) was followed. Performed on 1.1 g scale. The residue was purified over silica gel using EtOAc:Hexanes (1:1) as an eluent to afford 126 (1.13 g, 76%) as a colorless oil.

LC/MS: Expected for $C_{19}H_{33}N_5O_5$: 411.25. found: 434.2 (M+Na).

Preparation of (S)-4-(5-azido-6-(4-(ethoxycarbonyl)piperidin-1-yl)-6-oxohexyl amino)-4-oxobutanoic acid (127)

To a 100 mL round bottom flask containing 126 (1.1 g, 2.68 mmol) at 0° C., was added 4M HCl in dioxane (54 mL). The temperature was raised to RT and stirred for 2.5 h. After the reaction is done, dioxane removed in vacuo to get the colorless salt (0.928 g, 100%) and used for next step. To a 50 mL round bottom flask containing dihydrofuran-2,5-dione (6 mg, 0.06 mmol), catalytic amount of DMAP, amine (20 mg, 0.0576 mmol) was added and stirred at RT for 5 h. After the completion of reaction, silica added concentrated and purified by flash column chromatography using MeOH:CHCl₃ (1:9) as an eluent to get 127 as a colorless solid (16 mg, 73%).

LC/MS: Expected for $C_{18}H_{29}N_5O_6$: 411.21. found: 412.2 (M+H⁺).

Preparation of (S)-4-(6-(4-(ethoxycarbonyl)piperidin-1-yl)-6-oxo-5-(4-((2-sulfamoyl benzo[d]thiazol-6-yloxy)methyl)-1H-1,2,3-triazol-1-yl)hexylamino)-4-oxobutanoic acid (BD246)

To a 10 mL round bottomed flask equipped with a magnetic stir bar containing t-BuOH:THF:H₂O (1:1:1, 1 mL) was placed azide (16 mg, 0.0389 mmol) and alkyne (20 mg, 0.0389 mmol). To this solution CuSO₄ (2 mg, 0.0097 mmol), sodium ascorbate (1.5 mg, 0.0078 mmol) were added and stirred for 12 h. Silica added concentrated to dryness and purified over silica gel using MeOH:CH₂Cl₂ (1:4) as an eluent to afford BD246 (8.1 mg, 31%) as a light yellow solid.

LC/MS: Expected for $C_{28}H_{37}N_7O_9S_2$: 679.21. found: 680.3 (M+H⁺).

Preparation of BD247

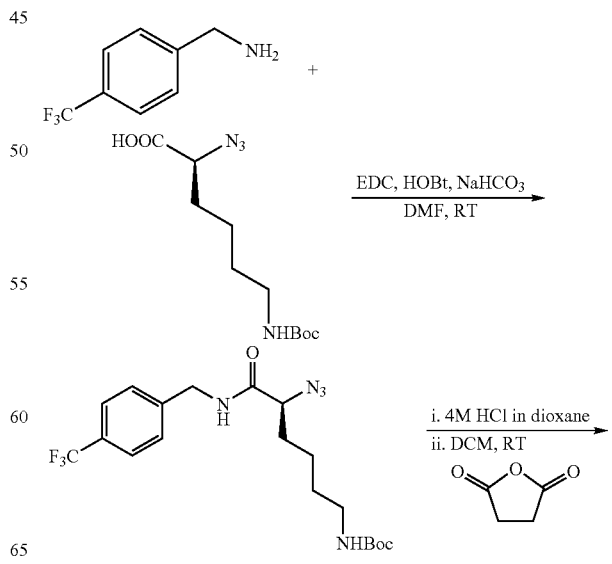

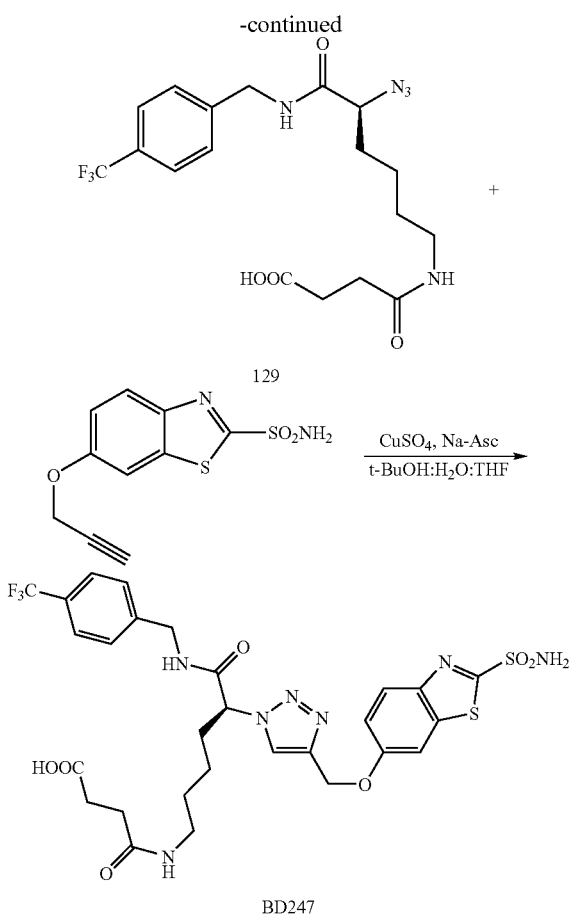

Preparation of (S)-tert-butyl 5-azido-6-oxo-6-(4-(trifluoromethyl)benzylamino)hexylcarbamate (128)

To a 200 mL round bottom flask containing acid (3.1 g, 11.55 mmol) in DMF (100 mL) was treated with HOBt (4.25 g, 31.5 mmol) and EDC (6.0 g, 31.5 mmol) at room temperature. After stirring for 1 h, a solution of amine (1.5 mL, 10.5 mmol) in DMF (2 mL) and NaHCO₃ (4.4 g, 52.5 mmol) was added to the reaction mixture and stirred for 12 h. The reaction was then poured into water (300 mL) and extracted with EtOAc (3×100 mL). The combined organic extracts were washed with water (100 mL), brine (100 mL), dried over MgSO₄ and concentrated in vacuo. The residue was purified over silica gel using EtOAc:Hexanes (1:2) as an eluent to afford 128 (3.9 g, 87%) as a colorless solid.
LC/MS: Expected for $C_{19}H_{26}F_3N_5O_3$: 429.2. found: 452.4 (M+Na⁺).

Preparation of (S)-4-(5-azido-6-oxo-6-(4-(trifluoromethyl)benzylamino)hexylamino)-4-oxobutanoic acid (129)

To a 500 mL round bottom flask containing 128 (3.9 g, 9.09 mmol) at 0° C., was added 4M HCl in dioxane (182 mL). The temperature was raised to RT and stirred for 2.5 h. After the reaction is done, dioxane removed in vacuo to get the colorless salt (3.3 g, 100%) and used for next step. To a 50 mL round bottom flask containing dihydrofuran-2,5-dione (5.4 mg, 0.0546 mmol), catalytic amount of DMAP, amine (19 mg, 0.052 mmol) was added and stirred at RT for 5 h. After the completion of reaction, silica added concentrated and purified by flash column chromatography using MeOH/CHCl₃ (10%) as an eluent to get 129 as colorless solid (6.6 mg, 31%).
LC/MS: Expected for $C_{18}H_{22}F_3N_5O_4$: 429.16. found: 430.2 (M+H).

Preparation of (S)-4-oxo-4-(6-oxo-5-(4-((2-sulfamoylbenzo[d]thiazol-6-yloxy)methyl)-1H-1,2,3-triazol-1-yl)-6-(4-(trifluoromethyl)benzylamino)hexylamino)butanoic acid (BD-2-47)

To a 10 mL round bottomed flask equipped with a magnetic stir bar containing t-BuOH:THF:H₂O (1:1:1, 1 mL) was placed 129 (6.6 mg, 0.0154 mmol) and alkyne (8 mg, 0.0154 mmol). To this solution CuSO₄ (1 mg, 0.0039 mmol), sodium ascorbate (0.6 mg, 0.0031 mmol) were added and stirred for 12 h. Silica added concentrated to dryness and purified over silica gel using MeOH:CH₂Cl₂ (1:4) as an eluent to afford BD-2-47 (9.3 mg, 93%) as a light yellow solid.
LC/MS: Expected for $C_{28}H_{30}F_3N_7O_7S_2$: 697.16. found: 698.3 (M+H).

Preparation of BD2120

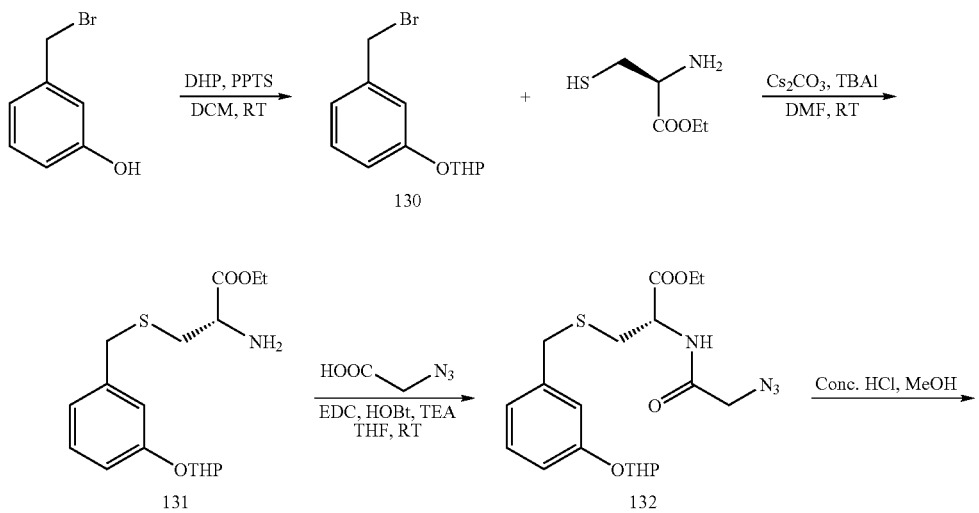

-continued
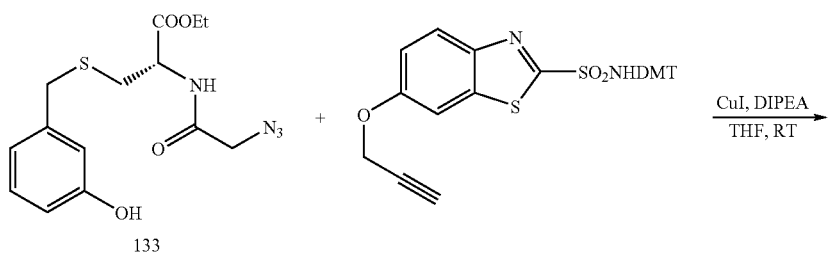
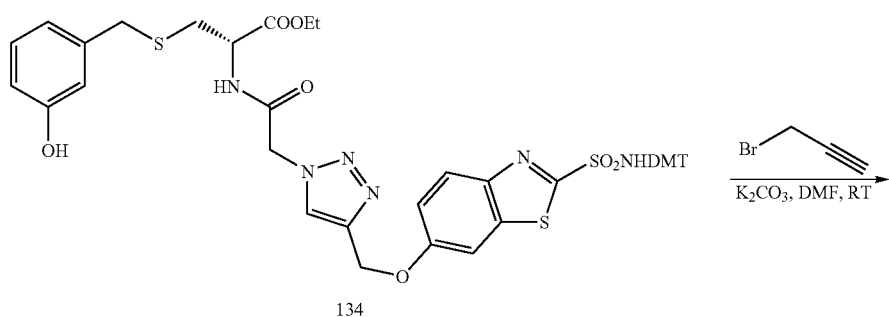
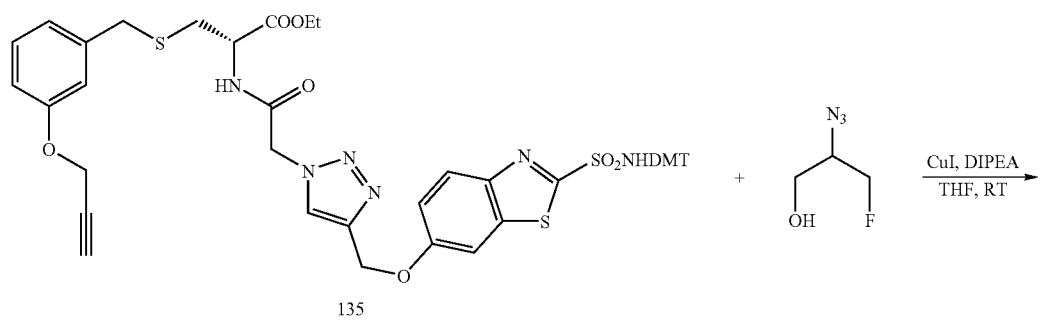
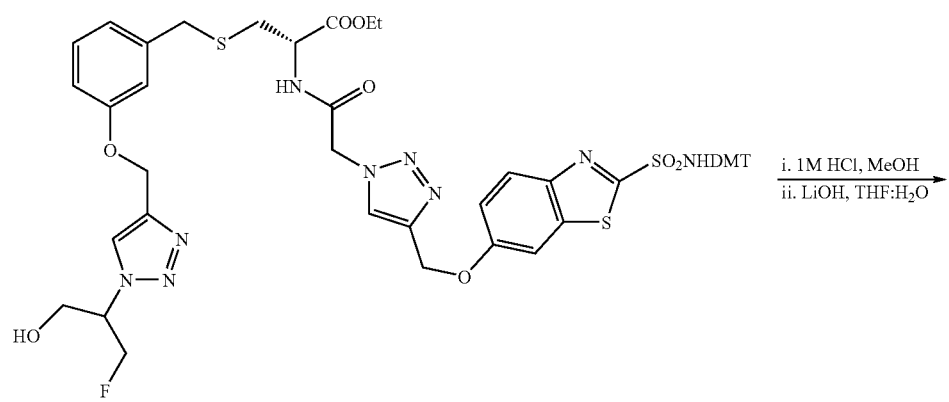

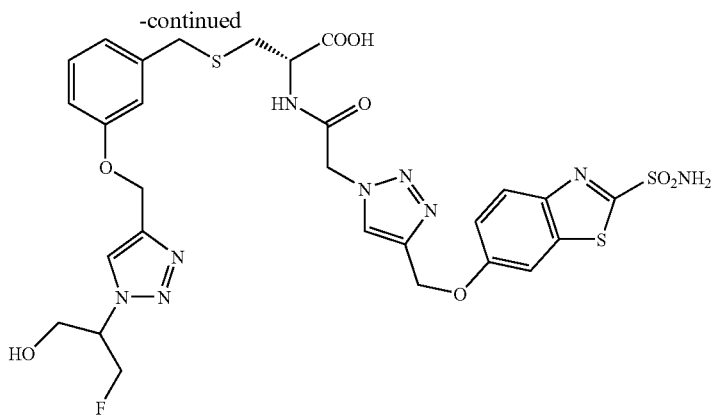

BD2120

Preparation of 2-(3-(bromomethyl)phenoxy)tetrahydro-2H-pyran (130)

To a 250 mL round bottomed flask equipped with a magnetic stir bar, rubber septum and argon inlet containing DCM (133 mL) was placed bromide (5 g, 26.7 mmol). To this solution DHP (4.83 mL, 53.4 mmol) and PPTS (1.0 g, 4.0 mmol) were added and the reaction was allowed to stir at RT for 12 h. The reaction was concentrated on silica and the residue was purified over silica gel using EtOAc:Hexanes (1:9) as an eluent to afford 130 (5.7 g, 79%) as a colorless oil.

Preparation of (2S)-ethyl 2-amino-3-(3-(tetrahydro-2H-pyran-2-yloxy)benzylthio)propanoate (131)

To a 500 mL round bottomed flask equipped with a magnetic stir bar, rubber septum and argon inlet containing DMF (200 mL) was placed 130 (5.7 g, 21.0 mmol). To this solution $Cs_2CO_3$ (6.8 g, 21.0 mmol) and TBAI (7.75 g, 21.0 mmol) were added at 0° C. and the reaction was allowed to stir at RT for 2 h. The reaction was then cooled to 0° C. and thiol was added and the reaction was allowed to stir at RT for 12 h. The reaction was poured into water (500 mL) and extracted into EtOAc (3×150 mL). The combined organic extracts were washed with water (150 mL), brine (150 mL), dried over $MgSO_4$ and concentrated in vacuo. The residue was purified over silica gel using EtOAc:Hexanes (9:1) as an eluent to afford 131 (5.9 g, 83%) as a colorless oil.

LC/MS: Expected for $C_{17}H_{25}NO_4S$: 339.15. found: 340.4 (M+H).

$^1$H NMR (400 MHz, $CDCl_3$) δ: 7.19 (t, J=7.6 Hz, 1H), 6.99-7.01 (m, 1H), 6.91-6.94 (m, 2H), 5.40 (t, J=3.2 Hz, 1H), 4.17 (q, J=7.2, 14 Hz, 2H), 3.85-3.92 (m, 1H), 3.7 (s, 2H), 3.56-3.66 (m, 2H), 2.84-2.88 (m, 1H), 2.71 (2dd, J=1.6, 7.6 Hz, 1H), 1.93-2.01 (m, 1H), 1.81-1.84 (m, 2H), 1.54-1.72 (m, 3H), 1.26 (t, J=7.2 Hz, 3H).

Preparation of (2S)-ethyl 2-(2-azidoacetamido)-3-(3-(tetrahydro-2H-pyran-2-yloxy)benzylthio)propanoate (132)

To a 500 mL round bottom flask containing 131 (5.9 g, 17.38 mmol) and azido acid (2.13 g, 20.8 mmol) in THF (174 mL) was treated with EDC (5.33 g, 27.81 mmol), HOBt (3.75 g, 27.81 mmol) and TEA (12.2 mL, 86.9 mmol) at room temperature and was stirred for 12 h. The reaction was concentrated on silica and was purified over silica gel using EtOAc:Hexanes (1:1) as an eluent to afford 132 (6.5 g, 89%) as a colorless oil.

LC/MS: Expected for $C_{19}H_{26}N_4O_5S$: 422.16. found: 445.2 (M+Na).

Preparation of (S)-ethyl 2-(2-azidoacetamido)-3-(3-hydroxybenzylthio)propanoate (133)

To a 250 mL round bottom flask containing 132 (6.5 g, 15.4 mmol) in MeOH (150 mL) at RT, was added Conc. HCl (1 mL) and stirred for 2.5 h. The reaction was concentrated on silica and purified over silica gel using EtOAc:Hexanes (1:1) as an eluent to afford 133 (4.8 g, 92%) as a colorless oil.

LC/MS: Expected for $C_{14}H_{18}N_4O_4S$: 338.1. found: 361.1 (M+Na).

Preparation of (S)-ethyl 2-(2-(4-((2-(N-(bis(4-methoxyphenyl)(phenyl)methyl)sulfamoyl)benzo[d]thiazol-6-yloxy)methyl)-1H-1,2,3-triazol-1-yl)acetamido)-3-(3-hydroxybenzylthio)propanoate (134)

To a 25 mL round bottomed flask equipped with a magnetic stir bar containing THF (5 mL) was placed alkyne (149 mg, 0.44 mmol) and azide (251 mg, 0.44 mmol). To this solution CuI (8 mg, 0.044 mmol) and DIPEA (0.084 mL, 0.484 mmol) were added and stirred for 12 h. Silica was added, concentrated to dryness and purified over silica gel using EtOAc:Hexanes (1:1) as an eluent to afford 134 (379 mg, 95%) as a light yellow solid.

$^1$H NMR (400 MHz, $CDCl_3$) δ: 7.81-7.84 (m, 2H), 7.05-7.35 (m, 12H), 6.68-6.77 (m, 3H), 6.52-6.55 (m, 4H), 5.19 (s, 2H), 5.07 (br, s, 2H), 4.66-4.69 (m, 1H), 4.06-4.12 (m, 2H), 3.60 (s, 6H), 3.53 (d, J=4.0 Hz, 2H), 2.83 (d, J=5.2 Hz, 2H), 1.16-1.25 (m, 3H).

Preparation of (S)-ethyl 2-(2-(4-((2-(N-(bis(4-methoxyphenyl)(phenyl)methyl)sulfamoyl)benzo[d]thiazol-6-yloxy)methyl)-1H-1,2,3-triazol-1-yl)acetamido)-3-(3-(prop-2-ynyloxy)benzylthio)propanoate (135)

To a 10 mL round bottomed flask equipped with a magnetic stir bar, rubber septum and argon inlet containing DMF (0.5 mL) was placed 134 (49 mg, 0.054 mmol). To this solution $K_2CO_3$ (22 mg, 0.162 mmol) and 3-bromoprop-1-yne (0.01 mL, 0.0702 mmol) were added and the reaction was allowed

Preparation of (2S)-ethyl 2-(2-(4-((2-(N-(bis(4-methoxyphenyl)(phenyl)methyl)sulfamoyl)benzo[d]thiazol-6-yloxy)methyl)-1H-1,2,3-triazol-1-yl)acetamido)-3-(3-((1-(1-fluoro-3-hydroxypropan-2-yl)-1H-1,2,3-triazol-4-yl)methoxy)benzylthio)propanoate (136)

To a 10 mL round bottomed flask equipped with a magnetic stir bar containing THF (1 mL) was placed 135 (46 mg, 0.0486 mmol) and azide (6 mg, 0.0486 mmol). To this solution CuI (1 mg, 0.00486 mmol) and DIPEA (0.09 mL, 0.0535 mmol) were added and stirred for 12 h. Silica added, concentrated to dryness and purified over silica gel using EtOAc:Hexanes (1:2) as an eluent to afford 136 (yield not determined) as a light yellow solid.

LC/MS: Expected for $C_{51}H_{52}FN_9O_{10}S_3$: 1065.3. found: 764.1 (M-DMT).

Preparation of (2S)-3-(3-(1-(1-fluoro-3-hydroxypropan-2-yl)-1H-1,2,3-triazol-4-yl)methoxy)benzylthio)-2-(2-(4-((2-sulfamoylbenzo[d]thiazol-6-yloxy)methyl)-1H-1,2,3-triazol-1-yl)acetamido)propanoic acid (BD2120)

To a 10 mL round bottom flask containing 136 (51 mg, 0.0486 mmol) in MeOH (2 mL) at RT, was added 1M HCl (1 mL) and stirred for 2 h. After the reaction is done, MeOH was removed and the residue was dissolved in THF:H$_2$O (1:1, 0.5 mL). To this LiOH (3 mg, 0.0309 mmol) was added and reaction was stirred at RT for 2 h, sample dilute with water (5 mL) and purified by HPLC using CH$_3$CN:H$_2$O (1:2) as an eluent to afford BD-2-120 (5.9 mg, 27%) as colorless solid.

LC/MS: Expected for $C_{28}H_{30}FN_9O_8S_3$: 735.1. found: 736.0 (M+H).

Preparation of BD336

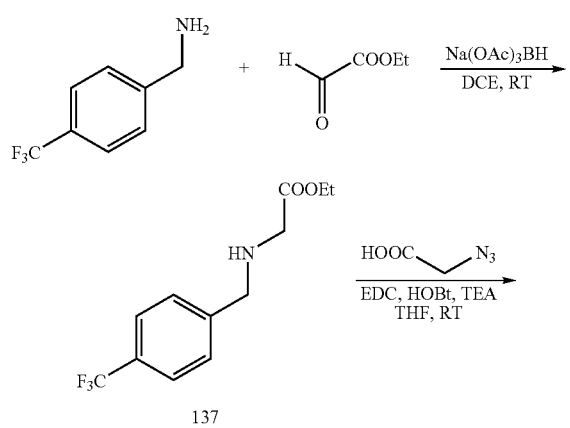

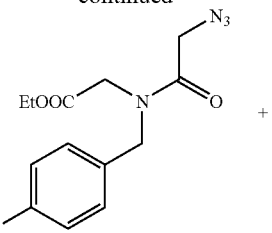

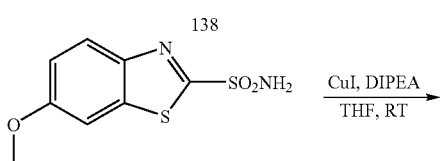

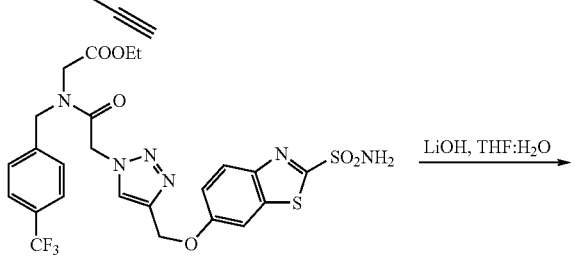

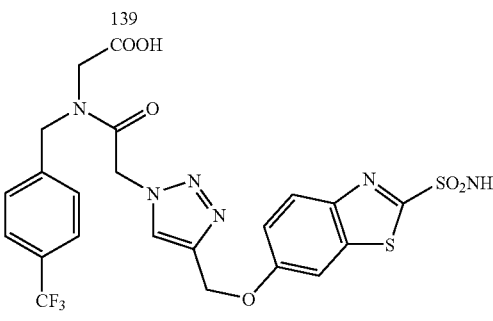

Preparation of ethyl 2-(4-(trifluoromethyl)benzylamino)acetate (137)

To a 200 mL round bottom flask containing amine (3 g, 17.1 mmol) in DCE (60 mL) at RT, was added aldehyde (1.83 g, 18.0 mmol) and sodium triacetoxyborohydride (5.07 g, 23.94 mmol) stirred for 2 h. After the reaction is done, reaction is poured into sat. NaHCO$_3$ (200 mL) and extracted with DCM (3×50 mL). The combined organics were washed with brine (50 mL), dried over MgSO$_4$ concentrated on silica and was purified over silica gel using EtOAc:Hexanes (1:2) as an eluent to afford 137 (3.91 g, 88%) as a yellow oil. LC/MS: Expected for $C_{12}H_{14}F_3NO_2$: 261.10. found: 262.1 (M+H).

Preparation of ethyl 2-(2-azido-N-(4-(trifluoromethyl)benzyl)acetamido)acetate (138)

To a 25 mL round bottom flask containing 137 (0.307 g, 1.18 mmol) and azido acid (0.89 g, 1.77 mmol) in THF (8 mL) was treated with EDC (0.362 g, 1.89 mmol), HOBt (0.255 g, 1.89 mmol) and TEA (0.83 mL, 5.9 mmol) at room temperature and was stirred for 12 h. The reaction was concentrated on silica and was purified over silica gel using EtOAc:Hexanes (2:1) as an eluent to afford 138 (0.259 g, 64%) as a yellow oil.

LC/MS: Expected for $C_{14}H_{15}F_3N_4O_3$: 344.11. found: 367.1 (M+Na).

Preparation of ethyl 2-(2-(4-((2-sulfamoylbenzo[d]thiazol-6-yloxy)methyl)-1H-1,2,3-triazol-1-yl)-N-(4-(trifluoromethyl)benzyl)acetamido)acetate (139)

To a 10 mL round bottomed flask equipped with a magnetic stir bar containing THF (4 mL) was placed 138 (0.259 mg, 0.75 mmol) and alkyne (0.201 mg, 0.75 mmol). To this solution CuI (0.014 g, 0.075 mmol) and DIPEA (0.2 mL, 1.125 mmol) were added and stirred for 4 h. Concentrated to dryness on silica and purified over silica gel using EtOAc:Hexanes (1:1) as an eluent to afford 139 (0.177 g, 38%) as a light yellow solid.
LC/MS: Expected for $C_{24}H_{23}F_3N_6O_6S_2$: 612.11. found: 613.1 (M+H).

Preparation of 2-(2-(4-((2-sulfamoylbenzo[d]thiazol-6-yloxy)methyl)-1H-1,2,3-triazol-1-yl)-N-(4-(trifluoromethyl)benzyl)acetamido)acetic acid (BD336)

To a 20 mL round bottomed flask equipped with a magnetic stir bar containing THF:$H_2O$ (1:1, 10 mL) was placed 139 (176 mg, 0.29 mmol). To this solution LiOH (61 mg, 1.45 mmol) was added and the reaction was allowed to stir at RT for 3 h. After the reaction was done, THF was removed and the aqueous layer was acidified to pH=3 with 6 M HCl. The reaction was then poured into brine (50 mL) and extracted into $CHCl_3$ (3×20 mL). The combined organic extracts were washed with water (20 mL), brine (20 mL), dried over $MgSO_4$ and concentrated in vacuo to afford BD336 (yield not determined) as a colorless solid.
LC/MS: Expected for $C_{22}H_{19}F_3N_6O_6S_2$: 584.08. found: 585.1 (M+H).

Preparation of UG3150

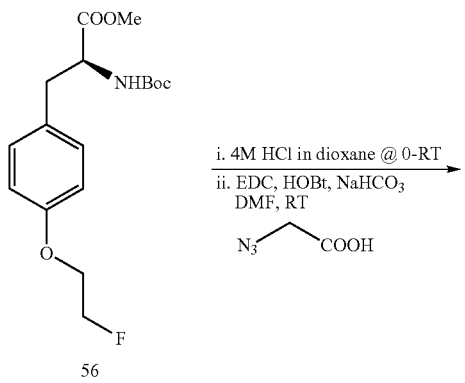

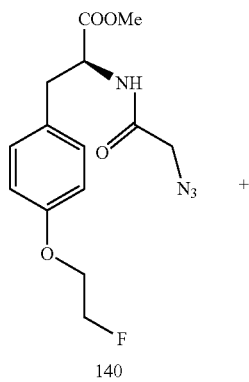

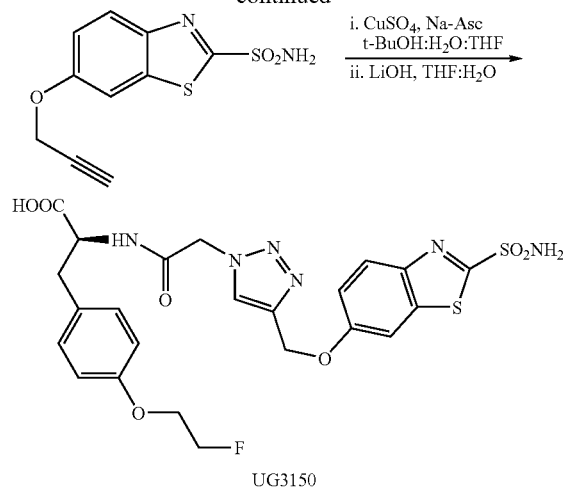

Preparation of (S)-methyl 2-(2-azidoacetamido)-3-(4-(2-fluoroethoxy)phenyl)propanoate (140)

To a 500 mL round bottom flask containing 56 (2.16 g, 6.33 mmol) at 0° C., was added 4M HCl in dioxane (127 mL). The temperature was raised to RT and stirred for 2.5 h. After the reaction is done, dioxane removed in vacuo to get the colorless salt (1.75 g, 100%) and used for next step. To a 100 mL round bottom flask containing azido acid (1.91 g, 18.9 mmol) in DMF (38 mL) was treated with EDC (3.61 g, 18.92 mmol) and HOBt (2.55 g, 18.92 mmol) at room temperature. After stirring for 1 hr, HCl salt (1.52 g, 5.49 mmol) and $NaHCO_3$ (2.65 g, 31.54 mmol) were added to the reaction mixture and stirred for 12 h. The reaction was then poured into water (150 mL) and extracted with EtOAc (3×50 mL). The combined organic extracts were washed with water (50 mL), brine (50 mL), dried over $MgSO_4$ and concentrated in vacuo. The residue was purified over silica gel using EtOAc:Hexanes (1:1) as an eluent to afford 140 (1.55 g, 87%) as a colorless oil.
LC/MS: Expected for $C_{14}H_{17}FN_4O_4$: 324.12. found: 325.2 (M+H).

Preparation of (S)-3-(4-(2-fluoroethoxy)phenyl)-2-(2-(4-((2-sulfamoylbenzo[d]thiazol-6-yloxy)methyl)-1H-1,2,3-triazol-1-yl)acetamido)propanoic acid (UG3150)

To a 25 mL round bottomed flask equipped with a magnetic stir bar containing t-BuOH:THF:$H_2O$ (1:1:1, 9 mL) was placed 140 (0.39 g, 1.194 mmol) and alkyne (0.32 g, 1.194 mmol). To this solution $CuSO_4$ (0.015 g, 0.056 mmol), sodium ascorbate (0.024 g, 0.119 mmol) were added and stirred for 12 h. Reaction was concentrated to dryness and used for next step. To this LiOH (0.012 g, 0.279 mmol) was added and reaction was stirred at RT for 2 h, sample dilute with water (25 mL) and purified by HPLC using $CH_3CN$:$H_2O$ (1:2) as an eluent to afford UG3150 (0.09 g, 84%) as a colorless solid.
LC/MS: Expected for $C_{23}H_{23}FN_6O_7S_2$: 578.11. found: 579.1 (M+H).

Fluorescent Tag:
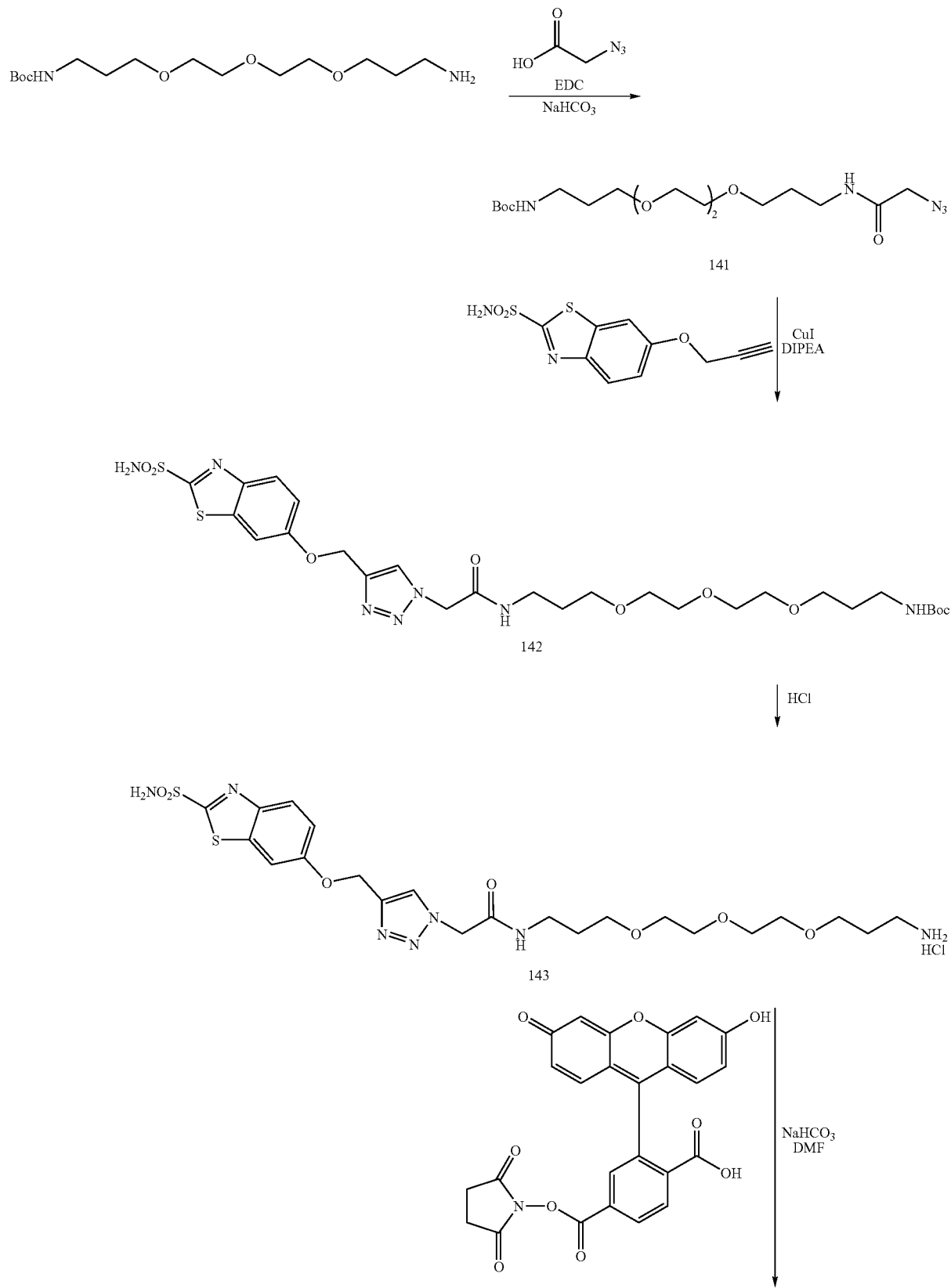

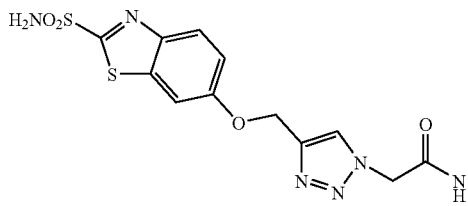
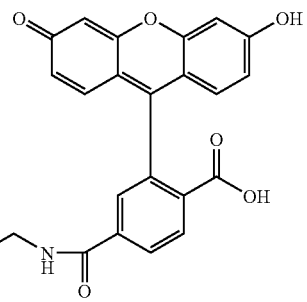

144

Preparation of tent-Butyl 1-azido-2-oxo-7,10,13-trioxa-3-azahexadecan-16-ylcarbamate (141)

To a 25 mL round bottomed flask equipped with a magnetic stir bar, rubber septum, and argon inlet containing tert-butyl 3-(2-(2-(3-aminopropoxy)ethoxy)ethoxy)propylcarbamate (amine, 160 mg, 0.5 mmol), 2-azidoacetic acid (56 mg, 0.55 mmol, in 50% DCM solution), NaHCO$_3$ (168 mg, 2 mmol), and 1 mL DMF was added EDC (115 mg, 0.6 mmol). The mixture was stirred at rt for 3 h and concentrated in vacuo. The crude product was purified by silica chromatography (gradient 5% to 90% EtOAc in hexane) to afford compound 141 as a clear oil (130 mg, 65%). MS (ESI) m/z 426 (M+Na$^+$).

Preparation of tert-Butyl 2-oxo-1-(4-((2-sulfamoylbenzo[d]thiazol-6-yloxy)methyl)-1H-1,2,3-triazol-1-yl)-7,10,13-trioxa-3-azahexadecan-16-ylcarbamate (142)

To a 25 mL round bottomed flask equipped with a magnetic stir bar, rubber septum, and argon inlet containing tert-butyl 1-azido-2-oxo-7,10,13-trioxa-3-azahexadecan-16-ylcarbamate (130 mg, 0.36 mmol), 6-(prop-2-ynyloxy)benzo[d]thiazole-2-sulfonamide (Alkyne, 107 mg, 0.4 mmol), CuI (6.9 mg, 0.036 mmol), and THF (3 mL) was added DIPEA (52 mg, 0.4 mmol). The mixture was stirred at rt for 15 h and concentrated. The crude material was purified with silical chromatography (gradient 10% to 90% EtOAc in hexane) to afford compound 142 as a clear wax (125 mg, 52%). MS (ESI) m/z 694(M+Na$^+$).

Preparation of 2-(6-Hydroxy-3-oxo-3H-xanthen-9-yl)-4-(2-oxo-1-(4-((2-sulfamoylbenzo[d]thiazol-6-yloxy)methyl)-1H-1,2,3-triazol-1-yl)-7,10,13-trioxa-3-azahexadecan-16-ylcarbamoyl)benzoic acid) (144)

To a 25 mL round bottomed flask equipped with a magnetic stir bar, rubber septum, and argon inlet containing tert-Butyl 2-oxo-1-(4-((2-sulfamoylbenzo[d]thiazol-6-yloxy)methyl)-1H-1,2,3-triazol-1-yl)-7,10,13-trioxa-3-azahexadecan-16-ylcarbamate (142, 125 mg, 0.18 mmol) was added 4 M HCl in dioxane (2 mL). The mixture was stirred at rt for 1 h and concentrated in vacuo and further dried under high vacuum to afford hydrochloride salt 143 as a clear wax (140 mg, 100%). MS (ESI) m/z 572 (M+H$^+$).

To this hydrochloride salt (30 mg, 0.049 mmol) in 1 mL DMF was added NaHCO$_3$ (21 mg, 0.25 mmol) and the mixture was stirred for 3 min. To this solution covered with alumina foil was added 4-((2,5-dioxopyrrolidin-1-yloxy)carbonyl)-2-(6-hydroxy-3-oxo-3H-xanthen-9-yl)benzoic acid (fluorescine, 25 mg, 0.054 mmol). The reaction was stirred at rt in dark for 2 h and concentrated, and diluted with 10 mL of MeOH and 10 mL of water. The solution was loaded on preparative RP-HPLC and eluted with TFA (0.05%) buffered MeCN and water (gradient 10% to 80% MeCN). The fractions containing the desired product 144 was lyophilized to afford a yellow solid (20 mg, 40%). MS (ESI) m/z 930(M+H$^+$).

Preparation of DHK33

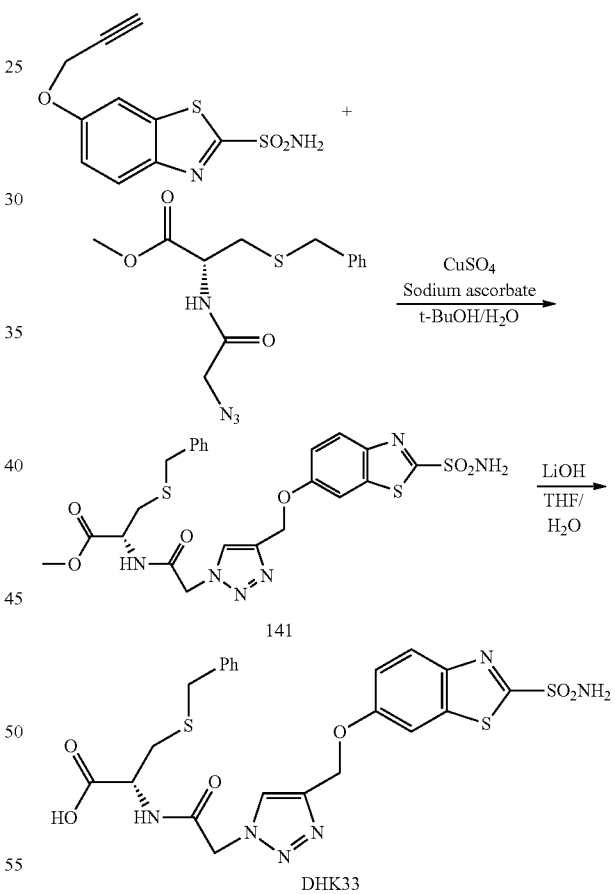

Preparation of (R)-methyl 3-(benzylthio)-2-(2-(4-((2-sulfamoylbenzo[d]thiazol-6-yloxy)methyl)-1H-1,2,3-triazol-1-yl)acetamido)propanoate (141)

Acetylene (6.1 mg, 0.023 mmol, 1.05 equiv) was treated with azide (6.7 mg, 0.022 mmol, 1 equiv) and CuSO$_4$.5H$_2$O (0.04 M aqueous solution in pH 7.4 phosphate buffer, 0.2 equiv), sodium ascorbate (0.1 M aqueous solution in pH 7.4 phosphate buffer, 0.4 equiv) in t-BuOH (0.5 mL) and H$_2$O (0.5 mL). The mixture was stirred at room temperature for 24 h. After the reaction was complete, the mixture was diluted with 1 mL of water and 1 mL of ether. The solid product was filtered, washed with an aqueous 0.1% NH$_4$OH solution (1 mL), water (1 mL) and ether (1 mL) and dried under vacuum. Yield: 0.011 g, 88%.

Preparation of (R)-3-(benzylthio)-2-(2-(4-((2-sulfamoylbenzo[d]thiazol-6-yloxy)methyl)-1H-1,2,3-triazol-1-yl)acetamido)propanoic acid (DHK33)

Compound 141 (5.0 mg, 0.0087 mmol, 1 equiv) in a THF/H$_2$O mixture (1:1, 1 mL) was treated with LiOH (0.4 mg, 0.010 mmol, 1.2 equiv) and irradiated in a Biotage Emrys Optimizer microwave reactor (250 W) at 100° C. for 10 min. After cooling the contents of the tube to room temperature, the solvent was removed and the crude product was purified by HPLC. Yield: 3 mg, 63%.

Preparation of (S)-3-phenyl-2-(4-((2-sulfamoylbenzo[d]thiazol-6-yloxy)methyl)-1H-1,2,3-triazol-1-yl)-N-(4-(trifluoromethyl)benzyl)propanamide (DHK251)

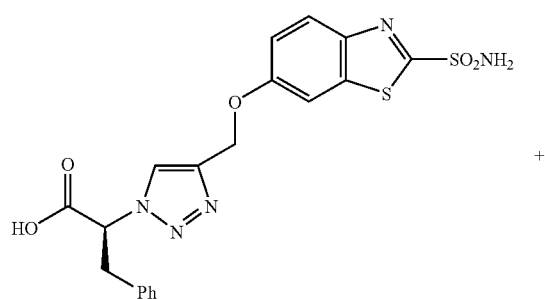

A 5 mL microwave tube was charged with acid (14 mg, 0.030 mmol, 1 equiv), PS-Carbodiimide (49 mg, 0.061 mmol, 2 equiv), 1-hydroxybenzotriazole (4.0 mg, 0.030 mmol, 1 equiv) and 4-trifluoromethylbenzylamine (0.004 mL, 0.027 mmol, 0.9 equiv) in dichloromethane (1 mL) and dimethylformamide (0.1 mL). The suspension was irradiated in a Biotage Emrys Optimizer microwave reactor (250 W) at 100° C. for 10 min. After cooling to room temperature the reaction mixture was filtered through an SPE-cartridge (pre-packed with 500 mg silica-bound carbonate and preconditioned with 2 mL of CH$_2$Cl$_2$) and washed with dichloromethane (2 mL). The dichloromethane washes were discarded. The cartridge was further washed with methanol (3×2 mL) and the eluents were collected via gravity filtration in a scintillation vial. Evaporation of all volatile components in a centrifugal vacuum evaporator (Genevac HT-4) provided the desired product (0.078 g, 42%).

Preparation of (DHK2120 precursor)

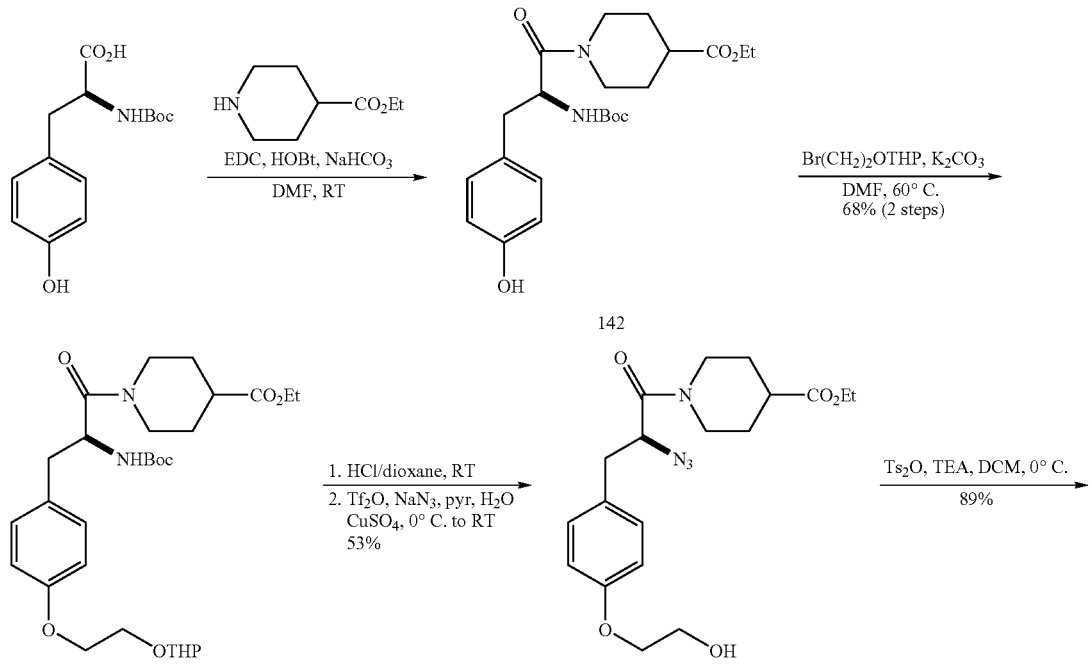

-continued

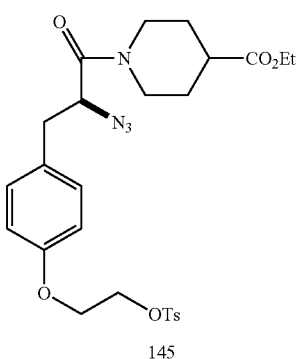

145

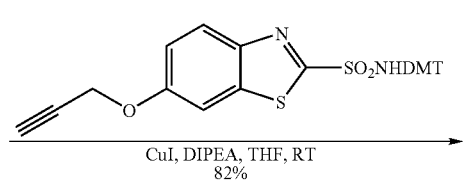

CuI, DIPEA, THF, RT
82%

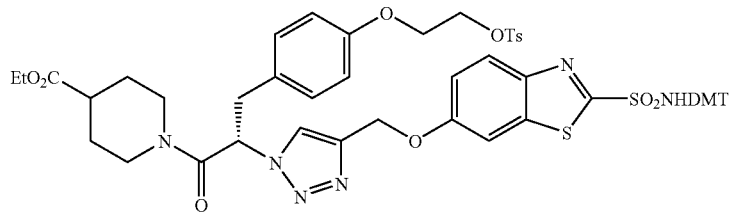

DHK2-120 precursor

Preparation of Ethyl 1-((2S)-2-(tert-Butoxycarbonylamino)-3-(4-(2-(tetrahydro-2H-pyran-2-yloxy)ethoxy)phenyl)propanoyl)piperidine-4-carboxylate (143)

To a stirring slurry of commercially available amine (10 g, 35.5 mmol) in DMF (250 mL) was added, sequentially, EDC (13.6 g, 71.1 mmol), HOBt (9.6 g, 71.1 mmol), NaHCO$_3$ (10 g, 118.5 mmol), and ethyl piperidine-4-carboxylate (3.72 g, 23.7 mmol). The mixture was stirred at 23° C. overnight. The reaction mixture was then poured into water, extraced 3×EtOAc, and the combined organic extracts were then washed 1×H$_2$O, 1×brine, and dried over MgSO$_4$. Solvents were removed in vacuo and the crude residue purified by flash chromatgraphy on silica gel using hexanes/ethyl actetate on a Biotage purification system yielding the amide 142 as a colorless, viscous oil. The amide 142 (9.96 g, 23.7 mmol) was then dissolved in DMF (80 mL) and K$_2$CO$_3$ (6.6 g, 47.4 mmol) was added followed by 2-(2-bromoethoxy)tetrahydro-2H-pyran (7.16 mL, 47.4 mmol). The mixture was heated to 60° C. and left to stir overnight. The reaction mixture was then poured into water, extraced 3×EtOAc, and the combined organic extracts were washed 1×H$_2$O, 1×brine, and dried over MgSO$_4$. Solvents were removed in vacuo and the crude residue purified by flash chromatgraphy on silica gel using hexanes/ethyl actetate on a Biotage purification system yielding the amide 143 as a colorless, viscous oil (8.8 g, 68%).

Preparation of (S)-Ethyl 1-(2-azido-3-(4-(2-hydroxyethoxy)phenyl)propanoyl)piperidine-4-carboxylate (144)

To a stirring solution of the amide 143 (8.8 g, 16 mmol) in dioxane (20 mL) at 23° C. was added a solution of 4 M HCl in dioxane (320 mL). The mixture was stirred for 9 h and concentrated in vacuo to afford a crude, clear, viscous pale-yellow oil. A slurry of NaN$_3$ (1.56 g, 24 mmol) in pyridine (25 mL) was then cooled to 0° C. and trifluoromethanesulfonic anhydride (4 mL, 24 mmol) was added dropwise before allowing the mixture to warm to 23° C. and stir for 3 h. A solution of the amine hydrochloride (6.4 g, 16 mmol) in H$_2$O (11 mL) was then added followed by CuSO$_4$.5H$_2$O (600 mg, 2.4 mmol). The combined mixture was allowed to stir at 23° C. overnight. An aqueous saturated solution of NaHCO$_3$ was then added and the organic layer was extracted 3×EtOAc. The combined organic extracts were washed 1×10% CuSO$_4$, 2×1 M HCl, 1×brine, and dried over MgSO$_4$. Solvents were removed in vacuo and the crude residue purified by flash chromatgraphy on silica gel using hexanes/ethyl actetate on a Biotage purification system yielding the azide 144 as a colorless, viscous oil (3.3 g, 53%).

Preparation of (S)-Ethyl 1-(2-azido-3-(4-(2-(tosyloxy)ethoxy)phenyl)propanoyl)piperidine-4-carboxylate (145)

To a stirring solution of the alcohol 144 (650 mg, 1.67 mmol) in DCM (17 mL) cooled to 0° C. was added triethylamine (0.7 mL, 5 mmol) followed by p-toluenesulfonic anhydride (1.09 g, 3.34 mmol). The mixture was stirred at 0° C. for 20 min and the solvents were removed in vacuo. The crude residue was purified by flash chromatgraphy on silica gel using hexanes/ethyl actetate on a Biotage purification system yielding the tosylate 145 as a colorless, viscous oil (807 mg, 89%).

Preparation of (S)-Ethyl 1-(2-(4-(2-(N-(bis(4-methoxyphenyl)(phenyl)methyl)sulfamoyl)benzo[d]thiazol-6-yloxy)methyl)-1H-1,2,3-triazol-1-yl)-3-(4-(2-(tosyloxy)ethoxy)phenyl)propanoyl)piperidine-4-carboxylate (DHK2-120 precursor)

To a stirring solution of N-(bis(4-methoxyphenyl)(phenyl)methyl)-6-(prop-2-ynyloxy)benzo[d]thiazole-2-sulfonamide (91 mg, 0.159 mmol) and the tosylate 145 (87 mg, 0.159 mmol) in THF (1 mL) was added copper(I) iodide (3 mg, 0.0159 mmol) then diisopropylethylamine (30 µL, 0.175 mmol). The mixture was allowed to stir for 2 h at 23° C. then concentrated in vacuo and the crude residue purified by flash chromatgraphy on silica gel using hexanes/ethyl actetate on a Biotage purification system yielding the desired product as a white, crystalline solid (145 mg, 82%).

Example 6
Preparation of (S)-Methyl 2-((S)-2-(4-((2-(N-(bis(4-methoxyphenyl)(phenyl)methyl)sulfamoyl)benzo[d]thiazol-6-yloxy)methyl)-1H-1,2,3-triazol-1-yl)-N-(tert-butoxycarbonyl)-3-(4-(2-(tosyloxy)ethoxy)phenyl)propanamido)-3-(4-(trifluoromethyl)phenyl)propanoate (DHK2-134 precursor)
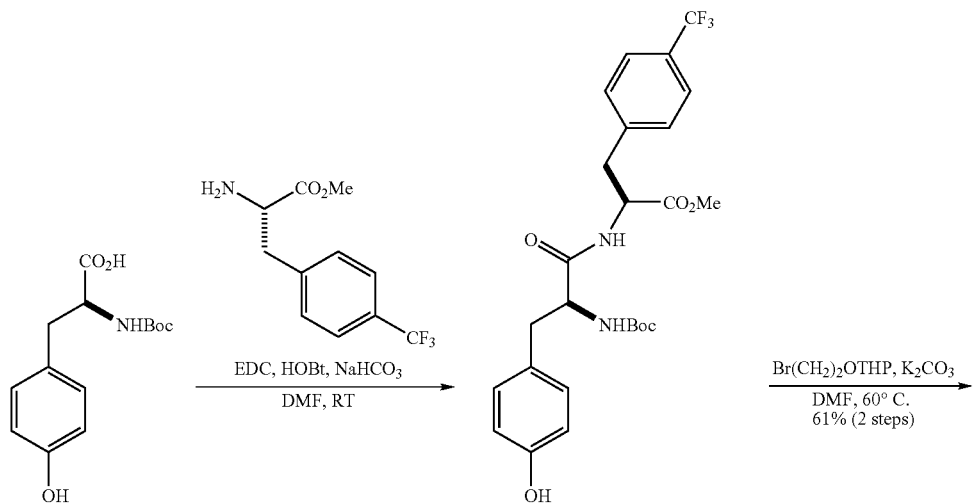
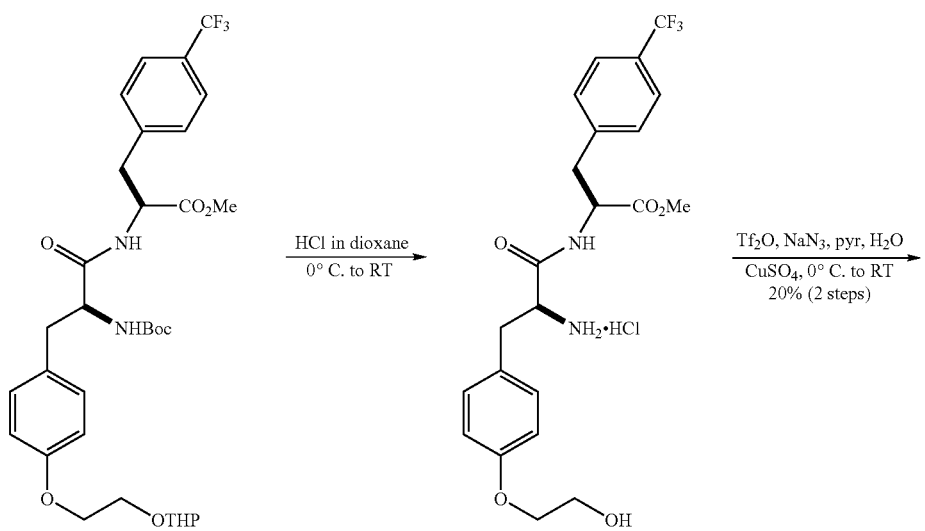

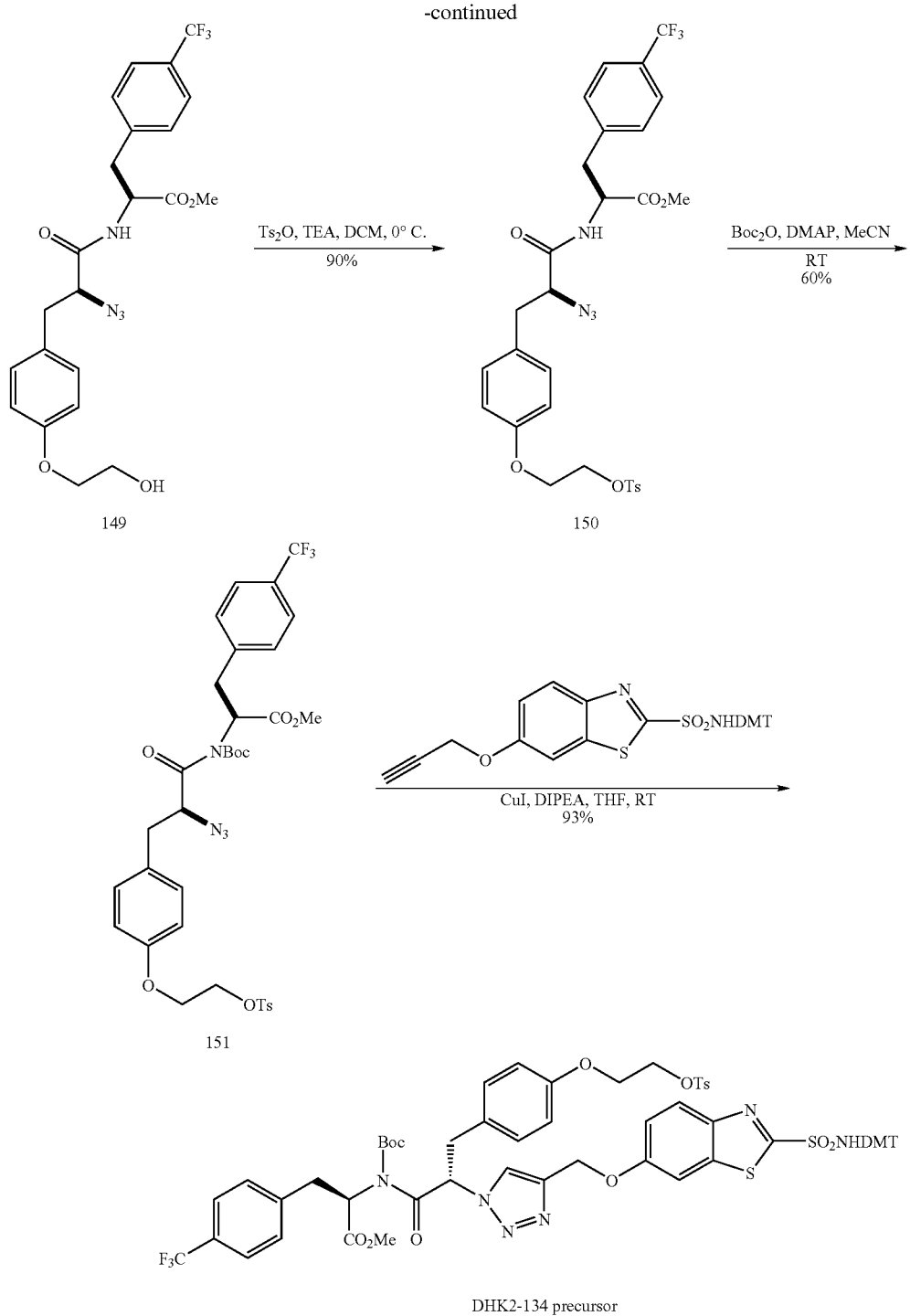

DHK2-134 precursor

Preparation of (2S)-Methyl 2-((2S)-2-(tert-butoxycarbonylamino)-3-(4-(2-(tetrahydro-2H-pyran-2-yloxy)ethoxy)phenyl)propanamido)-3-(4-(trifluoromethyl)phenyl)propanoate (147)

To a stirring slurry of commercially available 145 (5.9 g, 21.2 mmol) in DMF (140 mL) was added, sequentially, EDC (8.1 g, 42.3 mmol), HOBt (5.7 g, 42.3 mmol), NaHCO₃ (5.92 g, 70.5 mmol), and (S)-methyl 2-amino-3-(4-(trifluoromethyl)phenyl)propanoate (3.5 g, 14.1 mmol). The mixture was stirred at 23° C. overnight. The reaction mixture was then poured into water, extraced 3×EtOAc, and the combined organic extracts were then washed 1×H₂O, 1×brine, and dried over MgSO₄. Solvents were removed in vacuo and the crude residue purified by flash chromatgraphy on silica gel using hexanes/ethyl actetate on a Biotage purification system yielding the amide 146 as a colorless, viscous oil. The amide 146 (7.19 g, 21.2 mmol) was then dissolved in DMF (50 mL) and K₂CO₃ (3.89 g, 28.2 mmol) was added followed by 2-(2-bromoethoxy)tetrahydro-2H-pyran (4.26 mL, 28.2 mmol).

The mixture was heated to 60° C. and left to stir overnight. The reaction mixture was then poured into water, extraced 3×EtOAc, and the combined organic extracts were washed 1×H$_2$O, 1×brine, and dried over MgSO$_4$. Solvents were removed in vacuo and the crude residue purified by flash chromatgraphy on silica gel using hexanes/ethyl actetate on a Biotage purification system yielding the amide 147 as a pale yellow, viscous oil (5.5 g, 61%).

Preparation of (S)-Methyl 2-((S)-2-azido-3-(4-(2-hydroxyethoxy)phenyl)propanamido)-3-(4-(trifluoromethyl)phenyl)propanoate (149)

To a stirring solution of the amide 147 (5.5 g, 8.6 mmol) in dioxane (20 mL) at 23° C. was added a solution of 4 M HCl in dioxane (172 mL). The mixture was stirred for 4 h and concentrated in vacuo to afford crude, clear, viscous pale-yellow oil. A slurry of NaN$_3$ (839 mg, 12.9 mmol) in pyridine (13 mL) was then cooled to 0° C. and trifluoromethanesulfonic anhydride (2.17 mL, 12.9 mmol) was added dropwise before allowing the mixture to warm to 23° C. and stir for 3 h. A solution of the amine hydrochloride 148 (4.22 g, 8.6 mmol) in H$_2$O (6 mL) was then added followed by CuSO$_4$.5H$_2$O (321 mg, 1.29 mmol). The combined mixture was allowed to stir at 23° C. overnight. An aqueous saturated solution of NaHCO$_3$ was then added and the organic layer was extracted 3×EtOAc. The combined organic extracts were washed 1×10% CuSO$_4$, 2×1 M HCl, 1×brine, and dried over MgSO$_4$. Solvents were removed in vacuo and the crude residue purified by flash chromatgraphy on silica gel using hexanes/ethyl actetate on a Biotage purification system yielding the azide 149 as a pale yellow, viscous oil (800 mg, 20%).

Preparation of (S)-Methyl 2-((S)-2-azido-3-(4-(2-(tosyloxy)ethoxy)phenyl)propanamido)-3-(4-(trifluoromethyl)phenyl)propanoate (150)

To a stirring solution of the alcohol 149 (800 mg, 1.67 mmol) in DCM (17 mL) cooled to 0° C. was added triethylamine (0.7 mL, 5 mmol) followed by p-toluenesulfonic anhydride (1.09 g, 3.34 mmol). The mixture was stirred at 0° C. for 20 min and the solvents were removed in vacuo. The crude residue was purified by flash chromatgraphy on silica gel using hexanes/ethyl actetate on a Biotage purification system yielding the tosylate 150 as a viscous amber oil (945 mg, 90%).

Preparation of (S)-Methyl 2-((S)-2-azido-N-(tert-butoxycarbonyl)-3-(4-(2-(tosyloxy)ethoxy)phenyl) propanamido)-3-(4-(trifluoromethyl)phenyl)propanoate (151)

To a stirring solution of the tosylate 150 (376 mg, 0.59 mmol) in acetonitrile (5 mL) was added di-tent-butyl dicarbonate (193 mg, 0.89 mmol) followed by 4-dimethylaminopyridine (4 mg, 0.03 mmol). The solution was allowed to stir overnight at 23° C. Solvents were removed in vacuo and the crude residue purified by flash chromatgraphy on silica gel using hexanes/ethyl actetate on a Biotage purification system yielding the Boc-protected amide 151 as a pale yellow, viscous oil (262 mg, 60%).

Preparation of (S)-Methyl 2-((S)-2-(4-((2-(N-(bis(4-methoxyphenyl)(phenyl)methyl)sulfamoyl)benzo[d] thiazol-6-yloxy)methyl)-1H-1,2,3-triazol-1-yl)-N-(tert-butoxycarbonyl)-3-(4-(2-(tosyloxy)ethoxy) phenyl)propanamido)-3-(4-(trifluoromethyl)phenyl) propanoate (DHK2134 precursor)

To a stirring solution of N-(bis(4-methoxyphenyl)(phenyl) methyl)-6-(prop-2-ynyloxy)benzo[d]thiazole-2-sulfonamide (83 mg, 0.145 mmol) and the Boc-protected amide 151 (107 mg, 0.145 mmol) in THF (0.7 mL) was added copper(I) iodide (3 mg, 0.0145 mmol) then diisopropylethylamine (28 μL, 0.16 mmol). The mixture was allowed to stir for 2 h at 23° C. then concentrated in vacuo and the crude residue purified by flash chromatgraphy on silica gel using hexanes/ethyl actetate on a Biotage purification system yielding the desired product as a yellow, crystalline solid (145 mg, 82%).

Preparation of (S)-2-(4-(4-(N-(bis(4-Ethoxyphenyl) (phenyl)methyl)sulfamoyl)phenyl)-1H-1,2,3-triazol-1-yl)-3-methylbutanoic acid (DHK2-97 precursor)

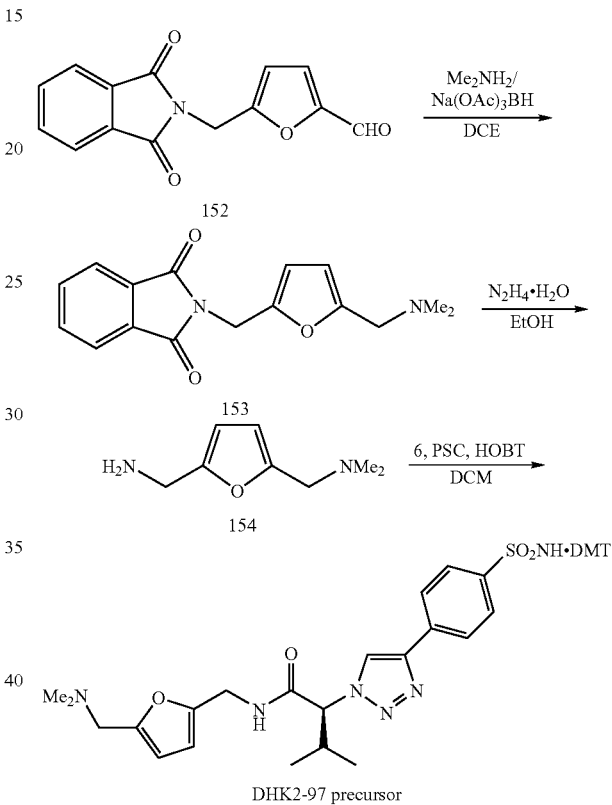

Aldehyde 152 (57 mg, 0.22 mmol, 1.0 equiv) in 1,2-dichloroethane (2 mL) was treated with dimethylamine (2 M solution in THF) (0.17 mL, 0.34 mmol, 1.5 equiv) and the mixture was stirred at room temperature for 1 h. Sodium triacetoxyborohydride (71 mg, 0.34 mmol, 1.5 equiv) and acetic acid (0.01 mL) were added and stirred for 1 h at room temperature. The reaction mixture was diluted with 25 mL of dichloromethane, washed with 2×10 mL of saturated aqueous sodium bicarbonate solution, 50 mL of water, dried over sodium sulphate and evaporated under vacuo to yield the amine 153 (60 mg, 95%). Amine 153 (0.86 g, 3.0 mmol, 1 equiv) in ethanol (50 mL) was treated with hydrazine hydrate (0.40 mL, 3.6 mmol, 1.2 equiv) and the mixture was heated to reflux overnight. White solid precipitated by cooling the reaction mixture to room temperature, filtered and the solid was discarded. The filtrate was concentrated under vacuo and purified by column chromatography over SiO$_2$ using a gradient of 100% EtOAc to 10% MeOH/90% EtOAc mixture to give 1-(5-(aminomethyl)furan-2-yl)-N,N-dimethylmethanamine 154 (0.17 g, 37%).

A 5 mL microwave tube was charged with acid 6 (62 mg, 0.099 mmol, 1 equiv), PS-Carbodiimide (0.16 g, 0.20 mmol, 2 equiv), 1-hydroxybenzotriazole (13 mg, 0.098 mmol, 0.99 equiv) and 1-(5-(aminomethyl)furan-2-yl)-N,N-dimethylmethanamine 154 (15 mg, 0.097 mmol, 0.98 equiv) in dichloromethane (3 mL). The suspension was irradiated in an Emrys Optimizer microwave reactor (250 W) at 60° C. for 5 min. After cooling to room temperature the reaction mixture was filtered through an SPE-cartridge (prepacked with 500 mg silica-bound carbonate and preconditioned with 2 mL of $CH_2Cl_2$) and washed with dichloromethane (2 mL). The dichloromethane washes were discarded. The cartridge was again washed with methanol (3×2 mL) and the eluants were collected via gravity filtration in a scintillation vial. Evaporation of all volatile components in a centrifugal vacuum evaporator (Genevac HT-4) provided the desired product (S)-2-(4-(4-(N-(bis(4-methoxyphenyl)(phenyl)methyl)sulfamoyl)phenyl)-1H-1,2,3-triazol-1-yl)-3-methylbutanoic acid, DHK297 precursor (60 mg, 80%).

DHK297 precursor (25 mg, 0.033 mmol, 1 equiv) in THF (5 mL) was treated with 2-fluoroethyl 4-methylbenzenesulfonate (7.3 mg, 0.033 mmol, 1.02 equiv) and stirred overnight at 75° C. Solvents were removed under vacuum and the resulting residue was washed with diethyl ether (5 mL) and dried under vacuum to yield the tosylate salt protected DHK2-97 (28 mg, 88%).

Protected DHK2-97 (10 mg, 0.001 mmol, 1 equiv) in THF (2 mL) was treated with TFA (1 mL) and stirred at room temperature for 1 h. Solvents were evaporated under vacuum and the resulting residue was purified by HPLC to yield (S)-2-fluoro-N,N-dimethyl-N-((5-((3-methyl-2-(4-(4-sulfamoylphenyl)-1H-1,2,3-triazol-1-yl)butanamido)methyl)furan-2-yl)methyl)ethanaminium 4-methylbenzenesulfonate, DHK297 (5 mg, 72%).

General Procedure for Radiolabeling of Compound
Preparation of dry, activated [F-18]fluoride using K222/K2CO3

Oxygen-18 water was irradiated using 11 MeV protons (RDS-111 Eclipse, Siemens Molecular Imaging) to generate [$^{18}$F]fluoride ion in the usual way. At the end of the bombardment, the [$^{18}$O] water containing [$^{18}$F]fluoride ion was transferred from the tantalum target to an automated nucleophilic fluorination module (explora RN, Siemens Biomarker Solutions). Under computer control, the [$^{18}$O]water/[$^{18}$F]fluoride ion solution was transferred to a small anion exchange resin Preparation of (S)-2-Fluoro-N,N-dimethyl-N-((5-((3-methyl-2-(4-(4-sulfamoylphenyl)-1H-1,2,3-triazol-1-yl)butanamido)methyl)furan-2-yl)methyl)ethanaminium 4-methylbenzenesulfonate (DHK2-97)

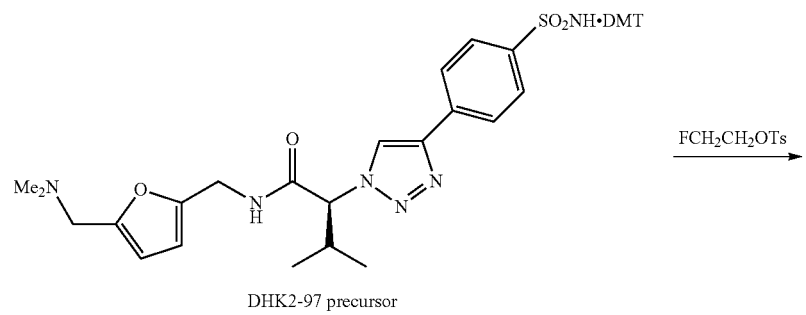

DHK2-97 precursor

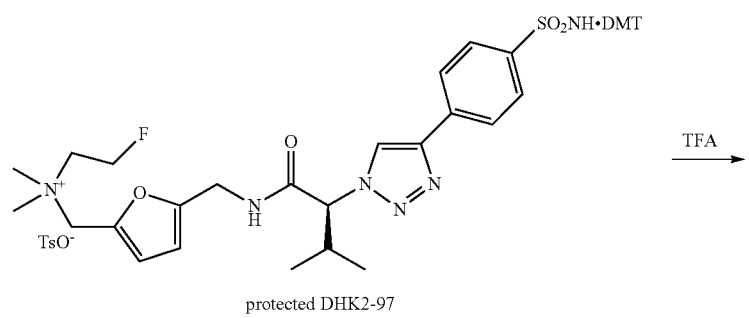

protected DHK2-97

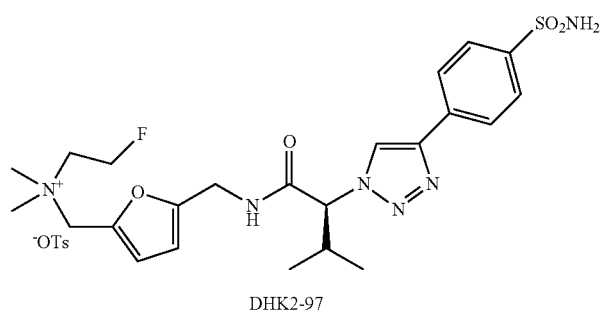

DHK2-97 column (Chromafix 45-PS-HCO$_3$, Machery-Nagel) which had previously been rinsed with water (10 mL). The [$^{18}$O] water (1.8 mL) was recovered for subsequent purification and reuse. The trapped [$^{18}$F]fluoride ion was eluted into the reaction vessel with a solution of potassium carbonate (3.0 mg) in water (0.4 mL). A solution of Kryptofix 222 (20 mg) in acetonitrile (1.0 mL) was added, and the mixture was heated (70 to 95° C.) under vacuum and a stream of argon to evaporate the acetonitrile and water.

Preparation of dry, activated [F-18]fluoride using tetra-N-butyl ammonium bicarbonate Oxygen-18 water was irradiated using 11 MeV protons (RDS-111 Eclipse, Siemens Molecular Imaging) to generate [$^{18}$F]fluoride ion in the usual way. At the end of the bombardment, the [$^{18}$O] water containing [$^{18}$F]fluoride ion was transferred from the tantalum target to an automated nucleophilic fluorination module (explora RN, Siemens Biomarker Solutions). Under computer control, the [$^{18}$O]water/[$^{18}$F]fluoride ion solution was transferred to a small anion exchange resin column (Chromafix 45-PS-HCO$_3$, Machery-Nagel) which had previously been rinsed with water (5 mL). The [$^{18}$O] water (1.8 mL) was recovered for subsequent purification and reuse. The trapped [$^{18}$F]fluoride ion was eluted into the reaction vessel with a solution of tetra-N-butyl ammonium bicarbonate (14 mg) in water (0.4 mL). A solution of acetonitrile (1.0 mL) was added, and the mixture was heated (70 to 95° C.) under vacuum and a stream of argon to evaporate the acetonitrile and water.

General Two-Pot Procedure for Radiolabelling of CA-IX Compounds:

After cooling, to the residue of "dry" reactive [$^{18}$F]-fluoride ion was added a solution of the appropriate precursor (15±5 mg) in anhydrous MeCN (1 mL) was then added to the reaction vessel of the Explora RN synthesis module and the reaction was heated at 95±5° C. for 5 min. The reaction was then cooled to 35° C. and diluted with HPLC solvent (1.5 mL). The mixture was passed through an alumina-light seppak and then purified directly by semi-preparative HPLC (column: 10.0 mm×250.0 mm Phenomenex Gemini, mobile phase: 60% MeCN (+0.05% v/v TFA): 40% water (+0.05% v/v TFA), flow rate=5 mL/min) and the fraction corresponding to the protected intermediate was collected. Collection began when the peak reached 10 counts on the γ-detector chart recorder and stopped when the signal dropped below 10 counts.

To the collected HPLC fraction was then added LiOH (2M, 0.25 mL) and the reaction was allowed was maintained at rt for 30 min After this time, HCl (6M-12M, 1.0±0.1 mL) was added and the reaction was heated to 100° C. for 10 min. The reaction was then cooled and subsequently purified by semi-preparative HPLC (Column: 10.0 mm×250.0 mm Phenomenex Gemini, Flow rate=5 mL/min)

Preparation of $^{18}$F-VM2133

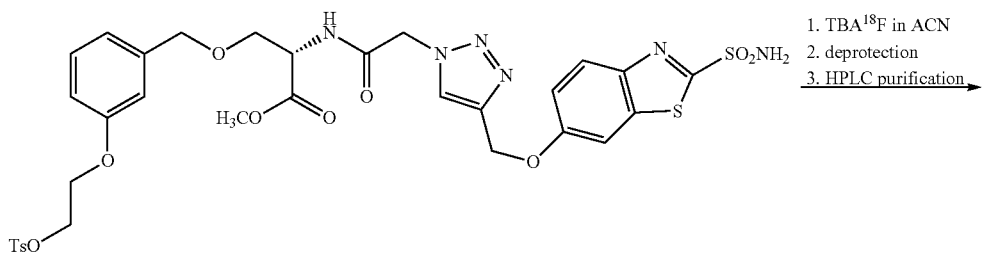

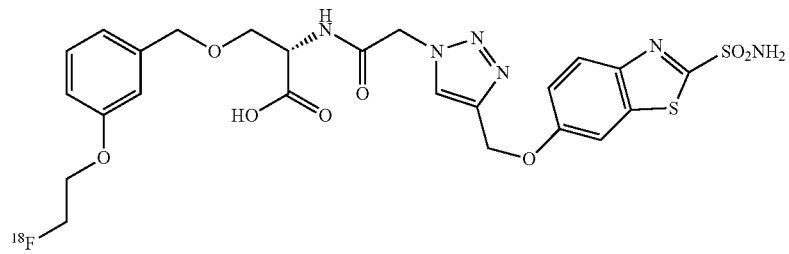

VM2133

Mobile phase: Gradient 5% MeCN (+0.05% v/v TFA): 95% water (+0.05% v/v TFA)-95% MeCN (+0.05% v/v TFA): 5% water (+0.05% v/v TFA) over 30 min; Yield: 4.0-112 mCi (n=9); Radiochemical Purity: >99%; Specific Activity: 20-36 Ci/μmol.

Preparation of $^{18}$F-VM391
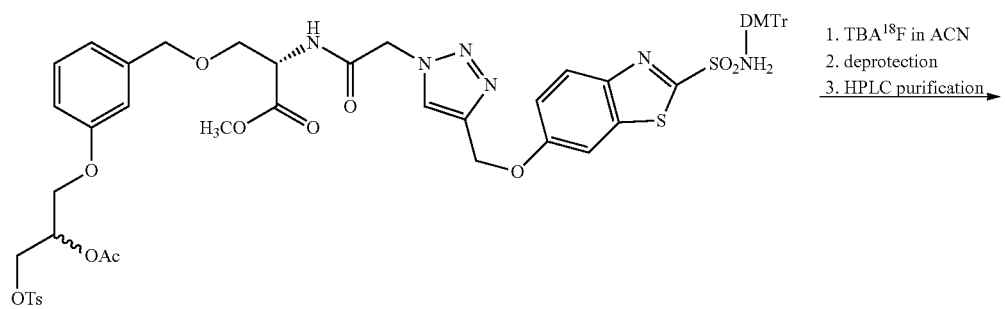
28
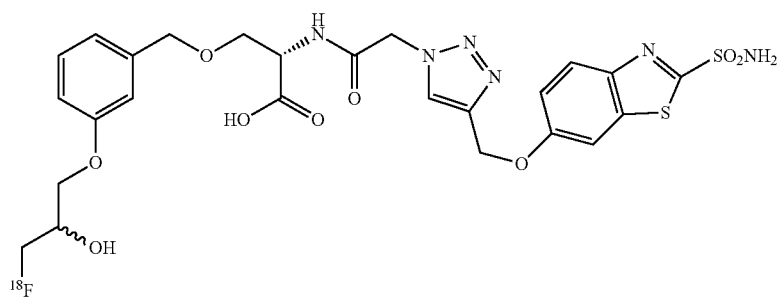
VM391
Mobile phase: Gradient 5% MeCN (+0.05% v/v TFA): 95% water (+0.05% v/v TFA)-95% MeCN (+0.05% v/v TFA): 5% water (+0.05% v/v TFA) over 30 min; Yield: 4.0-10.4 mCi (n=9); Radiochemical Purity: >99%; Specific Activity: Not determined.
Preparation of $^{18}$F-VM4037
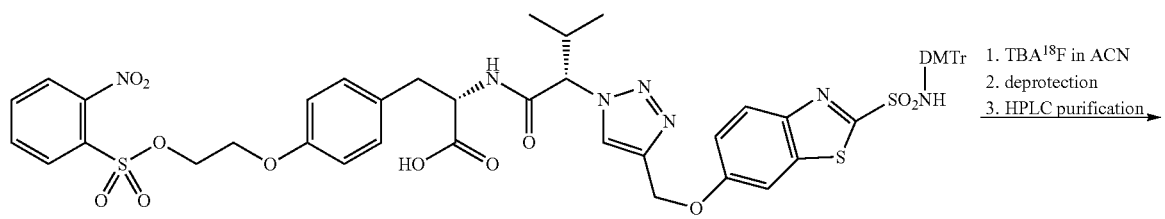
55
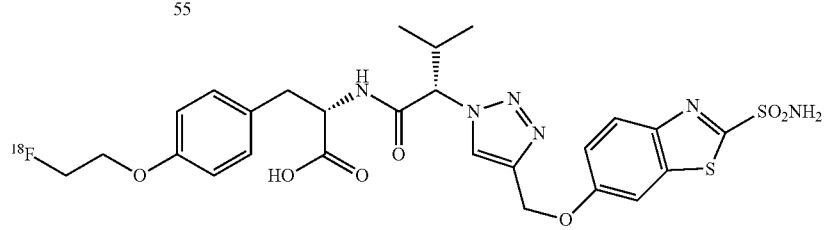
VM4037A
Mobile phase: 38% MeCN (+0.05% v/v TFA): 62% water (+0.05% v/v TFA); Yield: 1.3-193 mCi (n=16); Radiochemical Purity: >99%; Specific Activity: 1.8-8.2 Ci/μmol Preparation of $^{18}$F-VM4047
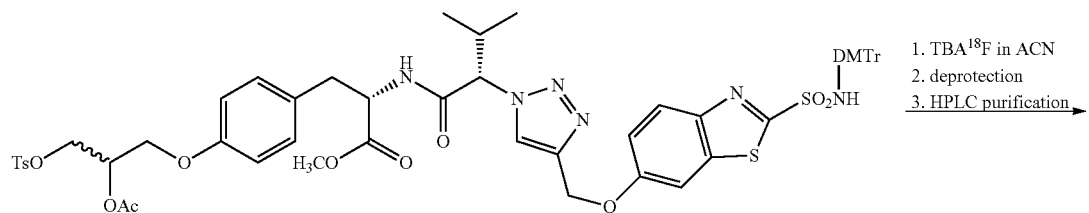
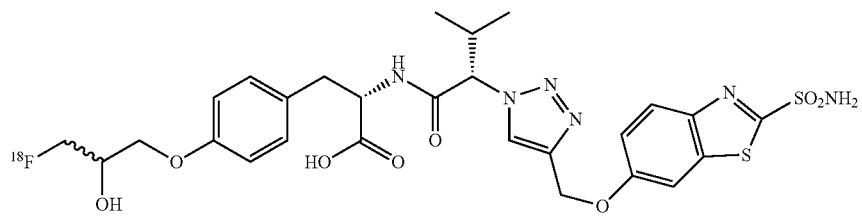
VM4047A and VM4047B
Mobile phase: 30% MeCN (+0.05% v/v TFA): 70% water (+0.05% v/v TFA); Yield: 1.0-14.7 mCi (n=9); Radiochemical Purity: >99%; Specific Activity: 1.8-2.8 Ci/μmol.
Preparation of $^{18}$F-DHK-2134
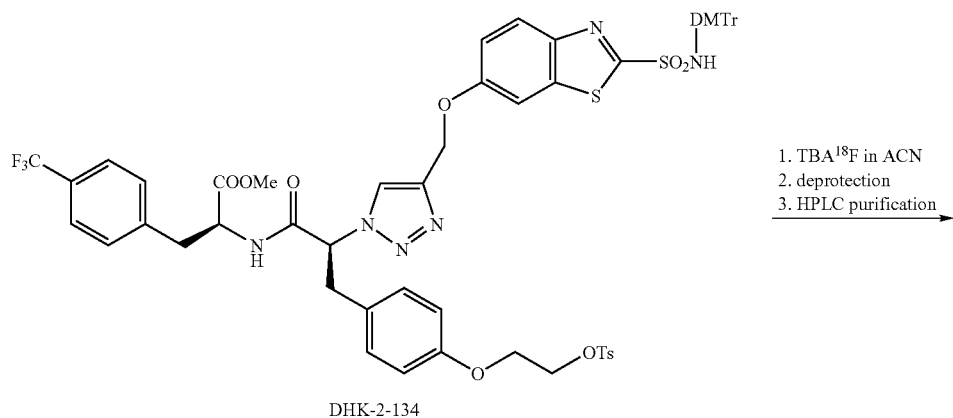
DHK-2-134
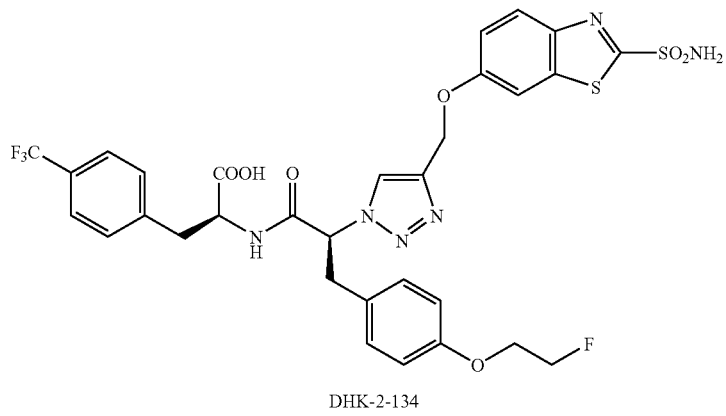
DHK-2-134

Mobile phase: 45% MeCN (+0.05% v/v TFA): 55% water (+0.05% v/v TFA); Yield: 2.75 mCi (n=1); Radiochemical Purity: >99%; Specific Activity: Not determined.

General Procedure for Reformulation of Radiolabelled Compounds into 10% ethanol: 90% Sterile Water Formulations Suitable for Injection:

The HPLC fraction corresponding to the radiolabelled compound was collected, diluted into sterile water (40 mL) and this was passed through a C-18 sep-pak. Compound remained bound to the sep-pak whilst residual HPLC solvent was washed away and the sep-pak was then washed with further sterile water (10 mL). The radiolabelled compound was then eluted with USP ethanol (1.0 mL) and diluted with sterile water (9 mL). Alternatively, the product is eluted with 60% EtOH: Water (1.0 mL) and diluted with sterile water (5 mL). This provided radiolabelled compound formulated in either 5 or 10 mL of 10% ethanol.

Activity was recorded using the hot-cell dose calibrator and then QC analysis was performed immediately (Chemical and radiochemical purity were determined by analytical HPLC: Column: 4.6 mm×150.0 mm Phenomenex Gemini; Mobile phase: Gradient 5% MeCN (+0.05% v/v TFA): 95% water (+0.05% v/v TFA)-95% MeCN (+0.05% v/v TFA): 5% water (+0.05% v/v TFA) over 30 min; Flow rate=1 mL/min).

Procedures for Preparation of Other Radiolabelled CA-IX Biomarkers: Typical One-Pot Labelling Procedure Preparation of VM3147 and VM241

[18F]Fluoride was prepared using TBAB according to the typical procedure described above. After cooling, a solution of the appropriate precursor (15±5 mg) in anhydrous MeCN (1 mL) was added to the residue of "dry" reactive [$^{18}$F]-fluoride ion in the reaction vessel of the Explora RN synthesis module and the reaction was heated at 95±5° C. for 5 min. The reaction was then cooled to room temperature, LiOH (2M, 0.25 mL) was added and the reaction was maintained at rt for 30 min. After this time, HCl (6M, 0.3±0.01 mL) was added and the reaction was heated to 100° C. for 10 min. The reaction was then cooled and subsequently purified by semi-preparative HPLC (Column: 10.0 mm×250.0 mm Phenomenex Gemini, Mobile phase: Gradient 5% MeCN (+0.05% v/v TFA): 95% water (+0.05% v/v TFA)-95% MeCN (+0.05% v/v TFA): 5% water (+0.05% v/v TFA) over 30 min, Flow rate=5 mL/min). The collected HPLC fraction was then reformulated into a 10% EtOH formulation suitable for injection using the general procedure described above.

Preparation of $^{18}$F-VM3147

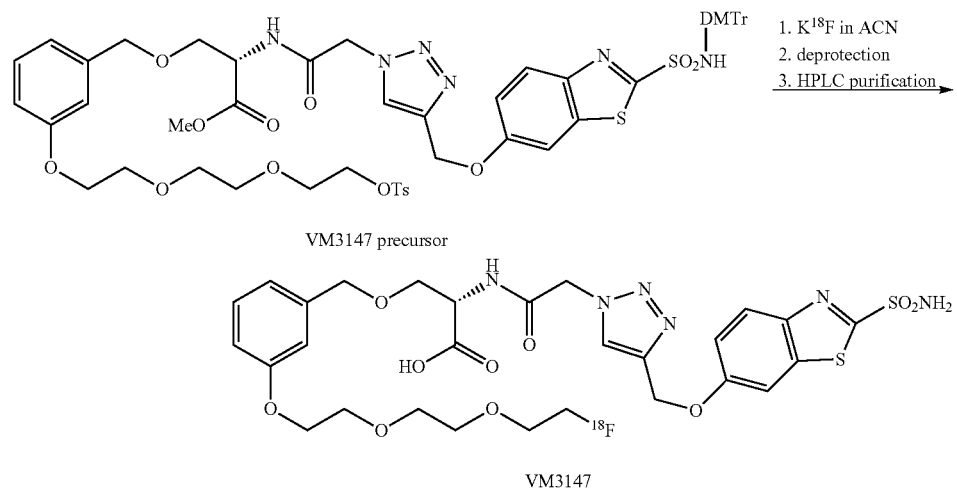

Yield: 58 mCi from 933 mCi fluoride; Radiochemical Purity: >99%; Specific Activity: Not determined.

Preparation of $^{18}$F-VM241

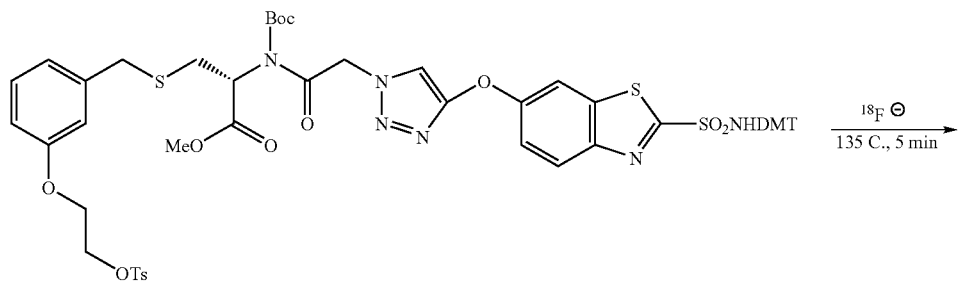

-continued

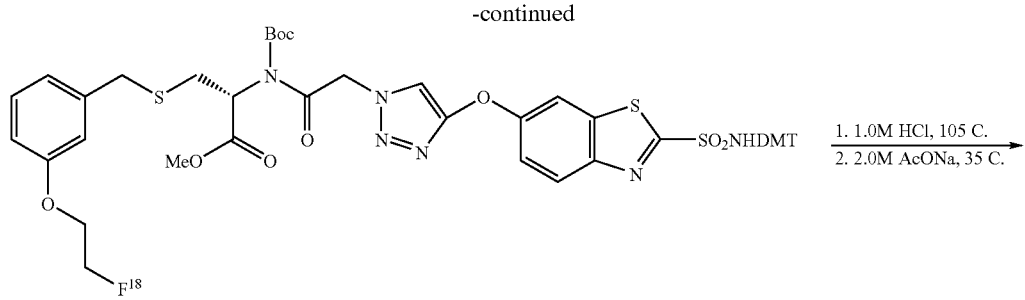

1. 1.0M HCl, 105 C.
2. 2.0M AcONa, 35 C.

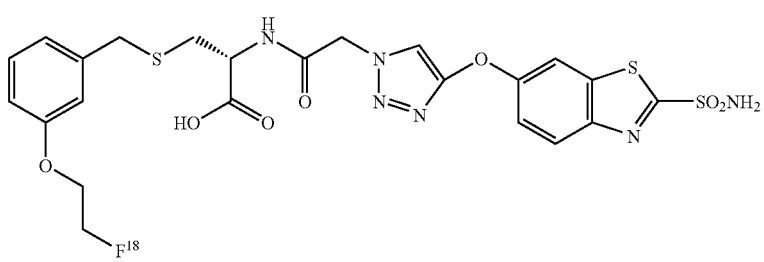

Yield: 33 mCi from 1000 mCi fluoride; Radiochemical Purity: >90%; Specific Activity: Not determined.

Radiolabelling via "Click" Chemistry

General Procedure for Preparation of [18F]-Fluoropentyne

[18F]Fluoride was prepared using $K_2CO_3$ and Kryptofix-2.2.2 according to the typical procedure described above. After cooling, a solution of tosyl pentyne (20±2.5 mg) in anhydrous MeCN (0.8 mL) was then added to the residue of "dry" reactive [$^{18}$F]-fluoride ion in the reaction vessel of the Explora RN synthesis module and the reaction was heated at 110±5° C. for 3 min. After this time, the crude material was purified by distillation and pure [18F]fluoropentyne was isolated in a solution of MeCN and collected in a cold-trap at −78° C. (dry-ice/acetone).

VM3135 by "Click" Chemistry

The solution of [18F]fluoropentyne was warmed up to room temperature and to this was added a mixture of sodium ascorbate (40 mg), tris-(benzyltriazolylmethyl)amine (TBTA ligand, 25 mg), copper(II) sulfate (1M aqueous solution, 0.25 mL) and VM3135 precursor (3 mg) in DMF (0.35 mL): $H_2O$ (0.2 mL): MeCN (0.1 mL). and the mixture was left at rt for 45 min with occasional agitation. After this the reaction was diluted with water (2 mL) and purified by semi-preparative HPLC (column: 10.0 mm×250.0 mm Phenomenex Luna C18, mobile phase: Gradient 5% MeCN (+0.05% v/v TFA): 95% water (+0.05% v/v TFA)-95% MeCN (+0.05% v/v TFA): 5% water (+0.05% v/v TFA) over 30 min; Flow rate=1 mL/min) and the fraction corresponding to the protected intermediate was collected. Collection began when the peak reached 10 counts on the γ-detector chart recorder and stopped when the signal dropped below 10 counts. The collected HPLC fraction was then reformulated into a 10% EtOH formulation suitable for injection using the general procedure described above.

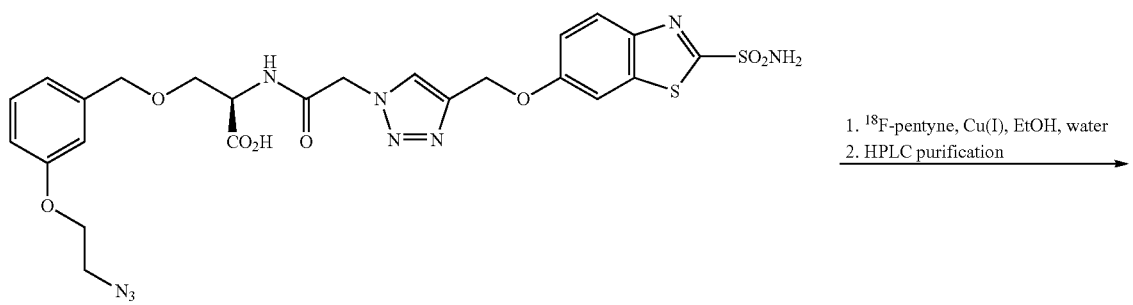

1. $^{18}$F-pentyne, Cu(I), EtOH, water
2. HPLC purification

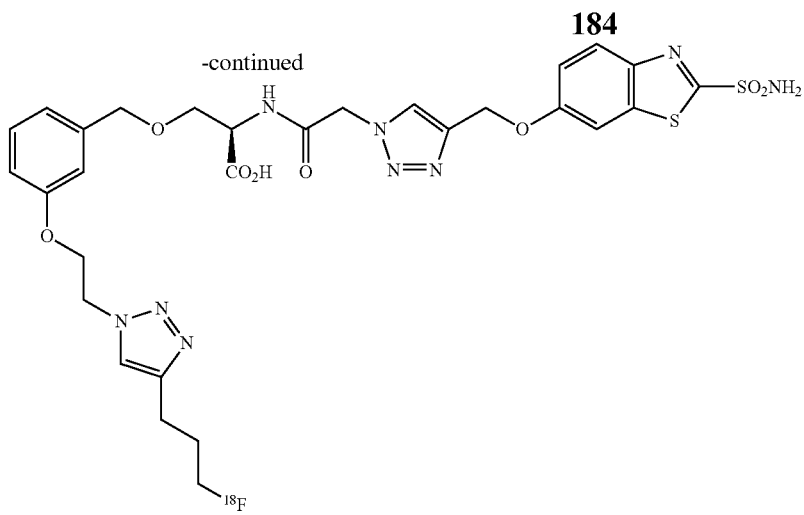

Yield 73 mCi from 560 mCi fluoride; Radiochemical Purity: >95%; Specific Activity: Not determined.

BW2-13 by "Click" Chemistry

The solution of [18F]fluoropentyne was warmed up to room temperature and to this was added a mixture of sodium ascorbate (29 mg), ammonia (0.7 M in MeOH, 0.1 mL), copper(I) acetate (1.5 mg) and BW2-13 precursor (2 mg) in DMF (0.2 mL): H$_2$O (0.25 mL): MeCN (0.25 mL). and the mixture was left at rt for 30 min with occasional agitation. After this the reaction was diluted with water (2 mL) and purified by semi-preparative HPLC (column 10.0 mm×250.0 mm Phenomenex Luna-C18, mobile phase: Gradient 5% MeCN (+0.05% v/v TFA): 95% water (+0.05% v/v TFA)-95% MeCN (+0.05% v/v TFA): 5% water (+0.05% v/v TFA) over 30 min; Flow rate=1 mL/min) and the fraction corresponding to the protected intermediate was collected. Collection began when the peak reached 10 counts on the γ-detector chart recorder and stopped when the signal dropped below 10 counts. The collected HPLC fraction was then reformulated into a 10% EtOH formulation suitable for injection using the general procedure described above.

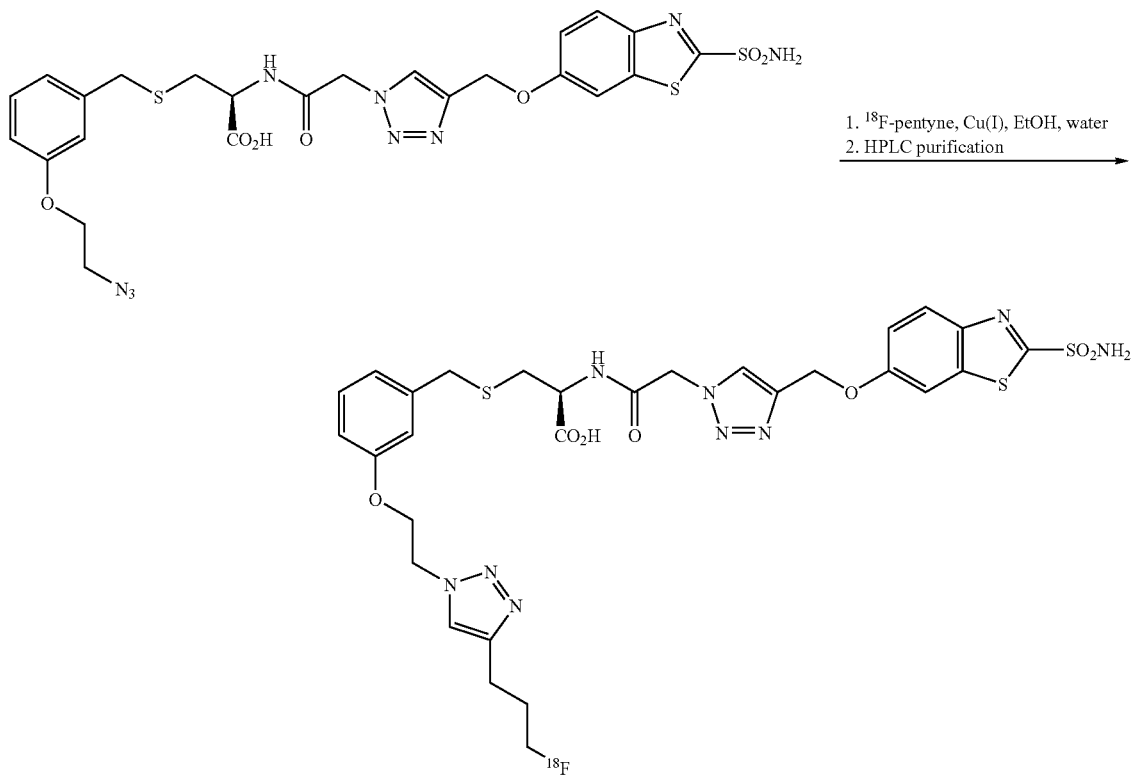

Yield 18.4 mCi; Radiochemical Purity: Not determined; Specific Activity: Not determined Typical [18F]-Fluoroethyltosvlate Labelling Procedure

[18F]Fluoride was prepared using K$_2$CO$_3$ and Kryptofix-2.2.2 according to the typical procedure described above. After cooling, a solution of ethylene ditosylate (9±1 mg) in anhydrous MeCN (0.9 mL) was added to the residue of "dry"

reactive [$^{18}$F]-fluoride ion in the reaction vessel of the Explora RN synthesis module and the reaction was heated at 115±5° C. for 10 min. The reaction was then cooled to room temperature, and purified by semi-preparative HPLC (column: 10.0 mm×250.0 mm Phenomenex ACE-C18, mobile phase: 50% MeCN: 50% aqueous ammonium formate; Flow rate=5 mL/min).

The HPLC fraction corresponding to [18F]fluoroethyl tosylate was collected, diluted into sterile water (15 mL) and this was passed through a Phenomenex Strata-X 33 μm polymeric reverse-phase sep-pak. Compound remained bound to the sep-pak whilst residual HPLC solvent was washed away and the sep-pak was then washed with further sterile water (10 mL). [18F]fluoroethyl tosylate was then eluted off the sep-pak with DMSO (0.5 mL).

Preparation of DHK97

[18F]fluoroethyl tosylate was prepared as described above and eluted off with DMSO (0.5 mL) into a vial charged with DHK97 precursor (8±2 mg) in MeCN (0.8 mL). The reaction was heated at 100° C. for 10 min. After this time, HCl (1M, 0.9±0.1 mL) was added and the reaction was heated to 100° C. for 10 min The reaction was then cooled, neutralized with sodium acetate (2M, 0.45±0.05 mL) and subsequently purified by semi-preparative HPLC (Column: 10.0 mm×250.0 mm Phenomenex Luna-C18, Mobile phase: Gradient 5% MeCN (+0.05% v/v TFA): 95% water (+0.05% v/v TFA)-95% MeCN (+0.05% v/v TFA): 5% water (+0.05% v/v TFA) over 30 min, Flow rate=5 mL/min). The collected HPLC fraction was then reformulated into a 10% EtOH formulation suitable for injection using the general procedure described above.

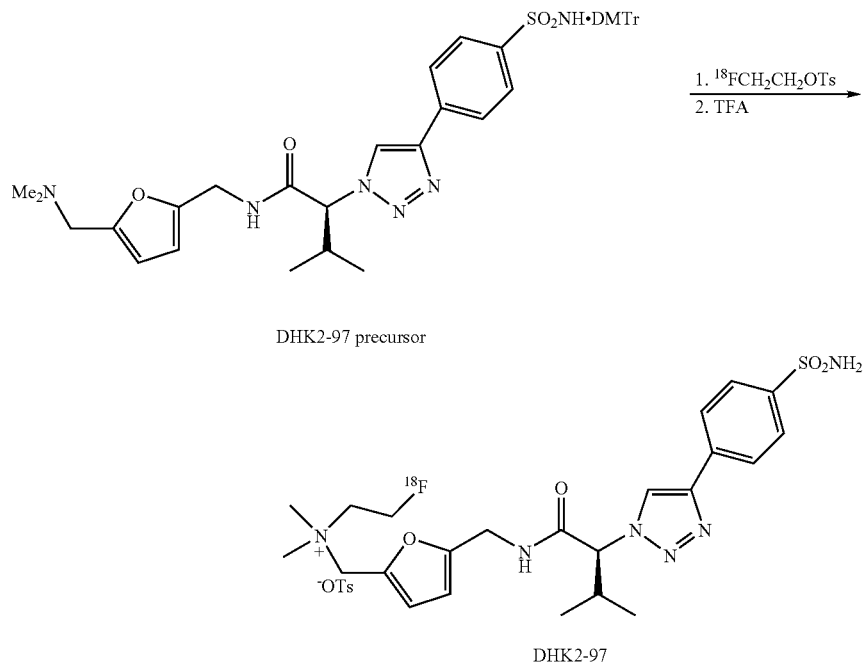

Yield: 0.2-2.2 mCi (n=3); Radiochemical Purity: >99%; Specific Activity: Not determined.

TABLE 1

| Entry | Code Name | Chemical Structure | Mol. Wt. | In Vitro Binding Assay (Library Screening) |
|---|---|---|---|---|
| Library 1 | | 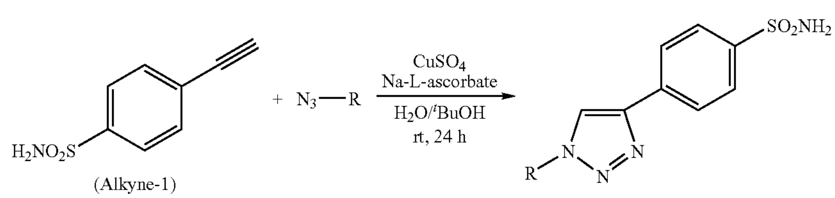 | | |

TABLE 1-continued

| Entry | Code Name | Chemical Structure | Mol. Wt. | In Vitro Binding Assay (Library Screening) |
|---|---|---|---|---|
| 1 | DHK3 | 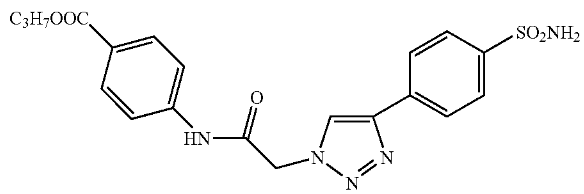 | 443.48 | x[a] |
| 2 | DHK4 | 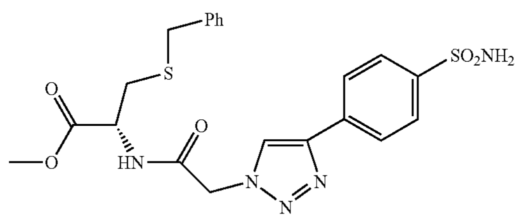 [SMILES: COC(=O)[C@H](CSCc1ccccc1)NC(=O)Cn1cc(-c2ccc(S(N)(=O)=O)cc2)nn1] | 489.57 | x |
| 3 | DHK5 | 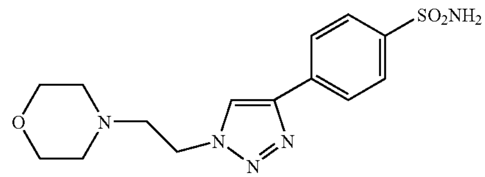 [SMILES: NS(=O)(=O)c1ccc(-c2cn(CCN3CCOCC3)nn2)cc1] | 337.40 | x |
| 4 | DHK7 | 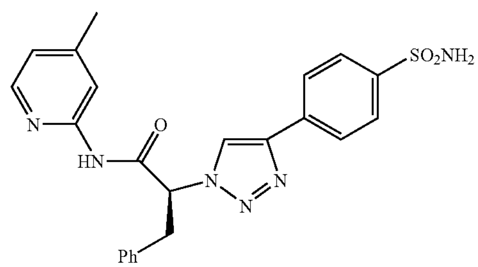 [SMILES: Cc1ccnc(NC(=O)[C@H](Cc2ccccc2)n2cc(-c3ccc(S(N)(=O)=O)cc3)nn2)c1] | 462.52 | ✓ |
| 5 | DHK8 | 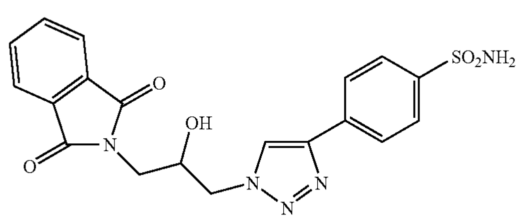 [SMILES: NS(=O)(=O)c1ccc(-c2cn(CC(O)CN3C(=O)c4ccccc4C3=O)nn2)cc1] | 427.43 | x |
| 6 | DHK11 | 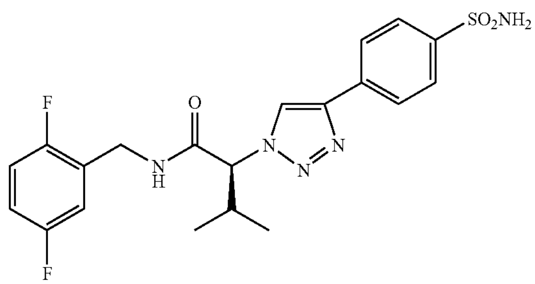 [SMILES: CC(C)[C@@H](C(=O)NCc1cc(F)ccc1F)n1cc(-c2ccc(S(N)(=O)=O)cc2)nn1] | 449.47 | x |

TABLE 1-continued

| Entry | Code Name | Chemical Structure | Mol. Wt. | In Vitro Binding Assay (Library Screening) |
|---|---|---|---|---|
| 7 | DHK12 | 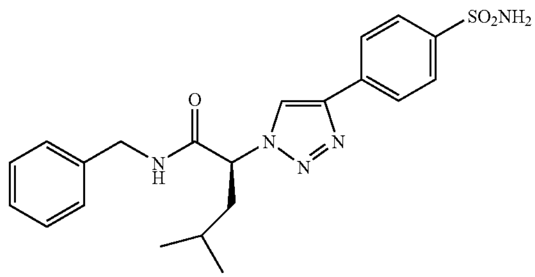 [SMILES: CC(C)C[C@@H](C(=O)NCc1ccccc1)n1cc(-c2ccc(S(N)(=O)=O)cc2)nn1] | 427.52 | x |
| 8 | DHK14 | 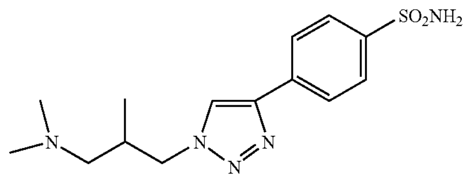 [SMILES: CC(CN(C)C)Cn1cc(-c2ccc(S(N)(=O)=O)cc2)nn1] | 323.41 | x |
| 9 | DHK15 | 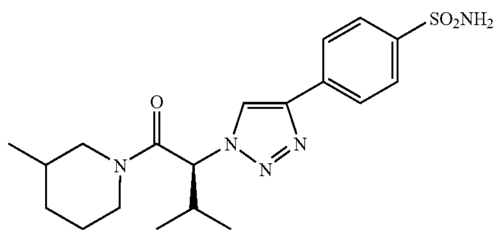 [SMILES: CC1CCCN(C(=O)[C@H](C(C)C)n2cc(-c3ccc(S(N)(=O)=O)cc3)nn2)C1] | 405.51 | x |
| 10 | DHK18 | 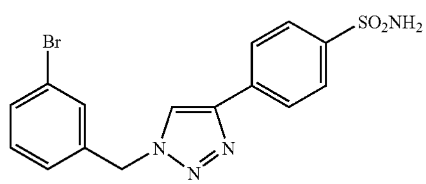 [SMILES: NS(=O)(=O)c1ccc(-c2cn(Cc3cccc(Br)c3)nn2)cc1] | 393.26 | x |
| 11 | DHK19 | 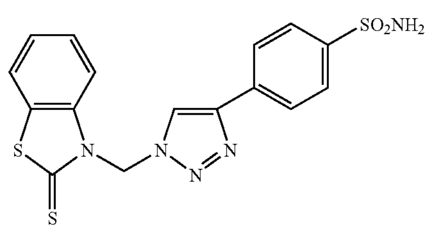 [SMILES: NS(=O)(=O)c1ccc(-c2cn(Cn3c(=S)sc4ccccc43)nn2)cc1] | 403.50 | ✓ |
| 12 | DHK20 | 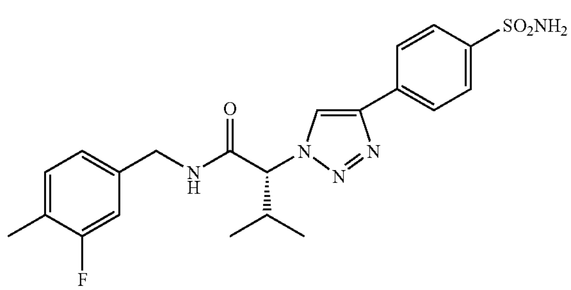 [SMILES: Cc1ccc(CNC(=O)[C@@H](C(C)C)n2cc(-c3ccc(S(N)(=O)=O)cc3)nn2)cc1F] | 445.51 | x |

TABLE 1-continued

| Entry | Code Name | Chemical Structure | Mol. Wt. | In Vitro Binding Assay (Library Screening) |
|---|---|---|---|---|
| 13 | DHK22 | 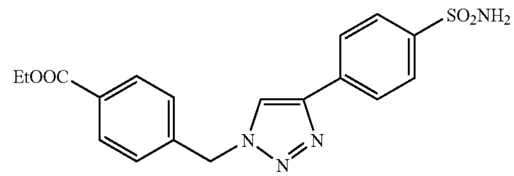 [SMILES: CCOC(=O)c1ccc(Cn2cc(-c3ccc(S(N)(=O)=O)cc3)nn2)cc1] | 386.42 | x |
| 14 | DHK23 | 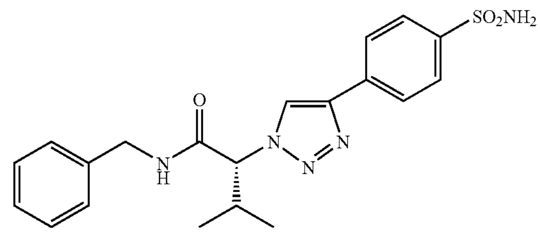 [SMILES: CC(C)[C@H](C(=O)NCc1ccccc1)n1cc(-c2ccc(S(N)(=O)=O)cc2)nn1] | 413.49 | x |
| 15 | DHK24 | 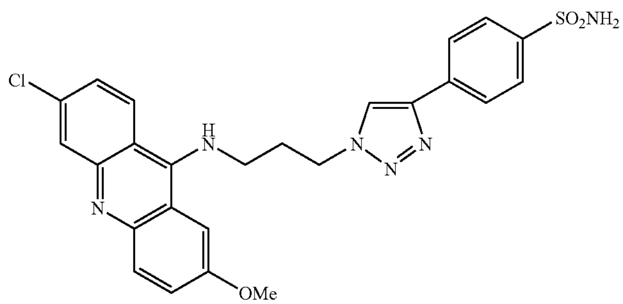 [SMILES: COc1ccc2nc3cc(Cl)ccc3c(NCCCn3cc(-c4ccc(S(N)(=O)=O)cc4)nn3)c2c1] | 523.01 | x |
| 16 | DHK25 | 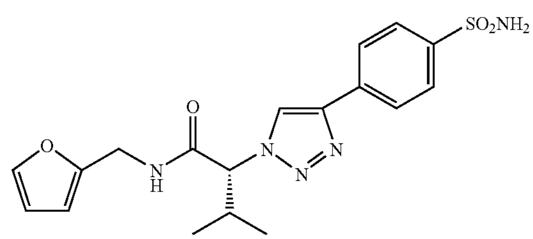 [SMILES: CC(C)[C@H](C(=O)NCc1ccco1)n1cc(-c2ccc(S(N)(=O)=O)cc2)nn1] | 403.46 | ✓✓ |
| 17 | DHK26 | 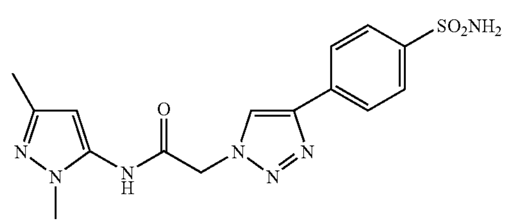 [SMILES: Cc1cc(NC(=O)Cn2cc(-c3ccc(S(N)(=O)=O)cc3)nn2)n(C)n1] | 375.41 | x |
| 18 | DHK27 | 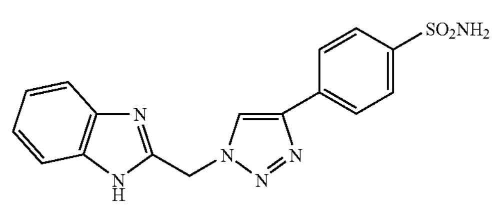 [SMILES: NS(=O)(=O)c1ccc(-c2cn(Cc3nc4ccccc4[nH]3)nn2)cc1] | 354.39 | x |

TABLE 1-continued
| Entry | Code Name | Chemical Structure | Mol. Wt. | In Vitro Binding Assay (Library Screening) |
|---|---|---|---|---|
| 19 | DHK29 | 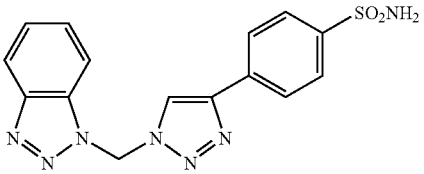 [SMILES: NS(=O)(=O)c1ccc(-c2cn(Cn3nnc4ccccc43)nn2)cc1] | 355.37 | ✓ |
| 20 | DHK63 | 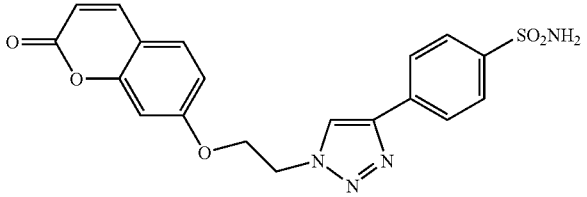 [SMILES: NS(=O)(=O)c1ccc(-c2cn(CCOc3ccc4ccc(=O)oc4c3)nn2)cc1] | 412.42 | x |
| 21 | DHK65 | 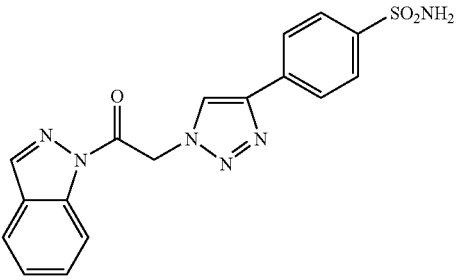 [SMILES: NS(=O)(=O)c1ccc(-c2cn(CC(=O)n3ncc4ccccc43)nn2)cc1] | 382.40 | x |
| 22 | DHK66 | 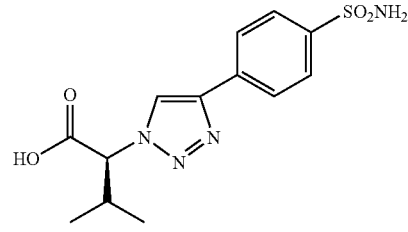 [SMILES: CC(C)[C@@H](C(=O)O)n1cc(-c2ccc(S(N)(=O)=O)cc2)nn1] | 324.36 | x |
| 23 | DHK67 | 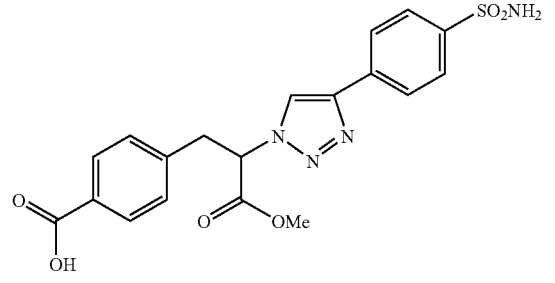 [SMILES: COC(=O)C(Cc1ccc(C(=O)O)cc1)n1cc(-c2ccc(S(N)(=O)=O)cc2)nn1] | 430.43 | x |
| 24 | DHK70 | 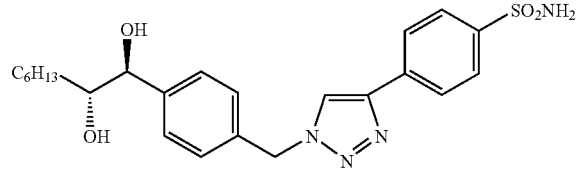 | 458.57 | x |

TABLE 1-continued
| Entry | Code Name | Chemical Structure | Mol. Wt. | In Vitro Binding Assay (Library Screening) |
|---|---|---|---|---|
| 25 | DHK71 | 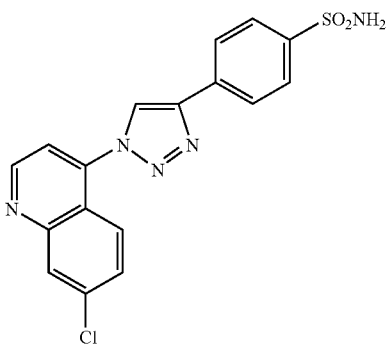 [SMILES: NS(=O)(=O)c1ccc(-c2cn(-c3ccnc4cc(Cl)ccc34)nn2)cc1] | 385.83 | x |
| 26 | DHK72 | 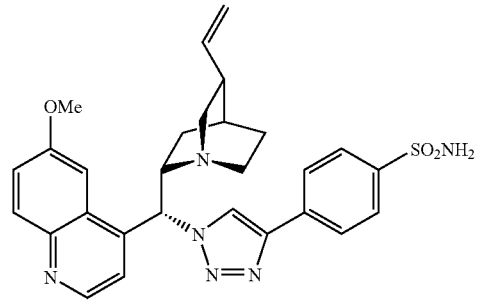 [SMILES: C=CC1C[N@@]2CCC1CC2[C@@H](c1ccnc2ccc(OC)cc12)n1cc(-c2ccc(S(N)(=O)=O)cc2)nn1] | 530.64 | x |
| 27 | DHK73 | 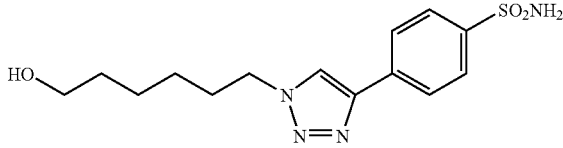 [SMILES: NS(=O)(=O)c1ccc(-c2cn(CCCCCCO)nn2)cc1] | 324.40 | x |
| 28 | DHK76 | 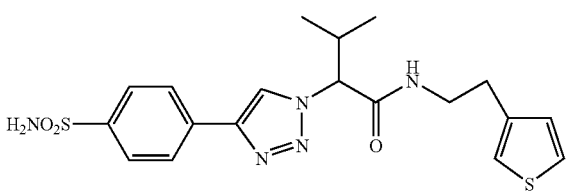 [SMILES: CC(C)C(C(=O)NCCc1ccsc1)n1cc(-c2ccc(S(N)(=O)=O)cc2)nn1] | 433.55 | x |
| 39 | DHK78 | 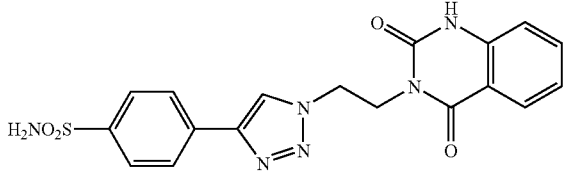 [SMILES: NS(=O)(=O)c1ccc(-c2cn(CCn3c(=O)[nH]c4ccccc4c3=O)nn2)cc1] | 412.42 | x |
| 30 | DHK82 | 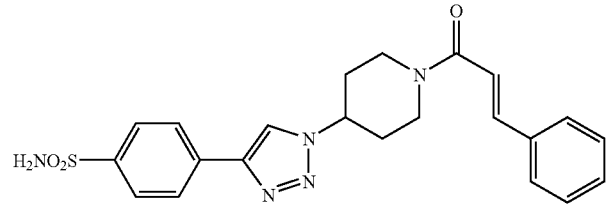 [SMILES: NS(=O)(=O)c1ccc(-c2cn(C3CCN(C(=O)/C=C/c4ccccc4)CC3)nn2)cc1] | 437.51 | x |

TABLE 1-continued

| Entry | Code Name | Chemical Structure | Mol. Wt. | In Vitro Binding Assay (Library Screening) |
|---|---|---|---|---|
| 31 | DHK101 | 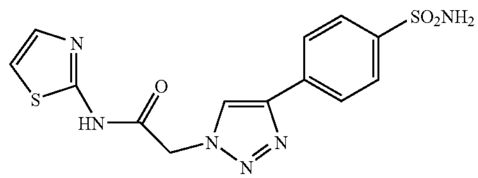 [SMILES: NS(=O)(=O)c1ccc(-c2cn(CC(=O)Nc3nccs3)nn2)cc1] | 364.40 | x |
| 32 | DHK102 | 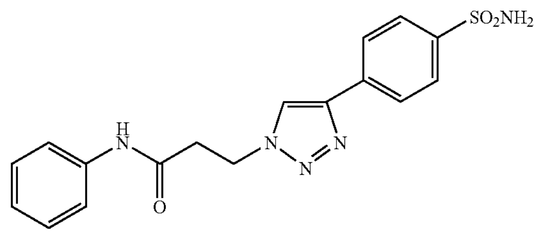 [SMILES: NS(=O)(=O)c1ccc(-c2cn(CCC(=O)Nc3ccccc3)nn2)cc1] | 371.41 | x |
| 33 | DHK104 | 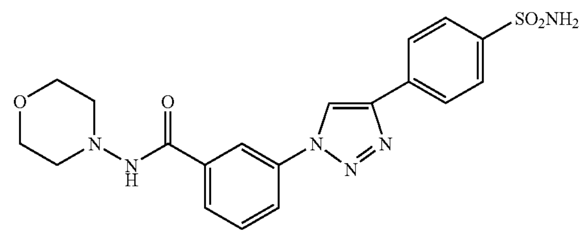 [SMILES: NS(=O)(=O)c1ccc(-c2cn(-c3cccc(C(=O)NN4CCOCC4)c3)nn2)cc1] | 428.46 | x |
| 34 | DHK106 | 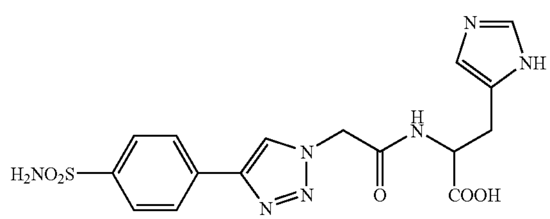 [SMILES: NS(=O)(=O)c1ccc(-c2cn(CC(=O)NC(Cc3cnc[nH]3)C(=O)O)nn2)cc1] | 419.42 | x |
| 35 | DHK107 | 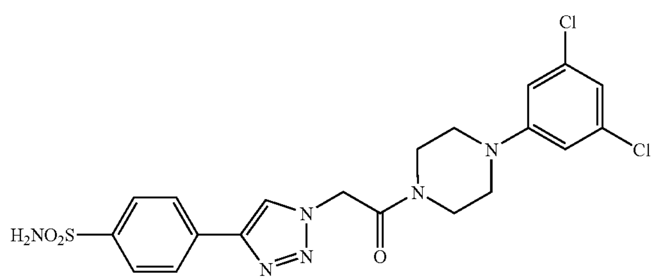 [SMILES: NS(=O)(=O)c1ccc(-c2cn(CC(=O)N3CCN(c4cc(Cl)cc(Cl)c4)CC3)nn2)cc1] | 495.38 | x |
| 36 | DHK108 | 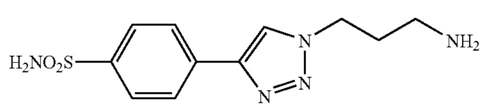 [SMILES: NCCCn1cc(-c2ccc(S(N)(=O)=O)cc2)nn1] | 281.33 | x |
| 37 | DHK109 | 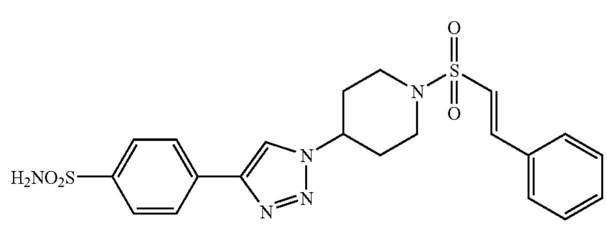 [SMILES: NS(=O)(=O)c1ccc(-c2cn(C3CCN(S(=O)(=O)/C=C/c4ccccc4)CC3)nn2)cc1] | 473.57 | x |

TABLE 1-continued

| Entry | Code Name | Chemical Structure | Mol. Wt. | In Vitro Binding Assay (Library Screening) |
|---|---|---|---|---|
| 38 | DHK111 | | 386.38 | x |
| Library 2 | | (Alkyne-2) + N₃—R → (triazole product), CuSO₄, Na-L-ascorbate, H₂O/ᵗBuOH, rt, 24 h | | |
| 39 | DHK33 | | 546.62 | x |
| 40 | DHK34 | | 394.45 | x |

TABLE 1-continued
| Entry | Code Name | Chemical Structure | Mol. Wt. | In Vitro Binding Assay (Library Screening) |
|---|---|---|---|---|
| 41 | DHK36 | 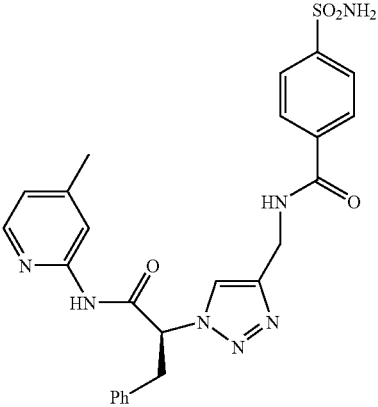 [SMILES: Cc1ccnc(NC(=O)[C@H](Cc2ccccc2)n2cc(CNC(=O)c3ccc(S(N)(=O)=O)cc3)nn2)c1] | 519.58 | x |
| 42 | DHK39 | 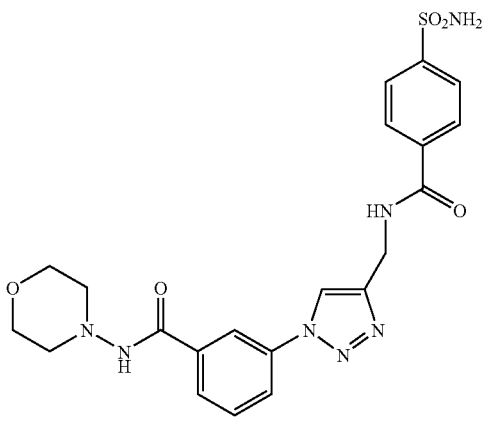 [SMILES: NS(=O)(=O)c1ccc(C(=O)NCc2cn(-c3cccc(C(=O)NN4CCOCC4)c3)nn2)cc1] | 485.52 | x |
| 43 | DHK40 | 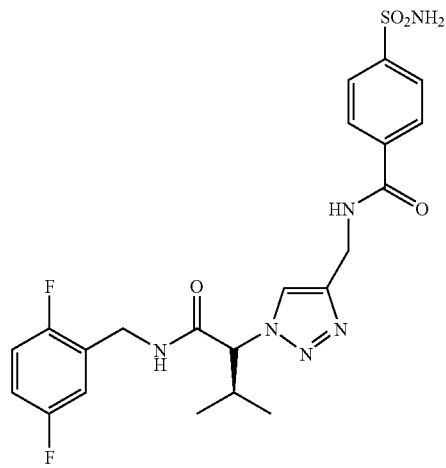 | 506.53 | x |

TABLE 1-continued
| Entry | Code Name | Chemical Structure | Mol. Wt. | In Vitro Binding Assay (Library Screening) |
|---|---|---|---|---|
| 44 | DHK41 | 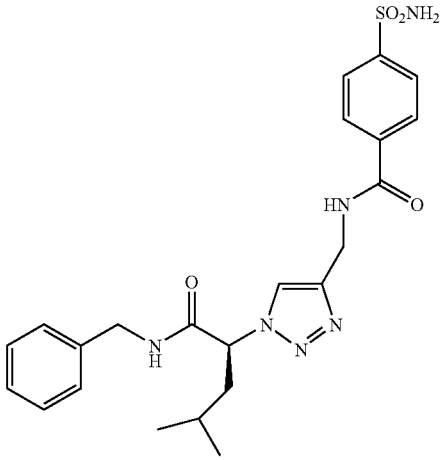 [SMILES: CC(C)C[C@@H](C(=O)NCc1ccccc1)n1cc(CNC(=O)c2ccc(S(N)(=O)=O)cc2)nn1] | 484.57 | x |
| 45 | DHK43 | 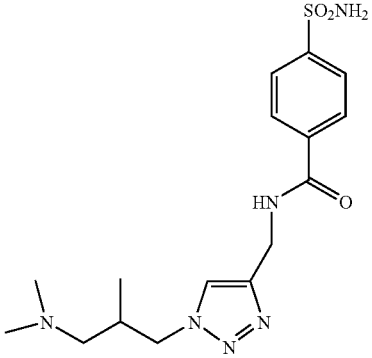 [SMILES: CC(CN(C)C)Cn1cc(CNC(=O)c2ccc(S(N)(=O)=O)cc2)nn1] | 380.47 | x |
| 46 | DHK44 | 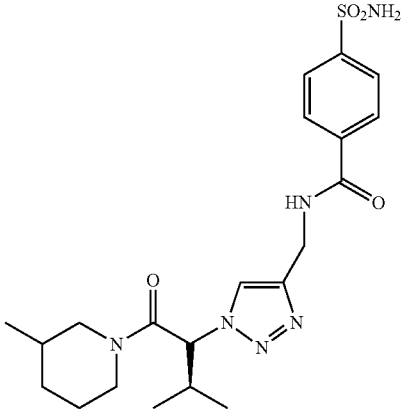 | 462.57 | x |

TABLE 1-continued
| Entry | Code Name | Chemical Structure | Mol. Wt. | In Vitro Binding Assay (Library Screening) |
|---|---|---|---|---|
| 47 | DHK45 | 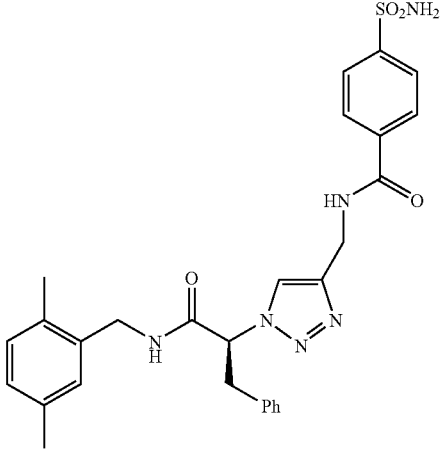 [SMILES: Cc1ccc(C)c(CNC(=O)[C@H](Cc2ccccc2)n2cc(CNC(=O)c3ccc(S(N)(=O)=O)cc3)nn2)c1] | 546.64 | x |
| 48 | DHK47 | 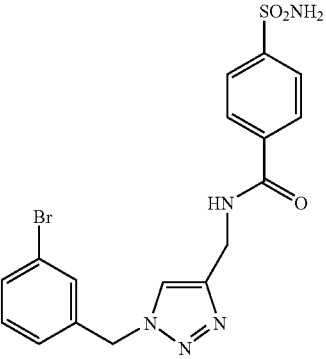 [SMILES: NS(=O)(=O)c1ccc(C(=O)NCc2cn(Cc3cccc(Br)c3)nn2)cc1] | 450.31 | x |
| 49 | DHK48 | 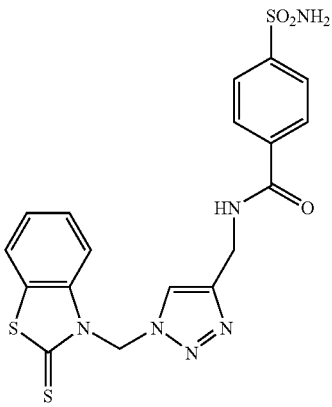 [SMILES: NS(=O)(=O)c1ccc(C(=O)NCc2cn(Cn3c(=S)sc4ccccc43)nn2)cc1] | 460.55 | x |

TABLE 1-continued

| Entry | Code Name | Chemical Structure | Mol. Wt. | In Vitro Binding Assay (Library Screening) |
|---|---|---|---|---|
| 50 | DHK49 | 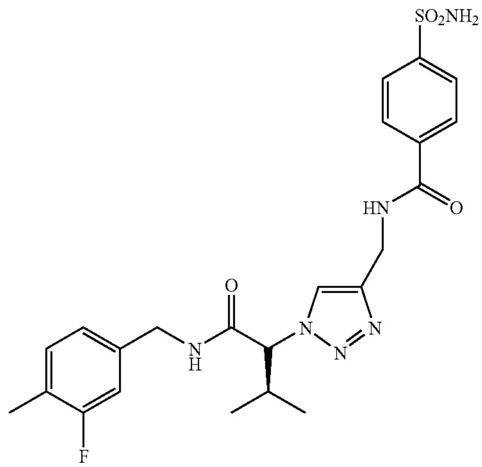 | 502.56 | x |
| 51 | DHK50 | 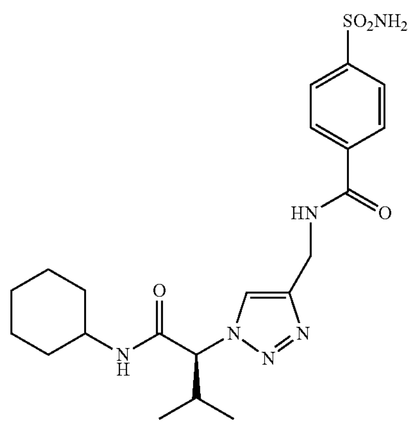 [SMILES: CC(C)[C@@H](C(=O)NC1CCCCC1)n1cc(CNC(=O)c2ccc(S(N)(=O)=O)cc2)nn1] | 462.57 | x |
| 52 | DHK51 | 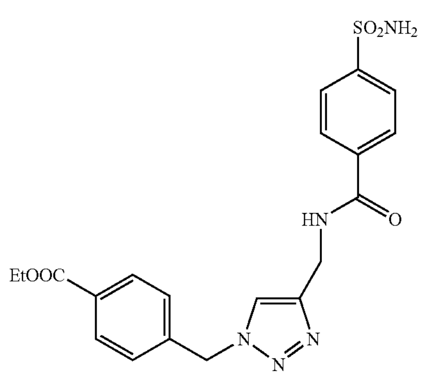 [SMILES: CCOC(=O)c1ccc(Cn2cc(CNC(=O)c3ccc(S(N)(=O)=O)cc3)nn2)cc1] | 443.48 | x |

TABLE 1-continued

| Entry | Code Name | Chemical Structure | Mol. Wt. | In Vitro Binding Assay (Library Screening) |
|---|---|---|---|---|
| 53 | DHK52 | 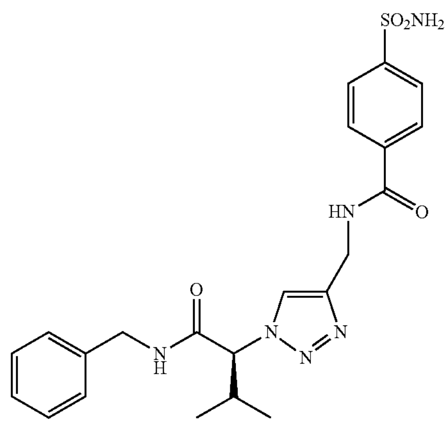 [SMILES: CC(C)[C@@H](C(=O)NCc1ccccc1)n1cc(CNC(=O)c2ccc(S(N)(=O)=O)cc2)nn1] | 470.54 | x |
| 54 | DHK54 | 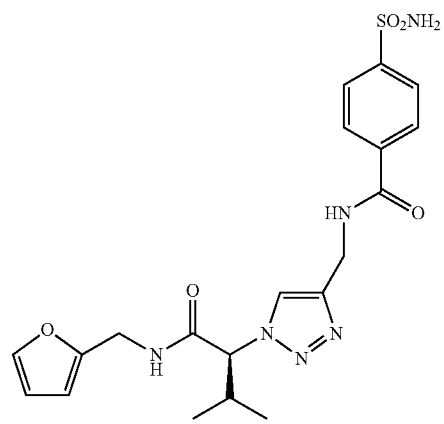 [SMILES: CC(C)[C@@H](C(=O)NCc1ccco1)n1cc(CNC(=O)c2ccc(S(N)(=O)=O)cc2)nn1] | 460.51 | x |
| 55 | DHK55 | 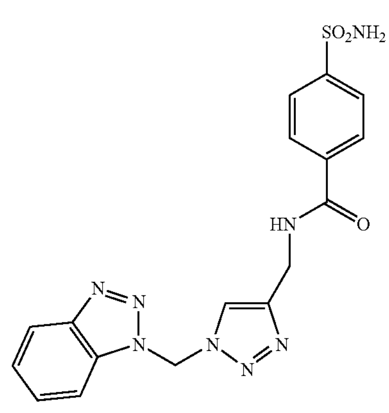 [SMILES: NS(=O)(=O)c1ccc(C(=O)NCc2cn(Cn3nnc4ccccc43)nn2)cc1] | 412.43 | x |

TABLE 1-continued
| Entry | Code Name | Chemical Structure | Mol. Wt. | In Vitro Binding Assay (Library Screening) |
|---|---|---|---|---|
| 56 | DHK56 | 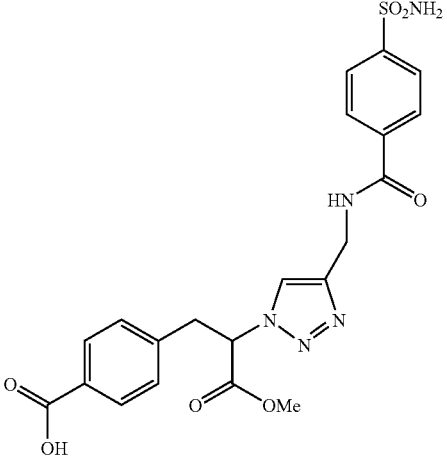 [SMILES: COC(=O)C(Cc1ccc(C(=O)O)cc1)n1cc(CNC(=O)c2ccc(S(N)(=O)=O)cc2)nn1] | 487.49 | x |
| 57 | DHK57 | 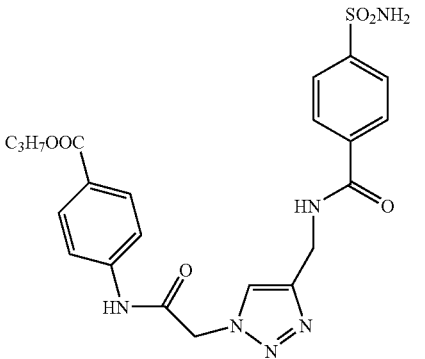 | 500.53 | x |
| 58 | DHK58 | 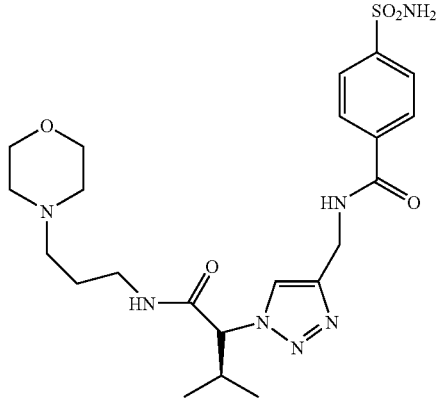 | 507.61 | x |

TABLE 1-continued
| Entry | Code Name | Chemical Structure | Mol. Wt. | In Vitro Binding Assay (Library Screening) |
|---|---|---|---|---|
| 59 | DHK59 | 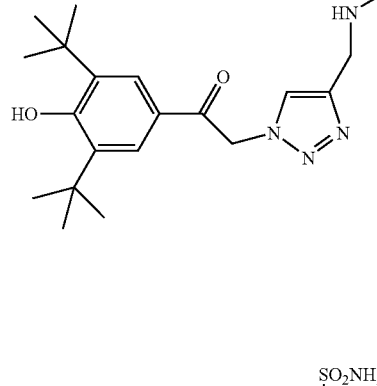 | 527.64 | x |
| 60 | DHK60 | 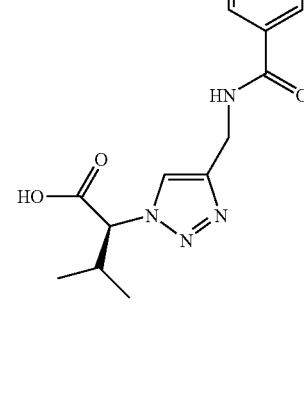 | 381.41 | x |
| 61 | DHK61 | 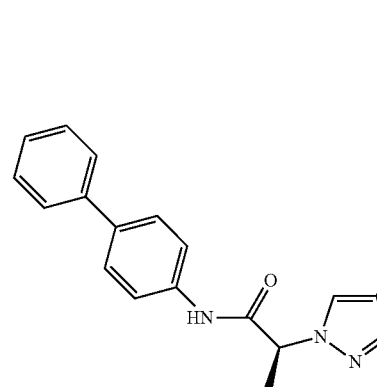 | 532.61 | x |

TABLE 1-continued
| Entry | Code Name | Chemical Structure | Mol. Wt. | In Vitro Binding Assay (Library Screening) |
|---|---|---|---|---|
| 62 | DHK85 | 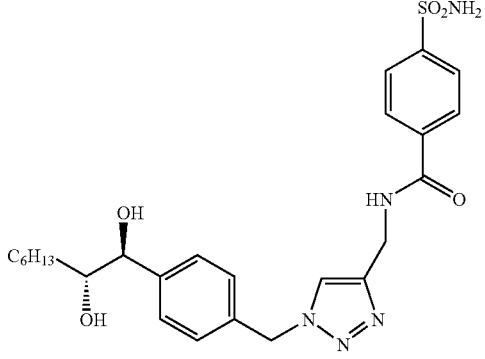 | 515.63 | x |
| 63 | DHK86 | 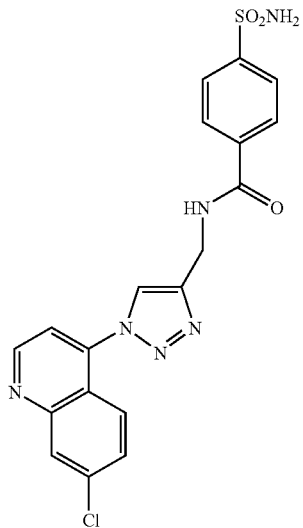 [SMILES: NS(=O)(=O)c1ccc(C(=O)NCc2cn(-c3ccnc4cc(Cl)ccc34)nn2)cc1] | 442.88 | x |
| 64 | DHK87 | 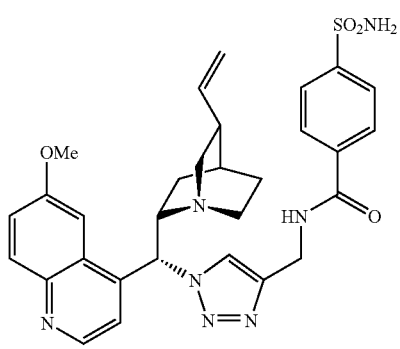 [SMILES: C=CC1C[N@@]2CCC1CC2[C@@H](c1ccnc2ccc(OC)cc12)n1cc(CNC(=O)c2ccc(S(N)(=O)=O)cc2)nn1] | 587.69 | x |

TABLE 1-continued
| Entry | Code Name | Chemical Structure | Mol. Wt. | In Vitro Binding Assay (Library Screening) |
|---|---|---|---|---|
| 65 | DHK88 | 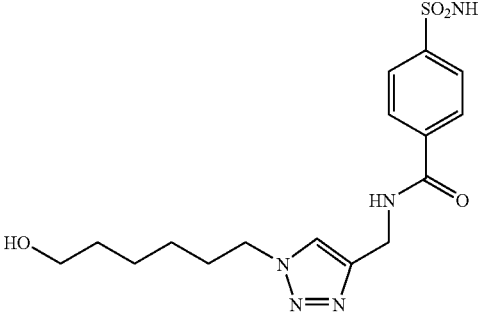 | 381.45 | x |
| 66 | DHK90 | 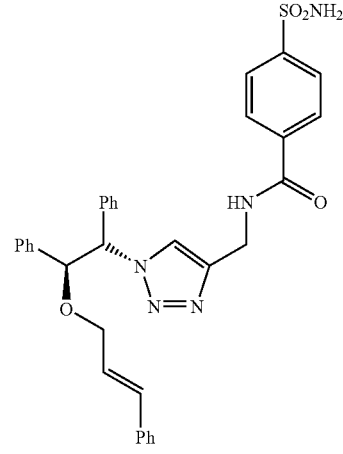 | 593.70 | x |
| 67 | DHK91 | 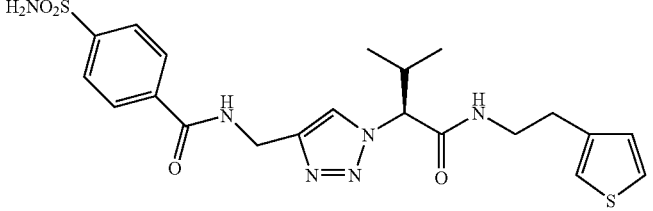 [SMILES: CC(C)[C@@H](C(=O)NCCc1ccsc1)n1cc(CNC(=O)c2ccc(S(N)(=O)=O)cc2)nn1] | 490.60 | x |
| 68 | DHK92 | 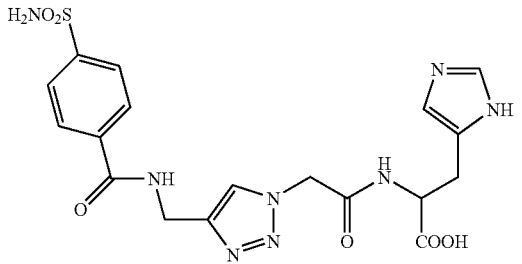 [SMILES: NS(=O)(=O)c1ccc(C(=O)NCc2cn(CC(=O)NC(Cc3cnc[nH]3)C(=O)O)nn2)cc1] | 476.47 | x |
| 69 | DHK93 | 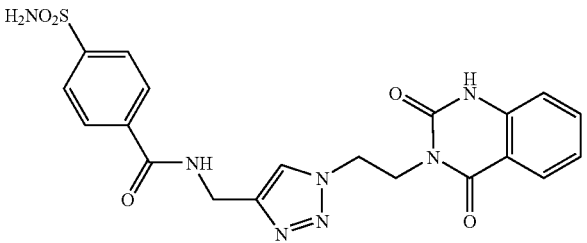 [SMILES: NS(=O)(=O)c1ccc(C(=O)NCc2cn(CCn3c(=O)[nH]c4ccccc4c3=O)nn2)cc1] | 469.47 | x |

TABLE 1-continued

| Entry | Code Name | Chemical Structure | Mol. Wt. | In Vitro Binding Assay (Library Screening) |
|---|---|---|---|---|
| 70 | DHK94 | 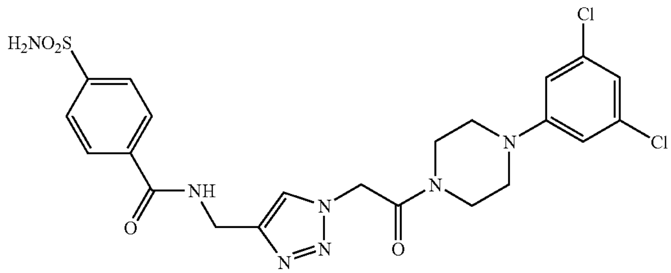 [SMILES: NS(=O)(=O)c1ccc(C(=O)NCc2cn(CC(=O)N3CCN(c4cc(Cl)cc(Cl)c4)CC3)nn2)cc1] | 552.43 | x |
| 71 | DHK95 | 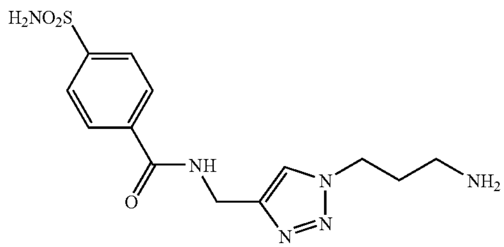 [SMILES: NCCCn1cc(CNC(=O)c2ccc(S(N)(=O)=O)cc2)nn1] | 338.39 | x |
| 72 | DHK96 | 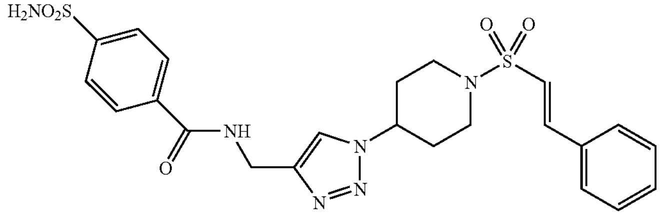 [SMILES: NS(=O)(=O)c1ccc(C(=O)NCc2cn(C3CCN(S(=O)(=O)/C=C/c4ccccc4)CC3)nn2)cc1] | 530.62 | x |
| 73 | DHK97 | 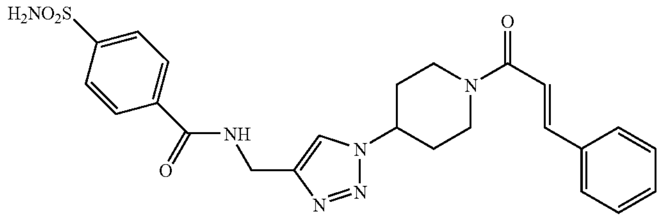 [SMILES: NS(=O)(=O)c1ccc(C(=O)NCc2cn(C3CCN(C(=O)/C=C/c4ccccc4)CC3)nn2)cc1] | 494.57 | x |
| 74 | DHK100 | 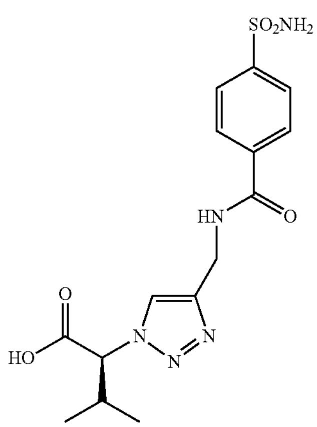 [SMILES: CC(C)[C@@H](C(=O)O)n1cc(CNC(=O)c2ccc(S(N)(=O)=O)cc2)nn1] | 381.41 | x |

TABLE 1-continued
| Entry | Code Name | Chemical Structure | Mol. Wt. | In Vitro Binding Assay (Library Screening) |
|---|---|---|---|---|
| 75 | DHK110 | 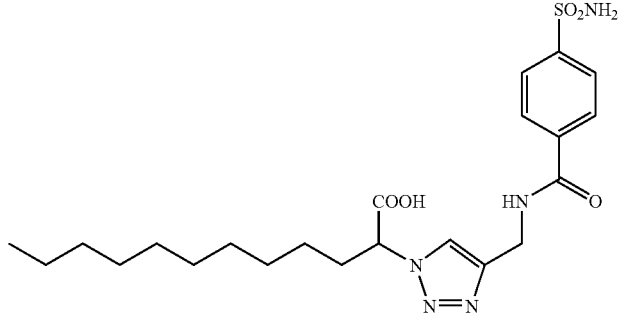 [SMILES: CCCCCCCCCCC(C(=O)O)n1cc(CNC(=O)c2ccc(S(N)(=O)=O)cc2)nn1] | 479.59 | x |
| 76 | DHK112 | 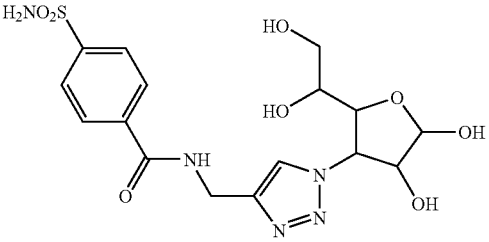 [SMILES: NS(=O)(=O)c1ccc(C(=O)NCc2cn(C3C(O)C(O)OC3C(O)CO)nn2)cc1] | 443.43 | x |
| Library 3 | | 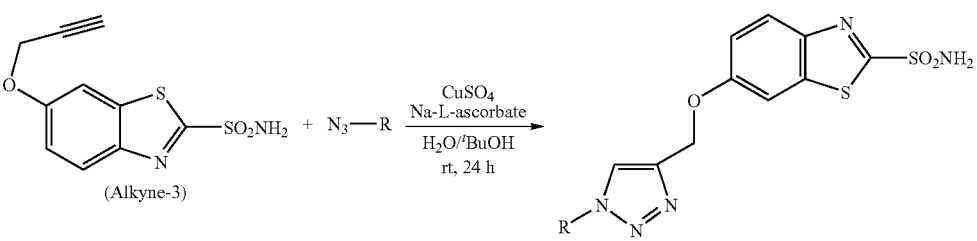 | | |
| 77 | DHK113 | 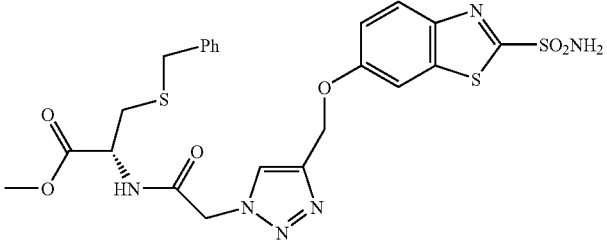 [SMILES: COC(=O)[C@H](CSCc1ccccc1)NC(=O)Cn1cc(COc2ccc3nc(S(N)(=O)=O)sc3c2)nn1] | 576.67 | ✓✓ |
| 78 | DHK114 | 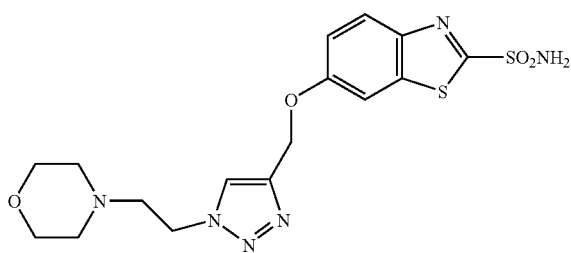 [SMILES: NS(=O)(=O)c1nc2ccc(OCc3cn(CCN4CCOCC4)nn3)cc2s1] | 424.50 | x[b] |

TABLE 1-continued
| Entry | Code Name | Chemical Structure | Mol. Wt. | In Vitro Binding Assay (Library Screening) |
|---|---|---|---|---|
| 79 | DHK115 | 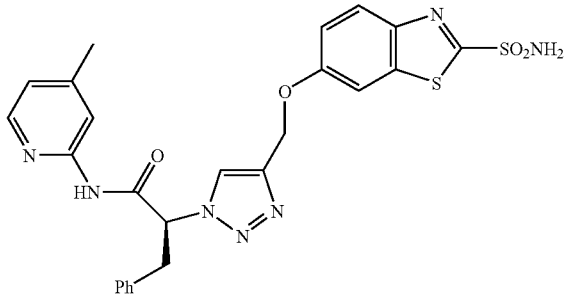 [SMILES: Cc1ccnc(NC(=O)[C@H](Cc2ccccc2)n2cc(COc3ccc4nc(S(N)(=O)=O)sc4c3)nn2)c1] | 549.62 | x |
| 80 | DHK116 | 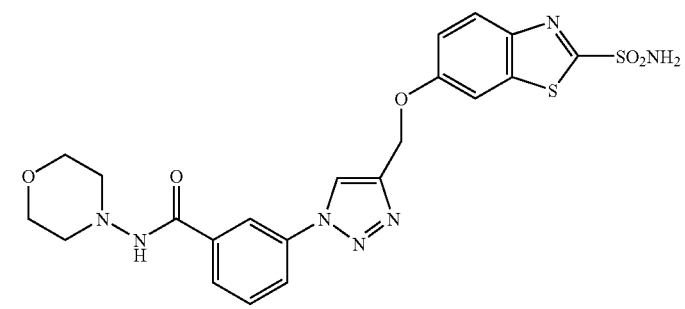 [SMILES: NS(=O)(=O)c1nc2ccc(OCc3cn(-c4cccc(C(=O)NN5CCOCC5)c4)nn3)cc2s1] | 515.57 | x |
| 81 | DHK117 | 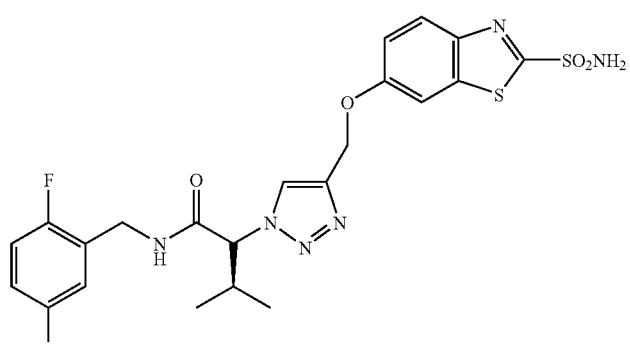 | 536.57 | ✓ |
| 82 | DHK118 | 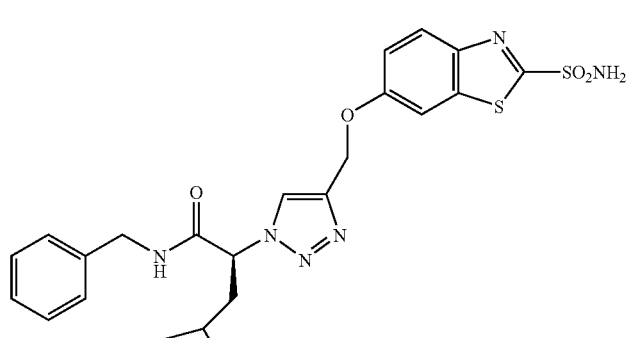 | 514.62 | x |

TABLE 1-continued

| Entry | Code Name | Chemical Structure | Mol. Wt. | In Vitro Binding Assay (Library Screening) |
|---|---|---|---|---|
| 83 | DHK119 | 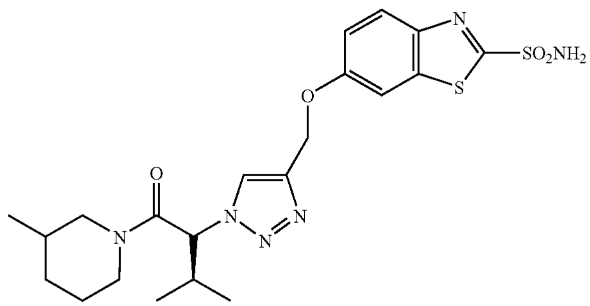 | 492.61 | x |
| 84 | DHK120 | 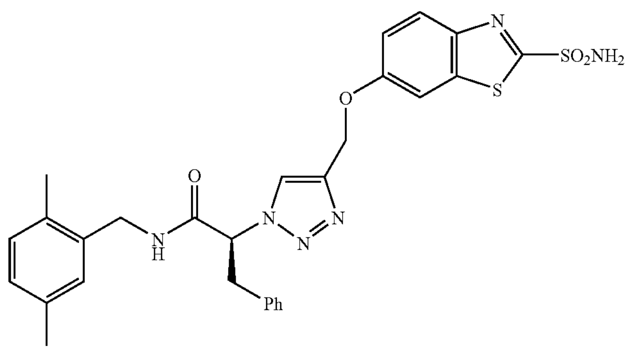 [SMILES: Cc1ccc(C)c(CNC(=O)[C@H](Cc2ccccc2)n2cc(COc3ccc4nc(S(N)(=O)=O)sc4c3)nn2)c1] | 576.69 | x |
| 85 | DHK121 | 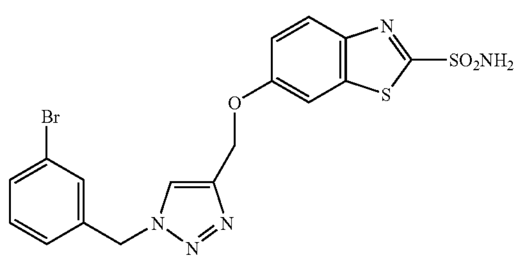 [SMILES: NS(=O)(=O)c1nc2ccc(OCc3cn(Cc4cccc(Br)c4)nn3)cc2s1] | 480.36 | ✓ |
| 86 | DHK123 | 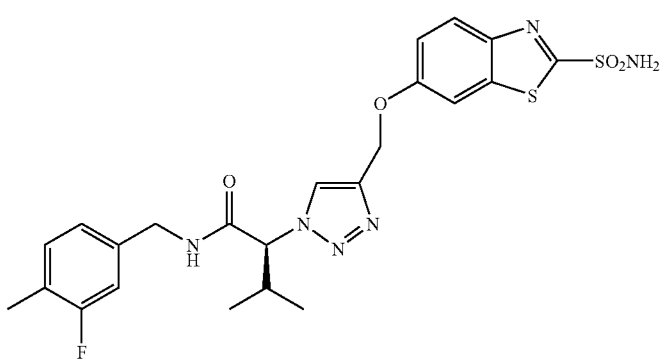 [SMILES: Cc1ccc(CNC(=O)[C@H](C(C)C)n2cc(COc3ccc4nc(S(N)(=O)=O)sc4c3)nn2)cc1F] | 532.61 | ✓ |

TABLE 1-continued

| Entry | Code Name | Chemical Structure | Mol. Wt. | In Vitro Binding Assay (Library Screening) |
|---|---|---|---|---|
| 87 | DHK124 | 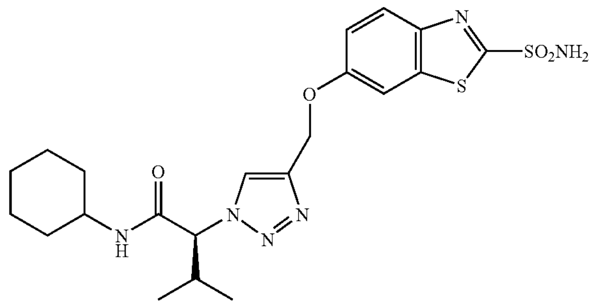 [SMILES: CC(C)[C@@H](C(=O)NC1CCCCC1)n1cc(COc2ccc3nc(S(N)(=O)=O)sc3c2)nn1] | 492.61 | x |
| 88 | DHK125 | 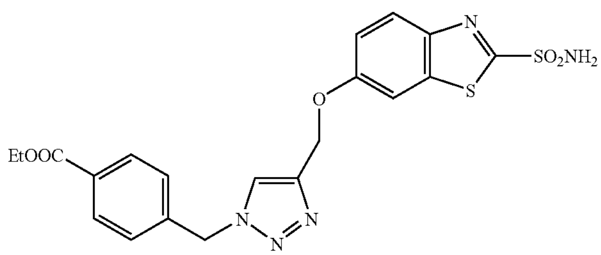 [SMILES: CCOC(=O)c1ccc(Cn2cc(COc3ccc4nc(S(N)(=O)=O)sc4c3)nn2)cc1] | 473.53 | ✓ |
| 89 | DHK126 | 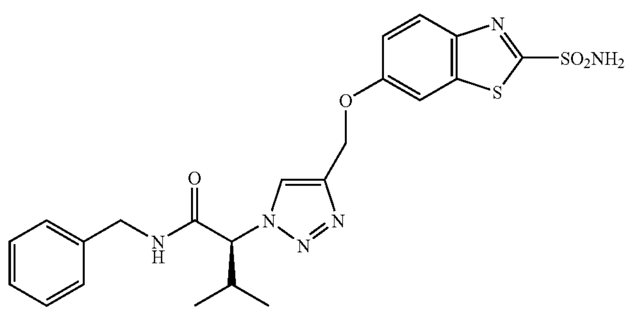 [SMILES: CC(C)[C@@H](C(=O)NCc1ccccc1)n1cc(COc2ccc3nc(S(N)(=O)=O)sc3c2)nn1] | 500.59 | x |
| 90 | DHK127 | 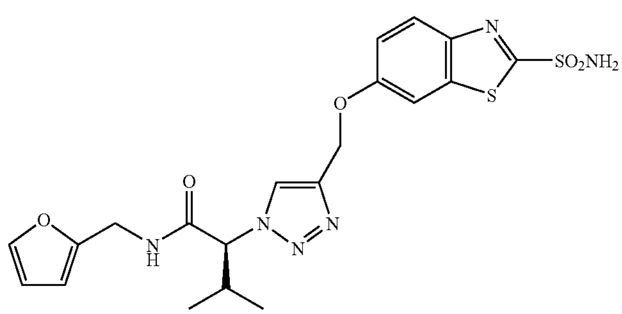 [SMILES: CC(C)[C@@H](C(=O)NCc1ccco1)n1cc(COc2ccc3nc(S(N)(=O)=O)sc3c2)nn1] | 490.56 | ✓ |
| 91 | DHK128 | 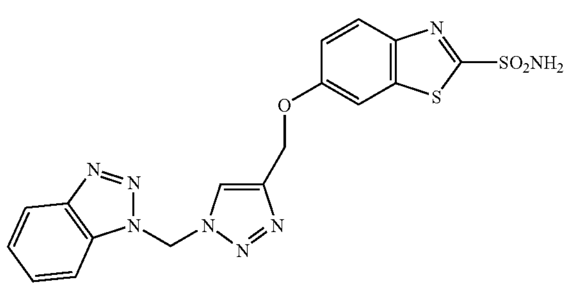 [SMILES: NS(=O)(=O)c1nc2ccc(OCc3cn(Cn4nnc5ccccc54)nn3)cc2s1] | 442.47 | ✓ |

TABLE 1-continued

| Entry | Code Name | Chemical Structure | Mol. Wt. | In Vitro Binding Assay (Library Screening) |
|---|---|---|---|---|
| 92 | DHK129 | 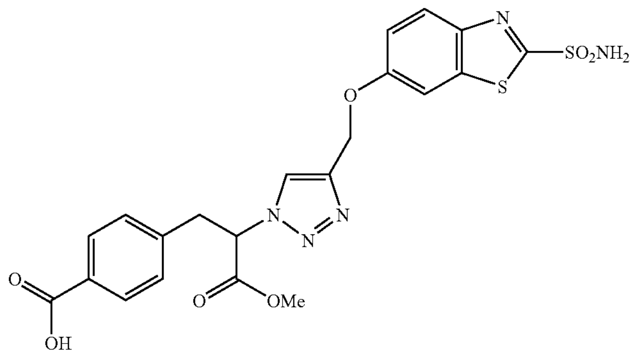 [SMILES: COC(=O)C(Cc1ccc(C(=O)O)cc1)n1cc(COc2ccc3nc(S(N)(=O)=O)sc3c2)nn1] | 517.53 | x |
| 93 | DHK130 | 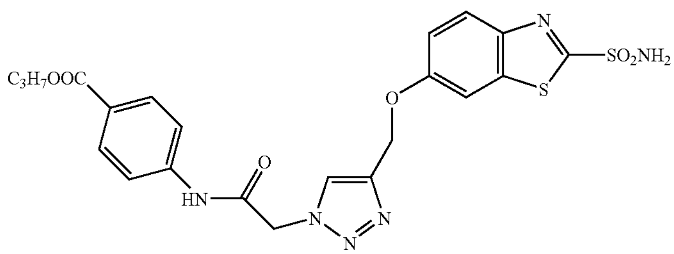 | 530.58 | x |
| 94 | DHK132 | 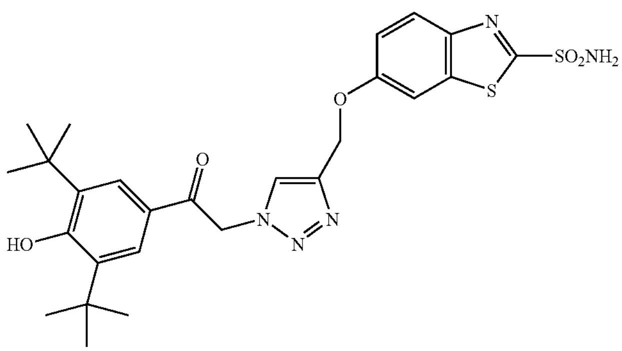 [SMILES: CC(C)(C)c1cc(C(=O)Cn2cc(COc3ccc4nc(S(N)(=O)=O)sc4c3)nn2)cc(C(C)(C)C)c1O] | 557.68 | x |
| 95 | DHK134 | 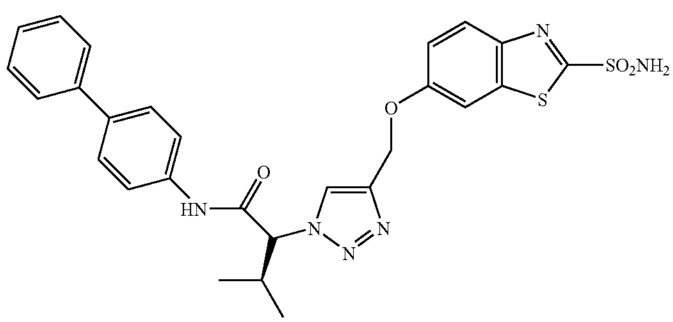 | 562.66 | x |
| 96 | DHK135 | 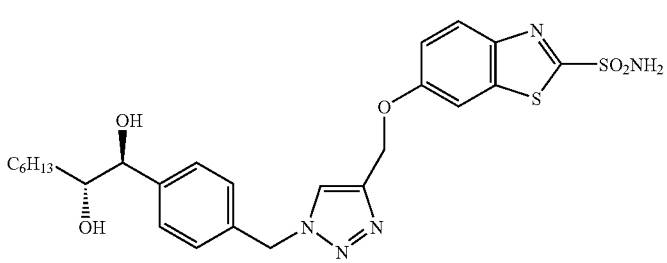 | 545.67 | x |

TABLE 1-continued

| Entry | Code Name | Chemical Structure | Mol. Wt. | In Vitro Binding Assay (Library Screening) |
|---|---|---|---|---|
| 97 | DHK136 | 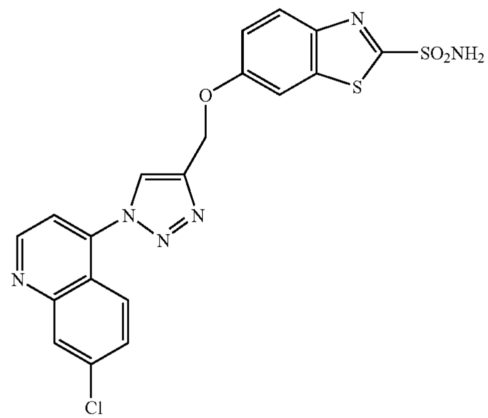 [SMILES: NS(=O)(=O)c1nc2ccc(OCc3cn(-c4ccnc5cc(Cl)ccc45)nn3)cc2s1] | 472.93 | x |
| 98 | DHK137 | 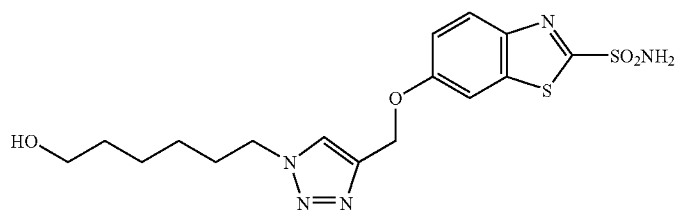 [SMILES: NS(=O)(=O)c1nc2ccc(OCc3cn(CCCCCCO)nn3)cc2s1] | 411.50 | x |
| 99 | DHK138 | 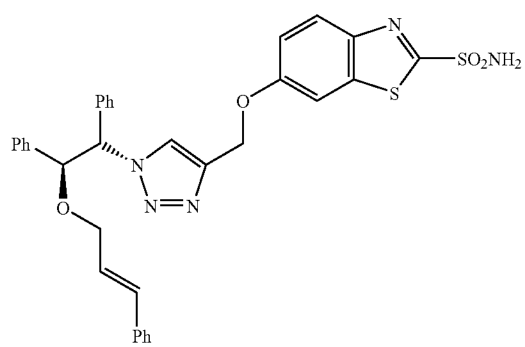 | 623.74 | x |
| 100 | DHK139 | 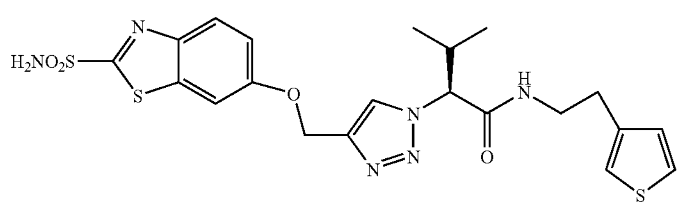 [SMILES: CC(C)[C@@H](C(=O)NCCc1ccsc1)n1cc(COc2ccc3nc(S(N)(=O)=O)sc3c2)nn1] | 520.65 | x |
| 101 | DHK140 | 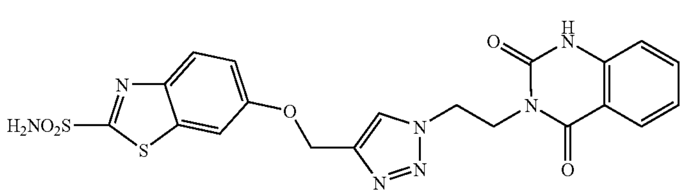 [SMILES: NS(=O)(=O)c1nc2ccc(OCc3cn(CCn4c(=O)[nH]c5ccccc5c4=O)nn3)cc2s1] | 499.52 | x |

TABLE 1-continued

| Entry | Code Name | Chemical Structure | Mol. Wt. | In Vitro Binding Assay (Library Screening) |
|---|---|---|---|---|
| 102 | DHK141 | 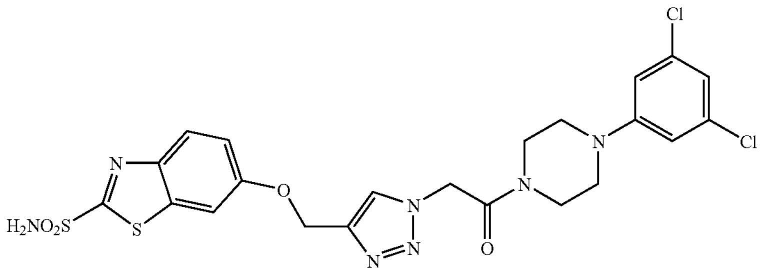 [SMILES: NS(=O)(=O)c1nc2ccc(OCc3cn(CC(=O)N4CCN(c5cc(Cl)cc(Cl)c5)CC4)nn3)cc2s1] | 582.48 | x |
| 103 | DHK143 | 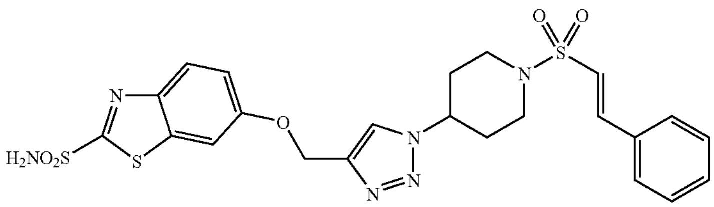 [SMILES: NS(=O)(=O)c1nc2ccc(OCc3cn(C4CCN(S(=O)(=O)/C=C/c5ccccc5)CC4)nn3)cc2s1] | 560.67 | x |
| 104 | DHK144 | 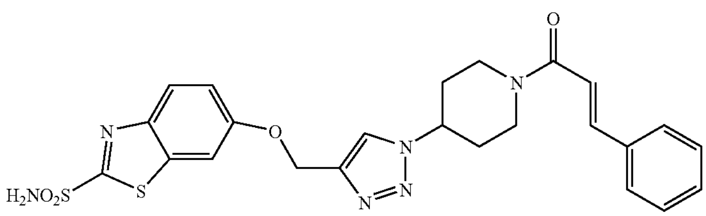 [SMILES: NS(=O)(=O)c1nc2ccc(OCc3cn(C4CCN(C(=O)/C=C/c5ccccc5)CC4)nn3)cc2s1] | 524.62 | x |

[a] Inhibition % is less than 40%.

TABLE 2

| Entry | Code Name | Chemical Structure | Mol. Wt. | In Vitro Binding Assay (Library Screening) |
|---|---|---|---|---|
| Library 4 | | 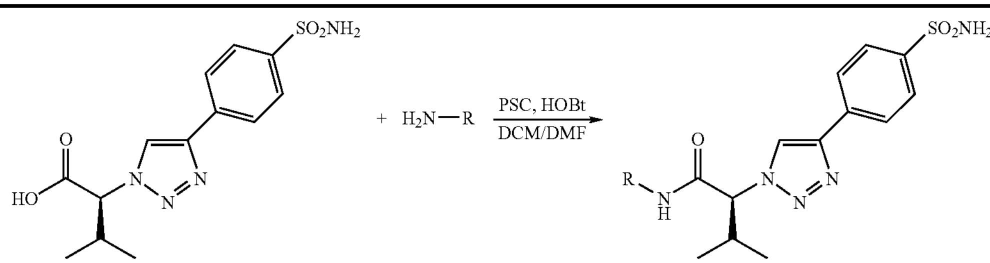 | | |
| 1 | DHK165 | 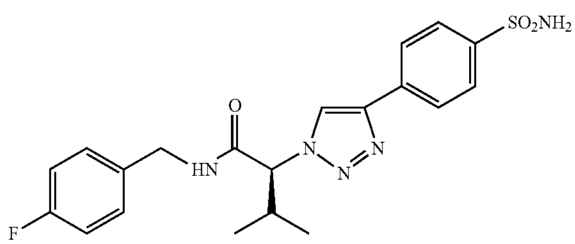 [SMILES: CC(C)[C@@H](C(=O)NCc1ccc(F)cc1)n1cc(-c2ccc(S(N)(=O)=O)cc2)nn1] | 431.48 | x[a] |

TABLE 2-continued

| Entry | Code Name | Chemical Structure | Mol. Wt. | In Vitro Binding Assay (Library Screening) |
|---|---|---|---|---|
| 2 | DHK166 | 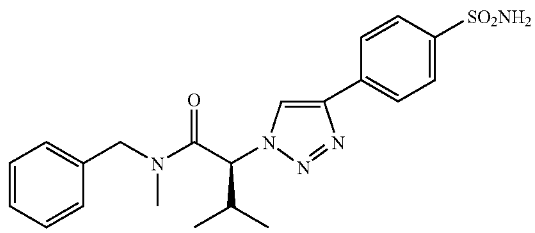 [SMILES: CC(C)[C@@H](C(=O)N(C)Cc1ccccc1)n1cc(-c2ccc(S(N)(=O)=O)cc2)nn1] | 427.52 | x |
| 3 | DHK168 | 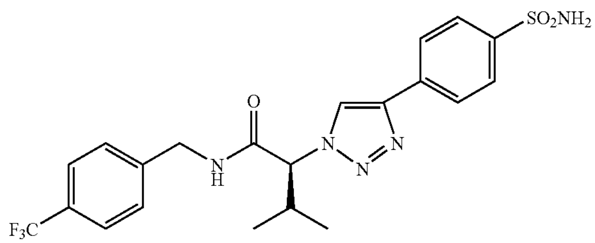 [SMILES: CC(C)[C@@H](C(=O)NCc1ccc(C(F)(F)F)cc1)n1cc(-c2ccc(S(N)(=O)=O)cc2)nn1] | 481.49 | x |
| 4 | DHK174 | 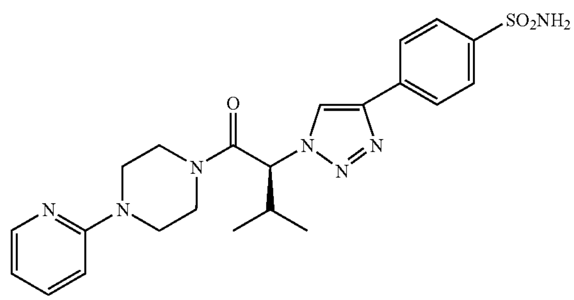 [SMILES: CC(C)[C@@H](C(=O)N1CCN(c2ccccn2)CC1)n1cc(-c2ccc(S(N)(=O)=O)cc2)nn1] | 469.56 | x |
| 5 | DHK175 | 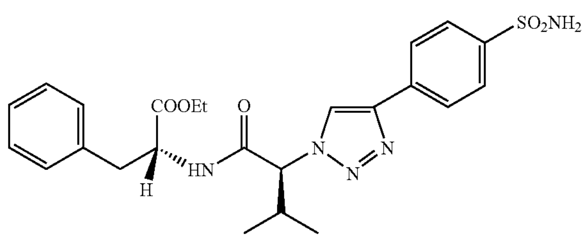 [SMILES: CCOC(=O)[C@@H](Cc1ccccc1)NC(=O)[C@H](C(C)C)n1cc(-c2ccc(S(N)(=O)=O)cc2)nn1] | 499.58 | x |
| 6 | DHK176 | 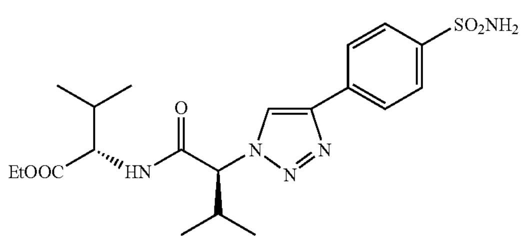 [SMILES: CCOC(=O)[C@@H](NC(=O)[C@H](C(C)C)n1cc(-c2ccc(S(N)(=O)=O)cc2)nn1)C(C)C] | 451.54 | x |
| 7 | DHK177 | 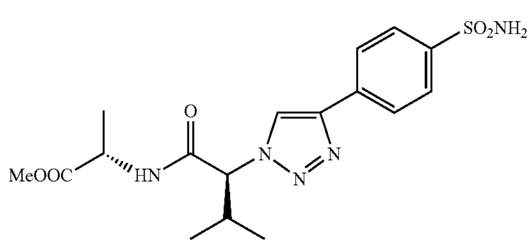 [SMILES: COC(=O)[C@H](C)NC(=O)[C@H](C(C)C)n1cc(-c2ccc(S(N)(=O)=O)cc2)nn1] | 409.46 | x |

TABLE 2-continued

| Entry | Code Name | Chemical Structure | Mol. Wt. | In Vitro Binding Assay (Library Screening) |
|---|---|---|---|---|
| 8 | DHK178 | 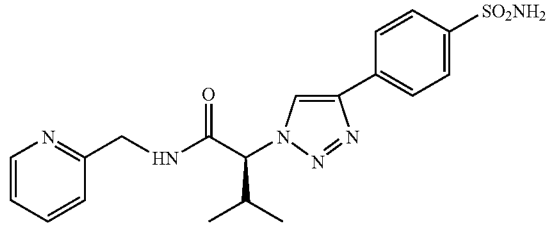 [SMILES: CC(C)[C@@H](C(=O)NCc1ccccn1)n1cc(-c2ccc(S(N)(=O)=O)cc2)nn1] | 414.48 | x |
| 9 | DHK179 | 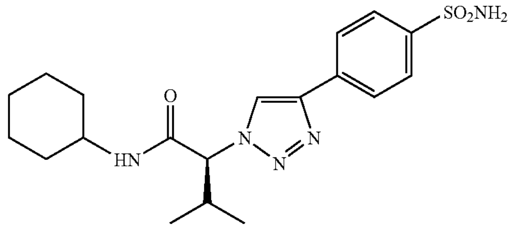 [SMILES: CC(C)[C@@H](C(=O)NC1CCCCC1)n1cc(-c2ccc(S(N)(=O)=O)cc2)nn1] | 405.51 | x |
| 10 | DHK180 | 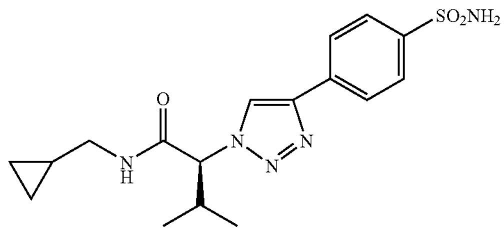 [SMILES: CC(C)[C@@H](C(=O)NCC1CC1)n1cc(-c2ccc(S(N)(=O)=O)cc2)nn1] | 377.46 | x |
| 11 | DHK181 | 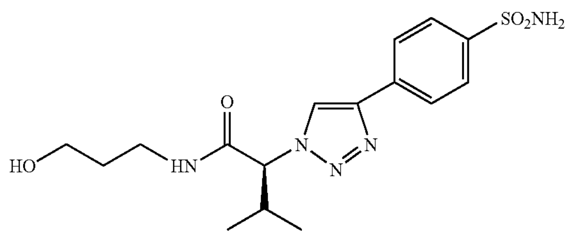 [SMILES: CC(C)[C@@H](C(=O)NCCCO)n1cc(-c2ccc(S(N)(=O)=O)cc2)nn1] | 381.45 | x |
| 12 | DHK182 | 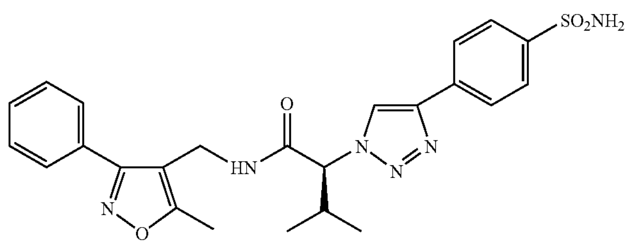 [SMILES: Cc1onc(-c2ccccc2)c1CNC(=O)[C@H](C(C)C)n1cc(-c2ccc(S(N)(=O)=O)cc2)nn1] | 494.57 | x |
| 13 | DHK183 | 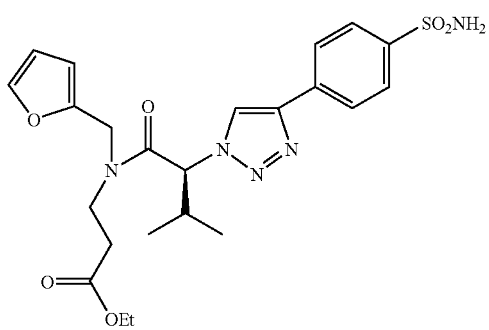 [SMILES: CCOC(=O)CCN(Cc1ccco1)C(=O)[C@H](C(C)C)n1cc(-c2ccc(S(N)(=O)=O)cc2)nn1] | 503.57 | x |

TABLE 2-continued
| Entry | Code Name | Chemical Structure | Mol. Wt. | In Vitro Binding Assay (Library Screening) |
|---|---|---|---|---|
| 14 | DHK184 | 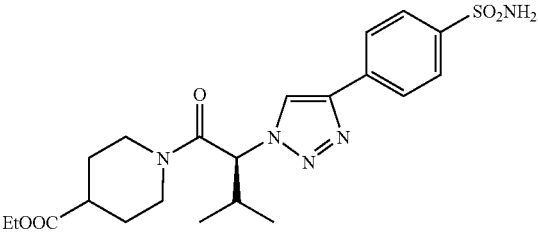 [SMILES: CCOC(=O)C1CCN(C(=O)[C@H](C(C)C)n2cc(-c3ccc(S(N)(=O)=O)cc3)nn2)CC1] | 463.55 | x |
| 15 | DHK185 | 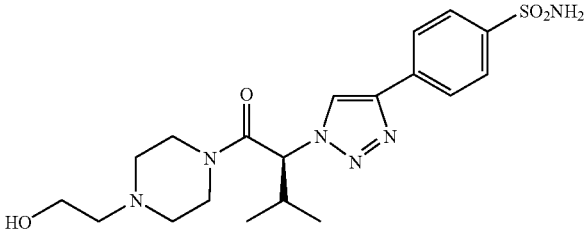 [SMILES: CC(C)[C@@H](C(=O)N1CCN(CCO)CC1)n1cc(-c2ccc(S(N)(=O)=O)cc2)nn1] | 436.53 | x |
| 16 | DHK186 | 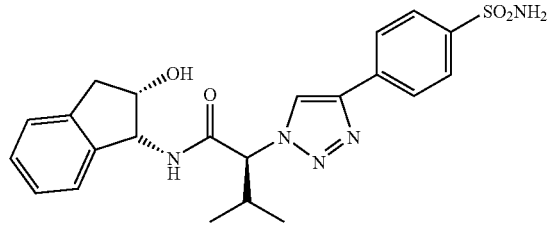 | 455.53 | x |
| 17 | DHK187 | 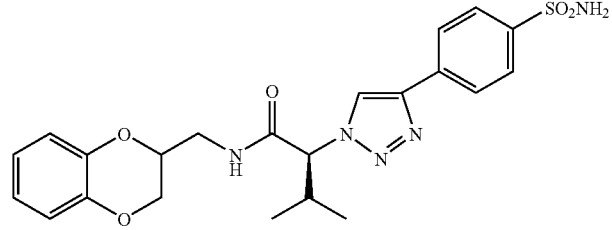 [SMILES: CC(C)[C@@H](C(=O)NCC1COc2ccccc2O1)n1cc(-c2ccc(S(N)(=O)=O)cc2)nn1] | 471.53 | x |
| 18 | DHK188 | 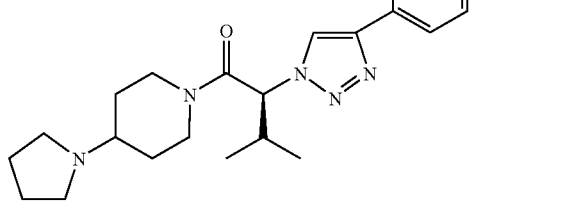 | 460.59 | x |
| 19 | DHK189 | 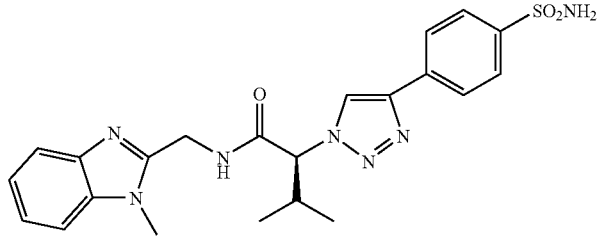 [SMILES: CC(C)[C@@H](C(=O)NCc1nc2ccccc2n1C)n1cc(-c2ccc(S(N)(=O)=O)cc2)nn1] | 467.54 | x |

TABLE 2-continued

| Entry | Code Name | Chemical Structure | Mol. Wt. | In Vitro Binding Assay (Library Screening) |
|---|---|---|---|---|
| 20 | DHK190 | 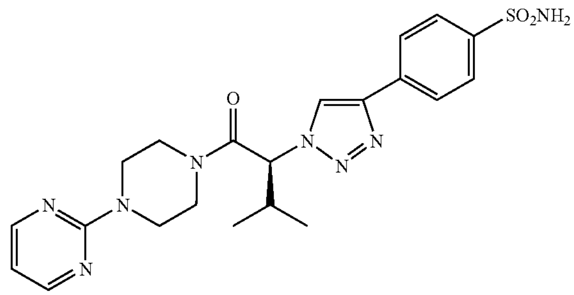 | 470.55 | x |
| 21 | DHK191 | 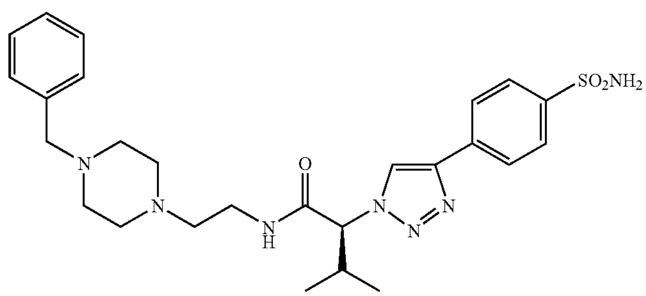 [SMILES: CC(C)[C@@H](C(=O)NCCN1CCN(Cc2ccccc2)CC1)n1cc(-c2ccc(S(N)(=O)=O)cc2)nn1] | 525.67 | x |
| Library 5 | | 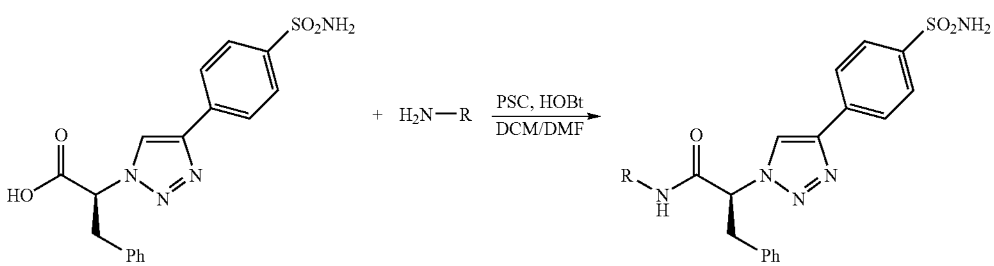 | | |
| 22 | DHK-2-1 | 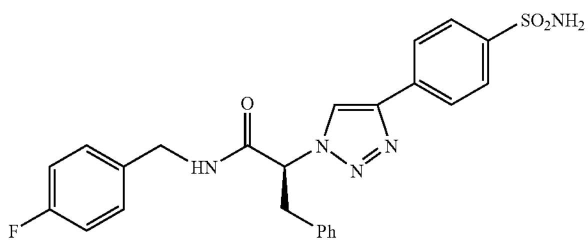 [SMILES: NS(=O)(=O)c1ccc(-c2cn([C@@H](Cc3ccccc3)C(=O)NCc3ccc(F)cc3)nn2)cc1] | 479.53 | x |
| 23 | DHK-2-2 | 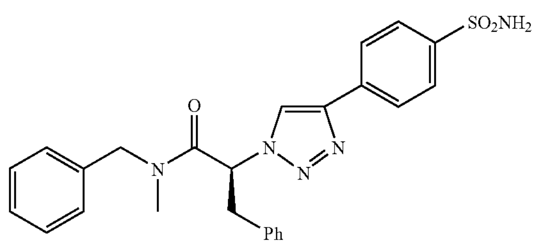 [SMILES: CN(Cc1ccccc1)C(=O)[C@H](Cc1ccccc1)n1cc(-c2ccc(S(N)(=O)=O)cc2)nn1] | 475.56 | x |

TABLE 2-continued
| Entry | Code Name | Chemical Structure | Mol. Wt. | In Vitro Binding Assay (Library Screening) |
|---|---|---|---|---|
| 24 | DHK-2-3 | 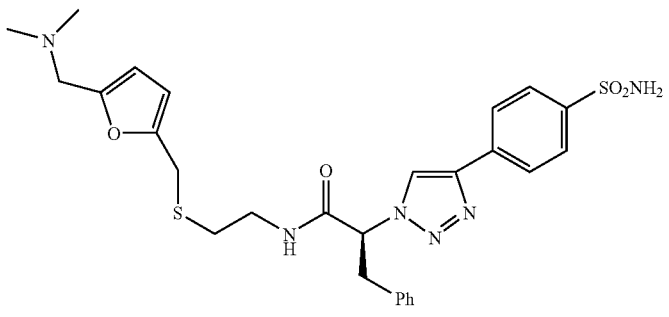 [SMILES: CN(C)Cc1ccc(CSCCNC(=O)[C@H](Cc2ccccc2)n2cc(-c3ccc(S(N)(=O)=O)cc3)nn2)o1] | 568.71 | x |
| 25 | DHK-2-4 | 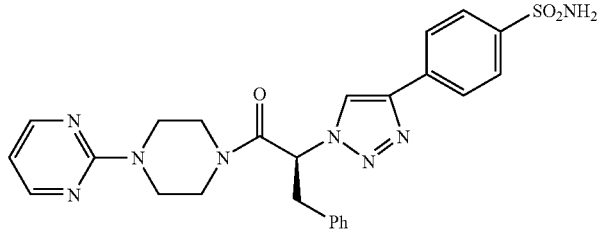 [SMILES: NS(=O)(=O)c1ccc(-c2cn([C@@H](Cc3ccccc3)C(=O)N3CCN(c4ncccn4)CC3)nn2)cc1] | 518.59 | x |
| 26 | DHK-2-5 | 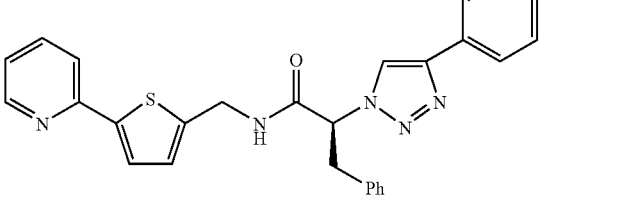 | 544.65 | x |
| 27 | DHK-2-6 | 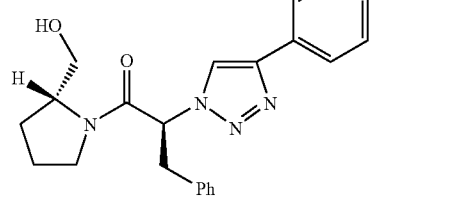 | 455.53 | x |
| 28 | DHK-2-7 | 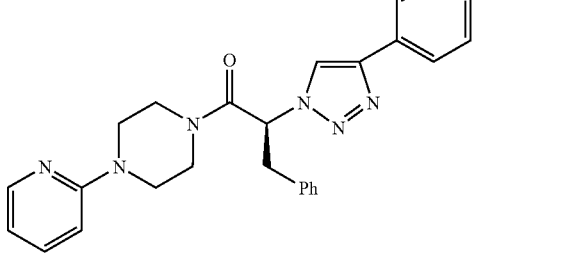 | 517.60 | x |

TABLE 2-continued

| Entry | Code Name | Chemical Structure | Mol. Wt. | In Vitro Binding Assay (Library Screening) |
|---|---|---|---|---|
| 29 | DHK-2-8 | 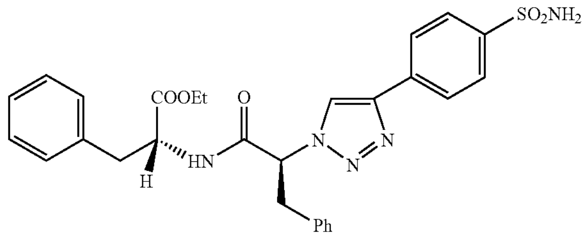 [SMILES: CCOC(=O)[C@@H](Cc1ccccc1)NC(=O)[C@H](Cc1ccccc1)n1cc(-c2ccc(S(N)(=O)=O)cc2)nn1] | 547.63 | x |
| 30 | DHK-2-9 | 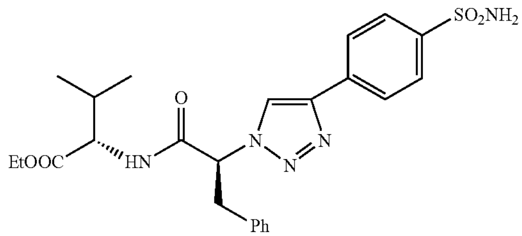 [SMILES: CCOC(=O)[C@@H](NC(=O)[C@H](Cc1ccccc1)n1cc(-c2ccc(S(N)(=O)=O)cc2)nn1)C(C)C] | 499.58 | x |
| 31 | DHK-2-10 | 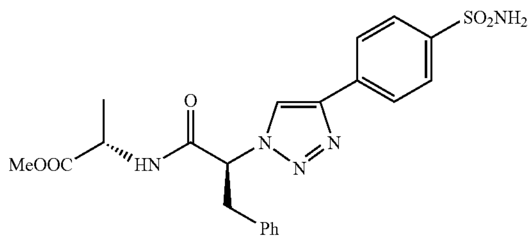 [SMILES: COC(=O)[C@H](C)NC(=O)[C@H](Cc1ccccc1)n1cc(-c2ccc(S(N)(=O)=O)cc2)nn1] | 457.50 | x |
| 32 | DHK-2-11 | 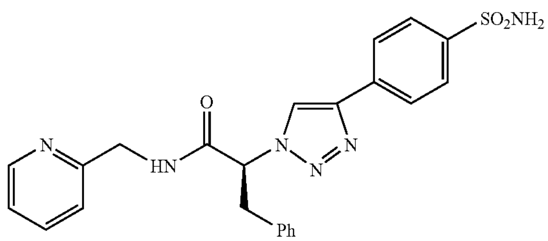 [SMILES: NS(=O)(=O)c1ccc(-c2cn([C@@H](Cc3ccccc3)C(=O)NCc3ccccn3)nn2)cc1] | 462.52 | x |
| 33 | DHK-2-12 | 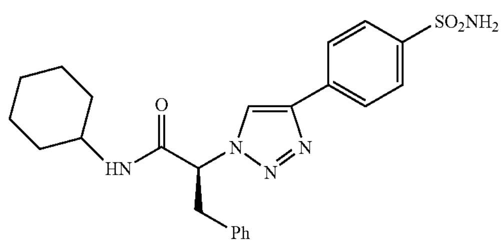 [SMILES: NS(=O)(=O)c1ccc(-c2cn([C@@H](Cc3ccccc3)C(=O)NC3CCCCC3)nn2)cc1] | 453.56 | x |
| 34 | DHK-2-13 | 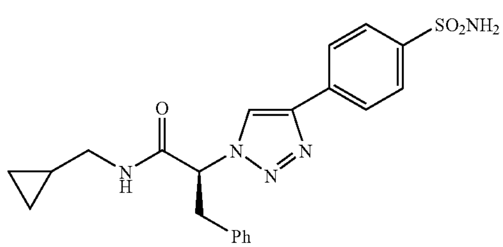 [SMILES: NS(=O)(=O)c1ccc(-c2cn([C@@H](Cc3ccccc3)C(=O)NCC3CC3)nn2)cc1] | 425.50 | x |

TABLE 2-continued

| Entry | Code Name | Chemical Structure | Mol. Wt. | In Vitro Binding Assay (Library Screening) |
|---|---|---|---|---|
| 35 | DHK-2-14 | 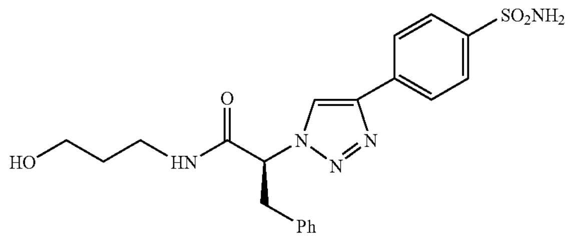 [SMILES: NS(=O)(=O)c1ccc(-c2cn([C@@H](Cc3ccccc3)C(=O)NCCCO)nn2)cc1] | 429.49 | x |
| 36 | DHK-2-15 | 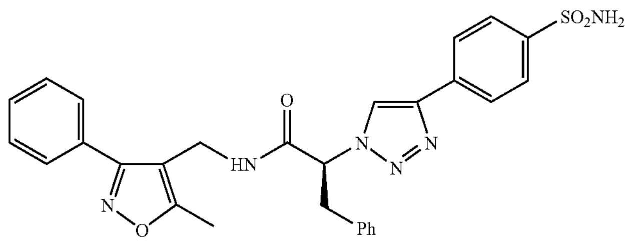 [SMILES: Cc1onc(-c2ccccc2)c1CNC(=O)[C@H](Cc1ccccc1)n1cc(-c2ccc(S(N)(=O)=O)cc2)nn1] | 542.61 | x |
| 37 | DHK-2-16 | 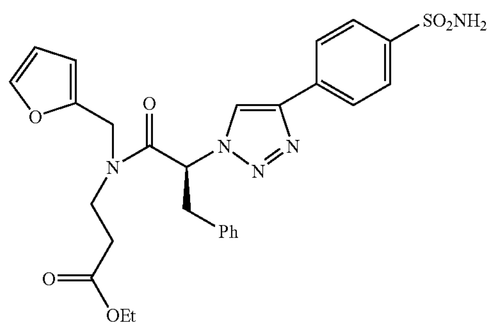 [SMILES: CCOC(=O)CCN(Cc1ccco1)C(=O)[C@H](Cc1ccccc1)n1cc(-c2ccc(S(N)(=O)=O)cc2)nn1] | 551.61 | x |
| 38 | DHK-2-17 | 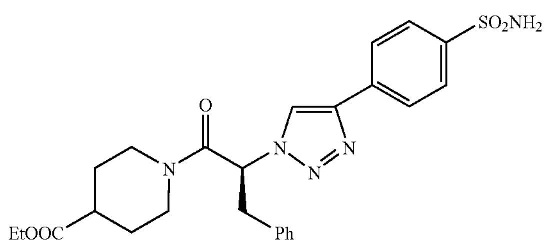 [SMILES: CCOC(=O)C1CCN(C(=O)[C@H](Cc2ccccc2)n2cc(-c3ccc(S(N)(=O)=O)cc3)nn2)CC1] | 511.59 | x |
| 39 | DHK-2-18 | 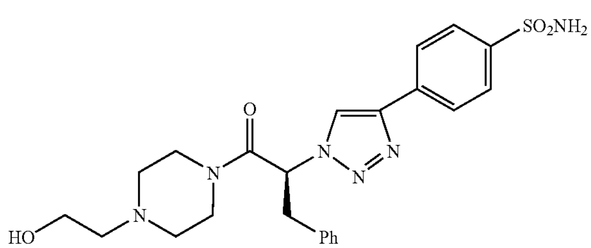 [SMILES: NS(=O)(=O)c1ccc(-c2cn([C@@H](Cc3ccccc3)C(=O)N3CCN(CCO)CC3)nn2)cc1] | 484.57 | x |

TABLE 2-continued

| Entry | Code Name | Chemical Structure | Mol. Wt. | In Vitro Binding Assay (Library Screening) |
|---|---|---|---|---|
| 40 | DHK-2-19 | 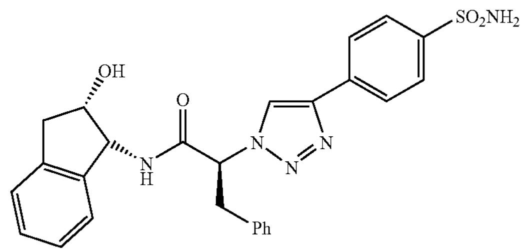 | 503.57 | x |
| 41 | DHK-2-20 | 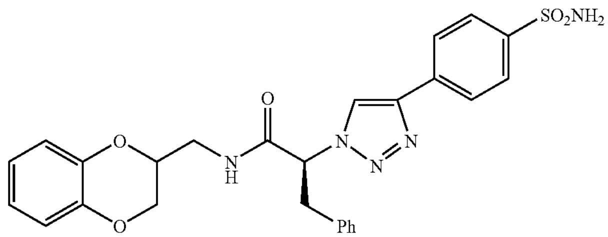 [SMILES: NS(=O)(=O)c1ccc(-c2cn([C@@H](Cc3ccccc3)C(=O)NCC3COc4ccccc4O3)nn2)cc1] | 519.57 | x |
| 42 | DHK-2-21 | 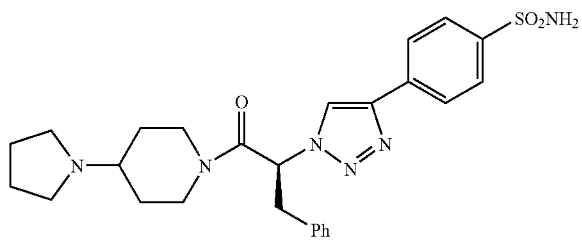 [SMILES: NS(=O)(=O)c1ccc(-c2cn([C@@H](Cc3ccccc3)C(=O)N3CCC(N4CCCC4)CC3)nn2)cc1] | 508.64 | x |
| 43 | DHK-2-22 | 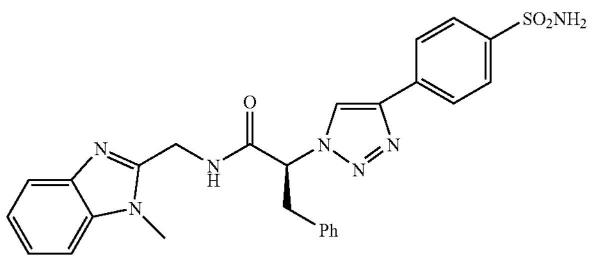 [SMILES: Cn1c(CNC(=O)[C@H](Cc2ccccc2)n2cc(-c3ccc(S(N)(=O)=O)cc3)nn2)nc2ccccc21] | 515.59 | x |
| 44 | DHK-2-23 | 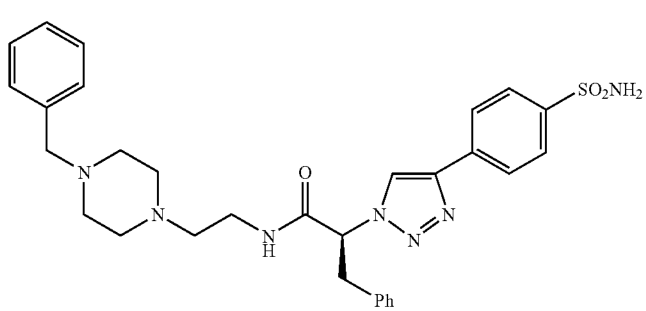 [SMILES: NS(=O)(=O)c1ccc(-c2cn([C@@H](Cc3ccccc3)C(=O)NCCN3CCN(Cc4ccccc4)CC3)nn2)cc1] | 573.71 | x |

TABLE 2-continued
| Entry | Code Name | Chemical Structure | Mol. Wt. | In Vitro Binding Assay (Library Screening) |
|---|---|---|---|---|
| Library 6 | | 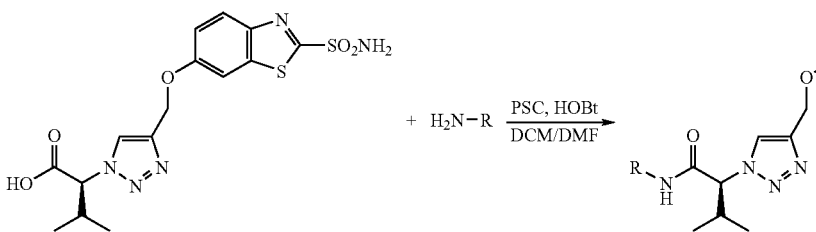 | | |
| 45 | DHK-2-24 | 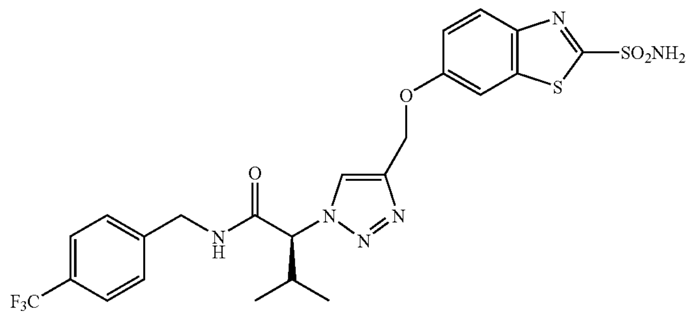 [SMILES: CC(C)[C@@H](C(=O)NCc1ccc(C(F)(F)F)cc1)n1cc(COc2ccc3nc(S(N)(=O)=O)sc3c2)nn1] | 568.59 | ✓✓ |
| 46 | DHK-2-25 | 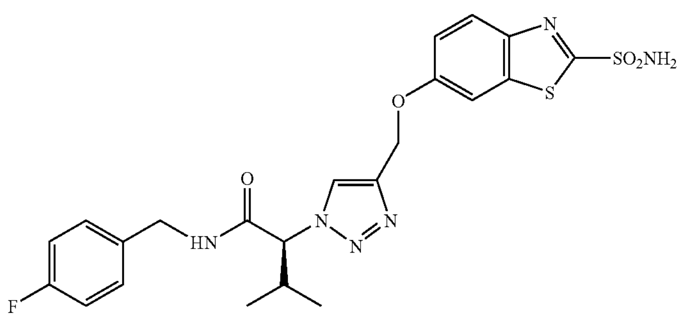 [SMILES: CC(C)[C@@H](C(=O)NCc1ccc(F)cc1)n1cc(COc2ccc3nc(S(N)(=O)=O)sc3c2)nn1] | 518.58 | x |
| 47 | DHK-2-26 | 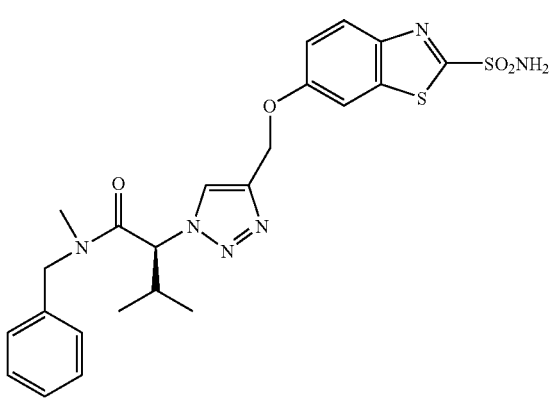 [SMILES: CC(C)[C@@H](C(=O)N(C)Cc1ccccc1)n1cc(COc2ccc3nc(S(N)(=O)=O)sc3c2)nn1] | 514.62 | x |

TABLE 2-continued
| Entry | Code Name | Chemical Structure | Mol. Wt. | In Vitro Binding Assay (Library Screening) |
|---|---|---|---|---|
| 48 | DHK-2-27 | 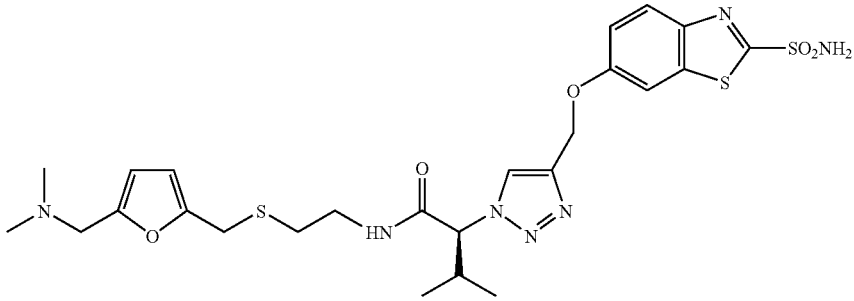 [SMILES: CC(C)[C@@H](C(=O)NCCSCc1ccc(CN(C)C)o1)n1cc(COc2ccc3nc(S(N)(=O)=O)sc3c2)nn1] | 607.77 | x |
| 49 | DHK-2-28 | 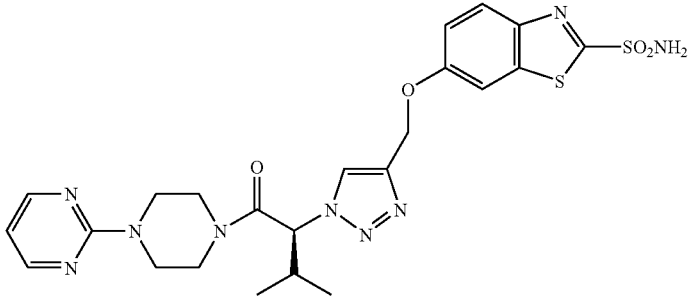 [SMILES: CC(C)[C@@H](C(=O)N1CCN(c2ncccn2)CC1)n1cc(COc2ccc3nc(S(N)(=O)=O)sc3c2)nn1] | 557.65 | x |
| 50 | DHK-2-29 | 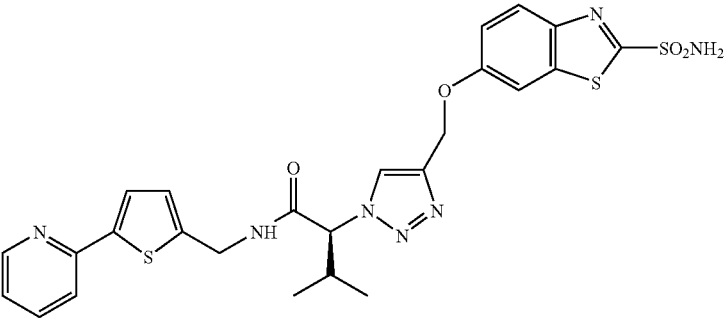 [SMILES: CC(C)[C@@H](C(=O)NCc1ccc(-c2ccccn2)s1)n1cc(COc2ccc3nc(S(N)(=O)=O)sc3c2)nn1] | 583.71 | x |
| 51 | DHK-2-30 | 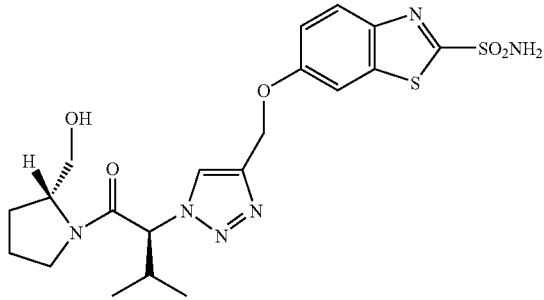 [SMILES: CC(C)[C@@H](C(=O)N1CCC[C@@H]1CO)n1cc(COc2ccc3nc(S(N)(=O)=O)sc3c2)nn1] | 494.59 | x |

TABLE 2-continued
| Entry | Code Name | Chemical Structure | Mol. Wt. | In Vitro Binding Assay (Library Screening) |
|---|---|---|---|---|
| 52 | DHK-2-31 | 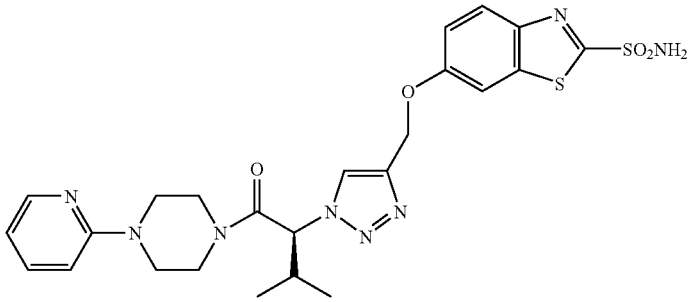 [SMILES: CC(C)[C@@H](C(=O)N1CCN(c2ccccn2)CC1)n1cc(COc2ccc3nc(S(N)(=O)=O)sc3c2)nn1] | 556.66 | x |
| 53 | DHK-2-32 | 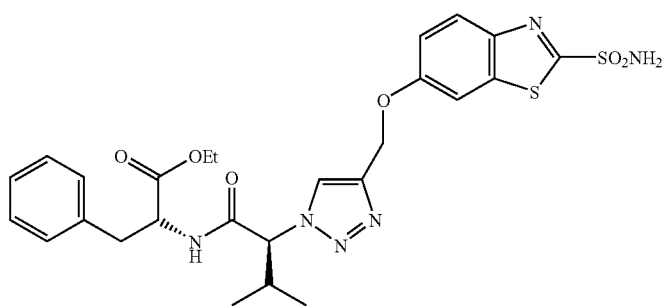 | 586.68 | x |
| 54 | DHK-2-33 | 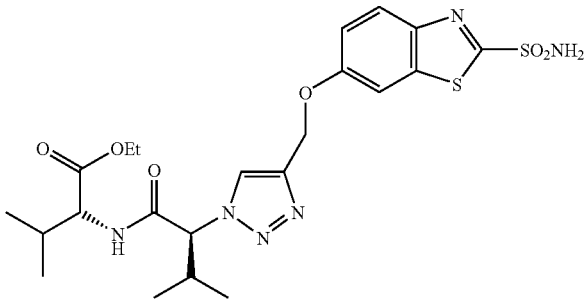 | 538.64 | x |
| 55 | DHK-2-34 | 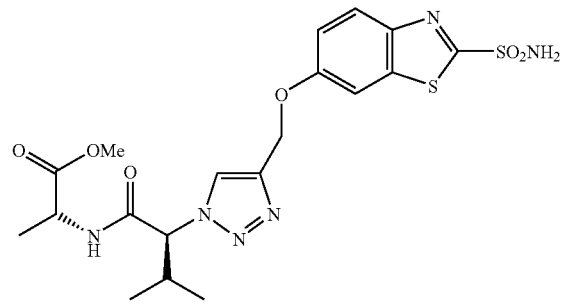 | 496.56 | x |
| 56 | DHK-2-35 | 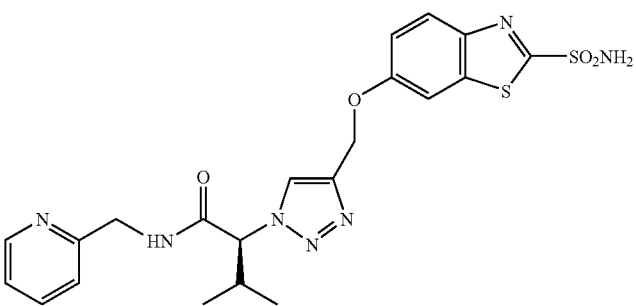 [SMILES: CC(C)[C@@H](C(=O)NCc1ccccn1)n1cc(COc2ccc3nc(S(N)(=O)=O)sc3c2)nn1] | 501.58 | x |

TABLE 2-continued

| Entry | Code Name | Chemical Structure | Mol. Wt. | In Vitro Binding Assay (Library Screening) |
|---|---|---|---|---|
| 57 | DHK-2-36 | 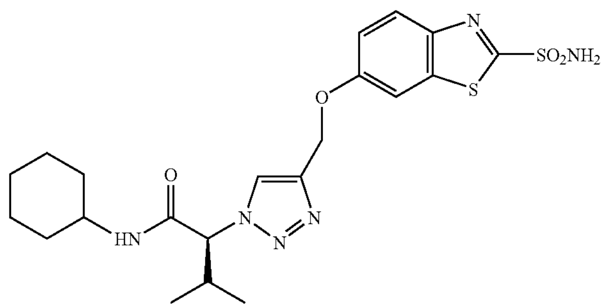 [SMILES: CC(C)[C@@H](C(=O)NC1CCCCC1)n1cc(COc2ccc3nc(S(N)(=O)=O)sc3c2)nn1] | 492.61 | x |
| 58 | DHK-2-37 | 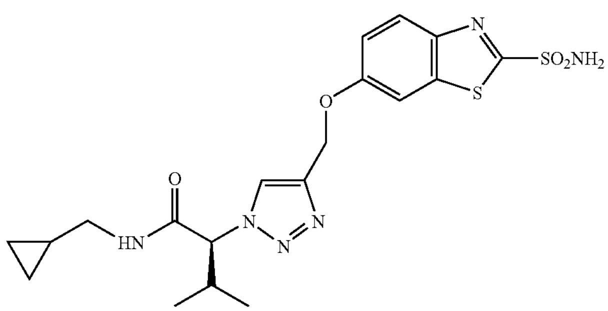 [SMILES: CC(C)[C@@H](C(=O)NCC1CC1)n1cc(COc2ccc3nc(S(N)(=O)=O)sc3c2)nn1] | 464.56 | x |
| 59 | DHK-2-38 | 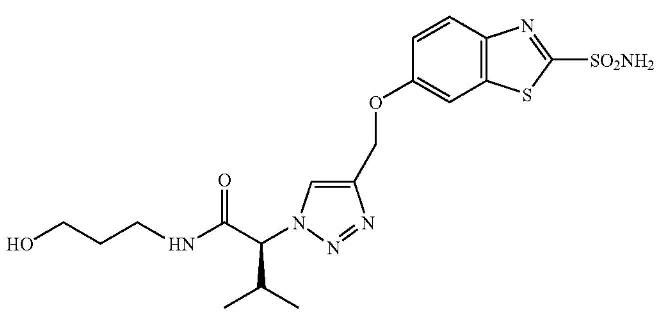 [SMILES: CC(C)[C@@H](C(=O)NCCCO)n1cc(COc2ccc3nc(S(N)(=O)=O)sc3c2)nn1] | 468.55 | x |
| 60 | DHK-2-39 | 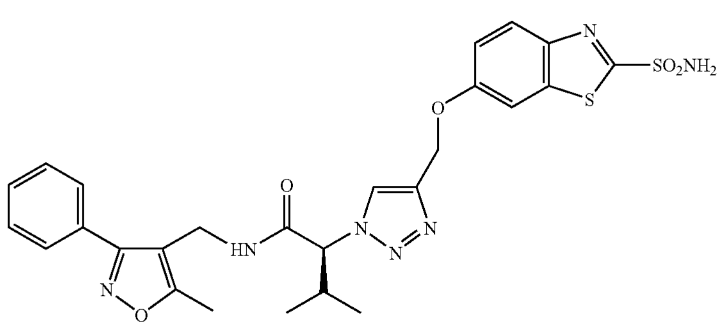 [SMILES: Cc1onc(-c2ccccc2)c1CNC(=O)[C@H](C(C)C)n1cc(COc2ccc3nc(S(N)(=O)=O)sc3c2)nn1] | 581.67 | x |

TABLE 2-continued
| Entry | Code Name | Chemical Structure | Mol. Wt. | In Vitro Binding Assay (Library Screening) |
|---|---|---|---|---|
| 61 | DHK-2-41 | 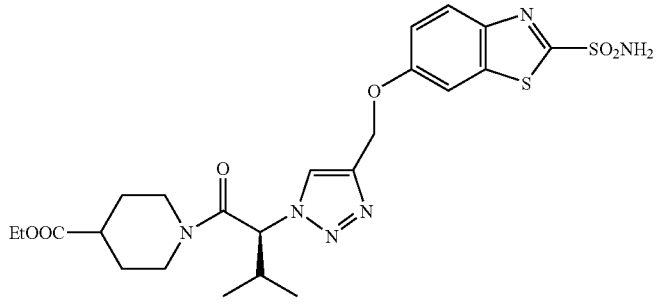 [SMILES: CCOC(=O)C1CCN(C(=O)[C@H](C(C)C)n2cc(COc3ccc4nc(S(N)(=O)=O)sc4c3)nn2)CC1] | 550.65 | ✓ |
| 62 | DHK-2-42 | 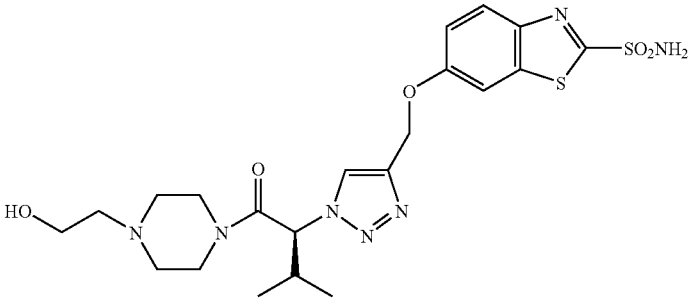 [SMILES: CC(C)[C@@H](C(=O)N1CCN(CCO)CC1)n1cc(COc2ccc3nc(S(N)(=O)=O)sc3c2)nn1] | 523.63 | x |
| 63 | DHK-2-43 | 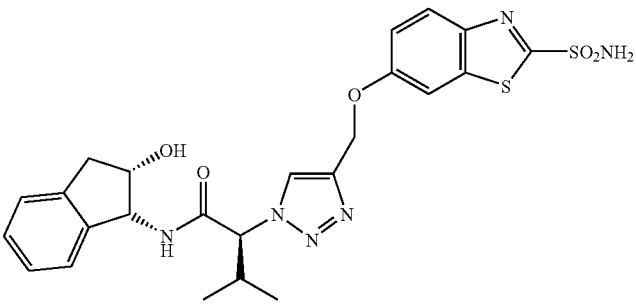 | 542.63 | x |
| 64 | DHK-2-44 | 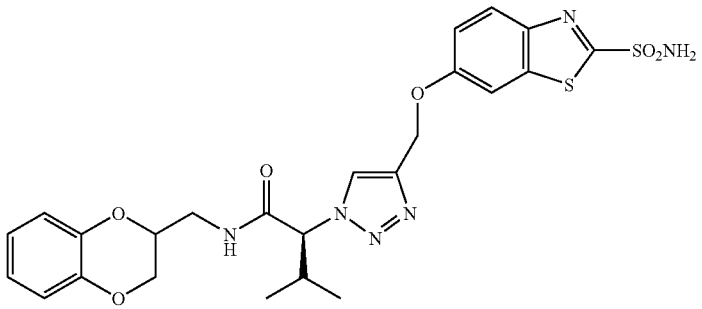 [SMILES: CC(C)[C@@H](C(=O)NCC1COc2ccccc2O1)n1cc(COc2ccc3nc(S(N)(=O)=O)sc3c2)nn1] | 558.63 | ✓ |

TABLE 2-continued

| Entry | Code Name | Chemical Structure | Mol. Wt. | In Vitro Binding Assay (Library Screening) |
|---|---|---|---|---|
| 65 | DHK-2-45 | 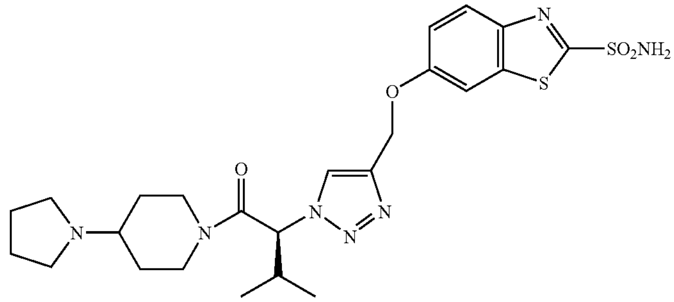 [SMILES: CC(C)[C@@H](C(=O)N1CCC(N2CCCC2)CC1)n1cc(COc2ccc3nc(S(N)(=O)=O)sc3c2)nn1] | 547.69 | x |
| 66 | DHK-2-47 | 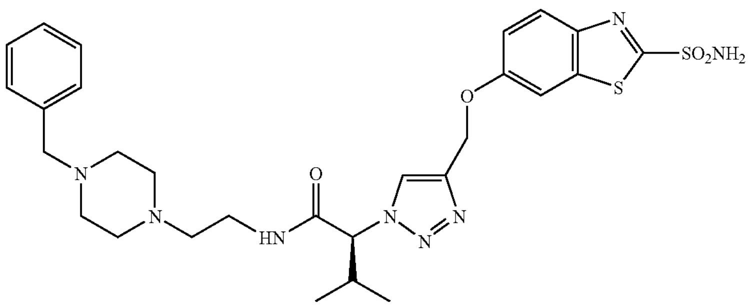 [SMILES: CC(C)[C@@H](C(=O)NCCN1CCN(Cc2ccccc2)CC1)n1cc(COc2ccc3nc(S(N)(=O)=O)sc3c2)nn1] | 612.77 | x |
| 67 | DHK-2-48 | 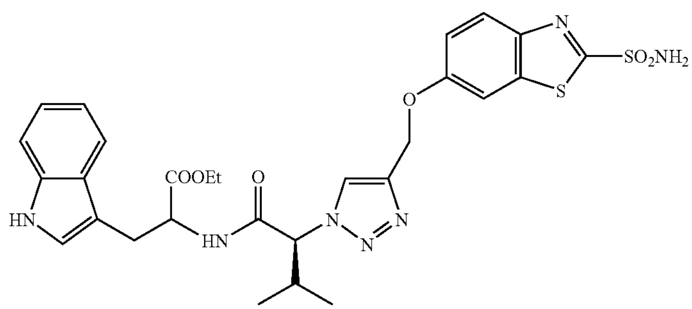 [SMILES: CCOC(=O)C(Cc1c[nH]c2ccccc12)NC(=O)[C@H](C(C)C)n1cc(COc2ccc3nc(S(N)(=O)=O)sc3c2)nn1] | 625.72 | x |
| Library 7 | | | | |
| 68 | DHK-2-51 | | 616.63 | ✓ |

TABLE 2-continued
| Entry | Code Name | Chemical Structure | Mol. Wt. | In Vitro Binding Assay (Library Screening) |
|---|---|---|---|---|
| 69 | DHK-2-52 | 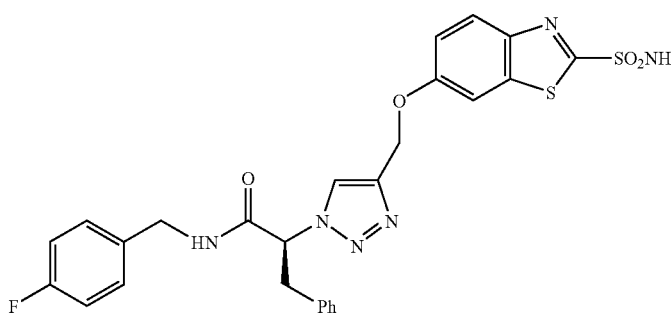 | 566.63 | x |
| 70 | DHK-2-53 | 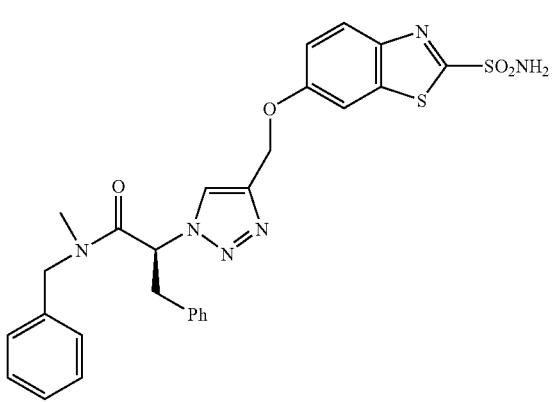 [SMILES: CN(Cc1ccccc1)C(=O)[C@H](Cc1ccccc1)n1cc(COc2ccc3nc(S(N)(=O)=O)sc3c2)nn1] | 562.66 | x |
| 71 | DHK-2-54 | 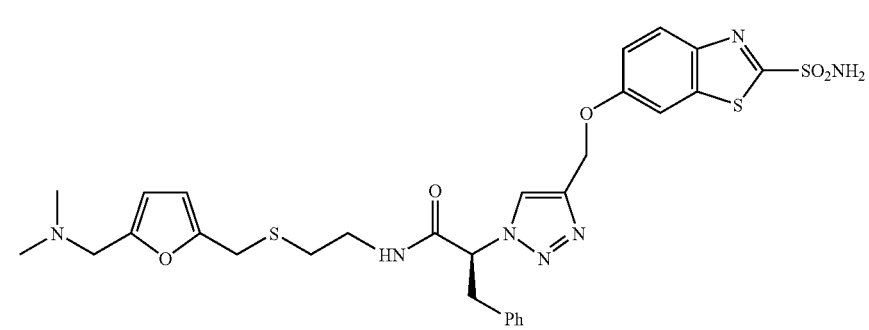 [SMILES: CN(C)Cc1ccc(CSCCNC(=O)[C@H](Cc2ccccc2)n2cc(COc3ccc4nc(S(N)(=O)=O)sc4c3)nn2)o1] | 655.81 | x |
| 72 | DHK-2-55 | 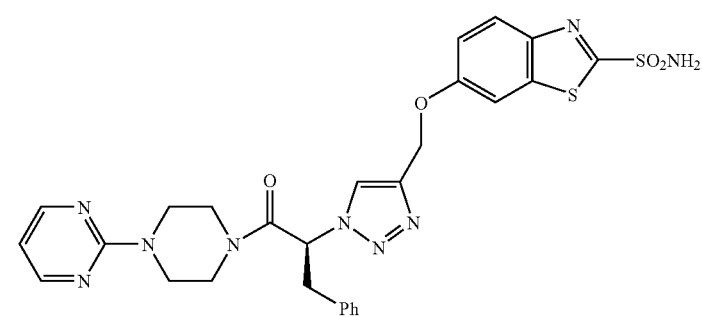 [SMILES: NS(=O)(=O)c1nc2ccc(OCc3cn([C@@H](Cc4ccccc4)C(=O)N4CCN(c5ncccn5)CC4)nn3)cc2s1] | 605.69 | x |

TABLE 2-continued
| Entry | Code Name | Chemical Structure | Mol. Wt. | In Vitro Binding Assay (Library Screening) |
|---|---|---|---|---|
| 73 | DHK-2-56 | 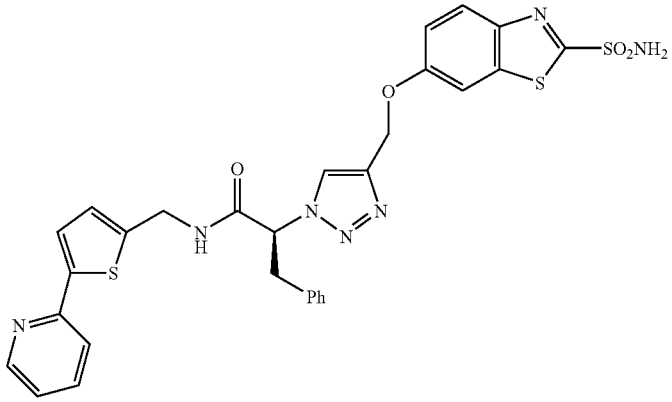 [SMILES: NS(=O)(=O)c1nc2ccc(OCc3cn([C@@H](Cc4ccccc4)C(=O)NCc4ccc(-c5ccccn5)s4)nn3)cc2s1] | 631.75 | x |
| 74 | DHK-2-57 | 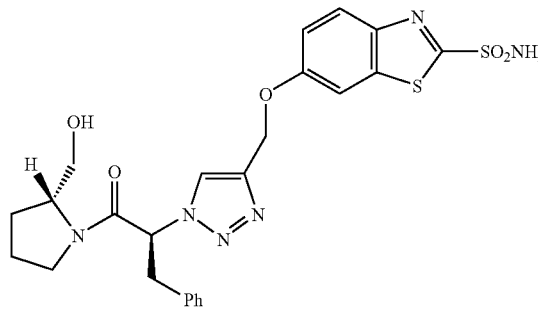 | 542.63 | x |
| 75 | DHK-2-58 | 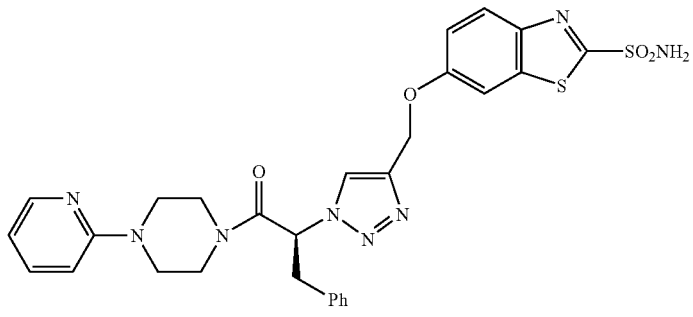 [SMILES: NS(=O)(=O)c1nc2ccc(OCc3cn([C@@H](Cc4ccccc4)C(=O)N4CCN(c5ccccn5)CC4)nn3)cc2s1] | 604.70 | x |
| 76 | DHK-2-59 | 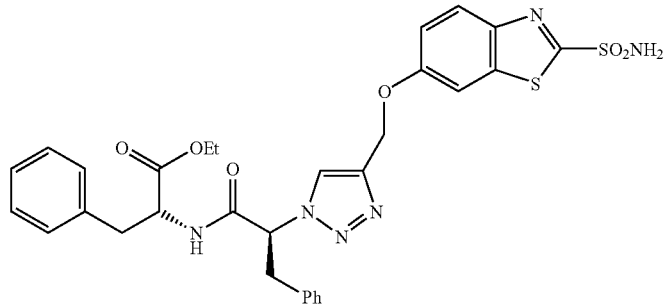 | 634.73 | x |

TABLE 2-continued

| Entry | Code Name | Chemical Structure | Mol. Wt. | In Vitro Binding Assay (Library Screening) |
|---|---|---|---|---|
| 77 | DHK-2-60 | 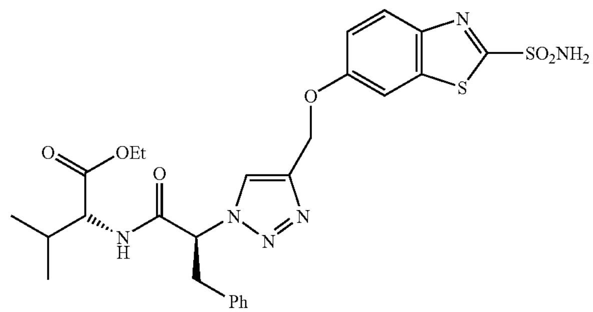 | 586.68 | x |
| 78 | DHK-2-61 | 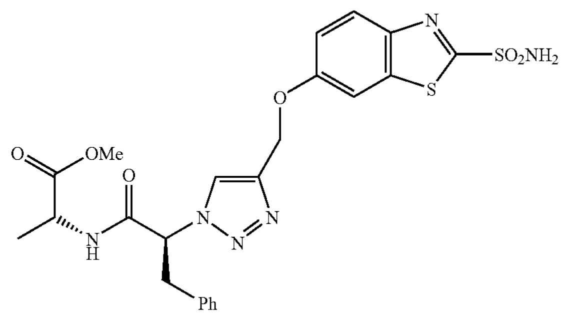 | 544.60 | ✓ |
| 79 | DHK-2-62 | 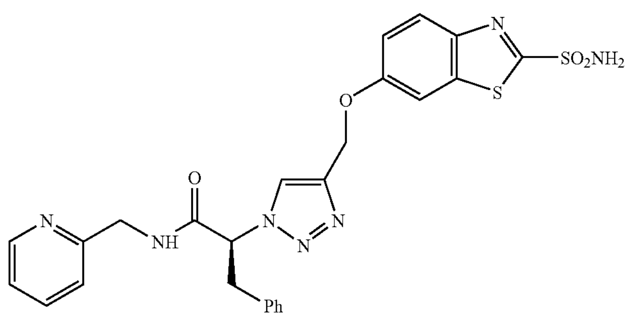 [SMILES: NS(=O)(=O)c1nc2ccc(OCc3cn([C@@H](Cc4ccccc4)C(=O)NCc4ccccn4)nn3)cc2s1] | 549.62 | x |
| 80 | DHK-2-63 | 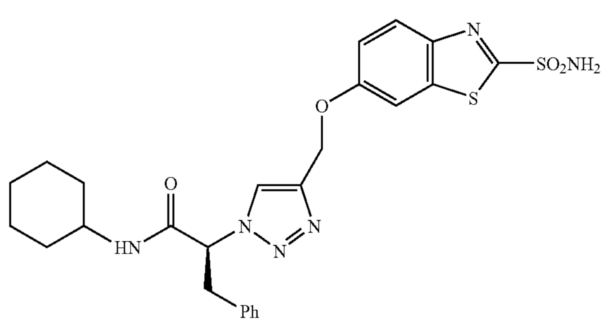 [SMILES: NS(=O)(=O)c1nc2ccc(OCc3cn([C@@H](Cc4ccccc4)C(=O)NC4CCCCC4)nn3)cc2s1] | 540.66 | x |

TABLE 2-continued

| Entry | Code Name | Chemical Structure | Mol. Wt. | In Vitro Binding Assay (Library Screening) |
|---|---|---|---|---|
| 81 | DHK-2-64 | 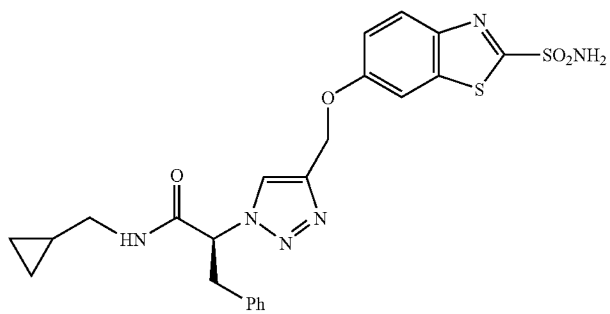 [SMILES: NS(=O)(=O)c1nc2ccc(OCc3cn([C@@H](Cc4ccccc4)C(=O)NCC4CC4)nn3)cc2s1] | 512.60 | x |
| 82 | DHK-2-65 | 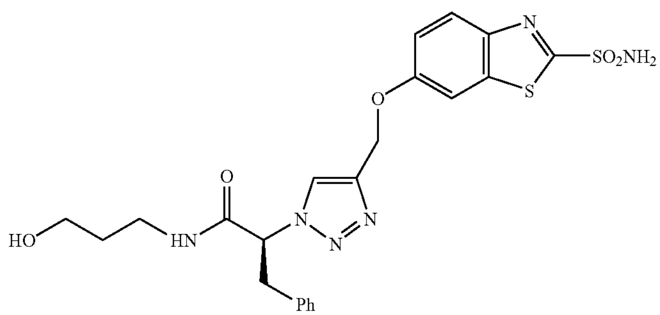 [SMILES: NS(=O)(=O)c1nc2ccc(OCc3cn([C@@H](Cc4ccccc4)C(=O)NCCCO)nn3)cc2s1] | 516.59 | x |
| 83 | DHK-2-66 | 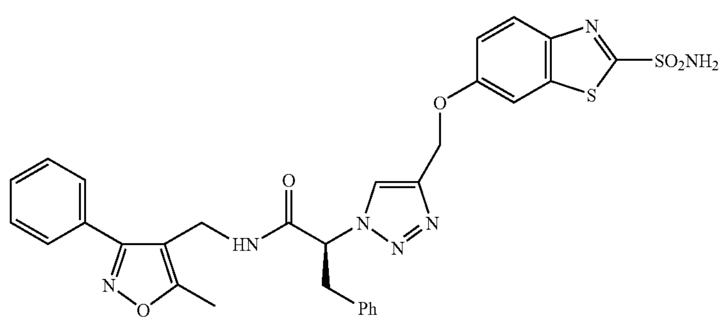 [SMILES: Cc1onc(-c2ccccc2)c1CNC(=O)[C@H](Cc1ccccc1)n1cc(COc2ccc3nc(S(N)(=O)=O)sc3c2)nn1] | 629.71 | ✓✓ |
| 84 | DHK-2-67 | 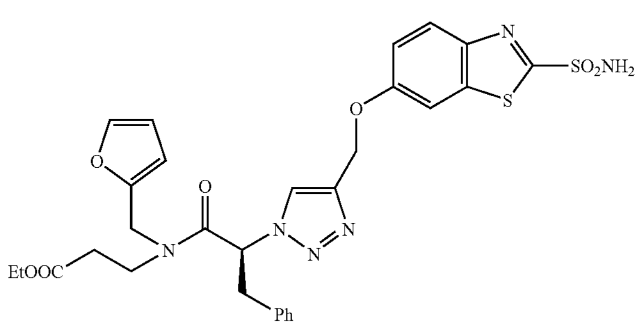 [SMILES: CCOC(=O)CCN(Cc1ccco1)C(=O)[C@H](Cc1ccccc1)n1cc(COc2ccc3nc(S(N)(=O)=O)sc3c2)nn1] | 638.71 | x |

TABLE 2-continued

| Entry | Code Name | Chemical Structure | Mol. Wt. | In Vitro Binding Assay (Library Screening) |
|---|---|---|---|---|
| 85 | DHK-2-68 | 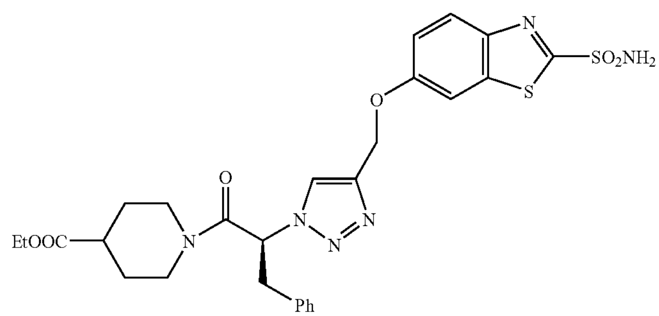 [SMILES: CCOC(=O)C1CCN(C(=O)[C@H](Cc2ccccc2)n2cc(COc3ccc4nc(S(N)(=O)=O)sc4c3)nn2)CC1] | 598.69 | ✓ |
| 86 | DHK-2-69 | 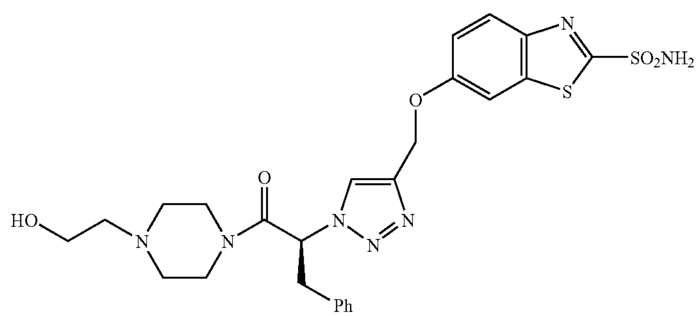 [SMILES: NS(=O)(=O)c1nc2ccc(OCc3cn([C@@H](Cc4ccccc4)C(=O)N4CCN(CCO)CC4)nn3)cc2s1] | 571.67 | x |
| 87 | DHK-2-70 | 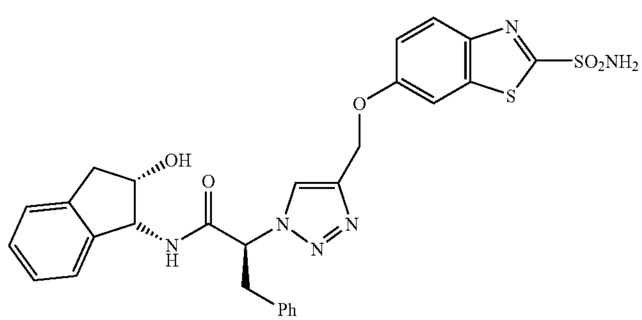 | 590.67 | x |
| 88 | DHK-2-71 | 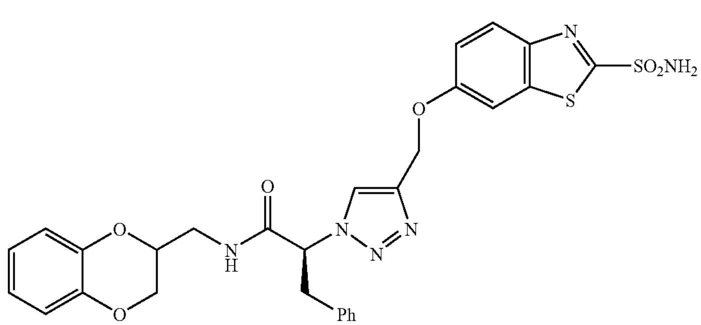 [SMILES: NS(=O)(=O)c1nc2ccc(OCc3cn([C@@H](Cc4ccccc4)C(=O)NCC4COc5ccccc5O4)nn3)cc2s1] | 606.67 | ✓ |

TABLE 2-continued
| Entry | Code Name | Chemical Structure | Mol. Wt. | In Vitro Binding Assay (Library Screening) |
|---|---|---|---|---|
| 89 | DHK-2-72 | 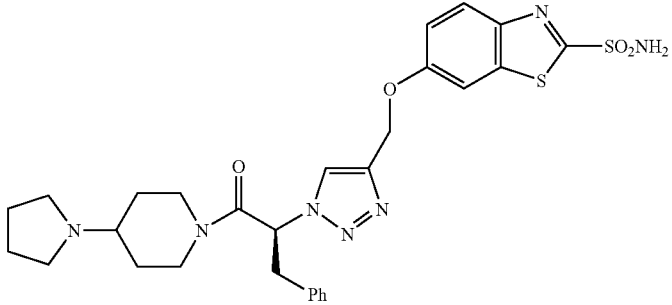 [SMILES: NS(=O)(=O)c1nc2ccc(OCc3cn([C@@H](Cc4ccccc4)C(=O)N4CCC(N5CCCC5)CC4)nn3)cc2s1] | 595.74 | x |
| 90 | DHK-2-73 | 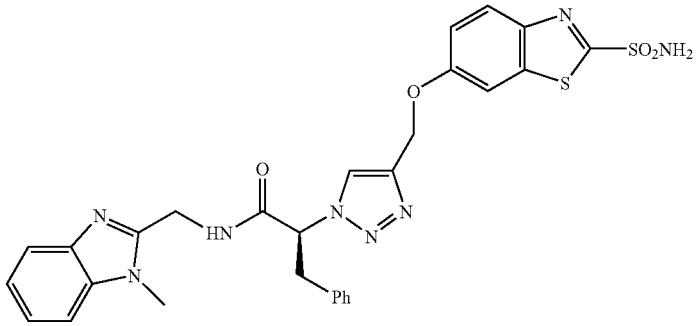 [SMILES: Cn1c(CNC(=O)[C@H](Cc2ccccc2)n2cc(COc3ccc4nc(S(N)(=O)=O)sc4c3)nn2)nc2ccccc21] | 602.69 | x |
| 91 | DHK-2-74 | 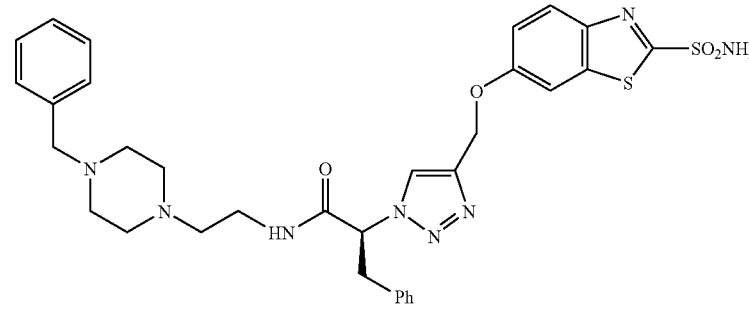 | 660.81 | x |
| 92 | DHK-2-75 | 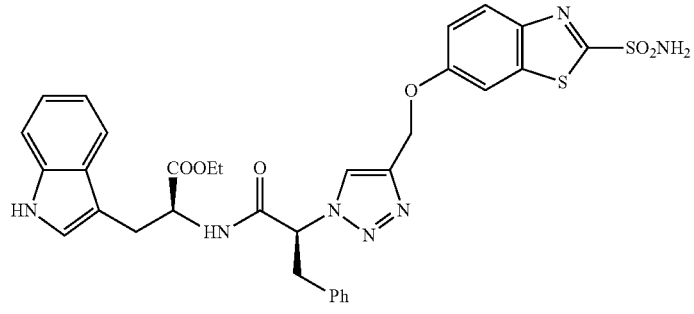 [SMILES: CCOC(=O)[C@H](Cc1c[nH]c2ccccc12)NC(=O)[C@H](Cc1ccccc1)n1cc(COc2ccc3nc(S(N)(=O)=O)sc3c2)nn1] | 673.76 | x |
[a] Inhibition % is less than 40%.

TABLE 3

| Name | Chemical Structure | $K_d$ (nM) CA-IX |
|---|---|---|
| DHK7 | 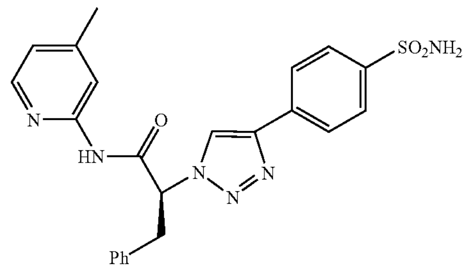 [SMILES: Cc1ccnc(NC(=O)[C@H](Cc2ccccc2)n2cc(-c3ccc(S(N)(=O)=O)cc3)nn2)c1] | 17 |
| DHK19 | 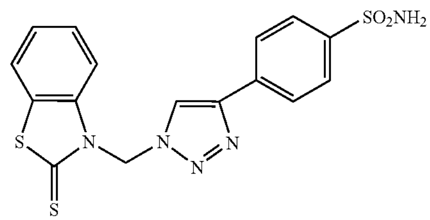 [SMILES: NS(=O)(=O)c1ccc(-c2cn(Cn3c(=S)sc4ccccc43)nn2)cc1] | 14 |
| DHK25 | 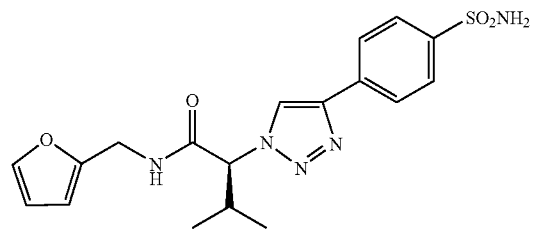 [SMILES: CC(C)[C@@H](C(=O)NCc1ccco1)n1cc(-c2ccc(S(N)(=O)=O)cc2)nn1] | 5<br>CLogP: 1.3936 |
| DHK29 | 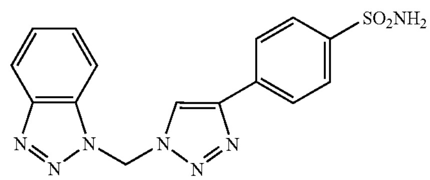 [SMILES: NS(=O)(=O)c1ccc(-c2cn(Cn3nnc4ccccc43)nn2)cc1] | 20 |
| DHK113 | 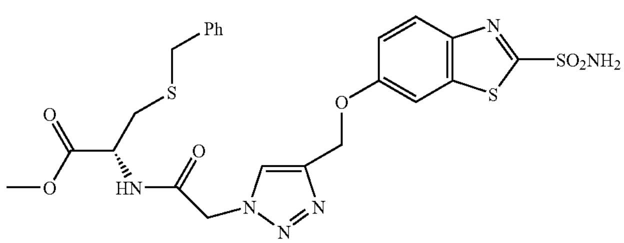 [SMILES: COC(=O)[C@H](CSCc1ccccc1)NC(=O)Cn1cc(COc2ccc3nc(S(N)(=O)=O)sc3c2)nn1] | 10 |
| DHK117 | 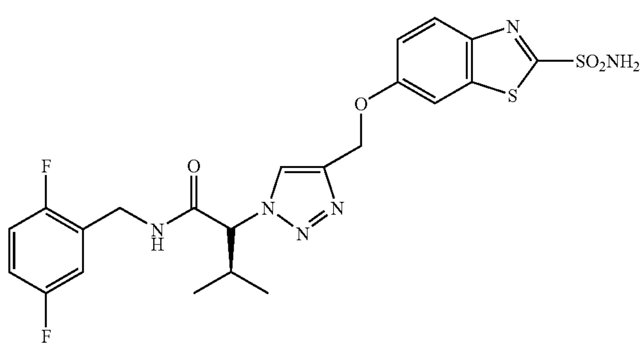 | 14.1 |

TABLE 3-continued

| Name | Chemical Structure | $K_d$ (nM) CA-IX |
|---|---|---|
| DHK121 | 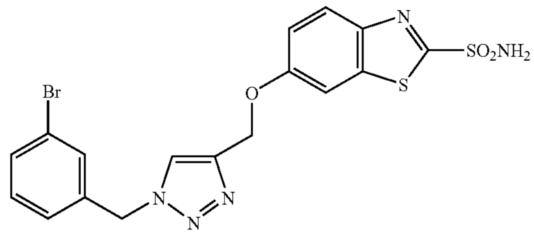 [SMILES: NS(=O)(=O)c1nc2ccc(OCc3cn(Cc4cccc(Br)c4)nn3)cc2s1] | 25 |
| DHK123 | 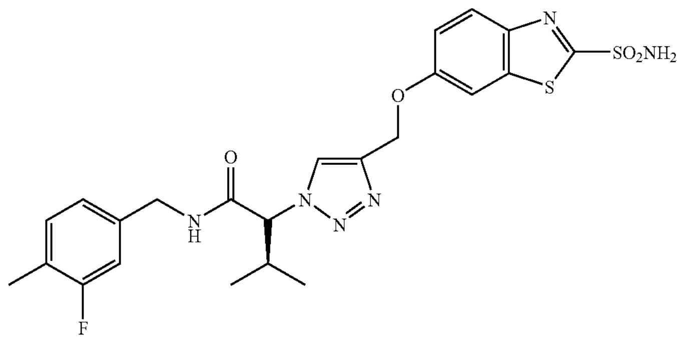 | 12.5 |
| DHK125 | 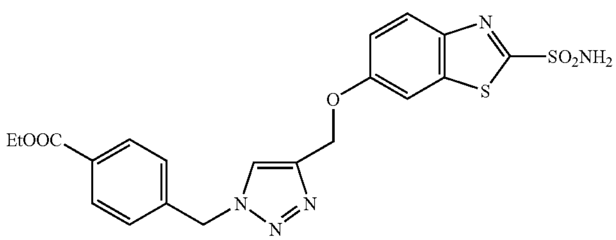 [SMILES: CCOC(=O)c1ccc(Cn2cc(COc3ccc4nc(S(N)(=O)=O)sc4c3)nn2)cc1] | 16.7 |
| DHK127 | 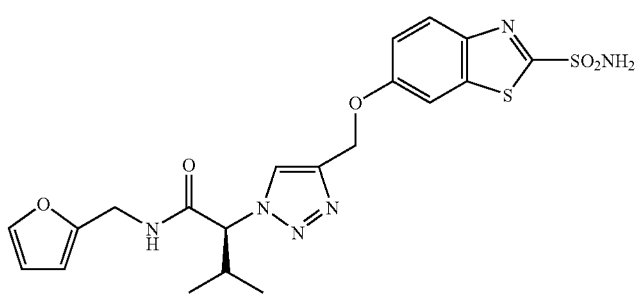 [SMILES: CC(C)[C@@H](C(=O)NCc1ccco1)n1cc(COc2ccc3nc(S(N)(=O)=O)sc3c2)nn1] | 25 |
| DHK128 | 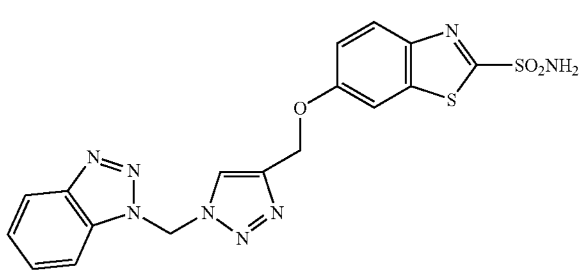 [SMILES: NS(=O)(=O)c1nc2ccc(OCc3cn(Cn4nnc5ccccc54)nn3)cc2s1] | 12.5 |

TABLE 3-continued

| Name | Chemical Structure | $K_d$ (nM) CA-IX |
|---|---|---|
| DHK159 | 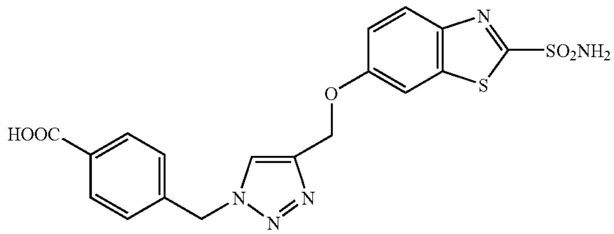 [SMILES: NS(=O)(=O)c1nc2ccc(OCc3cn(Cc4ccc(C(=O)O)cc4)nn3)cc2s1] | 14.1 |
| DHK160 | 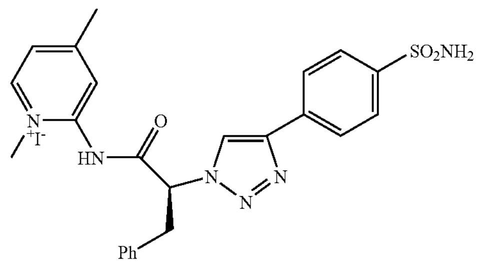 | 20 |
| DHK161 | 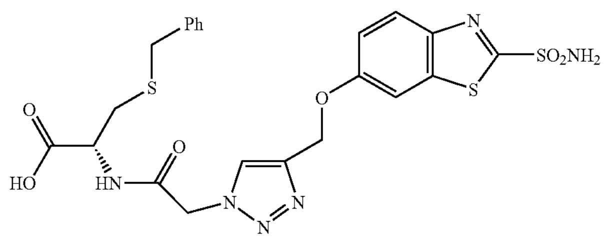 [SMILES: NS(=O)(=O)c1nc2ccc(OCc3cn(CC(=O)N[C@@H](CSCc4ccccc4)C(=O)O)nn3)cc2s1] | 10 |
| DHK2-24 | (DHK-2-24) | 1<br>CLogP: 3.85914 |
| DHK2-44 | (DHK-2-44) | 5<br>CLogP: 3.22094 |

TABLE 3-continued
| Name | Chemical Structure | $K_d$ (nM) CA-IX |
|---|---|---|
| DHK2-51 | 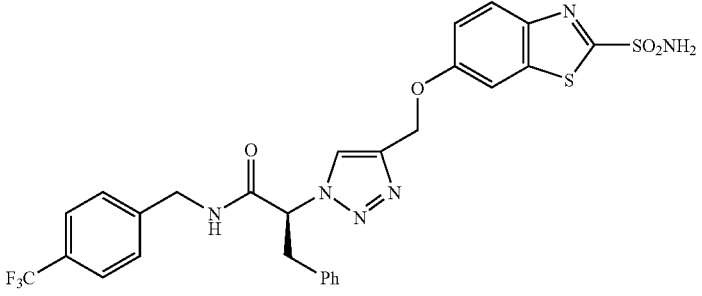 DHK-2-51 | 2.5 |
| DHK2-66 | 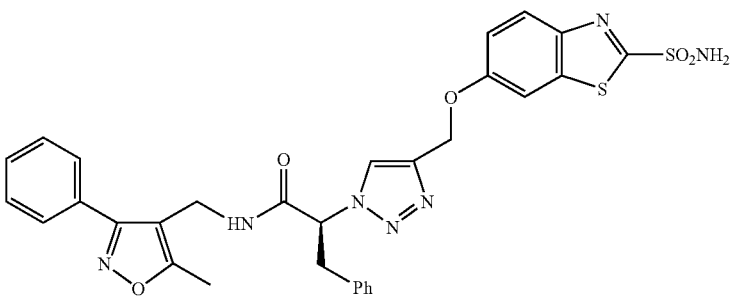 DHK-2-66 | 2 CLogP: 3.69214 |
| DHK2-71 | 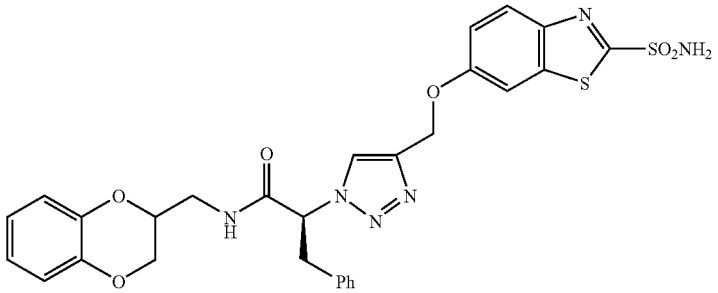 DHK-2-71 | 2.5 CLogP: 3.71094 |
| DHK2-68 | 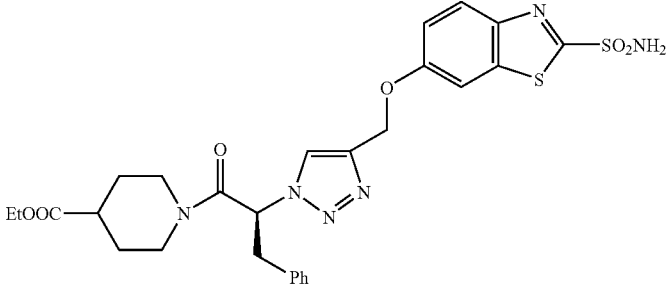 DHK-2-68 | 3.4 CLogP: 1.78814 |

TABLE 3-continued
| Name | Chemical Structure | $K_d$ (nM) CA-IX |
|---|---|---|
| DHK2-41 | 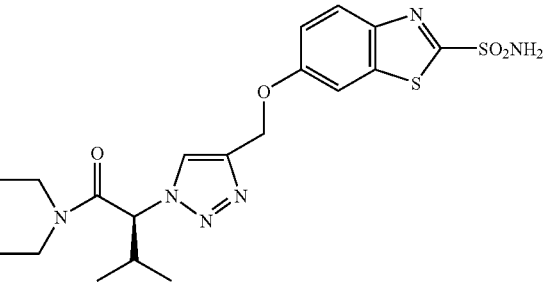 DHK-2-41 | 5 CLogP: 1.29814 |
| VM2-36 | 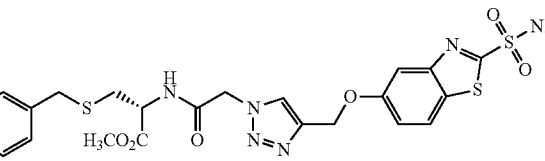 | 10 |
| VM2-41 | 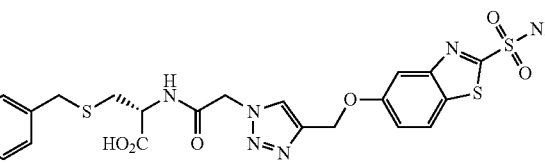 | 5 CLogP: 2.74794 |
| DHK2-84 | 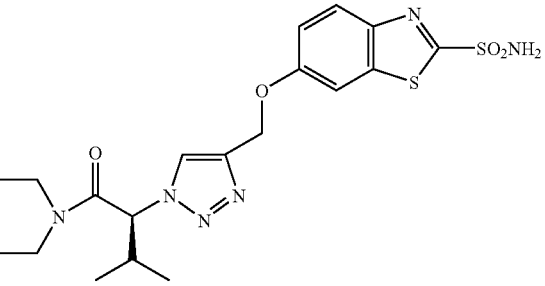 DHK-2-84 | 10 |
| DHK2-94 | 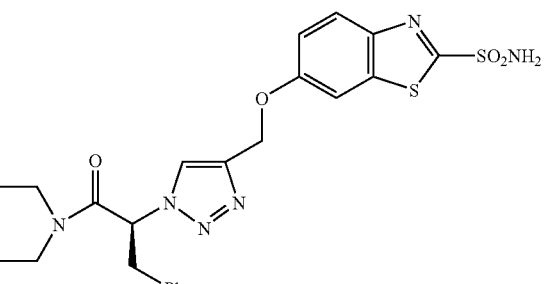 DHK-2-94 | 10 |
| DHK2-95 | 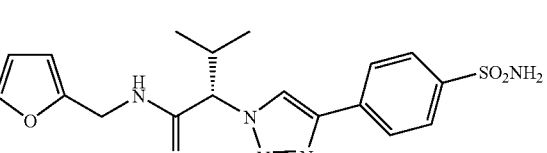 | 25 |

TABLE 3-continued
| Name | Chemical Structure | $K_d$ (nM) CA-IX |
|---|---|---|
| DHK2-97 | 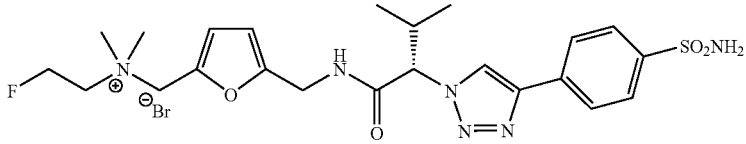 [SMILES: CC(C)[C@@H](C(=O)NCc1ccc(C[N+](C)(C)CCF)o1)n1cc(-c2ccc(S(N)(=O)=O)cc2)nn1 ; [Br-]] | 34 |
| DHK2-118 | 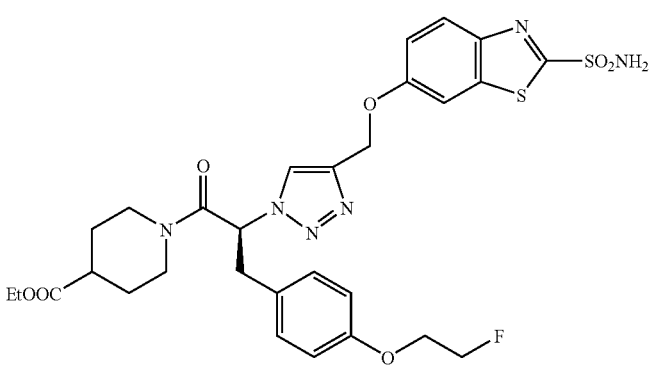 [SMILES: CCOC(=O)C1CCN(C(=O)[C@H](Cc2ccc(OCCF)cc2)n2cc(COc3ccc4nc(S(N)(=O)=O)sc4c3)nn2)CC1] | 5<br>CLogP: 1.95914 |
| DHK2-120 | 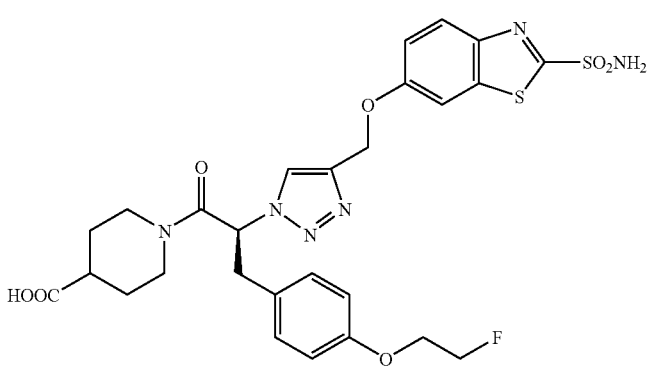 [SMILES: NS(=O)(=O)c1nc2ccc(OCc3cn([C@@H](Cc4ccc(OCCF)cc4)C(=O)N4CCC(C(=O)O)CC4)nn3)cc2s1] | 5<br>CLogP: 1.58314 |
| DHK2-127 | 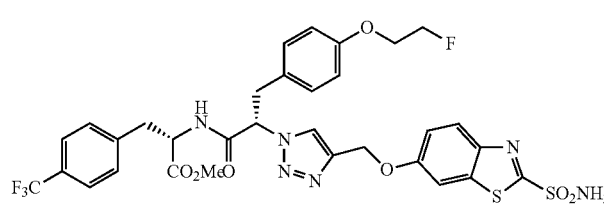 | 2 |
| DHK2-134 | 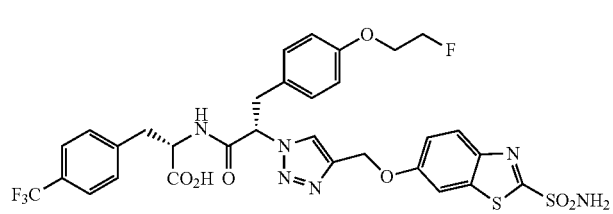 [SMILES: NS(=O)(=O)c1nc2ccc(OCc3cn([C@@H](Cc4ccc(OCCF)cc4)C(=O)N[C@@H](Cc4ccc(C(F)(F)F)cc4)C(=O)O)nn3)cc2s1] | 0.5 |
| DHK2-130 | 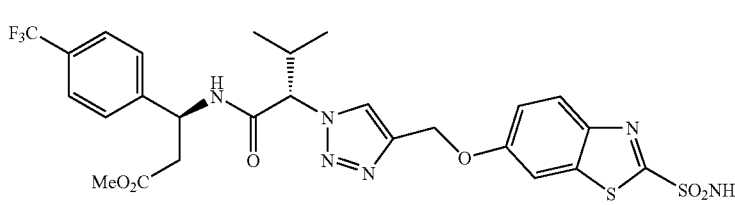 | 5 |

TABLE 3-continued

| Name | Chemical Structure | $K_d$ (nM) CA-IX |
|---|---|---|
| DHK2-133 | 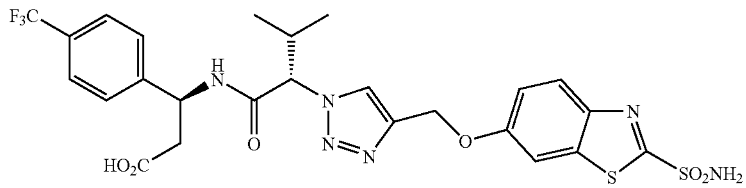 [SMILES: CC(C)[C@@H](C(=O)N[C@@H](CC(=O)O)c1ccc(C(F)(F)F)cc1)n1cc(COc2ccc3nc(S(N)(=O)=O)sc3c2)nn1] | 1.7 |
| DHK2-119 | 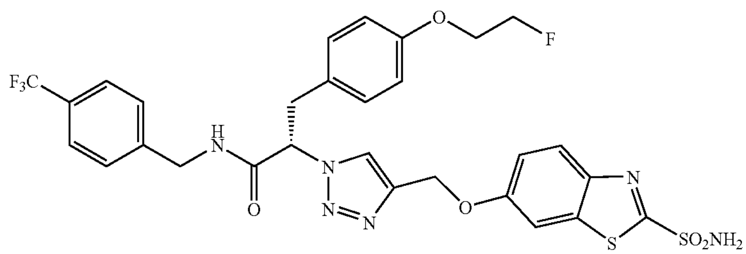 [SMILES: NS(=O)(=O)c1nc2ccc(OCc3cn([C@@H](Cc4ccc(OCCF)cc4)C(=O)NCc4ccc(C(F)(F)F)cc4)nn3)cc2s1] | 3.4 |
| BD2-09 | 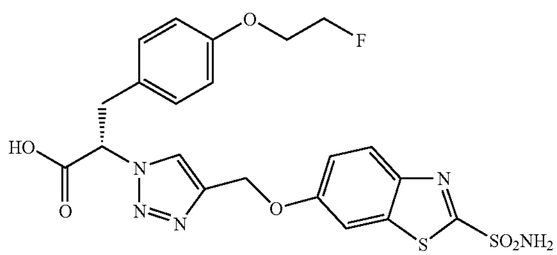 [SMILES: NS(=O)(=O)c1nc2ccc(OCc3cn([C@@H](Cc4ccc(OCCF)cc4)C(=O)O)nn3)cc2s1] | 17 |
| DHK2-129 | 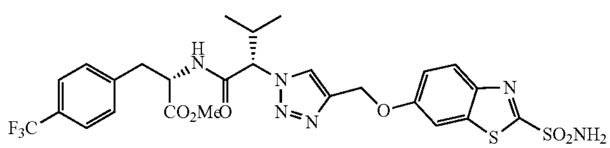 [SMILES: COC(=O)[C@H](Cc1ccc(C(F)(F)F)cc1)NC(=O)[C@H](C(C)C)n1cc(COc2ccc3nc(S(N)(=O)=O)sc3c2)nn1] | 1.2 |
| DHK2-132 | 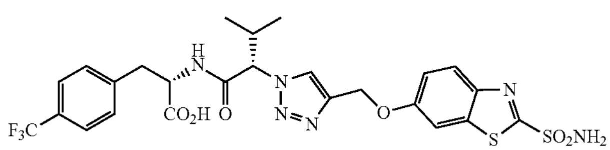 [SMILES: CC(C)[C@@H](C(=O)N[C@@H](Cc1ccc(C(F)(F)F)cc1)C(=O)O)n1cc(COc2ccc3nc(S(N)(=O)=O)sc3c2)nn1] | 0.5 |
| DHK2-128 | 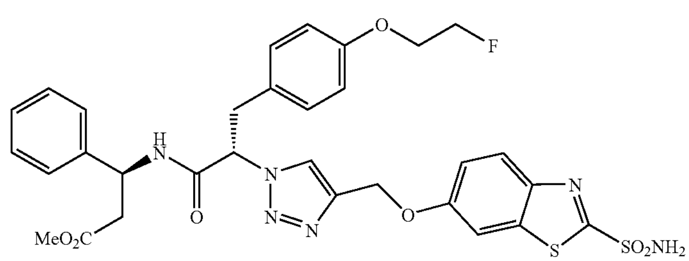 [SMILES: COC(=O)C[C@H](NC(=O)[C@H](Cc1ccc(OCCF)cc1)n1cc(COc2ccc3nc(S(N)(=O)=O)sc3c2)nn1)c1ccccc1] | 10 |
| DHK2-135 | 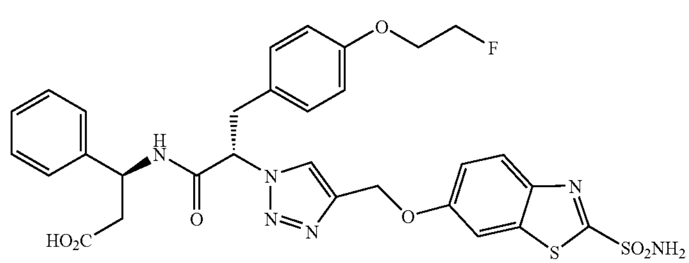 [SMILES: NS(=O)(=O)c1nc2ccc(OCc3cn([C@@H](Cc4ccc(OCCF)cc4)C(=O)N[C@@H](CC(=O)O)c4ccccc4)nn3)cc2s1] | 5 |

TABLE 3-continued
| Name | Chemical Structure | $K_d$ (nM) CA-IX |
|---|---|---|
| BD2-46 | 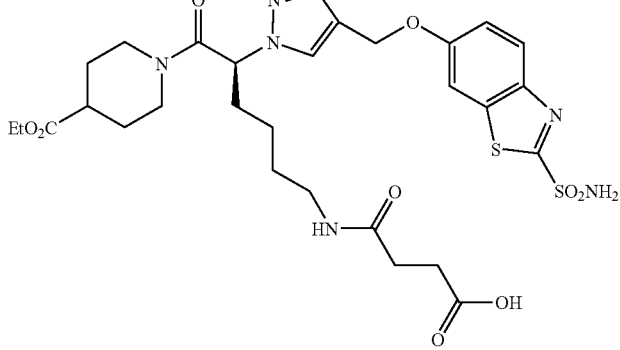 | 34 |
| BD2-47 | 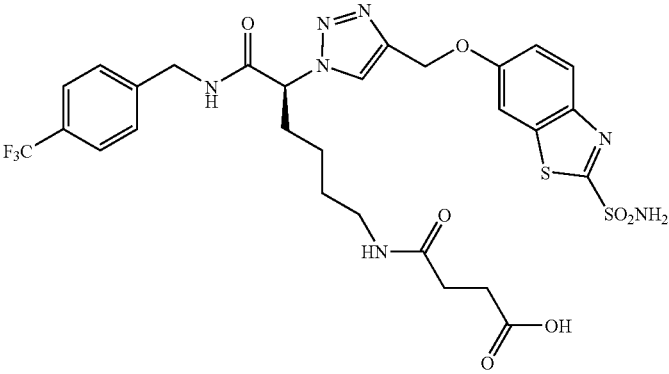 [SMILES: NS(=O)(=O)c1nc2ccc(OCc3cn([C@@H](CCCCNC(=O)CCC(=O)O)C(=O)NCc4ccc(C(F)(F)F)cc4)nn3)cc2s1] | 20 |
| DHK2-148 | 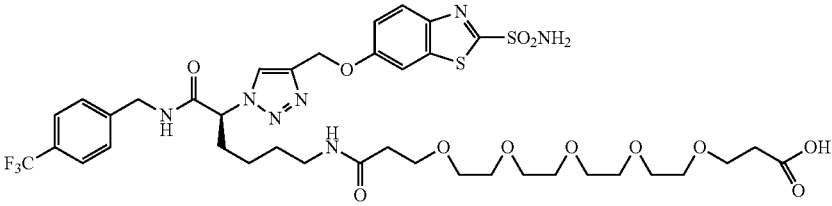 [SMILES: NS(=O)(=O)c1nc2ccc(OCc3cn([C@@H](CCCCNC(=O)CCOCCOCCOCCOCCOCCC(=O)O)C(=O)NCc4ccc(C(F)(F)F)cc4)nn3)cc2s1] | 34 |
| DHK2-147 | 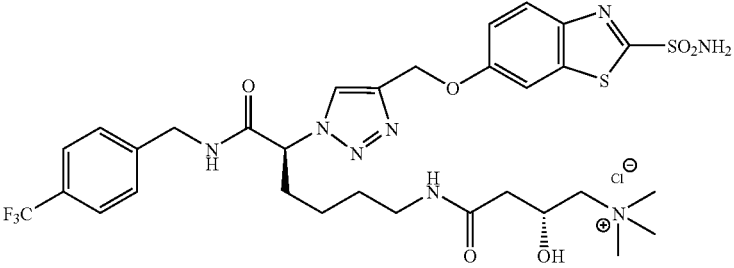 [SMILES: C[N+](C)(C)C[C@H](O)CC(=O)NCCCC[C@@H](C(=O)NCc1ccc(C(F)(F)F)cc1)n1cc(COc2ccc3nc(S(N)(=O)=O)sc3c2)nn1 ; [Cl-]] | 11 |
| DHK2-157 | 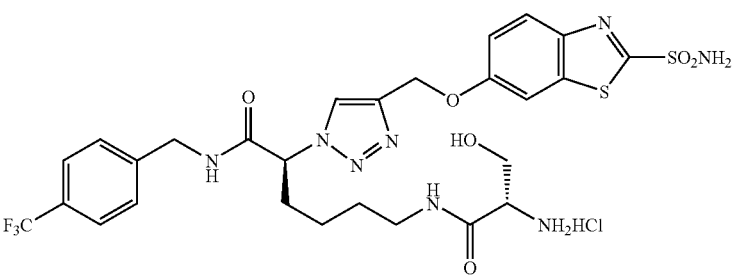 | 25 |

TABLE 3-continued

| Name | Chemical Structure | $K_d$ (nM) CA-IX |
|---|---|---|
| DHK2-141 | 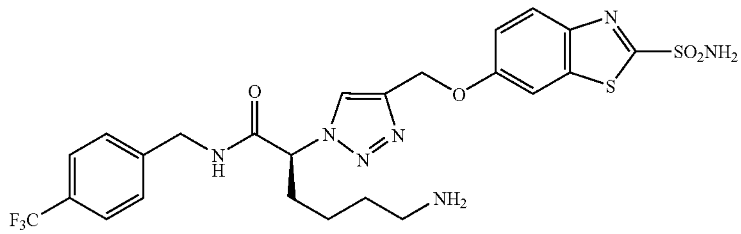 [SMILES: NCCCC[C@@H](C(=O)NCc1ccc(C(F)(F)F)cc1)n1cc(COc2ccc3nc(S(N)(=O)=O)sc3c2)nn1] | 34 |
| DHK2-160-F1 | 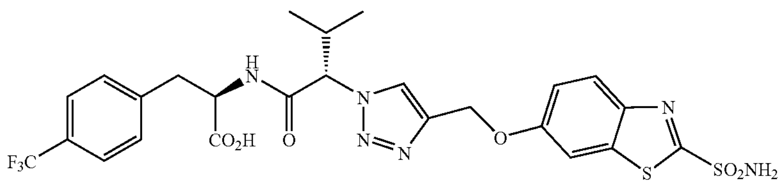 [SMILES: CC(C)[C@@H](C(=O)N[C@H](Cc1ccc(C(F)(F)F)cc1)C(=O)O)n1cc(COc2ccc3nc(S(N)(=O)=O)sc3c2)nn1] | 10 |
| DHK2-160-F2 | 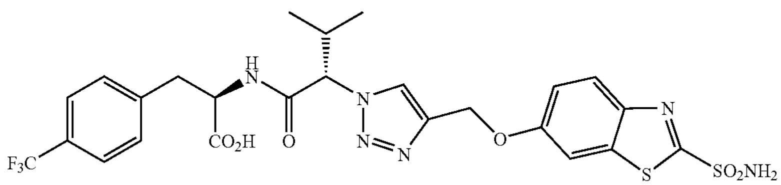 [SMILES: CC(C)[C@@H](C(=O)N[C@H](Cc1ccc(C(F)(F)F)cc1)C(=O)O)n1cc(COc2ccc3nc(S(N)(=O)=O)sc3c2)nn1] | 5 |
| DHK2-161 | 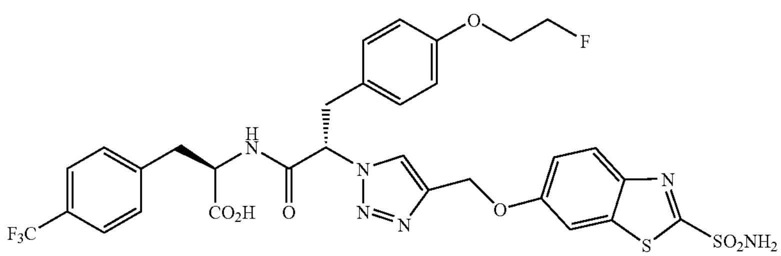 [SMILES: NS(=O)(=O)c1nc2ccc(OCc3cn([C@@H](Cc4ccc(OCCF)cc4)C(=O)N[C@H](Cc4ccc(C(F)(F)F)cc4)C(=O)O)nn3)cc2s1] | 5 |
| DHK2-173 | 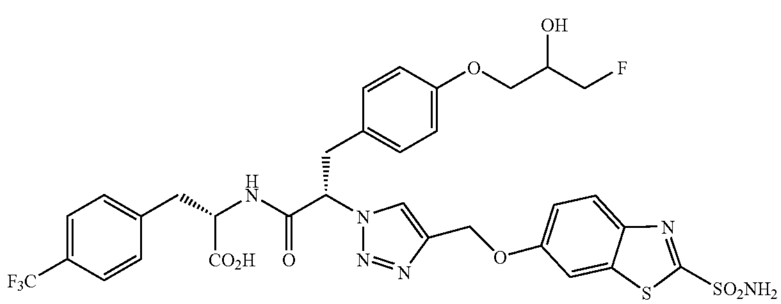 [SMILES: NS(=O)(=O)c1nc2ccc(OCc3cn([C@@H](Cc4ccc(OCC(O)CF)cc4)C(=O)N[C@@H](Cc4ccc(C(F)(F)F)cc4)C(=O)O)nn3)cc2s1] | 2 |
| DHK2-176 | 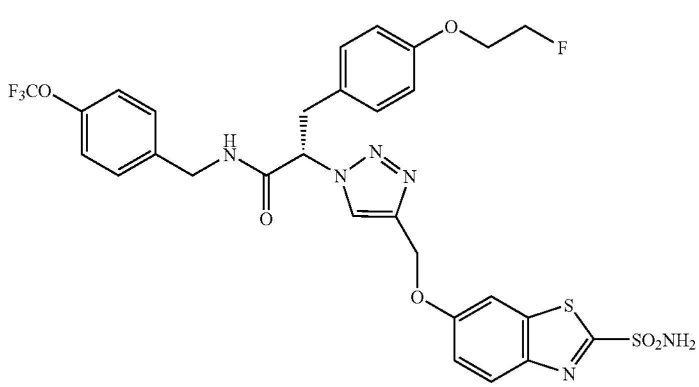 [SMILES: NS(=O)(=O)c1nc2ccc(OCc3cn([C@@H](Cc4ccc(OCCF)cc4)C(=O)NCc4ccc(OC(F)(F)F)cc4)nn3)cc2s1] | 5 |

TABLE 3-continued

| Name | Chemical Structure | $K_d$ (nM) CA-IX |
|---|---|---|
| DHK2-180 | 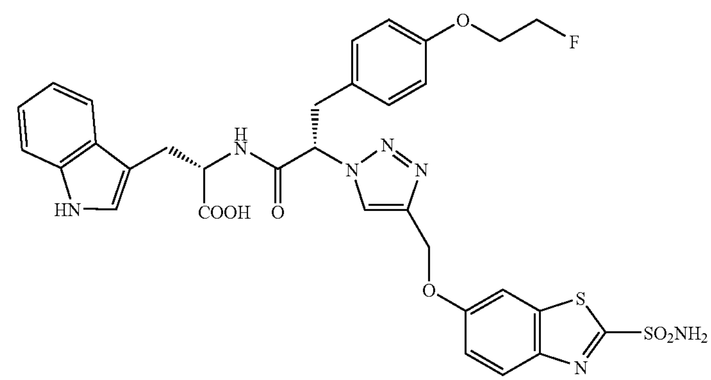 [SMILES: NS(=O)(=O)c1nc2ccc(OCc3cn([C@@H](Cc4ccc(OCCF)cc4)C(=O)N[C@@H](Cc4c[nH]c5ccccc45)C(=O)O)nn3)cc2s1] | 14 |
| DHK2-181 | 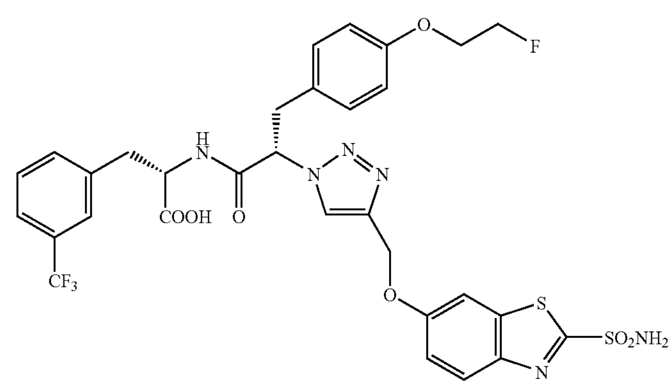 [SMILES: NS(=O)(=O)c1nc2ccc(OCc3cn([C@@H](Cc4ccc(OCCF)cc4)C(=O)N[C@@H](Cc4cccc(C(F)(F)F)c4)C(=O)O)nn3)cc2s1] | 2 |
| DHK2-187 | CLogP: 3.08694 | 17 |
| BW-96 | 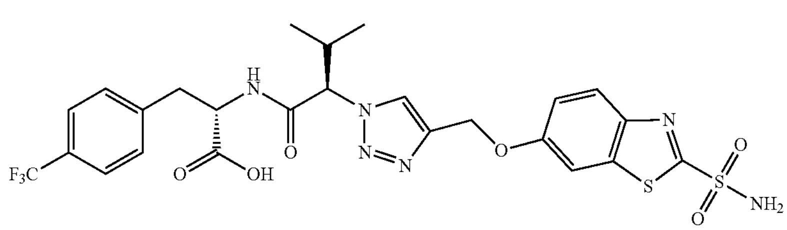 [SMILES: CC(C)[C@H](C(=O)N[C@@H](Cc1ccc(C(F)(F)F)cc1)C(=O)O)n1cc(COc2ccc3nc(S(N)(=O)=O)sc3c2)nn1] | 1.7 |

TABLE 3-continued

| Name | Chemical Structure | $K_d$ (nM) CA-IX |
|---|---|---|
| VM2-106 | 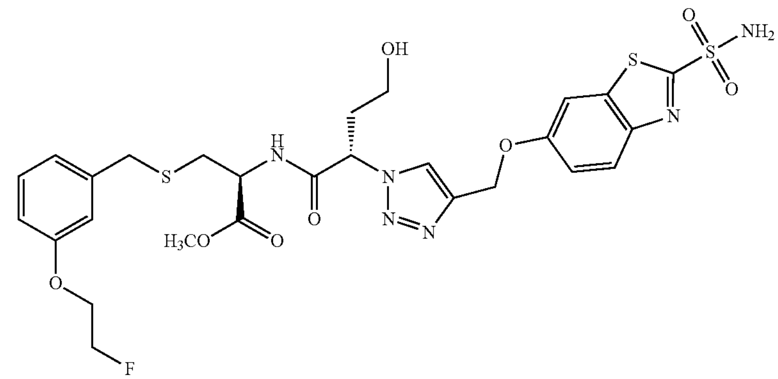 [SMILES: COC(=O)[C@@H](CSCc1cccc(OCCF)c1)NC(=O)[C@H](CCO)n1cc(COc2ccc3nc(S(N)(=O)=O)sc3c2)nn1] | 5 |
| VM2-107a | 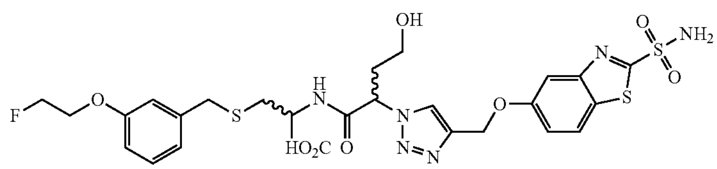 [SMILES: NS(=O)(=O)c1nc2cc(OCc3cn(C(CCO)C(=O)NC(CSCc4cccc(OCCF)c4)C(=O)O)nn3)ccc2s1] | 10 |
| BW-139-1A | 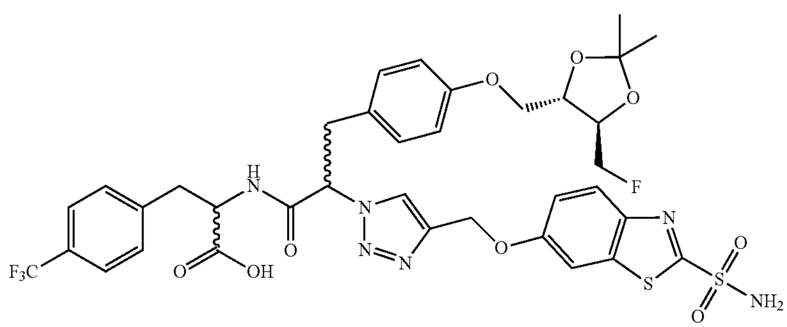 [SMILES: CC1(C)O[C@@H](CF)[C@H](COc2ccc(CC(C(=O)NC(Cc3ccc(C(F)(F)F)cc3)C(=O)O)n3cc(COc4ccc5nc(S(N)(=O)=O)sc5c4)nn3)cc2)O1] | 1.7 |
| BW-139-1B | 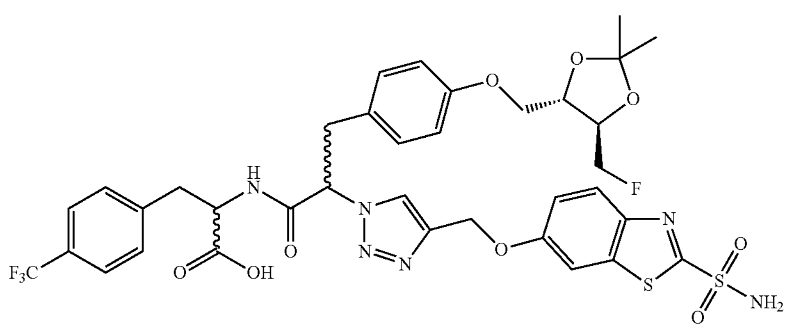 [SMILES: CC1(C)O[C@@H](CF)[C@H](COc2ccc(CC(C(=O)NC(Cc3ccc(C(F)(F)F)cc3)C(=O)O)n3cc(COc4ccc5nc(S(N)(=O)=O)sc5c4)nn3)cc2)O1] | 2.5 |
| BW-139-2C | 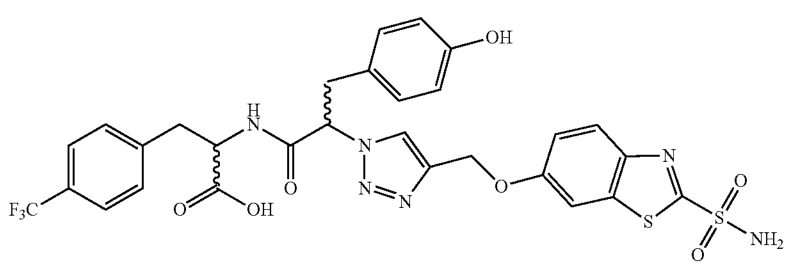 [SMILES: NS(=O)(=O)c1nc2ccc(OCc3cn(C(Cc4ccc(O)cc4)C(=O)NC(Cc4ccc(C(F)(F)F)cc4)C(=O)O)nn3)cc2s1] | 1.2 |

TABLE 3-continued

| Name | Chemical Structure | $K_d$ (nM) CA-IX |
|---|---|---|
| BW-139-2D | 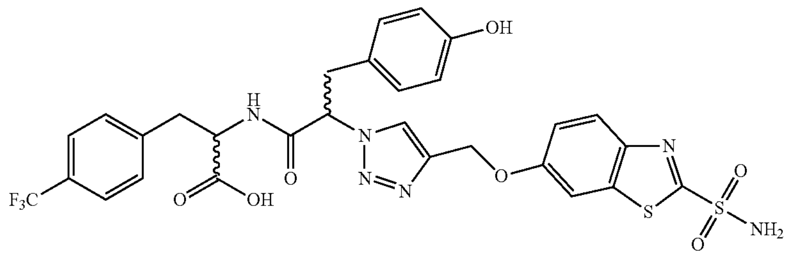 [SMILES: NS(=O)(=O)c1nc2ccc(OCc3cn(C(Cc4ccc(O)cc4)C(=O)NC(Cc4ccc(C(F)(F)F)cc4)C(=O)O)nn3)cc2s1] | 2.5 |
| VM2-93 | 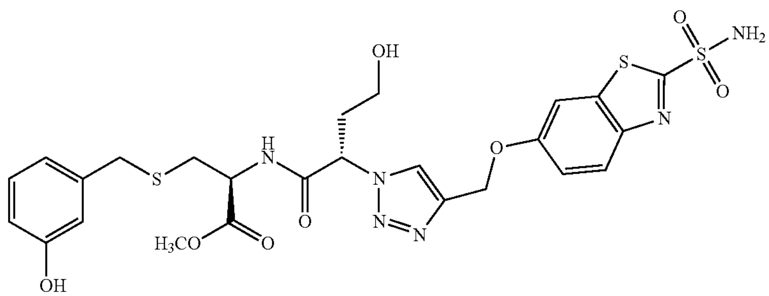 [SMILES: COC(=O)[C@@H](CSCc1cccc(O)c1)NC(=O)[C@H](CCO)n1cc(COc2ccc3nc(S(N)(=O)=O)sc3c2)nn1] | 10 |
| VM2-107b | 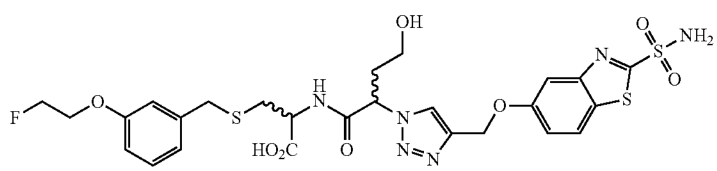 [SMILES: NS(=O)(=O)c1nc2cc(OCc3cn(C(CCO)C(=O)NC(CSCc4cccc(OCCF)c4)C(=O)O)nn3)ccc2s1] | 5 |
| BW-141-1 | 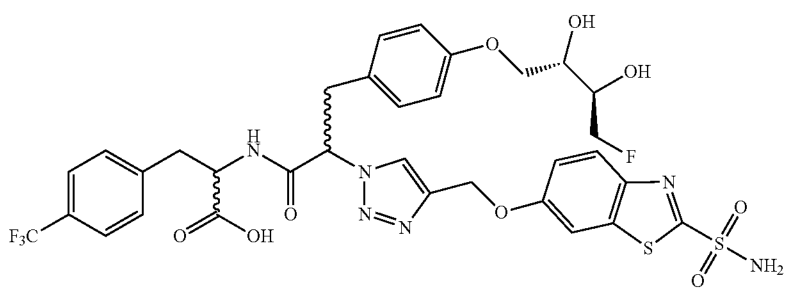 [SMILES: NS(=O)(=O)c1nc2ccc(OCc3cn(C(Cc4ccc(OC[C@H](O)[C@@H](O)CF)cc4)C(=O)NC(Cc4ccc(C(F)(F)F)cc4)C(=O)O)nn3)cc2s1] | 5 |
| BW-141-2 | 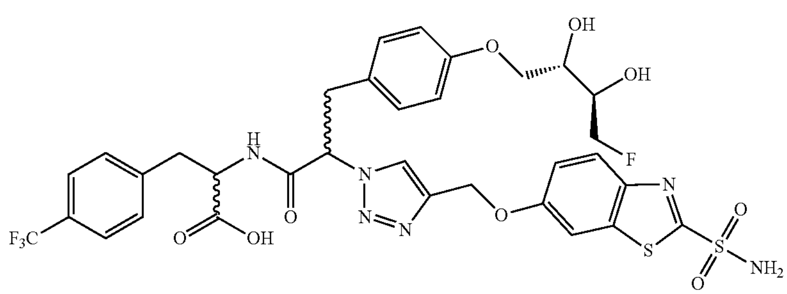 [SMILES: NS(=O)(=O)c1nc2ccc(OCc3cn(C(Cc4ccc(OC[C@H](O)[C@@H](O)CF)cc4)C(=O)NC(Cc4ccc(C(F)(F)F)cc4)C(=O)O)nn3)cc2s1] | 3.4 |
| BD2-120 | 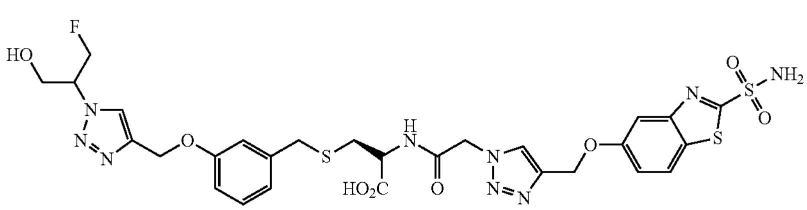 | 5 |

TABLE 3-continued

| Name | Chemical Structure | $K_d$ (nM) CA-IX |
|---|---|---|
| VM2-126 | 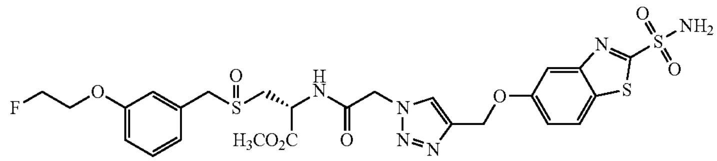 | 10 |
| VM2-128B | 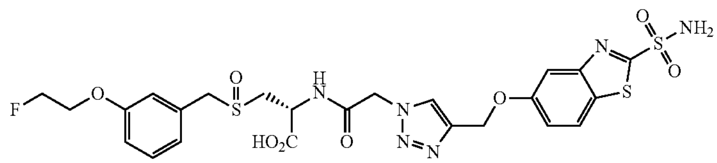 | 2.5 |
| VM2-128C | 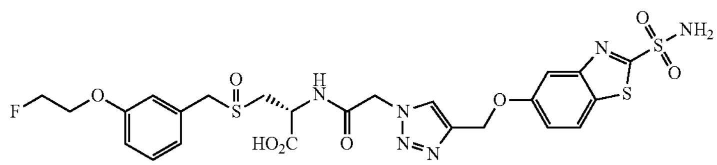 | 5 |
| VM2-131 | 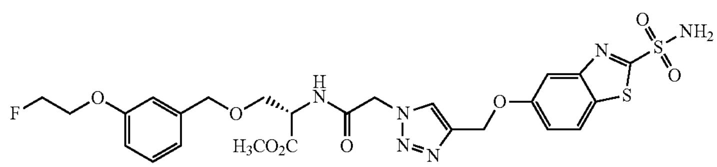 | 11 |
| VM2-133 | 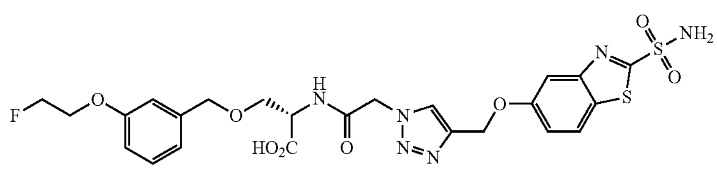 | 5 |
| BW2-23 | 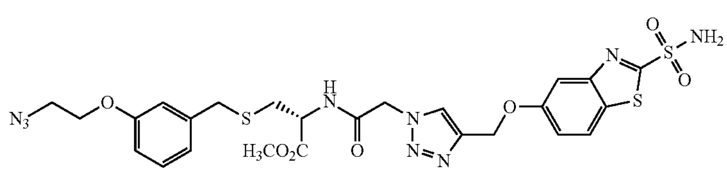 [SMILES: COC(=O)[C@H](CSCc1cccc(OCCN=[N+]=[N-])c1)NC(=O)Cn1cc(COc2ccc3sc(S(N)(=O)=O)nc3c2)nn1] | 10 |
| BW2-27 | 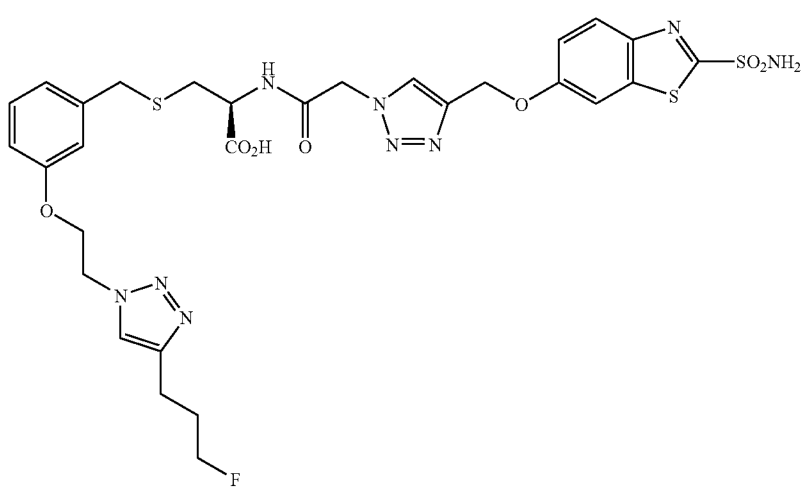 [SMILES: NS(=O)(=O)c1nc2ccc(OCc3cn(CC(=O)N[C@H](CSCc4cccc(OCCn5cc(CCCF)nn5)c4)C(=O)O)nn3)cc2s1] | 10 |

TABLE 3-continued
| Name | Chemical Structure | $K_d$ (nM) CA-IX |
|---|---|---|
| BW2-41 | 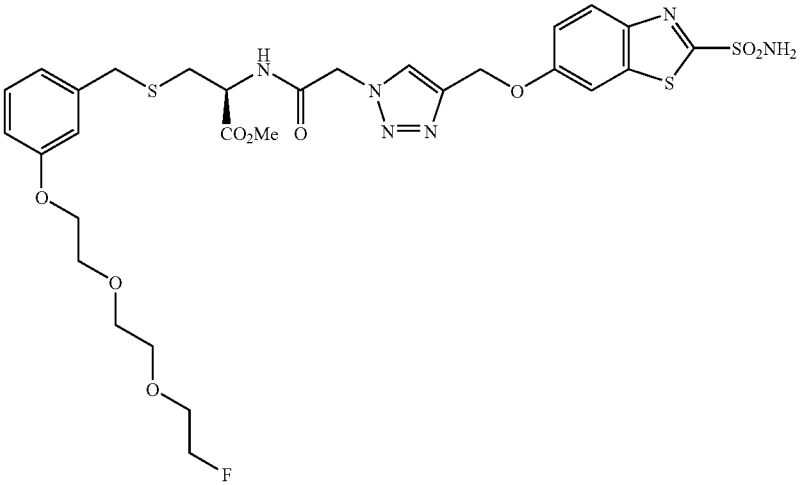 [SMILES: COC(=O)[C@@H](CSCc1cccc(OCCOCCOCCF)c1)NC(=O)Cn1cc(COc2ccc3nc(S(N)(=O)=O)sc3c2)nn1] | 5 |
| BW2-45 | 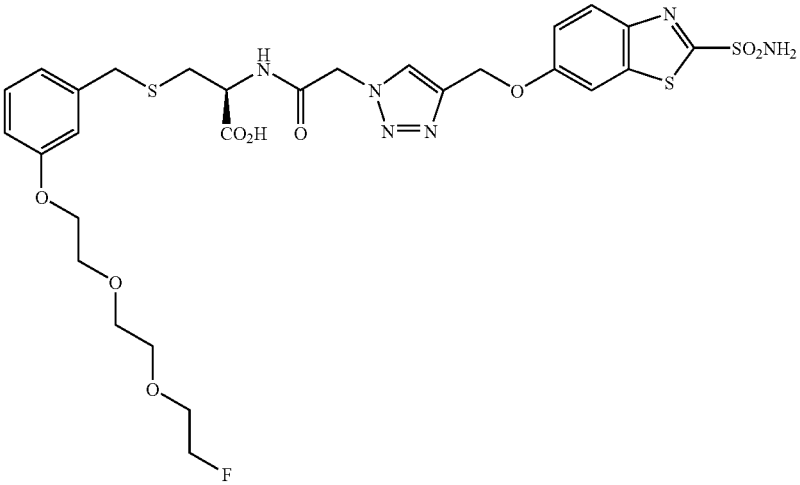 [SMILES: NS(=O)(=O)c1nc2ccc(OCc3cn(CC(=O)N[C@H](CSCc4cccc(OCCOCCOCCF)c4)C(=O)O)nn3)cc2s1] | 5 |

TABLE 3-continued
| Name | Chemical Structure | $K_d$ (nM) CA-IX |
|---|---|---|
| DHK3-48 | 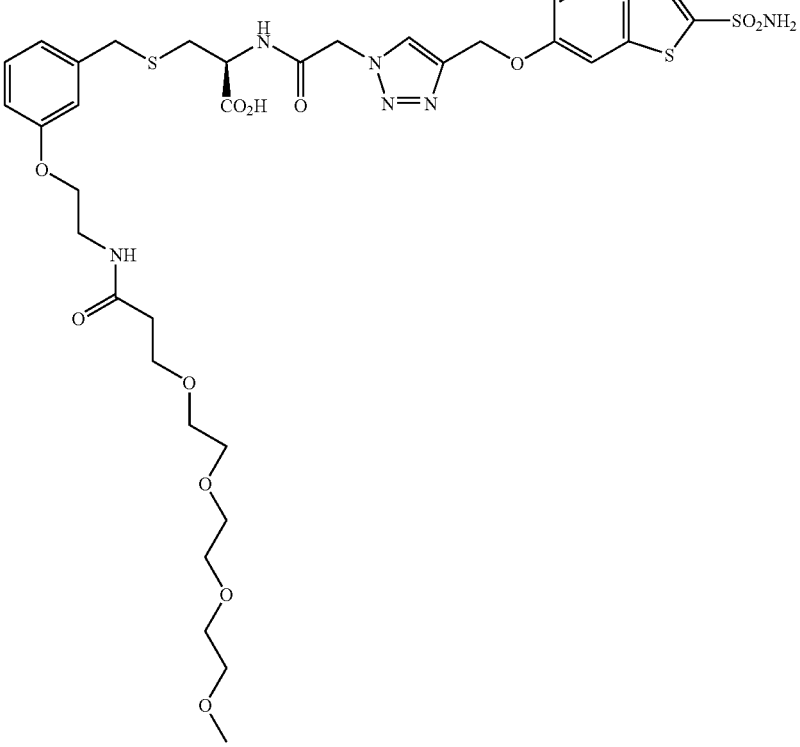 | 10 |
| VM3-91 | 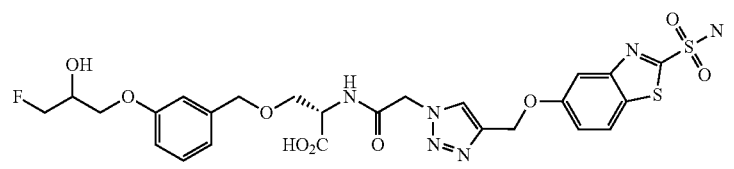 [SMILES: NS(=O)(=O)c1nc2cc(OCc3cn(CC(=O)N[C@@H](COCc4cccc(OCC(O)CF)c4)C(=O)O)nn3)ccc2s1] | 5<br>CLogP: 0.99834 |
| DHK3-158 | 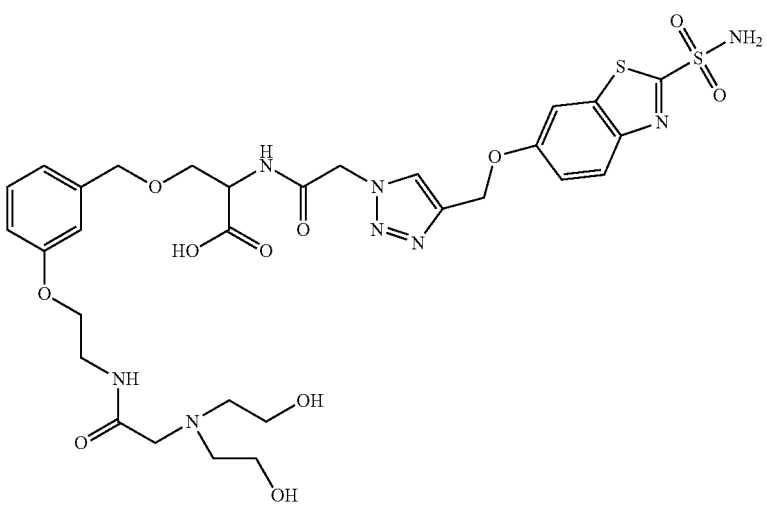 [SMILES: NS(=O)(=O)c1nc2ccc(OCc3cn(CC(=O)NC(COCc4cccc(OCCNC(=O)CN(CCO)CCO)c4)C(=O)O)nn3)cc2s1] | 14<br>(QPlogPo/w): −3.83 |

TABLE 3-continued
| Name | Chemical Structure | $K_d$ (nM) CA-IX |
|------|-------------------|------------------|
| DHK3-155 | 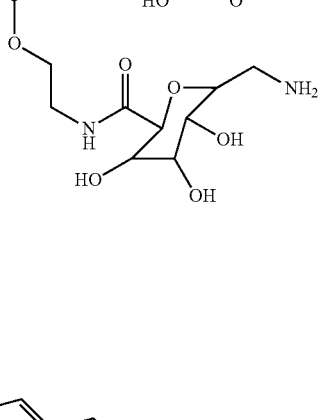 | 11 (QPlogPo/w): −5.14 |
| DHK3-154 | 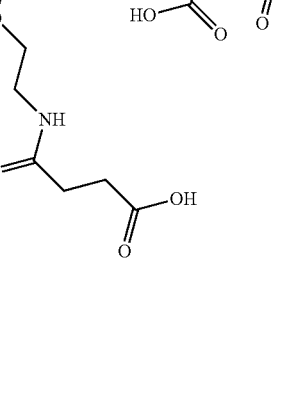 | 25 (QPlogPo/w): −0.47 |
| DHK3-156 | 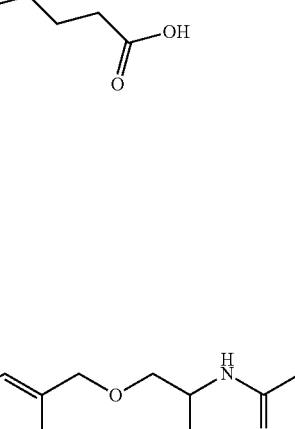 | 10 CLogP: −3.36606 |

TABLE 3-continued

| Name | Chemical Structure | $K_d$ (nM) CA-IX |
|---|---|---|
| DHK3-149 | 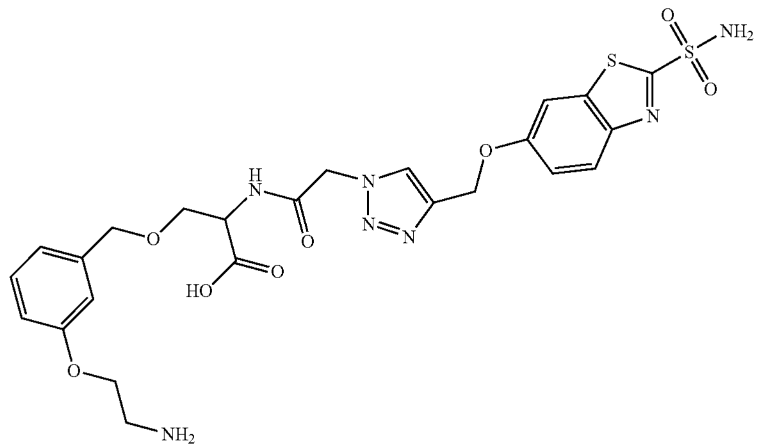 [SMILES: NCCOc1cccc(COCC(NC(=O)Cn2cc(COc3ccc4nc(S(N)(=O)=O)sc4c3)nn2)C(=O)O)c1] | 10 (QPlogPo/w): −2.35 |
| VM3-163 | 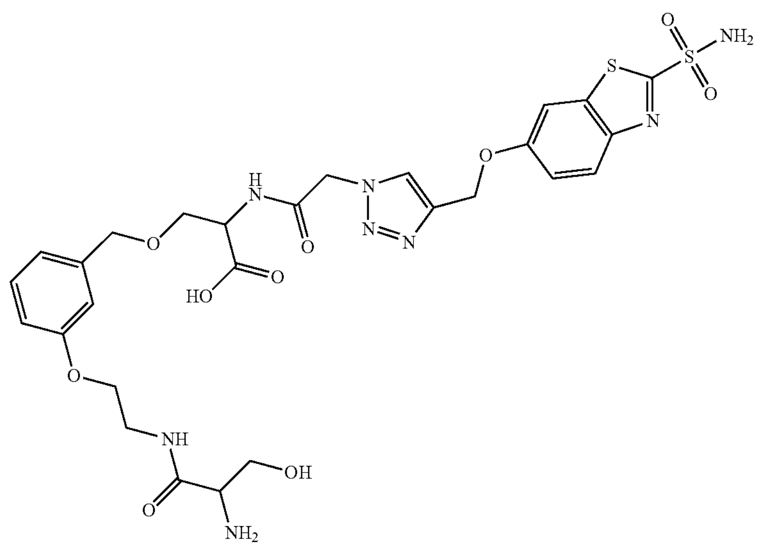 [SMILES: NC(CO)C(=O)NCCOc1cccc(COCC(NC(=O)Cn2cc(COc3ccc4nc(S(N)(=O)=O)sc4c3)nn2)C(=O)O)c1] | 10 (QPlogPo/w): −4.13 |
| VM3-165A/B | 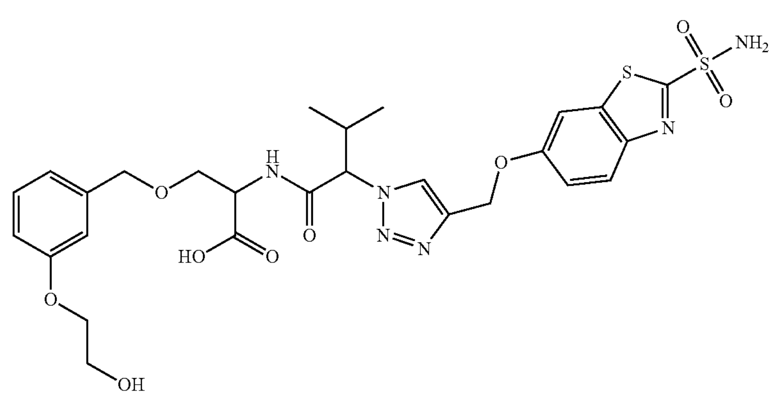 [SMILES: CC(C)C(C(=O)NC(COCc1cccc(OCCO)c1)C(=O)O)n1cc(COc2ccc3nc(S(N)(=O)=O)sc3c2)nn1] | 5/11 (QPlogPo/w): 0.95 |

TABLE 3-continued

| Name | Chemical Structure | $K_d$ (nM) CA-IX |
|---|---|---|
| VM3-167A/B | 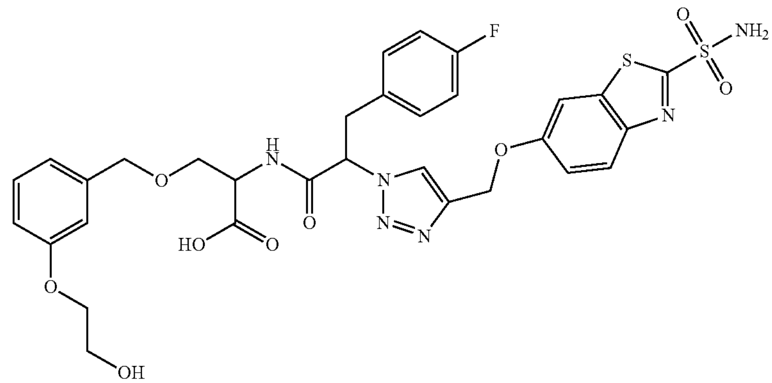 [SMILES: NS(=O)(=O)c1nc2ccc(OCc3cn(C(Cc4ccc(F)cc4)C(=O)NC(COCc4cccc(OCCO)c4)C(=O)O)nn3)cc2s1] | 5/10 (QPlogPo/w): 1.69 |
| BD3-36 | 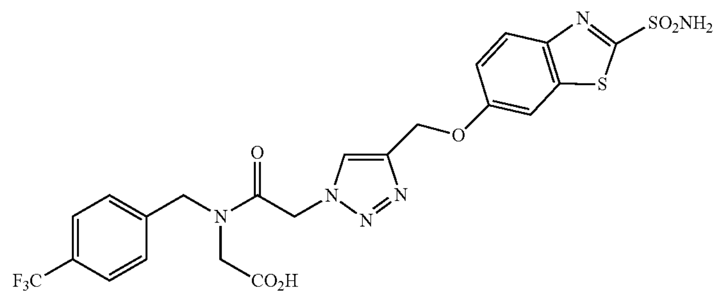 [SMILES: NS(=O)(=O)c1nc2ccc(OCc3cn(CC(=O)N(CC(=O)O)Cc4ccc(C(F)(F)F)cc4)nn3)cc2s1] | 14 CLogP: 3.16314 |
| VM4009 | 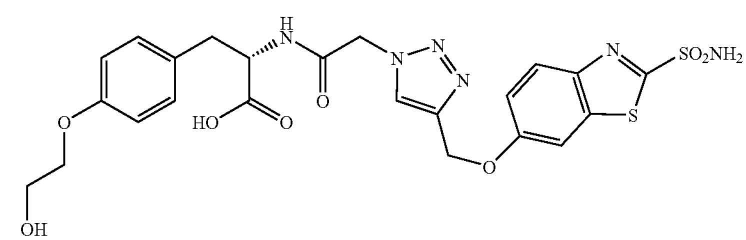 [SMILES: NS(=O)(=O)c1nc2ccc(OCc3cn(CC(=O)N[C@@H](Cc4ccc(OCCO)cc4)C(=O)O)nn3)cc2s1] | 5 CLogP: 0.80194 |
| VM4021 | 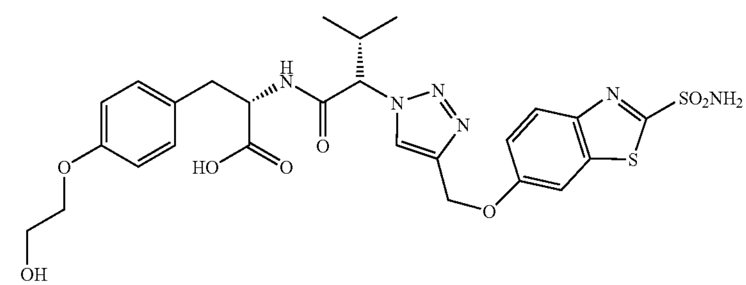 | 3.3 CLogP: 2.03894 |
| VM4047a | 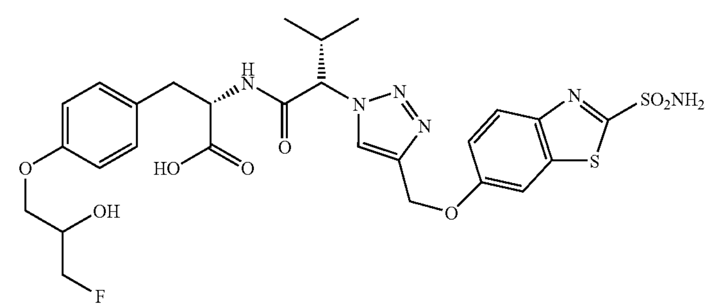 | 5 CLogP: 2.22094 |

TABLE 3-continued

| Name | Chemical Structure | $K_d$ (nM) CA-IX |
|---|---|---|
| VM4047b | 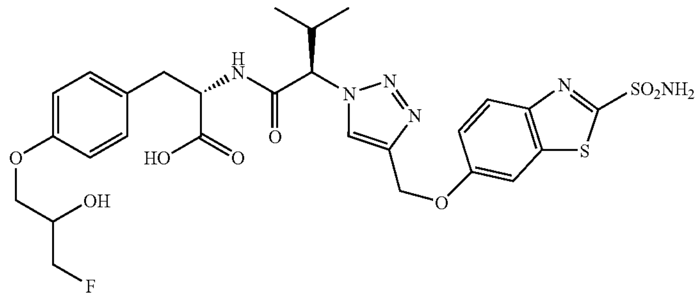 [SMILES: CC(C)[C@H](C(=O)N[C@@H](Cc1ccc(OCC(O)CF)cc1)C(=O)O)n1cc(COc2ccc3nc(S(N)(=O)=O)sc3c2)nn1] | 11<br>CLogP: 2.22094 |
| VM4037a | 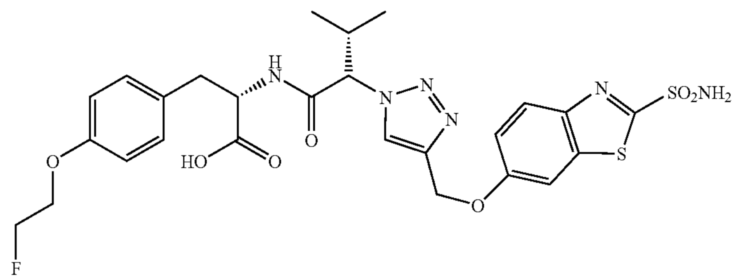 | 1.3<br>CLogP: 3.16394 |
| VM4037b | 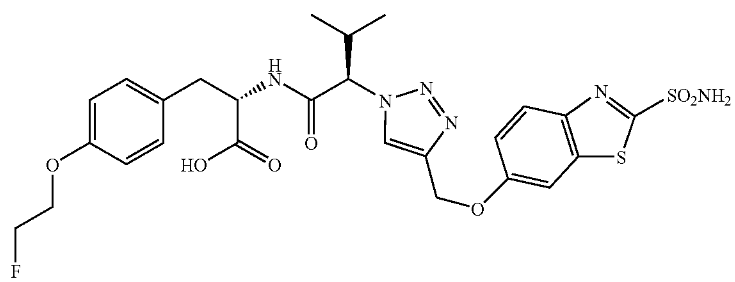 [SMILES: CC(C)[C@H](C(=O)N[C@@H](Cc1ccc(OCCF)cc1)C(=O)O)n1cc(COc2ccc3nc(S(N)(=O)=O)sc3c2)nn1] | 5<br>CLogP: 3.16394 |
| UG3150 | 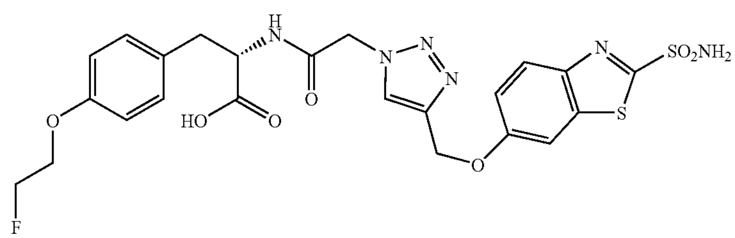 [SMILES: NS(=O)(=O)c1nc2ccc(OCc3cn(CC(=O)N[C@@H](Cc4ccc(OCCF)cc4)C(=O)O)nn3)cc2s1] | 3.3<br>CLogP: 1.92694 |
| VM4041 | 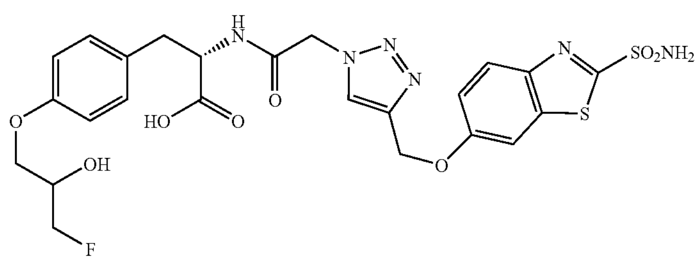 [SMILES: NS(=O)(=O)c1nc2ccc(OCc3cn(CC(=O)N[C@@H](Cc4ccc(OCC(O)CF)cc4)C(=O)O)nn3)cc2s1] | 5<br>CLogP: 0.983939 |
| WZ01101 | 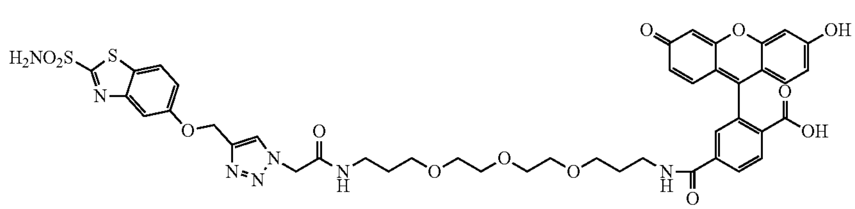 [SMILES: NS(=O)(=O)c1nc2cc(OCc3cn(CC(=O)NCCCOCCOCCOCCCNC(=O)c4ccc(C(=O)O)c(-c5c6ccc(=O)cc-6oc6cc(O)ccc56)c4)nn3)ccc2s1] | 14<br>CLogP: 3.16394 |

TABLE 3-continued

| Name | Chemical Structure | $K_d$ (nM) CA-IX |
|---|---|---|
| GGC121A | 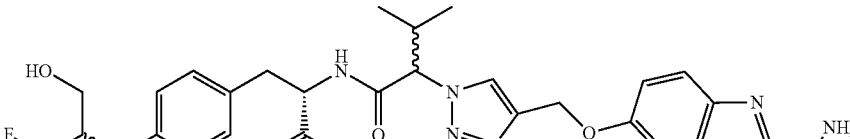 | 11<br>CLogP: 1.92694 |
| GGC121B | 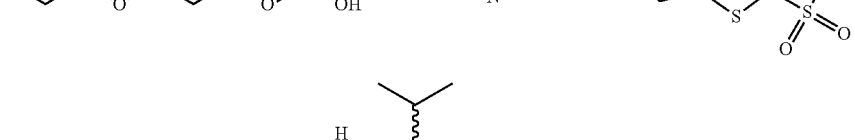 | 13<br>CLogP: 0.983939 |

We claim:

1. A compound comprising the Formula IIa$_2$:

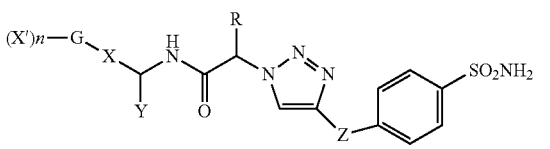

or a pharmaceutically acceptable salt thereof, optionally in the form of a single stereoisomer or mixtures of stereoisomers thereof, wherein:

G is a bond or is selected from the group consisting of cycloalkyl, aryl-CH(Y)—, heterocyclyl, aryl and heteroaryl, wherein said cycloalkyl, aryl-CH(Y)—, heterocyclyl, aryl and heteroaryl are substituted or unsubstituted;

n is 0, 1, 2 or 3;

X is a bond or is selected from the group consisting of —O—, —S—, —S(O)—, —S(O)$_2$—, —NR°— where R° is H, C$_{1-5}$alkyl or CH$_2$CO$_2$R'' wherein R'' is H or C$_1$-C$_3$-alkyl;

—NR°—C(O)—CH(R°)— where R° is H or C$_{1-5}$alkyl; heterocyclyl, aryl, heteroaryl and C$_{1-6}$alkyl wherein 1 or 2 carbon atoms of the C$_{1-6}$alkyl is replaced by a —O—, —C(O)—, —S—, —S(O)—, —S(O)$_2$— or —NR'''— where R''' is H or C$_{1-5}$alkyl, and where the C$_{1-6}$alkyl is optionally substituted with 1 or 2 substituents selected from the group consisting of —OH, —SH, NH$_2$, heterocyclyl, aryl and heteroaryl;

X' is selected from the group consisting of a quaternary ammonium salt, imidate salt, thiolate salt, oxonium cation, boron-amine salt, pyridinium salt, and Z'-D, where D comprises a charged moiety that is at least one of a cation or anion, —SO$_2$H, —SO$_3$H, —PO$_3$H, —OPO$_3$H, N-oxide, —B(OH)$_2$, —OH, amino, halo, —CF$_3$, —CH$_2$F, —CHF$_2$, —COOH, —COOC$_{1-5}$alkyl, —COC$_{1-5}$alkyl, —CO-aryl, —CO-heteroaryl, C$_{1-6}$alkyl, amino-C$_{1-5}$alkyl-, optionally substituted aryl, optionally substituted heteroaryl, halo-C$_{1-5}$alkyl, halo-C$_{1-5}$alkoxy-; Z'—C$_{1-6}$alkyl, Z'—C$_{2-6}$alkyl-O—, Z'—C$_{2-6}$alkyl-O—C$_{1-3}$alkyl-, Z'—C$_{2-6}$alkyl-S—, Z'—C$_{2-6}$alkyl-NH—, Z'—C$_{2-6}$alkyl-NH—C$_{1-3}$alkyl-, Z'—C$_{2-6}$alkyl-N(C$_{1-3}$alkyl)-C$_{1-3}$alkyl-, Z'—(CH$_2$CH$_2$—O)$_{1-5}$—, wherein Z' is selected from the group consisting of halo, radionuclide, —CF$_3$, —CH$_2$F, —CHF$_2$, aryl, and heteroaryl, wherein at least one H of aryl or heteroaryl is substituted with a halo or a radionuclide;

Y is H or is selected from the group consisting of a quaternary ammonium salt, imidate salt, thiolate salt, oxonium cation, boron-amine salt, pyridinium salt, —SO$_2$H, N-oxide, —B(OH)$_2$, —COOR'', —SO$_3$R'', —P(O)$_2$OR'' and —OP(O)$_2$OR'' wherein R'' is H or C$_{1-3}$alkyl;

R is H, or is selected from the group consisting of
a side chain of an amino acid,
halobenzyl,
—C$_{1-5}$alkyl-, —C$_{1-5}$alkyl-OR'', —C$_{1-5}$alkyl-N(R'')$_2$,—C$_{1-5}$alkyl-NR''C(O)—(CH$_2$CH$_2$O)$_m$—C$_1$-C$_5$-alkyl-CO$_2$R'' wherein m is 0-8, —C$_{1-5}$alkyl-NR''C(O)—C$_1$-C$_5$-alkyl wherein the —C$_{1-5}$alkyl is optionally substituted with OR'' or CH$_2$OR'', —C$_{1-5}$alkyl-o, m, or p-aryl- (O—CH$_2$CH$_2$)$_{1-5}$-halo wherein the —(O—CH$_2$CH$_2$)$_{1-5}$-halo is optionally substituted with one or more OR'', or —C$_{1-5}$alkyl-o, m, or p-aryl-(CH$_2$CH$_2$)$_{1-5}$-halo, wherein R'' is H or C$_1$-C$_3$-alkyl; and Z is a bond or is selected from the group consisting of —C(O)—NH—CH$_2$—, —CH$_2$O—, and —OCH$_2$— wherein at least one of X' or Y is comprised of an ionizable group.

2. The compound of claim 1, wherein X' is an ammonium ion and its respective salts.

3. The compound of claim 1, wherein X' comprises at least one of —COOH, —SO$_3$H, —PO$_3$H, —N(C$_{1-6}$alkyl)$_3$$^+$X$^-$ wherein X$^-$ is a counter anion.

4. The compound of claim 1, wherein R is H.

5. The compound of claim 1, wherein:
G is selected from the group consisting of a heterocyclyl, aryl and heteroaryl;
X' is selected from the group consisting of a quaternary ammonium salt, imidate salt, thiolate salt, oxonium cation, boron-amine salt, pyridinium salt, and Z'-D, where D comprises a charged moiety that is at least one of a cation or anion, wherein Z' is selected from the group consisting of halo, —CF₃, —CH₂F, —CHF₂, aryl and heteroaryl, wherein at least one H of aryl or heteroaryl is substituted with a halo or a radionuclide;

Y is selected from the group consisting of —SO₂H, N-oxide, —B(OH)₂, —COOR", —SO₃R", —P(O)₂OR" and —OP(O)₂OR" wherein R" is H or $C_{1-3}$alkyl;

R is H or a side chain of an amino acid; and

Z is selected from the group consisting of —CH₂O—, —OCH₂— or —C(O)—NH—CH₂—.

6. A compound of claim 5 wherein Z is —CH₂O—, —OCH₂—.

7. The compound of claim 1, wherein Z is a bond and R is Valine.

8. The compound of claim 1, wherein Z is a bond and R is —CH₂-phenyl.

9. The compound of claim 1, wherein X' comprises a radionuclide and wherein the radionuclide is selected from the group consisting of $^{11}C$, $^{18}F$, $^{13}N$ and $^{15}O$.

10. The compound of claim 1 that is:

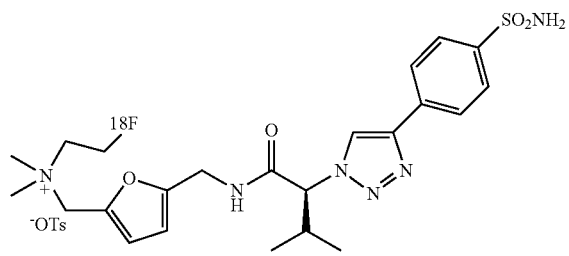

or a pharmaceutically acceptable salt thereof, optionally in the form of a single stereoisomer or mixtures of stereoisomers thereof.

11. The compound of claim 1, wherein Z is a bond.

12. The compound of claim 1, wherein X is $C_{1-6}$alkyl.

13. The compound of claim 11, wherein X is a bond.

14. The compound of claim 1 that is:

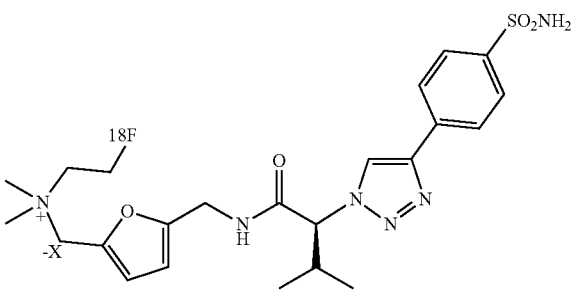

or a pharmaceutically acceptable salt thereof; optionally in the form of a single stereoisomer or mixtures of stereoisomers thereof,
wherein X is a counter ion.

15. The compound of claim 1, wherein X' is Z'-D and wherein D is $X^-[C(R^{4'})_2]_{1-5}$—, wherein $R^{4'}$ is $C_{1-5}$ alkyl, wherein one C is replaced by $N^+$, and wherein $X^-$ is a counter ion.

16. The compound of claim 1, wherein X' is Z'-D and wherein D is $X^-[C(R^{4'})_{1-2}]_{1-5}$—, wherein $R^{4'}$ is $C_{1-5}$ alkyl, wherein at least one $C(R^{4'})_{1-2}$ is $C(R^{4'})_1$ and wherein at least one C of $C(R^{4'})_1$ is replaced by $O^+$.

17. The compound of claim 1, wherein

X' is selected from the group consisting of —SO₂H, —SO₃H, —PO₃H, —OPO₃H, N-oxide, —B(OH)₂, —OH, amino, halo, —CF₃, —CH₂F, —CHF₂, —COOH, —COOC$_{1-5}$alkyl, —COC$_{1-5}$alkyl, —CO-aryl, —CO-heteroaryl, $C_{1-6}$alkyl, amino-$C_{1-5}$alkyl-, optionally substituted aryl, optionally substituted heteroaryl, halo-$C_{1-5}$alkyl, halo-$C_{1-5}$alkoxy-; Z'—$C_{1-6}$alkyl, Z'—$C_{2-6}$alkyl-O—, Z'—$C_{2-6}$alkyl-O—$C_{1-3}$alkyl-, Z'—$C_{2-6}$alkyl-S—, Z'—$C_{2-6}$alkyl-NH—, Z'—$C_{2-6}$alkyl-NH—$C_{1-3}$alkyl-, Z'—$C_{2-6}$alkyl-N($C_{1-3}$alkyl)-$C_{1-3}$alkyl-, Z'—(CH₂CH₂—O)$_{1-5}$—, wherein Z' is selected from the group consisting of halo, radionuclide, —CF₃, —CH₂F, —CHF₂, aryl, and heteroaryl, wherein at least one H of aryl or heteroaryl is substituted with a halo or a radionuclide; and Y is selected from the group consisting of a quaternary ammonium salt, imidate salt, thiolate salt, oxonium cation, boron-amine salt, pyridinium salt.

18. The compound of claim 13, wherein Y is H.

19. The compound of claim 15, wherein X of $X^-$ is a halo.

20. The compound of claim 15, wherein Z' is a radionuclide.

21. The compound of claim 15, wherein X of $X^-$ is an anion of a leaving group.

22. The compound of claim 18, wherein G is aryl or heteroaryl.

23. The compound of claim 21, wherein X of $X^-$ is Br.

24. A compound comprising the Formula IIa₃:

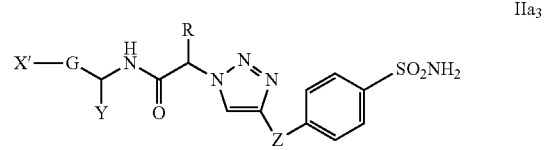

IIa₃ or a pharmaceutically acceptable salt thereof, optionally in the form of a single stereoisomer or mixtures of stereoisomers thereof,
wherein:

G is selected from the group consisting of aryl and heteroaryl;

X' is selected from the group consisting of a quaternary ammonium salt, imidate salt, thiolate salt, oxonium cation, boron-amine salt, pyridinium salt, and Z'-D, where D comprises a charged moiety that is at least one of a cation or anion, —SO₂H, —SO₃H, —PO₃H, —OPO₃H, N-oxide, —B(OH)₂, —OH, amino, halo, —CF₃, —CH₂F, —CHF₂, —COOH, —COOC$_{1-5}$alkyl, —COC$_{1-5}$alkyl, —CO-aryl, —CO-heteroaryl, $C_{1-6}$alkyl, amino-$C_{1-5}$alkyl-, optionally substituted aryl, optionally substituted heteroaryl, halo-$C_{1-5}$alkyl, halo-$C_{1-5}$alkoxy-; Z'—$C_{1-6}$alkyl, Z'—$C_{2-6}$alkyl-O—, Z'—$C_{2-6}$alkyl-O—$C_{1-3}$alkyl-, Z'—$C_{2-6}$alkyl-S—, Z'—$C_{2-6}$alkyl-NH—, Z'—$C_{2-6}$alkyl-NH—$C_{1-3}$alkyl-, Z'—$C_{2-6}$alkyl-N($C_{1-3}$alkyl)-$C_{1-3}$alkyl-, Z'—(CH₂CH₂—O)$_{1-5}$—, wherein Z' is selected from the group consisting of halo, radionuclide, —CF₃, —CH₂F, —CHF₂, aryl, and heteroaryl, wherein at least one H of aryl or heteroaryl is substituted with a halo or a radionuclide;

Y is H or is selected from the group consisting of a quaternary ammonium salt, imidate salt, thiolate salt, oxonium cation, boron-amine salt, pyridinium salt, —SO₂H, N-oxide, —B(OH)$_2$, —COOR", —SO$_3$R", —P(O)$_2$OR" and —OP(O)$_2$OR" wherein R" is H or C$_{1-3}$alkyl;

R is H, or is selected from the group consisting of
a side chain of an amino acid,
halobenzyl,
—C$_{1-5}$alkyl-, —C$_{1-5}$alkyl-OR", —C$_{1-5}$alkyl-N(R")$_2$, —C$_{1-5}$alkyl-NR"C(O)—(CH$_2$CH$_2$O)$_m$—C$_1$-C$_5$-alkyl-CO$_2$R" wherein m is 0-8, —C$_{1-5}$alkyl-NR"C(O)—C$_1$-C$_5$-alkyl wherein said —C$_{1-5}$alkyl is optionally substituted with OR" or CH$_2$OR", —C$_{1-5}$alkyl-o, m, or p-aryl-(O—CH$_2$CH$_2$)$_{1-5}$-halo wherein said —(O—CH$_2$CH$_2$)$_{1-5}$-halo is optionally substituted with one or more OR", or —C$_{1-5}$alkyl-o, m, or p-aryl-(CH$_2$CH$_2$)$_{1-5}$-halo, wherein R" is H or C$_1$-C$_3$-alkyl; and Z is a bond or is selected from the group consisting of —C(O)—NH—CH$_2$—, —CH$_2$O—, and —OCH$_2$—, wherein at least one of X' or Y is comprised of a charged moiety.

25. The compound of claim 24, wherein Z is a bond.
26. The compound of claim 24, wherein R is a side chain of an amino acid.
27. The compound of claim 24, wherein R is H.
28. The compound of claim 24, wherein X' is Z'-D and wherein D is X$^-$[C(R$^{4'}$)$_2$]$_{1-5}$—, wherein R$^{4'}$ is C$_{1-5}$ alkyl, wherein one C is replaced by N$^+$, and wherein X$^-$ is a counter ion.
29. The compound of claim 24, wherein G is heteroaryl.
30. The compound of claim 24, wherein Y is H.
31. The compound of claim 24, wherein
X' is selected from the group consisting of a quaternary ammonium salt, imidate salt, thiolate salt, oxonium cation, boron-amine salt, pyridinium salt, and Z'-D, where D comprises a charged moiety that is at least one of a cation or anion, wherein Z' is selected from the group consisting of halo, radionuclide, —CF$_3$, —CH$_2$F, —CHF$_2$, aryl, and heteroaryl, wherein at least one H of aryl or heteroaryl is substituted with a halo or a radionuclide; and
Y is selected from the group consisting of —SO$_2$H, N-oxide, —B(OH)$_2$, —COOR", —SO$_3$R", —P(O)$_2$OR" and —OP(O)$_2$OR" wherein R" is H or C$_{1-3}$alkyl.

32. The compound of claim 24, wherein
X' is selected from the group consisting of —SO$_2$H, —SO$_3$H, —PO$_3$H, —OPO$_3$H, N-oxide, —B(OH)$_2$, —OH, amino, halo, —CF$_3$, —CH$_2$F, —CHF$_2$, —COOH, —COOC$_{1-5}$alkyl, —COC$_{1-5}$alkyl, —CO-aryl, —CO-heteroaryl, C$_{1-6}$alkyl, amino-C$_{1-5}$alkyl-, optionally substituted aryl, optionally substituted heteroaryl, halo-C$_{1-5}$alkyl, halo-C$_{1-5}$alkoxy-; Z'—C$_{1-6}$alkyl, Z'—C$_{2-6}$alkyl-O—, Z'—C$_{2-6}$alkyl-O—C$_{1-3}$alkyl-, Z'—C$_{2-6}$alkyl-S—, Z'—C$_{2-6}$alkyl-NH—, Z'—C$_{2-6}$alkyl-NH—C$_{1-3}$alkyl-, Z'—C$_{2-6}$alkyl-N(C$_{1-3}$alkyl)-C$_{1-3}$alkyl-, Z'—(CH$_2$CH$_2$—O)$_{1-5}$—, wherein Z' is selected from the group consisting of halo, radionuclide, —CF$_3$, —CH$_2$F, —CHF$_2$, aryl, and heteroaryl, wherein at least one H of aryl or heteroaryl is substituted with a halo or a radionuclide; and Y is selected from the group consisting of a quaternary ammonium salt, imidate salt, thiolate salt, oxonium cation, boron-amine salt, pyridinium salt.

33. The compound of claim 28, wherein X of X$^-$ is a halo.
34. The compound of claim 28, wherein Z' is a radionuclide.
35. The compound of claim 34, wherein Z' is $^{18}$F.
36. A compound comprising the Formula IIa$_4$:

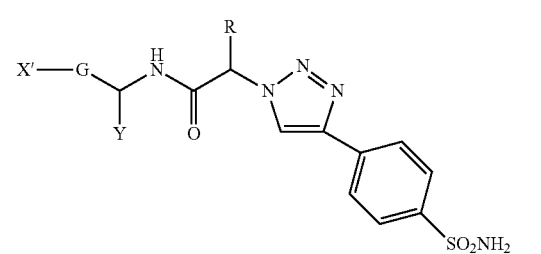

IIa$_4$ or a pharmaceutically acceptable salt thereof, optionally in the form of a single stereoisomer or mixtures of stereoisomers thereof,
wherein:
G is selected from the group consisting of aryl and heteroaryl;
X' is selected from the group consisting of a quaternary ammonium salt, imidate salt, thiolate salt, oxonium cation, boron-amine salt, pyridinium salt and Z'-D, where D comprises a charged moiety that is at least one of a cation or anion, wherein Z' is selected from the group consisting of halo, radionuclide, —CF$_3$, —CH$_2$F, —CHF$_2$, aryl, and heteroaryl, wherein at least one H of aryl or heteroaryl is substituted with a halo or a radionuclide;
Y is H or is selected from the group consisting of —SO$_2$H, N-oxide, —B(OH)$_2$, —COOR", —SO$_3$R", —P(O)$_2$OR" and —OP(O)$_2$OR" wherein R" is H or C$_{1-3}$alkyl; and
R is H, or is selected from the group consisting of
a side chain of an amino acid,
halobenzyl,
—C$_{1-5}$alkyl-, —C$_{1-5}$alkyl-OR", —C$_{1-5}$alkyl-N(R")$_2$, —C$_{1-5}$alkyl-NR"C(O)—(CH$_2$CH$_2$O)$_m$—C$_1$-C$_5$-alkyl-CO$_2$R" wherein m is 0-8, —C$_{1-5}$alkyl-NR"C(O)—C$_1$-C$_5$-alkyl wherein said —C$_{1-5}$alkyl is optionally substituted with OR" or CH$_2$OR", —C$_{1-5}$alkyl-o, m, or p-aryl-(O—CH$_2$CH$_2$)$_{1-5}$-halo wherein said —(O—CH$_2$CH$_2$)$_{1-5}$-halo is optionally substituted with one or more OR", or —C$_{1-5}$alkyl-o, m, or p-aryl-(CH$_2$CH$_2$)$_{1-5}$-halo, wherein R" is H or C$_1$-C$_3$-alkyl.

37. The compound of claim 36, wherein X' is Z'-D and wherein D is X$^-$[C(R$^{4'}$)$_{1-2}$]$_{1-5}$—, wherein R$^{4'}$ is C$_{1-5}$ alkyl, wherein at least one C(R$^{4'}$)$_{1-2}$ is C(R$^{4'}$)$_1$ and wherein at least one C of C(R$^{4'}$)$_1$ is replaced by O$^+$.
38. The compound of claim 37, wherein Z' is a radionuclide.

* * * * *